United States Patent
Hamilton

(10) Patent No.: US 7,625,756 B2
(45) Date of Patent: Dec. 1, 2009

(54) EXPRESSION OF CLASS 2 MANNOSIDASE AND CLASS III MANNOSIDASE IN LOWER EUKARYOTIC CELLS

(75) Inventor: Stephen Hamilton, Enfield, NH (US)

(73) Assignee: GycoFi, Inc., Lebanon, NH (US)

( * ) Notice: Subject to any disclaimer, the term of this patent is extended or adjusted under 35 U.S.C. 154(b) by 172 days.

(21) Appl. No.: 10/616,082

(22) Filed: Jul. 8, 2003

(65) Prior Publication Data
US 2004/0230042 A1 Nov. 18, 2004

Related U.S. Application Data

(63) Continuation-in-part of application No. 10/371,877, filed on Feb. 20, 2003, now Pat. No. 7,449,308.

(51) Int. Cl.
C12N 15/70 (2006.01)
C12N 1/15 (2006.01)
C07K 16/00 (2006.01)
C12N 15/63 (2006.01)

(52) U.S. Cl. .................. 435/471; 435/254.11; 530/395

(58) Field of Classification Search .................. None
See application file for complete search history.

(56) References Cited

U.S. PATENT DOCUMENTS

| | | | |
|---|---|---|---|
| 4,414,329 A | 11/1983 | Wegner | |
| 4,617,274 A | 10/1986 | Wegner | |
| 4,683,293 A | 7/1987 | Craig | |
| 4,775,622 A | 10/1988 | Hitzeman et al. | |
| 4,808,537 A | 2/1989 | Stroman et al. | |
| 4,812,405 A | 3/1989 | Lair et al. | |
| 4,818,700 A | 4/1989 | Cregg et al. | |
| 4,837,148 A | 6/1989 | Cregg | |
| 4,855,231 A | 8/1989 | Stroman et al. | |
| 4,857,467 A | 8/1989 | Sreekrishna et al. | |
| 4,879,231 A | 11/1989 | Stroman et al. | |
| 4,882,279 A | 11/1989 | Cregg | |
| 4,885,242 A | 12/1989 | Cregg | |
| 4,925,796 A | 5/1990 | Bergh et al. | |
| 4,929,555 A | 5/1990 | Cregg et al. | |
| 4,935,349 A | 6/1990 | McKnight et al. | |
| 5,002,876 A | 3/1991 | Sreekrishna et al. | |
| 5,004,688 A | 4/1991 | Craig et al. | |
| 5,032,516 A | 7/1991 | Cregg | |
| 5,032,519 A | 7/1991 | Paulson et al. | |
| 5,047,335 A | 9/1991 | Paulson et al. | |
| 5,122,465 A | 6/1992 | Cregg et al. | |
| 5,135,854 A | 8/1992 | MacKay et al. | |
| 5,166,329 A | 11/1992 | Cregg | |
| 5,324,663 A | 6/1994 | Lowe | |
| 5,595,900 A | 1/1997 | Lowe | |
| 5,602,003 A | 2/1997 | Pierse et al. | |
| 5,707,828 A | 1/1998 | Sreekrishna et al. | |
| 5,766,910 A | 6/1998 | Fukuda et al. | |
| 5,834,251 A | 11/1998 | Maras et al. | |
| 5,849,904 A | 12/1998 | Gerardy-Schahn et al. | |
| 5,854,018 A | 12/1998 | Hitzemane et al. | |
| 5,861,293 A | 1/1999 | Kojiri et al. | |
| 5,910,570 A | 6/1999 | Elhammer et al. | |
| 5,945,314 A | 8/1999 | Prieto et al. | |
| 5,945,322 A | 8/1999 | Gotschlich | |
| 5,955,347 A | 9/1999 | Lowe | |
| 5,955,422 A | 9/1999 | Lin | |
| 5,962,294 A | 10/1999 | Paulson et al. | |
| 6,017,743 A | 1/2000 | Tsuji et al. | |
| 6,096,512 A | 8/2000 | Elhammer et al. | |
| 6,204,431 B1 | 3/2001 | Prieto et al. | |
| 6,300,113 B1 | 10/2001 | Landry | |
| 6,410,246 B1 | 6/2002 | Zhu et al. | |
| 7,029,872 B2 | 4/2006 | Gerngross | |
| 7,064,191 B2 | 6/2006 | Shinkawa et al. | |
| 7,214,775 B2 | 5/2007 | Hanai et al. | |
| 2004/0018590 A1 | 1/2004 | Gerngross et al. | |
| 2004/0171826 A1 | 9/2004 | Hamilton | |
| 2004/0230042 A1 | 11/2004 | Hamilton | |
| 2005/0170452 A1 | 8/2005 | Wildt et al. | |
| 2005/0208617 A1 | 9/2005 | Bobrowicz et al. | |
| 2005/0260729 A1 | 11/2005 | Hamilton | |
| 2006/0024292 A1 | 2/2006 | Gerngross et al. | |

(Continued)

FOREIGN PATENT DOCUMENTS

EP 0 905 232 A1 3/1999

(Continued)

OTHER PUBLICATIONS

Vervecken et al. In vivo Synthesis of Mammalian-Like, Hybrid-Type N-Glycans in *Pichia pastoris*. Appl. Environ. Microbiol. 70(5): 2639-46, 2004.*

(Continued)

Primary Examiner—Nancy Vogel
Assistant Examiner—Michele K. Joike
(74) Attorney, Agent, or Firm—John David Reilly; Catherine D. Fitch

(57) ABSTRACT

A method for producing human-like glycoproteins by expressing a Class 2 α-mannosidase having a substrate specificity for Manα1,3 and Manα1,6 glycosidic linkages in a lower eukaryote is disclosed. Hydrolysis of these linkages on oligosaccharides produces substrates for further N-glycan processing in the secretory pathway.

28 Claims, 72 Drawing Sheets

U.S. PATENT DOCUMENTS

| | | |
|---|---|---|
| 2006/0024304 A1 | 2/2006 | Gerngross et al. |
| 2006/0029604 A1 | 2/2006 | Gerngross et al. |
| 2006/0034828 A1 | 2/2006 | Gerngross et al. |
| 2006/0034829 A1 | 2/2006 | Gerngross et al. |
| 2006/0034830 A1 | 2/2006 | Gerngross et al. |
| 2006/0040353 A1 | 2/2006 | Davidson et al. |
| 2006/0078963 A1 | 4/2006 | Gerngross |
| 2006/0148035 A1 | 7/2006 | Gerngross |
| 2006/0160179 A1 | 7/2006 | Bobrowicz et al. |
| 2006/0177898 A1 | 8/2006 | Gerngross |
| 2006/0211085 A1 | 9/2006 | Bobrowicz |
| 2006/0286637 A1 | 12/2006 | Hamilton |
| 2007/0105127 A1 | 5/2007 | Gerngross |

FOREIGN PATENT DOCUMENTS

| | | |
|---|---|---|
| EP | 1 054 062 A1 | 11/2000 |
| EP | 1 211 310 A | 6/2002 |
| EP | 1522590 | 4/2005 |
| EP | 1297172 | 11/2005 |
| JP | 8-336387 | 12/1996 |
| WO | WO 96/21038 A | 7/1996 |
| WO | WO 98/05768 | 2/1998 |
| WO | WO 99/31224 | 6/1999 |
| WO | WO 99/54342 | 10/1999 |
| WO | WO 00/61739 | 10/2000 |
| WO | WO 01/14522 A1 | 3/2001 |
| WO | WO 01/25406 | 4/2001 |
| WO | WO 01/36432 | 5/2001 |
| WO | WO 01/60860 | 8/2001 |
| WO | WO 02/00856 | 1/2002 |
| WO | WO 02/00879 | 1/2002 |
| WO | WO 02/097060 | 12/2002 |
| WO | WO 03/025148 | 3/2003 |
| WO | WO 03/031464 A | 4/2003 |
| WO | WO 03/056914 | 7/2003 |
| WO | WO 2004/003194 A | 1/2004 |
| WO | WO 2004/074458 | 9/2004 |
| WO | WO 2004/074461 | 9/2004 |
| WO | WO 2004/074497 | 9/2004 |
| WO | WO 2004/074498 | 9/2004 |
| WO | WO 2004/074499 | 9/2004 |
| WO | WO 2007/028144 | 3/2007 |

OTHER PUBLICATIONS

Bobrowicz et al. Engineering of an artificial glycosylation pathway blocked in core oligosaccharide assembly in the yeast *Pichia pastoris*: production of complex humanized glycoproteins with terminal galactose. Glycobiology 14(9): 757-766, 2004.*

Abeijon et al., "Molecular Cloning of the Golgi apparatus uridine diphosphate-N-acetylglucosamine transporter from *Kluyveromyces lactis*," *Proc. Natl. Acad. Sci.* USA 93:5963-5968 (1996).

Adachi et al., "Mus Musculus Adult Male Testis cDNA, Riken full length enriched library, clone: 4931438M07 product: mannosidase 2, alpha 2, full insert sequence" XP002293645, Database accession No. AK029913 Abstract, Database EMBL, Dec. 21, 2002.

Alani et al., "A Method for Gene Disruption that Allows Repeated Use of URA3 Selection in the Construction of Multiply Disrupted Yeast Strains," Genetics 116, 541-545, Aug. 1987.

Altman et al., "Processing of Asparagine-linked Oligosaccharides in Insect Cells: Evidence for Alpha-Mannosidase II," *Glycoconj. J* 12(2):150-155 (1995).

Altman et al., "Insect cells as hosts for the expression of recombinant glycoproteins," *Glycoconj. J.* 16(2):109-123 (1999).

Andersen et al., "The Effect of Cell-Culture Conditions on the Oligosaccharide Structures of Secreted Glycoproteins," *Curr Opin Biotechnol*, 5(5):546-549, Oct. 1994.

Aoki et al., "Expression and activity of chimeric molecules between human UDP-galactose transporter and CMP-sialic acid transporter," *J. Biochem.* (Tokyo), 126(5):940-50, Nov. 1999.

Bardor et al., "Analysis of the N-glycosylation of recombinant glycoproteins produced in transgenic plants," *Trends in Plant Science* 4(9): 376-380 (1999).

Beaudet et al., "High-level expression of mouse Mdr3 P-glycoprotein in yeast *Pichia pastoris* and characterization of ATPase activity," *Methods Enzymol* 292: 397-413 (1998).

Berka et al., "The Filamentous Fungus Aspergillus-Niger Var Awamori as Host for the Expression and Secretion of Fungal and Non-Fungal Heterologous Proteins," *Abstr Papers Amer Chem Soc* 203: 121-BIOT (1992).

Berninsone et al., "The Golgi Guanosine Diphophatase is Required For Transport of GDP-Mannose Into the Lumen of *Saccharomyces cerevisiae* Golgi Vesicles," *J. Biol. Chem.*, 269(1):207-211, Jan. 1994.

Berninsone et al., "Regulation of yeast Golgi glycosylation. Guanosine diphosphatase functions as a homodimer in the membrane," *J. Biol. Chem* 270(24): 14564-14567 (1995).

Berninsone et al., "Functional Expression of the Murine Golgi CMP-Sialic Acid Transporter in *Saccharomyces cerevisiae*," *J. Biol. Chem.* 272(19):12616-12619, May 1997.

Bianchi et al., "Transformation of the yeast *Kluyveromyces lactis* by new vectors derived from the 1.6 μm circular plasmid pKD1," *Current Genetics*, 12:185-192, 1987.

Boehm et al., "Disruption of the KEX1 Gene in *Pichia pastoris* Allows Expression of Full-Length Murine and Human Endostatin," *Yeast*, 15:563-572 (1999).

Bonneaud et al., "A family of low and high copy replicative, integrative and single-stranded *S. cerevisiae/E. coli* shuttle vectors," *Yeast* 7(6): 609-615 (1991).

Bretthauer et al., "Glycosylation of *Pichia pastoris*-derived proteins," *Biotechnol Appl Biochem* 30(Pt 3): 193-200 (1999).

Bretthauer et al., "Genetic engineering of *Pichia pastoris* to humanize N-glycosylation of proteins," *TRENDS in Biochem*, 21(11): 459-462 (2003).

Brockhausen et al., "Control of glycoprotein synthesis. The use of oligosaccharide substrates and HPLC to study the sequential pathway for N-acetylglucosaminyltransferases I, II, III, IV, V and VI in the biosynthesis of highly branched N-glycans by hen oviduct membranes," Biochem. Cell Biol. 66:1134-1151 (1988).

Callewaert et al., "Use of HDEL-Tagged *Trichoderma reesei* Mannosyl Oligosaccharide 1,2∀-D-Mannosidase for N-glycan Engineering in *Pichia pastoris*," FEBS Letters, 503(2-3):173-8, 2001.

Cereghino et al., "Heterologous protein expression in the methylotrophic yeast *Pichia pastoris*," *FEMS Microbiology Reviews*, 24(1): 45-66 (2000).

Cereghino et al., "New selectable marker/auxotrophic host strain combinations for molecular genetic manipulation of *Pichia pastoris*," Gene, 263:159-169(2001).

Chandrasekaran et al., "Purification and Properties of Alpha-D-Mannose:beta-1,2-N-acetylglucosaminyl-transferases and alpha-D-Mannosidases from Human Adenocarcinoma," *Cancer Res.*, 44(9):4059-68, Sep. 1984.

Chiba et al., "Production of Human Compatible High Mannose-type ($Man_5GlcNAc_2$) Sugar Chains in *Saccharomyces cerevisiae*," *J. Biol. Chem.*, 273(41):26298-26304, Oct. 1998.

Choi et al., "Use of combinatroial genetic libraries to humanize N-linked glycosylation in the yeast *Pichia pastoris*," *Proc. Natl. Acad. Sci.* USA 100(9):5022-5027, Apr. 2003.

Chui et al., "Genetic Remodeling of Protein Glycosylation in vivo Induces Autoimmune Disease," *Proc. Natl. Acad. Sci.*, USA 98:1142-1147, Jan. 2001.

Chui et al., "Alpha-mannosidase-II Deficiency Results in Dyserythropoiesis and Unveils and Alternate Pathway in Oligosaccharide Biosynthesis," *Cell*, Jul. 11, 1997; 90(1):157-67.

Daniel et al, "Mammalian Alpha—Mannosidases—Multiple Forms but a Common Purpose?", *Glycobiology*, 4, 551-566, Oct. 1994.

Davidson et al., "A PCR-Based Strategy to Generate Integrative Targeting Alleles With Large Regions of Homology," *Microbiology*, 148 (Pt 8):2607-15).

Dente, "Human alpha-1-acid glycoprotein genes," *Prog. Clin. Biol. Res* 300:85-98 (1989).

Duvet et al., "Cytosolic Deglycosylation Process of Newly Synthesized Glycoproteins Generates Oligomannosides Possessing One GlcNAc Residue at the Reducing End," *Biochem J.*, 335, 1998, 389-396.

Eades et al., "Characterization of the Class I alpha-Mannosidase Gene Family in the Filamentous Fungus *Aspergillus nidulans*," *Gene*, Sep. 5, 2000; 255(1):25-34.

Eckhardt et al., "Molecular Cloning of the Hamster CMP-Sialic Acid Transporter," *Eur. J. Biochem.*, 248(1):187-192 (1997).

Foster et al., "Cloning and Sequence Analysis of GmII, a Drosophila Melanogaster Homologue of the cDNA Encoding Murine Golgi alpha-Mannosidase II," *Gene* 154 (1995) 183-186.

Gleeson, Paul A. "Targeting of Proteins to the Golgi Apparatus," *Histochem. Cell Biol.*, 109:517-532 (1998).

Gonzalez, Daniel S et al: "The Alpha-Mannosidases: Phylogeny and Adaptive Diversification" Molecular Biology and Evolution, vol. 17, No. 2, Feb. 2000, pp. 292-300, XP002293609 ISSN: 0737-4038.

Graham et al., "Compartmental Organization of Golgi-specific Protein Modification and Vacuolar Protein Sorting Events Defined in Yeast sec18 (*NSF*) Mutant," *J. Cell. Biol.*, 114(2): 207-218 (1991).

Grard et al., "Oligomannosides or Oligosaccharide-lipids as Potential Substrates for Rat Liver Cytosolic ∀-D-Mannosidase," *Biochem. J.*, 316: 787-792 (1996).

Guillen et al., "Mammalian Golgi apparatus UDP-*N*-acetylglucosamine transporter: Molecular Cloning by Phenotypic Correction of a Yeast Mutant," *Proc. Natl. Acad. Sci. USA*, 95(14):7888-7892 (1998).

Hamilton et al., "Production of Complex Human Glycoproteins in Yeast," *Science* 301:1244-1246 (2003).

Harkki et al., "A Novel Fungal Express System —Secretion of Active Calf Chymosin from the Filamentous Fungus *Trichoderma-Reesei*," *Bio-Tech* 7:596-603 (1989).

Harris B.R.: "*Caenorhabditis elegans* Cosmid F58H1" XP002293610, Protein F58H1.1, Abstract, Databaase EMBL Jul. 13, 1996.

Ichishima et al., "Molecular and Enzymic Properties of Recombinant 1,2-∀-Mannosidase from *Aspergillus saitoi* Overexpressed in *Aspergillus oryzae* Cells," 1999; *Biochem. J.*, 339(Pt 3): 589-597.

Ishida et al., "Molecular Cloning and Functional Expression of the Human Golgi UDP-*N*-Acetylglucosamine Transporter," *J. Biochem.*, 126(1):68-77 (1999).

Jarvis et al., "Isolation and Characterization of a Class II alpha-mannosidase cDNA from Lepidopteran Insect Cells," *Glycobiology*, 1997; 7(1):113-127 (1997).

Jarvis et al., "Engineering N-glycosylation pathways in the baculovirus-insect cell system," *Curr Opin Biotechnol* 9(5): 528-33 (1998).

Kainuma et al., "Coexpression of α1,2 galactosyltransferase and UDP-galactose transporter efficiently galatosylates *N*- and *O*-glycan in *Saccharomyces cerevisiae*," *Glycobiology*, 9(2): 133-141 (1999).

Kalsner et al., "Insertion into *Aspergillus nidulans* of functional UDP-GlcNAc: α3-D-mannoside β-1,2-*N*-acetylglucosaminyltransferase I, the enzyme catalysing the first committed step from oligomannose to hybrid and complex N-glycans," *Glycoconj. J.*, 12(3):360-370 (1995).

Kawar et al., "Insect Cells Encode a Class II ∀-Mannosidase with Unique Properties," *J. Biol. Chem.*, 276(19):16335-16340 (2001).

Khatra et al., "Some kinetic properties of human milk galactosyltransferase," *Eur. J. Biochem.* 44:537-560 (1974).

Krezdorn et al., "Human β1,4 galactosyltransferase and α2,6 sialytransferase expressed in *Saccharomyces cerevisiae* are retained as active enzymes in the endoplasmic reticulum," *Eur. J. Biochem.*, 220(3): 809-17 (1994).

Lal et al., "Isolation and Expression of Murine and Rabbit cDNAs Encoding an α1,2-Mannosidase Involved in the Processing of Asparagine-Linked Oligosaccharides," *J. Biol. Chem.*, 1994. 269(13): 9872-9881.

Lal et al. "Substrate Specificities of Recombnant Murine Golgi α1,2-Mannosidase IA and IB and Comparison with Endoplasmic Reticulum and Golgi Processing α1,2-Mannosidases," *Glycobiology* 8(10):981-995, 1998.

Liao et al., "Cloning, Expression, Purification, and Characterization of the Human Broad Specificity Lysosomal Acid ∀-Mannosidase," *J. Biol Chem* 271(45): 28348-28358.

Lehle and Tanner, "Membrane-Bound Mannosyl Transferase in Yeast Glycoprotein Biosynthesis," *Biochem. Biophys. Acta*, 350(1): 225-235, 1974.

Lu et al., "Cloning and Disruption of the b-lsopropylmalate Dehydrogenase Gene of *Pichia stipitis* with URA3 and Recovery of the Double Auxotroph," *Appl. Microbiol. Biotechnol*, 49 (2): 141-146 (1998).

Lussier et al., "The *KTR* and *MNN1* mannosyltransferase families of *Saccharomyces cerevisiae*," *Biochimica et Biophysica Acta* 1426: 323-334 (1999).

Malissard et al., "Expression of functional soluble forms of human beta-1, 4-galactosyltransferase I, alpha-2-6-sialyltransferase, and alpha-1, 3-fucosyltransferase VI in the methylotrophic yeast *Pichia pastoris*," *Biochem Biophys Res Commun* 267(1): 169-173 (2000).

Maras et al., "In vitro conversion of the carbohydrate moiety of fungal glycoproteins to mammalian-type oligosaccharides," *Eur. J. Biochem.*, 249: 701-707 (1997).

Maras et al., "Filamentous fungi as production organisms for glycoproteins of bio-medical interest," *Glycoconjugate Journal*, 16:99-107 (1999).

Maras et al., "Molecular Cloning and Enzymatic Characterization of a Trichoderma *reeisi* 1,2-alpha-D-mannosidase," *J. Biotechnol*, 77(2-3):255-263, 2000.

Martinet et al., "Modification of the protein glycosylation pathway in the methylotrophic yeast *Pichia pastoris*," *Biotechnology Letters* 20(12): 1171-1177 (1998).

Maruyama et al., "A 1,2-alpha-D-Mannosidase from a Bacillus sp.: Purification, Characterization, and Mode of Action," *Carbohydrate Res.* 251:89-98 (1994).

McClure "Modeling the growth, survival and death of microorganisims in foods: the UK food micromodel approach," *Int J. Food Microbiol.*, 23(3-4) 265-265 (1994).

McGarvey et al., "Expression of the rabies virus glycoprotein in transgenic tomatoes," *Bio-Technology* 13(13): 1484-1487 (1995).

Merkle et al., "Cloning, Expression, Purification, and Characterixation of the Murine Lysosomal Acid Alpha-Mannosidase," *Biochim Biophys Acta*, 1336(2): 132-46 (1997).

Miele et al., "Glycosylation Properties of the *Pichia pastoris*-Expressed Recombinant Kringle 2 Domain of Tissue-Type Plasminogen Activator," *Biotechnol. Appl. Biochem.*, 25:151-157 (1997).

Moens et al., "Glycoproteins in prokaryotes," *Arch. Microbiol.* 168(3):169-175.

Moremen, "Golgi α-mannosidase II deficiency in vertebrate systems: implications for asparagine-linked oligosaccharide processing in mammals," *Biochimica Biophysica Acta*, 1573: 225-235 (2002).

Moremen et al., "Biosynthesis and Modification of Golgi Mannosidase II in HeLa and 3T3 Cells," *J. Biol. Chem.*, 260(11): 6654-6662 (1985).

Moremen et al., "Topology of Mannosidase II in Rat Liver Golgi Membranes and Release of the Catalytic Domain by Selective Proteolysis," *J. Biol. Chem.*, 261(23): 10945-10951 (1986).

Moremen, "Isolation of a Rat Liver Golgi Mannosidase II Clone by Mixed Oligonucleotide-Primed Amplication of cDNA," *Proc. Natl. Acad. Sci.*, USA Jul. 1989;86(14):5276-80.

Moremen et al., "Isolation, Characterization, and Expression of cDNAs Encoding Murine ∀-Mannosidase II, a Golgi Enzyme that Controls Conversion of High Mannose to Complex N-Glycans," *Journal of Cell Biology*, Dec. 1991; 115(6):1521-34.

Moremen et al., "Glycosidases of the Asparagine-Linked Oligosaccharide Processing Pathway," *Glycobiology* 4(2): 113-125 (1994).

Nakanishi-Shindo et al., "Structure of the N-Linked Oligosaccharides That Show the Complete Loss of α-1,6-Polymannose Outer Chain from och1, och1 mnn1, and och1 mnn1 alg3 Mutants in *Saccharomyces cerevisiae*," *J. Biol. Chem.*, 268(35):26338-45 (1993).

Nakayama et al., "OCHI1 Encodes a Novel Membrane Bound Mannosyltransferase: Outer Chain Elongation of Asparagine-Linked Oligosaccharides," *Embo J.*, 11(7):2511-19, 1992.

Nakayama et al. "Substrate Specificity of ∀-1,6-Mannosylatransferase that Initiates N-Linked Mannose Outer Chain Elongation in *Saccharomyces cerevisiae*", *FEBS Lett.*, 412(3):547-50, 1997.

Nikawa et al., "Structural and functional conservation of human and yeast HCP1 genese which can suppress the growth defect of the *Saccharomyces cerevisiae* irel5 mutant," Gene 171(1): 107-111(1996).

Ogawa et al., "Structure and Transcriptional Regulation of Human alpha-Mannosidase IIX (alpha-mannosidase II isotype) Gene," *Eur. J. Biochem.*, 242(3): 446-453 (1996).

Oh-eda et al., "Overexpression of the Golgi-Localized Enzyme ∀-mannosidase IIX in Chinese Hamster ovary Cells Results inthe Conversion of Hexamannosyl-N-acetylchitobiose to Tetramannosyl-N-acetylchitobiose in the N-glycan-processing Pathway," *Eur. J. Biochem.*, 268:1280-1288 (2001).

Papac et al., "A high-throughput microscale method to release N-linked oligosaccharides from glycoproteins for matrix-assisted laser desorption/ionization time-of-flight mass spectrometric analysis," *Glycobiology* 8(5): 445-454 (1998).

Perez et al., "Transport of Sugar Nucleotides into the Lumen of Vesicles Derived from Rat Liver Rough Endoplasmic Reticulum and Golgi Apparatus," *Methods in Enzymology*, 138: 709-715 (1987).

Puglielli et al., "Reconstitution, Identification, and Purification of the Rat Liver Golgi Membrane GDP-fucose Transporter," *J. Biol. Chem.* 274(50): 35596-35600 (1999).

Rabouille et al., "The *Drosophila GMII* Gene Encludes Golgi α-mannosidase II," *J. Cell Sci.*, Oct. 1999;112(Pt 19): 3319-30.

Raju et al., "Analysis of glycoconjugates," *Anal Biochem.* 283(2): 123-124 (2000).

Ren et al., "Purification and Properties of a Golgi-Derived (alpha 1,2)-mannosidase-I from Baculovirus-infected Lepidopteran Insect Cells (IPLB-SF21AE) with Preferential Activity Toward Mannose6-N-Acetylglucosamine2," *Biochem.*, 34(8): 2489-2495.

Roberts, D.B.: "Drosophila Melanogaster GMII gene, exons 1-5" XP002293614, Database accession No. AJ132715, Abstract, Database EMBL.

Romero et al., "Ktr1P is an ∀-1,2-mannosyltransferase of *Saccharomyces cerevisiae*," *Biochem. J.*, 321 (Pt 2): 289-295 (1997).

Romero et al., "Mutation of Arg$^{273}$ to Leu Alters the Specificity of the Yeast N-Glycan Processing Class I ∀1,2-Mannosidase," *J. Biol. Chem*, 275(15):11071-11074 (2000).

Ruther et al., "c-fos expression interferes with thymus development in transgenic mice," *Cell* 53(6): 847-856 (1988).

Schachter et al., "The 'Yellow Brick Road' to Branched Complex N-glycans," *Glycobiology* 1(5): 453-461, 1991.

Sato et al., "Arabidopsis Thaliana DNA Chromosome 5, BAC clone F2G14 (Essa project)", XP002293613, Database accession No. AL391146, gene "F2G14_70" encoding "alpha-mannosidase-like protein" of protein_id="CACO1814.1" Abstract, Database EMBL Aug. 7, 2000.

Satou and SatoH: "Ciona Intestinalis cDNA, clone: cieg014e11, full insert sequence." XP002293611, Database accession No. AK116684, the whole document, Database EMBL.

Schneikert et al., "Characterization of a Novem Mouse Recombinant Processing alpha-mannosidase," *Glycobiology*, 4(4):445-450 (1994).

Schwientek et al., "Golgi Localization in Yeast is Mediated by the Membrane Anchor Region in Rat Liver Sialyltransferase," *J. Biol. Chem.*, 270(10):5483-5489 (1995).

Segawa et al., "*Schizosaccharomyces pombe* UDP-galatose transporter: identification of its functional form through cDNA cloning and expression in mammalian cells," *FEBS Letters*, 451(3): 295-298 (1999).

Shinn et al: "Arabidopsis Thaliana AT5g14950/F2G14_70 mRNA, complete cds." XP002293612, Database accession No. AY052707, Abstract, Database EMBL.

Sikorski et al., "A system of shuttle vectors and yeast host strains designed for efficient manipulation of DNA in *Saccharomyces cerevisiae*," *Genetics* 122(1): 19-27 (1989).

Soderholm et al. "Vector for pop-in/pop-out Gene Replacement in *Pichia pastoris*," *Biotchniques*, 31 (2):306-10 (2001).

Sommers et al., "Transport of Sugar Nucleotides into Rat Liver Golgi," *J. Cell Biol.*, 91(2): A406-A406 (1981).

Sommers et al., "Transport of Sugar Nucleotides into Rat Liver Golgi. A New Golgi Marker Activity," *J Biolog Chem*, 257(18): 10811-10817 (1982).

Staub et al., "High-yield production of a human therapeutic protein in tobacco chloroplasts," *Nature Biotechnology* 18(3): 333-338 (2000).

Stix, "Supercharging Protein Manufacture," *Scientific Amer.*, Jan. 2004: 32-33.

Svetina et al., "Expression of Catalytic Subunit of Bovine Enterokinase in the Filamentous Fungus Aspergillus Niger," *J. Biotechnol.*, 76(2-3): 245-251 (200).

Swiss Prot P11655.
Swiss Prot P32906.
Swiss Prot P39107.
Swiss Prot P50108.
Swiss Prot P53008.

Takeuchi, "Trial for molecular breeding of yeast for the production of glycoprotein therapeutics," *Trends in Glycoscience and Glycotechnology* 9:S29-S35 (1997).

Umaña et al., "Engineered Glycoforms of an Antineuroblastoma IgG1 with Optimized Antibody-Dependent Cellular Cytotoxic Activity," *Nature Biotechnology*, 17(1):176-80 (1999).

Ware et al., "Expression of Human Platelet Glycoprotein lb-Alpha in Transgenic Mice," *Thrombosis and Haemostasis* 69(6): 1194-1194 (1993).

Weikert et al., "Engineering Chinese Hamster Ovary Cells to Maximize Sialic Acid Content of Recombinant Glycoproteins", *Nature Biotechnology*, 17(11): 1116-1121, Nov. 1999.

Werner et al., "Appropriate Mammalian Expression Systems for Biopharmaceuticals," *Arzneimittelforschung*, Aug. 1998;48(8):870-80.

Wiggins et al., "Activity of the yeast MNN1 alpha-1,3-mannosyltransferase requires a notif conserved in many other families of glycosyltransfereases," *Proc. Nat. Acad. Sci.* USA 95(14): 7945-7950 (1998).

Yamashita et al., "An α-Mannosidase purified from *Aspergillus saitoi* is specific for α1,2 linkages," *Biochemical and Biophysical Research Communications* 96(3): 1335-1342.

Yang et al., "Glycosylation and proteolytic processing of 70 kDa C-terminal recombinant polypeptides of *Plasmodium falciparum* merozoite surface protein 1 expressed in mammalian cells," *Glycobiology*, 9(12): (1999) 1347-55.

Yang et al., "Effects of Ammonia on CHO Cell Growth, Erythropoietin Production, and Glycosylation", *Biotechnol Bioeng.*, 68(4): 370-80 (2000).

Yip et al., "Cloning and analysis of the *Saccharomyces cerevisiae* MNN9 and MNN1 genes required for complex glycosylation of secreted proteins," *Proc. Natl. Acad. Sci.* USA, 91(7): 2723-2727 (1994).

Yoko-o et al., "*Schizosaccharomyces Pombe Ochl*(+) Encodes Alpha-1,6- Mannosyltranferase that is involved in Outer Chain Elongation of N-Linked Oligosaccharides," *FEBS Lett.*, 489(1): 75-80 (2001).

Yoshida et al., "1-2-alpha-D- mannosidase from *Penicillium citriunum*: molecular and enzymic properties of two isoenzymes," *Biochem. J.* 290 (Pt2): 349-354 (1993).

Yoshida et al., "Expression and charaterization of rat UDP-N-acetylgluocosamine: α-3-D-mannoside β-1,2-N-acetylglucosaminyltransferase I in *Saccharomyces cerevisiae*," *Glycobiology*, 9 (1): 53-58 (1999).

Genbank Accession No. AF005034.
Genbank Accession No. AF106080.
Genbank Accession No. AK116684.
Genbank Accession No. D55649.
Genbank Accession No. NM_073594.
Genbank Accession No. NM_121499.
Genbank Accession No. U31520.
Genbank Accession No. X77652.
Genbank Accession No. XM_218816.
Genbank Accession No. NM 002406.
Genbank Accession No. CAA98114.
Genbank Accession No. NM_088548 (Genbank AN 6678787).
Genbank Accession No. NM006715.

Genbank Accession No. X61172.
Genbank Accession No. NM_000528.
Li et al., Nature Biotech., vol. 24 (2006), pp. 210-215, "Optimization of humanized IgGs in glycoengineered *Pichia pastoris*".
Lifely et al., Glycobiology, vol. 5 (1995), pp. 813-822, "Glycosylation and biological activity of CAMPATH-1H expressed in different cell lines . . .".
Yamane-Ohnuki et al., Biotech. Bioengin., vol. 87 (2004), pp. 614-622, "Establishment of FUT8 knockout Chinese hamster ovary cells: an ideal host cell line for producing . . .".
Tatara et al., J. of Biol. Chem., vol. 278 (2003), pp. 25289-25294, "Identification of catalytic residues of Ca2+-independent 1,2-alpha-D-mannosidase from *Aspergillus saitoi*. . .".
EP 1297172 B1—Glycode Opposition Brief (French).
EP 1297172 B1—Glycode Opposition Brief (English translation).
EP 1297172 B1—Novozyme Opposition Brief.
EP 1297172 B1—Patentee's Reply to the Notice of Opinion.
EP 1297172 B1—EPO Non-Binding Opinion.
Fujita et al., Biochem. & Biophys. Res. Comm., vol. 238 (1997), pp. 779-783, "Five crucial carboxyl resideus of 1,2-alpha-mannosidase from *Aspergillus saitoi (A. phoenicis)*, . . .".
Schlegel et al., Database GSN Derwent No. ABV29386, XP002293375 (2002).
Voet et al., Biochemistry (1990), pp. 266-267, Section 10-3. Glycoproteins.
Strasser et al., Biochem., vol. 387 (2005), pp. 385-391, "Molecular basis of N-acetylglucosaminyltransferase I deficiency in *Arabidopsis thaliana*. . .".
Minowa et al., J. Biol. Chem., vol. 273 (1998), pp. 11556-11562, "cDNA cloning and expression of bovine UDP-N-acetylglucosamine: . . .".
Duman et al., Biotechnol. Appl. Biochem., vol. 28 (1998), pp. 39-45, "O-mannosylation of *Pichia pastoris* cellular and recombinant proteins".

Weng et al., Glycobiology, vol. 6 (1996), pp. 861-868, "Evaluation o the early procesing routes of N-linked oligosaccharides of glycoproteins through the characteization of Man8G1cNAc2 . . .".
Merriam-Webster, definition of "domain".
Lee et al., Biotechnol. Prog., vol. 13 (1997), pp. 368-373, "Sequential δ-integration for the regulated insertion of cloned genes . . .".
Zhu et al., Archives of Biochem. & Biophysics, vol. 352 (1998), pp. 1-8, "Structural studies of alpha-N-acetylgalactosaminidase: Effect of glycosylation . . .".
Fukuta et al., Glycobiology, vol. 10 (2000), pp. 421-430, Remodeling of sugar chain structures of human interferon-γ.
Spiro et al., J. Biol. Chem., vol. 272 (1997), pp. 29356-29363, "Molecular cloning and expression of rat liver endo-α-mannosidase . . .".
Spiro, J. Biol. Chem., vol. 275 (2000), pp. 35657-35660, "Glucose residues as key determinants in the biosynthesis and quality control . . .".
Tang et al., XP-002293372, WO2003025148-A2, Mar. 27, 2003, "New polynucleotides and secreted proteins, useful for treating myeloid or lymphoid cell disorders . . .".
Tang et al., XP-002293373, WO2003025148-A2, Mar. 27, 2003, "New polynucleotides and secreted proteins, useful for treating myeloid or lymphoid cell disorders . . .".
Swarnakar et al., XP-002293374, WO200297060-A2, Dec. 5, 2002, "Novel human carbohydrate associated polypeptide, useful in diagnosis, treatment and prevention . . .".
Carninci et al., XP-002293371, AK030141, dated Dec. 5, 2002, "Mus musculus adult male testis cDNA . . .".
Schlegel et al., XP-002293375, WO200160860-A2, Aug. 23, 2001, "Human prostate expression marker cDNA 29377".

* cited by examiner

M. musculus alpha-1,2-mannosidase IA open reading frame. The transmembrane and catalytic domains are highlighted in bold respectively. The sequence of the primers used to generate the N-terminal truncations are highlighted by underlining and the start of each respective protein fragment indicated by an arrow.

```
  1  atgcccgtgggggcctgttgccgctcttcagtagcccctggggcggcctgggcagtggcctgggcggcctggggcggagaagggg
  1▶ M  P  V  G  G  L  L  P  L  F  S  S  P  G  G  G  L  G  S  G  L  G  G  L  G  G  G  R  K  G 97  tctgtgcccgcctgcttccgcctcaccgagaagttcgtgctgcttgttcagcgccttcatcacgctctgcttcggcgcaatc
 33▶ S  G  P  A  A  F  R  L  T  E  K  F  V  L  L  V  F  S  A  F  I  T  L  C  F  G  A  I 184  ttcttcctgactgactctctccaagctgtctcagcgggtctgttcactccaacccctgcctgcagccggagcaagcccggctcg
 62▶ F  F  L  P  D  S  K  L  L  S  G  V  L  F  H  S  N  P  A  L  Q  P  P  A  E  H  K  P  G  L
             d65 primer 278  gggcgcgtgcgcggagggatgccgccgagggagagtccgcggcaccgcgcgggagcgcgcaggaagacaacttagcca
 93▶ G  R  A  E  D  A  A  E  G  R  V  R  H  R  E  E  G  A  P  G  D  P  G  A  G  L  E  D  N  L  A
                                    d105 primer 374  ggatccgcgaaaccacgagcgctcagggagcgctgcgaggagatccgcagaagctgcagaagactattctgctggagaagg
125▶ R  I  R  E  N  H  E  R  A  L  R  E  A  K  E  T  L  Q  K  L  P  E  E  I  Q  R  D  I  L  L  E  K 470  aaaaggtgccagaccagctgcgtgacaaggatctgttttaggggctgcccaaggtgcttgccaggtggacttcctgcccccgtcggggtagagaaccgggagc
157▶ E  K  V  A  Q  D  L  R  D  K  D  L  F  R  G  L  P  K  V  D  F  L  P  P  V  G  V  E  N  R  E
                                                                                d187 primer 566  ccgctgacgccaccatccgtgagaagaggcaaagatcaaagagagaggttgaataattataacgctatgcctgtggggc
189▶ P  A  D  A  T  I  R  E  K  R  A  K  I  K  E  M  M  T  H  A  W  N  N  Y  K  R  Y  A  W  G
```

FIG. 3

```
 655      ttgaacgaactgaaacctatatcaaagaaggccattcaagcagtttgtttggcaacatcaaggagctacaatagtagatg
 219 ►     L  N  E  L  K  P  I  S  K  E  G  H  S  S  S  L  F  G  N  I  K  G  A  T  I  V  D
 737      ccctggataccctttcattatgggcatgaagactgaagaattcaagaagctaaatcgtggattaaaaatattagattta
 246 ►  A  L  D  T  L  F  I  M  G  M  K  T  E  F  Q  E  A  K  S  W  I  K  K  Y  L  D  F  N
 819      tgtgaatgctgaagtttctgtttctgaagtcaacatacgcttcgtcggtggactgcttcagctacctattgtccggagag
 273 ►     V  N  A  E  V  S  V  F  E  V  N  I  R  F  V  G  G  L  L  S  A  Y  Y  L  S  G  E
 901      gagatattcgaaagacagtggaacttgggtaaaattgctatctcctctgaatacctgaatacctggcat
 301 ►  E  I  F  R  K  A  V  E  L  G  V  K  L  L  P  A  F  H  T  P  S  G  I  P  W  A
 983      tgctgaatatgaaaagtgggatcggcggaactggccgcatctggcctgtggaggcagaagtatcctggcgaattggaactct
 328 ►  L  L  N  M  K  S  G  I  G  R  N  W  P  W  A  S  G  G  S  S  I  L  A  E  F  G  T  L
1065      gcattagagtttatgcacttgtccacttatccagtcttcagggaccagcagtctttgccgaaaaggttcgaaaattcgaacagtgttg
 355 ►  H  L  E  F  M  H  L  S  G  D  P  V  F  A  E  K  V  M  K  I  R  T  V  L
1147      aacaaactggacaaaccagagcttgatgcttcaggcgacagctagcgacagtggggtcaacatcatgtgtcgg
 383 ►  N  K  L  D  K  P  E  G  L  Y  P  N  Y  L  N  P  S  S  G  Q  W  G  Q  H  V  S
1229      ttgaggagactggactgctgttcaggacaacaagatggccactgacctgctttgcactgttgcactcgcagatggagctc
 410 ►  V  G  G  L  G  D  S  F  Y  E  Y  L  L  K  A  W  L  M  S  D  K  T  D  L  E  A  K
1311      gatgtatttgatgctgttcaggacaacaagatggccactgacctgctttgcactgttgcactcgcagatggagctc
 437 ►  M  Y  F  D  A  V  Q  A  E  T  H  L  I  R  K  S  S  G  G  L  T  Y  I  A  E  W
1393      aaggggcctggctggaaactttgaattgcatgaattgtcatgaattctataatcgtacatatgt
 465 ►  K  G  G  L  L  E  H  K  M  G  H  L  T  C  F  A  G  G  M  F  A  L  G  A  D  G  A
1475      cggaagcccgactaccacttctgacctcgaggttgatggaagctgtgtggaagctgactgcagtacaggaccagcacgacccaagtgactgggctggaagccg
 492 ►  P  E  A  R  A  Q  H  Y  L  E  L  G  A  E  I  A  R  T  C  H  E  S  Y  N  R  T  Y  V
1557      gaagtgggaggaccgaagcgttcgattgatggcgttcgattggatggcgttcgattggatggaagctgtgtggaagctgactgcagt
 519 ►  K  L  G  P  E  A  F  R  F  D  G  G  V  E  A  I  A  T  R  Q  N  E  K  Y  I  L
1639      cggccgaggtcatcgagacatgccgcactgactgactgcagcacatgtggcgactactcacgaccagtacagg actacctggcctgggaagccg
 547 ►  R  P  E  V  I  E  T  Y  M  Y  M  W  R  L  T  H  D  P  K  Y  R  T  W  A  W  E  A
1721      tggagctctagaaagtcactgcagagacatgcaacggagaggctactcaggctactcattgcccgtgagagttatga
 574 ►  V  E  A  L  E  S  H  C  R  V  N  G  G  Y  S  G  L  R  D  V  Y  I  A  R  E  S  Y  D
1803      cgatgtccagcaaagtcttcttcctggcagacactgaagtatttcttgatattccgatgatgacttcttccact a
 601 ►  D  V  Q  Q  S  F  L  A  E  T  L  K  Y  L  Y  L  I  F  S  D  D  L  L  P  L
1885      gaacactggatcttcaacaccgaggctcatcctttccctatactccgtgaacagaagaaaattgatggcaagaaatga
 629 ►  E  H  W  I  F  N  T  E  A  H  P  F  P  I  L  R  E  Q  K  K  E  I  D  G  K  E  K
```

*FIG. 3 CONT*

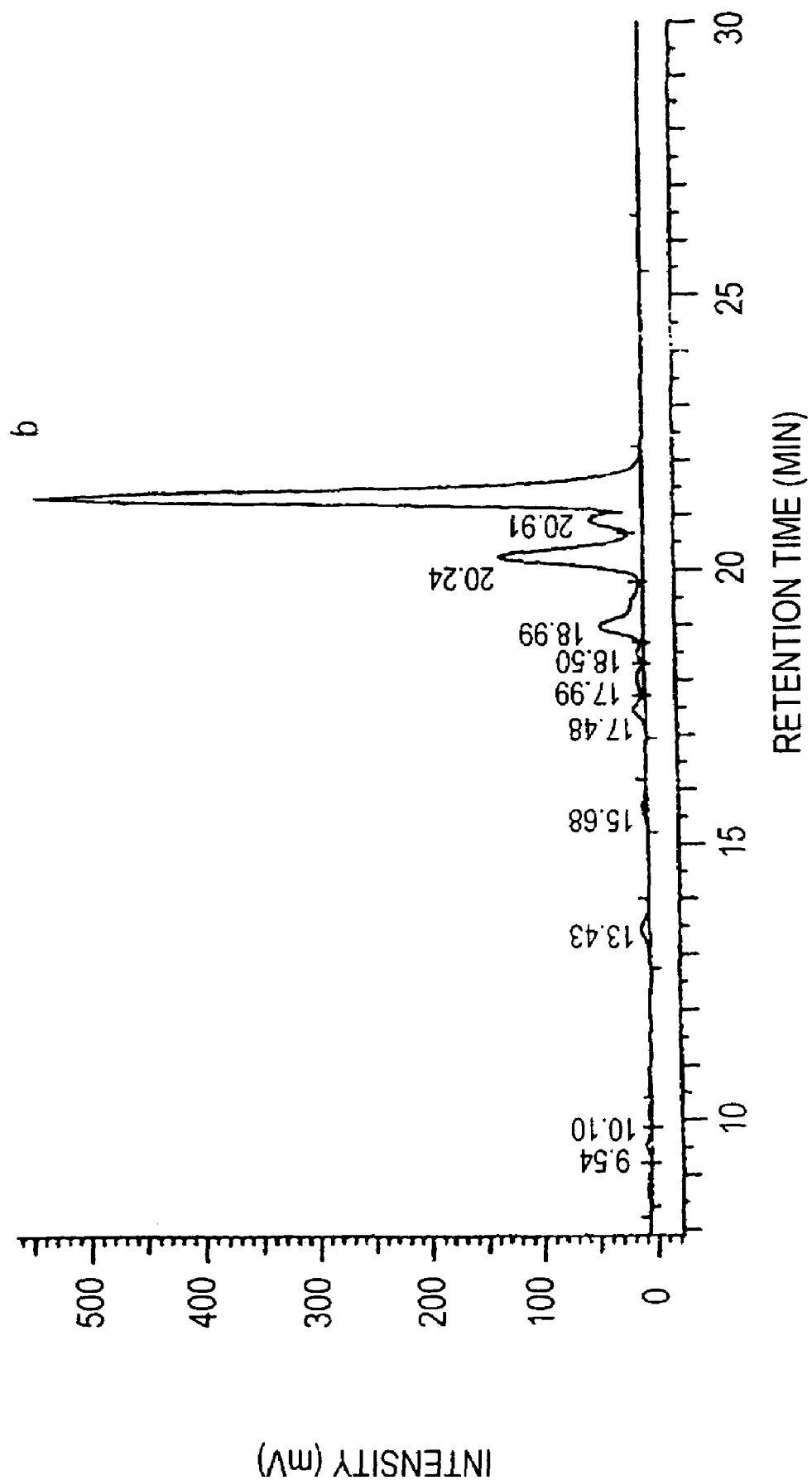

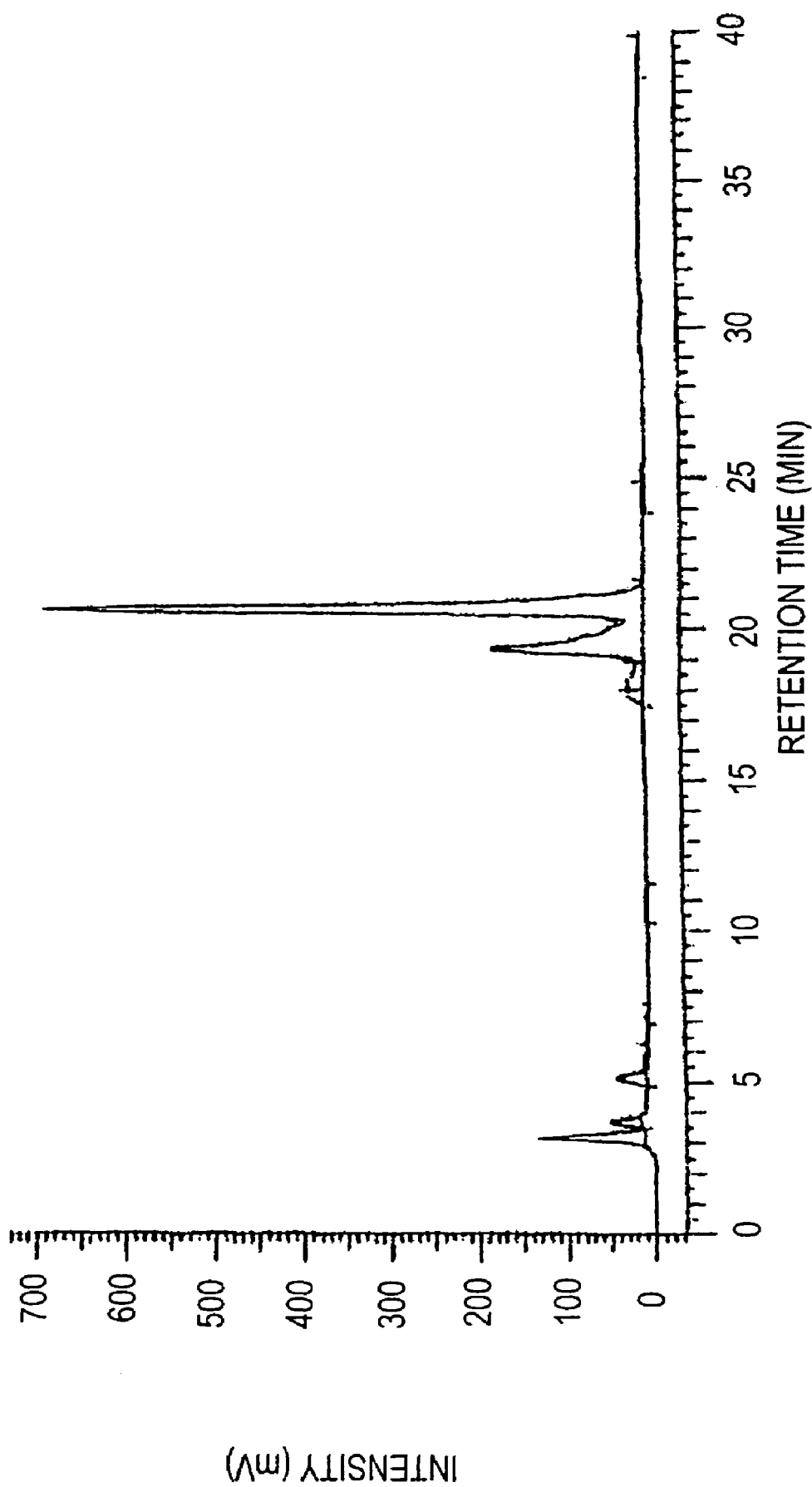

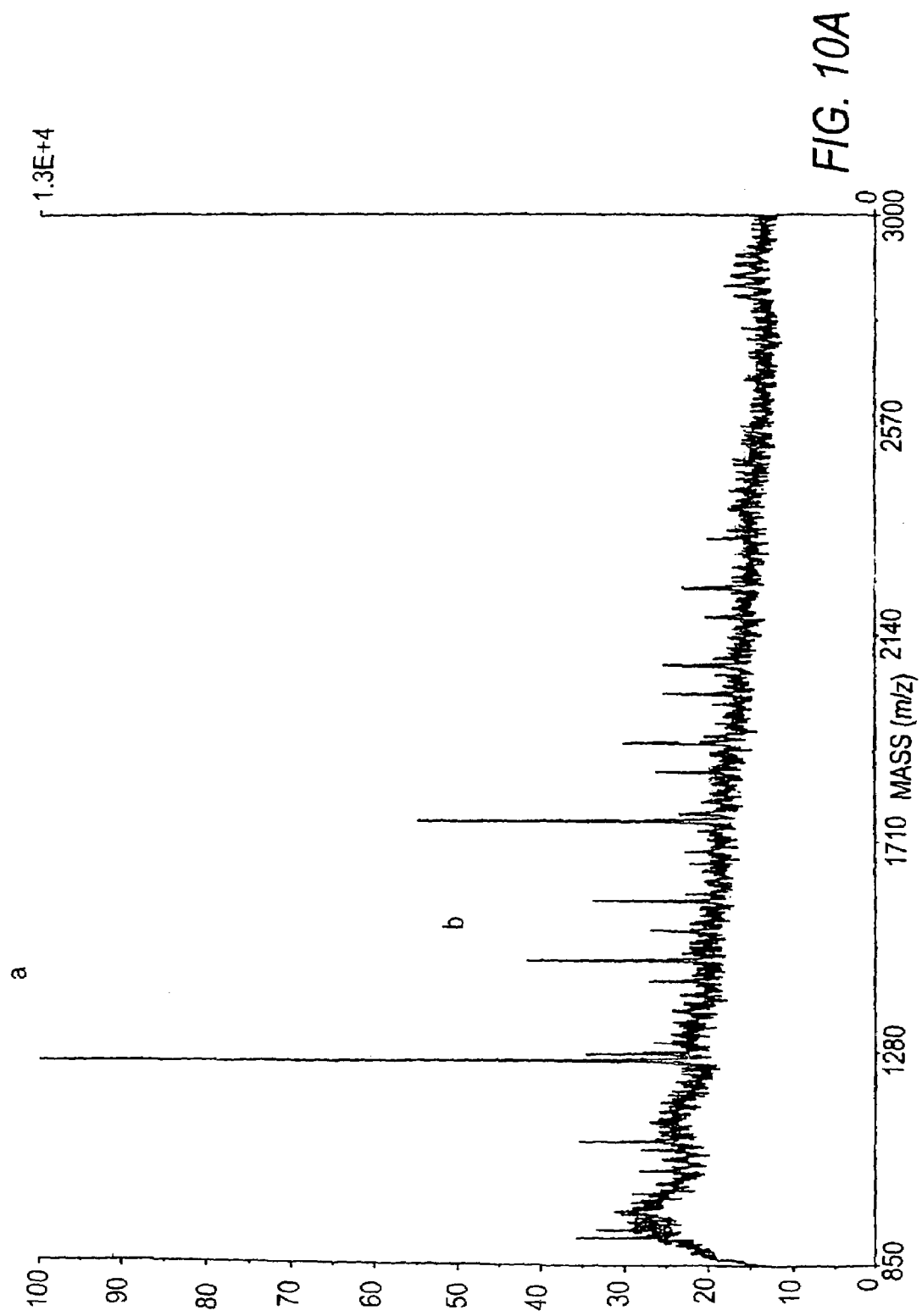

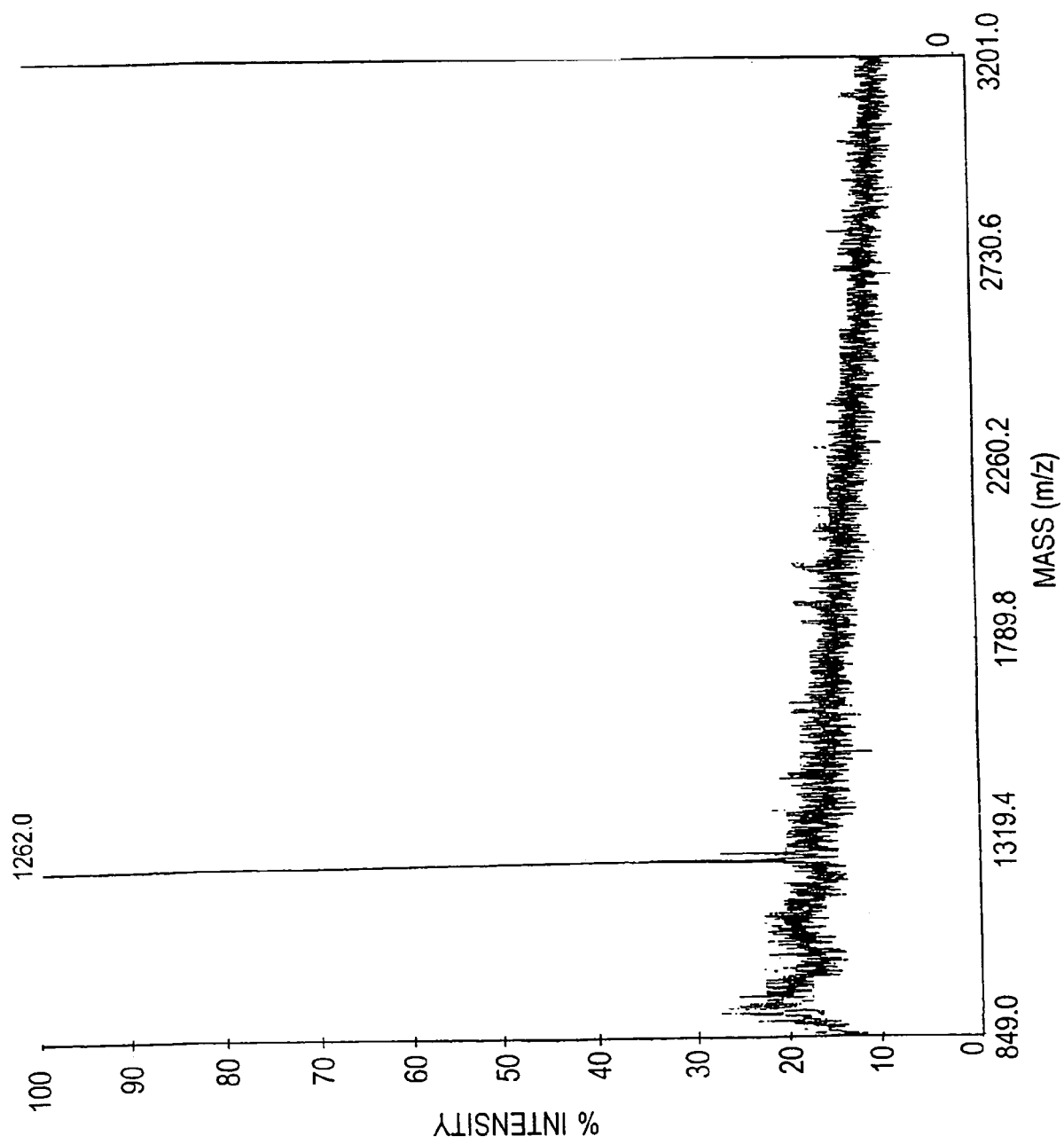

Version 3.2

BOXSHADE
Color-Coded Plots of Pre-Aligned Sequences

Selected Sequence(s)
- Droso MannII (X77652),
C.elegans MannII,
rMannII (XM_218816.1),
hMannIIx D55649,
Mouse MannII (X61172),
human MannII (U31520),
CionaMannII (AK116684),
ArabMannII,
Insect ManIII,
hLyso MannII,
hCyto MannII (NM_006715)

| Return | Help | Report Bugs |

Citation

Algorithm Citation:
Not given, but presumably Kay Hofmann and Michael D. Baron.
Program Citation:
Boxshade version 3.3.1, by Kay Hofmann and Michael D. Baron.

Copyright (C) 1999, Board of Trustees of the University of Illinois.

FIG. 25

Arabidopsis thaliana Mannosidase II (NM_121499)

FIG. 26

C. elegans Mannosidase II (NM_073594)

```
   1 ATGGGAAAACGCAATTTCTATATTATCCTATGTTTGGGAGTCTTTCTCACCGTATCACTCTATTTGTACAATGGAATTGAAACCGGAGCTGAAGCGCTCACCAAACGACA
   1 M  G  K  R  N  F  Y  I  I  L  C  L  G  V  F  L  T  V  S  L  Y  L  Y  N  G  I  E  T  G  A  E  A  L  T  K  R  Q
 111 AGCAAATGATTTACGCCGCAAAATCGGAAATTTGGAGCATGTAGCAGAAGAAAATGGAAGAACGATAGACCGCTTGGAACAAGAAGTTCAACGAGCAAAAGCTGAAAAAT
  37 A  N  D  L  R  R  K  I  G  N  L  E  H  V  A  E  E  N  G  R  T  I  D  R  L  E  Q  E  V  Q  R  A  K  A  E  K
 221 CGGTAGATTTTGATGAAGAAAAAGAAAAAACGGAAGAAAAAGAAGTAGAAAAAGAGGAAAAAGAAGTTGCACCAGTTCCAGTTCGAGGAAATCGTGGTGAAATGGCTCAT
  74 S  V  D  F  D  E  E  K  E  K  T  E  E  K  E  V  E  K  E  E  K  E  V  A  P  V  P  V  R  G  N  R  G  E  M  A  H
 331 ATTCATCAAGTAAAGCAACATATCAAGCCAACTCCATCGATGAAAGATGTTTGTGGAATTAGAGAAAACGTCAGCATTGCTCATTCAGACCTGCAGATGCTCGATCTCTA
 111 I  H  Q  V  K  Q  H  I  K  P  T  P  S  M  K  D  V  C  G  I  R  E  N  V  S  I  A  H  S  D  L  Q  M  L  D  L  Y
 441 TGACACCTGGAAGTTCGAAAATCCAGACGGAGGTGTATGGAAACAAGGATGGAAAATTGAATACGATGCAGAGAAAGTCAAATCTCTTCCACGTTTGGAAGTTATTGTGA
 147 D  T  W  K  F  E  N  P  D  G  G  V  W  K  Q  G  W  K  I  E  Y  D  A  E  K  V  K  S  L  P  R  L  E  V  I  V
 551 TACCTCATTCTCATTGTGATCCCGGATGGATTATGACTTTCGAAGAGTATTACAACACACAAACTCGCAATATTCTTGATGGAATGGCTAAACATTTGGCAGAAAAAGAC
 184 I  P  H  S  H  C  D  P  G  W  I  M  T  F  E  E  Y  Y  N  R  Q  T  R  N  I  L  D  G  M  A  K  H  L  A  E  K  D
 661 GAAATGCGGTTTATATATGCAGAAATATCATTTTTCGAAACTTGGTGGAGAGACCAGGCAGATGAAATAAAAAGAAAGTTAAAGGATATTTGGAAGCAGGAAAGTTTGA
 221 E  M  R  F  I  Y  A  E  I  S  F  F  E  T  W  W  R  D  Q  A  D  E  I  K  K  K  V  K  G  Y  L  E  A  G  K  F  E
 771 AATTGTTACTGGCGGATGGGTTATGACAGATGAAGCTAATGCACATTACACTCAATGATCACTGAATTGTTCGAAGGACATGAATTCAAAATCATTTGGGAAAAA
 257 I  V  T  G  G  W  V  M  T  D  E  A  N  A  H  Y  H  S  M  I  T  E  L  F  E  G  H  E  W  I  Q  N  H  L  G  K
 881 GCGCCATTCCACAATCTCATTGGTCAATTGATCCATTCGGTTTATCACCATCAATGCCACATCTTCTAACTTCTGCTAATATAACCAATGCTGTAATTCAAACAGTTCAT
 294 S  A  I  P  Q  S  H  W  S  I  D  P  F  G  L  S  P  S  M  P  H  L  L  T  S  A  N  I  T  N  A  V  I  Q  R  V  H
 991 TATTCGGTGAAACGTGAGCTTGCTCTGAAAAACAATCTTGAATTCTACTGGACACAATTATTTGGATCAACTGGACATCCTGATCTTCGTTCACATATTATGCCTTTCTA
 331 Y  S  V  K  R  E  L  A  L  K  K  N  L  E  F  Y  W  R  Q  L  F  G  S  T  G  H  P  D  L  R  S  H  I  M  P  F  Y
1101 CTCTTACGATATACCTCATACGTGTGGCCCAGAACCGTCTGTTTGCTGTCAATTCGATTTCCGTAGAATGCCAGAAGGTGGAAAATCATGTGATTGGGCAATCCCTCCAC
 367 S  Y  D  I  P  H  T  C  G  P  E  P  S  V  C  C  Q  F  D  F  R  R  M  P  E  G  G  K  S  C  D  W  G  I  P  P
1211 AGAAAATTAACGATGACAATGTGGCTCACAGAGCTGAAATGATTTATGATCAATATAGAAAGAAAAGTCAACTTTTCAAGAATAATGTGATTTTGCAACCACTTGGAGAT
 404 Q  K  I  N  D  D  N  V  A  H  R  A  E  M  I  Y  D  Q  Y  R  K  K  S  Q  L  F  K  N  N  V  I  F  Q  P  L  G  D
1321 GATTTCAGGTACGACATTGATTTTGAATGGAATTCACAATATGAAAACTATAAGAAATTGTTCGAATACATGAATTCCAAATCAGAATGGAATGTTCATGCTCAATTCGG
 441 D  F  R  Y  D  I  D  F  E  W  N  S  Q  Y  E  N  Y  K  K  L  F  E  Y  M  N  S  K  S  E  W  N  V  H  A  Q  F  G
1431 AACTCTTTCTGATTATTTCAAGAAGCTTGATACTGCAATTTCTGCGTCTGGCCAGCAACTTCCAACTTTTTCTGGAGATTTCTTCACTTATGCAGACAGAGATGATCATT
 477 T  L  S  D  Y  F  K  K  L  D  T  A  I  S  A  S  G  E  Q  L  P  T  F  S  G  D  F  F  T  Y  A  D  R  D  D  H
1541 ATTGGAGTGGATACTTCACTTCCCGTCCATTCTATAAACAGCTTGATCGGGTTCTCCAACATTATTTAAGATCAGCTGAAATCGCCTTTACCCTTGCAAATATTGAAGAA
 514 Y  W  S  G  Y  F  T  S  R  P  F  Y  K  Q  L  D  R  V  L  Q  H  Y  L  R  S  A  E  I  A  F  T  L  A  N  I  E  E
1651 GAAGGAATGGTTGAAGCGAAAATTTTTGAGAAGCTTGTGACTGCTCGAGCTCTTTCACTTTTCCAACATCACGATGGTCTAACTGGTACGGCAAAAGATCACGTCGT
 551 E  G  M  V  E  A  K  I  F  E  K  L  V  T  A  R  R  A  L  S  L  F  Q  H  H  D  G  V  T  G  T  A  K  D  H  V  V
1761 CTTGGATTATGGTCAGAAAATGATTGATGCTTTGAACGCATGTGAGGATATTCTTTCGGAAGCTCTTGTTGTATTGCTCGGGAATTGATTCAACGAATAAGATGCAGATGG
 587 L  D  Y  G  Q  K  M  I  D  A  L  N  A  C  E  D  I  L  S  E  A  L  V  V  L  L  G  I  D  S  T  N  K  M  Q  M
1871 ATGAGCATAGAGTTAATGAAAACCTTCTACCCGAAAAACGTGTCTATAAAATTGGGCAAAACGTCGTATTGTTCAATACTTTATCTAGAAATCGCAACGAGCCAATTTGT
 624 D  E  H  R  V  N  E  N  L  L  P  E  K  R  V  Y  K  I  G  Q  N  V  V  L  F  N  T  L  S  R  N  R  N  E  P  I  C
1981 ATTCAAGTTGATTCTCTTGACGCTGGTGTCCAAGCTCATCCTCCAATTAAAAAACAACAAGTTTCGCCGGTTATTGCATATGATGAAGAGAAGAAAACGCTTGTTGTCAA
 661 I  Q  V  D  S  L  D  A  G  V  E  A  D  P  P  I  K  K  Q  Q  V  S  P  V  I  A  Y  D  E  E  K  K  T  L  V  V  K
2091 AAACGGAATATTCGAACTTTGCTTCATGTTTATCACTTGGACCAATGGAGTCTGTCAGTTTCAGACTTGTGAAAAATACAACAACATCCAAAGTTGAAATAATCACCAATA
 697 N  G  I  F  E  L  C  F  M  L  S  L  G  P  M  E  S  V  S  F  R  L  V  K  N  T  T  T  S  K  V  E  I  I  T  N
2201 ATGCCGGCAGAATTCAAAGAAACAAGTTTTAAATCTTCATCCACTTCTGGAGACTTTACTGTGAAAAACGACAAAGTTGAAGCTGAATTTGATGGAGAAAATGGAATGATT
 734 N  A  A  E  F  K  E  T  S  F  K  S  S  S  T  S  G  D  F  T  V  K  N  D  K  V  E  A  E  F  D  G  E  N  G  M  I
2311 AAAAGAGCTACCAGTCTTGTTGATGATAAACCAATTGATTTGAATTCTCACTTTATTCATTATGGAGCGAGCAAGTCAAAGAGAAAGTTCGCAAATGGAAATGAAGACAA
 771 K  R  A  T  S  L  V  D  D  K  P  I  D  L  N  S  H  F  I  H  Y  G  A  R  K  S  K  R  K  F  A  N  G  N  E  D  N
2421 CCCGGCTGGCGCATACCTGTTCCTTCCCGATGGAGAAGCTAGAGAACTCAAAAAACAATCAAGTGATTGGATATTGGTAAAAGGAGAAGTTGTTCAAAAAGTGTTTGCAA
 807 P  G  A  Y  L  F  L  P  D  G  E  A  R  E  L  K  K  Q  S  S  D  W  I  L  V  K  G  E  V  V  Q  K  V  F  A
2533 CTCCAAACAATGATCTGAAAATATTGCAAACGTACACACTTTATCAAGGGCTTCCATGCATTGATTTGGATAATGAAGTTGATGTACGTTCCAAGGAGAATTTCGAGTTG
 844 T  P  N  N  D  L  K  I  L  Q  T  Y  Y  T  L  Y  Q  G  L  P  W  I  D  L  D  N  E  V  D  V  R  S  K  E  N  F  E  L
2641 GCACTCGAGATTCAGTTCTTCAGTAAATAGTCGTGATGAGTTTTTCACTGATCTCAATGGAATGCAAATGATAAAAAGGAGACACGAAACTAAATTACCAACACAGGCCAA
 881 A  L  R  F  S  S  S  V  N  S  G  D  E  F  F  T  D  L  N  G  M  Q  M  I  K  R  R  R  Q  T  K  L  P  T  Q  A  N
2751 TTTCTATCCCATGTCTGCTGGTGTTTACATTGAAGACGATACTACCAGAATGTCAATTCATTCGGCACAGGCTCTCGGAGTTAGCAGTCTCTCGTCGGGACAAATTGAAA
 917 F  Y  P  M  S  A  G  V  Y  I  E  D  D  T  T  R  M  S  I  H  S  A  Q  A  L  G  V  S  S  L  S  S  G  Q  I  E
2861 TAATGCTTGATCGACGACTTAGTTCAGATGACAACAGAGGTCTTCAGCAAGGAGTTAGAGACAACAAACGAACAGTTGCACATTTCCGTATTGTTATTGAGCCGATGTCT
 954 I  M  L  D  R  R  L  S  S  D  D  N  R  G  L  Q  Q  G  V  R  D  N  K  R  T  V  A  H  F  R  I  V  I  E  P  M  S
2971 TCATCGAGTGGTAATAAGAAGGAAGAAACGAGTTGCATTCCATTCACATGTTGGTCATCTCGCTACGTGGTCTCTTCATTATCCTCTTGTCAAAATGATTGGAGATGCAAC
 991 S  S  S  G  N  K  K  E  E  R  V  G  F  H  S  H  V  G  H  L  A  T  W  S  L  H  Y  P  L  V  K  M  I  G  D  A  T
3081 ACCAAAATCTATTTCTTCGAAAAATGTGGAACAAGAGCTGAACTCTGACCTGCATCTAGTGACATTTAGAACACTGGCATCGCCGACAACTTACGAAGCCAACGAAAGAT
1027 P  K  S  I  S  S  K  N  V  E  Q  E  L  N  C  D  L  H  L  V  T  F  R  T  L  A  S  P  T  T  Y  E  A  N  E  R
3191 CTACCGCAGCTGAGAAGAAAGCAGCCGATGGTGATGCATAGAGTTGTTCCAGACTGTAGATCCAGGCTTACCCTCCCAGACACGTCATGCTTAGCTACTGGATTAGAAATT
1064 S  T  A  A  E  K  K  A  A  M  V  M  H  R  V  V  P  D  C  R  S  R  L  T  L  P  D  T  S  C  L  A  T  G  L  E  I
3301 GAGCCCACTCAAATTGATCTCGACACTGAAGTCTGCGAAAAAAACGTCACTAACCAATCTTTATGAAGGAAACAAGGCTGAACAATTCCGACTCCAACCAAACGATATTTC
1101 E  P  L  K  L  I  S  T  L  K  S  A  K  K  T  S  L  T  N  L  Y  E  G  N  K  A  E  Q  F  R  L  Q  P  N  D  I  S
3411 CAGTATTCTTGTATCATTTTAA
1137 S  I  L  V  S  F
```

FIG. 27

Ciona intestinalis mannosidase II (AK116684)

```
   1 ATGAAGCTCAAACGCCAGTTCTTATTCTTTGGTGGAATTCTGTTCTTCGGGAGTATCTGGTTTATGATAGGTCAACTTGACACTCCTAATTCGCCACAGAAAGTCAAAT
   1▸M  K  L  K  R  Q  F  L  F  F  G  G  I  L  F  F  G  S  I  W  F  M  I  G  Q  L  D  T  P  N  S  P  Q  K  V  K
 110 TCTCGGAAGGCAGTGAAAATGACCAAGTTCGAACCCTTCAAGACAAACTTAGTCTGGTGGAAAAAGAATTGTTAGAAAATCGTAAAATAATGCACAAGGTGAAAGATAG
  37▸F  S  E  G  S  E  N  D  Q  V  R  T  L  Q  D  K  L  S  L  V  E  K  E  L  L  E  N  R  K  I  M  H  K  V  K  D  S
 219 TCTACAGGATATGACACCCATGAAAAATGTTCATGTGCCTATGCAGCGCGGAGAAATAAGAAACAACGTCAATAAACCTGTGCTACCACTTATAATGCCCAAGCAATTT
  73▸L  Q  D  M  T  P  M  K  N  V  H  V  P  M  Q  R  G  E  I  R  N  N  V  N  K  P  V  L  P  L  I  M  P  K  Q  F
 328 GCGAATGACTCCCGAATGAGTGACACGTGTCCTGTGCTCTCAGTATCCGGTGGCAAGTCCGATGTTAACATGATTAACGTCTATGATCATCTTCCATTTGATGATCCAG
 110▸A  N  D  S  R  M  S  D  T  C  P  V  L  S  Y  S  G  G  K  S  D  V  N  M  I  N  V  Y  D  H  L  P  F  D  D  P
 437 ATGGTGGAGTTTGGAAACAAGGTTGGGACATCCAGACATCGGATCAGGAATGGGCTGGGAGAAAATTGAAAGTGTTCATTGTCCCTCACTCACATAATGATCCTGGTTG
 146▸D  G  G  V  W  K  Q  G  W  D  I  Q  T  S  D  Q  E  W  A  G  R  K  L  K  V  F  I  V  P  H  S  H  N  D  P  G  W
 546 GTTAAAGACGGTGGAAAGATACTTCAGCGGATCAAACACAACATATTCTCAATAATATTGTGGATGCTTTGAGTCAAGACCCTGCAAGCGAAGTTTATCTGGGCAGAGATG
 182▸L  K  T  V  E  R  Y  F  S  D  Q  T  Q  H  I  L  N  N  I  V  D  A  L  S  Q  D  P  A  R  K  F  I  W  A  E  M
 655 TCGTATCTCTCAATGTGGTGGGACATTGCCACACCTGATCGTAAGCAGAAAATGCAGACACTCGTGAAGAATGGACAGCTTGAGATAGTTACGGGTGGTTGGGTCATGA
 219▸S  Y  L  S  M  W  W  D  I  A  T  P  D  R  K  Q  K  M  Q  T  L  V  K  N  G  Q  L  E  I  V  T  G  G  W  V  M
 764 ATGATGAAGCAAACACTCATTACTTTGCTATGATTGATCAACTCATTGAAGGTATGGAATGGTTGAGGCGAACATTGAATGTTGTTCCAAAAAGTGGGTGGGCGATTGA
 255▸M  D  E  A  N  T  H  Y  F  A  M  I  D  Q  L  I  E  G  M  E  W  L  R  R  T  L  N  V  V  P  K  S  G  W  A  I  D
 873 TCCCTTTGGTCACACCCCCACCATGGCTTATATACTGAAACAGATGAAGTTCAAAAACATGCTGATACAAAGAGTCCATTATGCAGTGAAGAAGTATCTTGCTCAGGAA
 291▸P  F  G  H  T  P  T  M  A  Y  I  L  K  Q  M  K  F  K  N  M  L  I  Q  R  V  H  Y  A  V  K  K  Y  L  A  Q  E
 982 AAGTCTCTGGAATTCAGATGGAGACAAATGTGGGATTCAGCTTCAAGTACAGACATGATGTCTCATCTCATGCCTTTCTATTCATATGATGTTCCTCATACTTGTGGCC
 328▸K  S  L  E  F  R  W  R  Q  M  W  D  S  A  S  S  T  D  M  M  C  H  L  M  P  F  Y  S  Y  D  V  P  H  T  C  G
1091 CAGACCCCAAGATTTGCTGCCAGTTTGATTTTGCTCGCTTACCCGGCGGCAAGATAACCTGCCCATGGAAAGTTCCTCCTGTTGCCATCACTGACTCCAATGTAGAAAC
 364▸P  D  P  K  I  C  C  Q  F  D  F  A  R  L  P  G  G  K  I  T  C  P  W  K  V  P  P  V  A  I  T  D  S  N  V  E  T
1200 ACGAGCCGGAATACTACTTGACCAATATAGAAAAAAGTCAAAACTCTTCAAAGTGACACCCTGCTTATTATATTAGGAGATGATTTTCGTTATTCGCTGAGCAAGGAA
 400▸R  A  G  I  L  L  D  Q  Y  R  K  K  S  K  L  F  K  S  D  T  L  L  I  I  L  G  D  D  F  R  Y  S  L  S  K  E
1309 ACCAACGATCAGTTTGACAACTACGCTCGAATTATCTCGTATGTGAATTCGCACCCAGAGTTAAACGCAAAACTTCAGTTTGGAACATTATCCGAATATTTTGATGCCA
 437▸T  N  D  Q  F  D  N  Y  A  R  I  I  S  Y  V  N  S  H  P  E  L  N  A  K  L  Q  F  G  T  L  S  E  Y  F  D  A
1418 TGAAATCTGAAGTGGGGGGAGAGGAAAAACTCCCAGCTTTAAGTGGTGATTTCTTCACTTATGCTGATAGAGAAGATCACTATTGGAGTGGTTACTACACTTCACGGCC
 473▸M  K  S  E  V  G  G  E  E  K  L  P  A  L  S  G  D  F  F  T  Y  A  D  R  E  D  H  Y  W  S  G  Y  Y  T  S  R  P
1527 TTACCACAAAATGCAGGAGAGAGTCCTGGAAAGCCACCTTCGAGGAGCAGAAATGTTGTTGCGCTCTCATGGCCCAAAATCCAGTGGACAGGACTTGGTGAAACATTT
 509▸Y  H  K  M  Q  E  R  V  L  E  S  H  L  R  G  A  E  M  L  F  A  L  S  W  P  K  I  Q  W  T  G  L  G  E  T  F
1636 TCACATGAACTTTACCCACTGCTGGTCCAAGCACGTCAAATCTTGGTTCTTGTTCAACACCACGATGGTATAACAGGCACAGCAAAGGATCATGTTGTTGTTGATTACG
 546▸S  H  E  L  Y  P  L  L  V  Q  A  R  Q  N  L  G  L  F  Q  H  H  D  G  I  T  G  T  A  K  D  H  V  V  V  D  Y
1745 GGAATAAACTCATGAAGAGTGTTATGGATGCAAAGAAGGTAATTTCATACAGTGCCCAAGTTCTGTTGCAAGAAATGATCACGTTTGATCCAAATACCATGGTACTTAA
 582▸G  N  K  L  M  K  S  V  M  D  A  K  K  V  I  S  Y  S  A  Q  V  L  L  Q  E  M  I  T  F  D  P  N  T  M  V  L  N
1854 CTATGATGAGGTGTATCAAGCTCAGAACCAACAACCTGCGCCTGTGGTTGTTAAGCTACCAACGAAGAATGAAGAAGCGCGGAAAGTCGTTCTCTACAACTCTCTGGAT
 618▸Y  D  E  V  Y  Q  A  Q  N  Q  Q  P  A  P  V  V  V  K  L  P  T  K  N  E  E  A  R  K  V  V  L  Y  N  S  L  D
1963 TACGACAGAACTGGTGTCGTGCGTCTAATTGTTACGTCACCCGACGTGGTTGTGATGTCAGAAAACAAAAACGTCGTTCCATCGCAAACCAGTCCGATCTGGTCAGATT
 655▸Y  D  R  T  G  V  V  R  L  I  V  T  S  P  D  V  V  M  S  E  N  K  N  V  V  P  S  Q  T  S  P  I  W  S  D
2072 CGACGGAGATCCGCACAGACCAGTTTGAACTGGCTTTTCCTTTCAACTGTTCCCGCGATAGGACTGGCGGTGTACAAGATATGGGAAGACAACGACGTAGCAGACACCAC
 691▸S  T  E  I  R  T  D  Q  F  E  L  V  F  L  S  T  V  P  A  I  G  L  A  V  Y  K  I  W  E  D  N  D  V  A  D  T  T
2181 GCACTCAACTGTTAAGTTTATCAACCCGAGAGTTGGGTTTTCGAAACGAACCCGCAGTAAGTTTGTACTCGACGTTGAGGATAGCGGGGAGTTTACCATCATGAATGAC
 727▸H  S  T  V  K  F  I  N  P  R  V  G  F  S  K  R  T  R  S  K  F  V  L  D  V  E  D  S  G  E  F  T  I  M  N  D
2290 CAATTAGTTGCGCATTTCTCTGGACAAAACGGGATGCTGCAGTCAGTCACCACTGTGCGTGACAACGTTAAAACCCAGCTCGGAATTGAATTCGTCGCTTATACTTCTC
 764▸Q  L  V  A  H  F  S  G  Q  N  G  M  L  Q  S  V  T  T  V  R  D  N  V  K  T  Q  L  G  I  E  F  V  A  Y  T  S
2399 GTAATAAGAAAGACAAGAGCGGCGCTTACTTGTTCCTGCCTGCTGGACCAGCACAACCGCATGTAACAGAATCCCACCGACCGTTAGTAAGGATCATCAGGGGTCCAGT
 800▸R  N  K  K  D  K  S  G  A  Y  L  F  L  P  A  G  P  A  Q  P  H  V  T  E  S  H  R  P  L  V  R  I  I  R  G  P  V
2508 GATGTCAACGGTGCATGTTCTACTACCGAACGTCTGCATAAAGTTACCCTATACACCGGTACTGGTGCAGGCACGCAGTCTTTAGGCGTCCACGTCTCTAACGACGTC
 836▸M  S  T  V  H  V  L  L  P  N  V  L  H  K  V  T  L  Y  T  G  T  G  E  A  G  T  Q  S  L  G  V  H  V  S  N  D  V
2617 GACGTTAGAACTGGCTACGACAACAAAGAACTCAGTATGAGGTTAAACAGCGAAGTTTTATCGGGAAGCAAATTCTTTACGGATTTAAACGGTTTCCAAATTCAACCCG
 873▸D  V  R  T  G  Y  D  N  K  E  L  S  M  R  L  N  S  E  V  L  S  G  S  K  F  T  D  L  N  G  F  Q  I  Q  P
2726 GAACCACGTATTCTAAACTGCCACTACAAGCAAACTTCTACCCAATACCCACAATGGCGTTCATACAAGACGAAAAATCAAGATTAACTTTGATGACGGCCCAACCACT
 909▸R  T  T  Y  S  K  L  P  L  Q  A  N  F  Y  P  I  P  T  M  A  F  I  Q  D  E  K  S  R  L  T  L  M  T  A  Q  P  L
2835 GGGTGTTGCCTCACTGAAGTCAGGTCAACTTGAGGTGGTTTTGGATCGCCGTTTAATGCAGGACGACAACAGGGGGTGGGTCAAGGTGTGAAAGATAATTTACCAACT
 945▸G  V  A  S  L  K  S  G  Q  L  E  V  V  L  D  R  R  L  M  Q  D  D  N  R  G  V  Q  G  V  K  D  N  L  P  T
2944 CCTGAGAGTTTCGTGATCATGCTGGAAAGATGGACCGCTATTGCAGCGAAAGAAAGCAAATCGTCAGCGAAGCTCGCCTATCCATCTATGGCTGTGTATCAGTCATCAT
 982▸P  E  S  F  V  I  M  L  E  R  W  T  A  I  A  A  K  E  S  K  S  S  A  K  L  A  Y  P  S  M  A  V  Y  Q  S  S
3053 GGGAATTGCTACACCCAATACGTCCAATGTCGGTAAATGGGCCGGTACATTTGAAAGAAGATTACCGCTCGCTGCCACAGCCTTTACCATCCGACGTGCACGTGTTAAA
1018▸W  E  L  L  H  P  I  R  P  M  S  V  N  G  P  V  H  L  K  E  D  Y  R  S  L  P  Q  L  P  C  D  V  H  V  L  N
3162 CTTGCGAGCAATTCATTCTAAAGATGCAGTTGCCCCTACCGACCAATCGGCTCTGCTTCTACACACAGTTGGGCGCGAATGCTCCTTGGACGCGGATAAGTATTTCCAC
1054▸L  R  A  I  H  S  K  D  A  V  A  P  T  D  Q  S  A  L  L  L  H  T  V  G  R  E  C  S  L  D  A  D  K  Y  F  H
3271 CCAACGTGCCTCATGCACGGCGTCGAGAAATTGCCTATCACGATCTCGACGCTTTTTACTAACTCTGGCATGCGGAAGACGTCGCTCGTCCTTACAACACGACGGCTCGT
1091▸P  T  C  L  M  H  G  V  E  K  L  A  I  T  I  S  T  L  F  T  N  S  G  M  R  K  T  S  L  S  L  Q  H  D  G  S
3380 TGCTGGACAACCAAGGCGGTATTACAGTTTCCCCAATGGAGATACAAGCTTACAAAATAGTACTGACGTAA
1127▸L  L  D  N  Q  G  G  I  T  V  S  P  M  E  I  Q  A  Y  K  I  V  L  T
```

FIG. 28

Drosophila mannosidase II (X77652)

FIG. 29

Human mannosidase II (U31520)

```
   1 ATGAAGTTAAGCCGCCAGTTCACCGTGTTCGGCAGTGCGATCTTCTGTGTGGTGATTTTCTCGCTCTACCTGATGCTGGACCGGGGTCACTTAGACTACCCCAGGAACC
   1▸ M  K  L  S  R  Q  F  T  V  F  G  S  A  I  F  C  V  V  I  F  S  L  Y  L  M  L  D  R  G  H  L  D  Y  P  R  N
 110 CGCGCCGCGAGGGCTCCTTCCCTCAGGGCCAGCTCTCAATGTTGCAAGAAAAAATAGACCATTTGCAGCCGTTTGCTAGCTGAGAATAATGAGATCATCTCAAATATTAG
  37▸ P  R  R  E  G  S  F  P  Q  G  Q  L  S  M  L  Q  E  K  I  D  H  L  E  R  L  L  A  E  N  N  E  I  I  S  N  I  R
 219 AGACTCAGTCATCAATTTGAGTGAGTCTGTGGAGGATGGTCCGAAAAGTTCACAAAGCAATTTCAGCCAAGGTGCTGGCTCACATCTTCTGCCCTCACAATTATCCCTC
  73▸ D  S  V  I  N  L  S  E  S  V  E  D  G  P  K  S  S  Q  S  N  F  S  Q  G  A  G  S  H  L  L  P  S  Q  L  S  L
 328 TCAGTTGACACTGCAGACTGTCTGTTTGCTTCACAAAGTGGAAGTCACAATTCAGATGTGCAGATGTTGGATGTTTACAGTCTAATTTCTTTTGACAATCCAGATGGTG
 110▸ S  V  D  T  A  D  C  L  F  A  S  Q  S  G  S  H  N  S  D  V  Q  M  L  D  V  Y  S  L  I  S  F  D  N  P  D  G
 437 GAGTTTGGAAGCAAGGATTTGACATTACTTATGAATCTAATGAATGGGACACTGAACCCCTTCAAGTCTTTGTGGTGCCTCATTCCCATAACGACCCAGGTTGGTTGAA
 146▸ G  V  W  K  Q  G  F  D  I  T  Y  E  S  N  E  W  D  T  E  P  L  Q  V  F  V  V  P  H  S  H  N  D  P  G  W  L  K
 546 GACTTTCAATGACTACTTTAGAGACAAGACTCAGTATATTTTTAATAACATGGTCCTAAAGCTGAAAGAAGACTCACGGAGGAAGTTTATTTGGTCTGAGATCTCTTAC
 182▸ T  F  N  D  Y  F  R  D  K  T  Q  Y  I  F  N  N  M  V  L  K  L  K  E  D  S  R  R  K  F  I  W  S  E  I  S  Y
 655 CTTTCAAAGTGGTGGGATATTATAGATATTCAGAAGAAGGATGCTGTTAAAAGTTTAATAGAAAATGGTCAGCTTGAAATTGTGACAGGTGGCTGGGTTATGCCTGATG
 219▸ L  S  K  W  W  D  I  I  D  I  Q  K  K  D  A  V  K  S  L  I  E  N  G  Q  L  E  I  V  T  G  G  W  V  M  P  D
 764 AAGCTACTCCACATTATTTTGCCTTAATTGATCAACTAATTGAAGGACATCAGTGGCTGGAAAATAATAGGAGTGAAACCTCGGTCCGGCTGGGCTATTGATCCCTT
 255▸ E  A  T  P  H  Y  F  A  L  I  D  Q  L  I  E  G  H  Q  W  L  E  N  N  I  G  V  K  P  R  S  G  W  A  I  D  P  F
 873 TGGACACTCACCAACAATGGCTTATCTTCTAAACCGTGCTGGACTTTCTCACATGCTTATCCAGAGAGTTCATTATGCAGTTCATTATGCACTGCATAAAACA
 291▸ G  H  S  P  T  M  A  Y  L  L  N  R  A  G  L  S  H  M  L  I  Q  R  V  H  Y  A  V  K  K  H  F  A  L  H  K  T
 982 TTGGAGTTTTTTTGGAGACAGAATTGGGATCTGGGATCTGTCACAGATATTTATGCCACATGATGCCCTTCTACAGCTATGACATCCCTCACACTTGTGGACCTGATC
 328▸ L  E  F  F  W  R  Q  N  W  D  L  G  S  V  T  D  I  L  C  H  M  M  P  F  Y  S  Y  D  I  P  H  T  C  G  P  D
1091 CTAAAATATGCTGCCAGTTTGATTTTAAACGTCTTCCTGGAGGCAGATTTGGTTGTCCCTGGGGAGTCCCCCCAGAAACAATACATCCTGGAAATGTCCAAAGCAGGGC
 364▸ P  K  I  C  C  Q  F  D  F  K  R  L  P  G  G  R  F  G  C  P  W  G  V  P  P  E  T  I  H  P  G  N  V  Q  S  R  A
1200 TCGGATGCTACTAGATCAGTACCGAAAGAAGTCAAAGCTTTTTCGAACCAAAGTTTCTTCCTGGCTCCACTAGGAGATGATTTCCGCTACTGTGAATACACGGAATGGGAT
 400▸ R  M  L  L  D  Q  Y  R  K  K  S  K  L  F  R  T  K  V  L  L  A  P  L  G  D  D  F  R  Y  C  E  Y  T  E  W  D
1309 TTACAGTTTAAGAATTATCAGCAGCTTTTTGATTATATGAATTCTCAGTCCAAGTTTAAAGTTAAGATACAGTTTGGACTTTATCAGATTTTTTGATGCCGCTGCATA
 437▸ L  Q  F  K  N  Y  Q  Q  L  F  D  Y  M  N  S  Q  S  K  F  K  V  K  I  Q  F  G  T  L  S  D  F  F  D  A  L  D
1418 AAGCAGATGAAACTCAGAGAGACAAGGGCCAATCGATGTTCCCTGTTTAAGTGGACATTTTTTCACTTATGCCGATCGAGATGATCATTACTGGAGTGGCTATTTTAC
 473▸ K  A  D  E  T  Q  R  D  K  G  Q  S  M  F  P  V  L  S  G  D  F  F  T  Y  A  D  R  D  D  H  Y  W  S  G  Y  F  T
1527 ATCCGACCCTTTTACAAACGAATGGACAGAATCATGGAAATCTCATTTAAGGGCTGCTGAAATTTCTTTACTATTTCGCCCTGAGACAAGCTCACAAATACAAGATAAAT
 509▸ S  R  P  F  Y  K  R  M  D  R  I  M  E  S  H  L  R  A  A  E  I  L  Y  Y  F  A  L  R  Q  A  H  K  Y  K  I  N
1636 AAATTTCTCTCATCATCACTTTACACGGCACTGACAGAAGCCAGAAGGAATTTGGGACTGTTTCAACATCATGATGCTATCACAGGAACTGCAAAAGACTGGGTGGTTG
 546▸ K  F  L  S  S  S  L  Y  T  A  L  T  E  A  R  R  N  L  G  L  F  Q  H  H  D  A  I  T  G  T  A  K  D  W  V  V
1745 TGGATTATGGTACCAGACTTTTTCATTCGTTAATGGTTTTGGAGAAGATAATTGGAAATTCTGCATTTCTTCTTATTGGGAAGGACAAACTCACATACGACTCTTACTC
 582▸ V  D  Y  G  T  R  L  F  H  S  L  M  V  L  E  K  I  I  G  N  S  A  F  L  L  I  G  K  D  K  L  T  Y  D  S  Y  S
1854 TCCTGATACCTTCCTGGAGATGGATTTGAAACAAAAATCACAGATTCTCTGCCACAAAAAAATATAATAAGGCTGAGTGCGGAGCCAAGGTACCTTGTGGTCTATAAT
 618▸ P  D  T  F  L  E  M  D  L  K  Q  K  S  Q  D  S  L  P  Q  K  N  I  I  R  L  S  A  E  P  R  Y  L  V  V  Y  N
1963 CCTTTAGAACAAGACCGAATCTCGTTGGTCTCAGTCTATGTGAGTTCCCCGACAGTGCAAGTGTTCTCTGCTTCAGGAAAACCTGTGGAAGTTCAAGTCAGCGCAGTTT
 655▸ P  L  E  Q  D  R  I  S  L  V  S  V  Y  V  S  S  P  T  V  Q  V  F  S  A  S  G  K  P  V  E  V  Q  V  S  A  V
2072 GGGATACAGCAAATACTATTTCAGAAACAGCCTATGAGATCTCTTTTCGAGCACATATACCGCCATTGGGACTGAAAGTGTATAAGATTTTGGAATCAGCAAGTTCAAA
 691▸ W  D  T  A  N  T  I  S  E  T  A  Y  E  I  S  F  R  A  H  I  P  P  L  G  L  K  V  Y  K  I  L  E  S  A  S  S  N
2181 TTCACATTTAGCTGATTATGTCTTGTATAAGAATAAAGTAGAAGATAGCGGAATTTTCACCATAAAGAATATGATAAATACTGAAGAAGGTATAACACTAGAGAACTCC
 727▸ S  H  L  A  D  Y  V  L  Y  K  N  K  V  E  D  S  G  I  F  T  I  K  N  M  I  N  T  E  E  G  I  T  L  E  N  S
2290 TTTGTTTTACTTCGGTTTGATCAAACTGGACTTATGAAGCAAATGATGACTAAAGAAGATGGTAAACACCATGAAGTAAATGTGCAATTTTCATGGTATGGAACCACAA
 764▸ F  V  L  L  R  F  D  Q  T  G  L  M  K  Q  M  M  T  K  E  D  G  K  H  H  E  V  N  V  Q  F  S  W  Y  G  T  T
2399 TTAAAAGAGACAAAAGTGGTGCCTACCTCTTCTTACCTGATGGTAATGCCAAGCCTTATGTTTACACAACACCGCCCTTTGTCAGAGTGACACATGGAAGGATTTATTC
 800▸ I  K  R  D  K  S  G  A  Y  L  F  L  P  D  G  N  A  K  P  Y  V  Y  T  T  P  P  F  V  R  V  T  H  G  R  I  Y  S
2508 GGAAGTGACTTGCTTTTTTGACCATGTTACTCATAGAGTCCGACTATACCACATACAGGGAATAGAAGGACAGTCTGTGGAAGTTTCCAATATTGTGGACATCCGAAAA
 836▸ E  V  T  C  F  F  D  H  V  T  H  R  V  R  L  Y  H  I  Q  G  I  E  G  Q  S  V  E  V  S  N  I  V  D  I  R  K
2617 GTATATAACCGTCAGATTGCAATGAAAATTTCTTCTGATATAAAAAGCCAAAATAGATTTTATACTGACCTAAATGGGTACCAGATTCAACCTAGAATGACACTGAGCA
 873▸ V  Y  N  R  E  I  A  M  K  I  S  S  D  I  K  S  Q  N  R  F  Y  T  D  L  N  G  Y  Q  I  Q  P  R  M  T  L  S
2726 AATTGCCTCTTCAAGCAAATGTCTATCCCATGACCACAATGGCCTATATCCAGGATGCCAAACATCGTTTGACACTGCTCTCTGCTCAGTCATTAGGGGTTTCGAGTTT
 909▸ K  L  P  L  Q  A  N  V  Y  P  M  T  T  M  A  Y  I  Q  D  A  K  H  R  L  T  L  L  S  A  Q  S  L  G  V  S  S  L
2835 GAATAGTGGTCAGATTGAAGTTATCATGCATCGAAGACTCATGCAAGATGATAATCGTGGCCTTGAGCAAGGTATCCAGGATAACAAGATTACAGCTAATCTATTTCGA
 945▸ N  S  G  Q  I  E  V  I  M  D  R  R  L  M  Q  D  D  N  R  G  L  E  Q  G  I  Q  D  N  K  I  T  A  N  L  F  R
2944 ATACTACTAGAAAAAAGAACTGCTGTTAATACGGAAGAAGAAAAAGAAGTCGGTCAGTTATCCTTCTCTCCTTAGCCACATAACTTCTTCTCTCATGAATCATCCAGTCA
 982▸ I  L  L  E  K  R  S  A  V  N  T  E  E  E  K  K  S  V  S  Y  P  S  L  L  S  H  I  T  S  S  L  M  N  H  P  V
3053 TTCCAATGGCAAATAAGTTCTCCTCACCTACCCTTGAGCTGCAAGGTGAATTCTCTCCATTACAGTCATCTTTGCCTTGTGACATTCATCTGGTTAATTTGAGAACAAT
1018▸ I  P  M  A  N  K  F  S  S  P  T  L  E  L  Q  G  E  F  S  P  L  Q  S  S  L  P  C  D  I  H  L  V  N  L  R  T  I
3162 ACAGTCAAAGGTGGGCAATGGGCACTCCAATGAGGCAGCCTTGATCCTCCACAGAAAAGGGTTTGATTGTCGGTTCTCTAGCAAAGGCACAGGGCTGTTTTGTTCTACT
1054▸ Q  S  K  V  G  N  G  H  S  N  E  A  A  L  I  L  H  R  K  G  F  D  C  R  F  S  S  K  G  T  G  L  F  C  S  T
3271 ACTCAGGGAAAGATATTGGTACAGAAACTTTTAAACAAGTTTATTGTCGAAAGTCTCACACCTTCATCACTATCCTTGATGCATTCACCTCCCGGCACTCAGAATATAA
1091▸ T  Q  G  K  I  L  V  Q  K  L  L  N  K  F  I  V  E  S  L  T  P  S  S  L  S  L  M  H  S  P  P  G  T  Q  N  I
3380 GTGAGATCAACTTGAGTCCAATGGAAATCAGCACATTCCGAATCCAGTTGAGGTGA
1127▸ S  E  I  N  L  S  P  M  E  I  S  T  F  R  I  Q  L  R
```

FIG. 30

Mouse mannosidase II (X61172)

```
   1 ATGAAGTTAAGTCGCCAGTTCACCGTGTTTGGCAGCGCGATCTTCTGCGTCGTAATCTTCTCACTCTACCTGATGCTGGACAGGGGTCACTTGGACTACCCTCGGGGCCC
   1▶ M  K  L  S  R  Q  F  T  V  F  G  S  A  I  F  C  V  V  I  F  S  L  Y  L  M  L  D  R  G  H  L  D  Y  P  R  G  P
 111 GCGCCAGGAGGGCTCCTTTCCGCAGGGCCAGCTTTCAATATTGCAAGAAAAGATTGACCATTTGGACCGTTTGCTCGCTGAGAACAACGAGATCATCTCAAATATCAGAG
  37▶ R  Q  E  G  S  F  P  Q  G  Q  L  S  I  L  Q  E  K  I  D  H  L  E  R  L  L  A  E  N  N  E  I  I  S  N  I  R
 221 ACTCAGTCATCAACCTGAGCGAGTCTGTGGAGGACGGCCCGCGGGGGTCACCAGGCAACGCCAGCCAAGGCTCCATCCACCTCCACTCGCCCACAGTTGGCCCTGCAGGCT
  74▶ D  S  V  I  N  L  S  E  S  V  E  D  G  P  R  G  S  P  G  N  A  S  Q  G  S  I  H  L  N  S  P  Q  L  A  L  Q  A
 331 GACCCCAGAGACTGTTTGTTTGCTTCACAGAGTGGGAGTCAGCCCCGGGATGTGCAGATGTTGGATGTTTACGATCTGATTCCTTTTGATAATCCAGATGGTGGAGTTTG
 111▶ D  P  R  D  C  L  F  A  S  Q  S  G  S  Q  P  R  D  V  Q  M  L  D  V  Y  D  L  I  P  F  D  N  P  D  G  G  V  W
 441 GAAGCAAGGATTTGACATTAAGTATGAAGCGGATGAGTGGGACCATGAGCCCCTGCAAGTGTTTGTGGTGCCTCACTCCCATAATGACCCAGGTTGGTTGAAGACTTTCA
 147▶ K  Q  G  F  D  I  K  Y  E  A  D  E  W  D  H  E  P  L  Q  V  F  V  V  P  H  S  H  N  D  P  G  W  L  K  T  F
 551 ATGACTACTTTAGAGACAAGACTCAGTATATTTTTAATAACATGGTCCTAAAGCTGAAAGAAGACTCAAGCAGGAAGTTTATGTGGTCTGAGATCTCTTACCTTGCAAAA
 184▶ N  D  Y  F  R  D  K  T  Q  Y  I  F  N  N  M  V  L  K  L  K  E  D  S  S  R  K  F  M  W  S  E  I  S  Y  L  A  K
 661 TGGTGGGATATTATAGATATTCCGAAGAAGGAAGCTGTTAAAAGTTTACTACAGAATGGTCAGCTGGAAATTGTGACCGGTGGCTGGGTTATGCCTGATGAAGCCACTCC
 221▶ W  W  D  I  I  D  I  P  K  K  E  A  V  K  S  L  L  Q  N  G  Q  L  E  I  V  T  G  G  W  V  M  P  D  E  A  T  P
 771 ACATTATTTTGCCTTAATTGACCAACTAATTGAAGGGCACCAATGGCTGGAAAAAAATCTACGAGTGAAACCTCGATCGGGCTGGGCCATAGATCCCTTTGGTCATTCAC
 257▶ H  Y  F  A  L  I  D  Q  L  I  E  G  H  Q  W  L  E  K  N  L  G  V  K  P  R  S  G  W  A  I  D  P  F  G  H  S
 881 CCACAATGGCTTATCTTCTAAAGCGTGCTGGATTTTCACACATGCTCATCCAGAGAGTCCATTATGCAATCAAAAAACACTTCTCTTTGCATAAAACGCTGGAGTTTTTC
 294▶ P  T  M  A  Y  L  L  K  R  A  G  F  S  H  M  L  I  Q  R  V  H  Y  A  I  K  K  H  F  S  L  H  K  T  L  E  F  F
 991 TGGAGACAGAATTGGGATCTTGGATCTGCTACACACATTTTGTGCCATATGATGCCCTTCTACAGCTACGACATCCCTCACACCTGTGGGCCTGATCCTAAATATGCTG
 331▶ W  R  Q  N  W  D  L  G  S  A  T  D  I  L  C  H  M  M  P  F  Y  S  Y  D  I  P  H  T  C  G  P  D  P  K  I  C  C
1101 CCAGTTTGATTTTAAACGGCTTCCTGGAGGCAGATATGGTTGTCCCTGGGGAGTTCCCCCACAAGCAATATCTCCTGGAAATGTCCAAAGCAGGGCTCAGATGCTATTGG
 367▶ Q  F  D  F  K  R  L  P  G  G  R  Y  G  C  P  W  G  V  P  P  E  A  I  S  P  G  N  V  Q  S  R  A  Q  M  L  L
1211 ATCAGTACCGGGAAAAAGTCAAAACTTTTCCGCACTAAAGTTCTGCTGGCTCCACTGGGAGACGACTTTCGGTTCAGTGAATACACAGAGTGGGATCTGCAGTGCAGGAAC
 404▶ D  Q  Y  R  K  K  S  K  L  F  R  T  K  V  L  L  A  P  L  G  D  D  F  R  F  S  E  Y  T  E  W  D  L  Q  C  R  N
1321 TACGACGCAACTGTTCAGTTACATGAACTCGCAGCCTCATCTGAAAGTGAAGATCCAGTTTGGACCTTGTCAGATTATTTCGACGCATTGGAGAAAGCGGTGGCAGCCGA
 441▶ Y  E  Q  L  F  S  Y  M  N  S  Q  P  H  L  K  V  K  I  Q  F  G  T  L  S  D  Y  F  D  A  L  E  K  A  V  A  A  E
1431 GAAGAAGAGTAGCCAGTCTGTGTTCCCTGCCCTGAGTGGAGACTTCTTCACGTACGCTGACAGAGACGACCATTACTGGAGTGGCTACTTCACGTCCAGACCTTTCTACA
 477▶ K  K  S  S  Q  S  V  F  P  A  L  S  G  D  F  F  T  Y  A  D  R  D  D  H  Y  W  S  G  Y  F  T  S  R  P  F  Y
1541 AACGAATGGACAGAATAATGGAATCTCGTATAAGGGCTGCTGAAATTCTTTACCAGTTGGCCTTGAAACAAGCTCAGAAATACAAGATAAATAAATTTCTTTCATCACCT
 514▶ K  R  M  D  R  I  M  E  S  R  I  R  A  A  E  I  L  Y  Q  L  A  L  K  Q  A  Q  K  Y  K  I  N  K  F  L  S  S  P
1651 CATTACACAACACTGACAGAAGCCAGAAGGAACTTAGGACTATTTCAGCATCATCATGCCATCACAGGAACCGCGAAAGACTGGGTGGTTGTGGACTATGGTACCAGACT
 551▶ H  Y  T  T  L  T  E  A  R  R  N  L  G  L  F  Q  H  H  D  A  I  T  G  T  A  K  D  W  V  V  V  D  Y  G  T  R  L
1761 CTTTCAGTCATTAAATTCTTTGGAGAAGATAATTGGAGATTCTGCATTTCTTCTCATTTTAAAGGACAAAAAGCTGTACCAGTCAGATCCTTCCAAAGCCTTCTTAGACA
 587▶ F  Q  S  L  N  S  L  E  K  I  I  G  D  S  A  F  L  L  I  L  K  D  K  K  L  Y  Q  S  D  P  S  K  A  F  L  E
1871 TGGATACGAAGCAAAGTTCACAAGATTCTCTGCCCCAAAAAATTATAATACAACTGAGCCGCACAGGAGCCAAGGTACCTTGTGGTCTACAATCCCTTTGAACAAGAACGG
 624▶ M  D  T  K  Q  S  S  Q  D  S  L  P  Q  K  I  I  I  Q  L  S  A  Q  E  P  R  Y  L  V  V  Y  N  P  F  E  Q  E  R
1981 CATTCAGTGGTGTCCATCCGGGTAAACTCCCGCCACAGGGAAAGTCCTCGTCGATTCGGGAAAACCCGTGGAGGTTCAAGTCAGTGCAGTTTGGAACGACATGAGGACAAT
 661▶ H  S  V  V  S  I  R  V  N  S  A  T  G  K  V  L  S  D  S  G  K  P  V  E  V  Q  V  S  A  V  W  N  D  M  R  T  I
2091 TTCACAAGCAGCCTATGAGGTTTCTTTTCTAGCTCATATACCACCACTGGGACTGAAAGTGTTTAAGATCTTAGAGTCACAAAGTTCAAGCTCACACTTGGCTGATTATG
 697▶ S  Q  A  A  Y  E  V  S  F  L  A  H  I  P  P  L  G  L  K  V  F  K  I  L  E  S  Q  S  S  S  H  L  A  D  Y
2201 TCCTATATAATAATGATGGACTAGCAGAAAATGGAATATTCCACGTGAAGAACATGGTGGATGCTGGAGATGCCATAACAATAGAGAATCCCTTCCTGGCCGATTTGGTTT
 734▶ V  L  Y  N  N  D  G  L  A  E  N  G  I  F  H  V  K  N  M  V  D  A  G  D  A  I  T  I  E  N  P  F  L  A  I  W  F
2311 GACCCGATCTCGGCCTGATGGAGAAAGTCAGGAGGAAGAACAGACTAGACAGCATGAACTGAAGGTCCAGTTCCTGTGGTACGGAACCACCAACAAAAGGGACAAGAGCGG
 771▶ D  R  S  G  L  M  E  K  V  R  R  K  E  D  S  R  Q  H  E  L  K  V  Q  F  L  W  Y  G  T  T  N  K  R  D  K  S  G
2421 TGCCTACCTCTTCCTGCCTGACGGGCAGGGCCAGCCATATGTTTCCCTAAGACCGCCCTTTGTCAGAGTGACACGTGGAAGGATCTACTCAGATGTGACCTGTTTCCTCG
 807▶ A  Y  L  F  L  P  D  G  Q  G  Q  P  Y  V  S  L  R  P  P  F  V  R  V  T  R  G  R  I  Y  S  D  V  T  C  F  L
2531 AACACGTTACTCACAAAGTCCGCCTCTACAACATTCAGGGAATAGAAGCTCACTCCATGGAAGTTTCTAATATTGTAAACATCAGGAATGTGCATAACCGTGAGATTGTA
 844▶ E  H  V  T  H  K  V  R  L  Y  N  I  Q  G  I  E  G  Q  S  M  E  V  S  N  I  V  N  I  R  N  V  H  N  R  E  I  V
2641 ATGCAGAATTTCATCTAAAATAAACAACCAAAATAGATATTATACTGACCTAAATGGATATCAGATTCAGCCTAGAACGACCATGAGCAAATTGCCTCTTCAAGCCAACGT
 881▶ M  R  I  S  S  K  I  N  N  Q  N  R  Y  Y  T  D  L  N  G  Y  Q  I  Q  P  R  R  T  M  S  K  L  P  L  Q  A  N  V
2751 TTACCCGATGTGCACAATGGCGTATATCCAGGATGCTGAGCACCGGCTCACCGTCCTCTGCTCAGTCTCTAGGTGCTTCCAGCATGGCTTCTGGTCAGATTGAAGTCT
 917▶ Y  P  M  C  T  M  A  Y  I  Q  D  A  E  H  R  L  T  L  L  S  A  Q  S  L  G  A  S  S  M  A  S  G  Q  I  E  V
2861 TCATGGATCGAAGGCTCATGCAGGATGATAACCGTGGCTTGGGCAAGGCGTCCATGACAATAAGATTACAGCTAATTTGTTTCGAATCCTCCTCGAAGAAGAACCGCT
 954▶ F  M  D  R  R  L  M  Q  D  D  N  R  G  L  G  Q  G  V  H  D  N  K  I  T  A  N  L  F  R  I  L  L  E  K  R  S  A
2971 GTGAACATGGAAGAAGAAAAAGAAGAGCCCTGTCAGCTACCCTTCCCTCCTCAGCCACATGACTTCGTCCTTCCTCAACCATCCCTTTCTCCCCATGGTACTAAGTGGCCA
 991▶ V  N  M  E  E  E  K  K  S  P  V  S  Y  P  S  L  L  S  H  M  T  S  S  F  L  N  H  P  F  L  P  M  V  L  S  G  Q
3081 GCTCCCCTCCCCTGCCTTTGAGCTGCTGAGTCAATTTCCTGCTGCTGCAGTCCTCTCTACCTTGTGATATCCATCTGGTCAACCTGCCGCAATACAATCAAAGATGGGCA
1027▶ L  P  S  P  A  F  E  L  L  S  E  F  P  L  L  Q  S  S  L  P  C  D  I  H  L  V  N  L  R  T  I  Q  S  K  M  G
3191 AAGGCTATTCGGATGAGGCAGCCTTGATCCTCCACAGGAAAGGGTTTGATTGCCAGTTCTCCAGCAGAGGCATCGGGCTACCCTGTTCCACTACTCACGGAAAGATGTCA
1064▶ K  G  Y  S  D  E  A  A  L  I  L  H  R  K  G  F  D  C  Q  F  S  S  R  G  I  G  L  P  C  S  T  T  Q  G  K  M  S
3301 GTTCTGAAACTTTTCAACAAGTTTGCTGTGGAGAGTCTCGTCCCTTCCTCTCTGTCCTTGATGCACTCCCCTCCAGATGCCCAGAACATGAGTGAAGTCAGCCTGAGCCC
1101▶ V  L  K  L  F  N  K  F  A  V  E  S  L  V  P  S  S  L  S  L  M  H  S  P  P  D  A  Q  N  M  S  E  V  S  L  S  P
3411 CATGGAGATCAGCACGTTCCGTATCCGCTTGCGTTGGACCTGA
1137▶ M  E  I  S  T  F  R  I  R  L  R  W  T
```

FIG. 31

Rat mannosidase II (XM_218816)

```
   1 ATGGCCTGTATAGGTGGAGCCCAGGGGCAACGGCAGGCCGTGGAAAAGGAACCTTCCCACCAAGGGTATCCGTGGAAGCCAATGACCAATGGCAGCTGCTCAGAACTG
   1  M  A  C  I  G  G  A  Q  G  Q  R  Q  A  V  E  K  E  P  S  H  Q  G  Y  P  W  K  P  M  T  N  G  S  C  S  E  L
 109 GCATTGCTCAGCAAAACCCGAATGTACTGTCACCAGGGATGTGTCAGGCCACCCAGGACTGACGTGAAAAACTTCAAGACCACAACTGATACTCAGAGTGTGCCTGGT
  37  A  L  L  S  K  T  R  M  Y  C  H  Q  G  C  V  R  P  P  R  T  D  V  K  N  F  K  T  T  T  D  T  Q  S  V  P  G
 217 GTCAGTATGAAGCTGAAAAAGCAGGTGACAGTGTGCGGGGCTGCTATCTTCTGTGTGGCCGTCTTTTCCCTGTACCTAATGCTGGACCGAGTGCAGCATGATCCTGCC
  73  V  S  M  K  L  K  K  Q  V  T  V  C  G  A  A  I  F  C  V  A  V  F  S  L  Y  L  M  L  D  R  V  Q  H  D  P  A
 325 AGACACCAGAATGGTGGGAACTTCCCCAGGAGCCAAATTTCTGCTACAGAACCGGATCGAACAGCTGCTGGAAGAAAACCATGAGATCATAAGCCAT
 109  R  H  Q  N  G  G  N  F  P  R  S  Q  I  S  V  L  Q  N  R  I  E  Q  L  E  Q  L  L  E  E  N  H  E  I  I  S  H
 433 ATCAAGGACTCTGTGCTGGAACTGACAGCCAATGCGGAGGGCCCACCCAGCCCTGCTGCCCTACCACACAGCCAACGGCTCCTGGGCTGTGCTCCCCGAGCCCCGGCCC
 145  I  K  D  S  V  L  E  L  T  A  N  A  E  G  P  P  A  L  L  P  Y  H  T  A  N  G  S  W  A  V  L  P  E  P  R  P
 541 AGCTTCTTCTCTGTATCCCCTGAGGACTGCCAGTTTGCTTTGGGGGGCCGGGGTCAGAAGCCAGAGCTACAGATGTTAACTGTGTCTGAGGATTTGCCGTTTGACAAT
 181  S  F  F  S  V  S  P  E  D  C  Q  F  A  L  G  G  R  G  Q  K  P  E  L  Q  M  L  T  V  S  E  D  L  P  F  D  N
 649 GTGGAGGGCGGCGTGTGGAGGCAAGGCTTCGACATCTCCTACAGCCCAAATGACTGGGATGCTGAAGACCTGCAGGTGTTTGTGGTGCCTCACTCCCACAATGATCCA
 217  V  E  G  G  V  W  R  Q  G  F  D  I  S  Y  S  P  N  D  W  D  A  E  D  L  Q  V  F  V  V  P  H  S  H  N  D  P
 757 GGTGAAGAGCCAGCAGGCCCCAGCCGCAGCGTGCAGGGTGGGCTTTCTGGTGACAGGCGCTGGATCAAGACTTTTGACAAGTACTACACGGAACAAACCCAACACATC
 253  G  E  E  P  A  G  P  S  R  S  V  Q  G  G  L  S  G  D  R  R  W  I  K  T  F  D  K  Y  Y  T  E  Q  T  Q  H  I
 865 CTCAACAGCATGGTGTCAAGCTGCAGGAAGATCCCCGACGGCGCTTTCTCTGGGCAGAAGTCTCCTTCTTCGCCAAGTGGTGGGACAACATCAGTGCCCAGAAAAGG
 289  L  N  S  M  V  S  K  L  Q  E  D  P  R  R  R  F  L  W  A  E  V  S  F  F  A  K  W  W  D  N  I  S  A  Q  K  R
 973 GCAGCAGTTCGAAGGCTGGTGGGAAATGGGCAGCTGGAAATTGCAACGGGTGGATGGGTGATGCCAGATGAGGCCAACTCCCATTACTTTGCCCTGGTGGGGCAGCTC
 325  A  A  V  R  R  L  V  G  N  G  Q  L  E  I  A  T  G  G  W  V  M  P  D  E  A  N  S  H  Y  F  A  L  V  G  Q  L
1081 ATCGAGGGGCCCCCCCCGGTACGCAGGGCAGTGGACCCCTTTGGACACAGCTCCACCATGCCTTACCTGCTGCGCCGTGCCAACCTGACCAGCATGCTAATTCAGAGG
 361  I  E  G  P  P  P  V  R  R  A  V  D  P  F  G  H  S  S  T  M  P  Y  L  L  R  R  A  N  L  T  S  M  L  I  Q  R
1189 GTGCATTACGCCATCAAGAAGCACTTTGCGGCCACTCACAGCCTGGAGTTCATGTGGAGGCAGACATGGATTCAGATCCAGCACAGACATCTTCTGCCACATGATG
 397  V  H  Y  A  I  K  K  H  F  A  A  T  H  S  L  E  F  M  W  R  Q  T  W  D  S  D  S  S  T  D  I  F  C  H  M  M
1297 CCCTTCTACAGCTACGACGTCCCACACACCTGTGGCCCTGATCCCAAGATCTGCTGCCAGTTTGATTTCAAACGTCTGCCGGGTGGGAGAATCAATTGTCCTTGGAAG
 433  P  F  Y  S  Y  D  V  P  H  T  C  G  P  D  P  K  I  C  C  Q  F  D  F  K  R  L  P  G  G  R  I  N  C  P  W  K
1405 GTGCCGCCGCGGGCTATCACAGAGGCCAACGTGGCAGACAGGGCAGCCCTGCTCCTGGACCAGTACCGGAAGAAGTCCCGGCTGTTTCGAAGCAGTGTCCTCCTTGTG
 469  V  P  P  R  A  I  T  E  A  N  V  A  D  R  A  A  L  L  L  D  Q  Y  R  K  K  S  R  L  F  R  S  S  V  L  L  V
1513 CCGCTGGGTGATGACTTCCGATATGACAAGCCCCAGGAATGGGATGCCCAGTTCTTCAACTATCAACGGCTCTTTGACTTCCTCAACAGCAAGCCGGAGTTCCACGTA
 505  P  L  G  D  D  F  R  Y  D  K  P  Q  E  W  D  A  Q  F  F  N  Y  Q  R  L  F  D  F  L  N  S  K  P  E  F  H  V
1621 CAGGCACAGTTTGGGACCCTCTCTGAGTATTTTGATGCCCTGTATAAGAGGACAGGAGTGGAGCCTGGTGCCCGGCCTTCCAGGGTTTCCTGTGCTGAGTGGGGACTTC
 541  Q  A  Q  F  G  T  L  S  E  Y  F  D  A  L  Y  K  R  T  G  V  E  P  G  A  R  P  P  G  F  P  V  L  S  G  D  F
1729 TTCTCCTATGCTGACCGGGAGGACCACTACTGGACAGGCTATTACACTTCCCGGCCTTTCTATAAGAGCTTGGACCGCGTGCTAGAAACTCACCTTCGTGGGGCAGAG
 577  F  S  Y  A  D  R  E  D  H  Y  W  T  G  Y  Y  T  S  R  P  F  Y  K  S  L  D  R  V  L  E  T  H  L  R  G  A  E
1837 GTTCTATACAGCCTGGCTTTGGCCATGCCCGCCGTTCTGGACTGACTGGCCAGTATCCGTCTGATTACGCTGTCCTGACGGAAGCTCGTCGTACACTGGGCCTC
 613  V  L  Y  S  L  A  L  A  H  A  R  R  S  G  L  T  G  Q  Y  P  L  S  D  Y  A  V  L  T  E  A  R  R  T  L  G  L
1945 TTCCAGCACCACGATGCCATCACCGGAACTGCCAAGGAGGCAGTTGTAGTAGACTATGGGGTCAGGTTGCTGCGTTCCCTGGTCAGCCTAAAGCAGGTCATCATCAAT
 649  F  Q  H  H  D  A  I  T  G  T  A  K  E  A  V  V  D  Y  G  V  R  L  L  R  S  L  V  S  L  K  Q  V  I  I  N
2053 GCTGCCCACTACCTGGTGCTGGGCGACAAGGAGACCTACAGCTTTGACCCTAGGGCACCCTTCCTCCAAATGGTGAGCCAGGCCTGGCGAGGCTCTCAGAGCACCCTC
 685  A  A  H  Y  L  V  L  G  D  K  E  T  Y  S  F  D  P  R  A  P  F  L  Q  M  V  S  Q  A  W  R  G  S  Q  S  T  L
2161 CACCCCAGCGCGGCCCTTGTTCCTGCTGCTGCTGCTCTGCCCTGCTGCCGCAGGACTCCTAGGTTTGTGGTGGTCTTTAACCCACTGGAACAGGAGCGGCTCAGT
 721  H  P  S  A  A  L  V  P  A  A  A  A  S  A  L  L  P  Q  R  A  P  F  V  V  V  F  N  P  L  E  Q  E  R  L  S
2269 GTGGTGTCCCTGCTGGTCAACTCACCCCGAGTGCGAGTGCTTTCAGAGGCAGGGTCAGCCCTTGTCTGTGCAGATCAGTGTGCAGTGGAGCTCCGCCACCAACATGGTC
 757  V  V  S  L  L  V  N  S  P  R  V  R  V  L  S  E  E  G  Q  P  L  S  V  Q  I  S  V  Q  W  S  S  A  T  N  M  V
2377 CCCGATGTCTACCAGGTGTCAGTGCCTGTCCGCCTGCCAGCCCTGGGGCTGGGTGTGCTGCAGCTGCAGCCAGATCTCGATGGACCCTACACACTGCAGTCTTCGGTG
 793  P  D  V  Y  Q  V  S  V  P  V  R  L  P  A  L  G  L  G  V  L  Q  L  Q  P  D  L  D  G  P  Y  T  L  Q  S  S  V
2485 CATGTCTACCTGAACGGCGTGAAACTGTCTGTCAGCAGGCAAACAACATTCCCTCCCGTTGTGGACTCGGGCACCAGTGACTTCGCCATCAGCAATCGATACATG
 829  H  V  Y  L  N  G  V  K  L  S  V  S  R  Q  T  T  F  P  L  R  V  V  D  S  G  T  S  D  F  A  I  S  N  R  Y  M
2593 CAGGTCTGGTTCTCCGGCCTTACTGGGCTTCTCAAGAGCGTCCGACGTGTGGACGAAGAGCAGGAACAGCAGGTGGACATGAAGCTCTTCGTCTATGGAACCCGCACA
 865  Q  V  W  F  S  G  L  T  G  L  L  K  S  V  R  R  V  D  E  E  Q  E  Q  Q  V  D  M  K  L  F  V  Y  G  T  R  T
2701 TCCAAGGATAAGAGTGGTGCCTACCTCTTCCTGCCCTGATAACGAGGCTAAGCCCTATGTCCCTAAGAAACCTCCTGTGCTGCGCGTCACCGAAGGCCCTTTCTTCTCA
 901  S  K  D  K  S  G  A  Y  L  F  L  P  D  N  E  A  K  P  Y  V  P  K  K  P  P  V  L  R  V  T  E  G  P  F  F  S
2809 GAGGTGGCTGCGTATTATGAGCACTTTCACCAAGTGATTCGACTTTACAACCTGCCAGGGGTAGAGGGGCTGTCTCTGGACGTGTCGTTCCAGGTGGACATCAGGGAC
 937  E  V  A  A  Y  Y  E  H  F  H  Q  V  I  R  L  Y  N  L  P  G  V  E  G  L  S  L  D  V  S  F  Q  V  D  I  R  D
2917 TACGTGAACAAGGAGCTAGCCCTGCGCATCCACACAGACATCGACAGCCAGGGCACTTTCTTCACAGACCTCAATGGCTTTCAGGTACAGCCCCGGAAGTATCTGAAG
 973  Y  V  N  K  E  L  A  L  R  I  H  T  D  I  D  S  Q  G  T  F  F  T  D  L  N  G  F  Q  V  Q  P  R  K  Y  L  K
3025 AAGTTGCCCCTGCAGGCTAATTTCTACCCTATGCCAGTCATGGCCTACATCCAGGATTCCCAGAGGCGCCTCACGCTGCACACTGCTCAGGCTCTGGGTGTCTCCAGC
1009  K  L  P  L  Q  A  N  F  Y  P  M  P  V  M  A  Y  I  Q  D  S  Q  R  R  L  T  L  H  T  A  Q  A  L  G  V  S  S
3133 CTCGGCAATGGCCAGCTGGAGGTGATCTTGGACCGAAGGCTAATGCAGGATGACAACCGGGACTAGGCCAAGGGCTCAAAGACAACAAGATCACCTGCAACCATTTC
1045  L  G  N  G  Q  L  E  V  I  L  D  R  R  L  M  Q  D  D  N  R  G  L  G  Q  G  L  K  D  N  K  I  T  C  N  H  F
3241 CGGCTCCTGTTAGAACGTCGAACCCTGATGAGCCCTGAGGTCCAACAGGAGCGCTCTACAAGCTACCCGTCCTCTCCTCAGCCACATGACTTCCATGTACCTCAACACA
1081  R  L  L  E  R  R  T  L  M  S  P  E  V  Q  Q  E  R  S  T  S  Y  P  S  L  L  S  H  M  T  S  M  Y  L  N  T
3349 CCTCCTCTGGTCTTACCGGTGGCCAAGAGGGAGAGCACCAGCCCCACTCTGCACTCTTTCACCCCTCTGGCTTCTCCGTTGCCCTGCCGATTTCCATCTGCTCAATCTG
1117  P  P  L  V  L  P  V  A  K  R  E  S  T  S  P  T  L  H  S  F  H  P  L  A  S  P  L  P  C  D  F  H  L  L  N  L
3457 CGCATGCTCCCCGCCGAGGTGAGTGTCCCGGTCCGTGCCAATCCTCACCATCAGGCTGAGCCTTGCCTTCTTGGCAGACATGCTGCTGACCCTCCACCGCTCTTGTCC
1153  R  M  L  P  A  E  V  S  V  P  V  R  A  N  P  H  H  Q  A  E  P  C  L  L  G  R  H  A  A  D  P  P  P  L  L  S
3565 CTGACTGTCTTCCAGGACACCTTGCCCGCGGCTGATGCTGCTCTCATCCTACACCGCAAGGGTTTTGACTGTGGCCTTGAAGCCAAGAACCTGGGCTTCAACTGTACC
1189  L  T  V  F  Q  D  T  L  P  A  A  D  A  A  L  I  L  H  R  K  G  F  D  C  G  L  E  A  K  N  L  G  F  N  C  T
3673 ACAAGCCAAGGCAAGCTGGCCCTGGGGAGCCTCTTCCATGGCCTGGATGTGCTATTCCTGCAGCCCACCTCTTTGACTTTGCTATACCCTCTGGCCTCGCCCTCCAAC
1225  T  S  Q  G  K  L  A  L  G  S  L  F  H  G  L  D  V  L  F  L  Q  P  T  S  L  T  L  L  Y  P  L  A  S  P  S  N
3781 AGCACTGACATCTCTCTGGAGCCCATGGAAGATCAGCACCTTCCGCCTGCGCTTGGGTTAG
1261  S  T  D  I  S  L  E  P  M  E  I  S  T  F  R  L  R  L  G
```

FIG. 32

Human mannosidase IIx (D55649)

```
   1 ATGAAGCTGAAAAAGCAGGTGACAGTGTGTGGGGCTGCCATCTTCTGTGTGGCAGTCTTCTCGCTCTACCTCATGCTGGACCGAGTGCAACACGATCCCACCCGACACC
   1▸M  K  L  K  K  Q  V  T  V  C  G  A  A  I  F  C  V  A  V  F  S  L  Y  L  M  L  D  R  V  Q  H  D  P  T  R  H
 110 ACAATGGTGGGAACTTCCCCCGGAGCCAAATTTCTGTGCTGCAGAACCGCATTGAGCAGCTGGAGCAGCTTTTGGAGGAGAACCATGAGATTATCAGCCATATCAAGGA
  37▸Q  N  G  G  N  F  P  R  S  Q  I  S  V  L  Q  N  R  I  E  Q  L  E  Q  L  L  E  E  N  H  E  I  I  S  H  I  K  D
 219 CTCCGTGCTGGAGCTGACAGCCAACGCAGAGGGCCCGCCCGCCATGCTGCCCTACTACACGGTCAATGGCTCCTGGGTGGTGCCACCGGAGCCCCGGCCCAGCTTCTTC
  73▸S  V  L  E  L  T  A  N  A  E  G  P  P  A  M  L  P  Y  Y  T  V  N  G  S  W  V  V  P  P  E  P  R  P  S  F  F
 328 TCCATCTCCCCGCAGGACTGCCAGTTTGCTTTGGGGGGCCGGGGTCAGAAGCCAGAGCTGCAGATGCTCACTGTGTCGGAGGAGCTGCCGTTTGACAACGTGGATGGTG
 110▸S  I  S  P  Q  D  C  Q  F  A  L  G  G  R  G  Q  K  P  E  L  Q  M  L  T  V  S  E  E  L  P  F  D  N  V  D  G
 437 GTGTGTGGAGGCAAGGCTTCGACATCTCCTACGACCCGCACGACTGGGATGCTGAAGACCTGCAGGTGTTTGTGGTGCCCCACTCTCACAATGACCCAGGCTGGATCAA
 146▸G  V  W  R  Q  G  F  D  I  S  Y  D  P  H  D  W  D  A  E  D  L  Q  V  F  V  V  P  H  S  H  N  D  P  G  W  I  K
 546 GACCTTTGACAAGTACTACACAGAGCAGACCCAACACATCCTCAATAGCATGGTGTCTAAGCTGCAGGAGGACCCCCGGCGGCGTTCCTCTCTGGGCAGAGGTCTCCTTC
 182▸T  F  D  K  Y  Y  T  E  Q  T  Q  H  I  L  N  S  M  V  S  K  L  Q  E  D  P  R  R  R  F  L  W  A  E  V  S  F
 655 TTCGCCAAGTGGTGGGACAACATCAATGTCCAAAAGAGAGCGGCAGTCCGAAGGCTGGTGGGAAACGGGCAGCTGGAGATTGCCGACAGGAGGCTCGGCTGATGCCACATG
 219▸F  A  K  W  W  D  N  I  N  V  Q  K  R  A  A  V  R  R  L  V  G  N  G  Q  L  E  I  A  T  G  G  W  V  M  P  D
 764 AGGCCAATTCCCACTACTTTGCATTGATTGACCAGCTCATCGAAGGACACCAGTGGCTGGAGAGAAATCTTGGTGCAACCCCCCGCTCTGGCTGGGCAGTGGACCCCTT
 255▸E  A  N  S  H  Y  F  A  L  I  D  Q  L  I  E  G  H  Q  W  L  E  R  N  L  G  A  T  P  R  S  G  W  A  V  D  P  F
 873 TGGATACAGCTCCACCATGCCTTACCTGCTGCGCCGTGCCAACCTCACCAGCATGCTGATTCAGAGAGTGCACTATGCCATCAAGAAGCACTTTGCTGCCACCCACAGC
 291▸G  Y  S  S  T  M  P  Y  L  L  R  R  A  N  L  T  S  M  L  I  Q  R  V  H  Y  A  I  K  K  H  F  A  A  T  H  S
 982 CTAGAGTTCATGTGGAGGCAGACATGGGACTCGGACTCCAGCACAGACATCTTCTGTCACATGATGCCCTTCTACAGCTATGACGTCCCCCATACCTGTGGCCCAGATC
 328▸L  E  F  M  W  R  Q  T  W  D  S  D  S  S  T  D  I  F  C  H  M  M  P  F  Y  S  Y  D  V  P  H  T  C  G  P  D
1091 CCAAGATCTGCTGCCAATTTGATTTCAAACGCCTGCCTGGTGGGCGCATCAACTGCCCTTGGAAGGTGCCACCCCGGGCCATCACAGAGGCCAACGTGGCAGAGAGGGC
 364▸P  K  I  C  C  Q  F  D  F  K  R  L  P  G  G  R  I  N  C  P  W  K  V  P  P  R  A  I  T  E  A  N  V  A  E  R  A
1200 AGCCCTGCTTCTGGACCAATACCGGAAGAAGTCCCAGCTGTTCCGAAGCAACGTCCTCCTGGTGCCTCTTGGAGATGACTTCCGATATGACAAGCCCCAGGAGTGGGAT
 400▸A  L  L  L  D  Q  Y  R  K  K  S  Q  L  F  R  S  N  V  L  L  V  P  L  G  D  D  F  R  Y  D  K  P  Q  E  W  D
1309 GCCCAGTTCTTCAACTACCAACGGCTCTTTGACTTCTTCAACAGCAGGCCTAACCTCCATGTGCAGGCCCAGTTTGGCACTCTTTCTGACTATTTTGATGCCCTGTACA
 437▸A  Q  F  F  N  Y  Q  R  L  F  D  F  F  N  S  R  P  N  L  H  V  Q  A  Q  F  G  T  L  S  D  Y  F  D  A  L  Y
1418 AGAGGACAGGGGTGGAGCCAGGGGCCCGGCCTCCAGGGTTTCCTGTCCTGAGCGGGGATTTCTTCTCCTATGCGGACCGGGAGGATCATTACTGGACAGGCTATTACAC
 473▸K  R  T  G  V  E  P  G  A  R  P  P  G  F  P  V  L  S  G  D  F  F  S  Y  A  D  R  E  D  H  Y  W  T  G  Y  Y  T
1527 TTCCCGGCCCTTCTACAAGAGCTTAGACCGAGTCCTGGAAGCCCACCTGCCGGGGGGCAGAGGTTCTGTACAGCCTGGCTGCAGCTCACGCTCGCCGCTCTGTCTGGCT
 509▸S  R  P  F  Y  K  S  L  D  R  V  L  E  A  H  L  R  G  A  E  V  L  Y  S  L  A  A  A  H  A  R  R  S  G  L  A
1636 GGCCGGTACCCACTGTCTGATTTCACCCTCCTGACGGAAGCTCGGCGCACATTGGGGCTCTTCCAGCATCACGATGCCATCACTGGCACGGCCAAGGAGGCTGTGGTGG
 546▸G  R  Y  P  L  S  D  F  T  L  L  T  E  A  R  R  T  L  G  L  F  Q  H  H  D  A  I  T  G  T  A  K  E  A  V  V
1745 TGGACTATGGGGTCAGGCTTCTGCGCTCCCTTGTCAACCTGAAGCAGGTCATCATTCATGCAGCCCACTATCTGGTGCTGGGGGACAAGGAGACCTACCACTTTGACCC
 582▸V  D  Y  G  V  R  L  L  R  S  L  V  N  L  K  Q  V  I  I  H  A  A  H  Y  L  V  L  G  D  K  E  T  Y  H  F  D  P
1854 TGAGGCGCCCTTCCTCCAAGTGGATGACACTCGCTTAAGTCACGACGCCCTCCCAGAGCGCACCGTGATCCAGCTGGATTCCTCGCCCAGGTTTGTGGTCCTATTCAAC
 618▸E  A  P  F  L  Q  V  D  D  T  R  L  S  H  D  A  L  P  E  R  T  V  I  Q  L  D  S  S  P  R  F  V  V  L  F  N
1963 CCACTGGAACAGGAGCGATTCAGCATGGTGTCCCTGCTGGTCAACTCTCCCCGCGTGCGTGTCCTTTCGGAGGAGGGTCAGCCCCTGGCCGTGCAGATCAGCGCACACT
 655▸P  L  E  Q  E  R  F  S  M  V  S  L  L  V  N  S  P  R  V  R  V  L  S  E  E  G  Q  P  L  A  V  Q  I  S  A  H
2072 GGAGCTCTGCCACCGAGGCGGTCCCTGACGTCTACCAGGTGTCTGTGCCTGTCCGCCTGCCAGCCCTGGGCCTGGGCGTGCTGCAGCTACAGCTGGGCCTGGATGGGCA
 691▸W  S  S  A  T  E  A  V  P  D  V  Y  Q  V  S  V  P  V  R  L  P  A  L  G  L  G  V  L  Q  L  Q  L  G  L  D  G  H
2181 CCGCACGCTGCCCTCCTCTCTGTGCGCATCTACCTGCACGGCCGGCAGCTGTCCGTCAGCAGGCACGAAGCGTTTCCTCTCCGTGTCATTGACTCTGGCACCAGCGACTTC
 727▸R  T  L  P  S  S  V  R  I  Y  L  H  G  R  Q  L  S  V  S  R  H  E  A  F  P  L  R  V  I  D  S  G  T  S  D  F
2290 GCCCTCAGCAACCGCTACATGCAGGTCTGGTTCTCAGGGCCTTACTGGGCCTCCTCAAGAGCATCCGAAGGGGTGGATGAGGAGCACGAGCAGCAGGTGGACATGCAGGTCC
 764▸A  L  S  N  R  Y  M  Q  V  W  F  S  G  L  T  G  L  L  K  S  I  R  R  V  D  E  E  H  E  Q  Q  V  D  M  Q  V
2399 TTGTCTATGGCACCCGTACGTCCAAAGACAAGAGTGGAGCCTACCTCTTCCTGCCCGATGGCGAGGCTAGCCCTACGTCCCCAAGGAGCCCCCCGTGCTGCGTGTCACT
 800▸L  V  Y  G  T  R  T  S  K  D  K  S  G  A  Y  L  F  L  P  D  G  E  A  S  P  T  S  P  R  S  P  P  C  C  V  S  L
2508 GAAGGCCCTTCTTCTCAGAGGTGGTTGCGTACTATGAGCACATTCACCAGGCGGTCCGGCTTTACAATCTGCCAGGGGTGGAGGGCTGTCTCTGGACATATCATCCC
 836▸K  A  L  S  S  Q  R  W  L  R  T  M  S  T  F  T  R  S  G  F  T  I  C  Q  G  W  R  G  C  L  W  T  Y  H  P
2617 TGGTGGACATCCGGGACTACGTCAACAAGGAGCTGGCCCTGCACATCCATACAGACATCGACAGCCAGGGTGCAGCCCCGACGGTATCTGAAGAAGCTCCCCCTCCAGG
 873▸W  W  T  S  G  T  T  S  T  R  S  W  P  C  T  S  I  Q  T  S  T  A  R  V  Q  P  R  R  Y  L  K  K  L  P  L  Q
2726 CCAACTTCTACCCCATGCCAGTCATGGCCTATATCCAGGACGCACAGAAGCGCCTCACGCTGCACACTGCCCAGGCCCTGGGTGTCTCTAGCCTCAAAGATGGCCAGCT
 909▸A  N  F  Y  P  M  P  V  M  A  Y  I  Q  D  A  Q  K  R  L  T  L  H  T  A  Q  A  L  G  V  S  S  L  K  D  G  Q  L
2835 GCAGGTGATCTTGGACCGGCGGCTGATGCAGGATGACAACCGGGGCCTAGGCCAAGGGCTCAAGGACAACAAGAGAACCTGCAACCGTTTCCGCCTCCTGCTAGAGCGG
 945▸E  V  I  L  D  R  R  L  M  Q  D  D  N  R  G  L  G  Q  G  L  K  D  N  K  R  T  C  N  R  F  R  L  L  L  E  R
2944 CGAACCGTGGGCAGTGAGGTCCAAGATAGCCACTCTACCAGCTACCCATCCCTCCTCAGCCACCTGACCTCCATGTACCTGAACGCCCCGGCGCTCGCTCTGCCTGTAG
 982▸R  T  V  G  S  E  V  Q  D  S  H  S  T  S  Y  P  S  L  L  S  H  L  T  S  M  Y  L  N  A  P  A  L  A  L  P  V
3053 CCAGGATGCAGCTCCCAGGCCCTGGTCTGCCGCTCATTTCATCTCTGGCTTCCTCACTGCCCTGTGACTTCCACCTGCTCAACCTACGTACGCTCCAGGCTGAGGAGGA
1018▸A  R  M  Q  L  P  G  P  G  L  R  S  F  H  P  L  A  S  S  L  P  C  D  F  H  L  L  N  L  R  T  L  Q  A  E  E  D
3162 CACCCTACCCTCGGCGGAGACCGCACTCATCTTACACCGCAAGGGTTTTGACTGCGGCCTGGAGGCCAAGAACTTGGGCTTCAACTGCACCACAAGCCAAGGCAAGGTA
1054▸T  L  P  S  A  E  T  A  L  I  L  H  R  K  G  F  D  C  G  L  E  A  K  N  L  G  F  N  C  T  T  S  Q  G  K  V
3271 GCCCTGGGCAGCCTTTTCCATGGCCTGGATGTGGTATTCCTTCAGCCAACCTCCTTGACGTTACTGTACCCTCTGGCCTCCCCGTCCAACAGCACTGACGTCTATTTGG
1091▸A  L  G  S  L  F  H  G  L  D  V  V  F  L  Q  P  T  S  L  T  L  L  Y  P  L  A  S  P  S  N  S  T  D  V  Y  L
3380 AGCCCATGGAGATTGCTACCTTTCGCCTCCGCTTGGGTTAG
1127▸E  P  M  E  I  A  T  F  R  L  R  L  G
```

FIG. 33

Insect cell mannosidase III (AF005034)

*[Figure shows a DNA sequence and corresponding protein sequence translation for insect cell mannosidase III (GenBank accession AF005034). The sequence begins with ATGAGGACTCGTGTCCTTCGTTGCCGGCCGTTCT... encoding the protein starting with MRTRVLRCRPFS... and continues for approximately 1,100 amino acids ending with ...NAMEVKTYKIRF.]*

FIG. 34

Human lysosomal mannosidase II (NM_000528)

```
   1 ATGGGCTACGCGCGGGCTTCGGGGGTCTGCGCTCGCGGCTGCCTGGACTCAGCAGGCCCCTGGACCATGTCCCGCGCCCTGCGGCCACCGCTCCCGCCTCTCTGCTTTT
   1▶ M  G  Y  A  R  A  S  G  V  C  A  R  G  C  L  D  S  A  G  P  W  T  M  S  R  A  L  R  P  P  L  P  P  L  C  F
 110 TCCTTTTGTTGCTGGCGGCTGCCGGTGCTCGGGCCGGGGGATACGAGACATGCCCCACAGTGCAGCCGAACATGCTGAACGTGCACCTGCTGCCTCACACACATGATGA
  37▶ F  L  L  L  L  A  A  A  G  A  R  A  G  G  Y  E  T  C  P  T  V  Q  P  N  M  L  N  V  H  L  L  P  H  T  D  D
 219 CCTGGGCTGGCTCAAAACCGTGGACCAGTACTTTTATGGAATCAAGAATGACATCCAGCACGCCGGTGTGCAGTATATCCTGGACTCGGTCATCTCTGCCTTGCTGGCA
  73▶ V  G  W  L  K  T  V  D  Q  Y  F  Y  G  I  K  N  D  I  Q  H  A  G  V  Q  Y  I  L  D  S  V  I  S  A  L  L  A
 328 GATCCCACCCGTCGCTTCATTTACGTGGAGATTGCCTTCTTCTCCCGTTGGTGGCACCAGCAGACAAATGCCACACAGGAAGTCGTGCCGAGACCTTGTGCCCCAGGGGC
 110▶ D  P  T  R  R  F  I  Y  V  E  I  A  F  F  S  R  W  W  H  Q  Q  T  N  A  T  Q  E  V  V  R  D  L  V  R  Q  G
 437 GCCTGGAGTTCGCCAATGGTGGCTGGGTGATGAACGATGAGGCAGCCACCCACTACGGTGCCATCGTGGACCAGATGACACTTGGGCTGCGCTTTCTGGAGGACATT
 146▶ R  L  E  F  A  N  G  G  W  V  M  N  D  E  A  A  T  H  Y  G  A  I  V  D  Q  M  T  L  G  L  R  F  L  E  D  T  F
 546 TGGCAATGATGGGCGACCCCGTGTGGCCTGGCACATTGACCCCTTCGGCCACTCTCGGGAGCAGGCCTCGCTGTTTGCGCAGATGGGCTTCGACGGCTTCTTCTTTGGG
 182▶ G  N  D  G  R  P  R  V  A  W  H  I  D  P  F  G  H  S  R  E  Q  A  S  L  F  A  Q  M  G  F  D  G  F  F  F  G
 655 CGCCTTGATTATCAAGATAAGTGGGTACCGATGCAGAAGCTGGAGATGGAGCAGGTGTGGCGGGCCAGCACCAGCCTGAAGCCCCCGACCGCGGACCTCTTCACTGGTG
 219▶ R  L  D  Y  Q  D  K  W  V  R  M  Q  K  L  E  M  E  Q  V  W  R  A  S  T  S  L  K  P  P  T  A  D  L  F  T  G
 764 TGCTTCCCAATGGTTACAACCCGCCAAGGAATCTGTGCTGGGATGTGCTGTGTGTCGATCAGCCGCTGGTGGAGGACCCTCGCAGCCCCGAGTACAACGCCAAGGAGCT
 255▶ V  L  P  N  G  Y  N  P  P  R  N  L  C  W  D  V  L  C  V  D  Q  P  L  V  E  D  P  R  S  P  E  Y  N  A  K  E  L
 873 GGTCGATTACTTCCTAAATGTGGCCACTGCCCAGGGCCGGTATTACCGCACCAACACACTGTGATGACCATGGGCTCGGACTTCCAATATGAGAATGCCAACATGTGG
 291▶ V  D  Y  F  L  N  V  A  T  A  Q  G  R  Y  Y  R  T  N  H  T  V  M  T  M  G  S  D  F  Q  Y  E  N  A  N  M  W
 982 TTCAAGAACCTTGACAAGCTCATCCGGCTGGTAAATGCGCAGCAGGCAAAAGGGAAGCAGTGTCCATGTTCTCTACTCCACCCCGCTTGTTACCTCTGGGAGCTGAACA
 328▶ F  K  N  L  D  K  L  I  R  L  V  N  A  Q  Q  A  K  G  S  S  V  H  V  L  Y  S  T  P  A  C  Y  L  W  E  L  N
1091 AGGCCAACCTCACCTGGTCAGTGAAACATGACGACTTCTTCCCTTACGGCGGATGGCCCCCACCAGTTCTGGACCGGTTACTTTTCCAGTCGGCCGGCCCTCAAACGCTA
 364▶ K  A  N  L  T  W  S  V  K  H  D  D  F  F  P  Y  A  D  G  P  H  Q  F  W  T  G  Y  F  S  S  R  P  A  L  K  R  Y
1200 CGAGCGCCTCAGCTACAACTTCCTGCAGGTGTGCAATCAGCTGGAGGCGCTGGTGGGCGTGGCGGCCAACGTGGGACCCTATGGCTCCGGAGACAGTGCACCCCTCAAT
 400▶ E  R  L  S  Y  N  F  L  Q  V  C  N  Q  L  E  A  L  V  G  L  A  A  N  V  G  P  Y  G  S  G  D  S  A  P  L  N
1309 GAGGCGATGGCTGTGCTCCAGCATCACGACGCCGTCAGCGGCACCTCCCCGCCAGCACGTGGCCAACGACTACGCGCGCCAGCTTGCGGCAGGCTGGGGGCCTTGCGAGG
 437▶ E  A  M  A  V  L  Q  H  H  D  A  V  S  G  T  S  R  Q  H  V  A  N  D  Y  A  R  Q  L  A  A  G  W  G  P  C  E
1418 TTCTTCTGAGCAACGCGCTGGCCGCGGCTCAGAGGCTTCAAAGATCACTTCACCTTTTGCCAACAGCTAAACATCAGCATCTGCCCGCTCAGCCAGACGGCCGCGGCGCTT
 473▶ V  L  L  S  N  A  L  A  R  L  R  G  F  K  D  H  F  T  F  C  Q  Q  L  N  I  S  I  C  P  L  S  Q  T  A  A  R  F
1527 CCAGGTCATCGTTTATAATCCCCTGGGGCGGAAGGTGAATTGGATGGTACGGCTGCCGGTCAGCGAAGGCGTTTTCGTTGTGAAGGACCCCAATGGCAGGACAGTGCCC
 509▶ Q  V  I  V  Y  N  P  L  G  R  K  V  N  W  M  V  R  L  P  V  S  E  G  V  F  V  V  K  D  P  N  G  R  T  V  P
1636 AGCGATGTGGTAATATTTCCCAGCTCAGACAGCCAGGCGCACCCTCCGGAGCTGCTGTTCTCAGCCTCACTGCCCGCCCTGGGCTTCAGCACCTATTCAGTAGCCCAGG
 546▶ S  D  V  V  I  F  P  S  S  D  S  Q  A  H  P  P  E  L  L  F  S  A  S  L  P  A  L  G  F  S  T  Y  S  V  A  Q
1745 TGCCTCGCTGGAAGCCCCAGGCCCCGCGCACCACAGCCCATCCCCAGAAGATCCTGGTCCCCTGCTTTAACCATCGAAAATGAGCACATCCGGGCAACGTTTGATCCTGA
 582▶ V  P  R  W  K  P  Q  A  R  A  P  Q  P  I  P  R  R  S  W  S  P  A  L  T  I  E  N  E  H  I  R  A  T  F  D  P  D
1854 CACACAGGGCTGTTGATGGACATTATGAACATGAATCAGCAACTCCTGCTGCCTGTTCGCCAGACCTTCTTCTGGTACAACGCCAGTATAGGTGACAACGAAAGTGACCAG
 618▶ T  G  L  L  M  E  I  M  N  M  N  Q  Q  L  L  P  V  R  Q  T  F  F  W  Y  N  A  S  I  G  D  N  E  S  D  Q
1963 GCCCTCAGGTGCCTACATCTTCAGACCCAACCAACAGAAACCGCTGCCTGTCAGCCGCTGGGCTCAGATCCACCTGGTGAAGACACCCTTGGTGCAGGAGGTGCACCAGA
 655▶ A  S  G  A  Y  I  F  R  P  N  Q  Q  K  P  L  P  V  S  R  W  A  Q  I  H  L  V  K  T  P  L  V  Q  E  V  H  Q
2072 ACTTCTCAGCTTGGTGTTCCCAGGTGGTTCGCCTGTACCCAGGACAGCGGCACCTGGAGCTAGAGTGGTCGGTGGGGCCGATACCTGTGGGCGACACCTGGGGGAAGGA
 691▶ N  F  S  A  W  C  S  Q  V  V  R  L  Y  P  G  Q  R  H  L  E  L  E  W  S  V  G  P  I  P  V  G  D  T  W  G  K  E
2181 GGTCATCAGCCGTTTTGACACACCGCTGGAGACAAAGGGACGCTTCTACACAGACAGCAATGGCCGGAGATCCTGGAGACGAGGCGGGATTATCGACCCACCTGGAAA
 727▶ V  I  S  R  F  D  T  P  L  E  T  K  G  R  F  Y  T  D  S  N  G  R  E  I  L  E  R  R  R  D  Y  R  P  T  W  K
2290 CTGAACCAGACGGAGCCCGTGGCAGGAAACTACTATCCAGTCAACACCCGGATTTACATCACGGATGGAAACATGCAGCTGACTGTGCTGACTGACCGCTCCCAGGGGG
 764▶ L  N  Q  T  E  P  V  A  G  N  Y  Y  P  V  N  T  R  I  Y  I  T  D  G  N  M  Q  L  T  V  L  T  D  R  S  Q  G
2399 GCAGCAGCCTGAGAGATGGCTCGCTGGAGCTCATGGTGCACCGAAGGCTGCTGAAGGACGATGGACGCGGAGTATCGGAGCCACTAATGGAGAACGGGTCGGGGGCGTG
 800▶ G  S  S  L  R  D  G  S  L  E  L  M  V  H  R  R  L  L  K  D  D  G  R  G  V  S  E  P  L  M  E  N  G  S  A  W
2508 GGTCCCAGGGCCCCACCTGGTGCTGCTGGACACAGCCCAGGCTGCAGCCGCCGGACACCGGCTCCTGGCCGAGCAGGAGGTCCTGGCCCCTCAGGTGGTGCTGGCCCCG
 836▶ V  R  G  R  H  L  V  L  L  D  T  A  Q  A  A  A  A  G  H  R  L  L  A  E  Q  E  V  L  A  P  Q  V  V  L  A  P
2617 GGTGGCGGCGCCGCCTACAATCTCGGGGCTCCTCCGCGCACGCAGTTCTCAGGGCTGCGCAGGGACCTGCCGCCCTCGGTGCACCTGCTCACGCTGGCCAGCTGGGGCC
 873▶ G  G  G  A  A  Y  N  L  G  A  P  P  R  T  Q  F  S  G  L  R  R  D  L  P  P  S  V  H  L  L  T  L  A|S  W  G
2726 CCGAAATGGTGCTGCTGCGCTTGGAGCACCAGTTTGCCGTAGGAGAGGATTCCGGACCTAACCTGAGCGCCCCCGTTACCTTGAACTTGAGGGACCTGTTCTCCACCTT
 909▶ P  E  M  V  L  L  R  L  E  H  Q  F  A  V  G  E  D  S  G  R  N  L  S  A  P  V  T  L  N  L  R  D  L  F  S  T  F
2835 CACCATCACCCGCCTGCAGGAGACCACGCTGGTGGCCAACCAGCTCCGCGAGGCAGCCTCCAGGCTCAAGTGGACAACAAACACAGGCCCCACACCCCACCAAACTCCG
 945▶ T  I  T  R  L  Q  E  T  T  L  V  A  N  Q  L  R  E  A  A  S  R  L  K  W  T  T  N  T  G  P  T  P  H  Q  T  P
2944 TACCAGCTGGACCCGGCCAACATCACGCTGGAACCCATGGAAATCCGCACTTTCCTGGCCTCAGTTCAATGGAAGGAGGTGGATGGTTAG
 982▶ Y  Q  L  D  P  A  N  I  T  L  E  P  M  E  I  R  T  F  L  A  S  V  Q  W  K  E  V  D  G
```

FIG. 35

Human cytoplasmic mannosidase II (NM_006715)

```
   1 ATGGCGGCAGCGCCGTTCTTGAAGCACTGGCGCACCACTTTTGAGCGGGTGGAGAAGTTCGTGTCCCCGATCTACTTCACCGACTGTAACCTCCGCGGCAGGCTTTTTG
   1 M  A  A  A  P  F  L  K  H  W  R  T  T  F  E  R  V  E  K  F  V  S  P  I  Y  F  T  D  C  N  L  R  G  R  L  F
 110 CGGCCAGCTGCCCTGTGGCTGTGCTCTCCAGCTTCCTGACGCCGGAGAGACTTCCCTACCAGGAGGCAGTCCAGCGGGACTTCCGCCCCGCGCAGGTCGGCGACAGCTT
  37 G  A  S  C  P  V  A  V  L  S  S  F  L  T  P  E  R  L  P  Y  Q  E  A  V  Q  R  D  F  R  P  A  Q  V  G  D  S  F
 219 CGGACCCACATGGTGGACCTGCTGGTTCCGGGTGGAGCTGACCATCCCAGAGGCCATGGGTGGGCCAGGAAGTTCACCTTTGCTGGGAAAGTGATGGAGAAGGTCGGTG
  73 G  P  T  W  W  T  C  W  F  R  V  E  L  T  I  P  E  A  W  V  G  Q  E  V  H  L  C  W  E  S  D  G  E  G  L  V
 328 TGGCGTGATGGAGAACCTGTCCAGGGTTTAACCAAAGAGGGTGAGAAGACCAGCTATGTCCTCACTGACAGGCTGGGGGAAAGAGACCCCCGAAGCCTCACTCTCTATG
 110 W  R  D  G  E  P  V  Q  G  L  T  K  E  G  E  K  T  S  Y  V  L  T  D  R  L  G  E  R  D  P  R  S  L  T  L  Y
 437 TGGAAGTAGCCTGCAATGGGCTCCTGGGGGCCGGGAAGGGAAGCATGATTGCAGCCCCTGACCCTGAGAAGATATTCCAGCTGAGCCGGGCTGAGCTAGCTGTGTTCCA
 146 V  E  V  A  C  N  G  L  L  G  A  G  K  G  S  M  I  A  A  P  D  P  E  K  I  F  Q  L  S  R  A  E  L  A  V  F  H
 546 CCCGGATGTCCACATGCTCCTGGTGGATCTGGAGCTGCTGCTGGGCATAGCCAAGGGCCTCGGGAAGGACAACCAGCGCAGCTTCCAGGCCCTGTACACAGCCAATCAG
 182 R  D  V  H  M  L  L  V  D  L  E  L  L  L  G  I  A  K  G  L  G  K  D  N  Q  R  S  F  Q  A  L  Y  T  A  N  Q
 655 ATGGTGAACGTGTGTGACCCTGCCCAGCCCGAGACCTTCCCAGTGGCCCAGGCCCTGGCCTCCAGGTTCTTTGGCCAACATGGGGGTGAAAGCCAACACACCATTCATG
 219 M  V  N  V  C  D  P  A  Q  P  E  T  F  P  V  A  Q  A  L  A  S  R  F  F  G  Q  H  G  G  E  S  Q  H  T  I  H
 764 CCACAGGGCACTGCCACATTGATACAGCCTGGCTTTGGCCCTTCAAAGAGACTGTGAGGAAATGTGCCCGGAGCTGGGTGACCGCCCTGCAGCTCATGGAGCGGAACCC
 255 A  T  G  H  C  H  I  D  T  A  W  L  W  P  F  K  E  T  V  R  K  C  A  R  S  W  V  T  A  L  Q  L  M  E  R  N  P
 873 TGAGTTCATCTTTGCCTGCTCCCAGGCGCAGCAGCTGGAATGGGTGAAGAGCCGCTACCCTGGCCTGTACTCCCGCATCCAGGAGTTTGCGTGCCGTGGGCAGTTTGTG
 291 E  F  I  F  A  C  S  Q  A  Q  Q  L  E  W  V  K  S  R  Y  P  G  L  Y  S  R  I  Q  E  F  A  C  R  G  Q  F  V
 982 CCTGTGGGGGGCACCTGGGTGGAAATGGATGGGAACCTGCCCAGTGGAGAGGCCATGGTGAGGCAGTTTTTGCAGGGCCAGAACTTCTTTCTGCAGGAGTTTGGGAAGA
 328 P  V  G  G  T  W  V  E  M  D  G  N  L  P  S  G  E  A  M  V  R  Q  F  L  Q  G  Q  N  F  F  L  Q  E  F  G  K
1091 TGTGCTCTGAGTTCTGGCTGCCCGACACCTTTGGCTACTCAGCACAGCTCCCCCAGATCATGCACGGCTGTGGCATCAGGCGCTTTCTCACCCAGAAATTGAGCTGGAA
 364 M  C  S  E  F  W  L  P  D  T  F  G  Y  S  A  Q  L  P  Q  I  M  H  G  C  G  I  R  R  F  L  T  Q  K  L  S  W  N
1200 TTTGGTGAACTCCTTCCCACACCATACATTTTTCTGGGAGGGCCTGGATGGCTCCCGTGTACTGGTCCACTTCCCACCTGGCGACTCCTATGGGATGCAGGGCAGCGTG
 400 L  V  N  S  F  P  H  H  T  F  F  W  E  G  L  D  G  S  R  V  L  V  H  F  P  P  G  D  S  Y  G  M  Q  G  S  V
1309 GAGGAGGTGCTGAAGACCGTGGCCAACAACCGGGACAAGGGGCGGGCCAACACACGTGCCTTCCTCTTTGGCTTTGGGGATGGGGGTGGTGGCCCCACCCAGACCATGC
 437 E  E  V  L  K  T  V  A  N  N  R  D  K  G  R  A  N  H  S  A  F  L  F  G  F  G  D  G  G  G  G  P  T  Q  T  M
1418 TGGACCGCCTGAAGCGCCTGAGCAATACCGATGGGCTGCCCAGGGTGCAGCTATCTTCTCCAAGACAGCTCTTCTCAGCACTGGAGAGTGACTCAGAGCAGCTGTGCAC
 473 L  D  R  L  K  R  L  S  N  T  D  G  L  P  R  V  Q  L  S  S  P  R  Q  L  F  S  A  L  E  S  D  S  E  Q  L  C  T
1527 GTGGGTTGGGGAGCTCTTCTTGGAGCTGCACAATGGCACATACACCACCCATGCCCAGATCAAGAAGGGGAACCGGGAATGTGAGCCGGATCCTGCACGACGTGGAGCTG
 509 V  W  V  G  E  L  F  L  E  L  H  N  G  T  Y  T  T  H  A  Q  I  K  K  G  N  R  E  C  E  R  I  L  H  D  V  E  L
1636 CTCAGTAGCCCTGGCCCTGGCCCGCAGTGCCCAGTTCCTATACCCAGCAGCCCAGCTGCAGCACCTCTGGAGGCTCCTTCTTCTGAACCAGTTCCATGATGGTGACTG
 546 L  S  S  L  A  L  A  R  S  A  Q  F  L  Y  P  A  A  Q  L  Q  H  L  W  R  L  L  L  L  N  Q  F  H  D  V  V  T
1745 GAAGCTGCATCCAGATGGTGGCAGAGGAAGCCATGTGCCATTATGAAGACATCCGTTCCCATGGCAATACACTGCTCAGCGCTGCAGCCGCAGCCCTGTGTGCTGGGGA
 582 G  S  C  I  Q  M  V  A  E  E  A  M  C  H  Y  E  D  I  R  S  H  G  N  T  L  L  S  A  A  A  A  A  L  C  A  G  E
1854 GCCAGGTCCTGAGGGCCTCCTCATCGTCAACACACTGCCCTGGAAGCGGATCGAAGTGATGGCCCTGCCCAAACCGGGCGGGGCCCACAGCCTAGCCCTGGTGACAGTG
 618 P  G  P  E  G  L  L  I  V  N  T  L  P  W  K  R  I  E  V  M  A  L  P  K  P  G  A  H  S  L  A  L  V  T  V
1963 CCCAGCATGGGCTATGCTCCTGTTCCTCCCCCCACCTCACTGCAGCCCCTGCTGCCCCAGCAGCCTGTGTTCGTAGTGCAAGAGACTGATGGCTCCGTGACTCTGGACA
 655 P  S  M  G  Y  A  P  V  P  P  P  T  S  L  Q  P  L  P  Q  Q  P  V  F  V  V  Q  E  T  D  G  S  V  T  L  D
2072 ATGGCATCATCCGAGTGAAGCTGGACCCCAACTGGTCGCCTGACCTCCTTGGTCCTGGTGGCCTCTGGCAGGGAGGCCATTGCTGAGGGCGCCGTGGGGAACCAGTTTGT
 691 N  G  I  I  R  V  K  L  D  P  T  G  R  L  T  S  L  V  L  V  A  S  G  R  E  A  I  A  E  G  A  V  G  N  Q  F  V
2181 GCTATTTGATGATGTCCCCCTTGTACTGGGATGCATGGGACGTCATGGACTACCACCTGGAGACACCGAAGCCTGTGCTGGGCCAGGCAGGGACCCTGGCAGTGGGCACC
 727 L  F  D  D  V  P  L  Y  W  D  A  W  D  V  M  D  Y  H  L  E  T  R  K  P  V  L  G  Q  A  G  T  L  A  V  G  T
2290 GAGGGCGGCCTGCGGGGCAGCGCCTGGTTCTTGCTACAGATCAGCCCCAACAGTCGGCTTAGCCAGGAGGTTGTGCTGGACGTTGGCTGCCCCTATGTCCGCTTCCACA
 764 E  G  G  L  R  G  S  A  W  F  L  L  Q  I  S  P  N  S  R  L  S  Q  E  V  V  L  D  V  G  C  P  Y  V  R  F  H
2399 CCGAGGTACACTGGCATGAGGCCCACAAGTTCCTGAAGGTGGAGTTCCCTGCTCGCGTGCGGAGTTCCCAGGCCACCTATGAGATCCAGTTTGGGCACCTGCAGCGACC
 800 T  E  V  H  W  H  E  A  H  K  F  L  K  V  E  F  P  A  R  V  R  S  S  Q  A  T  Y  E  I  Q  F  G  H  L  Q  R  P
2508 TACCCACTACAATACCTCTTGGGACTGGGCTCGATTTGAGGTGTGGGCCCATCGCTGGATGGATCTGTCAGAACACGGCTTTGGCTGGCCCTGCTCAACGACTGCAAG
 836 T  H  Y  N  T  S  W  D  W  A  R  F  E  V  W  A  H  R  W  M  D  L  S  E  H  G  F  G  L  A  L  L  N  D  C  K
2617 TATGCCGCGTCAGTGCGAGGCAGCATCCTCAGCCTCTCGCTCTTGCGGGCGCCTAAAGCCCCGGACGCTACTGCTGACACGGGCGCCACGAGTTCACCTATGCACTGA
 873 Y  G  A  S  V  R  G  S  I  L  S  L  S  L  L  R  A  P  K  A  P  D  A  T  A  D  T  G  R  H  E  F  I  Y  A  L
2726 TGCCGCACAAGGGCTCTTTCCAGGATGCTGGCGTTATCCAAGCTGCCTACAGCCTAAACTTCCCCCTGTTGGCTCTGCCAGCCCCCAGCCCAGCGCCCGCCACCTCCTG
 909 M  P  H  K  G  S  F  Q  D  A  G  V  I  Q  A  A  Y  S  L  N  F  P  L  L  A  L  P  A  P  S  P  A  P  A  T  S  W
2835 GAGTGCGTTTTCCGTGTCTTCACCCGCCGGTCGTATTGGAGACCGTCAAGCAGGCGGAGAGCAGCCCCAGCGCCGCTCGCTGGTCCTGAGGCCTGTATGAGCCCACGGC
 945 S  A  F  S  V  S  S  P  A  V  V  L  E  T  V  K  Q  A  E  S  S  P  Q  R  R  S  L  V  L  R  L  Y  E  A  H  G
2944 AGCCACGTGGACTGCTGGCTGCACTTGTCGCTGCCGGTTCAGGAGGCCATCCTCTGCGACTCTTGGAGCGACCAGACCCTGCTGGCCACTTGACTTCGGCACAACCGC
 982 S  H  V  D  C  W  L  H  L  S  L  P  V  Q  E  A  I  L  C  D  L  L  E  R  P  D  P  A  G  H  L  T  S  G  Q  P
3053 CTGAAGCTCACCTTTTCTCCCTTCCAAGTGCTGTCCCTGTTGCTCGTGCTTCAGCCTCCGCCACACTGAGTCCCTGGGGCTGGGGTTTTGTTTGTAGAAGGCTCTGGGG
1018 P  E  A  H  L  F  S  L  P  S  A  V  P  V  A  R  A  S  A  S  A  T  L  S  P  W  G  W  G  F  V  C  R  R  L  W  G
3162 ACTCCTAATTTCTGCTTCCCCAGCCTAA
1054 L  L  I  S  A  S  P  A
```

EXPRESSION OF CLASS 2 MANNOSIDASE AND CLASS III MANNOSIDASE IN LOWER EUKARYOTIC CELLS

CROSS REFERENCE TO RELATED APPLICATIONS

This application is a continuation-in-part of U.S. application Ser. No. 10/371,877, filed on Feb. 20, 2003, now issued U.S. Pat. No. 7,449,308 and which is incorporated herein by reference in its entirety.

STATEMENT OF FEDERALLY SPONSORED RESEARCH

This invention was made with government support under grant no. 70NANB2H3046 from the National Institute of Standards and Technology Advanced Technology Program (NIST-STP).

FIELD OF THE INVENTION

The present invention relates to the field of protein glycosylation in lower eukaryotes, specifically the introduction of a mannosidase enzyme having substrate specificity for hydrolysis of Manα1,3 and/or Manα1,6 glycosidic linkages. The present invention further relates to novel host cells comprising genes encoding a mannosidase enzyme and N-glycan or N-glycan-containing intermediates produced as a result of the hydrolysis.

BACKGROUND OF THE INVENTION

Glycosylation Pathways in Humans and Lower Eukaryotes

After DNA is transcribed and translated into a protein, further post-translational processing involves the attachment of sugar residues, a process known as glycosylation. Different organisms produce different glycosylation enzymes (glycosyltransferases and glycosidases), and have different substrates (nucleotide sugars) available, so that the glycosylation patterns as well as composition of the individual oligosaccharides, even of the same protein, will be different depending on the host system in which the particular protein is being expressed. Bacteria typically do not glycosylate proteins, and if so only in a very unspecific manner (Moens and Vanderleyden, 1997 *Arch Microbiol*. 168(3): 169-175). Lower eukaryotes such as filamentous fungi and yeast add primarily mannose and mannosylphosphate sugars. The resulting glycan is known as a "high-mannose" type glycan or a mannan. Plant cells and insect cells (such as Sf9 cells) glycosylate proteins in yet another way. By contrast, in higher eukaryotes such as humans, the nascent oligosaccharide side chain may be trimmed to remove several mannose residues and elongated with additional sugar residues that typically are not found in the N-glycans of lower eukaryotes. See, e.g., R. K. Bretthauer, et al. *Biotechnology and Applied Biochemistry*, 1999, 30, 193-200; W. Martinet, et al. *Biotechnology Letters*, 1998, 20, 1171-1177; S. Weikert, et al. *Nature Biotechnology*, 1999, 17, 1116-1121; M. Malissard, et al. *Biochemical and Biophysical Research Communications*, 2000, 267, 169-173; Jarvis, et al., *Current Opinion in Biotechnology*, 1998, 9:528-533; and M. Takeuchi, 1 *Trends in Glycoscience and Glycotechnology*, 1997, 9, S29-S35.

Synthesis of a mammalian-type oligosaccharide structure begins with a set of sequential reactions in the course of which sugar residues are added and removed while the protein moves along the secretory pathway in the host organism. The enzymes which reside along the glycosylation pathway of the host organism or cell determine the resulting glycosylation patterns of secreted proteins. Thus, the resulting glycosylation pattern of proteins expressed in lower eukaryotic host cells differs substantially from the glycosylation pattern of proteins expressed in higher eukaryotes such as humans and other mammals (Bretthauer, 1999). The structure of a typical fungal N-glycan is shown in FIG. 1A.

The early steps of human glycosylation can be divided into at least two different phases: (i) lipid-linked $Glc_3Man_9GlcNAc_2$ oligosaccharides, are assembled by a sequential set of reactions at the membrane of the endoplasmic reticulum (ER) and (ii) the transfer of this oligosaccharide from the lipid anchor dolichyl pyrophosphate onto de novo synthesized protein. The site of the specific transfer is defined by an asparagine (Asn) residue in the sequence Asn-Xaa-Ser/Thr where Xaa can be any amino acid except proline (Gavel and von Heijne, 1990 *Protein Eng*. 3:433-42). Further processing by glucosidases and mannosidases occurs in the ER before the nascent glycoprotein is transferred to the early Golgi apparatus, where additional mannose residues are removed by Golgi specific alpha (α-1,2-) mannosidases. Processing continues as the protein proceeds through the Golgi. In the medial Golgi, a number of modifying enzymes, including N-acetylglucosaminyl Transferases (GnTI, GnTII, GnTIII, GnTIV and GnTV), mannosidase II and fucosyltransferases, add and remove specific sugar residues. Finally, in the trans-Golgi, galactosyltranferases (GalT) and sialyltransferases (ST) produce a glycoprotein structure that is released from the Golgi. It is this structure, characterized by bi-, tri- and tetra-antennary structures, containing galactose, fucose, N-acetylglucosamine and a high degree of terminal sialic acid, that gives glycoproteins their human characteristics. The structure of a typical human N-glycan is shown in FIG. 1B.

In nearly all eukaryotes, glycoproteins are derived from a common lipid-linked oligosaccharide precursor $Glc_3Man_9GlcNAc_2$-dolichol-pyrophosphate. Within the endoplasmic reticulum, synthesis and processing of dolichol pyrophosphate bound oligosaccharides are identical between all known eukaryotes. However, further processing of the core oligosaccharide by fungal cells, e.g., yeast, once it has been transferred to a peptide leaving the ER and entering the Golgi, differs significantly from humans as it moves along the secretory pathway and involves the addition of several mannose sugars.

In yeast, these steps are catalyzed by Golgi residing mannosyl-transferases, like Och1p, Mnt1p and Mnn1p, which sequentially add mannose sugars to the core oligosaccharide. The resulting structure is undesirable for the production of human-like proteins and it is thus desirable to reduce or eliminate mannosyltransferase activity. Mutants of *S. cerevisiae*, deficient in mannosyl-transferase activity (for example och1 or mnn9 mutants) have been shown to be non-lethal and display reduced mannose content in the oligosaccharide of yeast glycoproteins, thus more closely resembling oligosaccharides of higher eukaryotes.

Sugar Nucleotide Precursors

The N-glycans of animal glycoproteins typically include galactose, fucose, and terminal sialic acid. These sugars are not found on glycoprofeins produced in yeast and filamentous fungi. In humans, the full range of nucleotide sugar precursors (e.g. UDP-N-acetylglucosamine, UDP-N-acetylgalactosamine, CMP-N-acetylneuraminic acid, UDP-galactose, GDP-fucose, etc.) are synthesized in the cytosol and transported into the Golgi, where they are attached to the core oligosaccharide by glycosyltransferases. (Sommers and Hirschberg, 1981 *J. Cell Biol.* 91(2): A406-A406; Sommers and Hirschberg 1982 *J. Biol. Chem.* 257(18): 811-817; Perez and Hirschberg 1987 *Methods in Enzymology* 138: 709-715).

Glycosyl transfer reactions typically yield a side product which is a nucleoside diphosphate or monophosphate. While monophosphates can be directly exported in exchange for nucleoside triphosphate sugars by an antiport mechanism, diphosphonucleosides (e.g. GDP) have to be cleaved by phosphatases (e.g. GDPase) to yield nucleoside monophosphates and inorganic phosphate prior to being exported. This reaction is important for efficient glycosylation; for example, GDPase from *Saccharomyces cerevisiae* (*S. cerevisiae*) has been found to be necessary for mannosylation. However that GDPase has 90% reduced activity toward UDP (Berninsone et al., 1994 *J. Biol. Chem.* 269(1):207-211). Lower eukaryotes typically lack UDP-specific diphosphatase activity in the Golgi since they do not utilize UDP-sugar precursors for Golgi-based glycoprotein synthesis. *Schizosaccharomyces pombe*, a yeast found to add galactose residues to cell wall polysaccharides (from UDP-galactose) has been found to have specific UDPase activity, indicating the potential requirement for such an enzyme (Berninsone et al. (1994) *J. Biol. Chem.* 269(1):207-211). UDP is known to be a potent inhibitor of glycosyltransferases and the removal of this glycosylation side product may be important to prevent glycosyltransferase inhibition in the lumen of the Golgi (Khatara et al., 1974). See Berninsone, P., et al. 1995. *J Biol. Chem.* 270(24): 14564-14567; Beaudet, L., et al. 1998 *Abc Transporters: Biochemical, Cellular, and Molecular Aspects.* 292: 397-413.

Sequential Processing of N-glycans by Compartmentalized Enzyme Activities

Sugar transferases and glycosidases (e.g., mannosidases) line the inner (luminal) surface of the ER and Golgi apparatus and thereby provide a "catalytic" surface that allows for the sequential processing of glycoproteins as they proceed through the ER and Golgi network. The multiple compartments of the cis, medial, and trans Golgi and the trans-Golgi Network (TGN), provide the different localities in which the ordered sequence of glycosylation reactions can take place. As a glycoprotein proceeds from synthesis in the ER to full maturation in the late Golgi or TGN, it is sequentially exposed to different glycosidases, mannosidases and glycosyltransferases such that a specific carbohydrate structure may be synthesized. Much work has been dedicated to revealing the exact mechanism by which these enzymes are retained and anchored to their respective organelle. The evolving picture is complex but evidence suggests that stem region, membrane spanning region and cytoplasmic tail, individually or in concert, direct enzymes to the membrane of individual organelles and thereby localize the associated catalytic domain to that locus (see, e.g., Gleeson, P. A. (1998) *Histochem. Cell Biol.* 109, 517-532).

In some cases, these specific interactions were found to function across species. For example, the membrane spanning domain of α2,6-ST from rats, an enzyme known to localize in the trans-Golgi of the animal, was shown to also localize a reporter gene (invertase) in the yeast Golgi (Schwientek et al. (1995) *J. Biol. Chem.* 270(10):5483-9). However, the very same membrane spanning domain as part of a full-length α2,6-ST was retained in the ER and not further transported to the Golgi of yeast (Krezdom et al. (1994) *Eur. J. Biochem.* 220(3):809-17). A full length GalT from humans was not even synthesized in yeast, despite demonstrably high transcription levels. In contrast, the transmembrane region of the same human GalT fused to an invertase reporter was able to direct localization to the yeast Golgi, albeit at low production levels. Schwientek and co-workers have shown that fusing 28 amino acids of a yeast mannosyltransferase (MNT1), a region containing a cytoplasmic tail, a transmembrane region and eight amino acids of the stem region, to the catalytic domain of human GalT are sufficient for Golgi localization of an active GalT. Other galactosyltransferases appear to rely on interactions with enzymes resident in particular organelles because, after removal of their transmembrane region, they are still able to localize properly.

Improper localization of a glycosylation enzyme may prevent proper functioning of the enzyme in the pathway. For example, *Aspergillus nidulans*, which has numerous α-1,2-mannosidases (Eades and Hintz, 2000 *Gene* 255(1):25-34), does not add GlcNAc to $Man_5GlcNAc_2$ when transformed with the rabbit GnTI gene, despite a high overall level of GnTI activity (Kalsner et al. (1995) *Glycoconj. J.* 12(3):360-370). GnTI, although actively expressed, may be incorrectly localized such that the enzyme is not in contact with both of its substrates: UDP-GlcNAc and a productive $Man_5GlcNAc_2$ substrate (not all $Man_5GlcNAc_2$ structures are productive; see below). Alternatively, the host organism may not provide an adequate level of UDP-GlcNAc in the Golgi or the enzyme may be properly localized but nevertheless inactive in its new environment. In addition, $Man_5GlcNAc_2$ structures present in the host cell may differ in structure from $Man_5GlcNAc_2$ found in mammals. Maras and coworkers found that about one third of the N-glycans from cellobiohydrolase I (CBHI) obtained from *T. reesei* can be trimmed to $Man_5GlcNAc_2$ by *A. saitoi* 1,2 mannosidase in vitro. Fewer than 1% of those N-glycans, however, could serve as a productive substrate for GnTI. Maras et al., 1997, *Eur. J. Biochem.* 249, 701-707. The mere presence of $Man_5GlcNAc_2$, therefore, does not assure that further in vivo processing of $Man_5GlcNAc_2$ can be achieved. It is formation of a productive, GnTI-reactive $Man_5GlcNAc_2$ structure that is required. Although $Man_5GlcNAc_2$ could be produced in the cell (about 27 mol %), only a small fraction could be converted to $Man_5GlcNAc_2$ (less than about 5%, see Chiba WO 01/14522).

To date, there is no reliable way of predicting whether a particular heterologously expressed glycosyltransferase or mannosidase in a lower eukaryote will be (1) sufficiently translated, (2) catalytically active or (3) located to the proper organelle within the secretory pathway. Because all three of these are necessary to affect glycosylation patterns in lower eukaryotes, a systematic scheme to achieve the desired catalytic function and proper retention of enzymes in the absence of predictive tools, which are currently not available, would be desirable.

Production of Therapeutic Glycoproteins

A significant number of proteins isolated from humans or animals are post-translationally modified, with glycosylation being one of the most significant modifications. An estimated 70% of all therapeutic proteins are glycosylated and thus currently rely on a production system (i.e., host cell) that is able to glycosylate in a manner similar to humans. Several studies have shown that glycosylation plays an important role in determining the (1) immunogenicity, (2) pharmacokinetic properties, (3) trafficking and (4) efficacy of therapeutic proteins. It is thus not surprising that substantial efforts by the pharmaceutical industry have been directed at developing processes to obtain glycoproteins that are as "humanoid" or "human-like" as possible. To date, most glycoproteins are made in a mammalian host system. This may involve the genetic engineering of such mammalian cells to enhance the degree of sialylation (i.e., terminal addition of sialic acid) of proteins expressed by the cells, which is known to improve pharmacokinetic properties of such proteins. Alternatively, one may improve the degree of sialylation by in vitro addition of such sugars using known glycosyltransferases and their respective nucleotide sugars (e.g., 2,3-sialyltransferase and CMP-sialic acid).

While most higher eukaryotes carry out glycosylation reactions that are similar to those found in humans, recombinant human proteins expressed in the above mentioned host systems invariably differ from their "natural" human counterpart (Raju et al. (2000) *Glycobiology* 10(5): 477-486). Extensive development work has thus been directed at finding ways to improve the "human character" of proteins made in these expression systems. This includes the optimization of fermentation conditions and the genetic modification of protein expression hosts by introducing genes encoding enzymes involved in the formation of human-like glycoforms. Goochee et al. (1999) *Biotechnology* 9(12):1347-55; Andersen and Goochee (1994) *Curr Opin Biotechnol*. 5(5):546-49; Werner et al. (1998) *Arzneimittelforschung*. 48(8):870-80; Weikert et al. (1999) *Nat Biotechnol*. 17(11):1116-21; Yang and Butler (2000) *Biotech. Bioeng*. 68:370-80. Inherent problems associated with all mammalian expression systems have not been solved.

Glycoprotein Production Using Eukaryotic Microorganisms

Although the core oligosaccharide structure transferred to a protein in the endoplasmic reticulum is basically identical in mammals and lower eukaryotes, substantial differences have been found in the subsequent processing reactions which occur in the Golgi apparatus of fungi and mammals. In fact, even amongst different lower eukaryotes there exist a great variety of glycosylation structures. This has historically prevented the use of lower eukaryotes as hosts for the production of recombinant human glycoproteins despite otherwise notable advantages over mammalian expression systems.

Therapeutic glycoproteins produced in a microorganism host such as yeast utilizing the endogenous host glycosylation pathway differ structurally from those produced in mammalian cells and typically show greatly reduced therapeutic efficacy. Such glycoproteins are typically immunogenic in humans and show a reduced half-life (and thus bioactivity) in vivo after administration (Takeuchi (1997) *Trends in Glycoscience and Glycotechnology* 9, S29-S35). Specific receptors in humans and animals (i.e., macrophage mannose receptors) can recognize terminal mannose residues and promote the rapid clearance of the foreign glycoprotein from the bloodstream. Additional adverse effects may include changes in protein folding, solubility, susceptibility to proteases, trafficking, transport, compartmentalization, secretion, recognition by other proteins or factors, antigenicity, or allergenicity.

Yeast and filamentous fungi have both been successfully used for the production of recombinant proteins, both intracellular and secreted (Cereghino, J. L. and J. M. Cregg 2000 *FEMS Microbiology Reviews* 24(1): 45-66; Harkki, A., et al. 1989 *Bio-Technology* 7(6): 596; Berka, R. M., et al. 1992 *Abstr. Papers Amer. Chem. Soc*. 203: 121-BIOT; Svetina, M., et al. 2000 *J. Biotechnol*. 76(2-3): 245-251). Various yeasts, such as *K. lactis, Pichia pastoris, Pichia methanolica*, and *Hansenula polymorpha*, have played particularly important roles as eukaryotic expression systems because they are able to grow to high cell densities and secrete large quantities of recombinant protein. Likewise, filamentous fungi, such as *Aspergillus niger, Fusarium* sp, *Neurospora crassa* and others, have been used to efficiently produce glycoproteins at the industrial scale. However, as noted above, glycoproteins expressed in any of these eukaryotic microorganisms differ substantially in N-glycan structure from those in animals. This has prevented the use of yeast or filamentous fungi as hosts for the production of many therapeutic glycoproteins.

Although glycosylation in yeast and fungi is very different than in humans, some common elements are shared. The first step, the transfer of the core oligosaccharide structure to the nascent protein, is highly conserved in all eukaryotes including yeast, fungi, plants and humans (compare FIGS. 1A and 1B). Subsequent processing of the core oligosaccharide, however, differs significantly in yeast and involves the addition of several mannose sugars. This step is catalyzed by mannosyltransferases residing in the Golgi (e.g. OCH1, MNT1, MNN1, etc.), which sequentially add mannose sugars to the core oligosaccharide. The resulting structure is undesirable for the production of humanoid proteins and it is thus desirable to reduce or eliminate mannosyltransferase activity. Mutants of *S. cerevisiae* deficient in mannosyltransferase activity (e.g. och1 or mnn9 mutants) have shown to be nonlethal and display a reduced mannose content in the oligosaccharide of yeast glycoproteins. Other oligosaccharide processing enzymes, such as mannosylphosphate transferases, may also have to be eliminated depending on the host's particular endogenous glycosylation pattern. After reducing undesired endogenous glycosylation reactions, the formation of complex N-glycans has to be engineered into the host system. This requires the stable expression of several enzymes and sugar-nucleotide transporters. Moreover, one has to localize these enzymes so that a sequential processing of the maturing glycosylation structure is ensured.

Several efforts have been made to modify the glycosylation pathways of eukaryotic microorganisms to provide glycoproteins more suitable for use as mammalian therapeutic agents. For example, several glycosyltransferases have been separately cloned and expressed in *S. cerevisiae* (GalT, GnTI), *Aspergillus nidulans* (GnTI) and other fungi (Yoshida et al. (1999) *Glycobiology* 9(1):53-8, Kalsner et al. (1995) *Glycoconj. J*. 12(3):360-370). However, N-glycans resembling those made in human cells were not obtained.

Yeasts produce a variety of mannosyltransferases (e.g., 1,3-mannosyltransferases such as MNN1 in *S. cerevisiae*; Graham and Emr, 1991 *J. Cell. Biol*. 114(2):207-218), 1,2-mannosyltransferases (e.g. KTR/KRE family from *S. cerevisiae*), 1,6-mannosyltransferases (e.g., OCH1 from *S. cerevisiae*), mannosylphosphate transferases and their regulators (e.g., MNN4 and MNN6 from *S. cerevisiae*) and additional enzymes that are involved in endogenous glycosylation reactions. Many of these genes have been deleted individually giving rise to viable organisms having altered glycosylation profiles. Examples are shown in Table 1.

TABLE 1

Examples of yeast strains having altered mannosylation

| Strain | N-glycan (wild type) | Mutation | N-glycan (mutant) | Reference |
|---|---|---|---|---|
| S. pombe | Man$_{>9}$GlcNAc$_2$ | OCH1 | Man$_8$GlcNAc$_2$ | Yoko-o et al., 2001 FEBS Lett. 489(1): 75-80 |
| S. cerevisiae | Man$_{>9}$GlcNAc$_2$ | OCH1/MNN1 | Man$_8$GlcNAc$_2$ | Nakanishi-Shindo et al., 1993 J. Biol. Chem. 268(35): 26338-26345 |
| S. cerevisiae | Man$_{>9}$GlcNAc$_2$ | OCH1/MNN1/MNN4 | Man$_8$GlcNAc$_2$ | Chiba et al., 1998 J. Biol. Chem. 273, 26298-26304 |
| P. pastoris | Hyperglycosylated | OCH1 (complete deletion) | Not hyperglycosylated | Welfide, Japanese Application Publication No. 8-336387 |
| P. pastoris | Man$_{>8}$GlcNAc$_2$ | OCH1 (disruption) | Man$_{>8}$GlcNAc$_2$ | Contreras et al. WO 02/00856 A2 |

Japanese Patent Application Publication No. 8-336387 discloses the deletion of an OCH1 homolog in *Pichia pastoris*. In *S. cerevisiae*, OCH1 encodes a 1,6-mannosyltransferase, which adds a mannose to the glycan structure Man$_8$GlcNAc$_2$ to yield Man$_9$GlcNAc$_2$. The Man$_9$GlcNAc$_2$ structure, which contains three 1,6 mannose residues, is then a substrate for further 1,2-, 1,6-, and 1,3-mannosyltransferases in vivo, leading to the hypermannosylated glycoproteins that are characteristic for *S. cerevisiae* and which typically may have 30-40 mannose residues per N-glycan. Because the Och1p initiates the transfer of 1,6 mannose to the Man$_8$GlcNAc$_2$ core, it is often referred to as the "initiating 1,6 mannosyltransferase" to distinguish it from other 1,6 mannosyltransferases acting later in the Golgi. In an och1 mnn1 mnn4 mutant strain of *S. cerevisiae*, proteins glycosylated with Man$_8$GlcNAc$_2$ accumulate and hypermannosylation does not occur. However, Man$_8$GlcNAc$_2$ is not a substrate for mammalian glycosyltransferases, such as human UDP-GlcNAc transferase I, and accordingly, the use of that mutant strain, in itself, is not useful for producing mammalian-like proteins, i.e., with complex or hybrid glycosylation patterns.

One can trim Man$_8$GlcNAc$_2$ structures to a Man$_5$GlcNAc$_2$ isomer in *S. cerevisiae* (although high efficiency trimming greater than 50% in vivo has yet to be demonstrated) by engineering a fungal mannosidase from *A. saitoi* into the endoplasmic reticulum (ER). The shortcomings of this approach are two-fold: (1) it is not clear whether the Man$_5$GlcNAc$_2$ structures formed are in fact formed in vivo (rather than having been secreted and further modified by mannosidases outside the cell); and (2) it is not clear whether any Man$_5$GlcNAc$_2$ structures formed, if in fact formed in vivo, are the correct isoform to be a productive substrate for subsequent N-glycan modification by GlcNAc transferase I (Maras et al., 1997, *Eur. J. Biochem.* 249, 701-707).

With the objective of providing a more humanlike glycoprotein derived from a fungal host, U.S. Pat. No. 5,834,251 discloses a method for producing a hybrid glycoprotein derived from *Trichoderma reseei*. A hybrid N-glycan has only mannose residues on the Manα1-6 arm of the core mannose structure and one or two complex antennae on the Manα1-3 arm. While this structure has utility, the method has the disadvantage that numerous enzymatic steps must be performed in vitro, which is costly and time-consuming. Isolated enzymes are expensive to prepare and need costly substrates (e.g. UDP-GlcNAc). The method also does not allow for the production of complex glycans on a desired protein.

Intracellular Mannosidase Activity Involved in N-Glycan Trimming

Alpha-1,2-mannosidase activity is required for the trimming of Man$_8$GlcNAc$_2$ to form Man$_5$GlcNAc$_2$, which is a major intermediate for complex N-glycan formation in mammals. Previous work has shown that truncated murine, fungal and human α-1,2-mannosidase can be expressed in the methylotropic yeast *P. pastoris* and display Man$_8$GlcNAc$_2$ to Man$_5$GlcNAc$_2$ trimming activity (Lal et al., *Glycobiology* 1998 October; 8(10):981-95; Tremblay et al., *Glycobiology* 1998 June; 8(6):585-95, Callewaert et al. (2001) *FEBS Lett.* 503(2-3):173-8). However, to date, no reports exist that show the high level in vivo trimming of Man$_8$GlcNAc$_2$ to Man$_5$GlcNAc$_2$ on a secreted glycoprotein from *P. pastoris*.

Moreover, the mere presence of an α-1,2-mannosidase in the cell does not, by itself, ensure proper intracellular trimming of Man$_8$GlcNAc$_2$ to Man$_5$GlcNAc$_2$. (See, e.g., Contreras et al. WO 02/00856 A2, in which an HDEL tagged mannosidase of *T. reesei* is localized primarily in the ER and co-expressed with an influenza haemagglutinin (HA) reporter protein on which virtually no Man$_5$GlcNAc$_2$ could be detected. See also Chiba et al. (1998) *J. Biol. Chem.* 273(41): 26298-26304, in which a chimeric α-1,2-mannosidase/Och1p transmembrane domain fusion localized in the ER, early Golgi and cytosol of *S. cerevisiae*, had no mannosidase trimming activity). Accordingly, mere localization of a mannosidase in the ER or Golgi is insufficient to ensure activity of the respective enzyme in that targeted organelle. (See also, Martinet et al. (1998) *Biotech. Letters* 20(12): 1171-1177, showing that α-1,2-mannosidase from *T. reesei*, while localizing intracellularly, increased rather than decreased the extent of mannosylation). To date, there is no report that demonstrates the intracellular localization of an active heterologous α-1,2-mannosidase in either yeast or fungi using a transmembrane localization sequence.

While it is useful to engineer strains that are able to produce Man$_5$GlcNAc$_2$ as the primary N-glycan structure, any attempt to further modify these high mannose precursor structures to more closely resemble human glycans requires additional in vivo or in vitro steps. Methods to further humanize glycans from fungal and yeast sources in vitro are described in U.S. Pat. No. 5,834,251 (supra). If Man$_5$GlcNAc$_2$ is to be further humanized in vivo, one has to ensure that the generated $Man_5GlcNAc_2$ structures are, in fact, generated intracellularly and not the product of mannosidase activity in the medium. Complex N-glycan formation in yeast or fungi will require high levels of $Man_5GlcNAc_2$ to be generated within the cell because only intracellular $Man_5GlcNAc_2$ glycans can be further processed to hybrid and complex N-glycans in vivo. In addition, one has to demonstrate that the majority of $Man_5GlcNAc_2$ structures generated are in fact a substrate for GnTI and thus allow the formation of hybrid and complex N-glycans.

Accordingly, the need exists for methods to produce glycoproteins characterized by a high intracellular $Man_5GlcNAc_2$ content which can be further processed into human-like glycoprotein structures in non-human eukaryotic host cells, and particularly in yeast and filamentous fungi.

Class 2 Mannosidases

A number of class 2 mannosidases of have been purified and characterized: mouse mannosidase II, human mannosidase II and Drosophila mannosidase II (FIG. 24 shows a phylogenetic tree of the classes of mannosidases). It has been found that Class 2 mannosidase enzymes are responsible for the hydrolysis of α1,3 and α1,6 mannose glycosidic linkages on N-linked oligosaccharides generally localized in the Golgi. At least five types of Class 2 mannosidases have been identified, namely: (1) Golgi α-mannosidase II; (2) Golgi α-mannosidase IIx; (3) lysosomal α-mannosidase; (4) cytosolic α-mannosidase; and (5) an enzyme characterized from mouse and pig sperm or epididymal tissues. Moremen K. W., *Biochimica Biophysica Acta* 1573 (2002) 225-235.

Human congenital dyserythropoietic anemia type II has been associated with the lack of functional α-mannosidase II gene as exhibited in mice. Chui et al. *Cell* 1997 July 11; 90(1):157-67. This genetic defect is referred to as HEMPAS (hereditary erythroblastic multinuclearity with positive acidified serum lysis test), and further research is underway to study the role of α-mannosidase II. For example, a mutation of a single gene encoding α-mannosidase II has been shown to result in a systemic autoimmune disease similar to human systemic lupus erythematosis. Chui et al., *Proc. Natl. Acad. Sci. USA* 2001 98:1142-1147.

The importance of the enzymatic activity in glycoprotein formation has been well-established; however, efficient expression of such activity for the production of therapeutic glycoproteins has not been accomplished in lower eukaryotic cells.

(1) Golgi α-Mannosidase II

The Golgi α-mannosidase II (EC. 3.2.1.114) is a Type II transmembrane protein, approximately 125 kDa in size, composed of a short N-terminal cytoplasmic tail, a single-span transmembrane domain connected by a stalk segment to a large luminal C-terminal catalytic portion. Moremen and Touster, *J. Biol. Chem.*, 260, 6654-6662; Moremen and Touster, *J. Biol. Chem.*, 261, 10945-10951. The function of the mannosidase II is essential in the processing of N-glycans in the secretory pathway. In mammalian cells, it has been established that this particular enzyme hydrolyzes the Manα1,3 and Manα1,6 glycosidic linkages on the substrate $GlcNAcMan_5GlcNAc_2$. Subsequent N-glycan processing is catalyzed by other glycosylation enzymes (e.g. N-acetylglucosaminyltransferases, galactosyltransferases, sialyltransferases) to produce the desired glycoforms with their substrates (UDP-GlcNAc, UDP-GalNAc, CMP-Sialic acid) and their respective transporters. See, e.g., WO 02/00879, which is incorporated by reference herein in its entirety.

A partial clone encoding the Golgi α-mannosidase II has been isolated from a rat liver λgt11 cDNA library. Moremen, K W. *Proc. Natl. Acad. Sci. USA* 1989 July; 86(14):5276-80. The mouse Golgi α-mannosidase II and the human α-mannosidase II have also been characterized and expressed in COS cells. Moremen and Robbins, *J. Cell. Biol.* 1991 December; 115(6):1521-34. Research conducted on Golgi α-mannosidase II enzyme shows that there is considerable similarity within the C-terminal domain of this class of enzyme. In addition, substrate specificity studies show that the hydrolysis of the α1,3 and/or α1,6 glycosidic linkages by the Golgi α-mannosidase II enzyme requires a terminal GlcNAc on the oligosaccharide substrate.

The *Drosophila melangaster* Golgi α-mannosidase II has been isolated using the murine Golgi α-mannosidase II cDNA and is shown to have considerable similarity to regions from other α-mannosidases. Foster et al. *Gene* 154 (1995) 183-186. Previous work has shown that the Drosophila and mouse cDNA sequences translate amino acid sequences of 41% identity and 61% similarity. Expression of the *Drosophila* Golgi α-mannosidase II sequence in CHOP cells (CHO cells stably expressing polyoma large T-antigen) was shown to be active and was also shown to localize mainly in the Golgi apparatus. Rabouille et al. *J. Cell. Sci.* 1999 October; 112 (Pt 19):3319-30.

(2) Golgi α-Mannosidase IIx

The gene encoding the human α-mannosidase IIx (α-mannosidase II isotype) has been characterized. Ogawa et al. *Eur. J. Biochem.* 242, 446-453 (1996). Overexpression of the α-mannosidase IIx enzyme leads to the conversion of $Man_6GlcNAc_2$ to $Man_4GlcNAc_2$ in CHO cells. Oh-eda et al. *Eur. J. Biochem.* 268, 1280-1288 (2001). The two types of mannosidases (II and IIx) are closely related to the processing of N-glycans in the Golgi. This Golgi α-mannosidase IIx has 66% identity to α-mannosidase II and has similar catalytic activity of hydrolyzing the Manα1,6 and Manα1,3 of the $Man_6GlcNAc_2$ oligosaccharide. More recent studies revealed an obvious phenotype of infertility in α-mannosidase IIx-deficient male mice. *Biochim Biophys Acta*. 2002 Dec. 19; 1573(3):382-7. One study found that α-mannosidase IIx-deficient mouse testis showed reduced levels of GlcNAc-terminated complex type N-glycans.

(3) Lysosomal α-Mannosidase

Another type of Class 2 mannosidase is found in the lysosome of eukaryotic cells and is involved in glycoprotein catabolism (breakdown). Unlike the Golgi mannosidase II enzyme, which has a neutral pH optimum, the lysosomal mannosidase II has a low pH optimum (pH 4.5), has broad natural substrate specificity, is active toward the synthetic substrate p-nitrophenyl-α-mannosidase and is sensitive to inhibition by swainsonine. Daniel et al., (1994) *Glycobiology* 4, 551-566; Moremen et al., (1994) *Glycobiology* 4, 113-125. Structurally, the lysosomal α-mannosidase has an N-terminal signal sequence in place of the cytoplasmic tail, transmembrane domain, and stem region of the Golgi enzyme. Moremen, K. W., *Biochimica Biophysica Acta* 1573 (2002) 225-235. The human lysosomal α-mannosidase (EC 3.2.1.24) has been cloned and expressed in *Pichia pastoris*. Liao et al., *J Biol Chem* 1996 Nov. 8; 271(45):28348-58. Based on regions of amino acid sequence conservation between the lysosomal α-mannosidase from *Dictyostelium discoideum* and the murine Golgi α-mannosidase II (a glycoprotein that processes α1,3/1,6-mannosidase activity) a cDNA encoding the murine lysosomal α-mannosidase was cloned. Merkle et al., *Biochim Biophys Acta* 1997 Aug. 29; 1336(2):132-46. A deficiency in the lysosomal α-mannosidase results in a human genetic disease termed α-mannosidosis.

(4) Cytosolic α-Mannosidase

The cytosolic α-mannosidase II is less-similar to the other Class 2 mannosidases and appears to prefer $Co^{2+}$ over $Zn^{2+}$ for catalytic activity. Moremen, K. W., *Biochimica Biophysica Acta* 1573 (2002) 225-235. Like the lysosomal α-mannosidase II, it is involved in the catabolism of glycoproteins. The cytosolic α-mannosidase II catabolizes the improperly folded glycoproteins in the lumen of the ER that have been retro-translocated into the cytoplasm for proteolytic disposal. Duvet et al., *Biochem. J.* 335 (1998) 389-396; Grard et al., *Biochem. J.* 316 (1996) 787-792. Structurally, this enzyme has no cleavable signal sequence or transmembrane domain.

Additional mannosidases that exhibit characteristics of Class 2 mannosidases have been described but have yet to be cloned for direct comparision by sequence alignment. Moremen, K. W., *Biochimica Biophysica Acta* 1573 (2002) 225-235.

Class III Mannosidases

Class III mannosidases, which are also involved in trimming of the Manα1,3 and Manα1,6 glycosidic linkages of an oligosaccharide, e.g. converting $Man_5GlcNAc_2$ to $Man_3GlcNAc_2$, have been recently cloned and identified. To date only two members of this class of proteins are known. The first member identified was from an anemic mouse that was deficient in the classic Golgi mannosidase II activity but possessed an alternative mechanism for converting $Man_5GlcNAc_2$ directly to $Man_3GlcNAc_2$, which was independent of the presence of GlcNAc on the core mannose-1,3 branch (D. Chui, et al. *Cell* 1997 90:157-167). This class III mannosidase has yet to be cloned but a protein with similar activity has been cloned from Sf9 cells (Z. Kawar, et al. *J. Biol. Chem.* 2001 276(19):16335-16340). The only member of the class III mannosidases to be cloned and characterized originates from lepidopteran insect cell line Sf9 (D. Jarvis, et al. *Glycobiology* 1997 7:113-127). This Sf9 Golgi mannosidase III converts $Man_5GlcNAC_2$ to $Man_3GlcNAc_2$, and, unlike the Golgi mannosidase II, does not process $GlcNAcMan_5GlcNAc_2$. A unique feature of this class of mannosidases is that, in addition to possessing Manα1,3/1,6 activity, they also possess α-1,2 mannosidase activity like a class I Golgi mannosidase. Furthermore, like the Golgi mannosidase I enzymes, this Sf9 mannosidase III trims $Man_8GlcNAc_2$ more efficiently than $Man_9GlcNAc_2$.

Given the utility of the mannosidase enzyme activities in processing N-glycans, it would be desirable to have a method for producing human-like glycoproteins in lower eukaroytic host cells comprising the step of expressing a catalytically active α-mannosidase II having substrate specificity for Manα1,3 and Manα1,6 on an oligosaccharide.

SUMMARY OF THE INVENTION

The invention provides a method for producing a human-like glycoprotein in a lower eukaryotic host cell comprising the step of expressing a catalytically active fragment of a Class 2 or a Class III mannosidase enzyme.

One embodiment of the invention provides a method for producing a human-like glycoprotein in a lower eukaryotic host cell comprising the step of expressing in the cell a mannosidase enzymatic activity that is capable of hydrolyzing an oligosaccharide substrate comprising either or both a Manα1,3 and Manα1,6 glycosidic linkage to the extent that at least 10% of the Manα1,3 and/or Manα1,6 linkages of the substrate are hydrolyzed in vivo.

Another embodiment of the invention provides a method for producing a desired N-glycan in a lower eukaryotic host cell comprising the step of expressing in the cell a mannosidase enzymatic activity that is capable of hydrolyzing in vivo an oligosaccharide substrate comprising either or both a Manα1,3 and Manα1,6 glycosidic linkage wherein the desired N-glycan is produced within the host cell at a yield of at least 10 mole percent.

Preferably, the desired N-glycan produced is selected from the group consisting of $Man_3GlcNAc_2$, $GlcNAcMan_3GlcNAc_2$ and $Man_4GlcNAc_2$. In another preferred embodiment, the desired N-glycan is characterized as having at least the oligosaccharide branch Manα1,3 (Manα1,6) Manβ1,4-GlcNAc β1,4-GlcNAc β1-Asn. The glycoprotein is preferably isolated from the host cell. In yet another preferred embodiment, the mannosidase enzymatic activity is capable of hydrolyzing in vivo both Manα1,3 and Manα1,6 linkages of an oligosaccharide substrate comprising a Manα1,3 and Manα1,6 glycosidic linkage.

In another preferred embodiment, the oligosaccharide substrate is characterized as Manα1,3 (Manα1,6 Manα1,6) Manβ1,4-GlcNAc β1,4-GlcNAc-Asn; Manα1,3 (Manα1,3 Manα1,6) Manβ1,4-GlcNAc β1,4-GlcNAc-Asn; GlcNAcβ1,2 Manα1,3 (Manα1,6 Manα1,6) Manβ1,4-GlcNAc β1,4-GlcNAc-Asn; GlcNAcβ1,2 Manα1,3 (Manα1,3 Manα1,6) Manβ1,4-GlcNAc β1,4-GlcNAc-Asn; Manα1,3 (Manα1,3 Manα1,6 Manα1,6) Manβ1,4-GlcNAc β1,4-GlcNAc-Asn; GlcNAcβ1,2 Manα1,3 (Manα1,3 Manα1,6 Manα1,6) Manβ1,4-GlcNAc β1,4-GlcNAc-Asn; Manα1,2 Manα1,3 (Manα1,3 Manα1,6 Manα1,6) Manβ1,4-GlcNAc β1,4-GlcNAc-Asn; Manα1,2 Manα1,3 (Manα1,3 Manα1,6) Manβ1,4-GlcNAc β1,4-GlcNAc-Asn; Manα1,2 Manα1,3 (Manα1,6 Manα1,6) Manβ1,4-GlcNAc β1,4-GlcNAc-Asn or high mannan.

In a preferred embodiment, the mannosidase activity is characterized as a Class 2 mannosidase activity. In a more preferred embodiment, the Class 2 mannosidase activity has a substrate specificity for GlcNAcβ1,2 Manα1,3 (Manα1,6 Manα1,6) Manβ1,4-GlcNAc β1,4-GlcNAc-Asn; GlcNAcβ1,2 Manα1,3 (Manα1,3 Manα1,6) Manβ1,4-GlcNAc β1,4-GlcNAc-Asn; or GlcNAcβ1,2 Manα1,3 (Manα1,3 Manα1,6 Manα1,6) Manβ1,4-GlcNAc β1,4-GlcNAc-Asn. In an even more preferred embodiment, the Class 2 mannosidase activity is one which is normally found in the Golgi apparatus of a higher eukaryotic host cell.

In another preferred embodiment, the mannosidase activity is characterized as a Class IIx mannosidase activity. In a more preferred embodiment, the Class IIx mannosidase activity has a substrate specificity for Manα1,3 (Manα1,6 Manα1,6) Manβ1,4-GlcNAc β1,4-GlcNAc-Asn; Manα1,3 (Manα1,3 Manα1,6) Manβ1,4-GlcNAc β1,4-GlcNAc-Asn; or Manα1,2 Manα1,3 (Manα1,3 Manα1,6 Manα1,6) Manβ1,4-GlcNAc β1,4-GlcNAc-Asn.

In yet another preferred embodiment, the mannosidase activity is characterized as a Class III mannosidase activity. In a more preferred embodiment, the Class III mannosidase activity has a substrate specificity for (Manα1,6 Manα1,6) Manβ1,4-GlcNAc β1,4-GlcNAc-Asn; (Manα1,3 Manα1,6) Manβ1,4-GlcNAc β1,4-GlcNAc-Asn; or high mannans.

In any one of the above embodiments, the mannosidase activity is preferably overexpressed. In another preferred embodiment, the mannosidase is further capable of hydrolyzing a Manα1,2 linkage. The mannosidase activities of the invention preferably have a pH optimum of from about 5.0 to about 8.0.

In another embodiment the mannosidase activity is localized within the secretory pathway of the host cell. Preferably, the mannosidase activity is expressed from a polypeptide localized within at least one of the ER, Golgi apparatus or the trans golgi network of the host cell.

In one preferred embodiment, the mannosidase activity is expressed from a nucleic acid encoding a polypeptide comprising a mannosidase catalytic domain fused to a cellular targeting signal peptide. In a more preferred embodiment, the mannosidase activity is expressed from a nucleic acid comprising sequences that encode a mannosidase catalytic domain native to the host cell. In another more preferred embodiment, the mannosidase activity is expressed from a nucleic acid comprising sequences that encode a mannosidase catalytic domain heterologous to the host cell.

In another preferred embodiment, the mannosidase enzymatic activity is selected from the group consisting of β*Arabidopsis thaliana* Mannosidase II, *C. elegans* Mannosidase II, *Ciona intestinalis* mannosidase II, *Drosophila* mannosidase II, Human mannosidase II, Mouse mannosidase II, Rat mannosidase II, Human mannosidase IIx, Insect cell mannosidase III, Human lysosomal mannosidase II and Human cytoplasmic mannosidase II.

In another preferred embodiment, the polypeptide is expressed from a nucleic acid comprising sequences that encode a target peptide native to the host cell.

In another preferred embodiment, the polypeptide is expressed from a nucleic acid comprising sequences that encode a target peptide heterologous to the mannosidase catalytic domain.

In a preferred embodiment, the host cell is selected from the group consisting of *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum* and *Neurospora crassa*. In a more preferred embodiment, the host cell is *Pichia pastoris*.

The invention further provides glycoproteins and N-glycans produced by one of the above methods. In a preferred embodiment, the glycoprotein is a therapeutic protein. In a more preferred embodiment, the therapeutic protein is selected from the group consisting of erythropoietin, cytokines, coagulation factors, soluble IgE receptor α-chain, IgG, IgG fragments, IgM, interleukins, urokinase, chymase, urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, (α-1-antitrypsin and α-feto protein.

The invention further provides a nucleic acid library comprising at least two different genetic constructs, wherein at least one genetic construct comprises a nucleic acid fragment encoding a mannosidase class 2, IIx or III catalytic domain ligated in-frame with a nucleic acid fragment encoding a cellular targeting signal peptide which it is not normally associated with.

In a preferred embodiment, the mannosidase catalytic domain is selected from the group consisting of: *Arabidopsis thaliana* Mannosidase II, *C. elegans* Mannosidase II, *Ciona intestinalis* mannosidase II, *Drosophila* mannosidase II, Human mannosidase II, Mouse mannosidase II, Rat mannosidase II, Human mannosidase IIx, Insect cell mannosidase III, Human lysosomal mannosidase II and Human cytoplasmic mannosidase II.

In another preferred embodiment, the nucleic acid fragment encoding a cellular targeting peptide is selected from the group consisting of: *Saccharomyces* GLS1, *Saccharomyces* MNS1, *Saccharoniyces* SEC12, *Pichia* SEC, *Pichia* OCH1, *Saccharomyces* MNN9, *Saccharomyces* VAN1, *Saccharomyces* ANP1, *Saccharomyces* HOC1, *Saccharomyces* MNN10, *Saccharomyces* MNN11, *Saccharomyces* MNT1, *Pichia* D2, *Pichia* D9, *Pichia* J3, *Saccharomyces* KTR1, *Saccharomyces* KTR2, *Kluyveromyces* GnTI, *Saccharomyces* MNN2, *Saccharomyces* MNN5, *Saccharomyces* YUR1, *Saccharomyces* MNN1 and *Saccharomyces* MNN6.

Another embodiment of the invention provides a vector comprising a fusion construct derived from any one of the above libraries linked to an expression control sequence, wherein said cellular targeting signal peptide is targeted to at least one of the ER, Golgi or trans-Golgi network. In a more preferred embodiment, the expression control sequence is inducible or constitutive. In an even more preferred embodiment, the vector, upon expression in a host cell, encodes a mannosidase activity involved in producing GlcNAcMan$_3$GlcNAc$_2$ Man$_3$GlcNAc$_2$ or Man$_4$GlcNAc$_2$ in vivo.

Another embodiment of the invention provides a host cell comprising at least one of the above vectors. In more preferred embodiments, the vector is selected from the group of vectors designated pKD53, pKD1, pKD5, pKD6 and pKD16.

Another embodiment of the invention provides a chimeric polypeptide comprising a mannosidase catalytic domain fused in-frame to a targeting signal peptide and, upon expression in a lower eukaryotic host cell, capable of hydrolyzing in vivo an oligosaccharide substrate comprising either or both a Manα1,3 and Manα1,6 glycosidic linkage to the extent that at least 10% of the Manα1,3 and/or Manα1,6 linkages of the substrate are hydrolyzed in vivo.

Another embodiment of the invention provides a chimeric polypeptide comprising a mannosidase catalytic domain fused in-frame to a targeting signal peptide and, upon expression in a lower eukaryotic host cell, capable of hydrolyzing in vivo an oligosaccharide substrate comprising a Manα1,3, Manα1,6, or Manα1,2 glycosidic linkage to the extent that a detectable moiety of the Manα1,3, Manα1,6 or Manα1,2 linkage of the substrate is hydrolyzed in vivo.

Another embodiment of the invention provides a nucleic acid encoding the above chimeric polypeptide or a host cell comprising the above chimeric polypeptide.

Another embodiment of the invention provides a host cell comprising the above nucleic acid.

Another embodiment of the invention provides a glycoprotein produced in the above host cell. In a more preferred embodiment, an N-glycan produced in the host cell is provided. More preferably, the glycoprotein is characterized as uniform.

Another embodiment of the invention provides an isolated polynucleotide comprising or consisting of a nucleic acid sequence selected from the group consisting of the conserved regions SEQ ID NO: 5-SEQ ID NO: 15.

BRIEF DESCRIPTION OF THE DRAWINGS

FIG. 2A diagrams the insertion of a targeting peptide fragment into pCR2.1-TOPO (Invitrogen, Carlsbad, Calif.). FIG. 2B shows the generated targeting peptide sub-library having restriction sites NotI-AscI. FIG. 2C diagrams the insertion of a catalytic domain region into pJN347, a modified pUC19 vector. FIG. 2D shows the generated catalytic domain sub-library having restriction sites NotI, AscI and PacI. FIG. 2E depicts one particular fusion construct generated from the targeting peptide sub-library and the catalytic domain sub-library.

FIG. 3 illustrates the *M. musculus* α-1,2-mannosidase IA open reading frame nucleic acid sequence (SEQ ID NO: 1) and encoded polypeptide sequence (SEQ ID NO: 2). The sequences of the PCR primers used to generate N-terminal truncations are underlined.

FIG. 5A depicts the standard $Man_5GlcNAc_2$ [a] glycan (Glyko, Novato, Calif.) and $Man_5GlcNAc_2$+Na+[b]. FIG. 5B shows PNGase—released glycans from K3 wild type. The N-glycans shown are as follows: $Man_9GlcNAc_2$ [d]; $Man_{10}GlcNAc_2$ [e]; $Man_{11}GlcNAc_2$ [f]; $Man_{12}GlcNAc_2$ [g]. FIG. 5C depicts the och1 deletion resulting in the production of $Man_8GlcNAc_2$ [c] as the predominant N-glycan. FIGS. 5D and 5E show the production of $Man_5GlcNAc_2$ [b] after in vivo trimming of $Man_8GlcNAc_2$ with a chimeric α-1,2-mannosidase. The predominant N-glycan is indicated by a peak with a mass (m/z) of 1253 consistent with its identification as $Man_5GlcNAc_2$ [b].

FIG. 6A shows the standard $Man_5GlcNAc_2$ [a] and $Man_5GlcNAc_2$+Na+[b] as the standard (Glyko, Novato, Calif.). FIG. 6B shows PNGase-released glycans from IFN-β wildtype. FIG. 6C depicts the och1 knock-out producing $Man_8GlcNAc_2$ [c]; $Man_9GlcNAc_2$ [d]; $Man_{10}GlcNAc_2$ [e]; $Man_{11}GlcNAc_2$ [f]; $Man_{12}GlcNAc_2$ [g]; and no production of $Man_5GlcNAc_2$ [b]. FIG. 6D shows relatively small amount of $Man_5GlcNAc_2$ [b] among other intermediate N-glycans $Man_8GlcNAc_2$ [c] to $Man_{12}GlcNAc_2$ [g]. FIG. 6E shows a significant amount of $Man_5GlcNAc_2$ [b] relative to the other glycans $Man_8GlcNAc_2$ [c] and $Man_9GlcNAc_2$ [d] produced by pGC5 (*Saccharomyces* MNS1(m)/mouse mannosidase IB Δ99). FIG. 6F shows predominant production of $Man_5GlcNAc_2$ [b] on the secreted glycoprotein IFN-β by pFB8 (*Saccharomyces* SEC 12 (m)/mouse mannosidase IA Δ187). The N-glycan is indicated by a peak with a mass (m/z) of 1254 consistent with its identification as $Man_5GlcNAc_2$ [b].

FIG. 10A depicts a *P. pastoris* strain (YSH-3) transformed with a human GnTI but without the UDP-GlcNAc transporter resulting in some production of $GlcNAcMan_5GlcNAc_2$ [b] but a predominant production of $Man_5GlcNAc_2$ [a]. FIG. 10B depicts the addition of UDP-GlcNAc transporter from *K. lactis* in a strain (PBP-3) transformed with the human GnTI, which resulted in the predominant production of $GlcNAcMan_5GlcNAc_2$ [b]. The single prominent peak of mass (m/z) at 1457 is consistent with its identification as $GlcNAcMan_5GlcNAc_2$ [b] as shown in FIG. 10B.

FIG. 12A shows the N-glycans released from wild-type cells, which includes high-mannose type N-glycans. FIG. 12B shows the N-glycans released from och1 mnn1 deleted cells, revealing a distinct peak of mass (m/z) at 1908 consistent with its identification as $Man_9GlcNAc_2$ [d]. FIG. 12C shows the N-glycans released from och1 mnn1 deleted cells after in vitro α-1,2-mannosidase digest corresponding to a peak consistent with $Man_5GlcNAc_2$.

Figure 18:
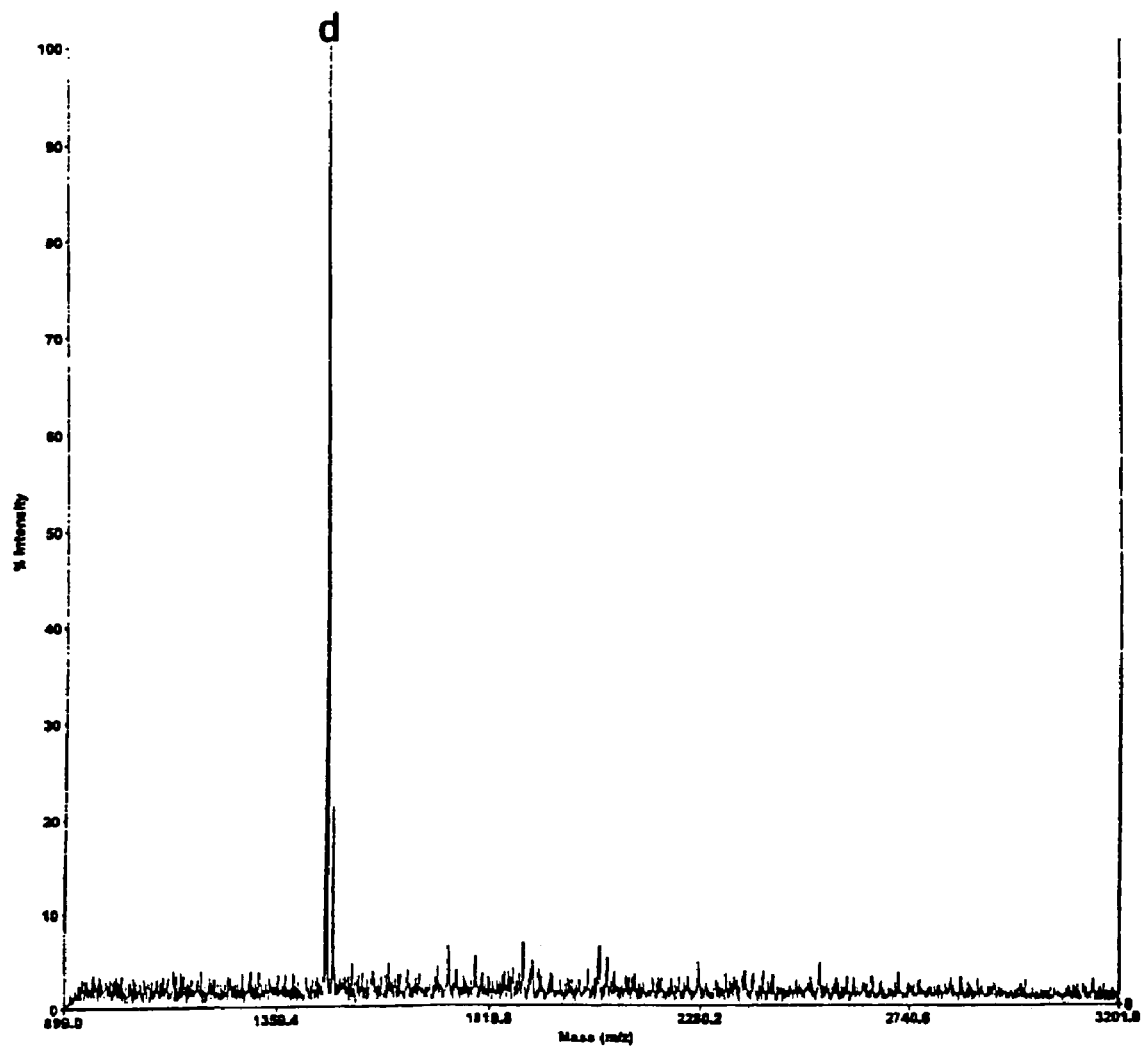

FIG. 18 shows a MALDI-TOF-MS analysis of N-glycans isolated from a kringle 3 glycoprotein produced in a *P. pastoris* YSH-1 transformed with *D. melanogaster* mannosidase IIΔ74/*S. cerevisiae* MNN9(m) showing a predominant peak at 1464 m/z corresponding to the mass of Man$_5$GlcNAc$_2$ [d].

Figure 19:
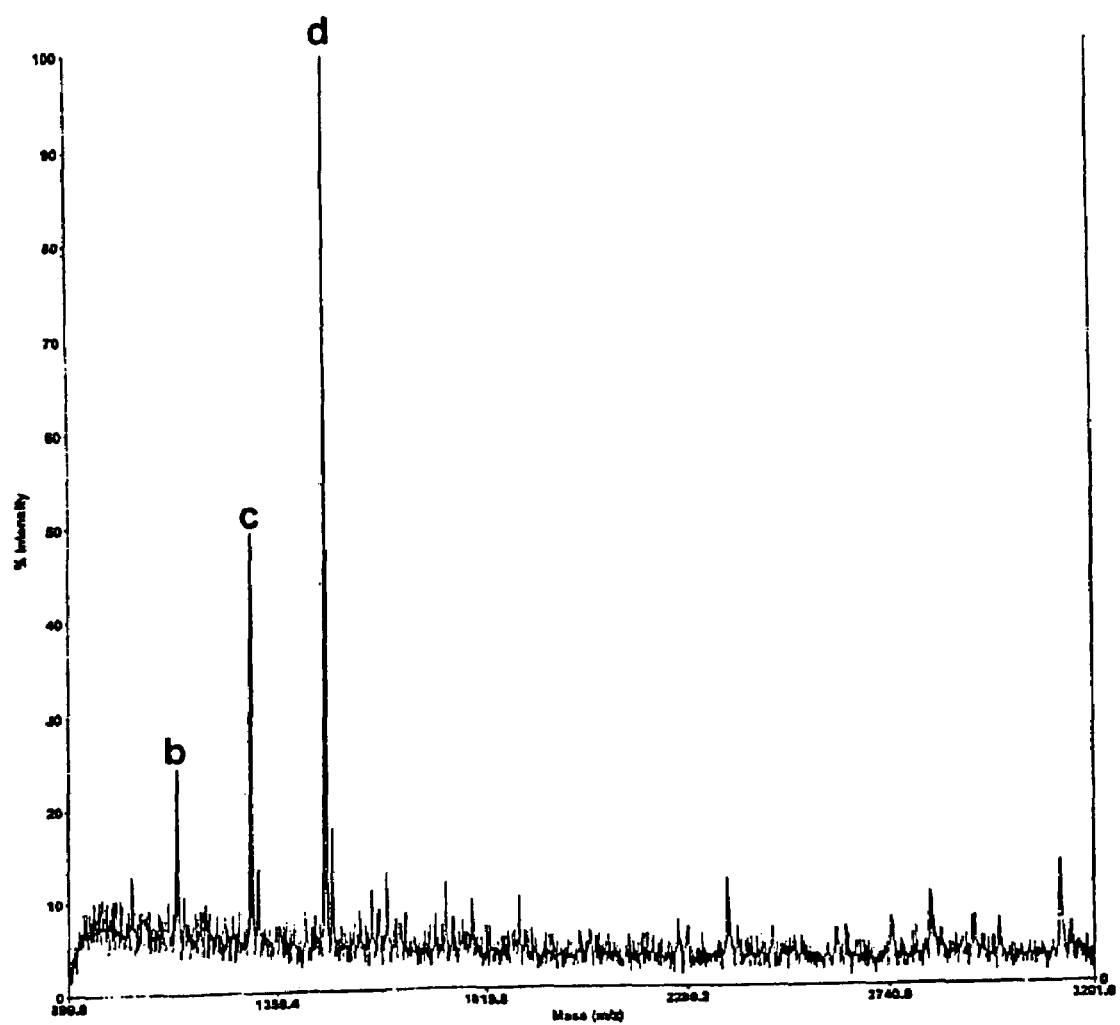

FIG. 19 shows a MALDI-TOF-MS analysis of N-glycans isolated from a kringle 3 glycoprotein produced in a *P. pastoris* YSH-1 transformed with *D. melanogaster* mannosidase IIΔ74/*S. cerevisiae* MNS1(1) showing a predominant peak at 1464 m/z corresponding to the mass of Man$_5$GlcNAc$_2$ [d] and other peaks corresponding to GlcNAcMan$_3$GlcNAc$_2$ [b] at 1139 m/z and GlcNAcMan$_4$GlcNAc$_2$ [c] at 1302 m/z.

Figure 20:
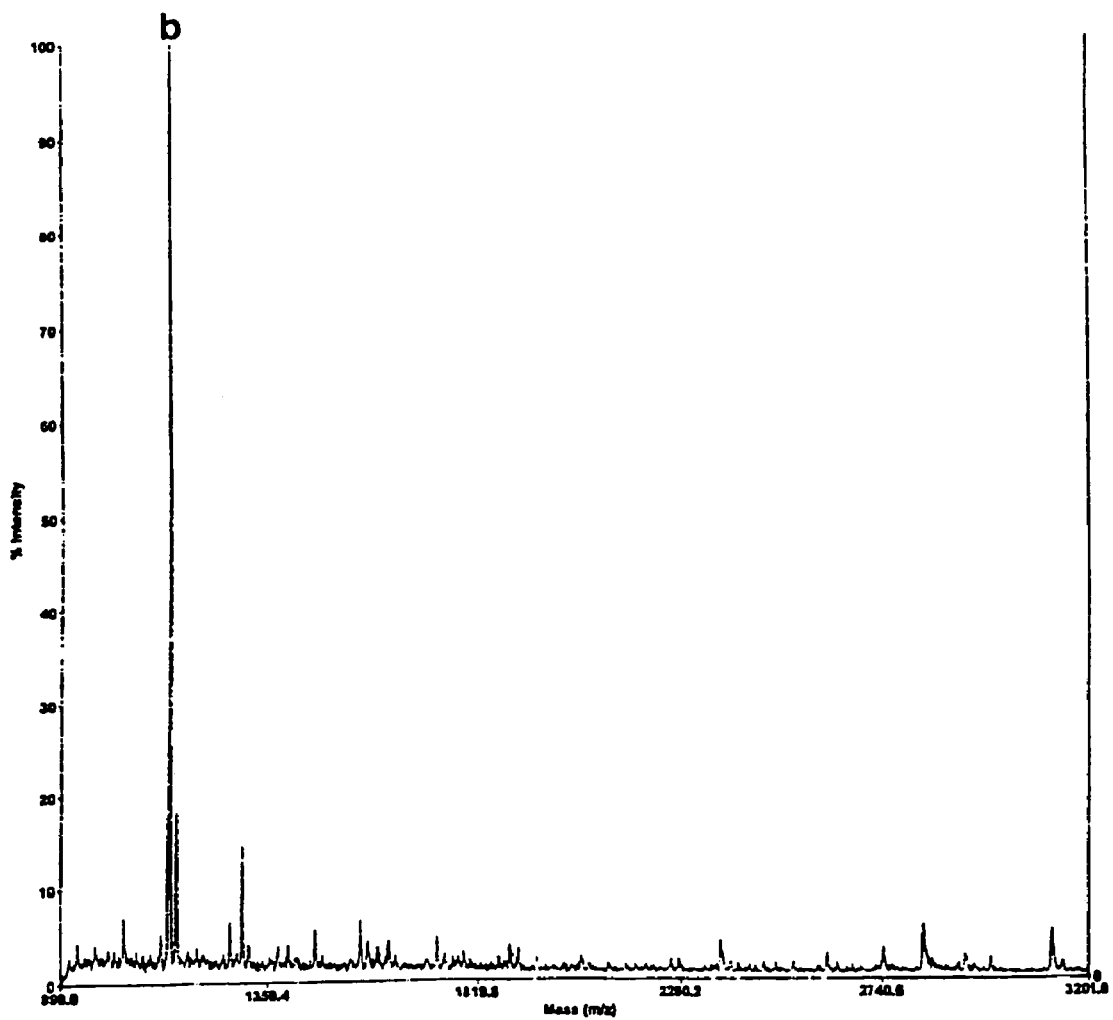

FIG. 20 shows a MALDI-TOF-MS analysis of N-glycans isolated from a kringle 3 glycoprotein produced in a *P. pastoris* YSH-1 transformed with *D. melanogaster* mannosidase IIΔ74/*S. cerevisiae* GLS1(s) showing a predominant peak at 1139 m/z corresponding to the mass of GlcNAcMan$_3$GlcNAc$_2$ [b]. This strain was designated YSH-27.

Figure 21:
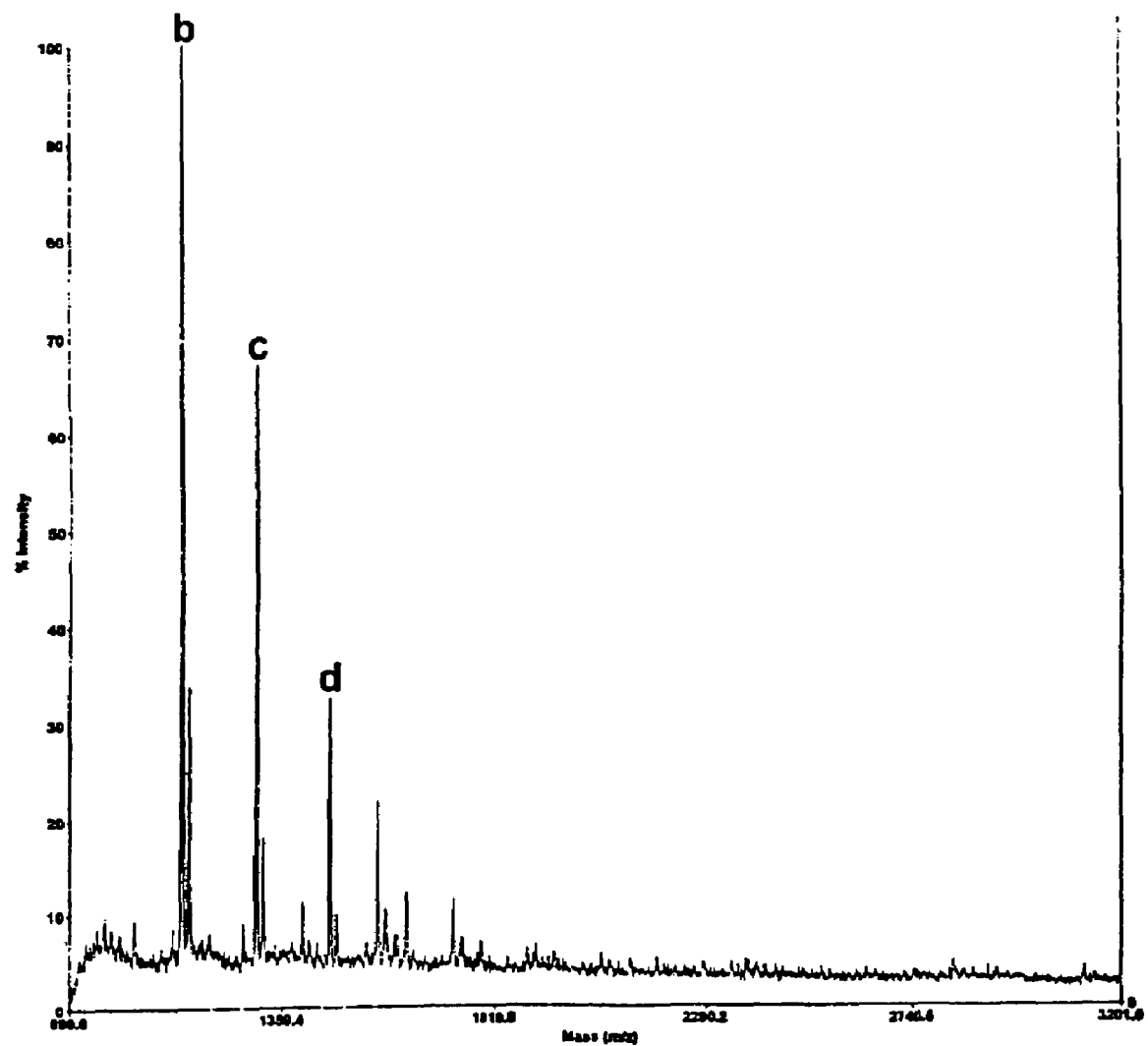

FIG. 21 shows a MALDI-TOF-MS analysis of N-glycans isolated from a kringle 3 glycoprotein produced in a *P. pastoris* YSH-1 transformed with *D. melanogaster* mannosidase IIΔ74/*S. cerevisiae* MNS1(m) showing a predominant peak at 1140 m/z corresponding to the mass of GlcNAcMan$_3$GlcNAc$_2$ [b] and other peaks corresponding to GlcNAcMan$_4$GlcNAc$_2$ [c] at 1302 m/z and GlcNAcMan$_5$GlcNAc$_2$ [d] at 1464 m/z. This strain was designated YSH-74.

Figure 22:
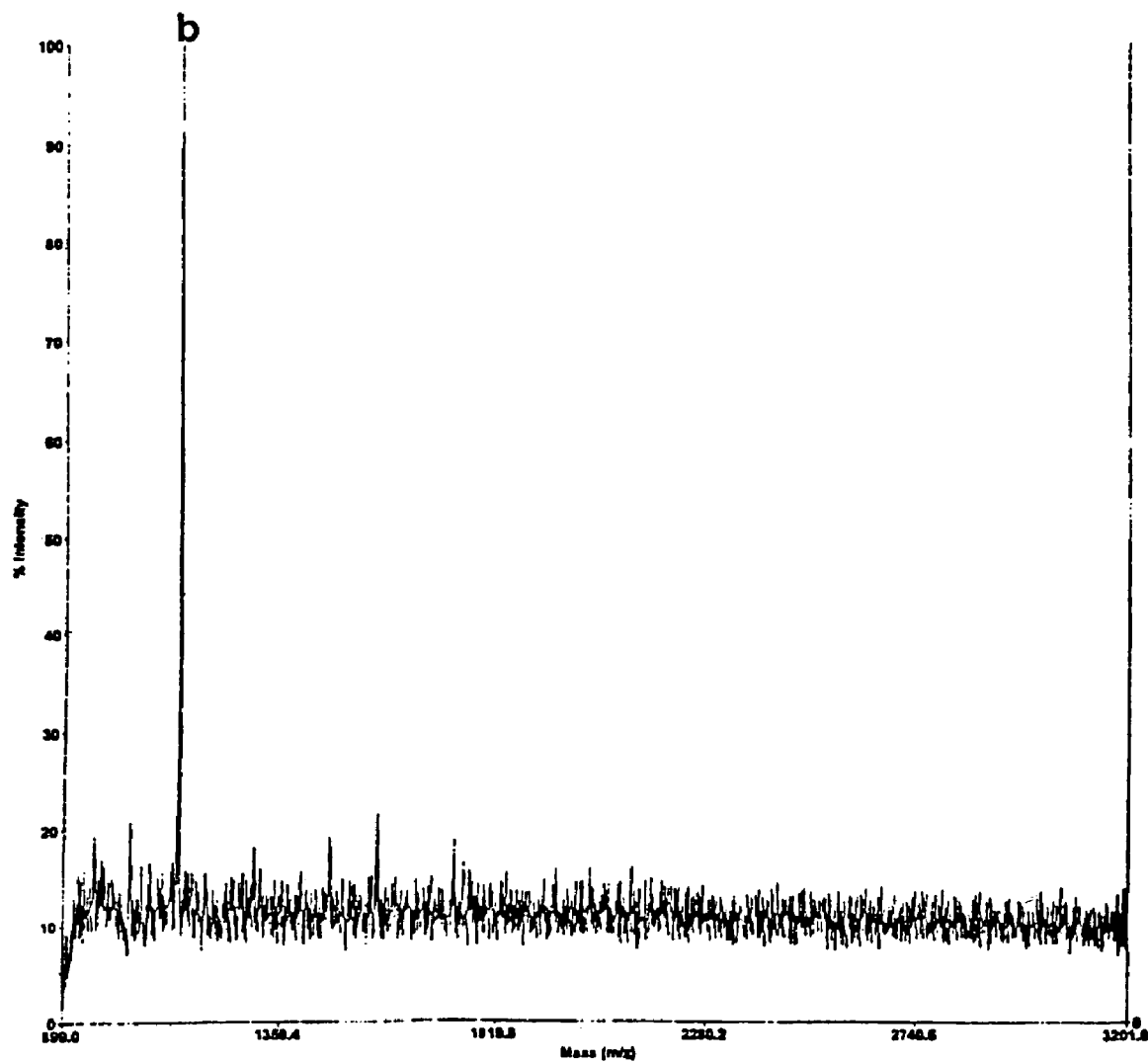

FIG. 22 shows a MALDI-TOF-MS analysis of N-glycans isolated from a kringle 3 glycoprotein produced in a *P. pastoris* YSH-74 digested with a *T. reesei/A. saitoi* α-1,2 mannosidase showing a predominant peak at 1141 m/z corresponding to the mass of GlcNAcMan$_3$GlcNAc$_2$ [b].

Figure 23:
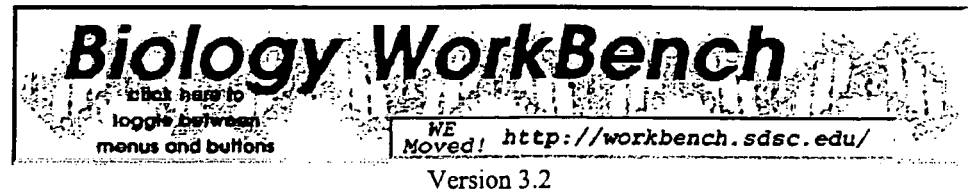
Figure 23:

FIG. 23 shows a BLAST Sequence Comparision of known and hypothetical mannosidase II, mannosidase fix and Class III mannosidases (SEQ ID NOS 96, 92, 93, 99, 98, 97, 94, 95, and 100-102, respectively in order of appearance).

Figure 24:
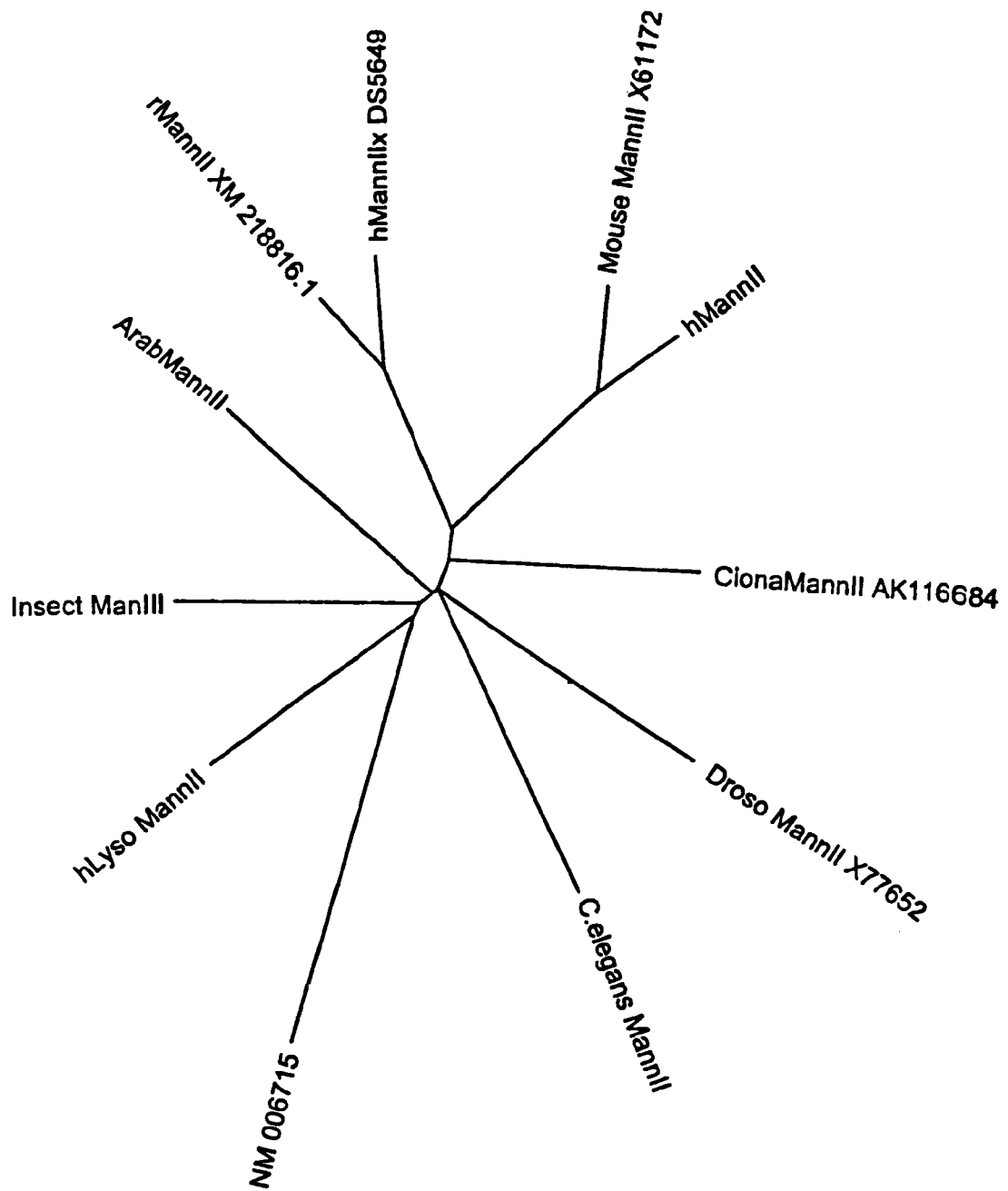

FIG. 24 shows a phylogenetic tree of the classes of mannosidase.

Figure 25:
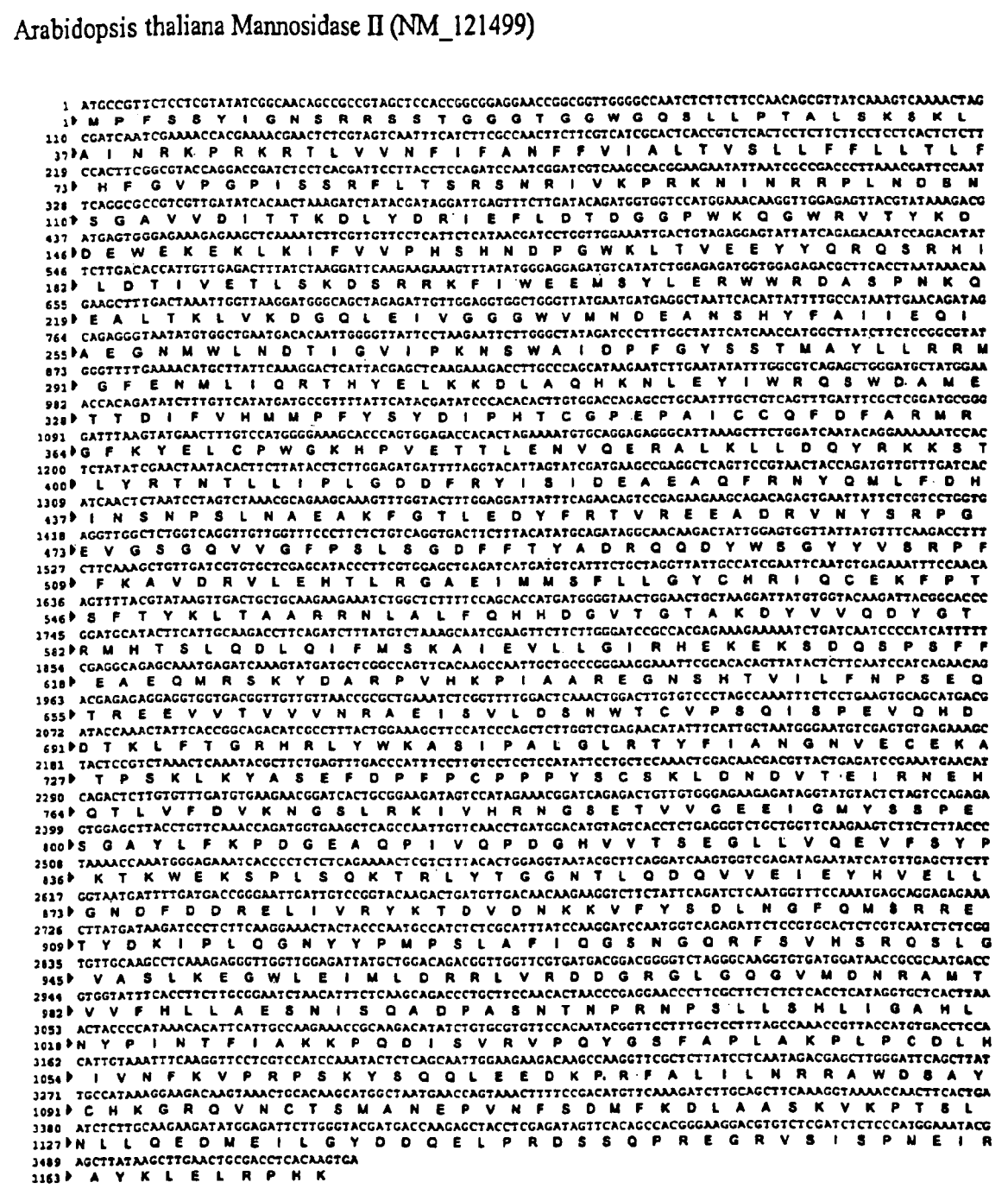

FIG. 25 shows an *Arabidopsis thaliana* Mannosidase II (NM_121499) nucleotide Sequence (SEQ ID NO: 49) and encoded protein (SEQ ID NO: 95).

FIG. 26 shows a *C. elegans* Mannosidase II (NM_073594) nucleotide Sequence (SEQ ID NO: 50) and encoded protein (SEQ ID NO: 92).

FIG. 27 shows a *Ciona intestinalis* mannosidase II (AK116684) nucleotide Sequence (SEQ ID NO: 51) and encoded protein (SEQ ID NO: 94).

Figure 28:
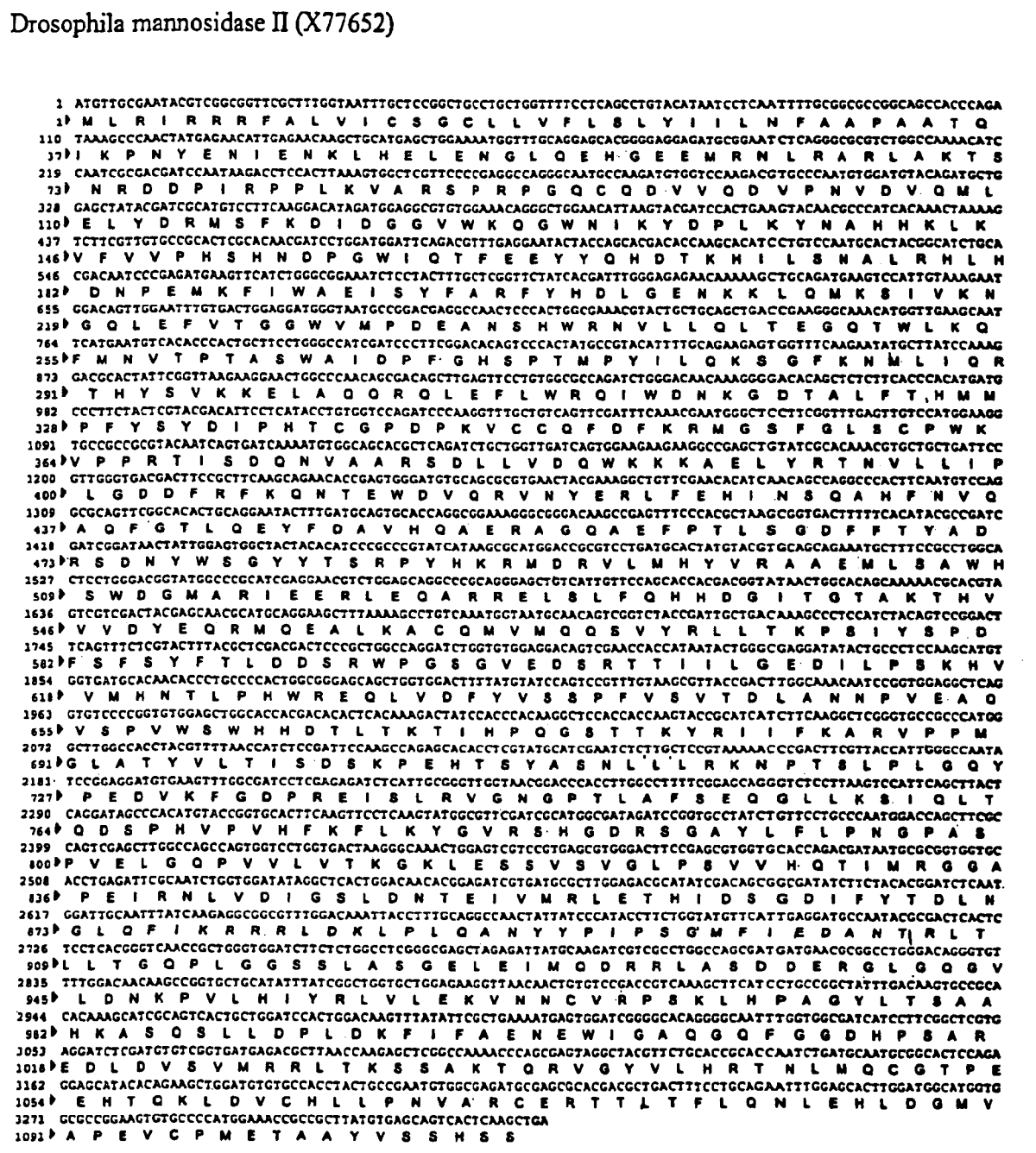

FIG. 28 shows a *D. melanogaster* mannosidase II (X77652) nucleotide Sequence (SEQ ID NO: 52) and encoded protein (SEQ ID NO: 96).

FIG. 29 shows a human mannosidase II (U31520) nucleotide Sequence (SEQ ID NO: 53) and encoded protein (SEQ ID NO: 97).

FIG. 30 shows a mouse mannosidase II (X61172) nucleotide Sequence (SEQ ID NO: 54) and encoded protein (SEQ ID NO: 98).

FIG. 31 shows a rat mannosidase II (XM_218816) nucleotide Sequence (SEQ ID NO: 55) and encoded protein (SEQ ID NO: 93).

FIG. 32 shows a human mannosidase IIx (D55649) nucleotide Sequence (SEQ ID NO: 56) and encoded protein (SEQ ID NO: 99).

FIG. 33 shows an insect cell mannosidase III (AF005034) nucleotide Sequence (SEQ ID NO: 57) and encoded protein (SEQ ID NO: 100).

FIG. 34 shows a human lysosomal mannosidase II (NM_000528) nucleotide Sequence (SEQ ID NO: 58) and encoded protein (SEQ ID NO: 101).

FIG. 35 shows a human cytoplasmic mannosidase II (NM_006715) nucleotide Sequence (SEQ ID NO: 59) and encoded protein (SEQ ID NO: 102).

FIG. 36 illustrates oligosaccharide intermediates produced using mannosidase II, mannosidase IIx and mannosidase III activities.

DETAILED DESCRIPTION OF THE INVENTION

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The methods and techniques of the present invention are generally performed according to conventional methods well known in the art. Generally, nomenclatures used in connection with, and techniques of biochemistry, enzymology, molecular and cellular biology, microbiology, genetics and protein and nucleic acid chemistry and hybridization described herein are those well-known and commonly used in the art.

The methods and techniques of the present invention are generally performed according to conventional methods well-known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane Antibodies: A Laboratory Manual Cold Spring Harbor Laboratory Press, Cold Spring Harbor, N.Y. (1990); Introduction to Glycobiology, Maureen E. Taylor, Kurt Drickamer, Oxford Univ. Press (2003); Worthington Enzyme Manual, Worthington Biochemical Corp. Freehold, N.J.; Handbook of Biochemistry: Section A Proteins Vol I 1976 CRC Press; Handbook of Biochemistry: Section A Proteins Vol II 1976 CRC Press; Essentials of Glycobiology, Cold Spring Harbor Laboratory Press (1999). The nomenclatures used in connection with, and the laboratory procedures and techniques of, molecular and cellular biology, protein biochemistry, enzymology and medicinal and pharmaceutical chemistry described herein are those well known and commonly used in the art.

All publications, patents and other references mentioned herein are incorporated by reference.

The following terms, unless otherwise indicated, shall be understood to have the following meanings:

As used herein, the term "N-glycan" refers to an N-linked oligosaccharide, e.g., one that is attached by an asparagine-N-acetylglucosamin linkage to an asparagine residue of a polypeptide. N-glycans have a common pentasaccharide core of Man$_3$GlcNAc$_2$ ("Man" refers to mannose; "Glc" refers to glucose; and "NAc" refers to N-acetyl; GlcNAc refers to N-acetylglucosamine). The term "trimannose core" used with respect to the N-glycan also refers to the structure Man$_3$GlcNAc$_2$ ("Man$_3$"). N-glycans differ with respect to the number of branches (antennae) comprising peripheral sugars (e.g., fucose and sialic acid) that are added to the Man$_3$ core structure. N-glycans are classified according to their branched constituents (e.g., high mannose, complex or hybrid).

A "high mannose" type N-glycan has five or more mannose residues. A "complex" type N-glycan typically has at least one GlcNAc attached to the 1,3 mannose arm and at least one GlcNAc attached to the 1,6 mannose arm of the trimannose core. Complex N-glycans may also have galactose ("Gal") residues that are optionally modified with sialic acid or derivatives ("NeuAc", where "Neu" refers to neuraminic acid and "Ac" refers to acetyl). A complex N-glycan typically has at least one branch that terminates in an oligosaccharide such as, for example: NeuNAc-; NeuAca2-6GalNAca1-; NeuAca2-3Galb1-3GalNAca1-; NeuAca2-3/6Galb1-4GlcNAcb1-; GlcNAca1-4Galb1-(mucins only); Fuca1-2Galb1-(blood group H). Sulfate esters can occur on galactose, GalNAc, and GlcNAc residues, and phosphate esters can occur on mannose residues. NeuAc (Neu: neuraminic acid; Ac: acetyl) can be O-acetylated or replaced by NeuGl (N-glycolylneuraminic acid). Complex N-glycans may also have intrachain substitutions comprising "bisecting" GlcNAc and core fucose ("Fuc"). A "hybrid" N-glycan has at least one GlcNAc on the terminal of the 1,3 mannose arm of the trimannose core and zero or more mannoses on the 1,6 mannose arm of the trimannose core.

The term "predominant" or "predominantly" used with respect to the production of N-glycans refers to a structure which represents the major peak detected by matrix assisted laser desorption ionization time of flight mass spectrometry (MALDI-TOF) analysis.

Abbreviations used herein are of common usage in the art, see, e.g., abbreviations of sugars, above. Other common abbreviations include "PNGase", which refers to peptide N-glycosidase F (EC 3.2.2.18); "GlcNAc Tr" or "GnT," which refers to N-acetylglucosaminyl Transferase enzymes; "NANA" refers to N-acetylneuraminic acid.

As used herein, a "humanized glycoprotein" or a "human-like glycoprotein" refers alternatively to a protein having attached thereto N-glycans having three or less mannose residues, and synthetic glycoprotein intermediates (which are also useful and can be manipulated further in vitro or in vivo). Preferably, glycoproteins produced according to the invention contain at least 20 mole %, preferably 20-30 mole %, more preferably 30-40 mole %, even more preferably 40-50 mole % and even more preferably 50-100 mole % of the GlcNAcMan$_3$GlcNAc$_2$ intermediate, at least transiently. This may be achieved, e.g., by engineering a host cell of the invention to express a "better", i.e., a more efficient glycosylation enzyme. For example, a mannosidase II is selected such that it will have optimal activity under the conditions present at the site in the host cell where proteins are glycosylated and is introduced into the host cell preferably by targeting the enzyme to a host cell organelle where activity is desired.

The term "enzyme", when used herein in connection with altering host cell glycosylation, refers to a molecule having at least one enzymatic activity, and includes full-length enzymes, catalytically active fragments, chimerics, complexes, and the like. A "catalytically active fragment" of an enzyme refers to a polypeptide having a detectable level of functional (enzymatic) activity. Enzyme activity is "substantially intracellular" when subsequent processing enzymes have the ability to produce about 51% of the desired glycoforms in vivo.

A lower eukaryotic host cell, when used herein in connection with glycosylation profiles, refers to any eukaryotic cell which ordinarily produces high mannose containing N-glycans, and thus is meant to include some animal or plant cells and most typical lower eukaryotic cells, including uni- and multicellular fungal and algal cells.

As used herein, the term "secretion pathway" refers to the assembly line of various glycosylation enzymes to which a lipid-linked oligosaccharide precursor and an N-glycan substrate are sequentially exposed, following the molecular flow of a nascent polypeptide chain from the cytoplasm to the endoplasmic reticulum (ER) and the compartments of the Golgi apparatus. Enzymes are said to be localized along this pathway. An enzyme X that acts on a lipid-linked glycan or an N-glycan before enzyme Y is said to be or to act "upstream" to enzyme Y; similarly, enzyme Y is or acts "downstream" from enzyme X.

The term "targeting peptide" as used herein refers to nucleotide or amino acid sequences encoding a cellular targeting signal peptide which mediates the localization (or retention) of an associated sequence to sub-cellular locations, e.g., organelles.

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. The term includes single and double stranded forms of DNA. A nucleic acid molecule of this invention may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

Unless otherwise indicated, a "nucleic acid comprising SEQ ID NO:X" refers to a nucleic acid, at least a portion of which has either (i) the sequence of SEQ ID NO:X, or (ii) a sequence complementary to SEQ ID NO:X. The choice between the two is dictated by the context. For instance, if the nucleic acid is used as a probe, the choice between the two is dictated by the requirement that the probe be complementary to the desired target.

An "isolated" or "substantially pure" nucleic acid or polynucleotide (e.g., an RNA, DNA or a mixed polymer) is one which is substantially separated from other cellular components that naturally accompany the native polynucleotide in its natural host cell, e.g., ribosomes, polymerases, and genomic sequences with which it is naturally associated. The term embraces a nucleic acid or polynucleotide that (1) has been removed from its naturally occurring environment, (2) is not associated with all or a portion of a polynucleotide in which the "isolated polynucleotide" is found in nature, (3) is operatively linked to a polynucleotide which it is not linked to in nature, or (4) does not occur in nature. The term "isolated" or "substantially pure" also can be used in reference to recombinant or cloned DNA isolates, chemically synthesized polynucleotide analogs, or polynucleotide analogs that are biologically synthesized by heterologous systems.

However, "isolated" does not necessarily require that the nucleic acid or polynucleotide so described has itself been physically removed from its native environment. For instance, an endogenous nucleic acid sequence in the genome of an organism is deemed "isolated" herein if a heterologous sequence (i.e., a sequence that is not naturally adjacent to this endogenous nucleic acid sequence) is placed adjacent to the endogenous nucleic acid sequence, such that the expression of this endogenous nucleic acid sequence is altered. By way of example, a non-native promoter sequence can be substituted (e.g., by homologous recombination) for the native promoter of a gene in the genome of a human cell, such that this gene has an altered expression pattern. This gene would now become "isolated" because it is separated from at least some of the sequences that naturally flank it.

A nucleic acid is also considered "isolated" if it contains any modifications that do not naturally occur to the corresponding nucleic acid in a genome. For instance, an endogenous coding sequence is considered "isolated" if it contains an insertion, deletion or a point mutation introduced artificially, e.g., by human intervention. An "isolated nucleic acid" also includes a nucleic acid integrated into a host cell chromosome at a heterologous site, a nucleic acid construct present as an episome. Moreover, an "isolated nucleic acid" can be substantially free of other cellular material, or substantially free of culture medium when produced by recombinant techniques, or substantially free of chemical precursors or other chemicals when chemically synthesized.

As used herein, the phrase "degenerate variant" of a reference nucleic acid sequence encompasses nucleic acid sequences that can be translated, according to the standard genetic code, to provide an amino acid sequence identical to that translated from the reference nucleic acid sequence.

The term "percent sequence identity" or "identical" in the context of nucleic acid sequences refers to the residues in the two sequences which are the same when aligned for maximum correspondence. The length of sequence identity comparison may be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides. There are a number of different algorithms known in the art that can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA provides alignments and percent sequence identity of the regions of the best overlap between the query and search sequences (Pearson, 1990, herein incorporated by reference). For instance, percent sequence identity between nucleic acid sequences can be determined using FASTA with its default parameters (a word size of 6 and the NOPAM factor for the scoring matrix) or using Gap with its default parameters as provided in GCG Version 6.1, herein incorporated by reference.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 50%, more preferably 60% of the nucleotide bases, usually at least about 70%, more usually at least about 80%, preferably at least about 90%, and more preferably at least about 95%, 96%, 97%, 98% or 99% of the nucleotide bases, as measured by any well-known algorithm of sequence identity, such as FASTA, BLAST or Gap, as discussed above.

Alternatively, substantial homology or similarity exists when a nucleic acid or fragment thereof hybridizes to another nucleic acid, to a strand of another nucleic acid, or to the complementary strand thereof, under stringent hybridization conditions. "Stringent hybridization conditions" and "stringent wash conditions" in the context of nucleic acid hybridization experiments depend upon a number of different physical parameters. Nucleic acid hybridization will be affected by such conditions as salt concentration, temperature, solvents, the base composition of the hybridizing species, length of the complementary regions, and the number of nucleotide base mismatches between the hybridizing nucleic acids, as will be readily appreciated by those skilled in the art. One having ordinary skill in the art knows how to vary these parameters to achieve a particular stringency of hybridization.

In general, "stringent hybridization" is performed at about 25° C. below the thermal melting point ($T_m$) for the specific DNA hybrid under a particular set of conditions. "Stringent washing" is performed at temperatures about 5° C. lower than the $T_m$ for the specific DNA hybrid under a particular set of conditions. The $T_m$ is the temperature at which 50% of the target sequence hybridizes to a perfectly matched probe. See Sambrook et al., supra, page 9.51, hereby incorporated by reference. For purposes herein, "high stringency conditions" are defined for solution phase hybridization as aqueous hybridization (i.e., free of formamide) in 6×SSC (where 20×SSC contains 3.0 M NaCl and 0.3 M-sodium citrate), 1% SDS at 65° C. for 8-12 hours, followed by two washes in 0.2×SSC, 0.1% SDS at 65° C. for 20 minutes. It will be appreciated by the skilled artisan that hybridization at 65° C. will occur at different rates depending on a number of factors including the length and percent identity of the sequences which are hybridizing.

The term "mutated" when applied to nucleic acid sequences means that nucleotides in a nucleic acid sequence may be inserted, deleted or changed compared to a reference nucleic acid sequence. A single alteration may be made at a locus (a point mutation) or multiple nucleotides may be inserted, deleted or changed at a single locus. In addition, one or more alterations may be made at any number of loci within a nucleic acid sequence. A nucleic acid sequence may be mutated by any method known in the art including but not limited to mutagenesis techniques such as "error-prone PCR" (a process for performing PCR under conditions where the copying fidelity of the DNA polymerase is low, such that a high rate of point mutations is obtained along the entire length of the PCR product. See, e.g., Leung, D. W., et al., *Technique*, 1, pp. 11-15 (1989) and Caldwell, R. C. & Joyce G. F., *PCR Methods Applic.*, 2, pp. 28-33 (1992)); and "oligonucleotide-directed mutagenesis" (a process which enables the generation of site-specific mutations in any cloned DNA segment of interest. See, e.g., Reidhaar-Olson, J. F. & Sauer, R. T., et al., *Science*, 241, pp. 53-57 (1988)).

The term "vector" as used herein is intended to refer to a nucleic acid molecule capable of transporting another nucleic acid to which it has been linked. One type of vector is a "plasmid", which refers to a circular double stranded DNA loop into which additional DNA segments may be ligated. Other vectors include cosmids, bacterial artificial chromosomes (BAC) and yeast artificial chromosomes (YAC). Another type of vector is a viral vector, wherein additional DNA segments may be ligated into the viral genome (discussed in more detail below). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of genes to which they are operatively linked. Such vectors are referred to herein as "recombinant expression vectors" (or simply, "expression vectors").

"Operatively linked" expression control sequences refers to a linkage in which the expression control sequence is contiguous with the gene of interest to control the gene of interest, as well as expression control sequences that act in trans or at a distance to control the gene of interest.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "recombinant host cell" (or simply "host cell"), as used herein, is intended to refer to a cell into which a nucleic acid such as a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

The term "peptide" as used herein refers to a short polypeptide, e.g., one that is typically less than about 50 amino acids long and more typically less than about 30 amino acids long. The term as used herein encompasses analogs and mimetics that mimic structural and thus biological function.

The term "polypeptide" as used herein encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "isolated protein" or "isolated polypeptide" is a protein or polypeptide that by virtue of its origin or source of derivation (1) is not associated with naturally associated components that accompany it in its native state, (2) when it exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well-known in the art. As thus defined, "isolated" does not necessarily require that the protein, polypeptide, peptide or oligopeptide so described has been physically removed from its native environment.

The term "polypeptide fragment" as used herein refers to a polypeptide that has an amino-terminal and/or carboxy-terminal deletion compared to a full-length polypeptide. In a preferred embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long.

A "modified derivative" refers to polypeptides or fragments thereof that are substantially homologous in primary structural sequence but which include, e.g., in vivo or in vitro chemical and biochemical modifications or which incorporate amino acids that are not found in the native polypeptide. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well-known in the art, and include radioactive isotopes such as $^{125}I$, $^{32}P$, $^{35}S$, and $^{3}H$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods for labeling polypeptides are well-known in the art. See Ausubel et al., *Current Potocols in Molecular Biology*, Greene Publishing Associates (1992, and supplements to 2002) hereby incorporated by reference.

A "polypeptide mutant" or "mutein" refers to a polypeptide whose sequence contains an insertion, duplication, deletion, rearrangement or substitution of one or more amino acids compared to the amino acid sequence of a native or wild type protein. A mutein may have one or more amino acid point substitutions, in which a single amino acid at a position has been changed to another amino acid, one or more insertions and/or deletions, in which one or more amino acids are inserted or deleted, respectively, in the sequence of the naturally-occurring protein, and/or truncations of the amino acid sequence at either or both the amino or carboxy termini. A mutein may have the same but preferably has a different biological activity compared to the naturally-occurring protein.

A mutein has at least 70% overall sequence homology to its wild-type counterpart. Even more preferred are muteins having 80%, 85% or 90% overall sequence homology to the wild-type protein. In an even more preferred embodiment, a mutein exhibits 95% sequence identity, even more preferably 97%, even more preferably 98% and even more preferably 99% overall sequence identity. Sequence homology may be measured by any common sequence analysis algorithm, such as Gap or Bestfit.

Preferred amino acid substitutions are those which: (1) reduce susceptibility to proteolysis, (2) reduce susceptibility to oxidation, (3) alter binding affinity for forming protein complexes, (4) alter binding affinity or enzymatic activity, and (5) confer or modify other physicochemical or functional properties of such analogs.

As used herein, the twenty conventional amino acids and their abbreviations follow conventional usage. See *Immunology—A Synthesis* ($2^{nd}$ Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as α-, α-disubstituted amino acids, N-alkyl amino acids, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, s-N-methylarginine, and other similar amino acids and imino acids (e.g., 4-hydroxyproline). In the polypeptide notation used herein, the left-hand direction is the amino terminal direction and the right hand direction is the carboxy-terminal direction, in accordance with standard usage and convention.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences). In a preferred embodiment, a homologous protein is one that exhibits 60% sequence homology to the wild type protein, more preferred is 70% sequence homology. Even more preferred are homologous proteins that exhibit 80%, 85% or 90% sequence homology to the wild type protein. In a yet more preferred embodiment, a homologous protein exhibits 95%, 97%, 98% or 99% sequence identity. As used herein, homology between two regions of amino acid sequence (especially with respect to predicted structural similarities) is interpreted as implying similarity in function.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson el al., 1994, herein incorporated by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1.

A preferred algorithm when comparing a inhibitory molecule sequence to a database containing a large number of sequences from different organisms is the computer program BLAST (Altschul, S. F. et al. (1990) *J. Mol. Biol*. 215:403-410; Gish and States (1993) *Nature Genet*. 3:266-272; Madden, T. L. et al. (1996) *Meth. Enzymol*. 266:131-141; Altschul, S. F. et al. (1997) *Nucleic Acids Res*. 25:3389-3402; Zhang, J. and Madden, T. L. (1997) *Genome Res*. 7:649-656), especially blastp or tblastn (Altschul et al., 1997). Preferred parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

The length of polypeptide sequences compared for homology will generally be at least about 16 amino acid residues, usually at least about 20 residues, more usually at least about 24 residues, typically at least about 28 residues, and preferably more than about 35 residues. When searching a database containing sequences from a large number of different organisms, it is preferable to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, 1990, herein incorporated by reference). For example, percent sequence identity between amino acid sequences can be determined using FASTA with its default parameters (a word size of 2 and the PAM250 scoring matrix), as provided in GCG Version 6.1, herein incorporated by reference.

The term "motif" in reference to the conserved regions denotes the amino acid residues usually found in proteins and conventionally known as alanine (Ala or A), valine (Val or V), leucine (Leu or L), isoleucine (Ile or I), proline (Pro or P), phenylalanine (Phe or F), tryptophan (Trp or W), methionine (Met or M), glycine (Gly or G), serine (Ser or S), threonine (Thr or T), cysteine (Cys or C), tyrosine (Tyr or Y), asparagine (Asn or N), glutamine (Gln or Q), aspartic acid (Asp or D), glutamic acid (Glu or E), lysine (Lys or K), arginine (Arg or R), and histidine (His or H).

The term "fusion protein" refers to a polypeptide comprising a polypeptide or fragment coupled to heterologous amino acid sequences. Fusion proteins are useful because they can be constructed to contain two or more desired functional elements from two or more different proteins. A fusion protein comprises at least 10 contiguous amino acids from a polypeptide of interest, more preferably at least 20 or 30 amino acids, even more preferably at least 40, 50 or 60 amino acids, yet more preferably at least 75, 100 or 125 amino acids. Fusion proteins can be produced recombinantly by constructing a nucleic acid sequence which encodes the polypeptide or a fragment thereof in-frame with a nucleic acid sequence encoding a different protein or peptide and then expressing the fusion protein. Alternatively, a fusion protein can be produced chemically by crosslinking the polypeptide or a fragment thereof to another protein.

The term "region" as used herein refers to a physically contiguous portion of the primary structure of a biomolecule. In the case of proteins, a region is defined by a contiguous portion of the amino acid sequence of that protein.

The term "domain" as used herein refers to a structure of a biomolecule that contributes to a known or suspected function of the biomolecule. Domains may be co-extensive with regions or portions thereof; domains may also include distinct, non-contiguous regions of a biomolecule. Examples of protein domains include, but are not limited to, an Ig domain, an extracellular domain, a transmembrane domain, and a cytoplasmic domain.

As used herein, the term "molecule" means any compound, including, but not limited to, a small molecule, peptide, protein, sugar, nucleotide, nucleic acid, lipid, etc., and such a compound can be natural or synthetic.

Unless otherwise defined, all technical and scientific terms used herein have the same meaning as commonly understood by one of ordinary skill in the art to which this invention pertains. Exemplary methods and materials are described below, although methods and materials similar or equivalent to those described herein can also be used in the practice of the present invention and will be apparent to those of skill in the art. All publications and other references mentioned herein are incorporated by reference in their entirety. In case of conflict, the present specification, including definitions, will control. The materials, methods, and examples are illustrative only and not intended to be limiting.

Throughout this specification and claims, the word "comprise" or variations such as "comprises" or "comprising", will be understood to imply the inclusion of a stated integer or group of integers but not the exclusion of any other integer or group of integers.

Methods for Producing Human-Like Glycoproteins in Lower Eukaryotic Host Cells

The invention provides methods for producing a glycoprotein having human-like glycosylation in a non-human eukaryotic host cell. As described in more detail below, a eukaryotic host cell that does not naturally express, or which is engineered not to express, one or more enzymes involved in production of high mannose structures is selected as a starting host cell. Such a selected host cell is engineered to express one or more enzymes or other factors required to produce human-like glycoproteins. A desired host strain can be engineered one enzyme or more than one enzyme at a time. In addition, a nucleic acid molecule encoding one or more enzymes or activities may be used to engineer a host strain of the invention. Preferably, a library of nucleic acid molecules encoding potentially useful enzymes (e.g., chimeric enzymes comprising a catalytically active enzyme fragment ligated in-frame to a heterologous subcellular targeting sequence) is created (e.g., by ligation of sub-libraries comprising enzymatic fragments and subcellular targeting sequences), and a strain having one or more enzymes with optimal activities or producing the most "human-like" glycoproteins may be selected by transforming target host cells with one or more members of the library.

In particular, the methods described herein enable one to obtain, in vivo, $Man_5GlcNAc_2$ structures in high yield, at least transiently, for the purpose of further modifying it to yield complex N-glycans. A successful scheme to obtain suitable $Man_5GlcNAc_2$ structures in appropriate yields in a host cell, such as a lower eukaryotic organism, generally involves two parallel approaches: (1) reducing high mannose structures made by endogenous mannosyltransferase activities, if any, and (2) removing 1,2-α-mannose by mannosidases to yield high levels of suitable $Man_5GlcNAc_2$ structures which may be further reacted inside the host cell to form complex, human-like glycoforms.

Accordingly, a first step involves the selection or creation of a eukaryotic host cell, e.g., a lower eukaryote, capable of producing a specific precursor structure of $Man_5GlcNAc_2$ that is able to accept in vivo GlcNAc by the action of a GlcNAc transferase I ("GnTI"). In one embodiment, the method involves making or using a non-human eukaryotic host cell depleted in a 1,6 mannosyltransferase activity with respect to the N-glycan on a glycoprotein. Preferably, the host cell is depleted in an initiating 1,6 mannosyltransferase activity (see below). Such a host cell will lack one or more enzymes involved in the production of high mannose structures which are undesirable for producing human-like glycoproteins.

One or more enzyme activities are then introduced into such a host cell to produce N-glycans within the host cell characterized by having at least 30 mol % of the $Man_5GlcNAc_2$ ("$Man_5$") carbohydrate structures. $Man_5GlcNAc_2$ structures are necessary for complex N-glycan formation: $Man_5GlcNAc_2$ must be formed in vivo in a high yield (e.g., in excess of 30%), at least transiently, as subsequent mammalian- and human-like glycosylation reactions require $Man_5GlcNAc_2$ or a derivative thereof.

This step also requires the formation of a particular isomeric structure of $Man_5GlcNAc_2$ within the cell at a high yield. While $Man_5GlcNAc_2$ structures are necessary for complex N-glycan formation, their presence is by no means sufficient. That is because $Man_5GlcNAc_2$ may occur in different isomeric forms, which may or may not serve as a substrate for GlcNAc transferase I. As most glycosylation reactions are not complete, a particular glycosylated protein generally contains a range of different carbohydrate structures (i.e. glycoforms) on its surface. Thus, the mere presence of trace amounts (i.e., less than 5%) of a particular structure like $Man_5GlcNAc_2$ is of little practical relevance for producing mammalian- or human-like glycoproteins. It is the formation of a GlcNAc transferase I-accepting $Man_5GlcNAc_2$ intermediate (FIG. 1B) in high yield (i.e., above 30%), which is required. The formation of this intermediate is necessary to enable subsequent in vivo synthesis of complex N-glycans on glycosylated proteins of interest (target proteins).

Accordingly, some or all of the $Man_5GlcNAc_2$ produced by the selected host cell must be a productive substrate for enzyme activities along a mammalian glycosylation pathway, e.g., can serve as a substrate for a GlcNAc transferase I activity in vivo, thereby forming the human-like N-glycan intermediate $GlcNAcMan_5GlcNAc_2$ in the host cell. In a preferred embodiment, at least 10%, more preferably at least 30% and most preferably 50% or more of the $Man_5GlcNAc_2$ intermediate produced in the host cell of the invention is a productive substrate for GnTI in vivo. It is understood that if, for example, $GlcNAcMan_5GlcNAc_2$ is produced at 10% and $Man_5GlcNAc_2$ is produced at 25% on a target protein, that the total amount of transiently produced $Man_5GlcNAc_2$ is 35% because $GlcNAcMan_5GlcNAc_2$ is a product of $Man_5GlcNAc_2$.

One of ordinary skill in the art can select host cells from nature, e.g., existing fungi or other lower eukaryotes that produce significant levels of $Man_5GlcNAc_2$ in vivo. As yet, however, no lower eukaryote has been shown to provide such structures in vivo in excess of 1.8% of the total N-glycans (see e.g. Maras et al., 1997, *Eur. J. Biochem.* 249, 701-707). Alternatively, such host cells may be genetically engineered to produce the $Man_5GlcNAc_2$ structure in vivo. Methods such as those described in U.S. Pat. No. 5,595,900 may be used to identify the absence or presence of particular glycosyltransferases, mannosidases and sugar nucleotide transporters in a target host cell or organism of interest.

Inactivation of Undesirable Host Cell Glycosylation Enzymes

The methods of the invention are directed to making host cells which produce glycoproteins having altered, and preferably human-like, N-glycan structures. In a preferred embodiment, the methods are directed to making host cells in which oligosaccharide precursors are enriched in $Man_5GlcNAc_2$. Preferably, a eukaryotic host cell is used that does not express one or more enzymes involved in the production of high mannose structures. Such a host cell may be found in nature or may be engineered, e.g., starting with or derived from one of many such mutants already described in yeasts. Thus, depending on the selected host cell, one or a number of genes that encode enzymes known to be characteristic of non-human glycosylation reactions will have to be deleted. Such genes and their corresponding proteins have been extensively characterized in a number of lower eukaryotes (e.g., *S. cerevisiae, T. reesei, A. nidulans* etc.), thereby providing a list of known glycosyltransferases in lower eukaryotes, their activities and their respective genetic sequence. These genes are likely to be selected from the group of mannosyltransferases e.g. 1,3 mannosyltransferases (e.g. MNN1 in *S. cerevisiae*) (Graham, 1991), 1,2 mannosyltransferases (e.g. KTR/KRE family from *S. cerevisiae*), 1,6 mannosyltransferases (OCH1 from *S. cerevisiae*), mannosylphosphate transferases and their regulators (MNN4 and MNN6 from *S. cerevisiae*) and additional enzymes that are involved in aberrant, i.e. non human, glycosylation reactions. Many of these genes have in fact been deleted individually giving rise to viable phenotypes with altered glycosylation profiles. Examples are shown in Table 1 (above).

Figure 1A:
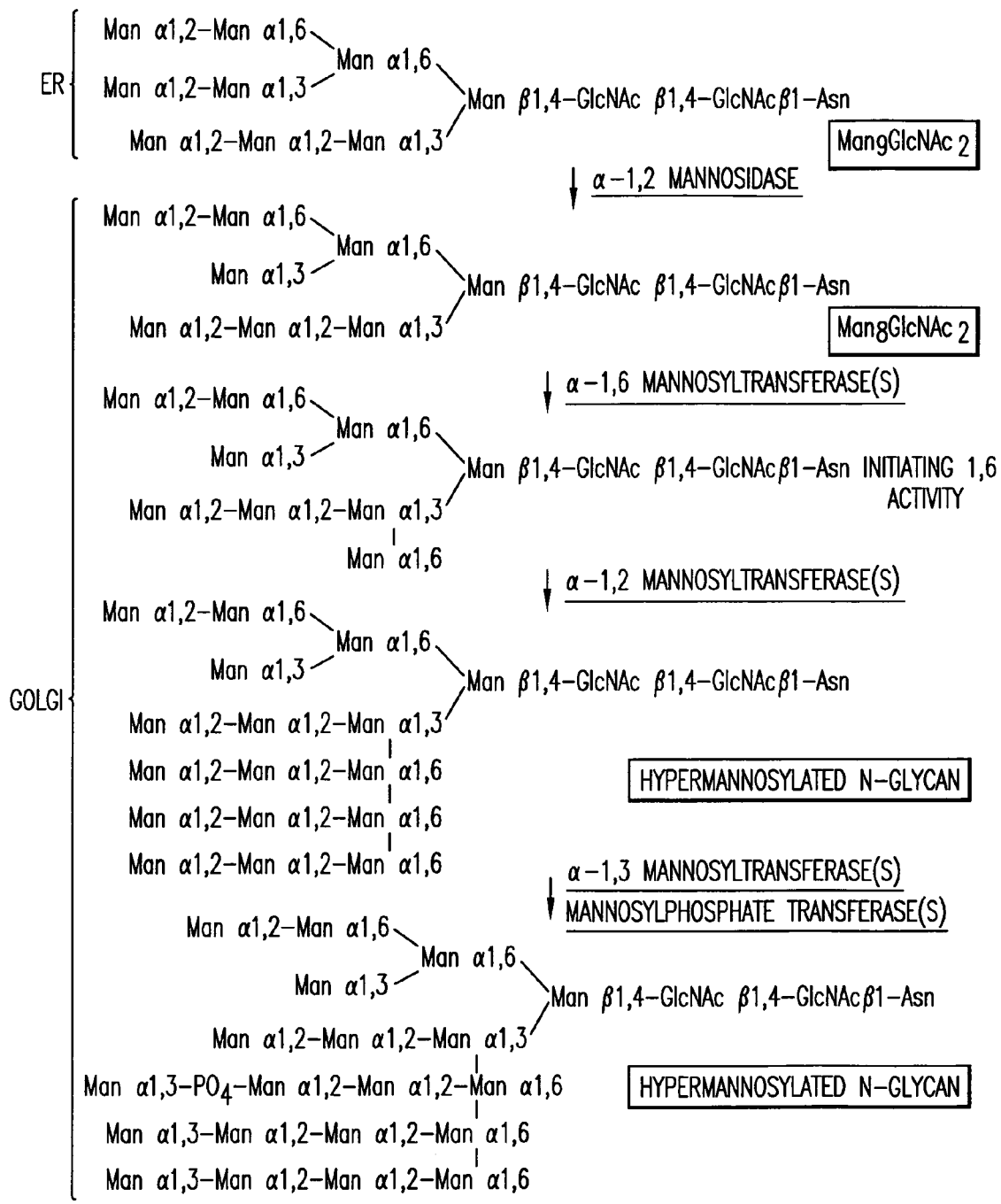
FIG. 1A is a schematic diagram of a typical fungal N-glycosylation pathway.

Preferred lower eukaryotic host cells of the invention, as described herein to exemplify the required manipulation steps, are hypermannosylation-minus (och1) mutants of *Pichia pastoris* or *K. lactis*. Like other lower eukaryotes, *P. pasioris* processes $Man_9GlcNAc_2$ structures in the ER with an α-1,2-mannosidase to yield $Man_8GlcNAc_2$ (FIG. 1A). Through the action of several mannosyltransferases, this structure is then converted to hypermannosylated structures ($Man_{>9}GlcNAc_2$), also known as mannans. In addition, it has been found that *P. pastoris* is able to add non-terminal phosphate groups, through the action of mannosylphosphate transferases, to the carbohydrate structure. This differs from the reactions performed in mammalian cells, which involve the removal rather than addition of mannose sugars. It is of particular importance to eliminate the ability of the eukaryotic host cell, e.g., fungus, to hypermannosylate an existing $Man_8GlcNAc_2$ structure. This can be achieved by either selecting for a host cell that does not hypermannosylate or by genetically engineering such a cell.

Genes that are involved in the hypermannosylation process have been identified, e.g., in *Pichia pastoris*, and by creating mutations in these genes, one can reduce the production of "undesirable" glycoforms. Such genes can be identified by homology to existing mannosyltransferases or their regulators (e.g., OCH1, MNN4, MNN6, MANN) found in other lower eukaryotes such as *C. albicans, Pichia angusta* or *S. cerevisiae* or by mutagenizing the host strain and selecting for a glycosylation phenotype with reduced mannosylation. Based on homologies amongst known mannosyltransferases and mannosylphosphate transferases, one may either design PCR primers (examples of which are shown in Table 2, SEQ ID Nos: 60-91 are additional examples of primers), or use genes or gene fragments encoding such enzymes as probes to identify homologs in DNA libraries of the target or a related organism. Alternatively, one may identify a functional homolog having mannosyltransferase activity by its ability to complement particular glycosylation phenotypes in related organisms.

TABLE 2

PCR Primers

| PCR primer A | PCR primer B | Target Gene(s) in *P. pastoris* | Homologs |
|---|---|---|---|
| ATGGCGAAGGCAG ATGGCAGT (SEQ ID NO: 18) | TTAGTCCTTCCA ACTTCCTTC (SEQ ID NO: 19) | 1,6-mannosyl-transferase | OCH1 *S. cerevisiae, Pichia albicans* |
| TAYTGGMGNGTNG ARCYNGAYATHAA (SEQ ID NO: 103) | GCRTCNCCCCAN CKYTCRTA (SEQ ID NO: 104) | 1,2 mannosyl-transferases | KTR/KRE family, *S. cerevisiae* |

Legend: M = A or C, R = A or G, W = A or T, S = C or G, Y = C or T, K = G or T, V = A or C or G, H = A or C or T, D = A or G or T, B = C or G or T, N = G or A or T or C.

To obtain the gene or genes encoding 1,6-mannosyltransferase activity in *P. pastoris*, for example, one would carry out the following steps: OCH1 mutants of *S. cerevisiae* are temperature sensitive and are slow growers at elevated temperatures. One can thus identify functional homologs of OCH1 in *P. pasioris* by complementing an OCH1 mutant of *S. cerevisiae* with a *P. pastoris* DNA or cDNA library. Mutants of *S. cerevisiae* are available, e.g., from Stanford University and are commercially available from ResGen, an Invitrogen Corp. (Carlsbad, Calif.). Mutants that display a normal growth phenotype at elevated temperature, after having been transformed with a *P. pastoris* DNA library, are likely to carry an OCH1 homolog of *P. pastoris*. Such a library can be created by partially digesting chromosomal DNA of *P. pastoris* with a suitable restriction enzyme and, after inactivating the restriction enzyme, ligating the digested DNA into a suitable vector, which has been digested with a compatible restriction enzyme.

Suitable vectors include, e.g., pRS314, a low copy (CEN6/ARS4) plasmid based on pBluescript containing the Trp1 marker (Sikorski, R. S., and Hieter, P., 1989, *Genetics* 122, pg 19-27) and pFL44S, a high copy (2μ) plasmid based on a modified pUC19 containing the URA3 marker (Bonneaud, N., et al., 1991, *Yeast* 7, pg. 609-615). Such vectors are commonly used by academic researchers and similar vectors are available from a number of different vendors (e.g., Invitrogen (Carlsbad, Calif.); Pharmacia (Piscataway, N.J.); New England Biolabs (Beverly, Mass.)). Further examples include pYES/GS, 2μ origin of replication based yeast expression plasmid from Invitrogen, or Yep24 cloning vehicle from New England Biolabs.

After ligation of the chromosomal DNA and the vector, one may transform the DNA library into a strain of *S. cerevisiae* with a specific mutation and select for the correction of the corresponding phenotype. After sub-cloning and sequencing the DNA fragment that is able to restore the wild-type phenotype, one may use this fragment to eliminate the activity of the gene product encoded by OCH1 in *P. pastoris* using in vivo mutagenesis and/or recombination techniques well-known to those skilled in the art.

Alternatively, if the entire genomic sequence of a particular host cell, e.g., fungus, of interest is known, one may identify such genes simply by searching publicly available DNA databases, which are available from several sources, such as NCBI, Swissprot. For example, by searching a given genomic sequence or database with sequences from a known 1,6 mannosyltransferase gene (e.g., OCH1 from *S. cerevisiae*), one can identify genes of high homology in such a host cell genome which may (but do not necessarily) encode proteins that have 1,6-mannosyltransferase activity. Nucleic acid sequence homology alone is not enough to prove, however, that one has identified and isolated a homolog encoding an enzyme having the same activity. To date, for example, no data exist to show that an OCH1 deletion in *P. pastoris* eliminates the crucial initiating 1,6-mannosyltransferase activity. (Martinet et al. *Biotech. Letters* 20(12) (December 1998): 1171-1177; Contreras et al. WO 02/00856 A2). Thus, no data prove that the *P. pastoris* OCH1 gene homolog actually encodes that function. That demonstration is provided for the first time herein.

Homologs to several *S. cerevisiae* mannosyltransferases have been identified in *P. pastoris* using these approaches. Homologous genes often have similar functions to genes involved in the mannosylation of proteins in *S. cerevisiae* and thus their deletion may be used to manipulate the glycosylation pattern in *P. pastoris* or, by analogy, in any other host cell, e.g., fungus, plant, insect or animal cells, with similar glycosylation pathways.

The creation of gene knock-outs, once a given target gene sequence has been determined, is a well-established technique in the art and can be carried out by one of ordinary skill in the art (see, e.g., R. Rothstein, (1991) Methods in Enzymology, vol. 194, p. 281). The choice of a host organism may be influenced by the availability of good transformation and gene disruption techniques.

If several mannosyltransferases are to be knocked out, the method developed by Alani and Kleckner, (*Genetics* 116: 541-545 (1987)), for example, enables the repeated use of a selectable marker, e.g., the URA3 marker in yeast, to sequentially eliminate all undesirable endogenous mannosyltransferase activity. This technique has been refined by others but basically involves the use of two repeated DNA sequences, flanking a counter selectable marker. For example: URA3 may be used as a marker to ensure the selection of a transformants that have integrated a construct. By flanking the URA3 marker with direct repeats one may first select for transformants that have integrated the construct and have thus disrupted the target gene. After isolation of the transformants, and their characterization, one may counter select in a second round for those that are resistant to 5-fluoroorotic acid (5-FOA). Colonies that are able to survive on plates containing 5-FOA have lost the URA3 marker again through a crossover event involving the repeats mentioned earlier. This approach thus allows for the repeated use of the same marker and facilitates the disruption of multiple genes without requiring additional markers. Similar techniques for sequential elimination of genes adapted for use in another eukaryotic host cells with other selectable and counter-selectable markers may also be used.

Eliminating specific mannosyltransferases, such as 1,6 mannosyltransferase (OCH1) or mannosylphosphate transferases (MNN6, or genes complementing lbd mutants) or regulators (MNN4) in *P. pastoris* enables one to create engineered strains of this organism which synthesize primarily $Man_8GlcNAc_2$ and which can be used to further modify the glycosylation pattern to resemble more complex glycoform structures, e.g., those produced in mammalian, e.g., human cells. A preferred embodiment of this method utilizes DNA sequences encoding biochemical glycosylation activities to eliminate similar or identical biochemical functions in *P. pastoris* to modify the glycosylation structure of glycoproteins produced in the genetically altered *P. pastoris* strain.

Methods used to engineer the glycosylation pathway in yeasts as exemplified herein can be used in filamentous fungi to produce a preferred substrate for subsequent modification. Strategies for modifying glycosylation pathways in *A. niger* and other filamentous fungi, for example, can be developed using protocols analogous to those described herein for engineering strains to produce human-like glycoproteins in yeast. Undesired gene activities involved in 1,2 mannosyltransferase activity, e.g., KTR/KRE homologs, are modified or eliminated. A filamentous fungus, such as *Aspergillus*, is a preferred host because it lacks the 1,6 mannosyltransferase activity and as such, one would not expect a hypermannosylating gene activity, e.g. OCH1, in this host. By contrast, other desired activities (e.g., α-1,2-mannosidase, UDP-GlcNAc transporter, glycosyltransferase (GnT), galactosyltransferase (GalT) and sialyltransferase (ST)) involved in glycosylation are introduced into the host using the targeting methods of the invention.

Engineering or Selecting Hosts Having Diminished Initiating α-1,6 Mannosyltransferase Activity In a preferred embodiment, the method of the invention involves making or using a host cell which is diminished or depleted in the activity of an initiating α-1,6-mannosyltransferase, i.e., an initiation specific enzyme that initiates outer chain mannosylation on the α-1,3 arm of the $Man_3GlcNAc_2$ core structure. In *S. cerevisiae*, this enzyme is encoded by the OCH1 gene. Disruption of the OCH1 gene in *S. cerevisiae* results in a phenotype in which N-linked sugars completely lack the poly-mannose outer chain. Previous approaches for obtaining mammalian-type glycosylation in fungal strains have required inactivation of OCH1 (see, e.g., Chiba et al. (1998) *J. Biol. Chem.* 273:26298-304). Disruption of the initiating α-1,6-mannosyltransferase activity in a host cell of the invention may be optional, however (depending on the selected host cell), as the Och1p enzyme requires an intact $Man_8GlcNAc_2$ for efficient mannose outer chain initiation. Thus, host cells selected or produced according to this invention which accumulate oligosaccharides having seven or fewer mannose residues may produce hypoglycosylated N-glycans that will likely be poor substrates for Och1p (see, e.g., Nakayama et al. (1997) *FEBS Lett.* 412(3):547-50).

The OCH1 gene was cloned from *P. pastoris* (Example 1) and *K. lactis* (Example 9), as described. The nucleic acid and amino acid sequences of the OCH1 gene from *K. lactis* are set forth in SEQ ID NOS: 3 and 4. Using gene-specific primers, a construct was made from each clone to delete the OCH1 gene from the genome of *P. pastoris* and *K. lactis* (Examples 1 and 9, respectively). Host cells depleted in initiating α-1,6-mannosyltransferase activity and engineered to produce N-glycans having a $Man_5GlcNAc_2$ carbohydrate structure were thereby obtained (see, e.g., Examples 4 and 9).

Thus, in another embodiment, the invention provides an isolated nucleic acid molecule having a nucleic acid sequence comprising or consisting of at least forty-five, preferably at least 50, more preferably at least 60 and most preferably 75 or more nucleotide residues of the *K. lactis* OCH1 gene (SEQ ID NO: 3), and homologs, variants and derivatives thereof. The invention also provides nucleic acid molecules that hybridize under stringent conditions to the above-described nucleic acid molecules. Similarly, isolated polypeptides (including muteins, allelic variants, fragments, derivatives, and analogs) encoded by the nucleic acid molecules of the invention are provided. Also provided are vectors, including expression vectors, which comprise the above nucleic acid molecules of the invention, as described further herein. Similarly, host cells transformed with the nucleic acid molecules or vectors of the invention are provided.

The invention further provides methods of making or using a non-human eukaryotic host cell diminished or depleted in an alg gene activity (i.e., alg activities, including equivalent enzymatic activities in non-fungal host cells) and introducing into the host cell at least one glycosidase activity. In a preferred embodiment, the glycosidase activity is introduced by causing expression of one or more mannosidase activities within the host cell, for example, by activation of a mannosidase activity, or by expression from a nucleic acid molecule of a mannosidase activity, in the host cell.

In yet another embodiment, the invention provides a method for producing a human-like glycoprotein in a non-human host, wherein the glycoprotein comprises an N-glycan having at least two GlcNAcs attached to a trimannose core structure.

Expression of Class 2 Mannosidases in Lower Eukaryotes

The present invention additionally provides a method for making more human-like glycoproteins in lower eukaryotic host cells by expressing a gene encoding a catalytically active Class 2 mannosidases (EC. 3.2.1.114) (homologs, variants, derivatives and catalytically active fragment thereof).

Using known techniques in the art, gene-specific primers are designed to complement the homologous regions of the Class 2 mannosidase genes (e.g. *D. melanogaster* α-mannosidase II) in order to PCR amplify the mannosidase gene.

Through the expression of an active Class 2 mannosidase in a cell from a nucleic acid encoding the Class 2 mannosidase a host cell (e.g. *P. pastoris*) is engineered to produce more human-like glycoproteins (see, e.g., Examples 17-25).

In one aspect of the invention, a method is provided for producing a human-like glycoprotein in a lower eukaryote (e.g. *P. pastoris*) by constructing a library of α-mannosidase II enzymes. In a preferred embodiment, a sub-library of *D. melanogaster* α-mannosidase II sequences (e.g. Genbank Accession No. X77652) is fused to a sub-library of *S. cerevisiae* MNN2 targeting peptide sequences. In a more preferred embodiment of the invention, a fusion construct comprising *D. melanogaster* Mannosidase II Δ74/MNN2(s) is transformed into a *P. pastoris* host producing $GlcNAcMan_5GlcNAc_2$. See Choi et al. *Proc Natl Acad Sci USA*. 2003 Apr. 29; 100(9):5022-7 and WO 02/00879, which disclose methods for making human-like glycoproteins in lower eukaryotes having the above N-glycan structure, which is now designated *P. pastoris* YSH-1.

In another embodiment, a Golgi α-mannosidase II sequence is selected from, rat, mouse, human, worms, plants and insects. Such sequences are available in databases such as Swissprot and Genbank. For example, sequences for the following genes were found in Genbank: *Arabidopsis thaliana* Mannosidase II (NM_121499); *C. elegans* Mannosidase II (NM_073594); *Ciona intestinalis* mannosidase II (AK116684); *Drosophila melanogaster* mannosidase II (X77652); human mannosidase II (U31520); mouse mannosidase II (X61172); rat mannosidase II (XM_218816); human mannosidase IIx (D55649); insect cell mannosidase III (AF005034); human lysosomal mannosidase II (NM_000528); and human cytosolic mannosidase II (NM_006715) (FIGS. 25-35, SEQ ID NOs: 49-59, respectively). Because of the high sequence similarity and the presence of the Manα1,3 and Manα1,6 activity, cytoplasmic mannosidase II and lysosomal mannosidase II will be collectively referred to herein as Class 2 mannosidases.

Other mannosidases that exhibit the Golgi α-mannosidase II activity include, inter alia, insect mannosidase III (AF005034) and human mannosidase IIx (D55649). As such, these mannosidases may also be used to generate a combinatorial DNA library of catalytically active enzymes.

In another aspect of the invention, a sub-library of targeting peptide sequences (leaders) selected from the group consisting of *Saccharomyces* GLS1, *Saccharomyces* MNS1, *Saccharomyces* SEC 12, *Pichia* SEC, *Pichia* OCH1, *Saccharomyces* MNN9, *Saccharomyces* VAN1, *Saccharomyces* ANP1, *Saccharomyces* HOC1, *Saccharomyces* MNN10, *Saccharomyces* MNN11, *Saccharomyces* MNT1, *Pichia* D2, *Pichia* D9, *Pichia* J3, *Saccharomyces* KTR1, *Saccharomyces* KTR2, *Kluyveromyces* GnTI, *Saccharomyces* MNN2, *Saccharomyces* MNN5, *Saccharomyces* YUR1, *Saccharomyces* MNN1, and *Saccharomyces* MNN6 are fused to sequences encoding catalytically active mannosidase II domains. The combination of the leader/catalytic domain library is illustrated in Table 11 (Example 14).

The Golgi α-mannosidase II fusion constructs generated according to the present invention display the α1,3 and α1,6 mannosidase trimming activity. For example, the catalytically active mannosidase II fusion construct cleaves the Manα1,3 and Manα1,6 glycosidic linkages present on $GlcNAcMan_5GlcNAc_2$ to $GlcNAcMan_3GlcNAc_2$ in *P. pastoris* YSH-1. In another example, a catalytically active mannosidase IIx fusion construct cleaves the Manα1,3 and Manα1,6 glycosidic linkages present on $Man_6GlcNAc_2$ to $Man_4GlcNAc_2$.

Class 2 Mannosidase Hydrolysis of Glycosidic Linkage

Figure 36A:
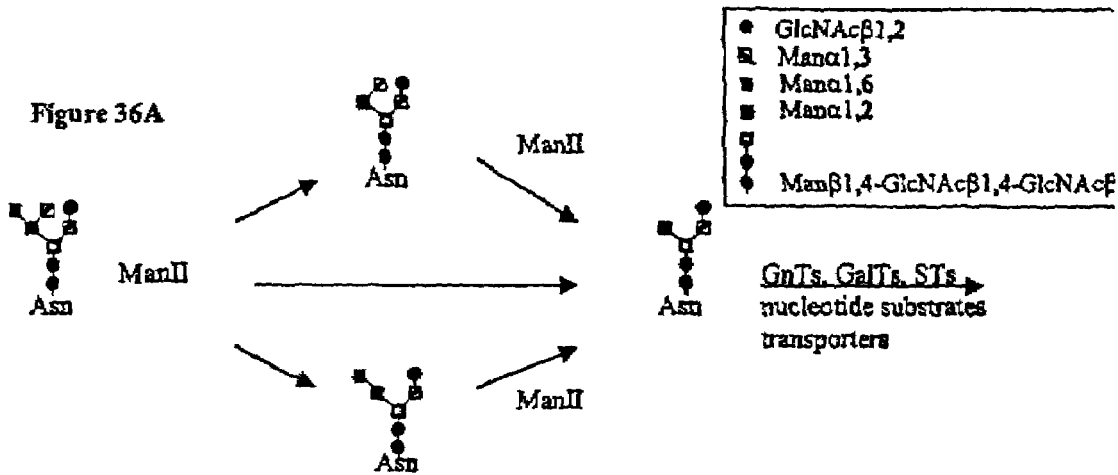
Figure 36B:
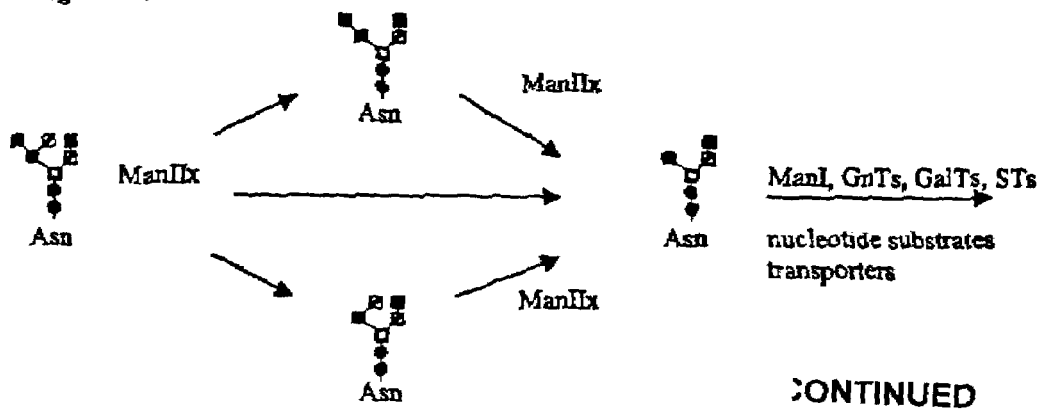

The present invention also encompasses the mechanism in which the catalytically active domain of Class 2 enzymes hydrolyze the Manα1,3 and/or Manα1,6 glycosidic linkages on an oligosaccharide e.g. GlcNAcMan$_5$GlcNAc$_2$ structure to produce GlcNAcMan$_3$GlcNAc$_2$, a desired intermediate for further N-glycan processing in a lower eukaryote. In a first embodiment, the hydrolysis of the glycosidic linkages occurs sequentially. The enzyme hydrolyzes at least one glycosidic linkage and conformationally rotates to hydrolyze the other glycosidic linkage. In a second embodiment, the hydrolysis of the glycosidic linkages occurs simultaneously. The intermediate produced is a substrate for further Golgi processing wherein other glycosylation enzymes such as N-acetylglucosaminyltransferases (GnTs), galactosyltransferases (GalTs) and sialyltransferases (STs) can subsequently modify it to produce a desired glycoform. FIG. 36A illustrates the oligosaccharide intermediates (e.g. GlcNAcMan$_3$GlcNAc$_2$, GlcNAcMan$_4$GlcNAc$_2$) produced via the mannosidase II pathway and FIG. 36B illustrates the oligosaccharide intermediates (e.g. Man$_4$GlcNAc$_2$, Man$_5$GlcNAc$_2$) produced via the mannosidase IIx pathway.

Conserved Regions of the Mannosidase II Enzymes

It is a feature of the present invention to express sequences encoding conserved regions of the mannosidase II enzyme. The present invention provides isolated nucleic acid molecules that comprise the conserved regions of the mannosidase II gene from various sources including insect, mammals, plants and worms.

Several full-length nucleic acid sequences encoding the mannosidase II enzyme have been identified and sequenced. The mannosidase II enzyme sequences are set forth in SEQ ID NO: 49 through SEQ ID NO: 59. An alignment of known mannosidase II sequences (i.e., *Drosophila melanogaster* aligned to other insect, animal and plant sequences) shows a highly conserved motif between amino acids 144-166 and amino acids 222-285 (FIG. 23). Accordingly, in another aspect, the invention relates to a method for providing to a host cell a nucleic acid encoding a Class 2 mannosidase enzyme activity wherein the nucleic acid is characterized by having the above conserved mannosidase II regions.

Moreover, the sequence alignment further reveals several highly conserved cystine-cystine disulfide bridges between amino acids 338-345 and amino acids 346-360 as shown in FIG. 23. These disulfide bridges may play an integral part in substrate binding and recognition, e.g., by maintaining protein architecture.

The present invention also provides catalytically active fragments of Class 2 mannosidases comprising conserved amino acid sequence regions, especially a first amino acid sequence consisting of 23 amino acid residues having the following sequence:

```
144
Leu Lys Val Phe Val Val Pro His Ser   (SEQ ID NO: 5)
His Asn Asp Pro Gly Trp Ile Gln Thr
Phe Glu Glu Tyr Try.
```

In another preferred embodiment, the amino acid residue at position 145 of the first sequence is selected from the group consisting of K E Q N and Y.

In another preferred embodiment, the amino acid residue at position 146 of the first sequence is selected from the group consisting of V and I.

In another preferred embodiment, the amino acid residue at position 147 of the first sequence is selected from the group consisting of F I H and L.

In another preferred embodiment, the amino acid residue at position 148 of the first sequence is selected from the group consisting of V I L and T.

In another preferred embodiment, the amino acid residue at position 149 of the first sequence is selected from the group consisting of V I L and D.

In another preferred embodiment, the amino acid residue at position 150 of the first sequence is selected from the group consisting of P and R.

In another preferred embodiment, the amino acid residue at position 151 of the first sequence is selected from the group consisting of H and L.

In another preferred embodiment, the amino acid residue at position 152 of the first sequence is selected from the group consisting of S T and G.

In another preferred embodiment, the amino acid residue at position 153 of the first sequence is selected from the group consisting of H and E.

In another preferred embodiment, the amino acid residue at position 154 of the first sequence is selected from the group consisting of N C D and R.

In another preferred embodiment, the amino acid residue at position 156 of the first sequence is selected from the group consisting of P and V.

In another preferred embodiment, the amino acid residue at position 157 of the first sequence is selected from the group consisting of G and R In another preferred embodiment, the amino acid residue at position 158 of the first sequence is selected from the group consisting of W and L In another preferred embodiment, the amino acid residue at position 159 of the first sequence is selected from the group consisting of I L K and T.

In another preferred embodiment, the amino acid residue at position 160 of the first sequence is selected from the group consisting of Q M K and L.

In another preferred embodiment, the amino acid residue at position 161 of the first sequence is selected from the group consisting of T and Y.

In another preferred embodiment, the amino acid residue at position 162 of the first sequence is selected from the group consisting of F and V.

In another preferred embodiment, the amino acid residue at position 163 of the first sequence is selected from the group consisting of E D and N.

In another preferred embodiment, the amino acid residue at position 164 of the first sequence is selected from the group consisting of E K D R Q and V.

In another preferred embodiment, the amino acid residue at position 165 of the first sequence is selected from the group consisting of Y and A.

In another preferred embodiment, the amino acid residue at position 166 of the first sequence is selected from the group consisting of Y F and C.

The present invention further provides a catalytically active fragment of a Class 2 mannosidase comprising conserved amino acid sequence regions, especially a second amino acid sequence consisting of 57 amino acid residues having the following sequence:

```
222
Glu Phe Val Thr Gly Gly Trp Val Met    (SEQ ID NO: 6)

Pro Asp Glu Ala Asn Ser Trp Arg Asn

Val Leu Leu Gln Leu Thr Glu Gly Gln

Thr Trp Leu Lys Gln Phe Met Asn Val

Thr Pro Thr Ala Ser Trp Ala Ile Asp

Pro Phe Gly His Ser Pro Thr Met Pro

Tyr Ile Leu.
```

In another preferred embodiment, the amino acid residue at position 222 of the first sequence is selected from the group consisting of E and R.

In another preferred embodiment, the amino acid residue at position 223 of the first sequence is selected from the group consisting of F I and S.

In another preferred embodiment, the amino acid residue at position 224 of the first sequence is selected from the group consisting of V A T and F In another preferred embodiment, the amino acid residue at position 225 of the first sequence is selected from the group consisting of T G N and Q.

In another preferred embodiment, the amino acid residue at position 226 of the first sequence is selected from the group consisting of G and A.

In another preferred embodiment, the amino acid residue at position 227 of the first sequence is selected from the group consisting of G and L.

In another preferred embodiment, the amino acid residue at position 228 of the first sequence is selected from the group consisting of W and Y.

In another preferred embodiment, the amino acid residue at position 229 of the first sequence is selected from the group consisting of V and T.

In another preferred embodiment, the amino acid residue at position 230 of the first sequence is selected from the group consisting of M and A.

In another preferred embodiment, the amino acid residue at position 231 of the first sequence is selected from the group consisting of P T and N.

In another preferred embodiment, the amino acid residue at position 232 of the first sequence is selected from the group consisting of D and Q.

In another preferred embodiment, the amino acid residue at position 233 of the first sequence is selected from the group consisting of E and M.

In another preferred embodiment, the amino acid residue at position 234 of the first sequence is selected from the group consisting of A and V.

In another preferred embodiment, the amino acid residue at position 235 of the first sequence is selected from the group consisting of N T C and A.

In another preferred embodiment, the amino acid residue at position 236 of the first sequence is selected from the group consisting of S A P T and V.

In another preferred embodiment, the amino acid residue at position 237 of the first sequence is selected from the group consisting of H and C.

In another preferred embodiment, the amino acid residue at position 238 of the first sequence is selected from the group consisting of W Y I and D.

In another preferred embodiment, the amino acid residue at position 239 of the first sequence is selected from the group consisting of R H F Y G and P.

In another preferred embodiment, the amino acid residue at position 240 of the first sequence is selected from the group consisting of N S and A.

In another preferred embodiment, the amino acid residue at position 241 of the first sequence is selected from the group consisting of V M L I and Q.

In another preferred embodiment, the amino acid residue at position 242 of the first sequence is selected from the group consisting of L I V and P.

In another preferred embodiment, the amino acid residue at position 243 of the first sequence is selected from the group consisting of L T G D and E.

In another preferred embodiment, the amino acid residue at position 244 of the first sequence is selected from the group consisting of Q E and T.

In another preferred embodiment, the amino acid residue at position 245 of the first sequence is selected from the group consisting of L M and F.

In another preferred embodiment, the amino acid residue at position 246 of the first sequence is selected from the group consisting of T F I A and P.

In another preferred embodiment, the amino acid residue at position 247 of the first sequence is selected from the group consisting of E L and V.

In another preferred embodiment, the amino acid residue at position 248 of the first sequence is selected from the group consisting of G and A.

In another preferred embodiment, the amino acid residue at position 249 of the first sequence is selected from the group consisting of Q H P M N and L.

In another preferred embodiment, the amino acid residue at position 250 of the first sequence is selected from the group consisting of T E P Q M H R and A.

In another preferred embodiment, the amino acid residue at position 251 of the first sequence is selected from the group consisting of W P F and L.

In another preferred embodiment, the amino acid residue at position 252 of the first sequence is selected from the group consisting of L I V and A.

In another preferred embodiment, the amino acid residue at position 253 of the first sequence is selected from the group consisting of K Q R E N and S.

In another preferred embodiment, the amino acid residue at position 254 of the first sequence is selected from the group consisting of Q N R K D and T.

In another preferred embodiment, the amino acid residue at position 255 of the first sequence is selected from the group consisting of F H N and T.

In another preferred embodiment, the amino acid residue at position 256 of the first sequence is selected from the group consisting of M I L and F.

In another preferred embodiment, the amino acid residue at position 257 of the first sequence is selected from the group consisting of N and G.

In another preferred embodiment, the amino acid residue at position 258 of the first sequence is selected from the group consisting of V A G and H.

In another preferred embodiment, the amino acid residue at position 259 of the first sequence is selected from the group consisting of T I K V R and G.

In another preferred embodiment, the amino acid residue at position 260 of the first sequence is selected from the group consisting of P and G.

In another preferred embodiment, the amino acid residue at position 261 of the first sequence is selected from the group consisting of T Q R K and E.

In another preferred embodiment, the amino acid residue at position 262 of the first sequence is selected from the group consisting of A S N T and V.

In another preferred embodiment, the amino acid residue at position 263 of the first sequence is selected from the group consisting of S H G A and Q.

in another preferred embodiment, the amino acid residue at position 264 of the first sequence is selected from the group consisting of W and H.

In another preferred embodiment, the amino acid residue at position 265 of the first sequence is selected from the group consisting of A S H and T.

In another preferred embodiment, the amino acid residue at position 266 of the first sequence is selected from the group consisting of I and V.

In another preferred embodiment, the amino acid residue at position 267 of the first sequence is selected from the group consisting of D and H.

In another preferred embodiment, the amino acid residue at position 268 of the first sequence is selected from the group consisting of P and A.

In another preferred embodiment, the amino acid residue at position 269 of the first sequence is selected from the group consisting of F and T.

In another preferred embodiment, the amino acid residue at position 271 of the first sequence is selected from the group consisting of H L and Y.

In another preferred embodiment, the amino acid residue at position 272 of the first sequence is selected from the group consisting of S T G and C.

, In another preferred embodiment, the amino acid residue at position 273 of the first sequence is selected from the group consisting of P S A R and H.

In another preferred embodiment, the amino acid residue at position 274 of the first sequence is selected from the group consisting of T S E and 1.

In another preferred embodiment, the amino acid residue at position 275 of the first sequence is selected from the group consisting of M V Q and D.

In another preferred embodiment, the amino acid residue at position 276 of the first sequence is selected from the group consisting of P A and T.

In another preferred embodiment, the amino acid residue at position 277 of the first sequence is selected from the group consisting of Y H S and A.

In another preferred embodiment, the amino acid residue at position 278 of the first sequence is selected from the group consisting of I L and W.

In another preferred embodiment, the amino acid residue at position 279 of the first sequence is selected from the group consisting of L and F.

In another preferred embodiment, the amino acid residue at position 280 of the first sequence is selected from the group consisting of Q T R K N D A and W.

In another preferred embodiment, the amino acid residue at position 281 of the first sequence is selected from the group consisting of K S R Q and P.

In another preferred embodiment, the amino acid residue at position 282 of the first sequence is selected from the group consisting of S A and M.

In another preferred embodiment, the amino acid residue at position 283 of the first sequence is selected from the group consisting of G N and K.

In another preferred embodiment, the amino acid residue at position 284 of the first sequence is selected from the group consisting of F I and L.

In another preferred embodiment, the amino acid residue at position 285 of the first sequence is selected from the group consisting of K T S E and D.

The present invention also provides a catalytically active fragment of a Class 2 mannosidase comprising conserved amino acid sequence regions, especially a third amino acid sequence consisting of 33 amino acid residues having the following sequence:

```
325
His Met Met Pro Phe Tyr Ser Tyr Asp    (SEQ ID NO: 7)
Ile Pro His Thr Cys Gly Pro Asp Pro
Arg Ile Cys Cys Gln Phe Asp Phe Arg
Arg Met Pro Gly Gly Arg.
```

In another preferred embodiment, the amino acid residue at position 325 of the first sequence is selected from the group consisting of H P and S.

In another preferred embodiment, the amino acid residue at position 326 of the first sequence is selected from the group consisting of M I L N T and R.

In another preferred embodiment, the amino acid residue at position 327 of the first sequence is selected from the group consisting of M Q A and Y.

In another preferred embodiment, the amino acid residue at position 328 of the first sequence is selected from the group consisting of P and D.

In another preferred embodiment, the amino acid residue at position 329 of the first sequence is selected from the group consisting of F L and G.

In another preferred embodiment, the amino acid residue at position 330 of the first sequence is selected from the group consisting of Y D F and L.

In another preferred embodiment, the amino acid residue at position 331 of the first sequence is selected from the group consisting of S I T and Y.

In another preferred embodiment, the amino acid residue at position 332 of the first sequence is selected from the group consisting of Y G and S.

In another preferred embodiment, the amino acid residue at position 333 of the first sequence is selected from the group consisting of D S V and R.

In another preferred embodiment, the amino acid residue at position 334 of the first sequence is selected from the group consisting of I V and L.

In another preferred embodiment, the amino acid residue at position 335 of the first sequence is selected from the group consisting of P K and Q.

In another preferred embodiment, the amino acid residue at position 336 of the first sequence is selected from the group consisting of H S N and E.

In another preferred embodiment, the amino acid residue at position 337 of the first sequence is selected from the group consisting of T G and F.

In another preferred embodiment, the amino acid residue at position 338 of the first sequence is selected from the group consisting of C Y and A.

In another preferred embodiment, the amino acid residue at position 339 of the first sequence is selected from the group consisting of G N and C.

In another preferred embodiment, the amino acid residue at position 340 of the first sequence is selected from the group consisting of P and R.

In another preferred embodiment, the amino acid residue at position 341 of the first sequence is selected from the group consisting of D E H P and G.

In another preferred embodiment, the amino acid residue at position 342 of the first sequence is selected from the group consisting of P R and Q.

In another preferred embodiment, the amino acid residue at position 343 of the first sequence is selected from the group consisting of K S A N and F.

In another preferred embodiment, the amino acid residue at position 344 of the first sequence is selected from the group consisting of V I and L.

In another preferred embodiment, the amino acid residue at position 345 of the first sequence is selected from the group consisting of C and P.

In another preferred embodiment, the amino acid residue at position 346 of the first sequence is selected from the group consisting of C L W and V.

In another preferred embodiment, the amino acid residue at position 347 of the first sequence is selected from the group consisting of Q S D and G.

In another preferred embodiment, the amino acid residue at position 348 of the first sequence is selected from the group consisting of F V and G.

In another preferred embodiment, the amino acid residue at position 349 of the first sequence is selected from the group consisting of D L and T.

In another preferred embodiment, the amino acid residue at position 350 of the first sequence is selected from the group consisting of F C and W.

In another preferred embodiment, the amino acid residue at position 351 of the first sequence is selected from the group consisting of R K A and V.

In another preferred embodiment, the amino acid residue at position 352 of the first sequence is selected from the group consisting of R K D and E.

In another preferred embodiment, the amino acid residue at position 353 of the first sequence is selected from the group consisting of M L I and Q.

In another preferred embodiment, the amino acid residue at position 354 of the first sequence is selected from the group consisting of G P R and D.

In another preferred embodiment, the amino acid residue at position 355 of the first sequence is selected from the group consisting of S E G In another preferred embodiment, the amino acid residue at position 356 of the first sequence is selected from the group consisting of F G and N.

In another preferred embodiment, the amino acid residue at position 357 of the first sequence is selected from the group consisting of G R K and L.

The present invention further provides a catalytically active fragment of a Class 2 mannosidase comprising conserved amino acid sequence regions, especially a fourth amino acid sequence consisting of 28 amino acid residues having the following sequence:

```
380
Leu Leu Leu Asp Gln Tyr Arg Lys Lys  (SEQ ID NO: 8)

Ser Glu Leu Phe Arg Thr Asn Val Leu

Leu Ile Pro Leu Gly Asp Asp Phe Arg

Tyr.
```

In another preferred embodiment, the amino acid residue at position 380 of the first sequence is selected from the group consisting of L M I K T and Y.

In another preferred embodiment, the amino acid residue at position 381 of the first sequence is selected from the group consisting of L I F and C.

In another preferred embodiment, the amino acid residue at position 382 of the first sequence is selected from the group consisting of V Y L I and S.

In another preferred embodiment, the amino acid residue at position 383 of the first sequence is selected from the group consisting of D E N and K.

In another preferred embodiment, the amino acid residue at position 384 of the first sequence is selected from the group consisting of Q E V and F.

In another preferred embodiment, the amino acid residue at position 385 of the first sequence is selected from the group consisting of W Y and A.

In another preferred embodiment, the amino acid residue at position 386 of the first sequence is selected from the group consisting of R D T and L.

In another preferred embodiment, the amino acid residue at position 387 of the first sequence is selected from the group consisting of K R A and P.

In another preferred embodiment, the amino acid residue at position 388 of the first sequence is selected from the group consisting of K I Q and D.

In another preferred embodiment, the amino acid residue at position 389 of the first sequence is selected from the group consisting of A S G and T.

In another preferred embodiment, the amino acid residue at position 390 of the first sequence is selected from the group consisting of E Q R K T S and F.

In another preferred embodiment, the amino acid residue at position 391 of the first sequence is selected from the group consisting of L Y and G.

In another preferred embodiment, the amino acid residue at position 392 of the first sequence is selected from the group consisting of Y F and T.

In another preferred embodiment, the amino acid residue at position 393 of the first sequence is selected from the group consisting of R P and S.

In another preferred embodiment, the amino acid residue at position 394 of the first sequence is selected from the group consisting of T N S H and A.

In another preferred embodiment, the amino acid residue at position 395 of the first sequence is selected from the group consisting of N S K D and Q.

In another preferred embodiment, the amino acid residue at position 396 of the first sequence is selected from the group consisting of V T H and L.

In another preferred embodiment, the amino acid residue at position 397 of the first sequence is selected from the group consisting of L I V T and P.

In another preferred embodiment, the amino acid residue at position 398 of the first sequence is selected from the group consisting of L F V and Q.

In another preferred embodiment, the amino acid residue at position 399 of the first sequence is selected from the group consisting of I Q V A and M.

In another preferred embodiment, the amino acid residue at position 400 of the first sequence is selected from the group consisting of P I T and M.

In another preferred embodiment, the amino acid residue at position 401 of the first sequence is selected from the group consisting of L M and H.

In another preferred embodiment, the amino acid residue at position 403 of the first sequence is selected from the group consisting of D S and C.

In another preferred embodiment, the amino acid residue at position 404 of the first sequence is selected from the group consisting of D and G.

In another preferred embodiment, the amino acid residue at position 405 of the first sequence is selected from the group consisting of F and I.

In another preferred embodiment, the amino acid residue at position 406 of the first sequence is selected from the group consisting of R and Q.

In another preferred embodiment, the amino acid residue at position 407 of the first sequence is selected from the group consisting of F Y and R.

The present invention also provides a catalytically active fragment of a Class 2 mannosidase comprising conserved amino acid sequence regions, especially a fifth amino acid sequence consisting of 12 amino acid residues having the following sequence:

```
438
Gln Phe Gly Thr Leu Ser Asp Tyr Phe  (SEQ ID NO: 9)
Asp Ala Leu.
```

In another preferred embodiment, the amino acid residue at position 438 of the first sequence is selected from the group consisting of Q K L and H.

In another preferred embodiment, the amino acid residue at position 439 of the first sequence is selected from the group consisting of F and Y.

In another preferred embodiment, the amino acid residue at position 440 of the first sequence is selected from the group consisting of G S and P.

In another preferred embodiment, the amino acid residue at position 441 of the first sequence is selected from the group consisting of T and P.

In another preferred embodiment, the amino acid residue at position 442 of the first sequence is selected from the group consisting of L P and G.

In another preferred embodiment, the amino acid residue at position 443 of the first sequence is selected from the group consisting of Q S E L A and D.

In another preferred embodiment, the amino acid residue at position 444 of the first sequence is selected from the group consisting of E D C and S.

In another preferred embodiment, the amino acid residue at position 445 of the first sequence is selected from the group consisting of Y and F.

In another preferred embodiment, the amino acid residue at position 446 of the first sequence is selected from the group consisting of F L and G.

In another preferred embodiment, the amino acid residue at position 447 of the first sequence is selected from the group consisting of D K R N W and M.

In another preferred embodiment, the amino acid residue at position 448 of the first sequence is selected from the group consisting of A K T E and Q.

In another preferred embodiment, the amino acid residue at position 449 of the first sequence is selected from the group consisting of V L M and G.

The present invention also provides a catalytically active fragment of a Class 2 mannosidase comprising conserved amino acid sequence regions, especially a sixth amino acid sequence consisting of 14 amino acid residues having the following sequence:

```
463
Leu Ser Gly Asp Phe Phe Thr Tyr  (SEQ ID NO: 10)
Ala Asp Arg Ser Asp His.
```

In another preferred embodiment, the amino acid residue at position 463 of the first sequence is selected from the group consisting of L F and K.

In another preferred embodiment, the amino acid residue at position 464 of the first sequence is selected from the group consisting of S K H and D.

In another preferred embodiment, the amino acid residue at position 465 of the first sequence is selected from the group consisting of G D and V.

In another preferred embodiment, the amino acid residue at position 466 of the first sequence is selected from the group consisting of D and A.

In another preferred embodiment, the amino acid residue at position 467 of the first sequence is selected from the group consisting of F and N.

In another preferred embodiment, the amino acid residue at position 468 of the first sequence is selected from the group consisting of F and N.

In another preferred embodiment, the amino acid residue at position 469 of the first sequence is selected from the group consisting of T S V P and R.

In another preferred embodiment, the amino acid residue at position 470 of the first sequence is selected from the group consisting of Y and D.

In another preferred embodiment, the amino acid residue at position 471 of the first sequence is selected from the group consisting of A S and K.

In another preferred embodiment, the amino acid residue at position 472 of the first sequence is selected from the group consisting of D and G.

In another preferred embodiment, the amino acid residue at position 473 of the first sequence is selected from the group consisting of R I and G.

In another preferred embodiment, the amino acid residue at position 474 of the first sequence is selected from the group consisting of S D E Q F P and A.

In another preferred embodiment, the amino acid residue at position 475 of the first sequence is selected from the group consisting of D Q S H and N.

In another preferred embodiment, the amino acid residue at position 476 of the first sequence is selected from the group consisting of N H D E and Q.

The present invention further provides a catalytically active fragment of a Class 2 mannosidase comprising conserved amino acid sequence regions, especially a seventh amino acid sequence consisting of 20 amino acid residues having the following sequence:

```
477
Tyr Trp Ser Gly Tyr Tyr Thr Ser  (SEQ ID NO: 11)
Arg Pro Phe Tyr Arg Arg Met Asp
Arg Val Leu Glu.
```

In another preferred embodiment, the amino acid residue at position 477 of the first sequence is selected from the group consisting of Y and F.

In another preferred embodiment, the amino acid residue at position 478 of the first sequence is selected from the group consisting of W and G.

In another preferred embodiment, the amino acid residue at position 479 of the first sequence is selected from the group consisting of S T and F.

In another preferred embodiment, the amino acid residue at position 481 of the first sequence is selected from the group consisting of Y and D.

In another preferred embodiment, the amino acid residue at position 482 of the first sequence is selected from the group consisting of Y F and G.

In another preferred embodiment, the amino acid residue at position 483 of the first sequence is selected from the group consisting of T V S and G.

In another preferred embodiment, the amino acid residue at position 484 of the first sequence is selected from the group consisting of S T and G.

In another preferred embodiment, the amino acid residue at position 485 of the first sequence is selected from the group consisting of R and G.

In another preferred embodiment, the amino acid residue at position 487 of the first sequence is selected from the group consisting of Y F A and T.

In another preferred embodiment, the amino acid residue at position 488 of the first sequence is selected from the group consisting of H Y F L and Q.

In another preferred embodiment, the amino acid residue at position 489 of the first sequence is selected from the group consisting of K and T.

In another preferred embodiment, the amino acid residue at position 490 of the first sequence is selected from the group consisting of R Q S M A and I.

In another preferred embodiment, the amino acid residue at position 491 of the first sequence is selected from the group consisting of M L Q V and Y.

In another preferred embodiment, the amino acid residue at position 492 of the first sequence is selected from the group consisting of D E and A.

In another preferred embodiment, the amino acid residue at position 494 of the first sequence is selected from the group consisting of V I Q and L.

In another preferred embodiment, the amino acid residue at position 495 of the first sequence is selected from the group consisting of L M F S and K.

In another preferred embodiment, the amino acid residue at position 496 of the first sequence is selected from the group consisting of M Q E Y and R.

The present invention also provides a catalytically active fragment of a Class 2 mannosidase comprising conserved amino acid sequence regions, especially a eighth amino acid sequence consisting of 27 amino acid residues having the following sequence:

```
524
Ala Arg Arg Glu Leu Gly Leu Phe    (SEQ ID NO: 12)

Gln His His Asp Ala Ile Thr Gly

Thr Ala Arg Asp His Val Val Val

Asp Tyr Gly.
```

In another preferred embodiment, the amino acid residue at position 524 of the first sequence is selected from the group consisting of A L and W.

In another preferred embodiment, the amino acid residue at position 525 of the first sequence is selected from the group consisting of R N and V.

In another preferred embodiment, the amino acid residue at position 526 of the first sequence is selected from the group consisting of R Q E and G.

In another preferred embodiment, the amino acid residue at position 527 of the first sequence is selected from the group consisting of E A T and N.

In another preferred embodiment, the amino acid residue at position 528 of the first sequence is selected from the group consisting of L and M.

In another preferred embodiment, the amino acid residue at position 529 of the first sequence is selected from the group consisting of S G A and F.

In another preferred embodiment, the amino acid residue at position 530 of the first sequence is selected from the group consisting of L and V.

In another preferred embodiment, the amino acid residue at position 531 of the first sequence is selected from the group consisting of F L and E.

In another preferred embodiment, the amino acid residue at position 532 of the first sequence is selected from the group consisting of Q and L.

In another preferred embodiment, the amino acid residue at position 534 of the first sequence is selected from the group consisting of H and N.

In another preferred embodiment, the amino acid residue at position 535 of the first sequence is selected from the group consisting of D and G.

In another preferred embodiment, the amino acid residue at position 536 of the first sequence is selected from the group consisting of G A and T.

In another preferred embodiment, the amino acid residue at position 537 of the first sequence is selected from the group consisting of I V and Y.

In another preferred embodiment, the amino acid residue at position 538 of the first sequence is selected from the group consisting of T and S.

In another preferred embodiment, the amino acid residue at position 539 of the first sequence is selected from the group consisting of G and T.

In another preferred embodiment, the amino acid residue at position 540 of the first sequence is selected from the group consisting of T and H.

In another preferred embodiment, the amino acid residue at position 541 of the first sequence is selected from the group consisting of A and S.

In another preferred embodiment, the amino acid residue at position 542 of the first sequence is selected from the group consisting of K R and Q.

In another preferred embodiment, the amino acid residue at position 543 of the first sequence is selected from the group consisting of T D E S Q and I.

In another preferred embodiment, the amino acid residue at position 544 of the first sequence is selected from the group consisting of H A W Y S and K.

In another preferred embodiment, the amino acid residue at position 545 of the first sequence is selected from the group consisting of V and K.

In another preferred embodiment, the amino acid residue at position 546 of the first sequence is selected from the group consisting of V M A and G.

In another preferred embodiment, the amino acid residue at position 547 of the first sequence is selected from the group consisting of V L Q and N.

In another preferred embodiment, the amino acid residue at position 548 of the first sequence is selected from the group consisting of D and R.

In another preferred embodiment, the amino acid residue at position 549 of the first sequence is selected from the group consisting of Y and E.

In another preferred embodiment, the amino acid residue at position 550 of the first sequence is selected from the group consisting of E G A and C.

The present invention also provides a catalytically active fragment of a Class 2 mannosidase comprising conserved amino acid sequence regions, especially a ninth amino acid sequence consisting of 11 amino acid residues having the following sequence:

```
788
Gly Ala Tyr Leu Phe Leu Pro Asp   (SEQ ID NO: 13)

Gly Glu Ala.
```

In another preferred embodiment, the amino acid residue at position 789 of the first sequence is selected from the group consisting of A and W.

In another preferred embodiment, the amino acid residue at position 790 of the first sequence is selected from the group consisting of Y and D.

In another preferred embodiment, the amino acid residue at position 791 of the first sequence is selected from the group consisting of L I and V.

In another preferred embodiment, the amino acid residue at position 792 of the first sequence is selected from the group consisting of F and M.

In another preferred embodiment, the amino acid residue at position 793 of the first sequence is selected from the group consisting of L K M R and D.

In another preferred embodiment, the amino acid residue at position 794 of the first sequence is selected from the group consisting of P and Y.

In another preferred embodiment, the amino acid residue at position 795 of the first sequence is selected from the group consisting of N D A and H.

In another preferred embodiment, the amino acid residue at position 796 of the first sequence is selected from the group consisting of G N Y Q and L.

In another preferred embodiment, the amino acid residue at position 797 of the first sequence is selected from the group consisting of P E Q N and D.

In another preferred embodiment, the amino acid residue at position 798 of the first sequence is selected from the group consisting of A G S K and T.

The present invention further provides a catalytically active fragment of a Class 2 mannosidase comprising conserved amino acid sequence regions, especially a tenth amino acid sequence consisting of 14 amino acid residues having the following sequence:

```
867
Phe Tyr Thr Asp Leu Asn Gly Phe   (SEQ ID NO: 14)
Gln Met Gln Lys Arg Arg.
```

In another preferred embodiment, the amino acid residue at position 867 of the first sequence is selected from the group consisting of F T and Y.

In another preferred embodiment, the amino acid residue at position 868 of the first sequence is selected from the group consisting of Y F S and E.

In another preferred embodiment, the amino acid residue at position 869 of the first sequence is selected from the group consisting of T I and S.

In another preferred embodiment, the amino acid residue at position 870 of the first sequence is selected from the group consisting of D and Q.

In another preferred embodiment, the amino acid residue at position 871 of the first sequence is selected from the group consisting of L T Q S and F.

In another preferred embodiment, the amino acid residue at position 872 of the first sequence is selected from the group consisting of N S and G.

In another preferred embodiment, the amino acid residue at position 873 of the first sequence is selected from the group consisting of G T and H.

In another preferred embodiment, the amino acid residue at position 874 of the first sequence is selected from the group consisting of L M F AY and R.

In another preferred embodiment, the amino acid residue at position 875 of the first sequence is selected from the group consisting of Q R and E.

In another preferred embodiment, the amino acid residue at position 876 of the first sequence is selected from the group consisting of F M V I Y and R.

In another preferred embodiment, the amino acid residue at position 877 of the first sequence is selected from the group consisting of I Q S L and P.

In another preferred embodiment, the amino acid residue at position 878 of the first sequence is selected from the group consisting of K P R E and T.

In another preferred embodiment, the amino acid residue at position 879 of the first sequence is selected from the group consisting of R and H.

In another preferred embodiment, the amino acid residue at position 880 of the first sequence is selected from the group consisting of R M T E V and Y.

The present invention further provides a catalytically active fragment of a Class 2 mannosidase comprising conserved amino acid sequence regions, especially a eleventh amino acid sequence consisting of 66 amino acid residues having the following sequence:

```
904
Lys Leu Pro Leu Gln Ala Asn Tyr   (SEQ ID NO: 15)

Tyr Pro Met Pro Ser Met Ala Tyr

Ile Gln Asp Ala Asn Thr Arg Leu

Thr Leu Leu Thr Gly Gln Pro Leu

Gly Val Ser Ser Leu Ala Ser Gly

Gln Leu Glu Val Met Leu Asp Arg

Arg Leu Met Ser Asp Asp Asn Arg

Gly Leu Gly Gln Gly Val Leu Asp

Asn Lys.
```

In another preferred embodiment, the amino acid residue at position 904 of the first sequence is selected from the group consisting of N T Q E and K.

In another preferred embodiment, the amino acid residue at position 905 of the first sequence is selected from the group consisting of T R K H S Q M and F.

In another preferred embodiment, the amino acid residue at position 906 of the first sequence is selected from the group consisting of R Q and G.

In another preferred embodiment, the amino acid residue at position 907 of the first sequence is selected from the group consisting of L M and F.

In another preferred embodiment, the amino acid residue at position 908 of the first sequence is selected from the group consisting of T S and A.

In another preferred embodiment, the amino acid residue at position 909 of the first sequence is selected from the group consisting of L 1 and V.

In another preferred embodiment, the amino acid residue at position 910 of the first sequence is selected from the group consisting of L H and M.

In another preferred embodiment, the amino acid residue at position 911 of the first sequence is selected from the group consisting of T S and N.

In another preferred embodiment, the amino acid residue at position 912 of the first sequence is selected from the group consisting of G A R N and D.

In another preferred embodiment, the amino acid residue at position 913 of the first sequence is selected from the group consisting of Q H R and C.

In another preferred embodiment, the amino acid residue at position 914 of the first sequence is selected from the group consisting of P A S and K.

In another preferred embodiment, the amino acid residue at position 915 of the first sequence is selected from the group consisting of L Q and Y.

In another preferred embodiment, the amino acid residue at position 917 of the first sequence is selected from the group consisting of G V and A.

In another preferred embodiment, the amino acid residue at position 918 of the first sequence is selected from the group consisting of S and A.

In another preferred embodiment, the amino acid residue at position 919 of the first sequence is selected from the group consisting of S and A.

In another preferred embodiment, the amino acid residue at position 920 of the first sequence is selected from the group consisting of L M and Y.

In another preferred embodiment, the amino acid residue at position 921 of the first sequence is selected from the group consisting of A S G K E R and V.

In another preferred embodiment, the amino acid residue at position 922 of the first sequence is selected from the group consisting of S N D E P and R.

In another preferred embodiment, the amino acid residue at position 924 of the first sequence is selected from the group consisting of E Q W R and S.

In another preferred embodiment, the amino acid residue at position 925 of the first sequence is selected from the group consisting of L and I.

In another preferred embodiment, the amino acid residue at position 926 of the first sequence is selected from the group consisting of E and L.

In another preferred embodiment, the amino acid residue at position 927 of the first sequence is selected from the group consisting of I V L and S.

In another preferred embodiment, the amino acid residue at position 928 of the first sequence is selected from the group consisting of M I F V and L.

In another preferred embodiment, the amino acid residue at position 929 of the first sequence is selected from the group consisting of Q L M V and S.

In another preferred embodiment, the amino acid residue at position 930 of the first sequence is selected from the group consisting of D H and L.

In another preferred embodiment, the amino acid residue at position 931 of the first sequence is selected from the group consisting of R and L.

In another preferred embodiment, the amino acid residue at position 933 of the first sequence is selected from the group consisting of L T and A.

In another preferred embodiment, the amino acid residue at position 934 of the first sequence is selected from the group consisting of A S M V L and P.

In another preferred embodiment, the amino acid residue at position 935 of the first sequence is selected from the group consisting of S Q R Y and K.

In another preferred embodiment, the amino acid residue at position 936 of the first sequence is selected from the group consisting of D and A.

In another preferred embodiment, the amino acid residue at position 937 of the first sequence is selected from the group consisting of D and P.

In another preferred embodiment, the amino acid residue at position 938 of the first sequence is selected from the group consisting of E N G F and D.

In another preferred embodiment, the amino acid residue at position 939 of the first sequence is selected from the group consisting of R and A.

In another preferred embodiment, the amino acid residue at position 940 of the first sequence is selected from the group consisting of G and T.

In another preferred embodiment, the amino acid residue at position 941 of the first sequence is selected from the group consisting of L V I and A.

In another preferred embodiment, the amino acid residue at position 942 of the first sequence is selected from the group consisting of G Q E S and D.

In another preferred embodiment, the amino acid residue at position 943 of the first sequence is selected from the group consisting of Q E and T.

In another preferred embodiment, the amino acid residue at position 944 of the first sequence is selected from the group consisting of G and P.

In another preferred embodiment, the amino acid residue at position 945 of the first sequence is selected from the group consisting of V L I and R.

In another preferred embodiment, the amino acid residue at position 946 of the first sequence is selected from the group consisting of L R K H Q M and V.

In another preferred embodiment, the amino acid residue at position 947 of the first sequence is selected from the group consisting of D and E.

In another preferred embodiment, the amino acid residue at position 948 of the first sequence is selected from the group consisting of N and F.

In another preferred embodiment, the amino acid residue at position 949 of the first sequence is selected from the group consisting of K L R G and T.

In another preferred embodiment, the amino acid residue at position 950 of the first sequence is selected from the group consisting of P R I A S and Y.

In another preferred embodiment, the amino acid residue at position 951 of the first sequence is selected from the group consisting of V T M G and A.

In another preferred embodiment, the amino acid residue at position 952 of the first sequence is selected from the group consisting of L V C A P T.

In another preferred embodiment, the amino acid residue at position 953 of the first sequence is selected from the group consisting of H A N E V F W and M.

In another preferred embodiment, the amino acid residue at position 954 of the first sequence is selected from the group consisting of I H R L S V Q and P.

In another preferred embodiment, the amino acid residue at position 955 of the first sequence is selected from the group consisting of Y F N R and H.

In another preferred embodiment, the amino acid residue at position 956 of the first sequence is selected from the group consisting of R V H W G and K.

In another preferred embodiment, the amino acid residue at position 957 of the first sequence is selected from the group consisting of L I R and G.

In another preferred embodiment, the amino acid residue at position 958 of the first sequence is selected from the group consisting of V L M H and S.

In another preferred embodiment, the amino acid residue at position 959 of the first sequence is selected from the group consisting of L I A F.

In another preferred embodiment, the amino acid residue at position 960 of the first sequence is selected from the group consisting of E V and Q.

In another preferred embodiment, the amino acid residue at position 961 of the first sequence is selected from the group consisting of K P R S L and D.

In another preferred embodiment, the amino acid residue at position 962 of the first sequence is selected from the group consisting of V M R W N L and A.

In another preferred embodiment, the amino acid residue at position 963 of the first sequence is selected from the group consisting of N S T I P D and G.

In another preferred embodiment, the amino acid residue at position 964 of the first sequence is selected from the group consisting of N S L V A G and T.

In another preferred embodiment, the amino acid residue at position 965 of the first sequence is selected from the group consisting of C S M G V I Q and A.

In another preferred embodiment, the amino acid residue at position 966 of the first sequence is selected from the group consisting of V S N A T and Q.

In another preferred embodiment, the amino acid residue at position 967 of the first sequence is selected from the group consisting of R G P M T A and D.

In another preferred embodiment, the amino acid residue at position 968 of the first sequence is selected from the group consisting of P N E K and A.

In another preferred embodiment, the amino acid residue at position 969 of the first sequence is selected from the group consisting of S K V E A K and Y.

In another preferred embodiment, the amino acid residue at position 970 of the first sequence is selected from the group consisting of K Q E S R and A.

In another preferred embodiment, the amino acid residue at position 971 of the first sequence is selected from the group consisting of L E Q D K N and G.

In another preferred embodiment, the amino acid residue at position 972 of the first sequence is selected from the group consisting of H E S K T and N.

In another preferred embodiment, the amino acid residue at position 973 of the first sequence is selected from the group consisting of P R S K and N.

In another preferred embodiment, the amino acid residue at position 974 of the first sequence is selected from the group consisting of A V T L P and Y.

In another preferred embodiment, the amino acid residue at position 975 of the first sequence is selected from the group consisting of G S A R and Q.

In another preferred embodiment, the amino acid residue at position 976 of the first sequence is selected from the group consisting of Y F N and V.

In another preferred embodiment, the amino acid residue at position 977 of the first sequence is selected from the group consisting of L H and P.

In another preferred embodiment, the amino acid residue at position 978 of the first sequence is selected from the group consisting of T S and L.

In another preferred embodiment, the amino acid residue at position 979 of the first sequence is selected from the group consisting of S H L M and Q.

In another preferred embodiment, the amino acid residue at position 980 of the first sequence is selected from the group consisting of A V L and T.

In another preferred embodiment, the amino acid residue at position 981 of the first sequence is selected from the group consisting of A G S V and L.

In another preferred embodiment, the amino acid residue at position 982 of the first sequence is selected from the group consisting of H Y D L and P.

In another preferred embodiment, the amino acid residue at position 983 of the first sequence is selected from the group consisting of K L M I Q Y and A.

In another preferred embodiment, the amino acid residue at position 984 of the first sequence is selected from the group consisting of A T S I L and P.

In another preferred embodiment, the amino acid residue at position 985 of the first sequence is selected from the group consisting of S T G and E.

In another preferred embodiment, the amino acid residue at position 986 of the first sequence is selected from the group consisting of Q W M S A R and P.

In another preferred embodiment, the amino acid residue at position 987 of the first sequence is selected from the group consisting of S Y F L E H M and A.

In another preferred embodiment, the amino acid residue at position 988 of the first sequence is selected from the group consisting of L M F V and P.

In another preferred embodiment, the amino acid residue at position 989 of the first sequence is selected from the group consisting of L H N and A.

In another preferred embodiment, the amino acid residue at position 990 of the first sequence is selected from the group consisting of D Y T A and H.

In another preferred embodiment, the amino acid residue at position 991 of the first sequence is selected from the group consisting of P and S.

In another preferred embodiment, the amino acid residue at position 992 of the first sequence is selected from the group consisting of L P A F V I Q and W.

In another preferred embodiment, the amino acid residue at position 993 of the first sequence is selected from the group consisting of D V L I R N and S.

In another preferred embodiment, the amino acid residue at position 994 of the first sequence is selected from the group consisting of K V A P and T.

In another preferred embodiment, the amino acid residue at position 995 of the first sequence is selected from the group consisting of F M L and Y.

In another preferred embodiment, the amino acid residue at position 996 of the first sequence is selected from the group consisting of I P V A S and L.

In another preferred embodiment, the amino acid residue at position 997 of the first sequence is selected from the group consisting of F G V L N A and P.

In another preferred embodiment, the amino acid residue at position 998 of the first sequence is selected from the group consisting of A D A S N K and G.

In another preferred embodiment, the amino acid residue at position 999 of the first sequence is selected from the group consisting of E A K R G T and S.

Expression of Class III Mannosidases in Lower Eukaryotes

The present invention also provides that a mannosidase having substrate specificity to Manα1,2/Manα1,3/Manα1,6 be introduced into a lower eukaryote host.

In one embodiment, a class III mannosidase capable of hydrolyzing Manα1,2/Manα1,3/Manα1,6 glycosidic linkages is expressed in a lower eukaryotic host. By expressing Class III mannosidases in vivo, either alone or in conjunction with other N-glycan modifying enzymes, efficient trimming of high mannose structures to $Man_3GlcNAc_2$ is obtained on host glycoproteins.

In a preferred embodiment, the Sf9 mannosidase III (Genbank gi:2245567 (D. Jarvis, et al. *Glycobiology* 1997 7:113-127)) is cloned into a yeast integration plasmid under the control of a constitutive or inducible promoter (see Example 26). The amount of Class III mannosidase activity is optimized while restricting adverse effects on the cell. This involves altering promoter strength and may include using an inducible or otherwise regulatable promoter to better control the expression of these proteins.

In addition to expressing the wild-type Class III mannosidase, modified forms of the Class III mannosidase can be expressed to enhance cellular localization and activity. This is achieved through the combinatorial DNA library approach of the invention by fusing varying lengths of the catalytic domain of Class III mannosidase(s) to endogenous yeast targeting regions, as described herein.

Class III Mannosidase Hydrolysis of Glycosidic Linkages

The method of the present invention also encompasses the mechanism in which the catalytically active domain of Class III enzymes hydrolyzes the Manα1,3 and/or Manα1,6 and/or Manα1,2 glycosidic linkages on an oligosaccharide e.g. $Man_5GlcNAc_2$ or $Man_8GlcNAc_2$ structures to produce $Man_3GlcNAc_2$, a desired intermediate for further N-glycan processing in a lower eukaryote.

In a first embodiment, the hydrolysis of the glycosidic linkages occurs sequentially. The enzyme hydrolyzes at least one glycosidic linkage and conformationally rotates to hydrolyze the other glycosidic linkages.

Figure 36C:
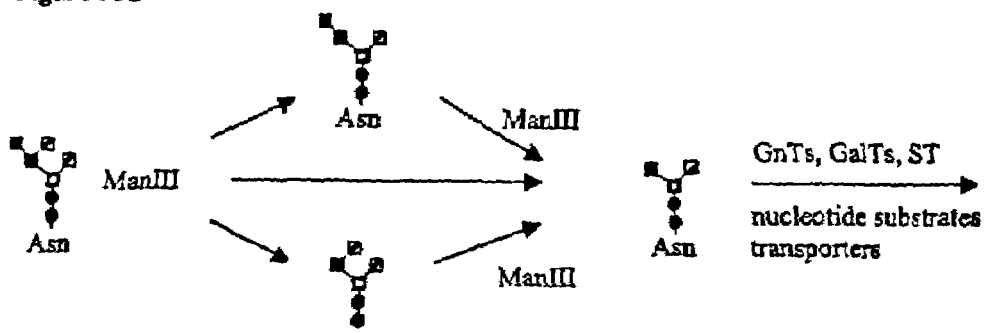

In a second embodiment, the hydrolysis of the Manα1,6 and Manα1,3 glycosidic linkages occurs simultaneously. In another embodiment, the enzyme specifically hydrolyzes Manα1,2 glycosidic linkages. The intermediate produced is a substrate for further Golgi processing wherein other glycosylation enzymes such as N-acetylglucosaminyltransferases (GnTs), galactosyltransferases (GalTs) and sialyltransferases (STs) can subsequently modify it to produce a desired glycoform. FIG. 36C illustrates the oligosaccharide intermediates (e.g. $Man_4GlcNAc_2$, $Man_3GlcNAc_2$) produced via the mannosidase III pathway.

Host Cells of the Invention

A preferred host cell of the invention is a lower eukaryotic cell, e.g., yeast, a unicellular and multicellular or filamentous fungus. However, a wide variety of host cells are envisioned as being useful in the methods of the invention. Plant cells or insect cells, for instance, may be engineered to express a human-like glycoprotein according to the invention. Likewise, a variety of non-human, mammalian host cells may be altered to express more human-like or otherwise altered glycoproteins using the methods of the invention. As one of skill in the art will appreciate, any eukaryotic host cell (including a human cell) may be used in conjunction with a library of the invention to express one or more chimeric proteins which is targeted to a subcellular location, e.g., organelle, in the host cell where the activity of the protein is modified, and preferably is enhanced. Such a protein is preferably—but need not necessarily be—an enzyme involved in protein glycosylation, as exemplified herein. It is envisioned that any protein coding sequence may be targeted and selected for modified activity in a eukaryotic host cell using the methods described herein.

Lower eukaryotes that are able to produce glycoproteins having the attached N-glycan $Man_5GlcNAc_2$ are particularly useful because (a) lacking a high degree of mannosylation (e.g. greater than 8 mannoses per N-glycan, or especially 30-40 mannoses), they show reduced immunogenicity in humans; and (b) the N-glycan is a substrate for further glycosylation reactions to form an even more human-like glycoform, e.g., by the action of GlcNAc transferase I (FIG. 1B; β1,2 GnTI) to form $GlcNAcMan_5GlcNAc_2$. A yield is obtained of greater than 30 mole %, more preferably a yield of 50-100 mole %, glycoproteins with N-glycans having a $Man_5GlcNAc_2$ structure. In a preferred embodiment, more than 50% of the $Man_5GlcNAc_2$ structure is shown to be a substrate for a GnTI activity and can serve as such a substrate in vivo.

Preferred lower eukaryotes of the invention include but are not limited to: *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reseei, Chrysosporium lucknowense, Fusarium* sp. *Fusarium gramineum, Fusarium venenatum* and *Neurospora crassa.*

In each above embodiment, the method is directed to making a host cell in which the oligosaccharide precursors are enriched in $Man_5GlcNAc_2$. These structures are desirable because they may then be processed by treatment in vitro, for example, using the method of Maras and Contreras, U.S. Pat. No. 5,834,251. In a preferred embodiment, however, precursors enriched in $Man_5GlcNAc_2$ are processed by at least one further glycosylation reaction in vivo—with glycosidases (e.g., α-mannosidases) and glycosyltransferases (e.g., GnTI)—to produce human-like N-glycans. Oligosaccharide precursors enriched in $Man_5GlcNAc_2$, for example, are preferably processed to those having $GlcNAcMan_xGlcNAc_2$ core structures, wherein X is 3, 4 or 5, and is preferably 3. N-glycans having a $GlcNAcMan_xGlcNAc_2$ core structure where X is greater than 3 may be converted to $GlcNAcMan_3GlcNAc_2$, e.g., by treatment with an α-1,3 and/or α-1,6 mannosidase activity, where applicable. Additional processing of $GlcNAcMan_3GlcNAc_2$ by treatment with glycosyltransferases (e.g., GnTII) produces $GlcNAc_2Man_3GlcNAc_2$ core structures which may then be modified, as desired, e.g., by ex vivo treatment or by heterologous expression in the host cell of additional glycosylation enzymes, including glycosyltransferases, sugar transporters and mannosidases (see below), to become human-like N-glycans.

Preferred human-like glycoproteins which may be produced according to the invention include those which comprise N-glycans having seven or fewer, or three or fewer, mannose residues; and which comprise one or more sugars selected from the group consisting of galactose, GlcNAc, sialic acid, and fucose.

While lower eukaryotic host cells are preferred, a wide variety of host cells having the aforementioned properties are envisioned as being useful in the methods of the invention. Plant cells, for instance, may be engineered to express a human-like glycoprotein according to the invention. Likewise, a variety of non-human, mammalian host cells may be altered to express more human-like glycoproteins using the methods of the invention. An appropriate host cell can be engineered, or one of the many such mutants already described in yeasts may be used. A preferred host cell of the invention, as exemplified herein, is a hypermannosylation-minus (OCH1) mutant in *Pichia pastoris*.

Formation of Complex N-Glycans

Formation of complex N-glycan synthesis is a sequential process by which specific sugar residues are removed and attached to the core oligosaccharide structure. In higher eukaryotes, this is achieved by having the substrate sequentially exposed to various processing enzymes. These enzymes carry out specific reactions depending on their particular location within the entire processing cascade. This "assembly line" consists of ER, early, medial and late Golgi, and the trans Golgi network all with their specific processing environment. To re-create the processing of human glycoproteins in the Golgi and ER of lower eukaryotes, numerous enzymes (e.g. glycosyltransferases, glycosidases, phosphatases and transporters) have to be expressed and specifically targeted to these organelles, and preferably, in a location so that they function most efficiently in relation to their environment as well as to other enzymes in the pathway.

Because one goal of the methods described herein is to achieve a robust protein production strain that is able to perform well in an industrial fermentation process, the integration of multiple genes into the host cell chromosome involves careful planning. As described above, one or more genes which encode enzymes known to be characteristic of non-human glycosylation reactions are preferably deleted. The engineered cell strain is transformed with a range of different genes encoding desired activities, and these genes are transformed in a stable fashion, thereby ensuring that the desired activity is maintained throughout the fermentation process.

Any combination of the following enzyme activities may be engineered singly or multiply into the host using methods of the invention: sialyltransferases, mannosidases, fucosyltransferases, galactosyltransferases, GlcNAc transferases, ER and Golgi specific transporters (e.g. syn- and antiport transporters for UDP-galactose and other precursors), other enzymes involved in the processing of oligosaccharides, and enzymes involved in the synthesis of activated oligosaccharide precursors such as UDP-galactose and CMP-N-acetylneuraminic acid. Preferably, enzyme activities are introduced on one or more nucleic acid molecules (see also below). Nucleic acid molecules may be introduced singly or multiply, e.g., in the context of a nucleic acid library such as a combinatorial library of the invention. It is to be understood, however, that single or multiple enzymatic activities may be introduced into a host cell in any fashion, including but not limited to protein delivery methods and/or by use of one or more nucleic acid molecules without necessarily using a nucleic acid library or combinatorial library of the invention.

Expression of Glycosyltransferases to Produce Complex N-Glycans:

With DNA sequence information, the skilled artisan can clone DNA molecules encoding GnT activities (e.g., Example 3). Using standard techniques well-known to those of skill in the art, nucleic acid molecules encoding GnTI, II, III, IV or V (or encoding catalytically active fragments thereof) may be inserted into appropriate expression vectors under the transcriptional control of promoters and other expression control sequences capable of driving transcription in a selected host cell of the invention, e.g., a fungal host such as *Pichia* sp., *Kluyveromyces* sp. and *Aspergillus* sp., as described herein, such that one or more of these mammalian GnT enzymes may be actively expressed in a host cell of choice for production of a humanlike complex glycoprotein (e.g., Examples 8, 15, 17, 19).

Several individual glycosyltransferases have been cloned and expressed in *S. cerevisiae* (GalT, GnTI), *Aspergillus nidulans* (GnTI) and other fungi, without however demonstrating the desired outcome of "humanization" on the glycosylation pattern of the organisms (Yoshida et al. (1999) *Glycobiology* 9(1):53-8; Kalsner et al. (1995) *Glycoconj. J.* 12(3):360-370). It was speculated that the carbohydrate structure required to accept sugars by the action of such glycosyltransferases was not present in sufficient amounts, which most likely contributed to the lack of complex N-glycan formation.

A preferred method of the invention provides the functional expression of a glycosyltransferase, such as GnTI, GnTII and GnTIII (or other GnTs such as GnTIV and GnTVI and combinations of any of the above) in the early, medial or late Golgi apparatus, as well as ensuring a sufficient supply of UDP-GlcNAc (e.g., by expression of a UDP-GlcNAc transporter; see below).

Methods for Providing Sugar Nucleotide Precursors to the Golgi Apparatus:

For a glycosyltransferase to function satisfactorily in the Golgi, the enzyme requires a sufficient concentration of an appropriate nucleotide sugar, which is the high-energy donor of the sugar moiety added to a nascent glycoprotein. In humans, the full range of nucleotide sugar precursors (e.g. UDP-N-acetylglucosamine, UDP-N-acetylgalactosamine, CMP-N-acetylneuraminic acid, UDP-galactose, etc.) are generally synthesized in the cytosol and transported into the Golgi, where they are attached to the core oligosaccharide by glycosyltransferases.

To replicate this process in non-human host cells such as lower eukaryotes, sugar nucleoside specific transporters have to be expressed in the Golgi to ensure adequate levels of nucleoside sugar precursors (Sommers and Hirschberg (1981) *J. Cell Biol.* 91(2):A406-A406; Sommers and Hirschberg (1982) *J. Biol. Chem.* 257(18):811-817; Perez and Hirschberg (1987) *Methods in Enzymology* 138:709-715). Nucleotide sugars may be provided to the appropriate compartments, e.g., by expressing in the host microorganism an exogenous gene encoding a sugar nucleotide transporter. The choice of transporter enzyme is influenced by the nature of the exogenous glycosyltransferase being used. For example, a GlcNAc transferase may require a UDP-GlcNAc transporter, a fucosyltransferase may require a GDP-fucose transporter, a galactosyltransferase may require a UDP-galactose transporter, and a sialyltransferase may require a CMP-sialic acid transporter.

The added transporter protein conveys a nucleotide sugar from the cytosol into the Golgi apparatus, where the nucleotide sugar may be reacted by the glycosyltransferase, e.g. to elongate an N-glycan. The reaction liberates a nucleoside diphosphate or monophosphate, e.g. UDP, GDP, or CMP. Nucleoside monophosphates can be directly exported from the Golgi in exchange for nucleoside triphosphate sugars by an antiport mechanism. Accumulation of a nucleoside diphosphate, however, inhibits the further activity of a glycosyltransferase. As this reaction appears to be important for efficient glycosylation, it is frequently desirable to provide an expressed copy of a gene encoding a nucleotide diphosphatase. The diphosphatase (specific for UDP or GDP as appropriate) hydrolyzes the diphosphonucleoside to yield a nucleoside monophosphate and inorganic phosphate.

Suitable transporter enzymes, which are typically of mammalian origin, are described below. Such enzymes may be engineered into a selected host cell using the methods of the invention.

Figure 1B:
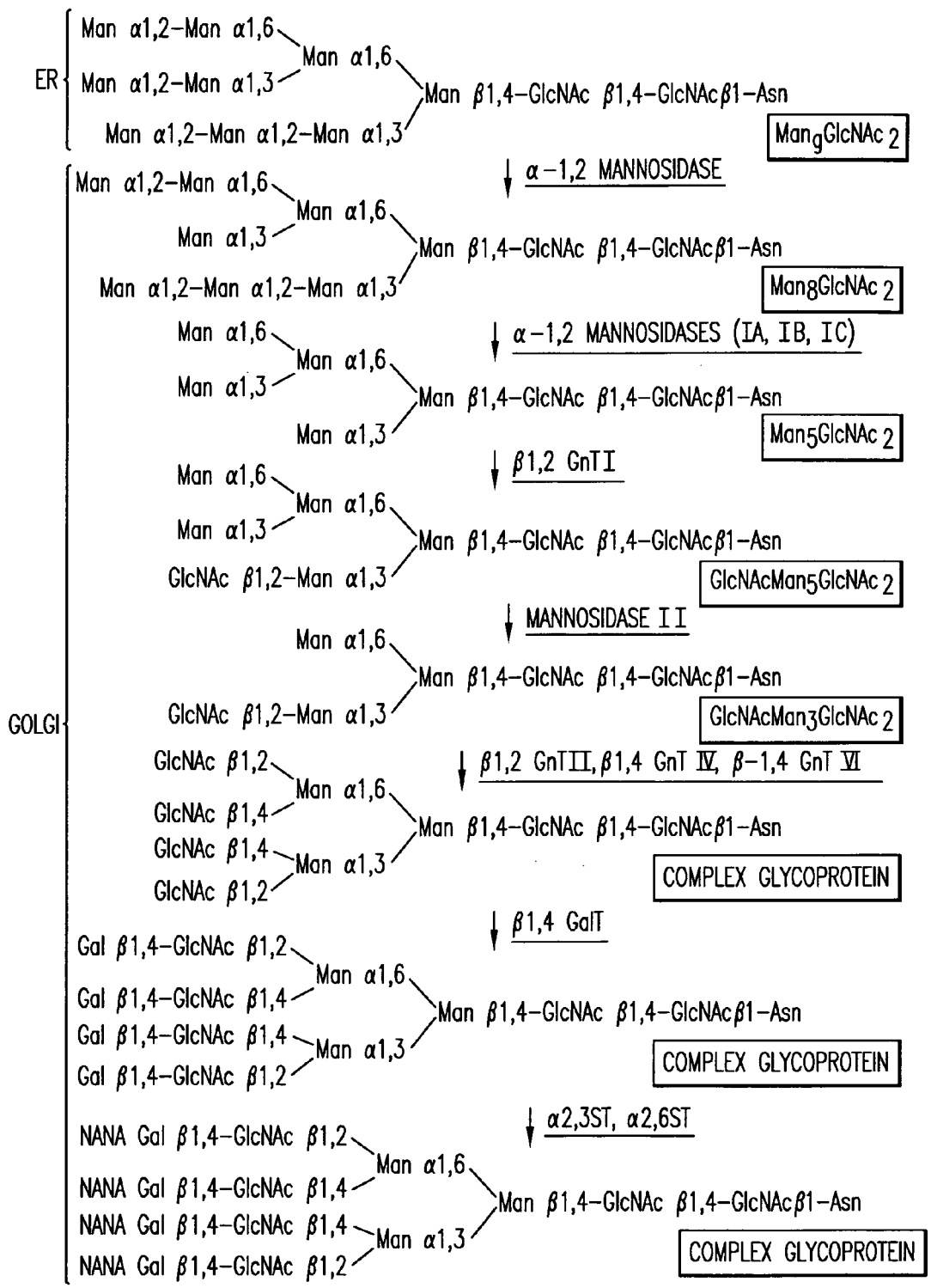
FIG. 1B is a schematic diagram of a typical human N-glycosylation pathway.

In another example, α2,3- or α2,6-sialyltransferase caps galactose residues with sialic acid in the trans-Golgi and TGN of humans leading to a mature form of the glycoprotein (FIG. 1B). To reengineer this processing step into a metabolically engineered yeast or fungus will require (1) α 2,3- or α 2,6-sialyltransferase activity and (2) a sufficient supply of CMP-N-acetyl neuraminic acid, in the late Golgi of yeast. To obtain sufficient α 2,3-sialyltransferase activity in the late Golgi, for example, the catalytic domain of a known sialyltransferase (e.g. from humans) has to be directed to the late Golgi in fungi (see above). Likewise, transporters have to be engineered to allow the transport of CMP-N-acetyl neuraminic acid into the late Golgi. There is currently no indication that fungi synthesize or can even transport sufficient amounts of CMP-N-acetyl neuraminic acid into the Golgi. Consequently, to ensure the adequate supply of substrate for the corresponding glycosyltransferases, one has to metabolically engineer the production of CMP-sialic acid into the fungus.

UDP-N-acetylglucosamine

The cDNA of human UDP-N-acetylglucosamine transporter, which was recognized through a homology search in the expressed sequence tags database (dbEST), has been cloned (Ishida, 1999 *J. Biochem.* 126(1): 68-77). The mammalian Golgi membrane transporter for UDP-N-acetylglucosamine was cloned by phenotypic correction with cDNA from canine kidney cells (MDCK) of a recently characterized *Kluyveromyces lactis* mutant deficient in Golgi transport of the above nucleotide sugar (Guillen et al. (1998) *Proc. Natl. Acad. Sci. USA* 95(14):7888-7892). Results demonstrate that the mammalian Golgi UDP-GlcNAc transporter gene has all of the necessary information for the protein to be expressed and targeted functionally to the Golgi apparatus of yeast and that two proteins with very different amino acid sequences may transport the same solute within the same Golgi membrane (Guillen et al. (1998) *Proc. Natl. Acad. Sci. USA* 95(14):7888-7892).

Figure 10:
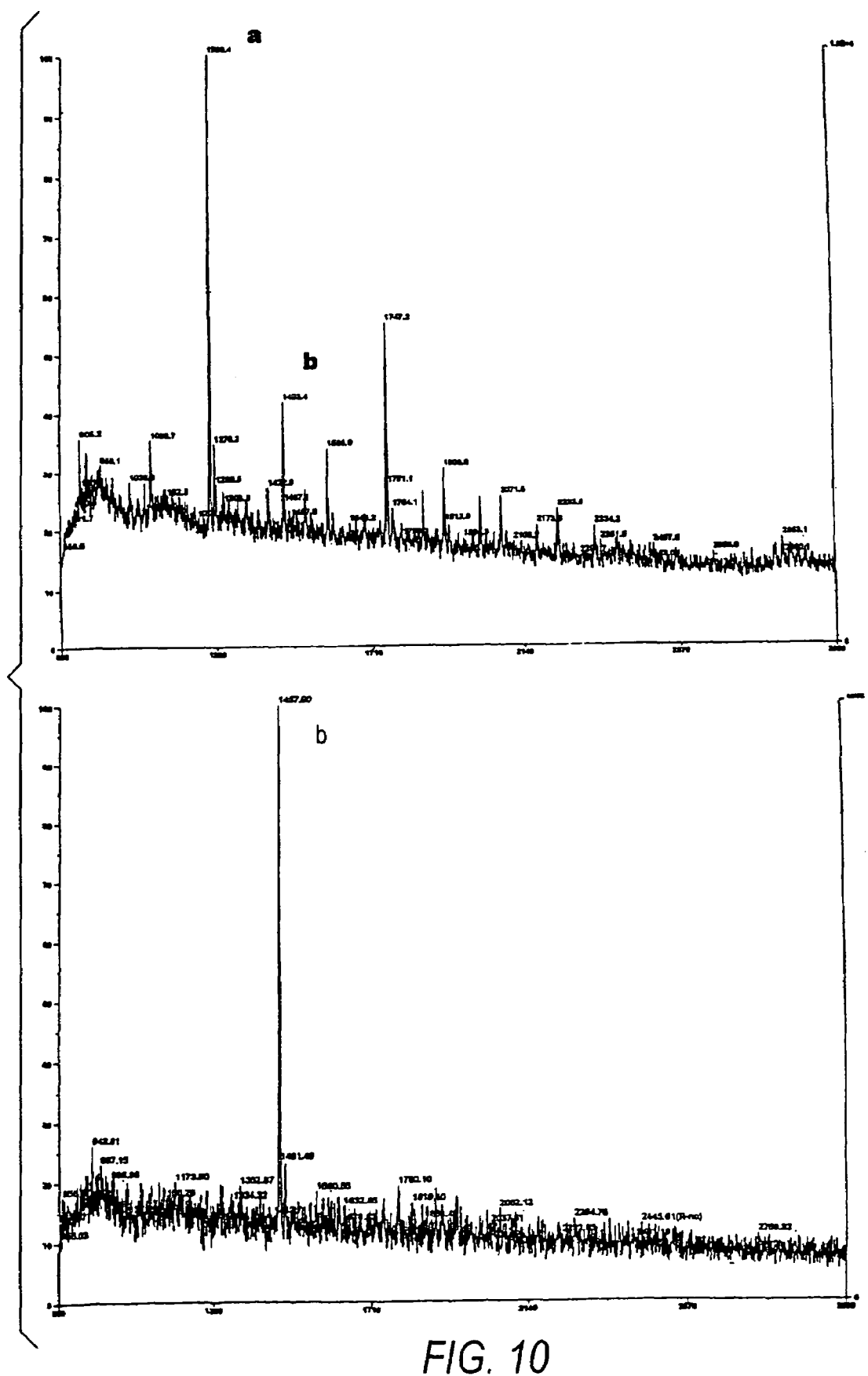
FIG. 10A-10B demonstrate the activity of an UDP-GlcNAc transporter in the production of $GlcNAcMan_5GlcNAc_2$ in *P. pastoris*.
Figure 10B:
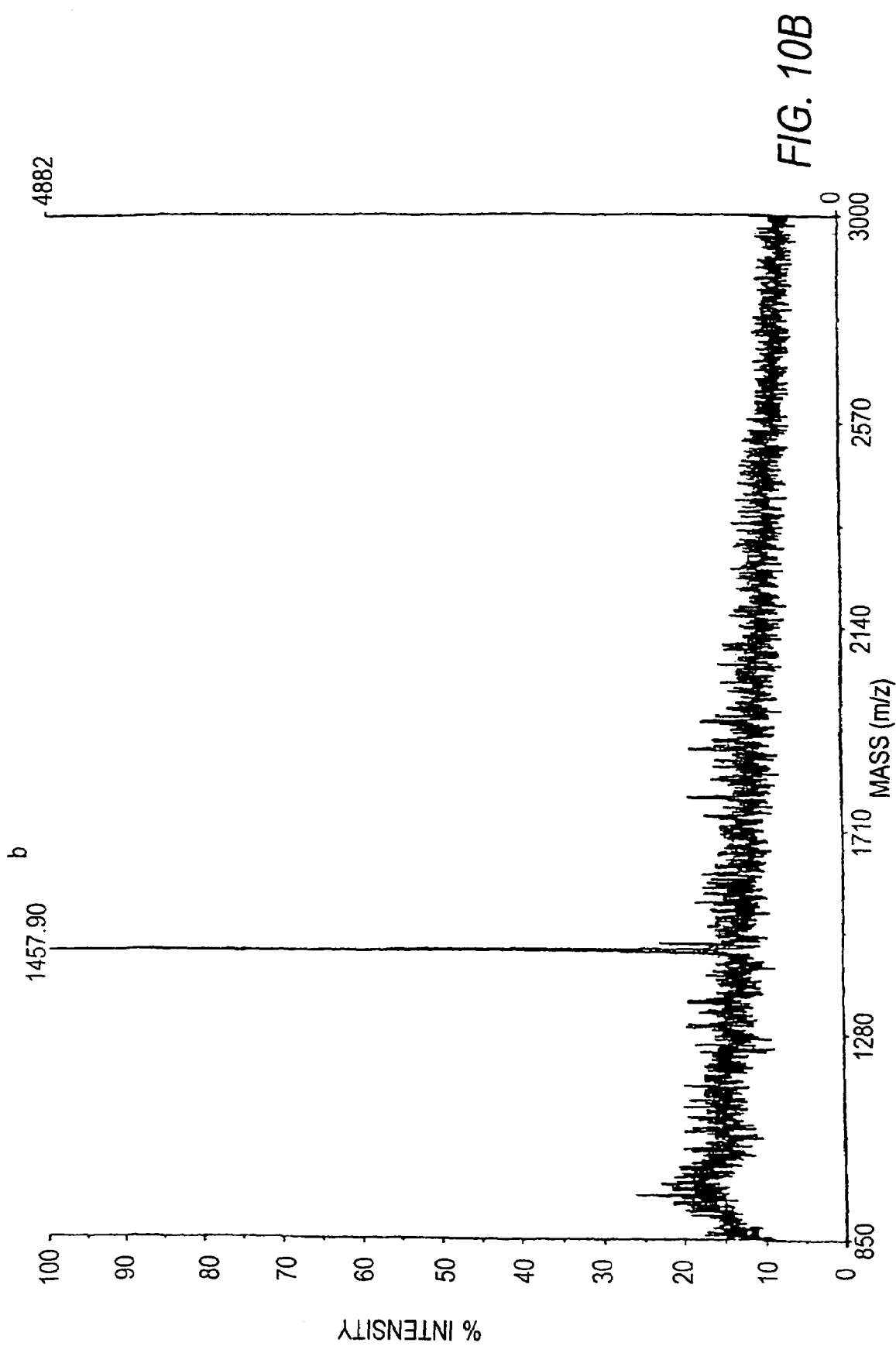

Accordingly, one may incorporate the expression of a UDP-GlcNAc transporter in a host cell by means of a nucleic acid construct which may contain, for example: (1) a region by which the transformed construct is maintained in the cell (e.g. origin of replication or a region that mediates chromosomal integration), (2) a marker gene that allows for the selection of cells that have been transformed, including counterselectable and recyclable markers such as ura3 or T-urf13 (Soderholm et al. (2001) *Biotechniques* 31 (2):306-10) or other well characterized selection-markers (e.g., his4, bla, Sh ble etc.), (3) a gene or fragment thereof encoding a functional UDP-GlcNAc transporter (e.g. from *K. lactis*, (Abeijon, (1996) *Proc. Natl. Acad. Sci. U.S.A.* 93:5963-5968), or from *H. sapiens* (Ishida et al. (1996) *J. Biochem.* (Tokyo) 120(6): 1074-8), and (4) a promoter activating the expression of the above mentioned localization/catalytic domain fusion construct library. Example 8 shows the addition of a *Kluyveromyces lactis* MNN2-2 gene (Genbank AN AF106080) encoding the UDP-GlcNAc transporter in a *P. pastoris* PBP-3. FIGS. 10A and 10B compares the MALDI-TOF N-glycan profiles of a *P. pastoris* strain without the UDP-GlcNAc transporter and a *P. pastoris* strain with the UDP-GlcNAc transporter (PBP-3), respectively. The *P. pastoris* PBP-3 exhibits a single prominent peak at 1457 (m/z) consistent with its identification as GlcNAcMan$_5$GlcNAc$_2$ [b].

GDP-Fucose

The rat liver Golgi membrane GDP-fucose transporter has been identified and purified by Puglielli, L. and C. B. Hirschberg (Puglielli, 1999 *J. Biol. Chem.* 274(50):35596-35600). The corresponding gene has not been identified, however, N-terminal sequencing can be used for the design of oligonucleotide probes specific for the corresponding gene. These oligonucleotides can be used as probes to clone the gene encoding for GDP-fucose transporter.

UDP-Galactose

Two heterologous genes, gmal2(+) encoding alpha 1,2-galactosyltransferase (alpha 1,2 GalT) from *Schizosaccharomyces pombe* and (hUGT2) encoding human UDP-galactose (UDP-Gal) transporter, have been functionally expressed in *S. cerevisiae* to examine the intracellular conditions required for galactosylation. Correlation between protein galactosylation and UDP-galactose transport activity indicated that an exogenous supply of UDP-Gal transporter, rather than alpha 1,2 GalT played a key role for efficient galactosylation in *S. cerevisiae* (Kainuma, 1999 *Glycobiology* 9(2): 133-141). Likewise, an UDP-galactose transporter from *S. pombe* was cloned (Segawa, 1999 *Febs Letters* 451(3): 295-298).

CMP-N-acetylneuraminic Acid (CMP-Sialic Acid).

Human CMP-sialic acid transporter (hCST) has been cloned and expressed in Lec 8 CHO cells (Aoki et al. (1999) *J. Biochem.* (Tokyo) 126(5):940-50; Eckhardt et al. (1997) *Eur. J. Biochem.* 248(1):187-92). The functional expression of the murine CMP-sialic acid transporter was achieved in *Saccharomyces cerevisiae* (Berninsone et al. (1997) *J. Biol. Chem.* 272(19):12616-9). Sialic acid has been found in some fungi, however it is not clear whether the chosen host system will be able to supply sufficient levels of CMP-Sialic acid. Sialic acid can be either supplied in the medium or alternatively fungal pathways involved in sialic acid synthesis can also be integrated into the host genome.

Expression of Diphosphatases:

When sugars are transferred onto a glycoprotein, either a nucleoside diphosphate or monophosphate is released from the sugar nucleotide precursors. While monophosphates can be directly exported in exchange for nucleoside triphosphate sugars by an antiport mechanism, diphosphonucleosides (e.g. GDP) have to be cleaved by phosphatases (e.g. GDPase) to yield nucleoside monophosphates and inorganic phosphate prior to being exported. This reaction appears to be important for efficient glycosylation, as GDPase from *S. cerevisiae* has been found to be necessary for mannosylation. However, the enzyme only has 10% of the activity towards UDP (Berninsone et al. (1994) *J. Biol. Chem.* 269(1):207-211). Lower eukaryotes often do not have UDP-specific diphosphatase activity in the Golgi as they do not utilize UDP-sugar precursors for glycoprotein synthesis in the Golgi. *Schizosaccharomyces pombe*, a yeast which adds galactose residues to cell wall polysaccharides (from UDP-galactose), was found to have specific UDPase activity, further suggesting the requirement for such an enzyme (Berninsone et al. (1994) *J. Biol. Chem.* 269(1):207-211). UDP is known to be a potent inhibitor of glycosyltransferases and the removal of this glycosylation side product is important to prevent glycosyltransferase inhibition in the lumen of the Golgi.

Recombinant Vectors

A variety of expression vectors may be used to express the nucleotide sequences of the present invention (see, e.g., Example 13). The sequences may be operatively linked to an expression control sequence in a suitable vector for transformation of a host cell. In one embodiment, a sequence of the present invention is operably linked to a vector designated pJN348, which comprises a GAPDH promoter, a NotI AscI PacI restriction site cassette, CycII transcriptional terminator, the ura3 selection cassette for expression in a *P. pastoris* YSH-1 (Amp$^r$).

In a preferred embodiment, the vector comprises a catalytically active fragment of a mannosidase II enzyme as set forth in the above description. Other suitable expression vectors for use in yeast and filamentous fungi are well-known in the art.

Methods for Altering N-Glycans in a Host by Expressing a Targeted Enzymatic Activity from a Nucleic Acid Molecule The present invention further provides a method for producing a human-like glycoprotein in a non-human host cell comprising the step of introducing into the cell one or more nucleic acid molecules which encode an enzyme or enzymes for production of the Man$_5$GlcNAc$_2$ carbohydrate structure. In one preferred embodiment, a nucleic acid molecule encoding one or more mannosidase activities involved in the production of Man$_5$GlcNAc$_2$ from Man$_8$GlcNAc$_2$ or Man$_9$GlcNAc$_2$ is introduced into the host. The invention additionally relates to methods for making altered glycoproteins in a host cell comprising the step of introducing into the host cell a nucleic acid molecule which encodes one or more glycosylation enzymes or activities. Preferred enzyme activities are selected from the group consisting of UDP-GlcNAc transferase, UDP-galactosyltransferase, GDP-fucosyltransferase, CMP-sialyltransferase, UDP-GlcNAc transporter, UDP-galactose transporter, GDP-fucose transporter, CMP-sialic acid transporter, and nucleotide diphosphatases. In a particularly preferred embodiment, the host is selected or engineered to express two or more enzymatic activities in which the product of one activity increases substrate levels of another activity, e.g., a glycosyltransferase and a corresponding sugar transporter, e.g., GnTI and UDP-GlcNAc transporter activities. In another preferred embodiment, the host is selected or engineered to expresses an activity to remove products which may inhibit subsequent glycosylation reactions, e.g. a UDP- or GDP-specific diphosphatase activity.

Preferred methods of the invention involve expressing one or more enzymatic activities from a nucleic acid molecule in a host cell and comprise the step of targeting at least one enzymatic activity to a desired subcellular location (e.g., an organelle) by forming a fusion protein comprising a catalytic domain of the enzyme and a cellular targeting signal peptide, e.g., a heterologous signal peptide which is not normally ligated to or associated with the catalytic domain. The fusion protein is encoded by at least one genetic construct ("fusion construct") comprising a nucleic acid fragment encoding a cellular targeting signal peptide ligated in the same translational reading frame ("in-frame") to a nucleic acid fragment encoding an enzyme (e.g., glycosylation enzyme), or catalytically active fragment thereof.

The targeting signal peptide component of the fusion construct or protein is preferably derived from a member of the group consisting of: membrane-bound proteins of the ER or Golgi, retrieval signals, Type II membrane proteins, Type I membrane proteins, membrane spanning nucleotide sugar transporters, mannosidases, sialyltransferases, glucosidases, mannosyltransferases and phosphomannosyltransferases.

The catalytic domain component of the fusion construct or protein is preferably derived from a glycosidase, mannosidase or a glycosyltransferase activity derived from a member of the group consisting of GnTI, GnTII, GnTIII, GnTIV, GnTV, GnTVI, GalT, Fucosyltransferase and Sialyltransferase. The catalytic domain preferably has a pH optimum within 1.4 pH units of the average pH optimum of other representative enzymes in the organelle in which the enzyme is localized, or has optimal activity at a pH between 5.1 and 8.0. In a preferred embodiment, the catalytic domain encodes a mannosidase selected from the group consisting of *C. elegans* mannosidase IA, *C. elegans* mannosidase IB, *D. melanogaster* mannosidase IA, *H. sapiens* mannosidase IB, *P. citrinum* mannosidase I, mouse mannosidase IA, mouse mannosidase IB, *A. nidulans* mannosidase IA, *A. nidulans* mannosidase IB, *A. nidulans* mannosidase IC, mouse mannosidase II, *C. elegans* mannosidase II, *H. sapiens* mannosidase II, and mannosidase III.

Selecting a Glycosylation Enzyme: pH Optima and Subcellular Localization

In one embodiment of the invention, a human-like glycoprotein is made efficiently in a non-human eukaryotic host cell by introducing into a subcellular compartment of the cell a glycosylation enzyme selected to have a pH optimum similar to the pH optima of other enzymes in the targeted subcellular compartment. For example, most enzymes that are active in the ER and Golgi apparatus of *S. cerevisiae* have pH optima that are between about 6.5 and 7.5 (see Table 3). Because the glycosylation of proteins is a highly evolved and efficient process, the internal pH of the ER and the Golgi is likely also in the range of about 6-8. All previous approaches to reduce mannosylation by the action of recombinant mannosidases in fungal hosts, however, have introduced enzymes that have a pH optimum of around pH 5.0 (Martinet et al. (1998) *Biotech. Letters* 20(12): 1171-1177, and Chiba et al. (1998) *J. Biol. Chem.* 273(41): 26298-26304). At pH 7.0, the in vitro determined activity of those mannosidases is reduced to less than 10%, which is likely insufficient activity at their point of use, namely, the ER and early Golgi, for the efficient in vivo production of Man$_5$GlcNAc$_2$ on N-glycans.

Accordingly, a preferred embodiment of this invention targets a selected glycosylation enzyme (or catalytic domain thereof), e.g., an α-mannosidase, to a subcellular location in the host cell (e.g., an organelle) where the pH optimum of the enzyme or domain is within 1.4 pH units of the average pH optimum of other representative marker enzymes localized in the same organelle(s). The pH optimum of the enzyme to be targeted to a specific organelle should be matched with the pH optimum of other enzymes found in the same organelle to maximize the activity per unit enzyme obtained. Table 3 summarizes the activity of mannosidases from various sources and their respective pH optima. Table 4 summarizes their typical subcellular locations.

TABLE 3

Mannosidases and their pH optimum.

| Source | Enzyme | pH optimum | Reference |
|---|---|---|---|
| Aspergillus saitoi | α-1,2-mannosidase | 5.0 | Ichishima et al., 1999 Biochem. J. 339(Pt 3): 589-597 |
| Trichoderma reesei | α-1,2-mannosidase | 5.0 | Maras et al., 2000 J. Biotechnol. 77(2-3): 255-263 |
| Penicillium citrinum | α-D-1,2-mannosidase | 5.0 | Yoshida et al., 1993 Biochem. J. 290(Pt 2): 349-354 |
| C. elegans | α-1,2-mannosidase | 5.5 | FIG. 11 herein |
| Aspergillus nidulans | α-1,2-mannosidase | 6.0 | Eades and Hintz, 2000 Gene 255(1): 25-34 |
| Homo sapiens IA(Golgi) | α-1,2-mannosidase | 6.0 | |
| Homo sapiens IB (Golgi) | α-1,2-mannosidase | 6.0 | |
| Lepidopteran insect cells | Type 1 α-1,2-Man$_6$-mannosidase | 6.0 | Ren et al., 1995 Biochem. 34(8): 2489-2495 |
| Homo sapiens | α-D-mannosidase | 6.0 | Chandrasekaran et al., 1984 Cancer Res. 44(9): 4059-68 |
| Xanthomonas manihotis | α-1,2,3-mannosidase | 6.0 | U.S. Pat. No. 6,300,113 |
| Drosophila melanogaster | α-1,2-mannosidase | 6.2 | Reported herein |
| Mouse IB (Golgi) | α-1,2-mannosidase | 6.5 | Schneikert and Herscovics, 1994 Glycobiology. 4(4): 445-50 |
| Bacillus sp. (secreted) | α-D-1,2-mannosidase | 7.0 | Maruyama et al., 1994 Carbohydrate Res. 251: 89-98 |

In a preferred embodiment, a particular enzyme or catalytic domain is targeted to a subcellular location in the host cell by means of a chimeric fusion construct encoding a protein comprising a cellular targeting signal peptide not normally associated with the enzymatic domain. Preferably, an enzyme or domain is targeted to the ER, the early, medial or late Golgi, or the trans Golgi apparatus of the host cell.

In a more preferred embodiment, the targeted glycosylation enzyme is a mannosidase, glycosyltransferase or a glycosidase. In an especially preferred embodiment, mannosidase activity is targeted to the ER or cis Golgi, where the early reactions of glycosylation occur. While this method is useful for producing a human-like glycoprotein in a non-human host cell, it will be appreciated that the method is also useful more generally for modifying carbohydrate profiles of a glycoprotein in any eukaryotic host cell, including human host cells.

Targeting sequences which mediate retention of proteins in certain organelles of the host cell secretory pathway are well-known and described in the scientific literature and public databases, as discussed in more detail below with respect to libraries for selection of targeting sequences and targeted enzymes. Such subcellular targeting sequences may be used alone or in combination to target a selected glycosylation enzyme (or catalytic domain thereof) to a particular subcellular location in a host cell, i.e., especially to one where the enzyme will have enhanced or optimal activity based on pH optima or the presence of other stimulatory factors.

When one attempts to trim high mannose structures to yield Man$_5$GlcNAc$_2$ in the ER or the Golgi apparatus of a host cell such as S. cerevisiae, for example, one may choose any enzyme or combination of enzymes that (1) has a sufficiently close pH optimum (i.e. between pH 5.2 and pH 7.8), and (2) is known to generate, alone or in concert, the specific isomeric Man$_5$GlcNAc$_2$ structure required to accept subsequent addition of GlcNAc by GnTI. Any enzyme or combination of enzymes that is shown to generate a structure that can be converted to GlcNAcMan$_5$GlcNAc$_2$ by GnTI in vitro would constitute an appropriate choice. This knowledge may be obtained from the scientific literature or experimentally.

For example, one may determine whether a potential mannosidase can convert Man$_8$GlcNAc$_2$-2AB (2-aminobenzamide) to Man$_5$GlcNAc$_2$-AB and then verify that the obtained Man$_5$GlcNAc$_2$-2AB structure can serve a substrate for GnTI and UDP-GlcNAc to give GlcNAcMan$_5$GlcNAc$_2$ in vitro. Mannosidase IA from a human or murine source, for example, would be an appropriate choice (see, e.g., Example 4). Examples described herein utilize 2-aminobenzamide labeled N-linked oligomannose followed by HPLC analysis to make this determination.

TABLE 4

Cellular location and pH optima of various glycosylation-related enzymes of S. cerevisiae.

| Gene | Activity | Location | pH optimum | Reference(s) |
|---|---|---|---|---|
| KTR1 | α-1,2 mannosyl-transferase | Golgi | 7.0 | Romero et al. (1997) Biochem. J. 321(Pt 2): 289-295 |
| MNS1 | α-1,2-mannosidase | ER | 6.5 | |
| CWH41 | glucosidase I | ER | 6.8 | |
| — | mannosyl-transferase | Golgi | 7-8 | Lehele and Tanner (1974) Biochim. Biophys. Acta 350(1): 225-235 |
| KRE2 | α-1,2 mannosyl-transferase | Golgi | 6.5-9.0 | Romero et al. (1997) Biochem. J. 321(Pt 2): 289-295 |

Accordingly, a glycosylation enzyme such as an α-1,2-mannosidase enzyme used according to the invention has an optimal activity at a pH of between 5.1 and 8.0. In a preferred embodiment, the enzyme has an optimal activity at a pH of between 5.5 and 7.5. The C. elegans mannosidase enzyme, for example, works well in the methods of the invention and has an apparent pH optimum of about 5.5). Preferred mannosidases include those listed in Table 3 having appropriate pH optima, e.g. *Aspergillus nidulans, Homo sapiens* IA (Golgi), *Homo sapiens* IB (Golgi), *Lepidopteran* insect cells (IPLB-SF21AE), *Homo sapiens*, mouse IB (Golgi), *Xanthomonas manihotis, Drosophila melanogaster* and *C. elegans*.

Figure 11:
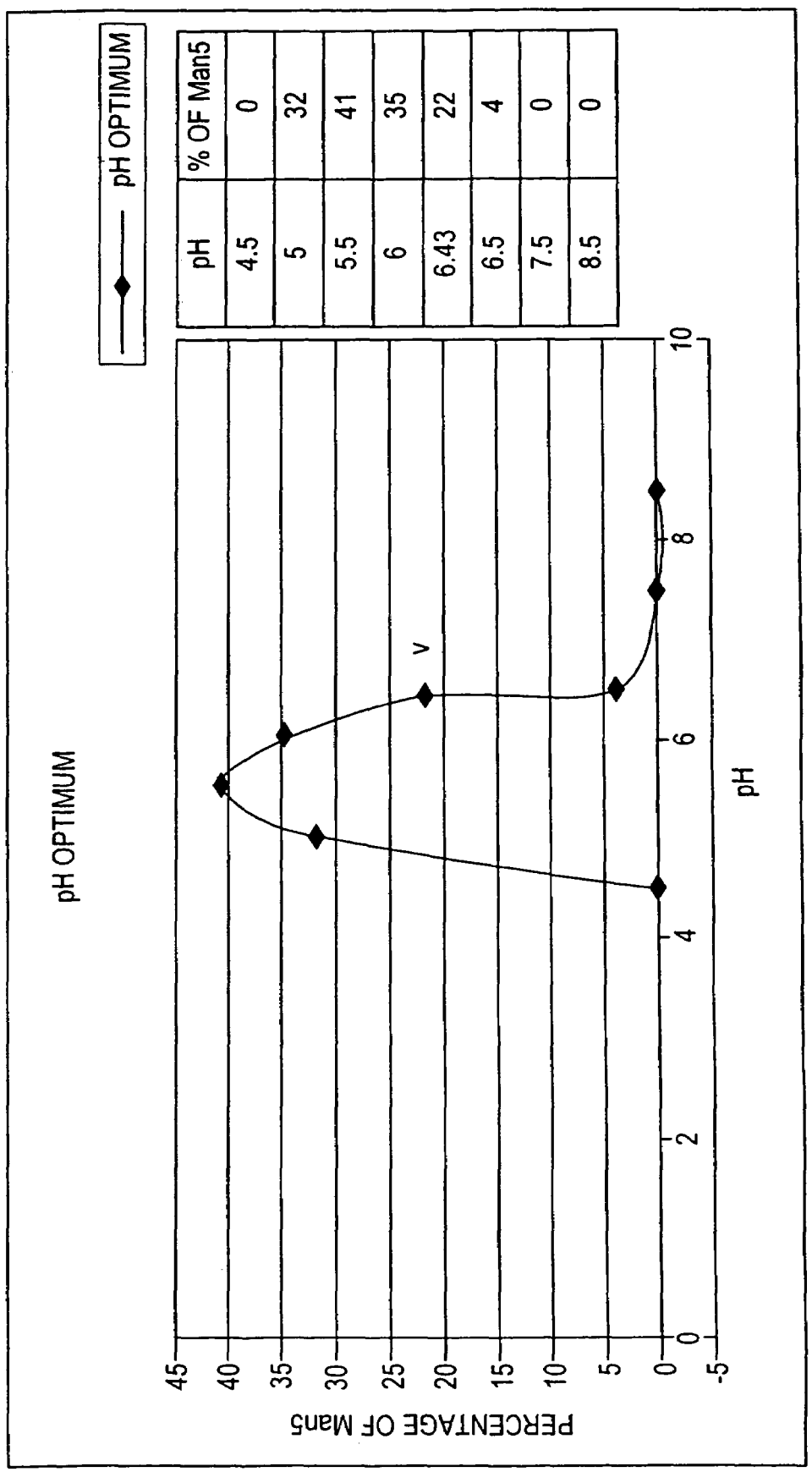
FIG. 11 shows a pH optimum of a heterologous mannosidase enzyme encoded by pBB27-2 (*Saccharomyces* MNN 10 (s)/*C. elegans* mannosidase IB Δ31) expressed in *P. pastoris*.

The experiment which illustrates the pH optimum for an α-1,2-mannosidase enzyme is described in Example 7. A chimeric fusion protein BB27-2 (*Saccharomyces* MNN10 (s)/*C. elegans* mannosidase IB Δ31), which leaks into the medium was subjected to various pH ranges to determine the optimal activity of the enzyme. The results of the experiment show that the α-1,2-mannosidase has an optimal pH of about 5.5 for its function (FIG. 11).

In a preferred embodiment, a single cloned mannosidase gene is expressed in the host organism. However, in some cases it may be desirable to express several different mannosidase genes, or several copies of one particular gene, in order to achieve adequate production of $Man_5GlcNAc_2$. In cases where multiple genes are used, the encoded mannosidases preferably all have pH optima within the preferred range of about 5.1 to about 8.0, or especially between about 5.5 and about 7.5. Preferred mannosidase activities include α-1,2-mannosidases derived from mouse, human, *Lepidoptera, Aspergillus nidulans*, or *Bacillus* sp., *C. elegans, D. melanogaster, P. citrinum, X. laevis* or *A. nidulans*.

In Vivo Alteration of Host Cell Glycosylation Using a Combinatorial DNA Library

Certain methods of the invention are preferably (but need not necessarily be) carried out using one or more nucleic acid libraries. An exemplary feature of a combinatorial nucleic acid library of the invention is that it comprises sequences encoding cellular targeting signal peptides and sequences encoding proteins to be targeted (e.g., enzymes or catalytic domains thereof, including but not limited to those which mediate glycosylation).

In one embodiment, a combinatorial nucleic acid library comprises: (a) at least two nucleic acid sequences encoding different cellular targeting signal peptides; and (b) at least one nucleic acid sequence encoding a polypeptide to be targeted. In another embodiment, a combinatorial nucleic acid library comprises: (a) at least one nucleic acid sequence encoding a cellular targeting signal peptide; and (b) at least two nucleic acid sequences encoding a polypeptide to be targeted into a host cell. As described further below, a nucleic acid sequence derived from (a) and a nucleic acid sequence derived from (b) are ligated to produce one or more fusion constructs encoding a cellular targeting signal peptide functionally linked to a polypeptide domain of interest. One example of a functional linkage is when the cellular targeting signal peptide is ligated to the polypeptide domain of interest in the same translational reading frame ("in-frame").

In a preferred embodiment, a combinatorial DNA library expresses one or more fusion proteins comprising cellular targeting signal peptides ligated in-frame to catalytic enzyme domains. The encoded fusion protein preferably comprises a catalytic domain of an enzyme involved in mammalian- or human-like modification of N-glycans. In a more preferred embodiment, the catalytic domain is derived from an enzyme selected from the group consisting of mannosidases, glycosyltransferases and other glycosidases which is ligated in-frame to one or more targeting signal peptides. The enzyme domain may be exogenous and/or endogenous to the host cell. A particularly preferred signal peptide is one normally associated with a protein that undergoes ER to Golgi transport.

The combinatorial DNA library of the present invention may be used for producing and localizing in vivo enzymes involved in mammalian- or human-like N-glycan modification. The fusion constructs of the combinatorial DNA library are engineered so that the encoded enzymes are localized in the ER, Golgi or the trans-Golgi network of the host cell where they are involved in producing particular N-glycans on a glycoprotein of interest. Localization of N-glycan modifying enzymes of the present invention is achieved through an anchoring mechanism or through protein-protein interaction where the localization peptide constructed from the combinatorial DNA library localizes to a desired organelle of the secretory pathway such as the ER, Golgi or the trans Golgi network.

An example of a useful N-glycan, which is produced efficiently and in sufficient quantities for further modification by human-like (complex) glycosylation reactions is $Man_5GlcNAc_2$. A sufficient amount of $Man_5GlcNAc_2$ is needed on a glycoprotein of interest for further human-like processing in vivo (e.g., more than 30 mole %). The $Man_5GlcNAc_2$ intermediate may be used as a substrate for further N-glycan modification to produce $GlcNAcMan_5GlcNAc_2$ (FIG. 1B; see above). Accordingly, the combinatorial DNA library of the present invention may be used to produce enzymes which subsequently produce $GlcNAcMan_5GlcNAc_2$, or other desired complex N-glycans, in a useful quantity.

A further aspect of the fusion constructs produced using the combinatorial DNA library of the present invention is that they enable sufficient and often near complete intracellular N-glycan trimming activity in the engineered host cell. Preferred fusion constructs produced by the combinatorial DNA library of the invention encode a glycosylation enzyme, e.g., a mannosidase, which is effectively localized to an intracellular host cell compartment and thereby exhibits very little and preferably no extracellular activity. The preferred fusion constructs of the present invention that encode a mannosidase enzyme are shown to localize where the N-glycans are modified, namely, the ER and the Golgi. The fusion enzymes of the present invention are targeted to such particular organelles in the secretory pathway where they localize and act upon N-glycans such as $Man_8GlcNAc_2$ to produce $Man_5GlcNAc_2$ on a glycoprotein of interest.

Figure 5:
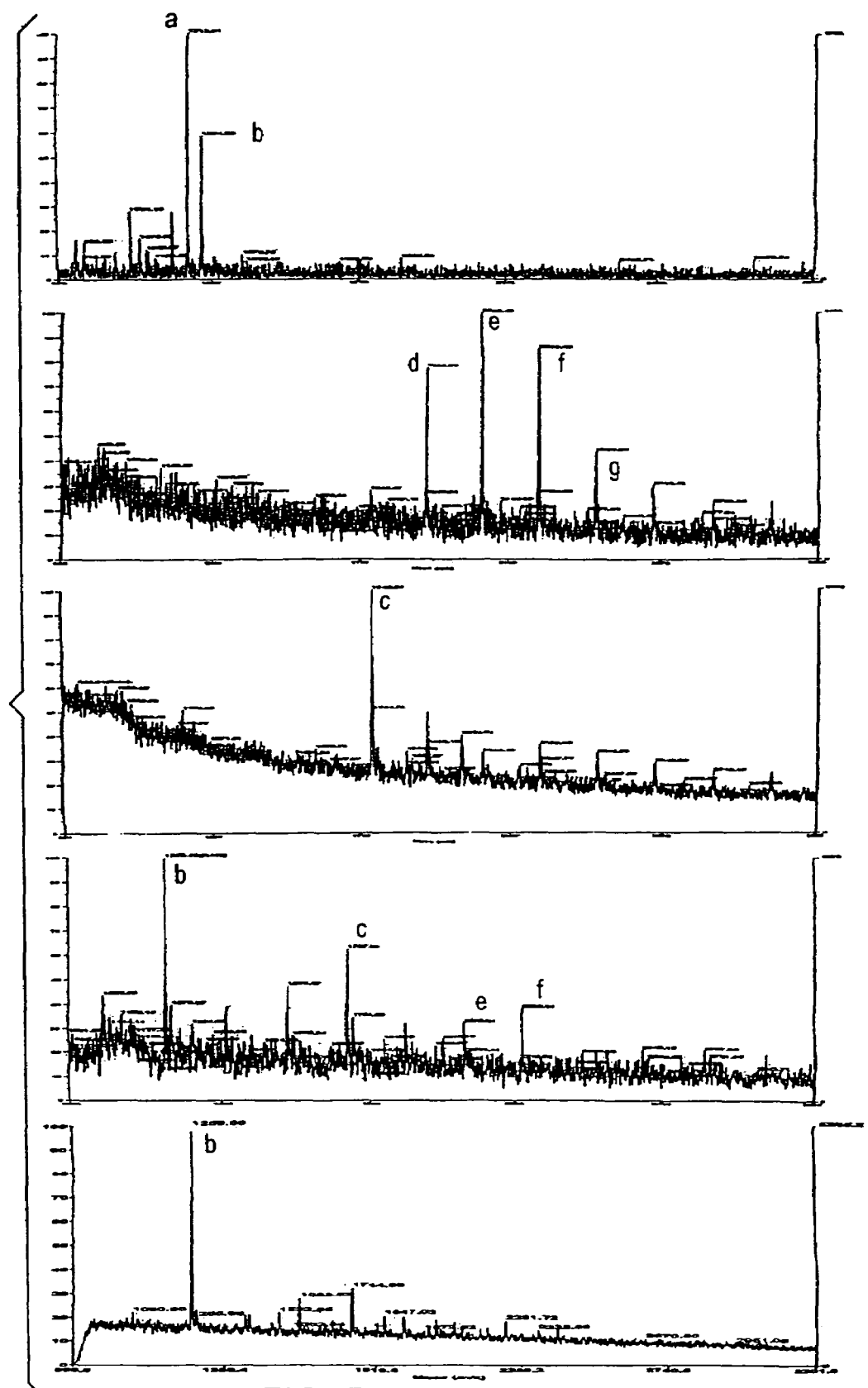
FIGS. 5A-5E show MALDI-TOF analysis demonstrating production of kringle 3 domain of human plasminogen (K3) glycoproteins having $Man_5GlcNAc_2$ as the predominant N-glycan structure in *P. pastoris*.
Figure 5A:
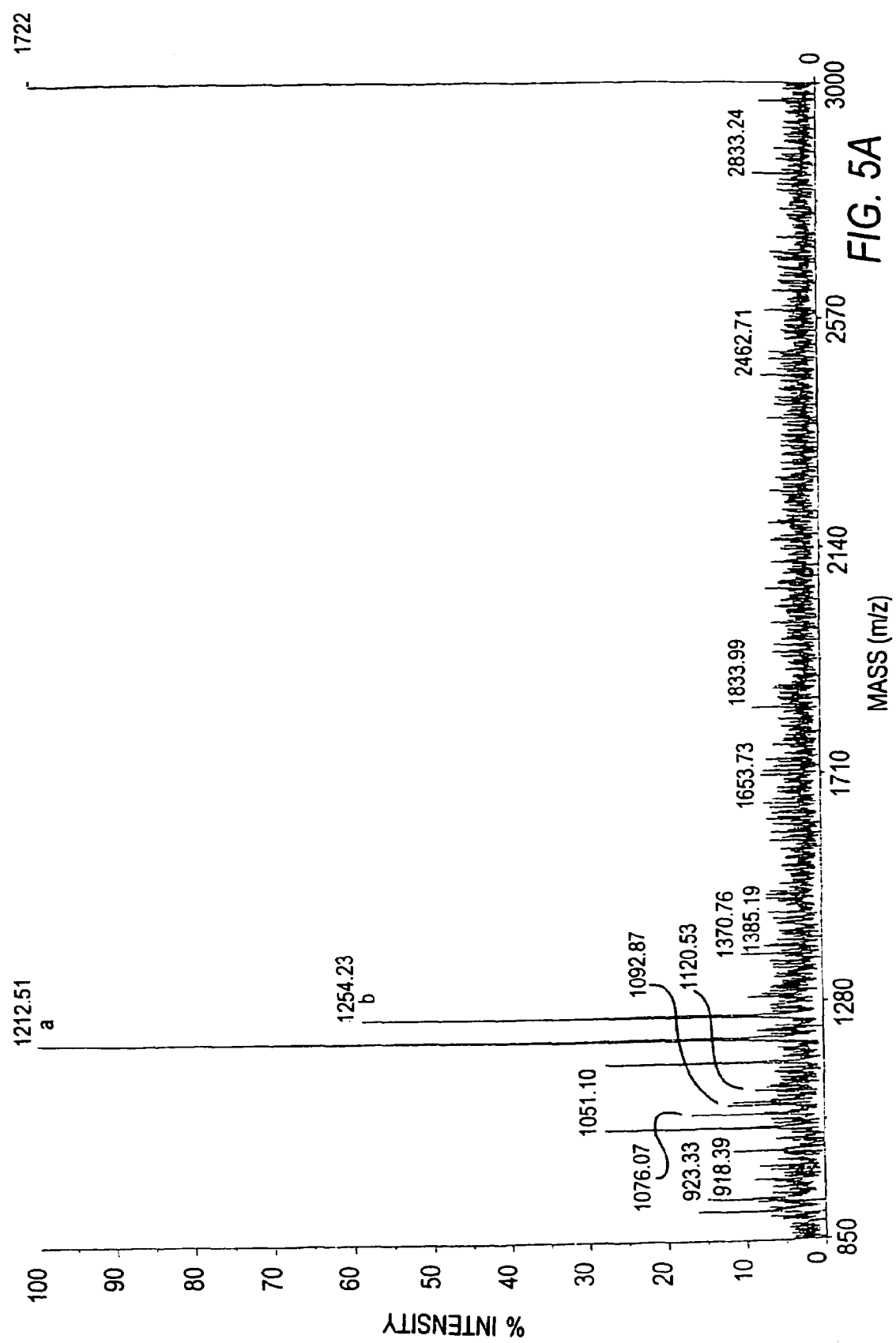
Figure 5B:
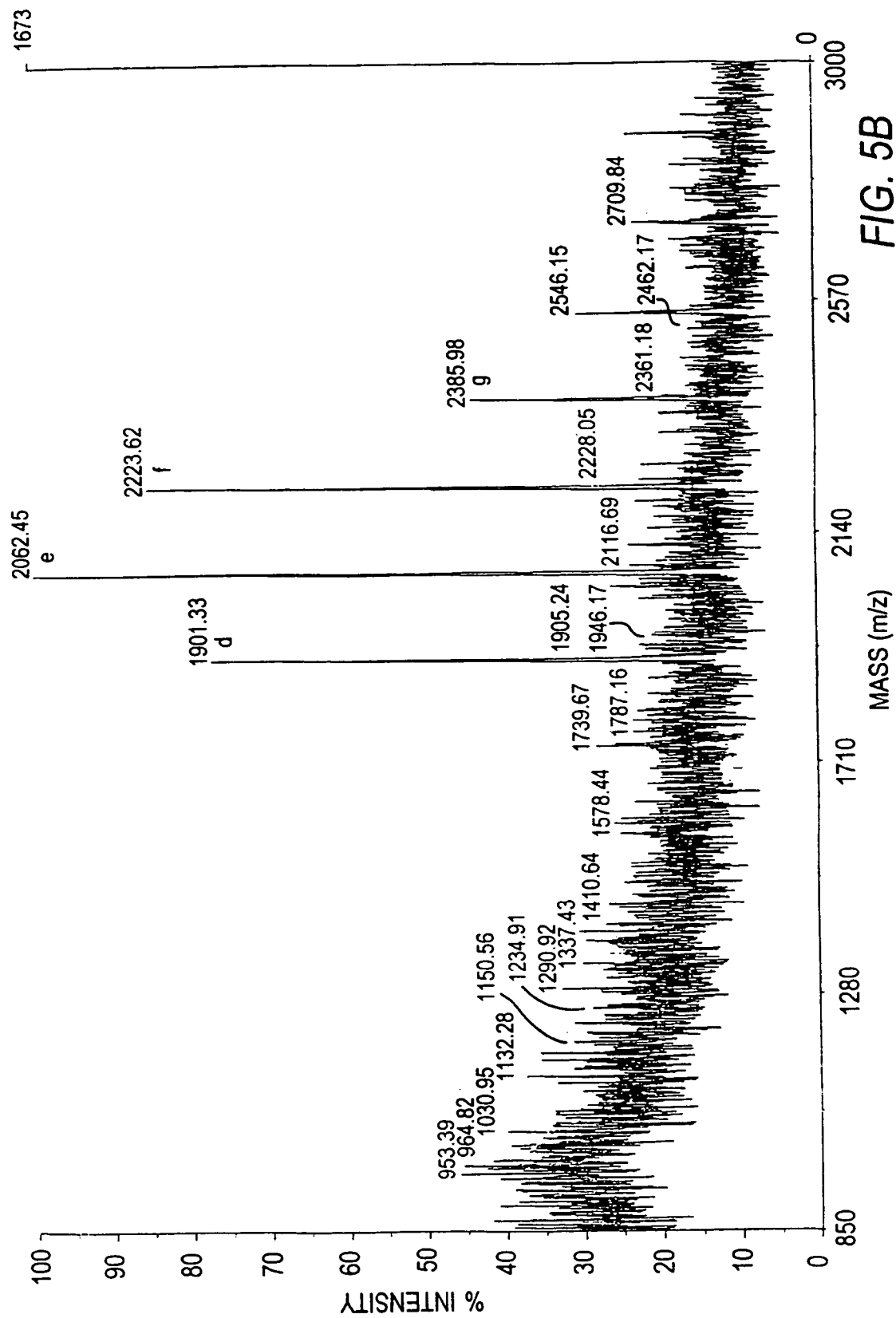
Figure 6:
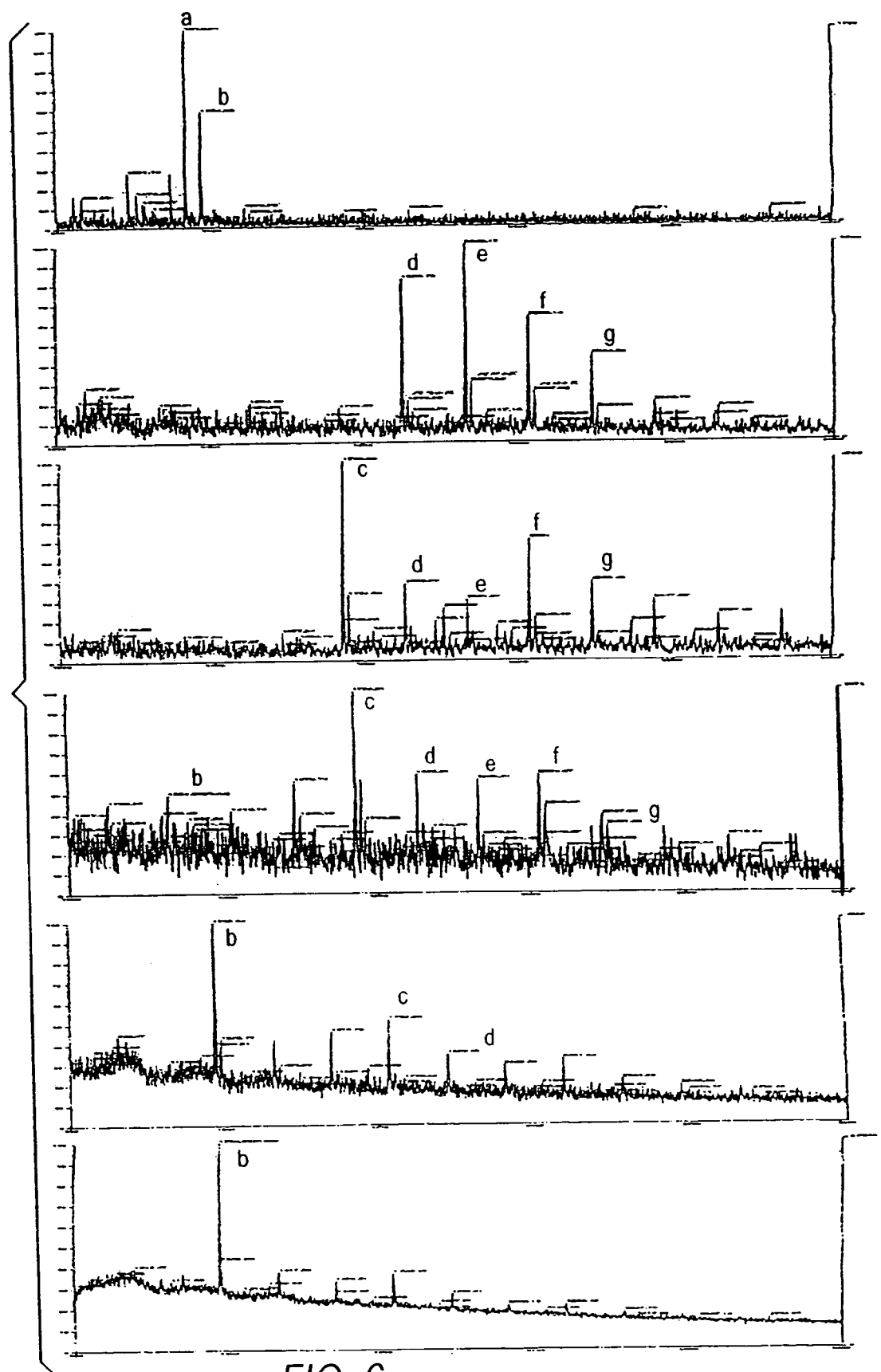
FIGS. 6A-6F show MALDI-TOF analysis demonstrating production of IFN-β glycoproteins having $Man_5GlcNAc_2$ as the predominant N-glycan structure in *P. pastoris*.
Figure 6A:
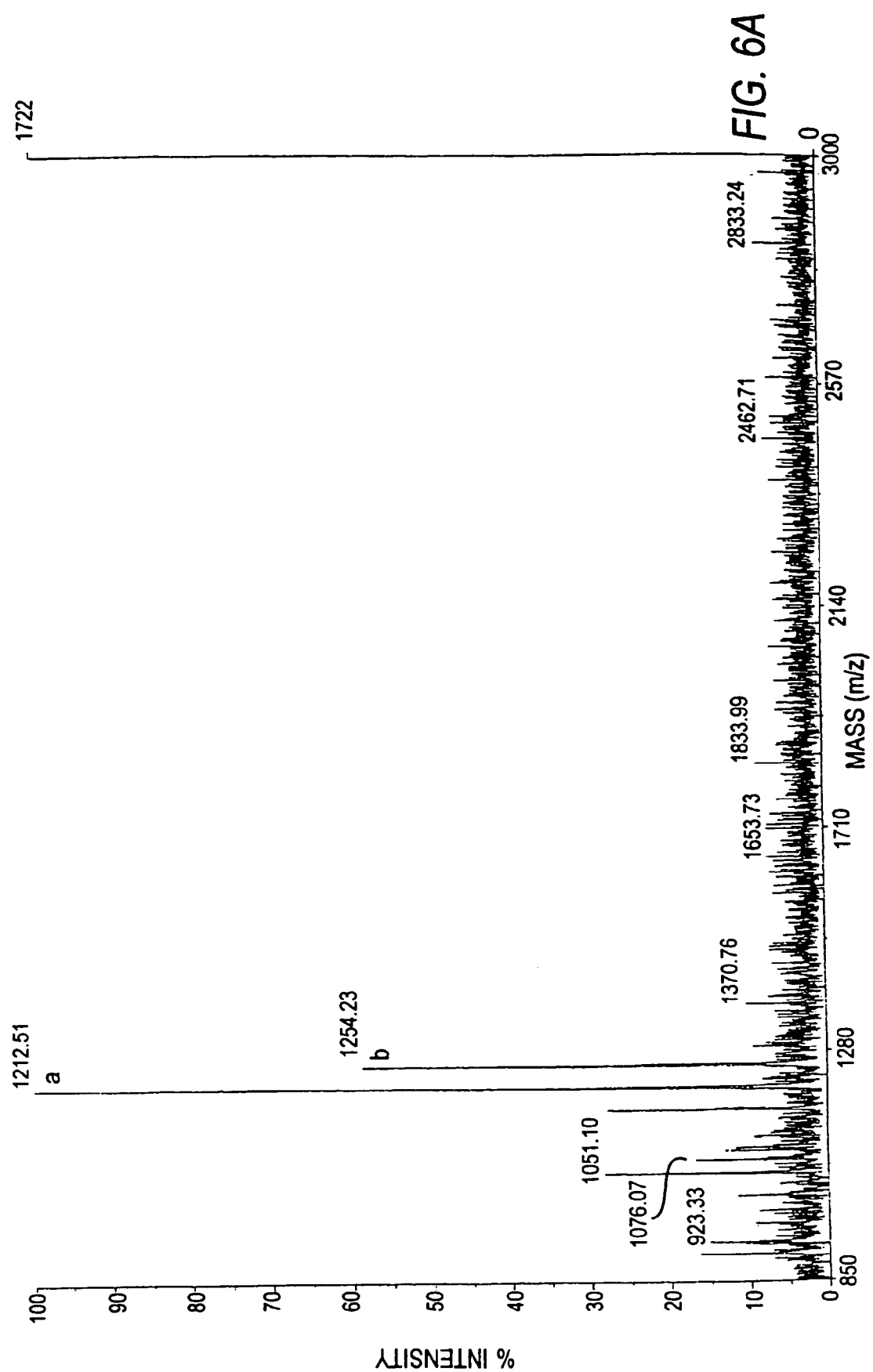
Figure 6B:
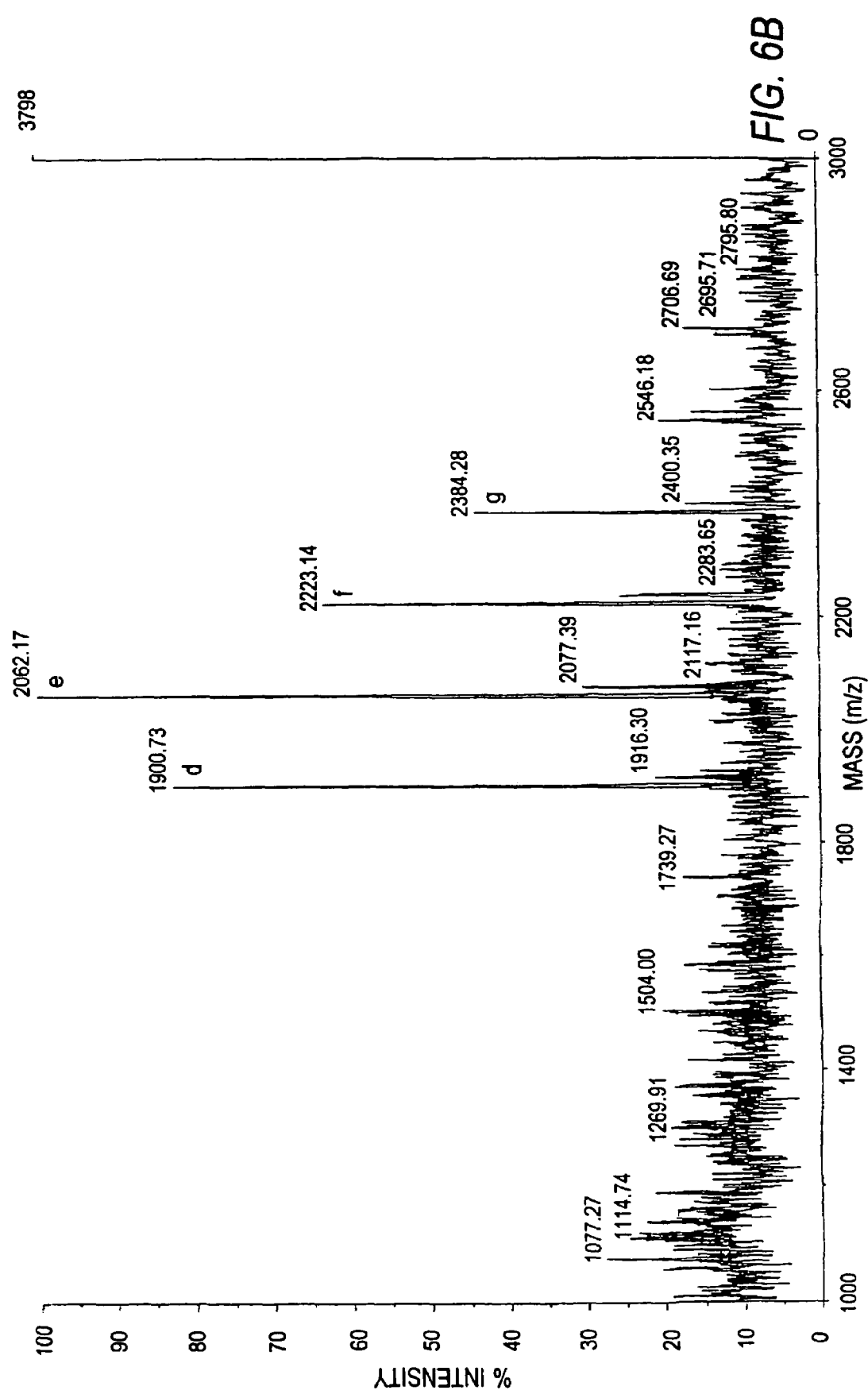
Figure 6C:
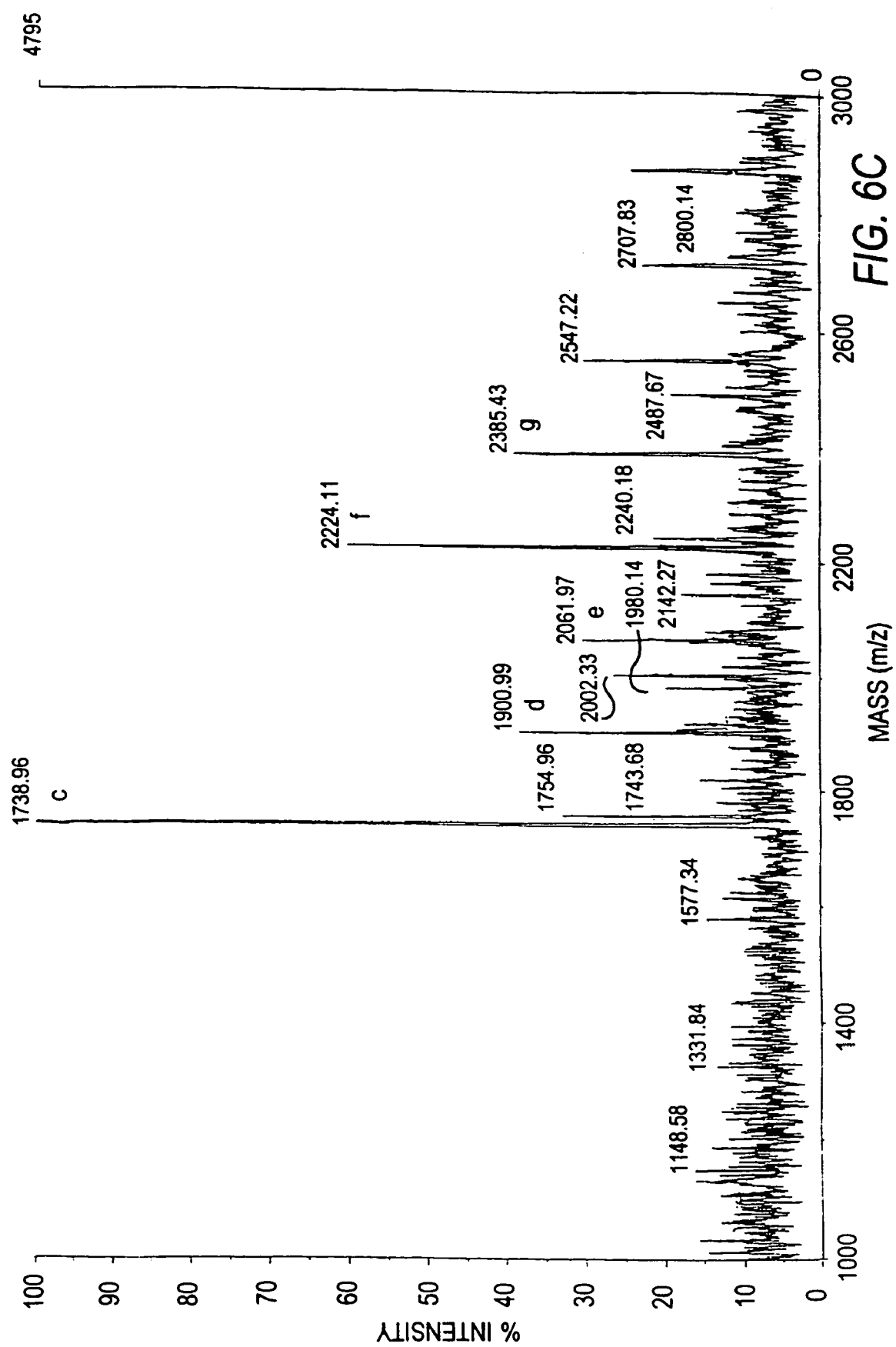
Figure 6D:
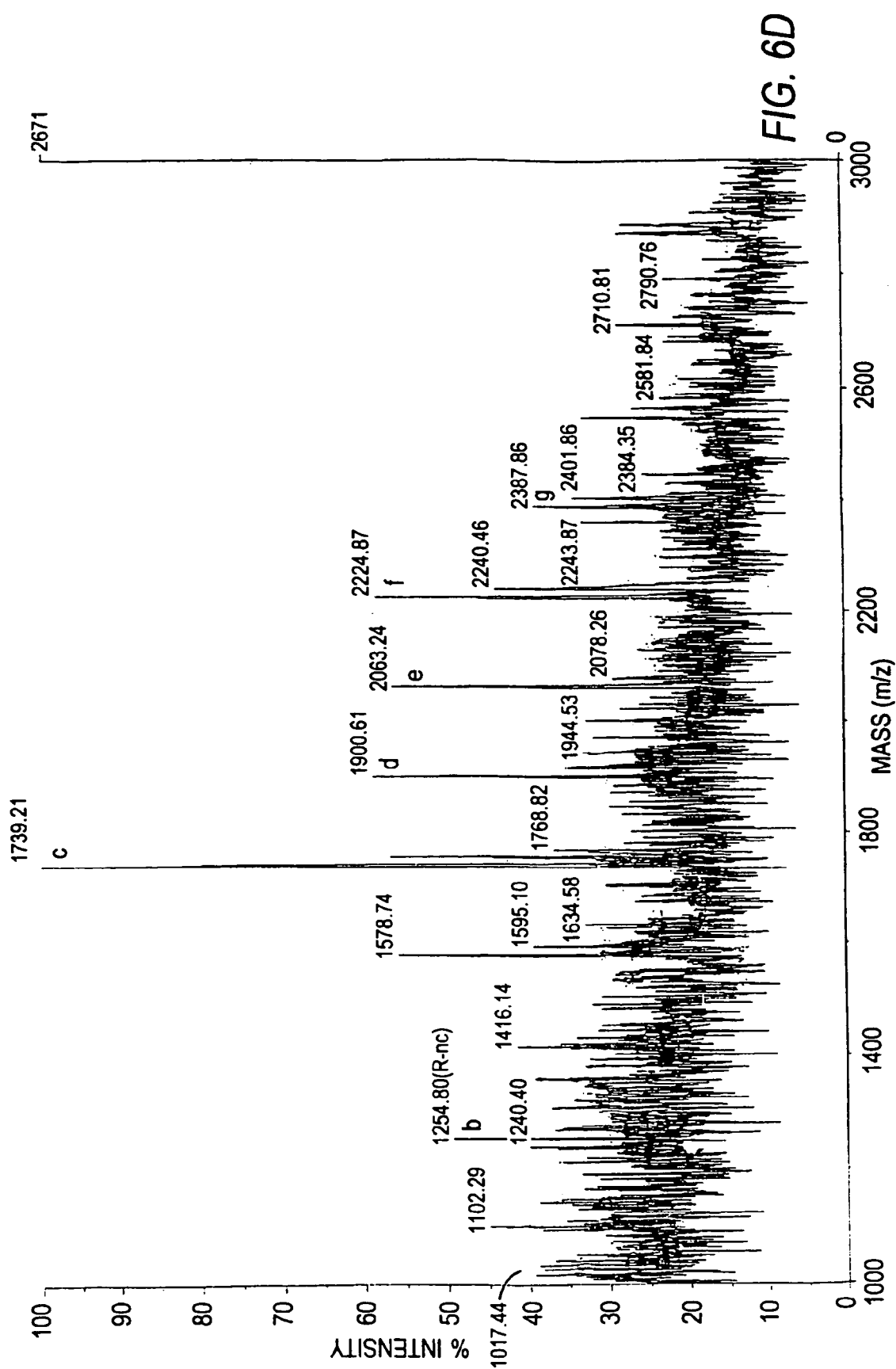
Figure 6E:
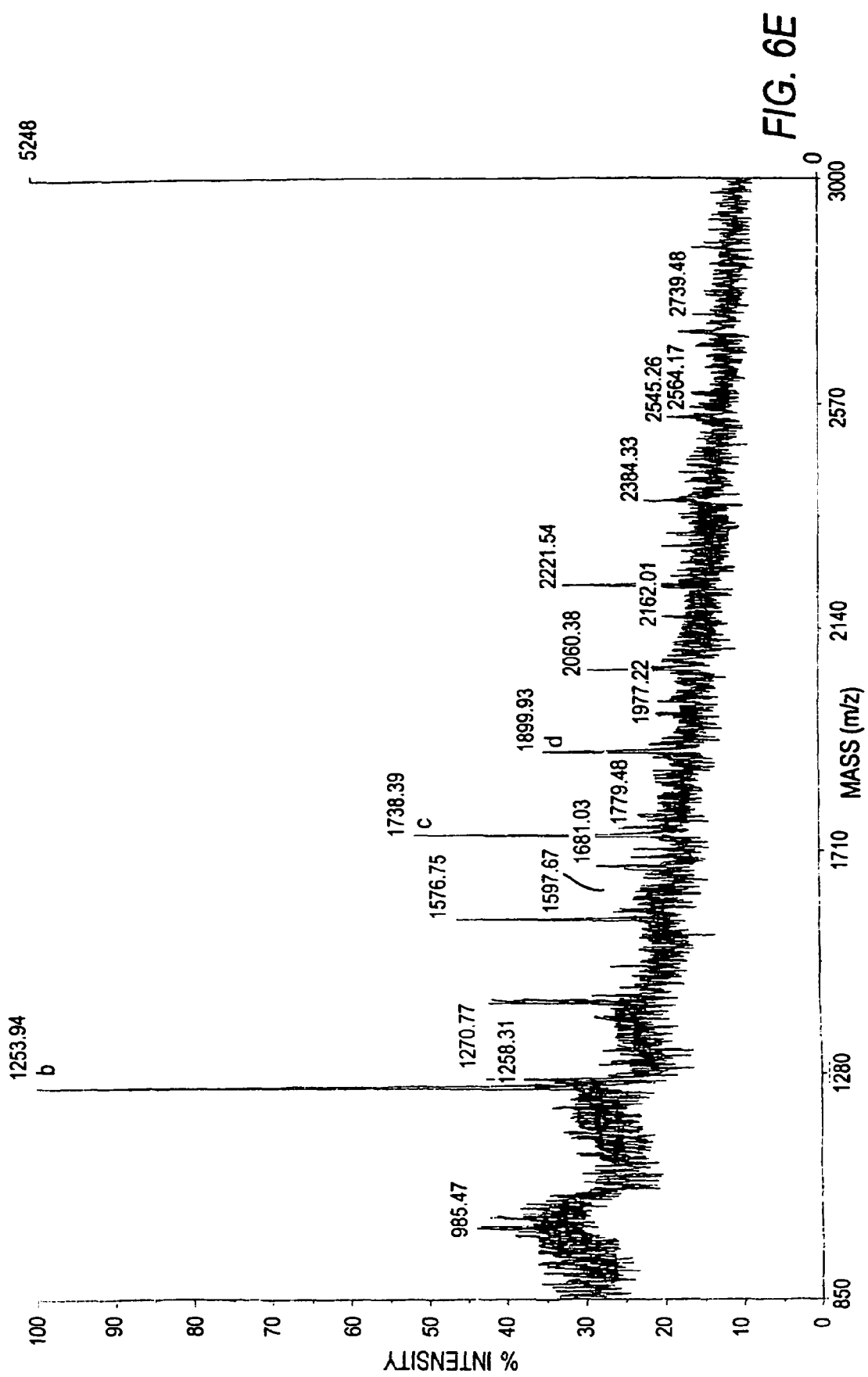

Enzymes produced by the combinatorial DNA library of the present invention can modify N-glycans on a glycoprotein of interest as shown for K3 or IFN-β proteins expressed in *P. pastoris*, as shown in FIGS. 5 and 6, respectively (see also Examples 2 and 4). It is, however, appreciated that other types of glycoproteins, without limitation, including erythropoietin, cytokines such as interferon-α, interferon-β, interferon-γ, interferon-ω, and granulocyte-CSF, coagulation factors such as factor VIII, factor IX, and human protein C, soluble IgE receptor α-chain, IgG, IgG fragments, IgM, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1 antitrypsin, DNase II and α-feto proteins may be glycosylated in this way.

Constructing a Combinatorial DNA Library of Fusion Constructs:

A combinatorial DNA library of fusion constructs features one or more cellular targeting signal peptides ("targeting peptides") generally derived from N-terminal domains of native proteins (e.g., by making C-terminal deletions). Some targeting peptides, however, are derived from the C-terminus of native proteins (e.g. SEC12). Membrane-bound proteins of the ER or the Golgi are preferably used as a source for targeting peptide sequences. These proteins have sequences encoding a cytosolic tail (ct), a transmembrane domain (tmd) and a stem region (sr) which are varied in length. These regions are recognizable by protein sequence alignments and comparisons with known homologs and/or other localized proteins (e.g., comparing hydrophobicity plots).

The targeting peptides are indicated herein as short (s), medium (m) and long (l) relative to the parts of a type II membrane. The targeting peptide sequence indicated as short (s) corresponds to the transmembrane domain (tmd) of the membrane-bound protein. The targeting peptide sequence indicated as long (l) corresponds to the length of the transmembrane domain (tmd) and the stem region (sr). The targeting peptide sequence indicated as medium (m) corresponds to the transmembrane domain (tmd) and approximately half the length of the stem region (sr). The catalytic domain regions are indicated herein by the number of nucleotide deletion with respect to its wild-type glycosylation enzyme.

Sub-Libraries

In some cases a combinatorial nucleic acid library of the invention may be assembled directly from existing or wild-type genes. In a preferred embodiment, the DNA library is assembled from the fusion of two or more sub-libraries. By the in-frame ligation of the sub-libraries, it is possible to create a large number of novel genetic constructs encoding useful targeted protein domains such as those which have glycosylation activities.

Catalytic Domain Sub-Libraries Encoding Glycosylation Activities

One useful sub-library includes DNA sequences encoding enzymes such as glycosidases (e.g., mannosidases), glycosyltransferases (e.g., fucosyl-transferases, galactosyltransferases, glucosyltransferases), GlcNAc transferases and sialyltransferases. Catalytic domains may be selected from the host to be engineered, as well as from other related or unrelated organisms. Mammalian, plant, insect, reptile, algal or fungal enzymes are all useful and should be chosen to represent a broad spectrum of biochemical properties with respect to temperature and pH optima. In a preferred embodiment, genes are truncated to give fragments some of which encode the catalytic domains of the enzymes. By removing endogenous targeting sequences, the enzymes may then be redirected and expressed in other cellular loci.

The choice of such catalytic domains may be guided by the knowledge of the particular environment in which the catalytic domain is subsequently to be active. For example, if a particular glycosylation enzyme is to be active in the late Golgi, and all known enzymes of the host organism in the late Golgi have a certain pH optimum, or the late Golgi is known to have a particular pH, then a catalytic domain is chosen which exhibits adequate, and preferably maximum, activity at that pH, as discussed above.

Targeting Peptide Sequence Sub-Libraries

Another useful sub-library includes nucleic acid sequences encoding targeting signal peptides that result in localization of a protein to a particular location within the ER, Golgi, or trans Golgi network. These targeting peptides may be selected from the host organism to be engineered as well as from other related or unrelated organisms. Generally such sequences fall into three categories: (1) N-terminal sequences encoding a cytosolic tail (ct), a transmembrane domain (tmd) and part or all of a stem region (sr), which together or individually anchor proteins to the inner (lumenal) membrane of the Golgi; (2) retrieval signals which are generally found at the C-terminus such as the HDEL (SEQ ID NO: 105) or KDEL tetrapeptide (SEQ ID NO: 106); and (3) membrane spanning regions from various proteins, e.g., nucleotide sugar transporters, which are known to localize in the Golgi.

In the first case, where the targeting peptide consists of various elements (ct, tmd and sr), the library is designed such that the ct, the tmd and various parts of the stem region are represented. Accordingly, a preferred embodiment of the sub-library of targeting peptide sequences includes ct, tmd, and/or sr sequences from membrane-bound proteins of the ER or Golgi. In some cases it may be desirable to provide the sub-library with varying lengths of sr sequence. This may be accomplished by PCR using primers that bind to the 5' end of the DNA encoding the cytosolic region and employing a series of opposing primers that bind to various parts of the stem region.

Still other useful sources of targeting peptide sequences include retrieval signal peptides, e.g. the tetrapeptides HDEL (SEQ ID NO: 105) or KDEL (SEQ ID NO: 106), which are typically found at the C-terminus of proteins that are transported retrograde into the ER or Golgi. Still other sources of targeting peptide sequences include (a) type II membrane proteins, (b) the enzymes listed in Table 3, (c) membrane spanning nucleotide sugar transporters that are localized in the Golgi, and (d) sequences referenced in Table 5.

TABLE 5

Sources of useful compartmental targeting sequences

| Gene or Sequence | Organism | Function | Location of Gene Product |
|---|---|---|---|
| MNSI | A. nidulans | α-1,2-mannosidase | ER |
| MNSI | A. niger | α-1,2-mannosidase | ER |
| MNSI | S. cerevisiae | α-1,2-mannosidase | ER |
| GLSI | S. cerevisiae | glucosidase | ER |
| GLSI | A. niger | glucosidase | ER |
| GLSI | A. nidulans | glucosidase | ER |
| HDEL (SEQ ID NO: 105) at C-terminus | Universal in fungi | retrieval signal | ER |
| SEC12 | S. cerevisiae | COPII vesicle protein | ER/Golgi |
| SEC12 | A. niger | COPII vesicle protein | ER/Golgi |
| OCH1 | S. cerevisiae | 1,6-mannosyltransferase | Golgi (cis) |

TABLE 5-continued

Sources of useful compartmental targeting sequences

| Gene or Sequence | Organism | Function | Location of Gene Product |
|---|---|---|---|
| OCH1 | P. pastoris | 1,6-mannosyltransferase | Golgi (cis) |
| MNN9 | S. cerevisiae | 1,6-mannosyltransferase complex | Golgi |
| MNN9 | A. niger | undetermined | Golgi |
| VAN1 | S. cerevisiae | undetermined | Golgi |
| VAN1 | A. niger | undetermined | Golgi |
| ANP1 | S. cerevisiae | undetermined | Golgi |
| HOC1 | S. cerevisiae | undetermined | Golgi |
| MNN10 | S. cerevisiae | undetermined | Golgi |
| MNN10 | A. niger | undetermined | Golgi |
| MNN11 | S. cerevisiae | undetermined | Golgi (cis) |
| MNN11 | A. niger | undetermined | Golgi (cis) |
| MNT1 | S. cerevisiae | 1,2-mannosyltransferase | Golgi (cis, medial |
| KTR1 | P. pastoris | undetermined | Golgi (medial) |
| KRE2 | P. pastoris | undetermined | Golgi (medial) |
| KTR3 | P. pastoris | undetermined | Golgi (medial) |
| MNN2 | S. cerevisiae | 1,2-mannosyltransferase | Golgi (medial) |
| KTR1 | S. cerevisiae | undetermined | Golgi (medial) |
| KTR2 | S. cerevisiae | undetermined | Golgi (medial) |
| MNN1 | S. cerevisiae | 1,3-mannosyltransferase | Golgi (trans) |
| MNN6 | S. cerevisiae | Phosphomannosyltransferase | Golgi (trans) |
| 2,6 ST | H. sapiens | 2,6-sialyltransferase | trans Golgi network |
| UDP-Gal T | S. pombe | UDP-Gal transporter | Golgi |

In any case, it is highly preferred that targeting peptide sequences are selected which are appropriate for the particular enzymatic activity or activities to function optimally within the sequence of desired glycosylation reactions. For example, in developing a modified host microorganism capable of terminal sialylation of nascent N-glycans, a process which occurs in the late Golgi in humans, it is desirable to utilize a sub-library of targeting peptide sequences derived from late Golgi proteins. Similarly, the trimming of $Man_8GlcNAc_2$ by an α-1,2-mannosidase to give $Man_5GlcNAc_2$ is an early step in complex N-glycan formation in humans (FIG. 1B). It is therefore desirable to have this reaction occur in the ER or early Golgi of an engineered host microorganism. A sub-library encoding ER and early Golgi retention signals is used.

A series of fusion protein constructs (i.e., a combinatorial DNA library) is then constructed by functionally linking one or a series of targeting peptide sequences to one or a series of sequences encoding catalytic domains. In a preferred embodiment, this is accomplished by the in-frame ligation of a sub-library comprising DNA encoding targeting peptide sequences (above) with a sub-library comprising DNA encoding glycosylation enzymes or catalytically active fragments thereof (see below).

The resulting library comprises synthetic genes encoding targeting peptide sequence-containing fusion proteins. In some cases it is desirable to provide a targeting peptide sequence at the N-terminus of a fusion protein, or in other cases at the C-terminus. In some cases, targeting peptide sequences may be inserted within the open reading frame of an enzyme, provided the protein structure of individual folded domains is not disrupted. Each type of fusion protein is constructed (in a step-wise directed or semi-random fashion) and optimal constructs may be selected upon transformation of host cells and characterization of glycosylation patterns in transformed cells using methods of the invention.

Generating Additional Sequence Diversity

The method of this embodiment is most effective when a nucleic acid, e.g., a DNA library transformed into the host contains a large diversity of sequences, thereby increasing the probability that at least one transformant will exhibit the desired phenotype. Single amino acid mutations, for example, may drastically alter the activity of glycoprotein processing enzymes (Romero et al. (2000) J. Biol. Chem. 275(15):11071-4). Accordingly, prior to transformation, a DNA library or a constituent sub-library may be subjected to one or more techniques to generate additional sequence diversity. For example, one or more rounds of gene shuffling, error prone PCR, in vitro mutagenesis or other methods for generating sequence diversity, may be performed to obtain a larger diversity of sequences within the pool of fusion constructs.

Expression Control Sequences

In addition to the open reading frame sequences described above, it is generally preferable to provide each library construct with expression control sequences, such as promoters, transcription terminators, enhancers, ribosome binding sites, and other functional sequences as may be necessary to ensure effective transcription and translation of the fusion proteins upon transformation of fusion constructs into the host organism.

Suitable vector components, e.g., selectable markers, expression control sequences (e.g., promoter, enhancers, terminators and the like) and, optionally, sequences required for autonomous replication in a host cell, are selected as a function of which particular host cell is chosen. Selection criteria for suitable vector components for use in a particular mammalian or a lower eukaryotic host cell are routine. Preferred lower eukaryotic host cells of the invention include Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oiyzae, Trichoderma reesei, Chrysosporium lucknowense, Fusarium sp. Fusarium gramineum, Fusarium venenatum and *Neurospora crassa*. Where the host is *Pichia pastoris*, suitable promoters include, for example, the AOX1, AOX2, GAPDH and P40 promoters.

Selectable Markers

It is also preferable to provide each construct with at least one selectable marker, such as a gene to impart drug resistance or to complement a host metabolic lesion. The presence of the marker is useful in the subsequent selection of transformants; for example, in yeast the URA3, HIS4, SUC2, G418, BLA, or SH BLE genes may be used. A multitude of selectable markers are known and available for use in yeast, fungi, plant, insect, mammalian and other eukaryotic host cells.

Transformation

The nucleic acid library is then transformed into the host organism. In yeast, any convenient method of DNA transfer may be used, such as electroporation, the lithium chloride method, or the spheroplast method. In filamentous fungi and plant cells, conventional methods include particle bombardment, electroporation and agrobacterium mediated transformation. To produce a stable strain suitable for high-density culture (e.g., fermentation in yeast), it is desirable to integrate the DNA library constructs into the host chromosome. In a preferred embodiment, integration occurs via homologous recombination, using techniques well-known in the art. For example, DNA library elements are provided with flanking sequences homologous to sequences of the host organism. In this manner, integration occurs at a defined site in the host genome, without disruption of desirable or essential genes.

In an especially preferred embodiment, library DNA is integrated into the site of an undesired gene in a host chromosome, effecting the disruption or deletion of the gene. For example, integration into the sites of the OCH1, MNN1, or MNN4 genes allows the expression of the desired library DNA while preventing the expression of enzymes involved in yeast hypermannosylation of glycoproteins. In other embodiments, library DNA may be introduced into the host via a nucleic acid molecule, plasmid, vector (e.g., viral or retroviral vector), chromosome, and may be introduced as an autonomous nucleic acid molecule or by homologous or random integration into the host genome. In any case, it is generally desirable to include with each library DNA construct at least one selectable marker gene to allow ready selection of host organisms that have been stably transformed. Recyclable marker genes such as URA3, which can be selected for or against, are especially suitable.

Screening and Selection Processes

After transformation of the host strain with the DNA library, transformants displaying a desired glycosylation phenotype are selected. Selection may be performed in a single step or by a series of phenotypic enrichment and/or depletion steps using any of a variety of assays or detection methods. Phenotypic characterization may be carried out manually or using automated high-throughput screening equipment. Commonly, a host microorganism displays protein N-glycans on the cell surface, where various glycoproteins are localized.

One may screen for those cells that have the highest concentration of terminal GlcNAc on the cell surface, for example, or for those cells which secrete the protein with the highest terminal GlcNAc content. Such a screen may be based on a visual method, like a staining procedure, the ability to bind specific terminal GlcNAc binding antibodies or lectins conjugated to a marker (such lectins are available from E.Y. Laboratories Inc., San Mateo, Calif.), the reduced ability of specific lectins to bind to terminal mannose residues, the ability to incorporate a radioactively labeled sugar in vitro, altered binding to dyes or charged surfaces, or may be accomplished by using a Fluorescence Assisted Cell Sorting (FACS) device in conjunction with a fluorophore labeled lectin or antibody (Guillen et al. (1998) *Proc. Natl. Acad. Sci. USA* 95(14):7888-7892).

Accordingly, intact cells may be screened for a desired glycosylation phenotype by exposing the cells to a lectin or antibody that binds specifically to the desired N-glycan. A wide variety of oligosaccharide-specific lectins are available commercially (e.g., from EY Laboratories, San Mateo, Calif.). Alternatively, antibodies to specific human or animal N-glycans are available commercially or may be produced using standard techniques. An appropriate lectin or antibody may be conjugated to a reporter molecule, such as a chromophore, fluorophore, radioisotope, or an enzyme having a chromogenic substrate (Guillen et al., 1998. *Proc. Natl. Acad. Sci. USA* 95(14): 7888-7892).

Screening may then be performed using analytical methods such as spectrophotometry, fluorimetry, fluorescence activated cell sorting, or scintillation counting. In other cases, it may be necessary to analyze isolated glycoproteins or N-glycans from transformed cells. Protein isolation may be carried out by techniques known in the art. In a preferred embodiment, a reporter protein is secreted into the medium and purified by affinity chromatography (e.g. Ni-affinity or glutathione-S-transferase affinity chromatography). In cases where an isolated N-glycan is preferred, an enzyme such as endo-β-N-acetylglucosaminidase (Genzyme Co., Boston, Mass.; New England Biolabs, Beverly, Mass.) may be used to cleave the N-glycans from glycoproteins. Isolated proteins or N-glycans may then be analyzed by liquid chromatography (e.g. HPLC), mass spectroscopy, or other suitable means. U.S. Pat. No. 5,595,900 teaches several methods by which cells with desired extracellular carbohydrate structures may be identified. In a preferred embodiment, MALDI-TOF mass spectrometry is used to analyze the cleaved N-glycans.

Prior to selection of a desired transformant, it may be desirable to deplete the transformed population of cells having undesired phenotypes. For example, when the method is used to engineer a functional mannosidase activity into cells, the desired transformants will have lower levels of mannose in cellular glycoprotein. Exposing the transformed population to a lethal radioisotope of mannose in the medium depletes the population of transformants having the undesired phenotype, i.e. high levels of incorporated mannose (Huffaker T C and Robbins P W., *Proc Natl Acad Sci U S A*. 1983 December; 80(24):7466-70). Alternatively, a cytotoxic lectin or antibody, directed against an undesirable N-glycan, may be used to deplete a transformed population of undesired phenotypes (e.g., Stanley P and Siminovitch L. *Somatic Cell Genet* 1977 July; 3(4):391-405). U.S. Pat. No. 5,595,900 teaches several methods by which cells with a desired extracellular carbohydrate structures may be identified. Repeatedly carrying out this strategy allows for the sequential engineering of more and more complex glycans in lower eukaryotes.

To detect host cells having on their surface a high degree of the human-like N-glycan intermediate GlcNAcMan$_3$GlcNAc$_2$, for example, one may select for transformants that allow for the most efficient transfer of GlcNAc by GlcNAc Transferase from UDP-GlcNAc in an in vitro cell assay. This screen may be carried out by growing cells harboring the transformed library under selective pressure on an agar plate and transferring individual colonies into a 96-well microtiter plate. After growing the cells, the cells are centrifuged, the cells resuspended in buffer, and after addition of UDP-GlcNAc and GnTII, the release of UDP is determined either by HPLC or an enzyme linked assay for UDP. Alternatively, one may use radioactively labeled UDP-GlcNAc and GnTII, wash the cells and then look for the release of radioactive GlcNAc by N-actylglucosaminidase. All this may be carried out manually or may be automated through the use of high throughput screening equipment. Transformants that release more UDP in the first assay, or more radioactively labeled GlcNAc in the second assay, are expected to have a higher degree of GlcNAcMan$_3$GlcNAc$_2$ on their surface and thus constitute the desired phenotype. Similar assays may be adapted to look at the N-glycans on secreted proteins as well.

Alternatively, one may use any other suitable screen such as a lectin binding assay that is able to reveal altered glycosylation patterns on the surface of transformed cells. In this case the reduced binding of lectins specific to terminal mannoses may be a suitable selection tool. *Galantus nivalis* lectin binds specifically to terminal α-1,3 mannose, which is expected to be reduced if sufficient mannosidase II activity is present in the Golgi. One may also enrich for desired transformants by carrying out a chromatographic separation step that allows for the removal of cells containing a high terminal mannose content. This separation step would be carried out with a lectin column that specifically binds cells with a high terminal mannose content (e.g., *Galantus nivalis* lectin bound to agarose, Sigma, St. Louis, Mo.) over those that have a low terminal mannose content.

In addition, one may directly create such fusion protein constructs, as additional information on the localization of active carbohydrate modifying enzymes in different lower eukaryotic hosts becomes available in the scientific literature. For example, it is known that human β1,4-GalTr can be fused to the membrane domain of MNT, a mannosyltransferase from *S. cerevisiae*, and localized to the Golgi apparatus while retaining its catalytic activity (Schwientek et al. (1995) *J. Biol. Chem.* 270(10):5483-9). If *S. cerevisiae* or a related organism is the host to be engineered one may directly incorporate such findings into the overall strategy to obtain complex N-glycans from such a host. Several such gene fragments in *P. pastoris* have been identified that are related to glycosyltransferases in *S. cerevisiae* and thus could be used for that purpose.

Figure 2:
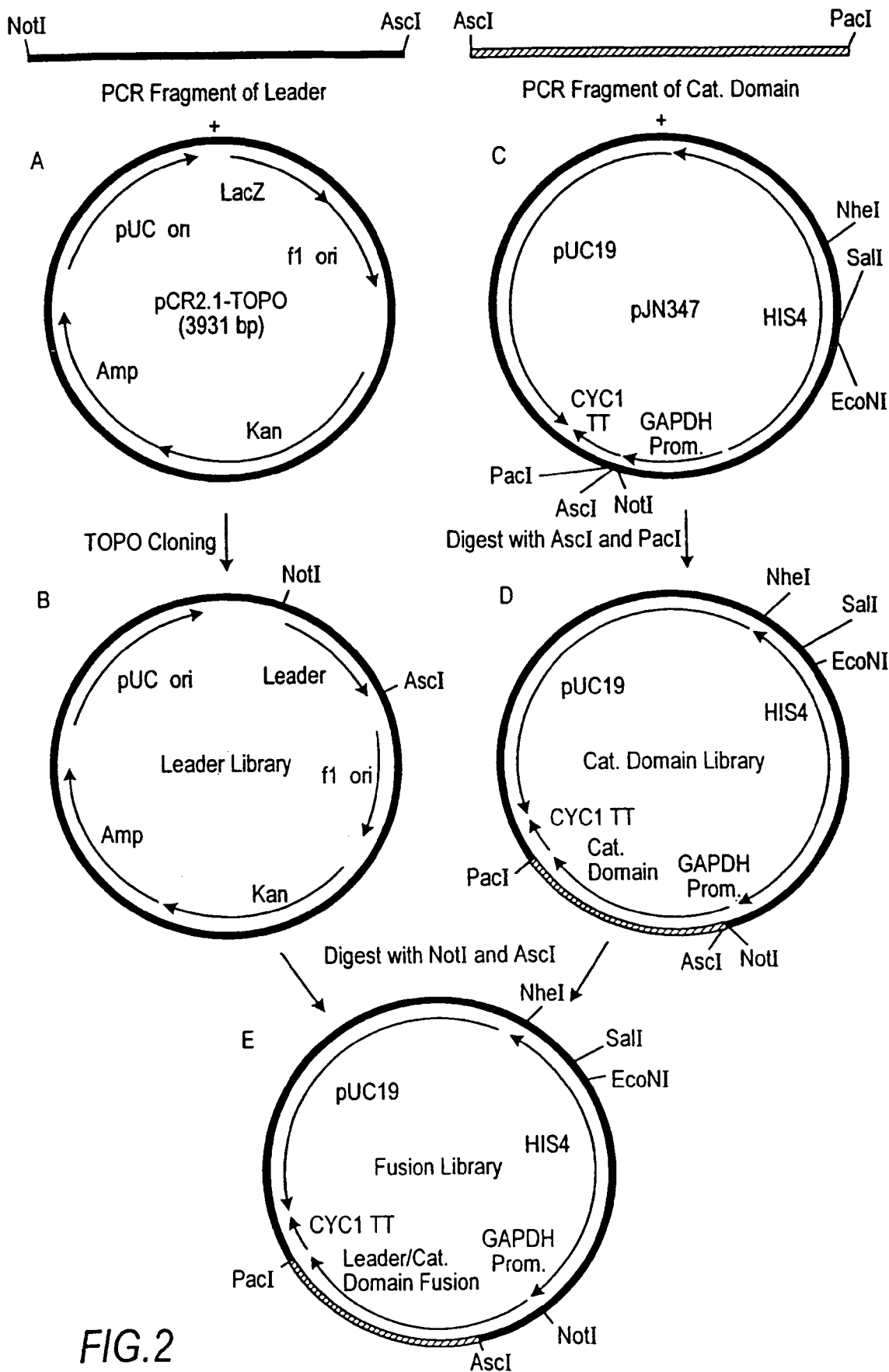
FIG. 2 depicts construction of a combinatorial DNA library of fusion constructs.

Alteration of Host Cell Glycosylation Using Fusion Constructs from Combinatorial Libraries The construction of a preferred combinatorial DNA library is illustrated schematically in FIG. 2 and described in Example 4. The fusion construct may be operably linked to a multitude of vectors, such as expression vectors well-known in the art. A wide variety of such fusion constructs were assembled using representative activities as shown in Table 6. Combinations of targeting peptide/catalytic domains may be assembled for use in targeting mannosidase, glycosyltransferase and glycosidase activities in the ER, Golgi and the trans Golgi network according to the invention. Surprisingly, the same catalytic domain may have no effect to a very profound effect on N-glycosylation patterns, depending on the type of targeting peptide used (see, e.g., Table 7, Example 4).

Mannosidase I Fusion Constructs

Figure 6F:
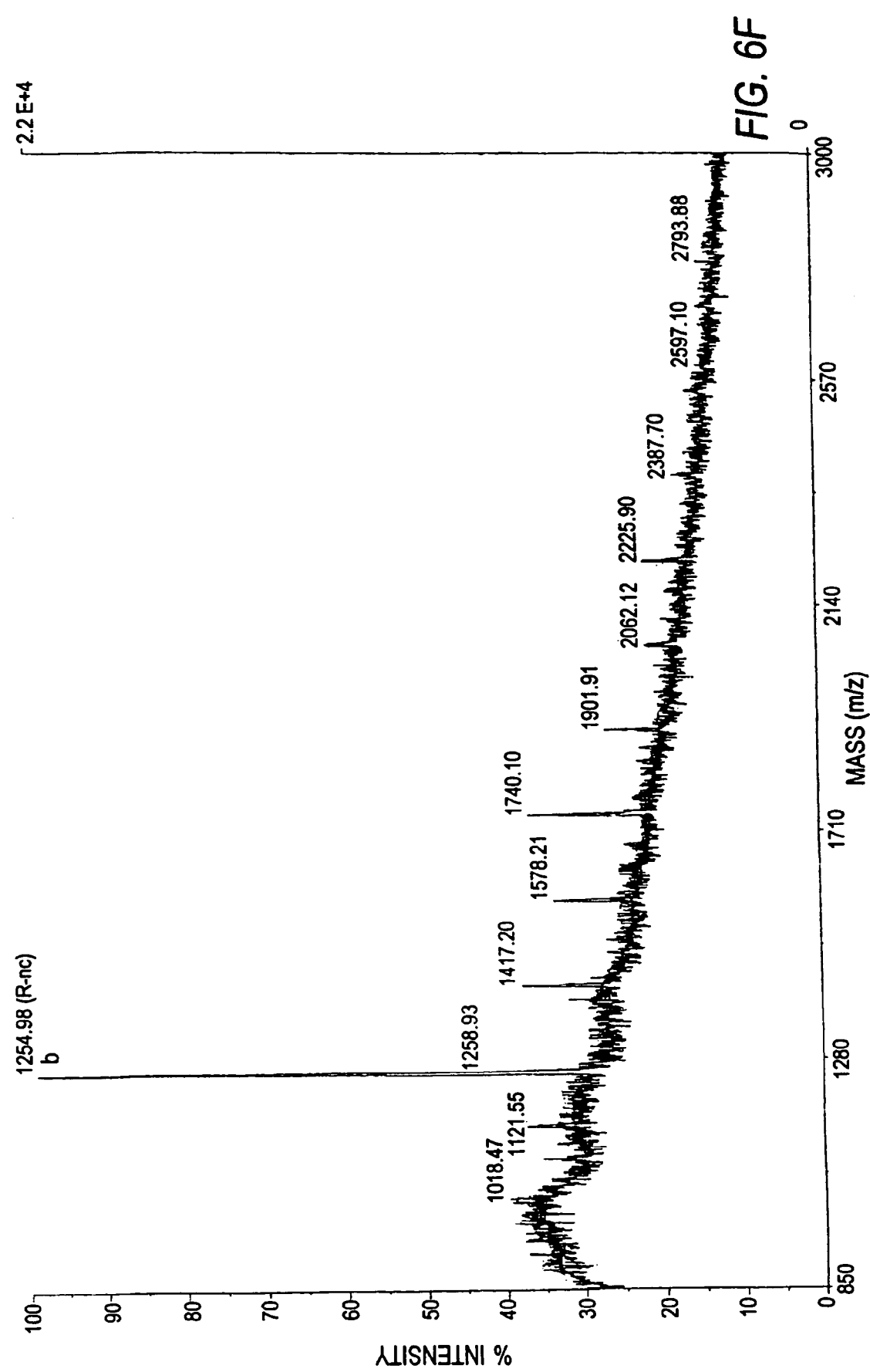
Figure 7:
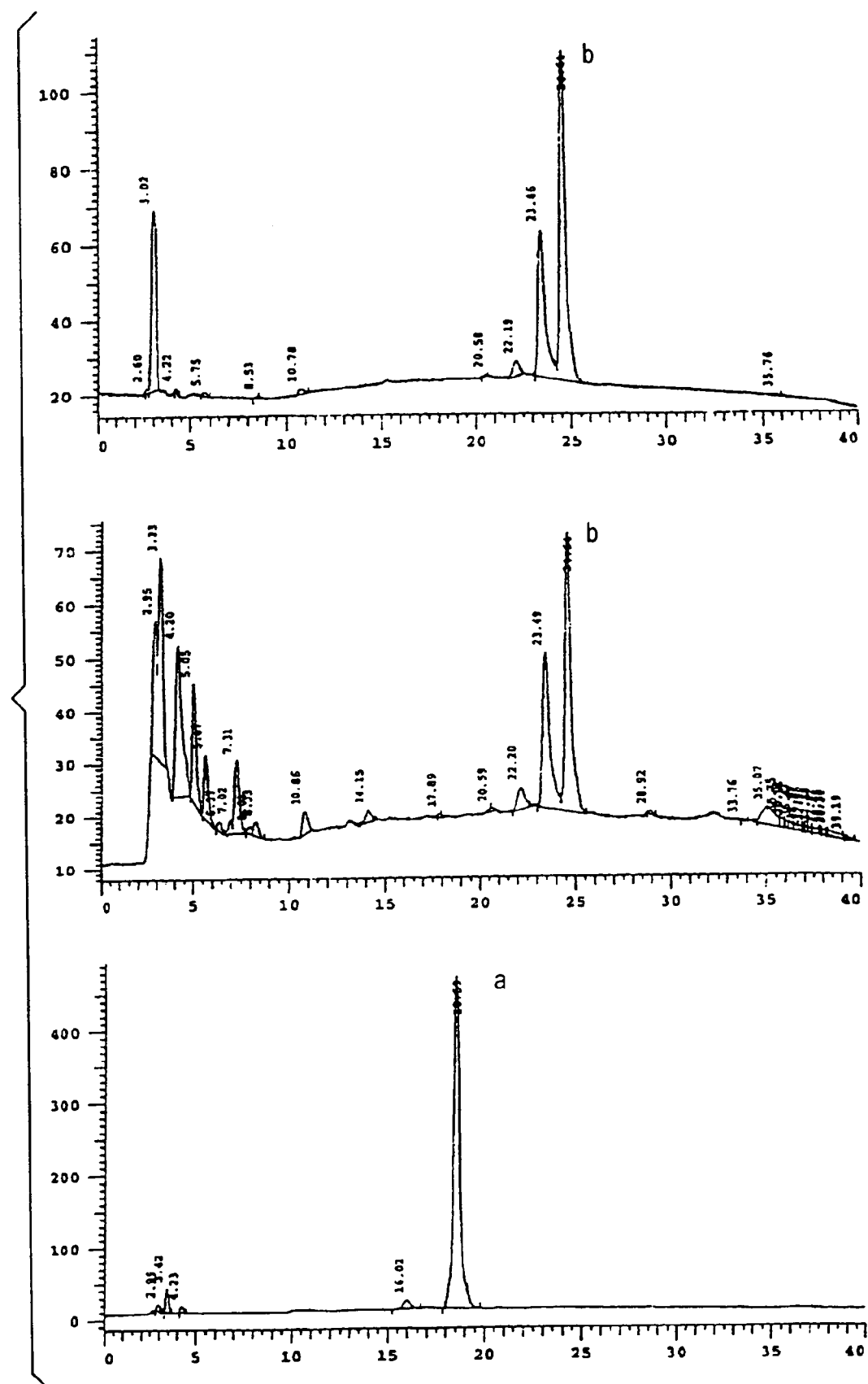
FIG. 7 shows a high performance liquid chromatogram for: (A) $Man_9GlcNAc_2$ standard labeled with 2-AB (negative control); (B) supernatant of growth medium from *P. pastoris*, Δ och1 transformed with pFB8 mannosidase, which demonstrates a lack of extracellular mannosidase activity in the supernatant; and (C) $Man_9GlcNAc_2$ standard labeled with 2-AB after exposure to *T. reesei* mannosidase (positive control).
Figure 7A:
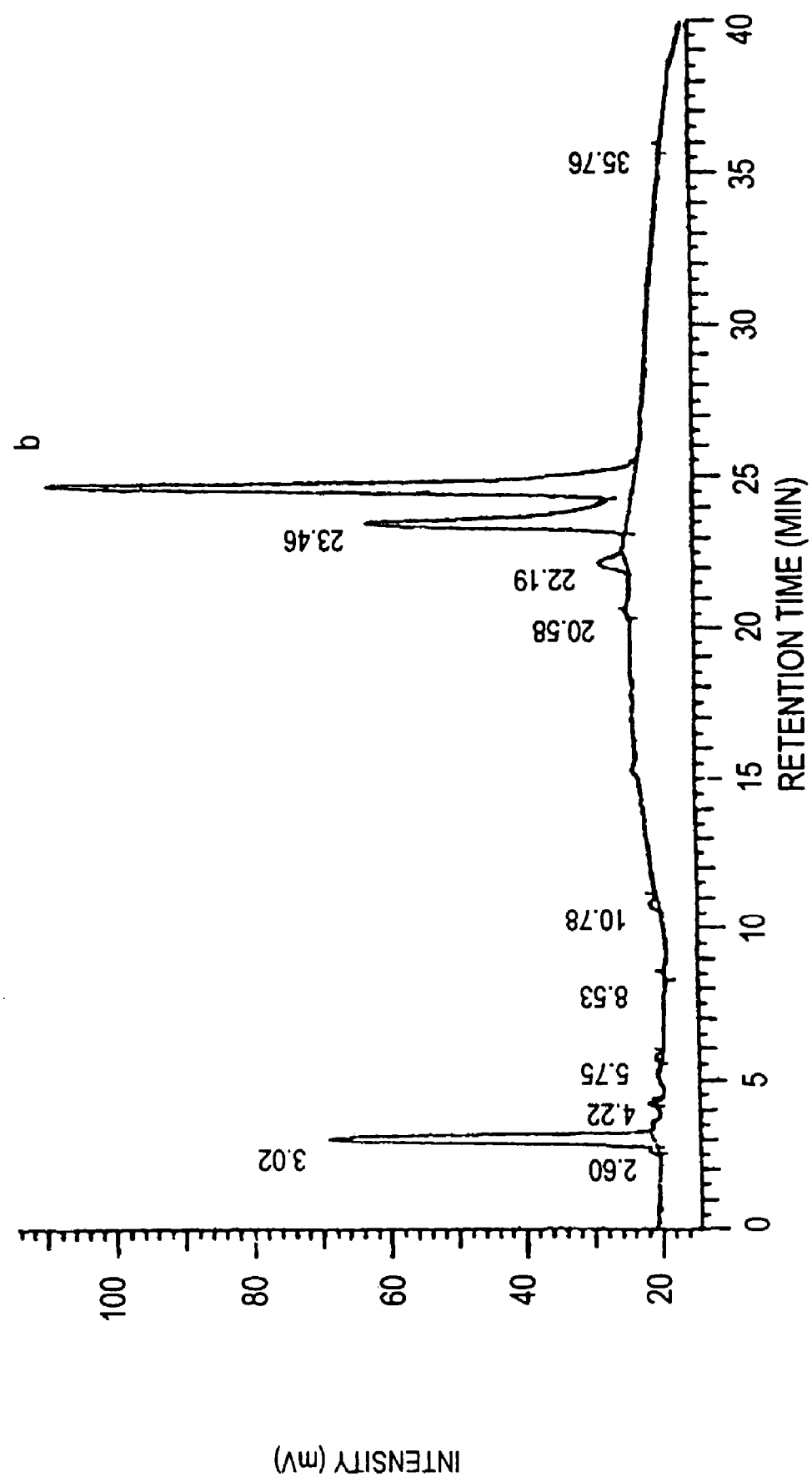
Figure 7B:
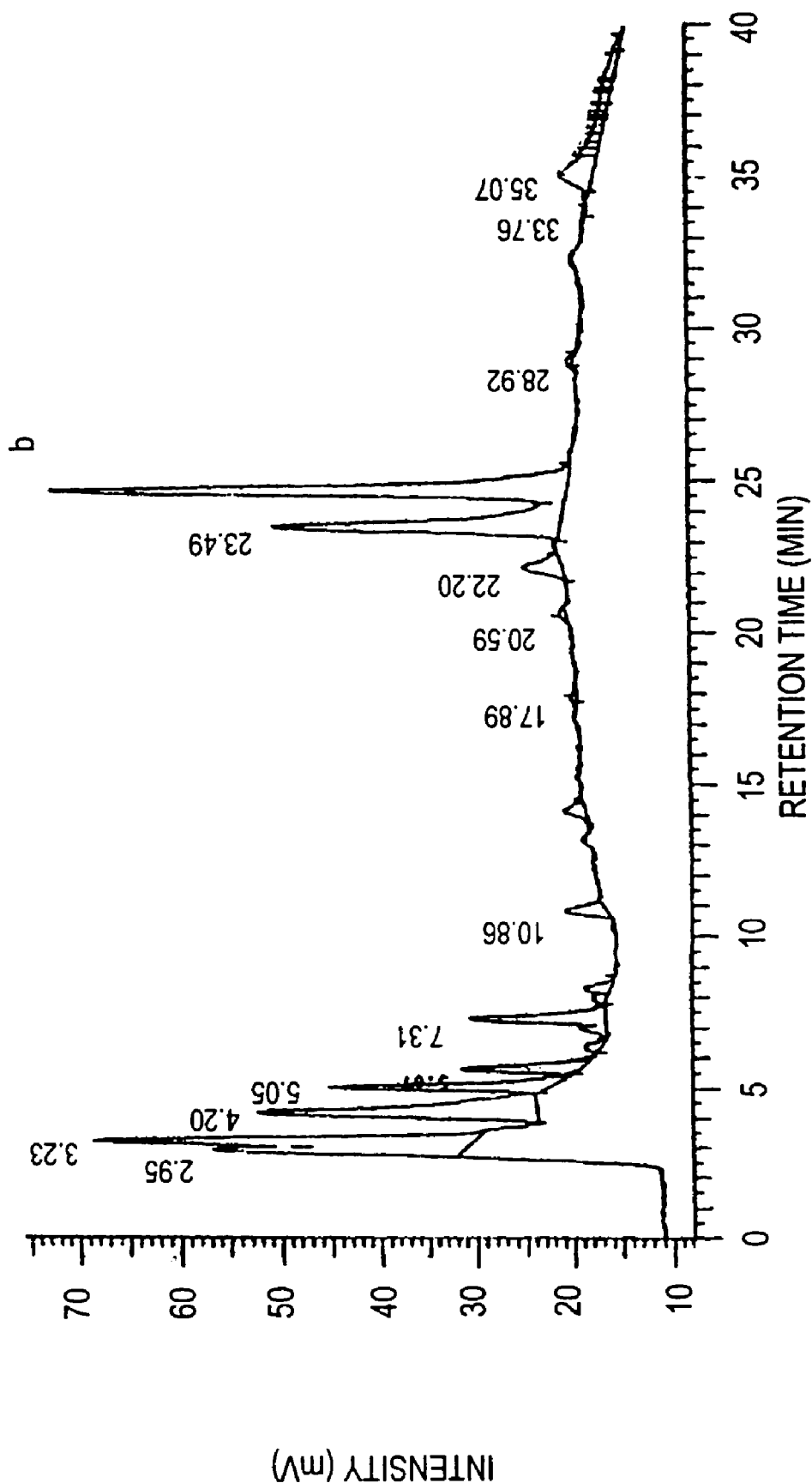

A representative example of a mannosidase fusion construct derived from a combinatorial DNA library of the invention is pFB8, which has a truncated *Saccharomyces* SEC12 (m) targeting peptide (988-1296 nucleotides of SEC12 from SwissProt P11655) ligated in-frame to a 187 N-terminal amino acid deletion of a mouse α-mannosidase IA (Genbank AN 6678787). The nomenclature used herein, thus, refers to the targeting peptide/catalytic domain region of a glycosylation enzyme as *Saccharomyces* SEC12 (m)/mouse mannosidase IA Δ187. The encoded fusion protein localizes in the ER by means of the SEC12 targeting peptide sequence while retaining its mannosidase catalytic domain activity and is capable of producing in vivo N-glycans having a Man$_5$GlcNAc$_2$ structure (Example 4; FIGS. 6F and 7B).

Figure 5C:
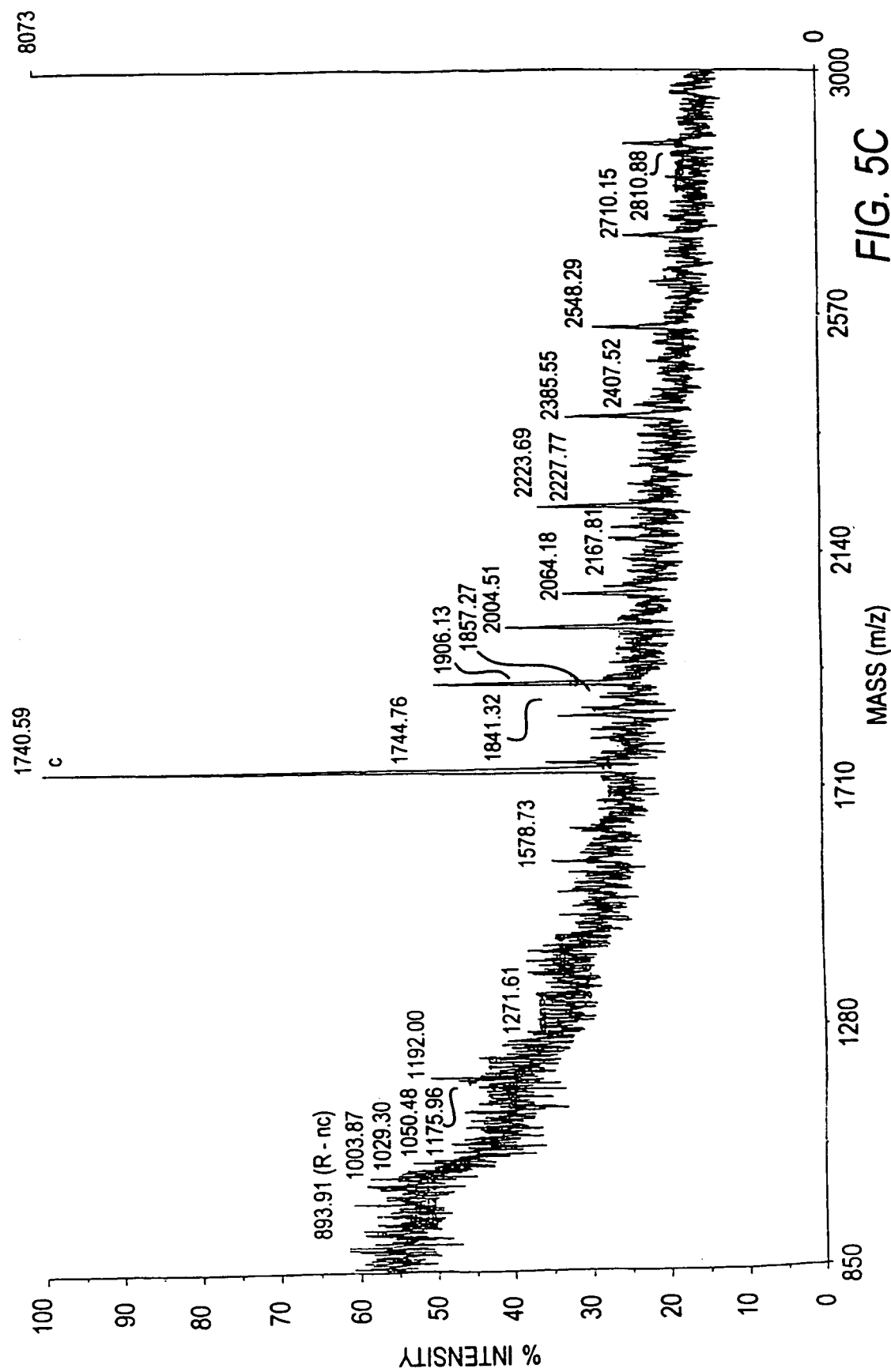
Figure 5D:
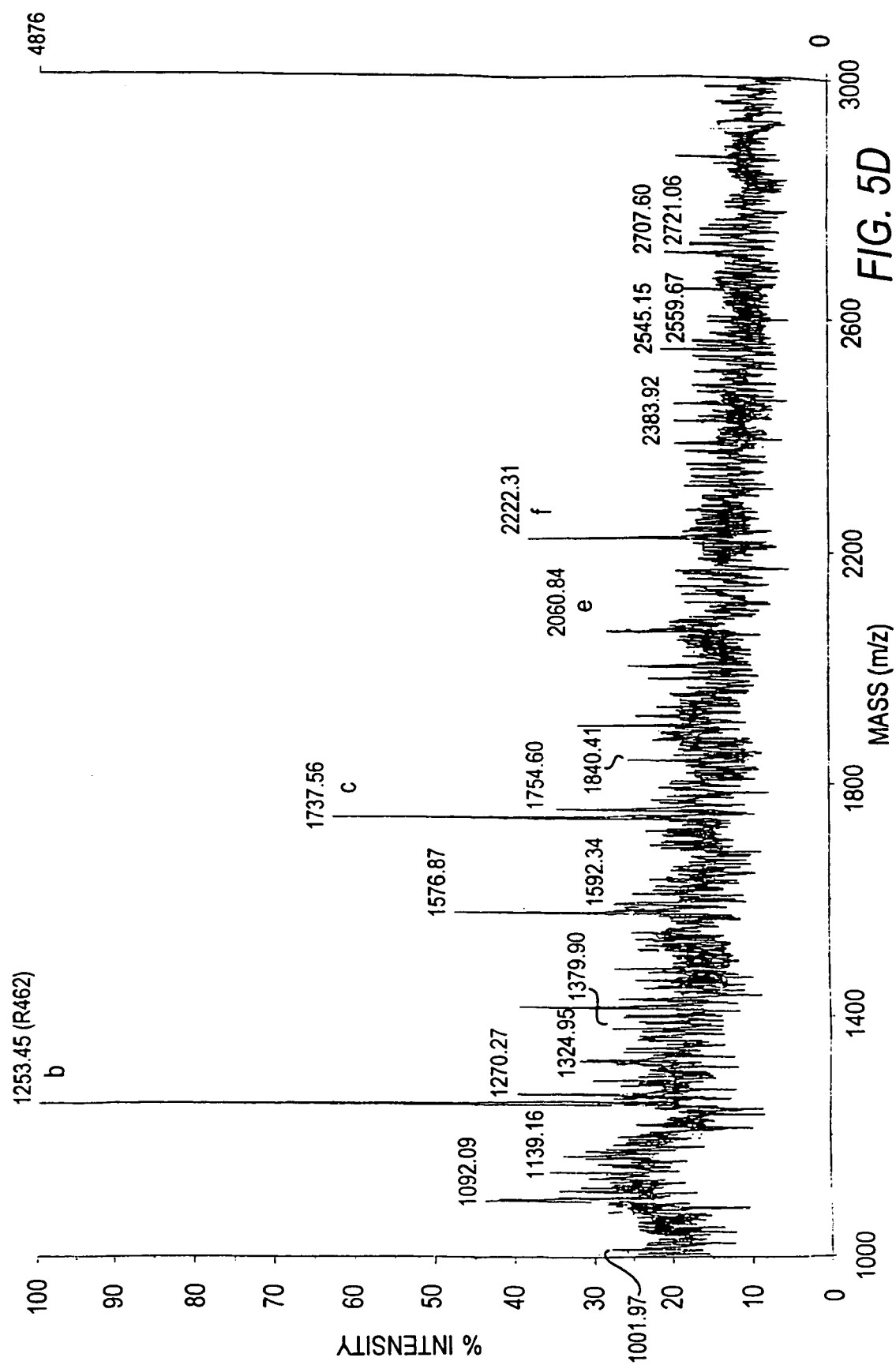

The fusion construct pGC5, *Saccharomyces* MNS1(m)/mouse mannosidase IB Δ99, is another example of a fusion construct having intracellular mannosidase trimming activity (Example 4; FIGS. 5D and 8B). Fusion construct pBC18-5 (*Saccharomyces* VAN1(s)/*C. elegans* mannosidase IB Δ80) is yet another example of an efficient fusion construct capable of producing in vivo N-glycans having a Man$_5$GlcNAc$_2$ structure. By creating a combinatorial DNA library of these and other such mannosidase fusion constructs according to the invention, a skilled artisan may distinguish and select those constructs having optimal intracellular trimming activity from those having relatively low or no activity. Methods using combinatorial DNA libraries of the invention are advantageous because only a select few mannosidase fusion constructs may produce a particularly desired N-glycan in vivo.

In addition, mannosidase trimming activity may be specific to a particular protein of interest. Thus, it is to be further understood that not all targeting peptide/mannosidase catalytic domain fusion constructs may function equally well to produce the proper glycosylation on a glycoprotein of interest. Accordingly, a protein of interest may be introduced into a host cell transfected with a combinatorial DNA library to identify one or more fusion constructs which express a mannosidase activity optimal for the protein of interest. One skilled in the art will be able to produce and select optimal fusion construct(s) using the combinatorial DNA library approach described herein.

It is apparent, moreover, that other such fusion constructs exhibiting localized active mannosidase catalytic domains (or more generally, domains of any enzyme) may be made using techniques such as those exemplified in Example 4 and described herein. It will be a matter of routine experimentation for one skilled in the art to make and use the combinatorial DNA library of the present invention to optimize, for example, Man$_5$GlcNAc$_2$ production from a library of fusion constructs in a particular expression vector introduced into a particular host cell.

Glycosyltransferase Fusion Constructs

Similarly, a glycosyltransferase combinatorial DNA library was made using the methods of the invention. A combinatorial DNA library of sequences derived from glycosyltransferase I (GnTI) activities were assembled with targeting peptides and screened for efficient production in a lower eukaryotic host cell of a GlcNAcMan$_5$GlcNAc$_2$ N-glycan structure on a marker glycoprotein. A fusion construct shown to produce GlcNAcMan$_5$GlcNAc$_2$ (pPB104), *Saccharomyces* MNN9(s)/human GnTI Δ38 was identified (Example 8). A wide variety of such GnTI fusion constructs were assembled (Example 8, Table 10). Other combinations of targeting peptide/GnTI catalytic domains can readily be assembled by making a combinatorial DNA library. It is also apparent to one skilled in the art that other such fusion constructs exhibiting glycosyltransferase activity may be made as demonstrated in Example 8. It will be a matter of routine experimentation for one skilled in the art to use the combinatorial DNA library method described herein to optimize GlcNAcMan$_5$GlcNAc$_2$ production using a selected fusion construct in a particular expression vector and host cell line.

As stated above for mannosidase fusion constructs, not all targeting peptide/GnTI catalytic domain fusion constructs will function equally well to produce the proper glycosylation on a glycoprotein of interest as described herein. However, one skilled in the art will be able to produce and select optimal fusion construct(s) using a DNA library approach as described herein. Example 8 illustrates a preferred embodiment of a combinatorial DNA library comprising targeting peptides and GnTI catalytic domain fusion constructs involved in producing glycoproteins with predominantly GlcNAcMan$_5$GlcNAc$_2$ structure.

Using Multiple Fusion Constructs to Alter Host Cell Glycosylation

In another example of using the methods and libraries of the invention to alter host cell glycosylation, a *P. pastoris* strain with an OCH1 deletion that expresses a reporter protein (K3) was transformed with multiple fusion constructs isolated from combinatorial libraries of the invention to convert high mannose N-glycans to human-like N-glycans (Example 8). First, the mannosidase fusion construct pFB8 (*Saccharomyces* SEC12 (m)/mouse mannosidase IA Δ187) was transformed into a *P. pastoris* strain lacking 1,6 initiating mannosyltransferases activity (i.e. och1 deletion; Example 1). Second, pPB103 comprising a *K. lactis* MNN2-2 gene (Genbank AN AF106080) encoding an UDP-GlcNAc transporter was constructed to increase further production of GlcNAcMan$_5$GlcNAc$_2$. The addition of the UDP-GlcNAc transporter increased production of GlcNAcMan$_5$GlcNAc$_2$ significantly in the *P. pastoris* strain as illustrated in FIG. 10B. Third, pPB104 comprising *Saccharomyces* MNN9 (s)/human GnTI Δ38 was introduced into the strain. This *P. pastoris* strain is referred to as "PBP-3."

It is understood by one skilled in the art that host cells such as the above-described yeast strains can be sequentially transformed and/or co-transformed with one or more expression vectors. It is also understood that the order of transformation is not particularly relevant in producing the glycoprotein of interest. The skilled artisan recognizes the routine modifications of the procedures disclosed herein may provide improved results in the production of the glycoprotein of interest.

Figure 5E:
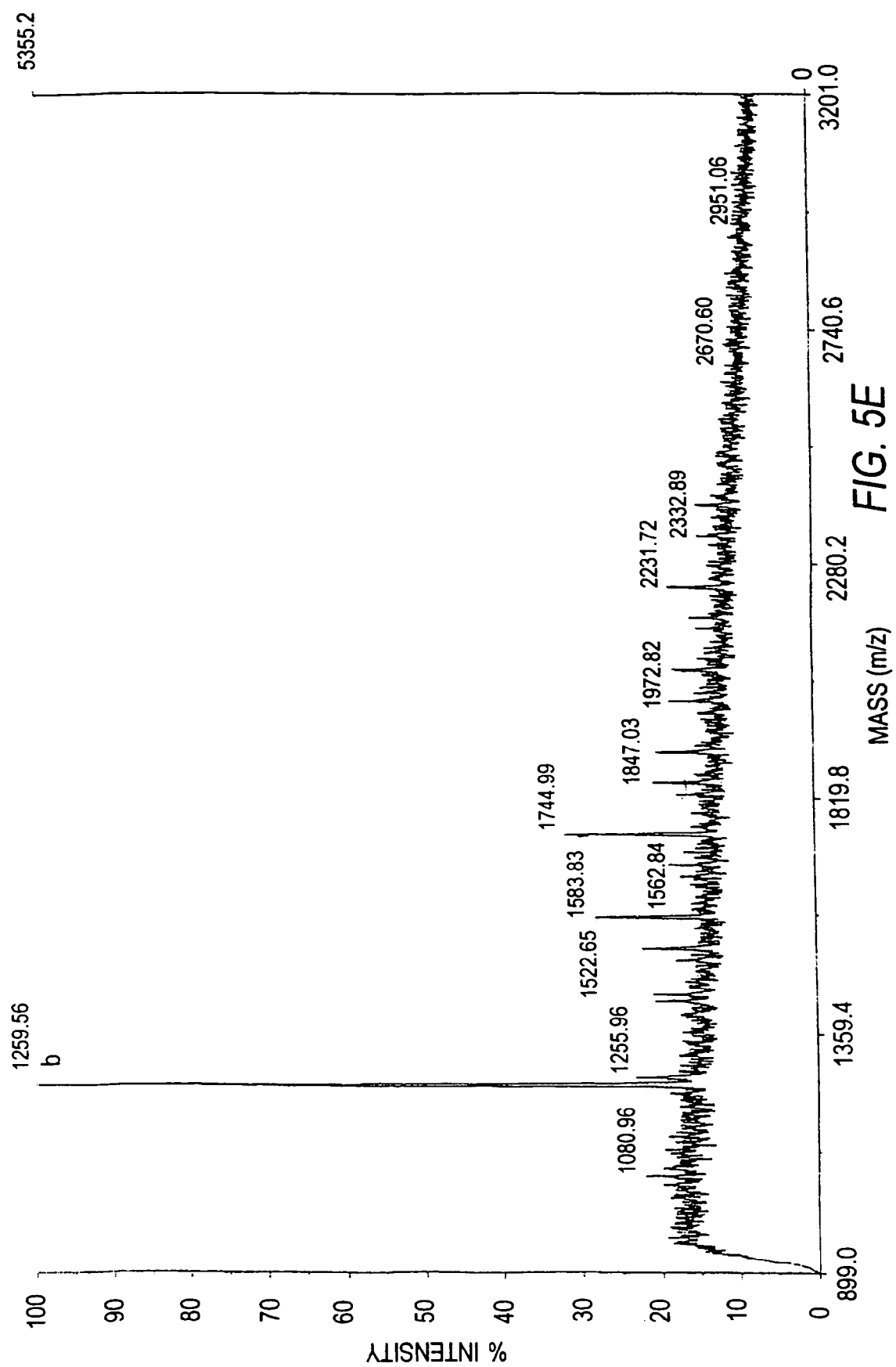

The importance of using a particular targeting peptide sequence with a particular catalytic domain sequence becomes readily apparent from the experiments described herein. The combinatorial DNA library provides a tool for constructing enzyme fusions that are involved in modifying N-glycans on a glycoprotein of interest, which is especially useful in producing human-like glycoproteins. (Any enzyme fusion, however, may be selected using libraries and methods of the invention.) Desired transformants expressing appropriately targeted, active α-1,2-mannosidase produce K3 with N-glycans of the structure Man$_5$GlcNAc$_2$ as shown in FIGS. 5D and 5E. This confers a reduced molecular mass to the cleaved glycan compared to the K3 of the parent OCH1 deletion strain, as was detected by MALDI-TOF mass spectrometry in FIG. 5C.

Similarly, the same approach was used to produce another secreted glycoprotein: IFN-β comprising predominantly Man$_5$GlcNAc$_2$. The Man$_5$GlcNAc$_2$ was removed by PNGase digestion (Papac et al. 1998 *Glycobiology* 8, 445-454) and subjected to MALDI-TOF as shown in FIGS. 6A-6F. A single prominent peak at 1254 (m/z) confirms Man$_5$GlcNA$_2$ production on IFN-β in FIG. 6E (pGC5) (*Saccharomyces* MNS1(m)/mouse mannosidase IB Δ99) and 6F (pFB8) (*Saccharomyces* SEC12 (m)/mouse mannosidase IA Δ187). Furthermore, in the *P. pastoris* strain PBP-3 comprising pFB8 (*Saccharomyces* SEC12 (m)/mouse mannosidase IA Δ187), pPB104 (*Saccharomyces* MNN9 (s)/human GnTI Δ38) and pPB103 (*K. lactis* MNN2-2 gene), the hybrid N-glycan GlcNAcMan$_5$GlcNAc$_2$ [b] was detected by MALDI-TOF (FIG. 10).

Figure 8:
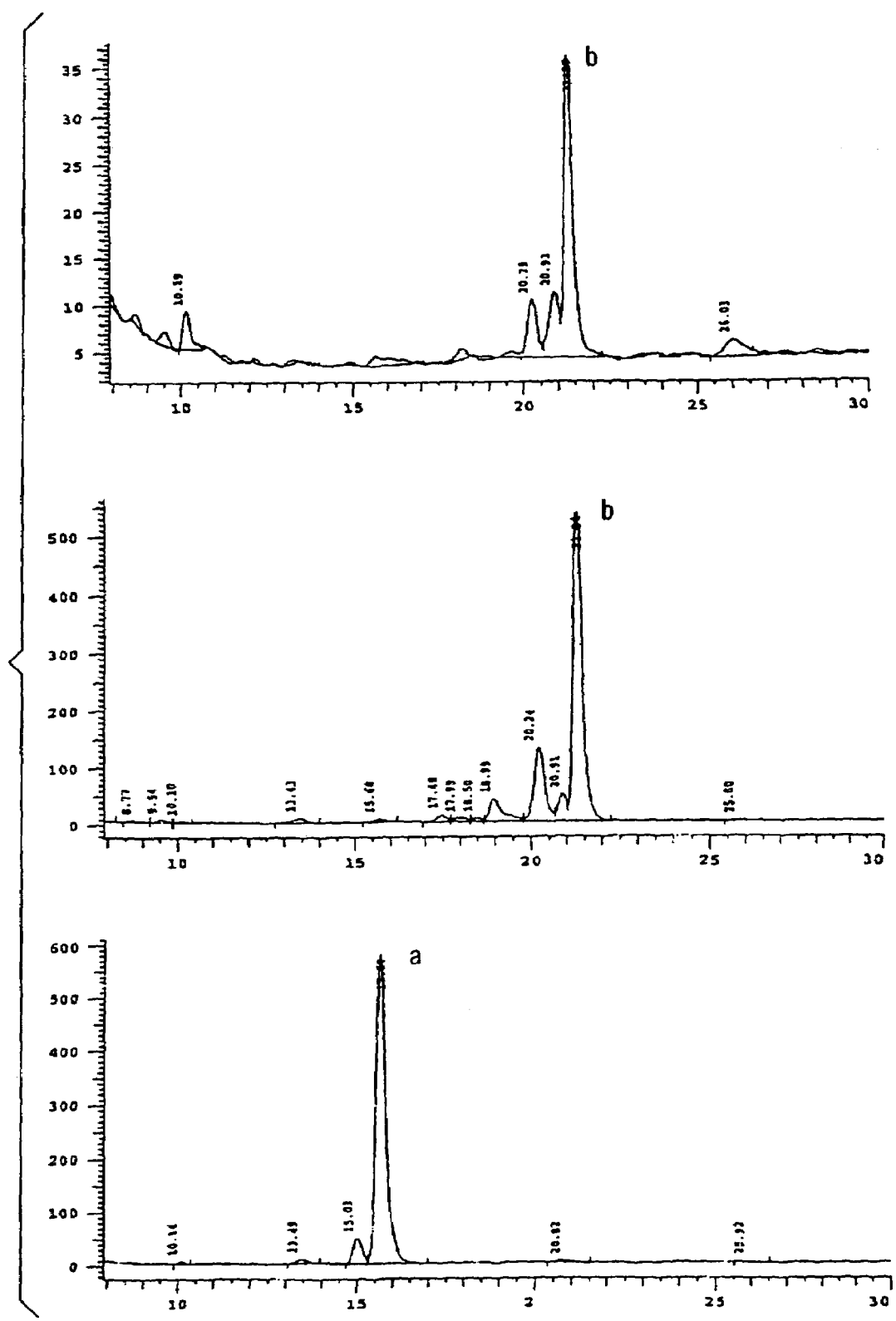
FIG. 8 shows a high performance liquid chromatogram for: (A) $Man_9GlcNAc_2$ standard labeled with 2-AB (negative control); (B) supernatant of growth medium from *P. pastoris*, Δ och1 transformed with pGC5 mannosidase, which demonstrates a lack of extracellular mannosidase activity in the supernatant; and (C) $Man_9GlcNAc_2$ standard labeled with 2-AB after exposure to *T. reesei* mannosidase (positive control).
Figure 9:
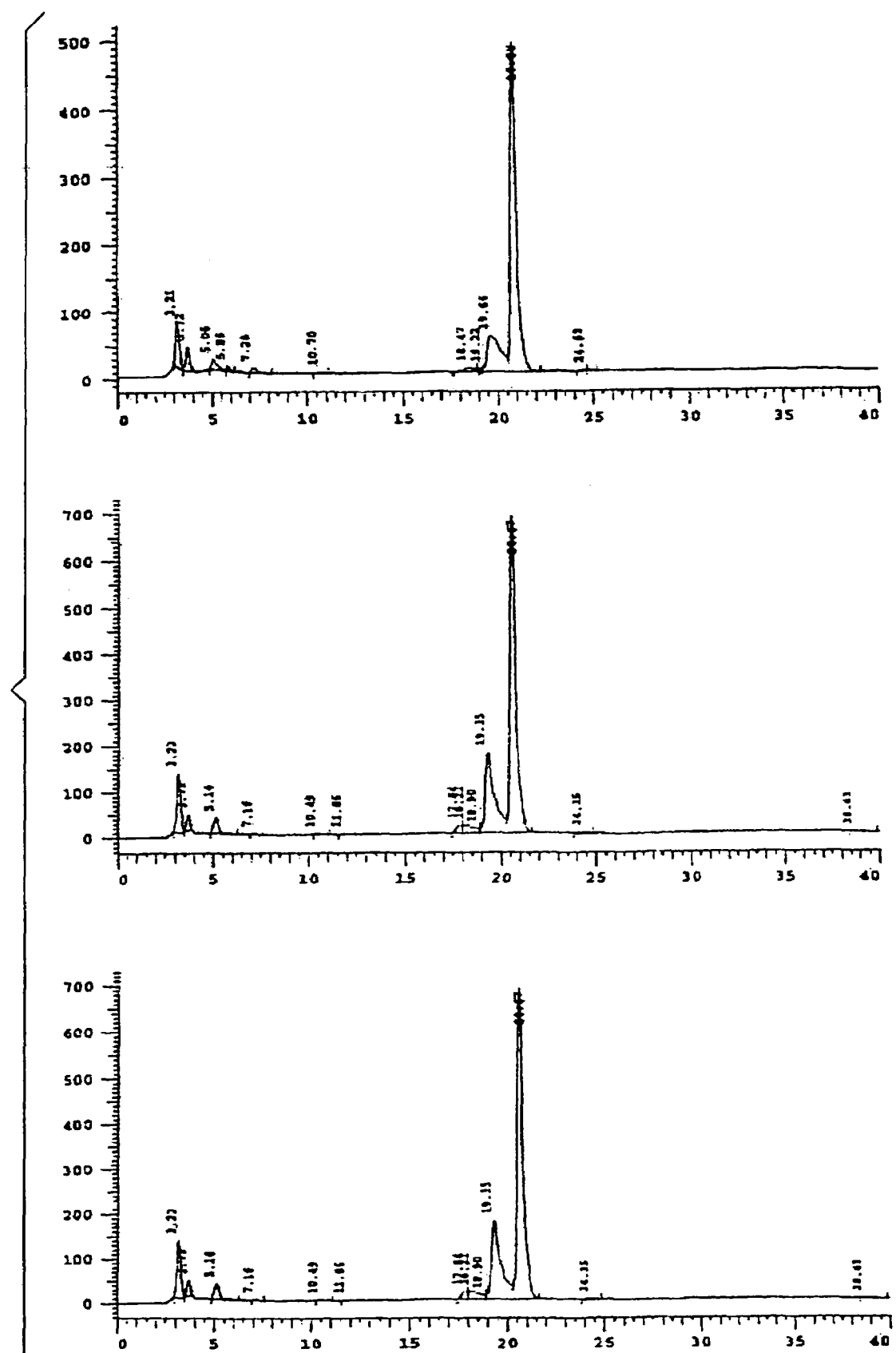
FIG. 9 shows a high performance liquid chromatogram for: (A) $Man_9GlcNAc_2$ standard labeled with 2-AB (negative control); (B) supernatant of growth medium from *P. pastoris*, Δ och1 transformed with pBC18-5 mannosidase, which demonstrates lack of extracellular mannosidase activity in the supernatant; and (C) supernatant of medium *P. pastoris*, Δ och1 transformed with pDD28-3, which demonstrates activity in the supernatant (positive control).

After identifying transformants with a high degree of mannose trimming, additional experiments were performed to confirm that mannosidase (trimming) activity occurred in vivo and was not predominantly the result of extracellular activity in the growth medium (Example 6; FIGS. 7-9).

Golgi α-Mannosidase II Fusion Constructs

As provided by the methods of the invention, a combinatorial DNA library of Golgi α-mannosidase II was made by fusing the catalytic domain of several mannosidase II enzymes to an array of cellular targeting peptide signals (Example 14). The resulting more than 500 combinatorial fusion constructs were introduced into a *P. pastoris* strain capable of producing the human precursor of complex glycosylation, GlcNAcMan$_5$GlcNAc$_2$ YSH-1 (Example 17) on the reporter K3. Only a small subset of strains about (<5%) were capable of quantitatively converting GlcNAcMan$_5$GlcNAc$_2$ to GlcNAcMan$_3$GlcNAc$_2$. These strains were isolated and subsequently transformed with a combinatorial library of several hundred GnTII/leader peptide fusions. Screening for the presence of GlcNAc$_2$Man$_3$GlcNAc$_2$ allowed for the isolation of strains that were able to secrete homogeneous complex glycan, as exemplified by strain YSII-44 (Example 19).

A representative example of a Golgi α-mannosidase II fusion construct derived from a combinatorial DNA library of the invention is pKD53, which a truncated *S. cerevisiae* MNN2(s) targeting peptide (1-108 nucleotides of MNN2 from SwissProt P38069) ligated in-frame to a 74 N-terminal amino acid deletion of a *D. melanogaster* golgi α-mannosidase II (Genbank AN X77652). The nomenclature used herein, thus, refers to the targeting peptide/catalytic domain region of a glycosylation enzyme as *S. cerevisiae* MNN2(s)/ *D. melanogaster* mannosidase II Δ74. The encoded fusion protein localizes in the Golgi by means of the MNN2(s) targeting peptide sequence while retaining its mannosidase catalytic domain activity and is capable of producing in vivo N-glycans having a predominant GlcNAcMan$_3$GlcNAc$_2$ structure (Example 18).

Another example of a Golgi α-mannosidase II fusion construct derived from a combinatorial DNA library of the invention is pKD1, which a truncated *Saccharomyces* GLS1(s) targeting peptide (1-102 nucleotides of GLS1 from SwissProt P53008) ligated in-frame to a 74 N-terminal amino acid deletion of a *D. melanogaster* golgi α-mannosidase II (Genbank AN X77652). The nomenclature used herein, thus, refers to the targeting peptide/catalytic domain region of a glycosylation enzyme as *Saccharomyces* GLS1 (s)/*D. melanogaster* mannosidase II Δ74. The encoded fusion protein localizes in the Golgi by means of the GLS1(s) targeting peptide sequence while retaining its mannosidase catalytic domain activity and is capable of producing in vivo N-glycans having a predominant GlcNAcMan$_3$GlcNAc$_2$ structure (Example 22).

Another example of a Golgi α-mannosidase II fusion construct derived from a combinatorial DNA library of the invention is pKD5, which a truncated *Saccharomyces* MNS1(m) targeting peptide (1-246 nucleotides of MNS1 from SwissProt P32906) ligated in-frame to a 74 N-terminal amino acid deletion of a *D. melanogaster* golgi α-mannosidase II (Genbank AN X77652). The nomenclature used herein, thus, refers to the targeting peptide/catalytic domain region of a glycosylation enzyme as *Saccharomyces* MNS1(m)/*D. mela-* nogaster mannosidase II Δ74. The encoded fusion protein localizes in the Golgi by means of the MNS1(m) targeting peptide sequence while retaining its mannosidase catalytic domain activity and is capable of producing in vivo N-glycans having a GlcNAcMan$_3$GlcNAc$_2$ structure (Example 23). Unlike the uniformity of N-glycans present in YSH-27, FIG. 21 shows heterogenous mixture of N-glycans produced YSH-74. The apparent mediocre trimming activity of this mannosidase II enzyme, however, indicates the heterogenity as Manα1,2 additions as suggested in FIG. 23, where the GlcNAcMan$_3$GlcNAc$_2$ peak appears after digestion of YSH-74 with *A. saitoi* α-1,2-mannosidase. By creating a combinatorial DNA library of these and other such mannosidase fusion constructs according to the invention, a skilled artisan may distinguish and select those constructs having optimal intracellular trimming activity from those having relatively low or no activity. Methods using combinatorial DNA libraries of the invention are advantageous because only a select few mannosidase fusion constructs may produce a particularly desired N-glycan in vivo.

In addition, mannosidase trimming activity may be specific to a particular protein of interest. Thus, it is to be further understood that not all targeting peptide/mannosidase catalytic domain fusion constructs may function equally well to produce the proper glycosylation on a glycoprotein of interest. FIG. 18 shows no apparent activity in a *P. pastoris* YSH-1 transformed a Golgi α-mannosidase II fusion construct derived from a combinatorial DNA library of the invention pKD16, which a truncated *Saccharomyces* MNN9(m) targeting peptide (1-273 nucleotides of MNN9 from SwissProt P39107) ligated in-frame to a 74 N-terminal amino acid deletion of a *D. melanogaster* golgi α-mannosidase II (Genbank AN X77652). Accordingly, a protein of interest may be introduced into a host cell transformed with a combinatorial DNA library to identify one or more fusion constructs which express a mannosidase activity optimal for the protein of interest. One skilled in the art will be able to produce and select optimal fusion construct(s) using the combinatorial DNA library approach described herein.

Host Cells

Figure 12:
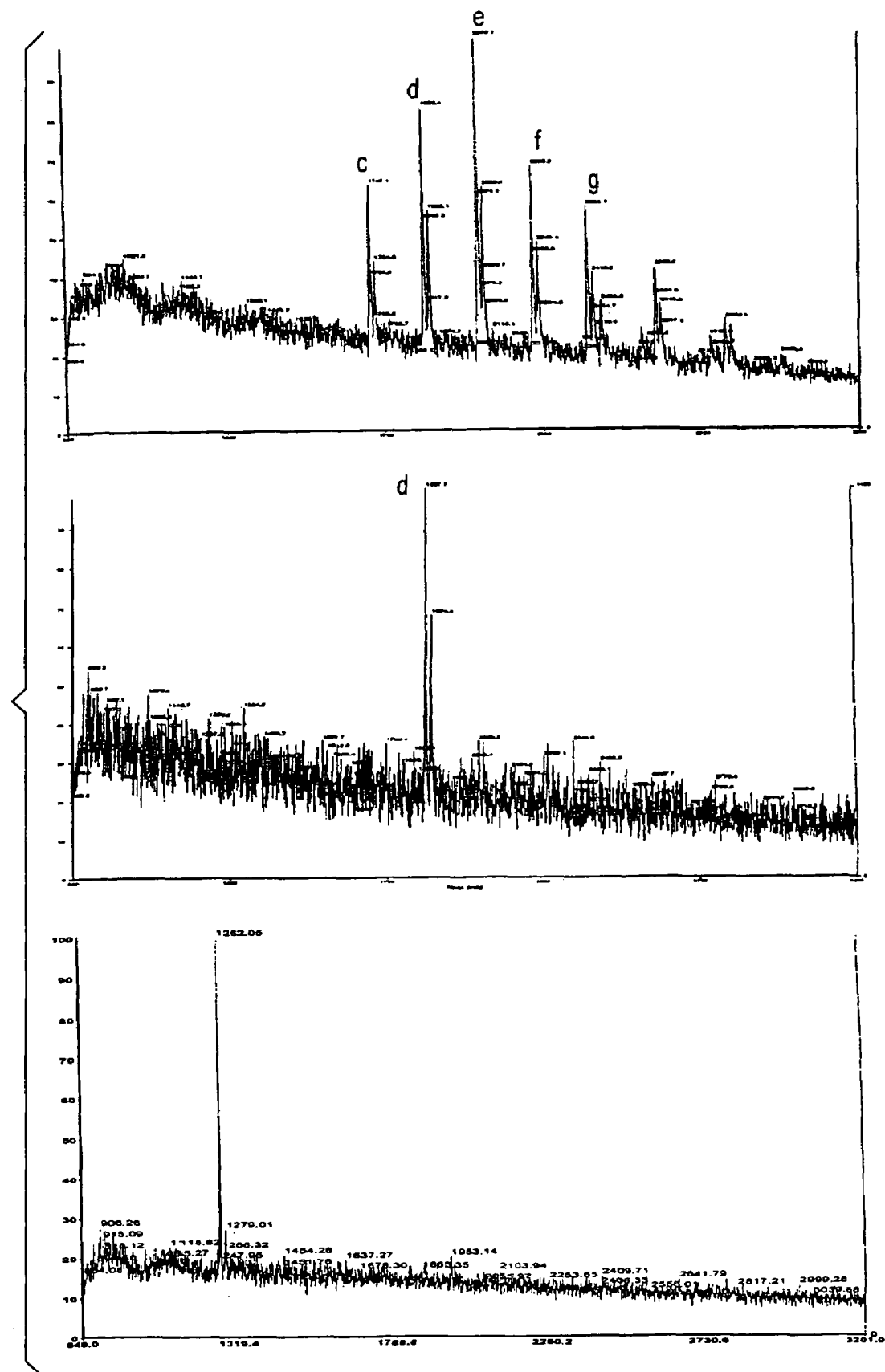
FIGS. 12A-12C show MALDI-TOF-MS analyses of N-glycans released from a cell free extract of *K. lactis*.

Although the present invention is exemplified using a *P. pastoris* host organism, it is to be understood by those skilled in the art that other eukaryotic host cells, including other species of yeast and fungal hosts, may be altered as described herein to produce human-like glycoproteins. The techniques described herein for identification and disruption of undesirable host cell glycosylation genes, e.g. OCH1, is understood to be applicable for these and/or other homologous or functionally related genes in other eukaryotic host cells such as other yeast and fungal strains. As described in Example 9, och1 mnn1 genes were deleted from *K. lactis* to engineer a host cell leading to N-glycans that are completely converted to Man$_5$GlcNAc$_2$ by 1,2-mannosidase (FIG. 12C).

The MNN1 gene was cloned from *K. lactis* as described in Example 9.

The nucleic acid and deduced amino acid sequences of the *K. lactis* MNN1 gene are shown in SEQ ID NOS: 16 and 17, respectively. Using gene-specific primers, a construct was made to delete the MNN1 gene from the genome of *K. lactis* (Example 9). Host cells depleted in och1 and mnn1 activities produce N-glycans having a Man$_9$GlcNAc$_2$ carbohydrate structure (see, e.g., FIG. 10). Such host cells may be engineered further using, e.g., methods and libraries of the invention, to produce mammalian- or human-like glycoproteins.

Thus, in another embodiment, the invention provides an isolated nucleic acid molecule having a nucleic acid sequence comprising or consisting of at least forty-five, preferably at least 50, more preferably at least 60 and most preferably 75 or more nucleotide residues of the *K. lactis* MNN1 gene (SEQ ID NO: 16), and homologs, variants and derivatives thereof. The invention also provides nucleic acid molecules that hybridize under stringent conditions to the above-described nucleic acid molecules. Similarly, isolated polypeptides (including muteins, allelic variants, fragments, derivatives, and analogs) encoded by the nucleic acid molecules of the invention are provided. In addition, also provided are vectors, including expression vectors, which comprise a nucleic acid molecule of the invention, as described further herein. Similarly host cells transformed with the nucleic acid molecules or vectors of the invention are provided.

Another aspect of the present invention thus relates to a non-human eukaryotic host strain expressing glycoproteins comprising modified N-glycans that resemble those made by human-cells. Performing the methods of the invention in species other than yeast and fungal cells is thus contemplated and encompassed by this invention. It is contemplated that a combinatorial nucleic acid library of the present invention may be used to select constructs that modify the glycosylation pathway in any eukaryotic host cell system. For example, the combinatorial libraries of the invention may also be used in plants, algae and insects, and in other eukaryotic host cells, including mammalian and human cells, to localize proteins, including glycosylation enzymes or catalytic domains thereof, in a desired location along a host cell secretory pathway. Preferably, glycosylation enzymes or catalytic domains and the like are targeted to a subcellular location along the host cell secretory pathway where they are capable of functioning, and preferably, where they are designed or selected to function most efficiently.

Preferred host cells of the present invention include *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum* and *Neurospora crassa*.

Plant and insect cells may also be engineered to alter the glycosylation of expressed proteins using the combinatorial library and methods of the invention. Furthermore, glycosylation in mammalian cells, including human cells, may also be modified using the combinatorial library and methods of the invention. It may be possible, for example, to optimize a particular enzymatic activity or to otherwise modify the relative proportions of various N-glycans made in a mammalian host cell using the combinatorial library and methods of the invention.

Examples of modifications to glycosylation which can be affected using a method according to this embodiment of the invention are: (1) engineering a eukaryotic host cell to trim mannose residues from Man$_8$GlcNAc$_2$ to yield a Man$_5$GlcNAc$_2$ N-glycan; (2) engineering eukaryotic host cell to add an N-acetylglucosamine (GlcNAc) residue to Man$_5$GlcNAc$_2$ by action of GlcNAc transferase 1; (3) engineering a eukaryotic host cell to functionally express an enzyme such as an N-acetylglucosaminyl Transferase (GnTI, GnTII, GnTIII, GnTIV, GnTV, GnTVI), mannosidase II, fucosyltransferase (FT), galactosyl tranferase (GalT) or a sialyltransferase (ST).

By repeating the method, increasingly complex glycosylation pathways can be engineered into a target host, such as a lower eukaryotic microorganism. In one preferred embodiment, the host organism is transformed two or more times with DNA libraries including sequences encoding glycosylation activities. Selection of desired phenotypes may be performed after each round of transformation or alternatively after several transformations have occurred. Complex glycosylation pathways can be rapidly engineered in this manner.

Sequential Glycosylation Reactions

In a preferred embodiment, such targeting peptide/catalytic domain libraries are designed to incorporate existing information on the sequential nature of glycosylation reactions in higher eukaryotes. Reactions known to occur early in the course of glycoprotein processing require the targeting of enzymes that catalyze such reactions to an early part of the Golgi or the ER. For example, the trimming of $Man_8GlcNAc_2$ to $Man_5GlcNAc_2$ by mannosidases is an early step in complex N-glycan formation. Because protein processing is initiated in the ER and then proceeds through the early, medial and late Golgi, it is desirable to have this reaction occur in the ER or early Golgi. When designing a library for mannosidase I localization, for example, one thus attempts to match ER and early Golgi targeting signals with the catalytic domain of mannosidase I.

Integration Sites

As one ultimate goal of this genetic engineering effort is a robust protein production strain that is able to perform well in an industrial fermentation process, the integration of multiple genes into the host (e.g., fungal) chromosome preferably involves careful planning. The engineered strain may likely have to be transformed with a range of different genes, and these genes will have to be transformed in a stable fashion to ensure that the desired activity is maintained throughout the fermentation process. As described herein, any combination of various desired enzyme activities may be engineered into the fungal protein expression host, e.g., sialyltransferases, mannosidases, fucosyltransferases, galactosyltransferases, glucosyltransferases, GlcNAc transferases, ER and Golgi specific transporters (e.g. syn and antiport transporters for UDP-galactose and other precursors), other enzymes involved in the processing of oligosaccharides, and enzymes involved in the synthesis of activated oligosaccharide precursors such as UDP-galactose, CMP-N-acetylneuraminic acid. Examples of preferred methods for modifying glycosylation in a lower eukaryotic host cell, such as Pichia pastoris, are shown in Table 6.

TABLE 6

Some preferred embodiments for modifying glycosylation in a lower eukaroytic microorganism

| Desired Structure | Suitable Catalytic Activities | Suitable Sources of Localization Sequences | Suitable Gene Deletions | Suitable Transporters and/or Phosphatases |
|---|---|---|---|---|
| $Man_5GlcNAc_2$ | α-1,2-mannosidase (murine, human, Bacillus sp., A. nidulans) | Mns1 (N-terminus, S. cerevisiae) Och1 (N-terminus, S. cerevisiae, P. pastoris) Ktr1 Mnn9 Mnt1 (S. cerevisiae) KDEL, HDEL (C-terminus) | OCH1 MNN4 MNN6 | none |
| $GlcNAcMan_5GlcNAc_2$ | GlcNAc Transferase 1, (human, murine, rat etc.) | Och1 (N-terminus, S. cerevisiae, P. pastoris) KTR1 (N-terminus) Mnn1 (N-terminus, S. cerevisiae) Mnt1 (N-terminus, S. cerevisiae) GDPase (N-terminus, S. cerevisiae) | OCH1 MNN4 MNN6 | UDP-GlcNAc transporter (human, murine, K. lactis) UDPase (human) |
| $GlcNAcMan_3GlcNAc_2$ | mannosidase II | Ktr1 Mnn1 (N-terminus, S. cerevisiae) Mnt1 (N-terminus, S. cerevisiae) Kre2/Mnt1 (S. cerevisiae) Kre2 (P. pastoris) Ktr1 (S. cerevisiae) Ktr1 (P. pastoris) Mnn1 (S. cerevisiae) | OCH1 MNN4 MNN6 | UDP-GlcNAc transporter (human, murine, K. lactis) UDPase (human) |
| $GlcNAc_{(2-4)}Man_3GlcNAc_2$ | GlcNAc Transferase II, III, IV, V (human, murine) | Mnn1 (N-terminus, S. cerevisiae) Mnt1 (N-terminus, S. cerevisiae) Kre2/Mnt1 (S. cerevisiae) Kre2 (P. pastoris) | OCH1 MNN4 MNN6 | UDP-GlcNAc transporter (human, murine, K. lactis) UDPase (human) |

TABLE 6-continued

Some preferred embodiments for modifying glycosylation in a lower eukaroytic microorganism

| Desired Structure | Suitable Catalytic Activities | Suitable Sources of Localization Sequences | Suitable Gene Deletions | Suitable Transporters and/or Phosphatases |
|---|---|---|---|---|
| Gal$_{(1-4)}$GlcNAc$_{(2-4)}$-Man$_3$GlcNAc$_2$ | β-1,4-Galactosyl transferase (human) | Ktr1 (S. cerevisiae)<br>Ktr1 (P. pastoris)<br>Mnn1 (S. cerevisiae)<br>Mnn1 (N-terminus, S. cerevisiae)<br>Mnt1(N-terminus, S. cerevisiae)<br>Kre2/Mnt1 (S. cerevisiae)<br>Kre2 (P. pastoris)<br>Ktr1 (S. cerevisiae)<br>Ktr1 (P. pastoris)<br>Mnn1 (S. cerevisiae) | OCH1<br>MNN4<br>MNN6 | UDP-Galactose transporter (human, S. pombe) |
| NANA$_{(1-4)}$-Gal$_{(1-4)}$GlcNAc$_{(2-4)}$-Man$_3$GlcNAc$_2$ | α-2,6-Sialyltransferase (human)<br>α-2,3-Sialyltransferase | KTR1<br>MNN1 (N-terminus, S. cerevisiae)<br>MNT1 (N-terminus, S. cerevisiae)<br>Kre2/Mnt1 (S. cerevisiae)<br>Kre2 (P. pastoris)<br>Ktr1 (S. cerevisiae)<br>Ktr1 (P. pastoris)<br>MNN1 (S. cerevisiae) | OCH1<br>MNN4<br>MNN6 | CMP-Sialic acid transporter (human) |

As any strategy to engineer the formation of complex N-glycans into a host cell such as a lower eukaryote involves both the elimination as well as the addition of particular glycosyltransferase activities, a comprehensive scheme will attempt to coordinate both requirements. Genes that encode enzymes that are undesirable serve as potential integration sites for genes that are desirable. For example, 1,6 mannosyltransferase activity is a hallmark of glycosylation in many known lower eukaryotes. The gene encoding alpha-α1,6 mannosyltransferase (OCH1) has been cloned from S. cerevisiae and mutations in the gene give rise to a viable phenotype with reduced mannosylation. The gene locus encoding alpha-α1,6 mannosyltransferase activity therefore is a prime target for the integration of genes encoding glycosyltransferase activity. In a similar manner, one can choose a range of other chromosomal integration sites that, based on a gene disruption event in that locus, are expected to: (1) improve the cell's ability to glycosylate in a more human-like fashion, (2) improve the cell's ability to secrete proteins, (3) reduce proteolysis of foreign proteins and (4) improve other characteristics of the process that facilitate purification or the fermentation process itself.

Target Glycoproteins

The methods described herein are useful for producing glycoproteins, especially glycoproteins used therapeutically in humans. Glycoproteins having specific glycoforms may be especially useful, for example, in the targeting of therapeutic proteins. For example, mannose-6-phosphate has been shown to direct proteins to the lysosome, which may be essential for the proper function of several enzymes related to lysosomal storage disorders such as Gaucher's, Hunter's, Hurler's, Scheie's, Fabry's and Tay-Sachs disease, to mention just a few. Likewise, the addition of one or more sialic acid residues to a glycan side chain may increase the lifetime of a therapeutic glycoprotein in vivo after administration. Accordingly, host cells (e.g., lower eukaryotic or mammalian) may be genetically engineered to increase the extent of terminal sialic acid in glycoproteins expressed in the cells. Alternatively, sialic acid may be conjugated to the protein of interest in vitro prior to administration using a sialic acid transferase and an appropriate substrate. Changes in growth medium composition may be employed in addition to the expression of enzyme activities involved in human-like glycosylation to produce glycoproteins more closely resembling human forms (Weikert et al. (1999) Nature Biotechnology 17, 1116-1121; Werner et al. (1998) Arzneimittelforschung 48(8):870-880; Andersen and Goochee (1994) Cur. Opin. Biotechnol. 5:546-549; Yang and Butler (2000) Biotechnol. Bioengin. 68(4):370-380). Specific glycan modifications to monoclonal antibodies (e.g. the addition of a bisecting GlcNAc) have been shown to improve antibody dependent cell cytotoxicity (Umana et al. (1999) Nat. Biotechnol. 17(2):176-80), which may be desirable for the production of antibodies or other therapeutic proteins.

Therapeutic proteins are typically administered by injection, orally, or by pulmonary or other means. Examples of suitable target glycoproteins which may be produced according to the invention include, without limitation: erythropoietin, cytokines such as interferon-α, interferon-β, interferon-γ, interferon-ω, and granulocyte-CSF, coagulation factors such as factor VIII, factor IX, and human protein C, soluble IgE receptor α-chain, IgG, IgG fragments, IgM, interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin and αfeto proteins.

Subsequent Glycosyltransferase Activities: N-Acetylglucosaminyltransferase II, Galactosyltransferase and Sialyltransferase In a further aspect of the invention, the newly formed glycans produced by the Golgi α-mannosidase II enzyme are substrates for subsequent glycosylation reactions. In one embodiment, GnT II, UDP-GlcNAc and optionally the UDP-GlcNAc transporter cap the newly formed Manα1,6 branch of the oligosaccharide produced in *P. pastoris* YSH-37 with a GlcNAc to form $GlcNAc_2Man_3GlcNAc_2$ (Example 19) In another embodiment, other GnTs (e.g. GnT III, GnT IV, GnT V) react upon the transient $GlcNAc_2Man_3GlcNAc_2$ substrate. This substrate in turn becomes a substrate for galactosyltransferases (Example 25) and further processing occurs with sialyltransferases.

The following are examples which illustrate the compositions and methods of this invention. These examples should not be construed as limiting: the examples are included for the purposes of illustration only.

Example 1

Cloning and Disruption of the OCH1 Gene in *P. pastoris*

A 1215 bp ORF of the *P. pastoris* OCH1 gene encoding a putative α-1,6 mannosyltransferase was amplified from *P. pastoris* genomic DNA (strain X-33, Invitrogen, Carlsbad, Calif.) using the oligonucleotides 5'-ATGGCGAAGGCA-GATGGCAGT-3' (SEQ ID NO: 18) and 5'-TTAGTCCTTC-CAACTTCCTTC-3' (SEQ ID NO: 19) which were designed based on the *P. pastoris* OCH1 sequence (Japanese Patent Application Publication No. 8-336387). Subsequently, 2685 bp upstream and 1175 bp downstream of the ORF of the OCH1 gene were amplified from a *P. pastoris* genomic DNA library (Boehm, T. et al. Yeast 1999 May; 15(7):563-72) using the internal oligonucleotides 5'-ACTGCCATCTGCCT-TCGCCAT-3' (SEQ ID NO: 20) in the OCH1 gene, and 5'-GTAATACGACTCACTATAGGGC-3' T7 (SEQ ID NO: 21) and 5'-AATTAACCCTCACTAAAGGG-3' T3 (SEQ ID NO: 22) oligonucleotides in the backbone of the library bearing plasmid lambda ZAP II (Stratagene, La Jolla, Calif.). The resulting 5075 bp fragment was cloned into the pCR2.1-TOPO vector (Invitrogen, Carlsbad, Calif.) and designated pBK9.

After assembling a gene knockout construct that substituted the OCH1 reading frame with a HIS4 resistance gene, *P. pastoris* was transformed and colonies were screened for temperature sensitivity at 37° C. OCH1 mutants of *S. cerevisiae* are temperature sensitive and are slow growers at elevated temperatures. One can thus identify functional homologs of OCH1 in *P. pastoris* by complementing an OCH1 mutant of *S. cerevisiae* with a *P. pastoris* DNA or cDNA library. About 20 temperature sensitive strains were further subjected to a colony PCR screen to identify colonies with a deleted och1 gene. Several och1 deletions were obtained.

The linearized pBK9.1, which has 2.1 kb upstream sequence and 1.5 kb down stream sequence of OCH1 gene cassette carrying Pichia HIS4 gene, was transformed into *P. pastoris* BK1 [GS115 (his4 Invitrogen Corp., San Diego, Calif.) carrying the human IFN-β gene in the AOX1 locus] to knock out the wild-type OCH1 gene. The initial screening of transformants was performed using histidine drop-out medium followed by replica plating to select the temperature sensitive colonies. Twenty out of two hundred histidine-positive colonies showed a temperature sensitive phenotype at 37° C. To exclude random integration of pBK9.1 into the *Pichia* genome, the 20 temperature-sensitive isolates were subjected to colony PCR using primers specific to the upstream sequence of the integration site and to HIS4 ORF. Two out of twenty colonies were och1 defective and further analyzed using a Southern blot and a Western blot indicating the functional och1 disruption by the och1 knock-out construct. Genomic DNA were digested using two separate restriction enzymes BglII and ClaI to confirm the och1 knock-out and to confirm integration at the open reading frame. The Western Blot showed och1 mutants lacking a discrete band produced in the GS115 wild type at 46.2 kDa.

Example 2

Engineering of *P. pastoris* with α-1,2-Mannosidase to Produce $Man_5GlcNAc_2$-Containing IFN-β Precursors An α-1,2-mannosidase is required for the trimming of $Man_8GlcNAc_2$ to yield $Man_5GlcNAc_2$, an essential intermediate for complex N-glycan formation. While the production of a $Man_5GlcNAc_2$ precursor is essential, it is not necessarily sufficient for the production of hybrid and complex glycans because the specific isomer of $Man_5GlcNAc_2$ may or may not be a substrate for GnTI. An och1 mutant of *P. pastoris* is engineered to express secreted human interferon-β under the control of an aox promoter. A DNA library is constructed by the in-frame ligation of the catalytic domain of human mannosidase IB (an α-1,2-mannosidase) with a sub-library including sequences encoding early Golgi and ER localization peptides. The DNA library is then transformed into the host organism, resulting in a genetically mixed population wherein individual transformants each express interferon-β as well as a synthetic mannosidase gene from the library. Individual transformant colonies are cultured and the production of interferon is induced by addition of methanol. Under these conditions, over 90% of the secreted protein is glycosylated interferon-β.

Supernatants are purified to remove salts and low-molecular weight contaminants by $C_{18}$ silica reversed-phase chromatography. Desired transformants expressing appropriately targeted, active α-1,2-mannosidase produce interferon-β including N-glycans of the structure $Man_5GlcNAc_2$, which has a reduced molecular mass compared to the interferon-β of the parent strain. The purified interferon-β is analyzed by MALDI-TOF mass spectroscopy and colonies expressing the desired form of interferon-β are identified.

Example 3

Generation of an och1 Mutant Strain Expressing an α-1,2-Mannosidase, GnTI for Production of a Human-Like Glycoprotein The 1215 bp open reading frame of the *P. pastoris* OCH1 gene as well as 2685 bp upstream and 1175 bp downstream was amplified by PCR (see also WO 02/00879), cloned into the pCR2.1-TOPO vector (Invitrogen) and designated pBK9. To create an och1 knockout strain containing multiple, auxotrophic markers, 100 μg of pJN329, a plasmid containing an och1::URA3 mutant allele flanked with SfiI restriction sites was digested with SfiI and used to transform *P. pastoris* strain JC308 (Cereghino et al. *Gene* 263 (2001) 159-169) by electroporation. Following incubation on defined medium lacking uracil for 10 days at room temperature, 1000 colonies were picked and re-streaked. $URA^+$ clones that were unable to grow at 37° C., but grew at room temperature, were subjected to colony PCR to test for the correct integration of the och1::URA3 mutant allele. One clone that exhibited the expected PCR pattern was designated YJN153. The Kringle 3 domain of human plasminogen (K3) was used as a model protein. A Neo[R] marked plasmid containing the K3 gene was transformed into strain YJN153 and a resulting strain, expressing K3, was named BK64-1.

Plasmid pPB103, containing the *Kluyveromyces lactis* MNN2-2 gene which encodes a Golgi UDP-N-acetylglucosamine transporter was constructed by cloning a blunt BglII-HindIII fragment from vector pDL02 (Abeijon et al. (1996) *Proc. Natl. Acad. Sci. U.S.A.* 93:5963-5968) into BglII and BamHI digested and blunt ended pBLADE-SX containing the *P. pastoris* ADE1 gene (Cereghino et al. (2001) *Gene* 263:159-169). This plasmid was linearized with EcoNI and transformed into strain BK64-1 by electroporation and one strain confirmed to contain the MNN2-2 by PCR analysis was named PBP1.

A library of mannosidase constructs was generated, comprising in-frame fusions of the leader domains of several type I or type II membrane proteins from *S. cerevisiae* and *P. pastoris* fused with the catalytic domains of several α-1,2-mannosidase genes from human, mouse, fly, worm and yeast sources (see, e.g., WO02/00879, incorporated herein by reference). This library was created in a *P. pastoris* HIS4 integration vector and screened by linearizing with SalI, transforming by electroporation into strain PBP1, and analyzing the glycans released from the K3 reporter protein. One active construct chosen was a chimera of the 988-1296 nucleotides (C-terminus) of the yeast SEC12 gene fused with a N-terminal deletion of the mouse α-1,2-mannosidase IA gene (FIG. 3), which was missing the 187 nucleotides. A *P. pastoris* strain expressing this construct was named PBP2.

A library of GnTI constructs was generated, comprising in-frame fusions of the same leader library with the catalytic domains of GnTI genes from human, worm, frog and fly sources (WO 02/00879). This library was created in a *P. pastoris* ARG4 integration vector and screened by linearizing with AatII, transforming by electroporation into strain PBP2, and analyzing the glycans released from K3. One active construct chosen was a chimera of the first 120 bp of the *S. cerevisiae* MNN9 gene fused to a deletion of the human GnTI gene, which was missing the first 154 bp. A *P. pastoris* strain expressing this construct was named PBP3.

Example 4

Engineering of *P. pastoris* to Produce Man$_5$GlcNAc$_2$ as the Predominant N-Glycan Structure Using a Combinatorial DNA Library An och1 mutant of *P. pastoris* (see Examples 1 and 3) was engineered to express and secrete proteins such as the kringle 3 domain of human plasminogen (K3) under the control of the inducible AOXI promoter. The Kringle 3 domain of human plasminogen (K3) was used as a model protein. A DNA fragment encoding the K3 was amplified using Pfu turbo polymerase (Strategene, La Jolla, Calif.) and cloned into EcoRI and XbaI sites of pPICZαA (Invitrogen, Carlsbad, Calif.), resulting in a C-terminal 6-His tag. In order to improve the N-linked glycosylation efficiency of K3 (Hayes et al. 1975 *J. Arch. Biochem. Biophys.* 171, 651-655), Pro$_{46}$ was replaced with Ser$_{46}$ using site-directed mutagenesis. The resulting plasmid was designated pBK64. The correct sequence of the PCR construct was confirmed by DNA sequencing.

A combinatorial DNA library was constructed by the in-frame ligation of murine α-1,2-mannosidase IB (Genbank AN 6678787) and IA (Genbank AN 6754619) catalytic domains with a sub-library including sequences encoding Cop II vesicle, ER, and early Golgi localization peptides according to Table 6. The combined DNA library was used to generate individual fusion constructs, which were then transformed into the K3 expressing host organism, resulting in a genetically mixed population wherein individual transformants each express K3 as well as a localization signal/mannosidase fusion gene from the library. Individual transformants were cultured and the production of K3 was induced by transfer to a methanol containing medium. Under these conditions, after 24 hours of induction, over 90% of the protein in the medium was K3. The K3 reporter protein was purified from the supernatant to remove salts and low-molecular weight contaminants by Ni-affinity chromatography. Following affinity purification, the protein was desalted by size exclusion chromatography on a Sephadex G10 resin (Sigma, St. Louis, Mo.) and either directly subjected to MALDI-TOF analysis described below or the N-glycans were removed by PNGase digestion as described below (Release of N-glycans) and subjected to MALDI-TOF analysis Miele et al. 1997 *Biotechnol. Appl. Biochem.* 25, 151-157.

Following this approach, a diverse set of transformants were obtained; some showed no modification of the N-glycans compared to the och1 knockout strain; and others showed a high degree of mannose trimming (FIGS. 5D and 5E). Desired transformants expressing appropriately targeted, active α-1,2-mannosidase produced K3 with N-glycans of the structure Man$_5$GlcNAc$_2$. This confers a reduced molecular mass to the glycoprotein compared to the K3 of the parent och1 deletion strain, a difference which was readily detected by MALDI-TOF mass spectrometry (FIG. 5). Table 7 indicates the relative Man$_5$GlcNAc$_2$ production levels.

TABLE 7

A representative combinatorial DNA library of localization sequences/catalytic domains exhibiting relative levels of Man$_5$GlcNAc$_2$ production.

| Catalytic Domains | Targeting peptide sequences | | | | |
| --- | --- | --- | --- | --- | --- |
| | MNS1(s) | MNS1(m) | MNS1(l) | SEC12(s) | SEC12(m) |
| Mouse mannosidase 1A Δ187 | FB4 ++ | FB5 + | FB6 − | FB7 ++ | FB8 ++++ |
| Mouse mannosidase 1B Δ58 | GB4 ++ | GB5 + | GB6 + | GB7 ++ | GB8 + |
| Mouse mannosidase 1B Δ99 | GC4 − | GC5 +++ | GC6 + | GC7 + | GC8 + |
| Mouse mannosidase 1B Δ170 | GD4 − | GD5 − | GD6 − | GD7 + | GD8 + |

TABLE 8

Another combinatorial DNA library of localization sequences/catalytic domains exhibiting relative levels of Man₅GlcNAc₂ production.

| Catalytic Domains | Targeting peptide sequences | | | | | |
|---|---|---|---|---|---|---|
| | VAN1(s) | VAN1(m) | VAN1(l) | MNN10(s) | MNN10(m) | MNN10(l) |
| C. elegans mannosidase 1B Δ80 | BC18-5 +++++ | BC19 ++++ | BC20 +++ | BC27 +++++ | BC28 +++++ | BC29 +++ |
| C. elegans mannosidase 1B Δ31 | BB18 +++++ | BB19 +++++ | BB20 ++++ | BB18 +++++ | BB19 +++++ | BB20 ++++ |

Targeting peptides were selected from MNS I (SwissProt P32906) in *S. cerevisiae* (long, medium and short) (see supra, Nucleic Acid Libraries; Combinatorial DNA Library of Fusion Constructs) and SEC12 (SwissProt P11655) in *S. cerevisiae* (988-1140 nucleotides: short) and (988-1296: medium). Although the majority of targeting peptide sequences were N-terminal deletions, some targeting peptide sequences, such as SEC12, were C-terminal deletions. Catalytic domains used in this experiment were selected from mouse mannosidase 1A with a 187 amino acid N-terminal deletion; and mouse mannosidase 1B with a 58, 99 and 170 amino acid deletion. The number of (+)s, as used herein, indicates the relative levels of Man₅GlcNAc₂ production. The notation (−) indicates no apparent production of Man₅GlcNAc₂ The notation (+) indicates less than 10% production of Man₅GlcNAc₂ The notation (++) indicates about 10-20% production of Man₅GlcNAc₂, The notation with (+++) indicates about 20-40% production of Man₅GlcNAc₂. The notation with (++++) indicates about 50% production of Man₅GlcNAc₂. The notation with (+++++) indicates greater than 50% production of Man₅GlcNAc₂.

Table 9 shows the relative amounts of Man₅GlcNAc₂ detected on a secreted K3 reporter glycoprotein. Six hundred and eight (608) different strains of *P. pastoris* (Δoch1) were generated by transforming each with a single construct from a combinatorial genetic library that was generated by fusing nineteen (19) α-1,2 mannosidase catalytic domains to thirty-two (32) fungal ER, and cis-Golgi leaders.

TABLE 9

| Amount of Man₅GlcNAc₂ on secreted K3 protein (% of total glycans) | Number of constructs (%) |
|---|---|
| N.D.* | 19 (3.1) |
| 0-10% | 341 (56.1) |
| 10-20% | 50 (8.2) |
| 20-40& | 75 (12.3) |
| 40-60% | 72 (11.8) |
| More than 60% | 51 (8.4)† |
| Total | 608 (100) |

*Several fusion constructs were not tested because the corresponding plasmids could not be propagated in *E. coli* prior to transformation into *P. pastoris*.
†Clones with the highest degree of Man₅GlcNAc₂ trimming (30/51) were further analyzed for mannosidase activity in the supernatant of the medium. The majority (28/30) displayed detectable mannosidase activity in the supernatant (e.g. FIG. 4B). Only two constructs displayed high Man₅GlcNAc₂ levels, while lacking mannosidase activity in the medium (e.g. FIG. 4C).

Table 7 shows two constructs pFB8 and pGC5, among others, which enable a transformed host cell to make K3 glycoprotein displaying Man₅GlcNAc₂.

Table 8 shows a more preferred construct, pBC18-5, a *S. cerevisiae* VAN1(s) targeting peptide sequence (from SwissProt 23642) ligated in-frame to a *C. elegans* mannosidase IB (Genbank AN CAA98114) with an 80 amino acid N-terminal deletion (*Saccharomyces* Van1(s)/*C. elegans* mannosidase IB Δ80). This fusion construct also produces a predominant Man₅GlcNAc₂ structure, as shown in FIG. 5E. This mannosidase fusion construct was shown to produce greater than 50% Man₅GlcNAc₂ (+++++).

Generation of a Combinatorial Localization/Mannosidase Library:

Generating a combinatorial DNA library of α-1,2-mannosidase catalytic domains fused to targeting peptides required the amplification of mannosidase domains with varying lengths of N-terminal deletions from a number of organisms. To approach this goal, the full length open reading frames (ORFs) of α-1,2-mannosidases were PCR amplified from either cDNA or genomic DNA obtained from the following sources: *Homo sapiens, Mus musculus, Drosophila melanogaster, Caenorhabditis elegans, Aspergillus nidulans* and *Penicillium citrinum*. In each case, DNA was incubated in the presence of oligonucleotide primers specific for the desired mannosidase sequence in addition to reagents required to perform the PCR reaction. For example, to amplify the ORF of the *M. musculus* α-1,2-mannosidase IA, the 5'-primer ATGCCCGTGGGGGGCCTGTTGC-CGCTCTTCAGTAGC (SEQ ID NO: 23) and the 3'-primer TCATTTCTCTTTGCCATCAATTTCCT-TCTTCTGTTCACGG (SEQ ID NO: 24) were incubated in the presence of Pfu DNA polymerase (Stratagene, La Jolla, Calif.) and amplified under the conditions recommended by Stratagene using the cycling parameters: 94° C. for 1 min (1 cycle); 94° C. for 30 sec, 68° C. for 30 sec, 72° C. for 3 min (30 cycles). Following amplification the DNA sequence encoding the ORF was incubated at 72° C. for 5 min with 1 U Taq DNA polymerase (Promega, Madison, Wis.) prior to ligation into pCR2.1-TOPO (Invitrogen, Carlsbad, Calif.) and transformed into TOP 10 chemically competent *E. coli*, as recommended by Invitrogen. The cloned PCR product was confirmed by ABI sequencing using primers specific for the mannosidase ORF.

To generate the desired N-terminal truncations of each mannosidase, the complete ORF of each mannosidase was used as the template in a subsequent round of PCR reactions wherein the annealing position of the 5'-primer was specific to the 5'-terminus of the desired truncation and the 3'-primer remained specific for the original 3'-terminus of the ORF. To facilitate subcloning of the truncated mannosidase fragment into the yeast expression vector, pJN347 (FIG. 2C) AscI and PacI restriction sites were engineered onto each truncation product, at the 5'- and 3'-termini respectively. The number and position of the N-terminal truncations generated for each mannosidase ORF depended on the position of the transmembrane (TM) region in relation to the catalytic domain (CD). For instance, if the stem region located between the TM and CD was less than 150 bp, then only one truncation for that protein was generated. If, however, the stem region was longer than 150 bp then either one or two more truncations were generated depending on the length of the stem region.

An example of how truncations for the *M. musculus* mannosidase IA (Genbank AN 6678787) were generated is described herein, with a similar approach being used for the other mannosidases. FIG. 3 illustrates the ORF of the *M. musculus* α-1,2-mannosidase IA with the predicted transmembrane and catalytic domains being highlighted in bold. Based on this structure, three 5'-primers were designed (annealing positions underlined in FIG. 3) to generate the Δ65-, Δ105- and Δ187-N-terminal deletions. Using the Δ65 N-terminal deletion as an example the 5'-primer used was 5'-GGCGCGCCGACTCCTCCAAGCTGCT-CAGCGGGGTCCTGTTCCAC-3' (SEQ ID NO: 25) (with the AscI restriction site highlighted in bold) in conjunction with the 3'-primer 5'-CCTTAATTAATCATTTCTCTTTGC-CATCAATTTCCTTCTTCTGTTCACGG-3' (SEQ ID NO: 26) (with the PacI restriction site highlighted in bold). Both of these primers were used to amplify a 1561 bp fragment under the conditions outlined above for amplifying the full length *M. musculus* mannosidase 1A ORF. Furthermore, like the product obtained for the full length ORF, the truncated product was also incubated with Taq DNA polymerase, ligated into pCR2.1-TOPO (Invitrogen, Carlsbad, Calif.), transformed into TOP 10 and ABI sequenced. After having amplified and confirmed the sequence of the truncated mannosidase fragment, the resulting plasmid, pCR2.1-Δ65mMannIA, was digested with AscI and PacI in New England Biolabs buffer #4 (Beverly, Mass.) for 16 h at 37° C. In parallel, the pJN347 (FIG. 2C) was digested with the same enzymes and incubated as described above. Post-digestion, both the pJN347 (FIG. 2C) back-bone and the truncated catalytic domain were gel extracted and ligated using the Quick Ligation Kit (New England Biolabs, Beverly, Mass.), as recommended by the manufacturers, and transformed into chemically competent DH5α cells (Invitrogen, Carlsbad, Calif.). Colony PCR was used to confirm the generation of the pJN347-mouse Mannosidase IAΔ65 construct.

Having generated a library of truncated α-1,2-mannosidase catalytic domains in the yeast expression vector pJN347 (FIG. 2C) the remaining step in generating the targeting peptide/catalytic domain library was to clone in-frame the targeting peptide sequences (FIG. 2). Both the pJN347-mannosidase constructs (FIG. 2D) and the pCR2.1TOPO-targeting peptide constructs (FIG. 2B) such as were incubated overnight at 37° C. in New England Biolabs buffer #4 in the presence of the restriction enzymes NotI and AscI. Following digestion, both the pJN347-mannosidase back-bone and the targeting peptide regions were gel-extracted and ligated using the Quick Ligation Kit (New England Biolabs, Beverly, Mass.), as recommended by the manufacturers, and transformed into chemically competent DH5α cells (Invitrogen, Carlsbad, Calif.). Subsequently, the pJN347-targeting peptide/mannosidase constructs were ABI sequenced to confirm that the generated fusions were in-frame. The estimated size of the final targeting peptide/alpha-α-1,2-mannosidase library contains over 1300 constructs generated by the approach described above. FIG. 2 illustrates construction of the combinatorial DNA library.

Engineering a *P. pastoris* OCH1 Knock-Out Strain with Multiple Auxotrophic Markers.

Figure 4A:
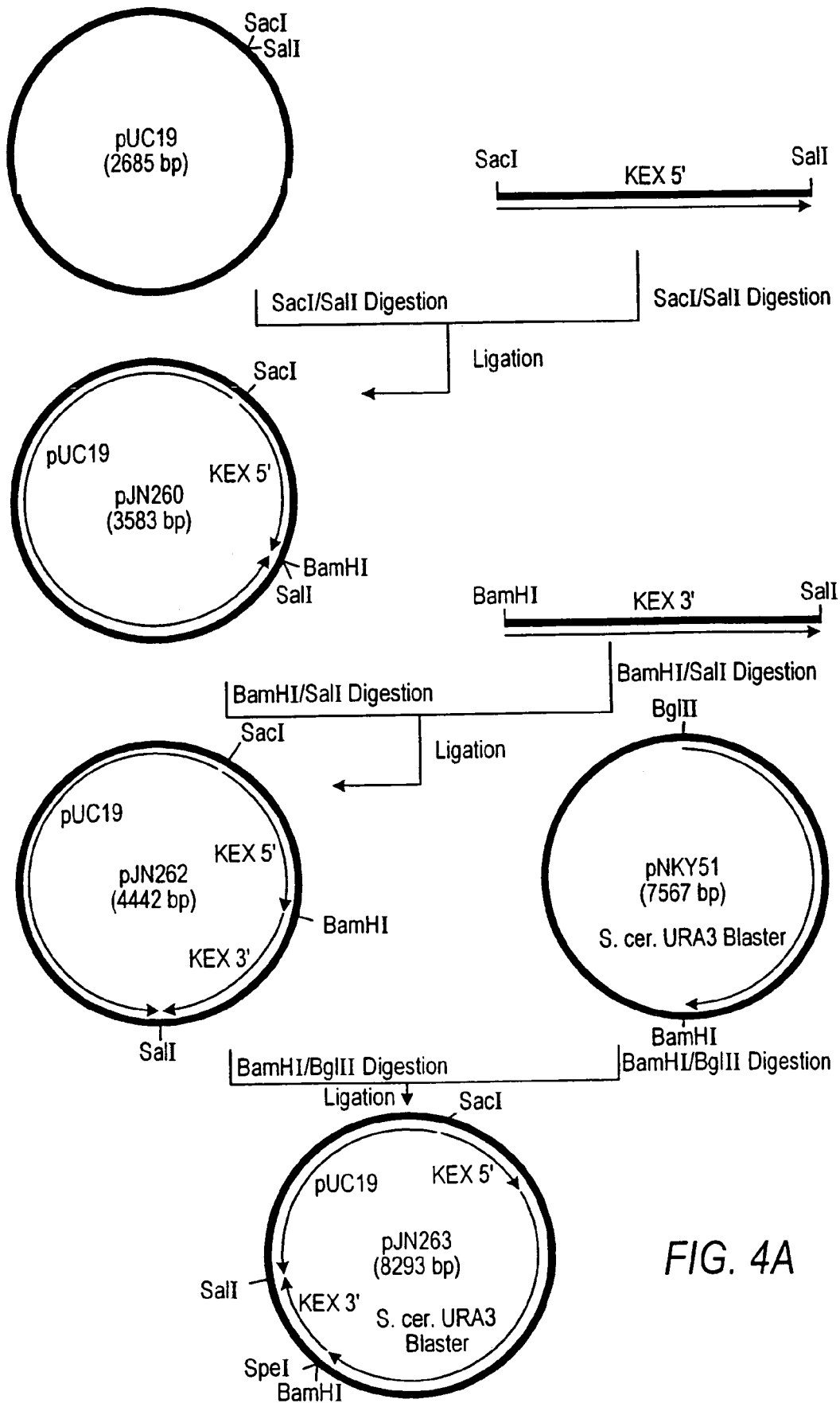
FIGS. 4A-4F illustrate engineering of vectors with multiple auxotrophic markers and genetic integration of target proteins in the *P. pastoris* OCH1 locus.
Figure 4B:
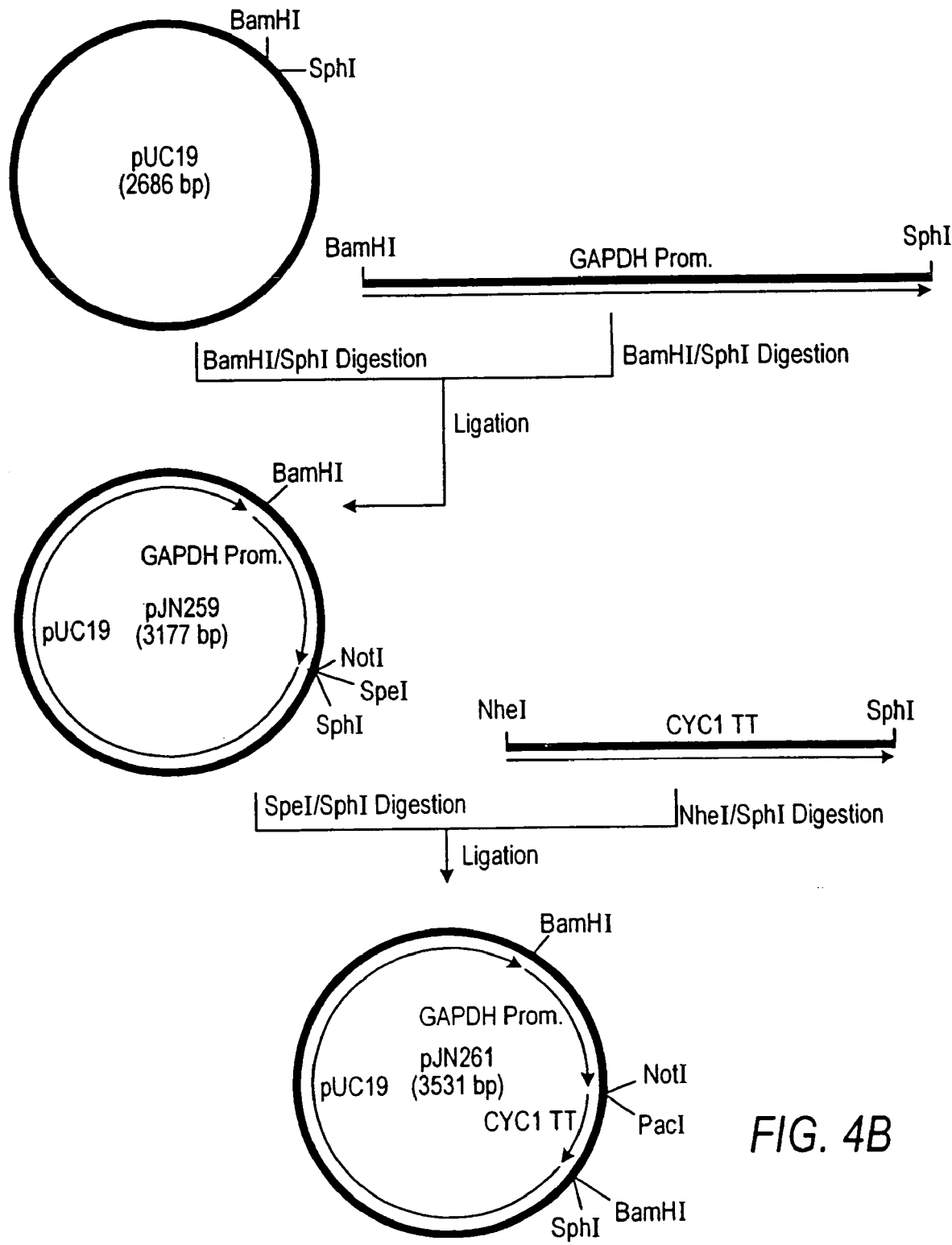

The first step in plasmid construction involved creating a set of universal plasmids containing DNA regions of the KEXI gene of *P. pastoris* (Boehm et al. Yeast 1999 May; 15(7):563-72) as space holders for the 5' and 3' regions of the genes to be knocked out. The plasmids also contained the *S. cerevisiae* Ura-blaster (Alani et al., *Genetics* 116, 541-545. 1987) as a space holder for the auxotrophic markers, and an expression cassette with a multiple cloning site for insertion of a foreign gene. A 0.9-kb fragment of the *P. pastoris* KEX1-5' region was amplified by PCR using primers GGC GAGCTCGGCCTACCCGGCCAAGGCTGAGATCATTT GTCCAGCTTCAGA (SEQ ID NO: 27) and GCCCAC GTCGACGGATCCGTTTAAACATCGATTGGAGAGGC TGACACCGCTACTA (SEQ ID NO: 28) and *P. pastoris* genomic DNA as a template and cloned into the SacI, SalI sites of pUC19 (New England Biolabs, Beverly, Mass.). The resulting plasmid was cut with BamHI and SalI, and a 0.8-kb fragment of the KEX1-3' region that had been amplified using primers CG GGATCCACTAGTATTTAAATCATATGTGCGAGTGTAC AACTCTTCCCACATGG (SEQ ID NO: 29) and GGACGC GTCGACGGCCTACCCGGCCGTACGAGGAATTTCTC GGATGACTCTTTTC (SEQ ID NO: 30) was cloned into the open sites-creating pJN262. This plasmid was cut with BamHI and the 3.8-kb BamHI, BglII fragment of pNKY51 (Alani et al., *Genetics* 116, 541-545. 1987) was inserted in both possible orientations resulting in plasmids pJN263 (FIG. 4A) and pJN284 (FIG. 4B).

An expression cassette was created with NotI and PacI as cloning sites. The GAPDH promoter of *P. pastoris* was amplified using primers CG GGATCCCTCGAGAGATCTTTTTTGTAGAAATGTCTT GGTGCCT (SEQ ID NO: 31) and GGACAT GCATGCACTAGTGCGGCCGCCACGTGATAGTTGTT CAATTGATTGAAATAGGGACAA (SEQ ID NO: 32) and plasmid pGAPZ-A (Invitrogen) as template and cloned into the BamHI, SphI sites of pUC19 (New England Biolabs, Beverly, Mass.) (FIG. 4B). The resulting plasmid was cut with SpeI and SphI and the CYC1 transcriptional terminator region ("TT") that had been amplified using primers CCTT GCTAGCTTAATTAACCGCGGCACGTCCGACGGCGG CCCACGGGTCCCA (SEQ ID NO: 33) and GGACAT GCATGCGGATCCCTTAAGA GCCGGCAGCTTGCAAATTAAAGCCTTCGAGCGTCCC (SEQ ID NO: 34) and plasmid pPICZ-A (Invitrogen) as a template was cloned into the open sites creating pJN261 (FIG. 4B).

Figure 4C:
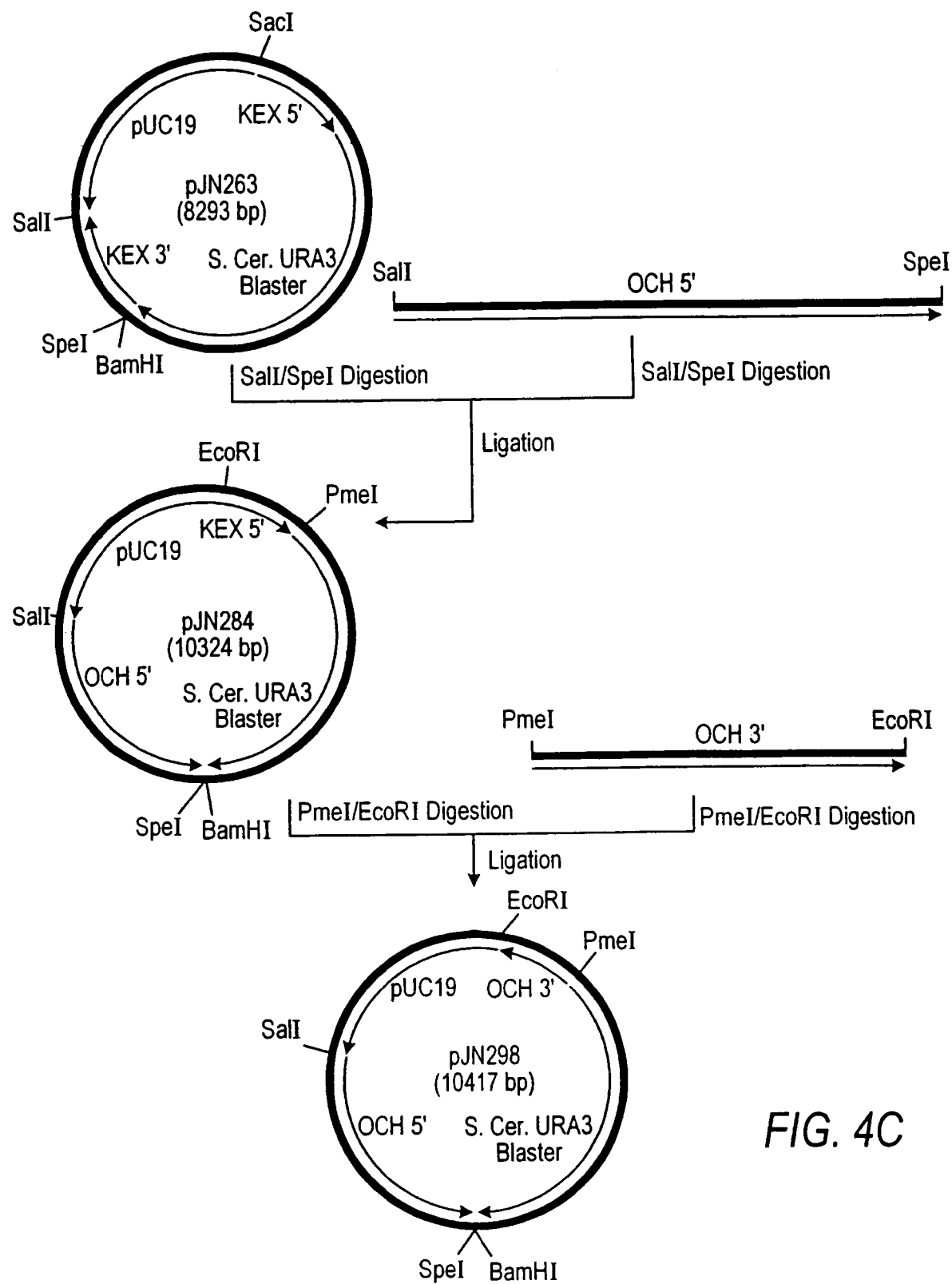
Figure 4D:
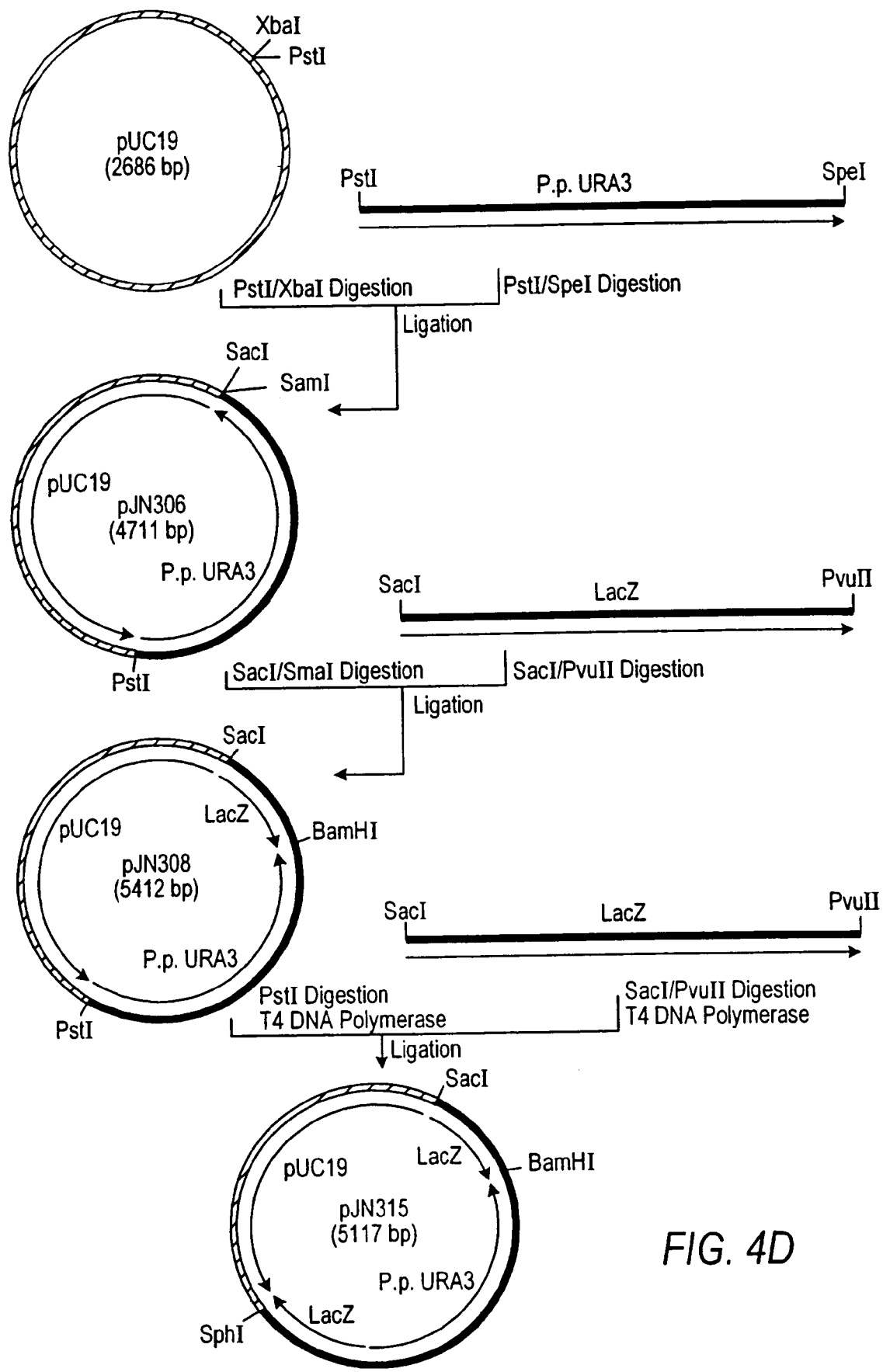
Figure 4E:
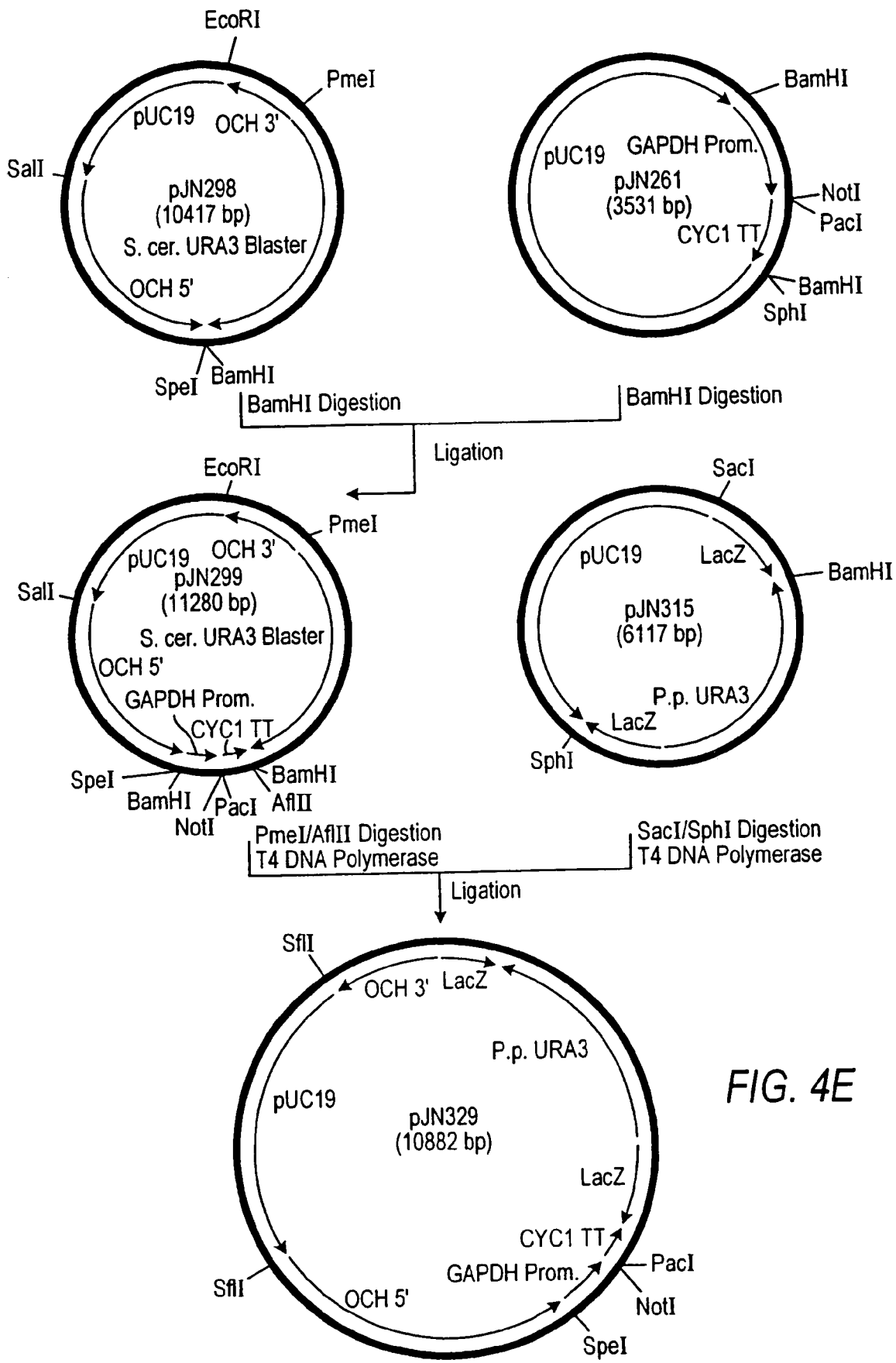

A knockout plasmid for the *P. pastoris* OCH1 gene was created by digesting pJN263 with SalI and SpeI and a 2.9-kb DNA fragment of the OCH1-5' region, which had been amplified using the primers GAACCAC GTCGACGGCCATTGCGGCCAAAACCTTTTTTCCTAT TCAAACACAAGGCATTGC (SEQ ID NO: 35) and CTC-CAAT ACTAGTCGAAGATTATCTTCTACGGTGCCTGGACTC (SEQ ID NO: 36) and *P. pastoris* genomic DNA as a template, was cloned into the open sites (FIG. 4C). The resulting plasmid was cut with EcoRI and PmeI and a 1.0-kb DNA fragment of the OCH1-3' region that had been generated using the primers TGGAAG GTTTAAACAAAGCTAGAGTAAAATAGATATAGCGAG ATTAGAGAATG (SEQ ID NO: 37) and AA GAATTCGGCTGGAAGGCCTTGTACCTTGATGTAGT TCCCGTTTTCATC (SEQ ID NO: 38) was inserted to generate pJN298 (FIG. 4C). To allow for the possibility to simultaneously use the plasmid to introduce a new gene, the BamHI expression cassette of pJN261 (FIG. 4B) was cloned into the unique BamHI site of pJN298 (FIG. 4C) to create pJN299 (FIG. 4E).

The *P. pastoris* Ura3-blaster cassette was constructed using a similar strategy as described in Lu et al. (1998) *Appl. Microbiol. Biotechnol.* 49:141-146. A 2.0-kb PstI, SpeI fragment of *P. pastoris* URA3 was inserted into the PstI, XbaI sites of pUC19 (New England Biolabs, Beverly, Mass.) to create pJN306 (FIG. 4D). Then a 0.7-kb SacI, PvuII DNA fragment of the lacZ open reading frame was cloned into the SacI, SmaI sites to yield pJN308 (FIG. 4D). Following digestion of pJN308 (FIG. 4D) with PstI, and treatment with T4 DNA polymerase, the SacI-PvuII fragment from lacZ that had been blunt-ended with T4 DNA polymerase was inserted generating pJN315 (FIG. 4D). The lacZ/URA3 cassette was released by digestion with SacI and SphI, blunt ended with T4 DNA polymerase and cloned into the backbone of pJN299 that had been digested with PmeI and AflII and blunt ended with T4 DNA polymerase. The resulting plasmid was named pJN329 (FIG. 4E).

Figure 4F:
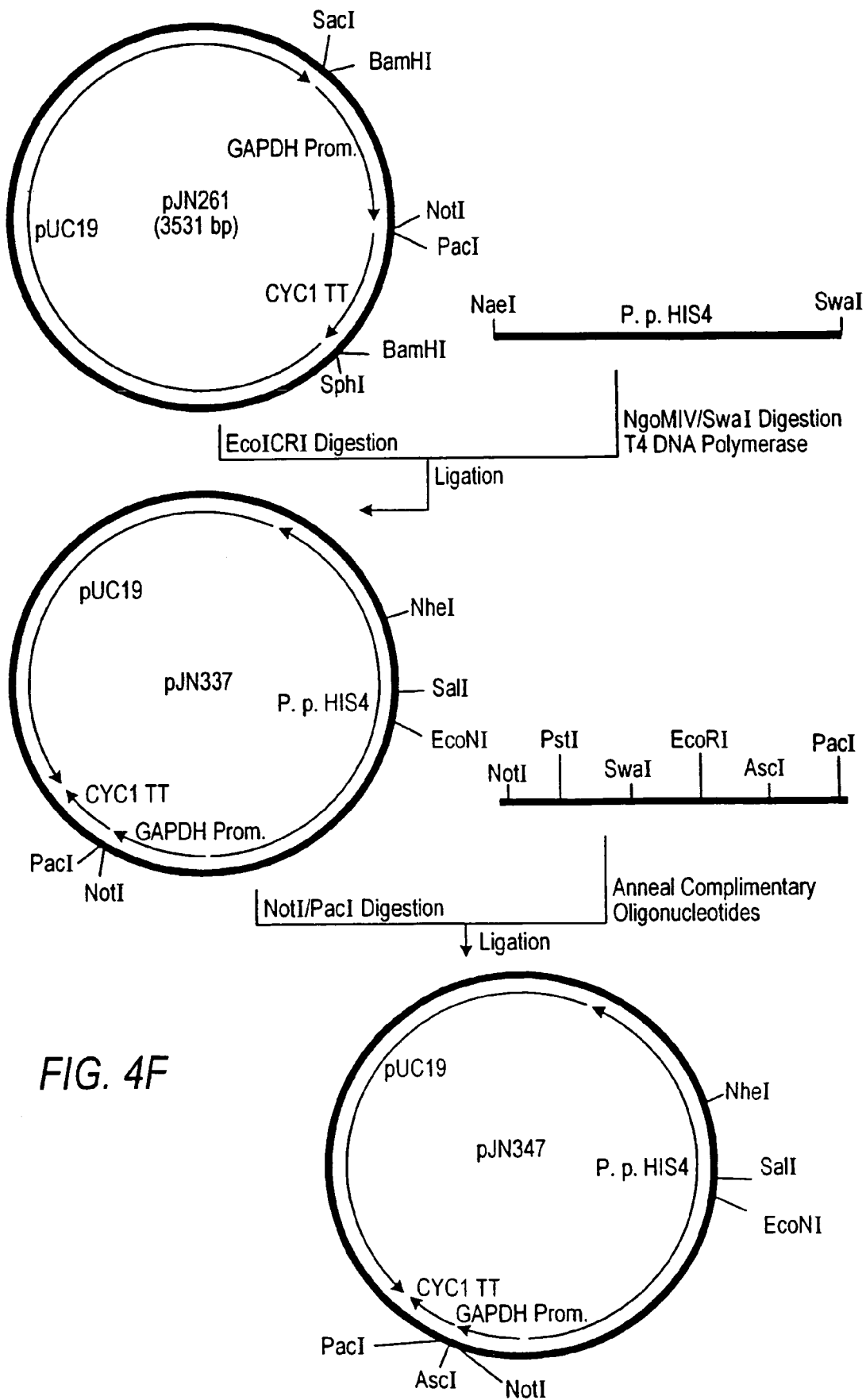

A HIS4 marked expression plasmid was created by cutting pJN261 (FIG. 4F) with EcoICRI (FIG. 4F). A 2.7 kb fragment of the *Pichia pastoris* HIS4 gene that had been amplified using the primers GCCCAA GCCGGCCTTAAGGGATCTCCTGATGACTGACTCAC TGATAATAAAAATACGG (SEQ ID NO: 39) and GGGCGCGT ATTTAAATACTAGTGGATCTATCGAATCTAAATGTAA GTTAAAATCTCTAA (SEQ ID NO: 40) cut with NgoMIV and SwaI and then blunt-ended using T4 DNA polymerase, was then ligated into the open site. This plasmid was named pJN337 (FIG. 4F). To construct a plasmid with a multiple cloning site suitable for fusion library construction, pJN337 was cut with NotI and PacI and the two oligonucleotides GGCCGCCTGCAGATTTAAATGAATTCGGCGCGCCT TAAT (SEQ ID NO: 41) and TAAGGCGCGCCGAATTCATTTAAATCTGCAGGGC (SEQ ID NO: 42), that had been annealed in vitro were ligated into the open sites, creating pJN347 (FIG. 4F).

To create an och1 knockout strain containing multiple auxotrophic markers, 100 µg of pJN329 was digested with SfiI and used to transform *P. pastoris* strain JC308 (Cereghino et al. *Gene* 263 (2001) 159-169) by electroporation. Following transformation, the URA dropout plates were incubated at room temperature for 10 days. One thousand (1000) colonies were picked and restreaked. All 1000 clones were then streaked onto 2 sets of URA dropout plates. One set was incubated at room temperature, whereas the second set was incubated at 37° C. The clones that were unable to grow at 37° C., but grew at room temperature, were subjected to colony PCR to test for the correct OCH1 knockout. One clone that showed the expected PCR signal (about 4.5 kb) was designated YJN153.

Example 5

Characterization of the Combinatorial Localization/Mannosidase Library

Positive transformants (Example 4) screened by colony PCR to confirm integration of the mannosidase construct into the *P. pastoris* genome were subsequently grown at room temperature in 50 ml BMGY buffered methanol-complex medium consisting of 1% yeast extract, 2% peptone, 100 mM potassium phosphate buffer, pH 6.0, 1.34% yeast nitrogen base, $4 \times 10^{-5}$% biotin, and 1% glycerol as a growth medium) until $OD_{600nm}$ 2-6 at which point they were washed with 10 ml BMMY (buffered methanol-complex medium consisting of 1% yeast extract, 2% peptone, 100 mM potassium phosphate buffer, pH 6.0, 1.34% yeast nitrogen base, $4 \times 10^{-5}$% biotin, and 1.5% methanol as a growth medium) prior to induction of the reporter protein for 24 hours at room temperature in 5 ml BMMY. Consequently, the reporter protein was isolated and analyzed as described in Example 3 to characterize its glycan structure. Using the targeting peptides in Table 6, mannosidase catalytic domains localized to either the ER or the Golgi showed significant level of trimming of a glycan predominantly containing $Man_8GlcNAc_2$ to a glycan predominantly containing $Man_5GlcNAc_2$. This is evident when the glycan structure of the reporter glycoprotein is compared between that of *P. pastoris* och1 knock-out in FIGS. 5C and 6C and the same strain transformed with *M. musculus* mannosidase constructs as shown in FIGS. 5D, 5E, 6D-6F. FIGS. 5 and 6 show expression of constructs generated from the combinatorial DNA library which show significant mannosidase activity in *P. pastoris*. Expression of pGC5 (*Saccharomyces* MNS1(m)/mouse mannosidase IB Δ99) (FIGS. 5D and 6E) produced a protein which has approximately 30% of all glycans trimmed to $Man_5GlcNAc_2$, while expression of pFB8 (*Saccharomyces* SEC12(m)/mouse mannosidase IA Δ187) (FIG. 6F) produced approximately 50% $Man_5GlcNAc_2$ and expression of pBC18-5 (*Saccharomyces* VAN1(s)/*C. elegans* mannosidase IB Δ80) (FIG. 5E) produced 70% $Man_5GlcNAc_2$.

Example 6

Trimming In Vivo by Alpha-1,2-Mannosidase

To ensure that the novel engineered strains of Example 4 in fact produced the desired $Man_5GlcNAc_2$ structure in vivo, cell supernatants were tested for mannosidase activity (see FIGS. 7-9). For each construct/host strain described below, HPLC was performed at 30° C. with a 4.0 mm×250 mm column of Altech (Avondale, Pa., USA) Econosil-NH$_2$ resin (5 µm) at a flow rate of 1.0 ml/min for 40 min. In FIGS. 7 and 8, degradation of the standard $Man_9GlcNAc_2$ [b] was shown to occur resulting in a peak which correlates to $Man_8GlcNAc_2$. In FIG. 7, the $Man_9GlcNAc_2$ [b] standard eluted at 24.61 min and $Man_5GlcNAc_2$ [a] eluted at 18.59 min. In FIG. 8, $Man_9GlcNAc_2$ eluted at 21.37 min and $Man_5GlcNAc_2$ at 15.67 min. In FIG. 9, the standard $Man_8GlcNAc_2$ [b] was shown to elute at 20.88 min.

Figure 7C:
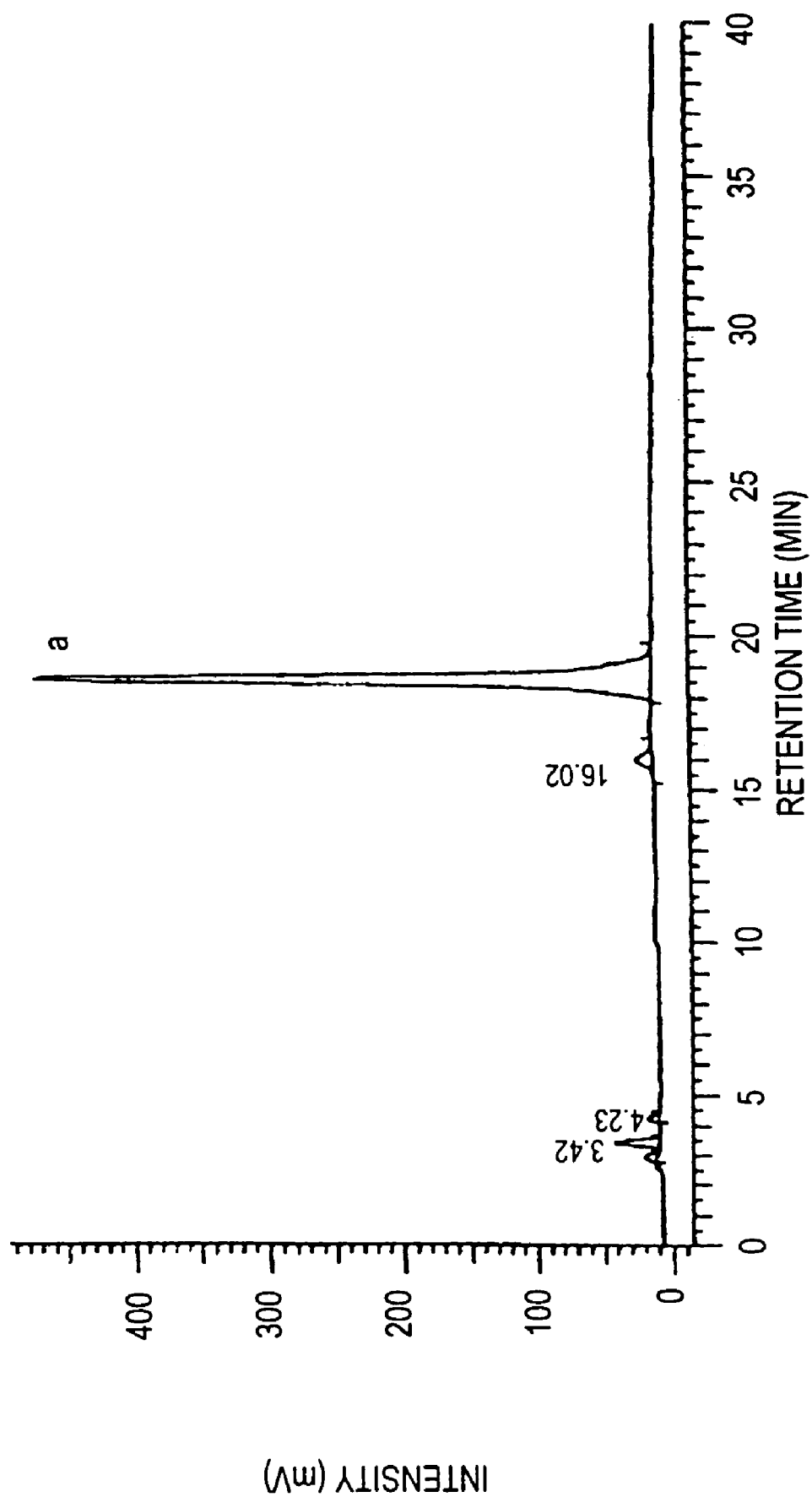

*P. pastoris* cells comprising plasmid pFB8 (*Saccharomyces* SEC12 (m)/mouse mannosidase IA Δ187) were grown at 30° C. in BMGY to an OD600 of about 10. Cells were harvested by centrifugation and transferred to BMMY to induce the production of K3 (kringle 3 from human plasminogen) under control of an AOX1 promoter. After 24 hours of induction, cells were removed by centrifugation to yield an essentially clear supernatant. An aliquot of the supernatant was removed for mannosidase assays and the remainder was used for the recovery of secreted soluble K3. A single purification step using CM-sepharose chromatography and an elution gradient of 25 mM NaAc, pH5.0 to 25 mM NaAc, pH5.0, 1M NaCl, resulted in a 95% pure K3 eluting between 300-500 mM NaCl. N-glycan analysis of the K3 derived glycans is shown in FIG. 6F. The earlier removed aliquot of the supernatant was further tested for the presence of secreted mannosidase activity. A commercially available standard of 2-aminobenzamide-labeled N-linked-type oligomannose 9 (Man9-2-AB) (Glyko, Novato, Calif.) was added to: BMMY (FIG. 7A), the supernatant from the above aliquot (FIG. 7B), and BMMY containing 10 ng of 75 mU/mL of α-1,2-mannosidase from *Trichoderma reesei* (obtained from Contreras et al., WO 02/00856 A2) (FIG. 7C). After incubation for 24 hours at room temperature, samples were analyzed by amino silica HPLC to determine the extent of mannosidase trimming.

Figure 8A:
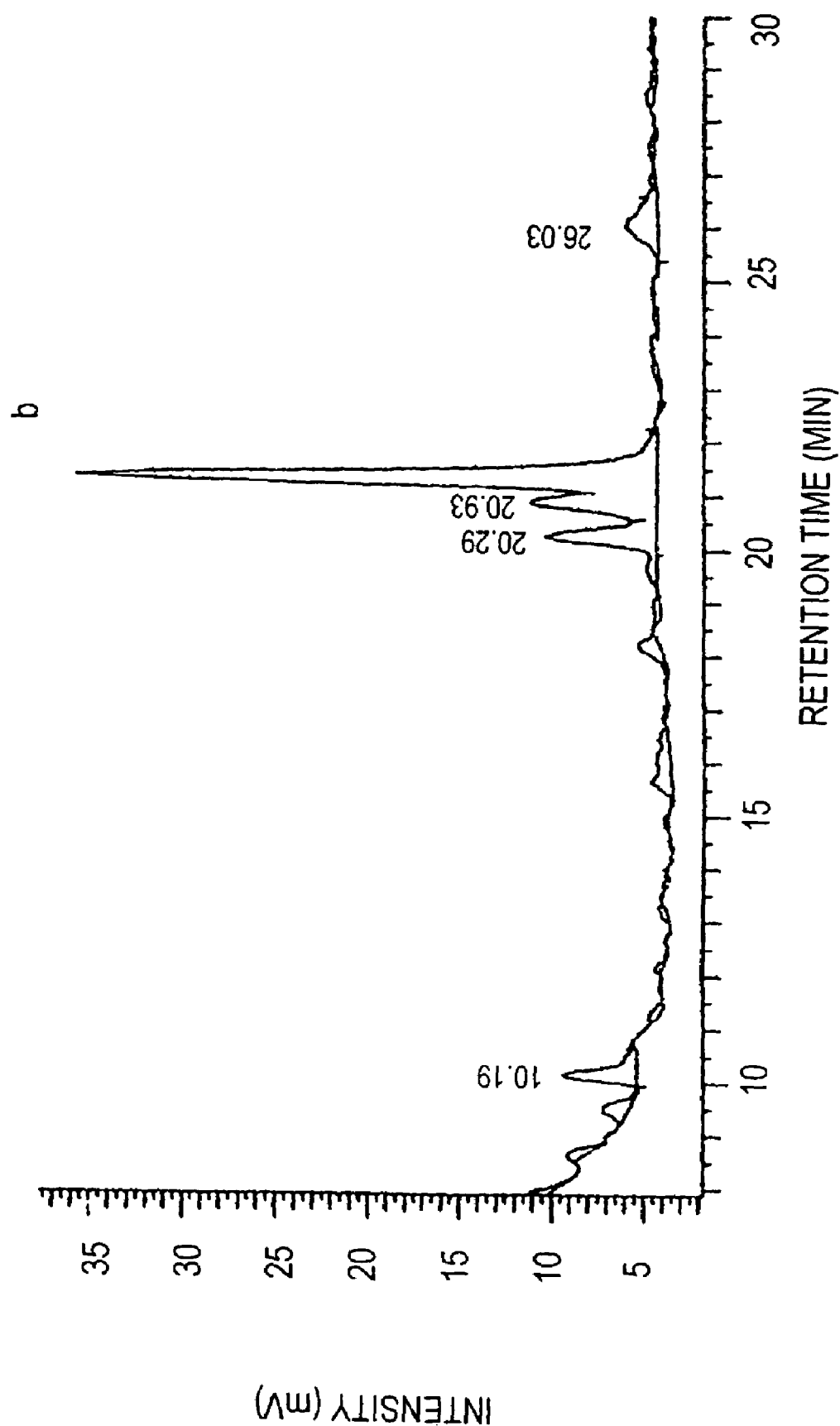
Figure 8C:
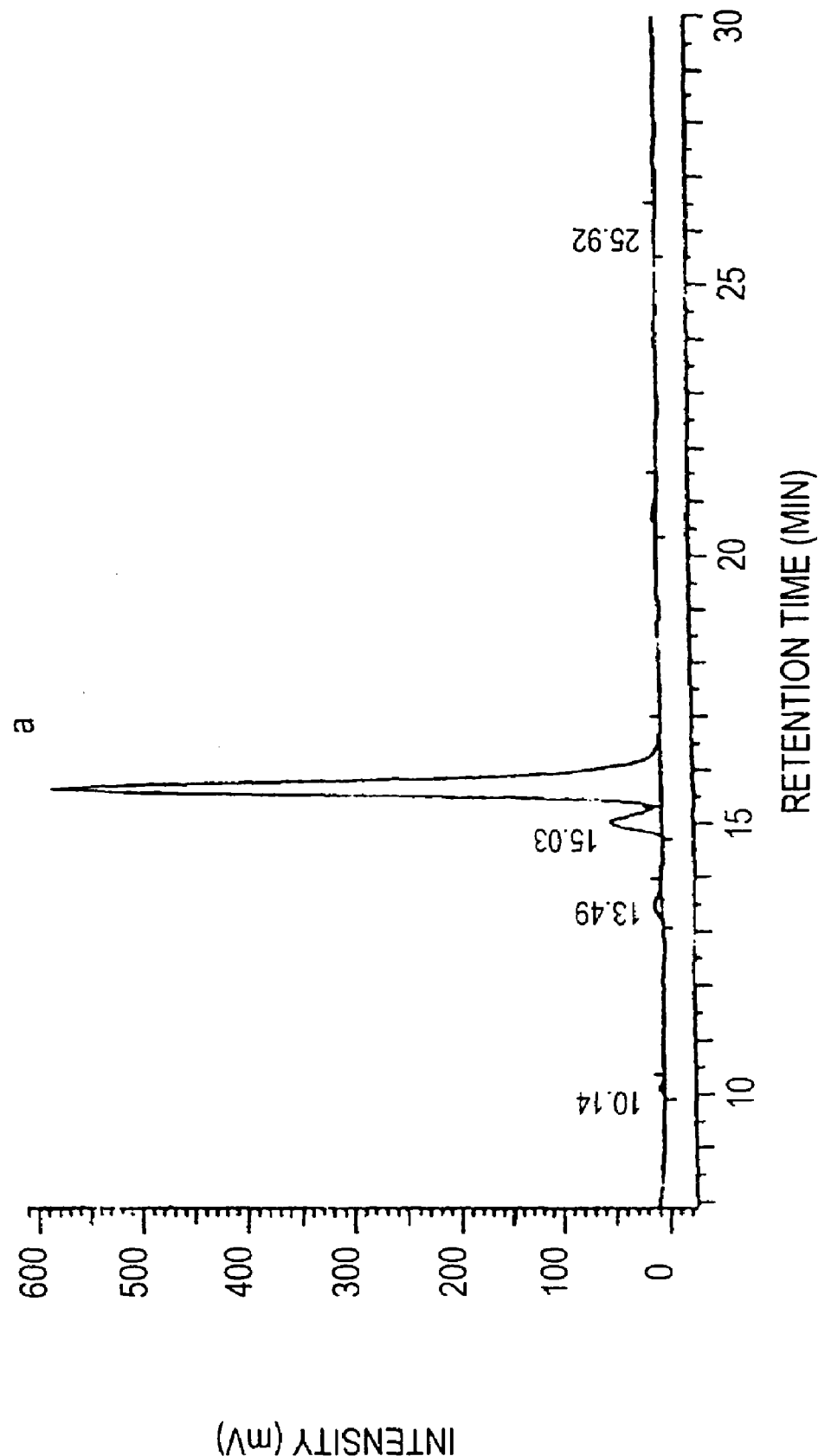

*P. pastoris* cells comprising plasmid pGC5 (*Saccharomyces* MNS1(m)/mouse mannosidase IB Δ99) were similarly grown and assayed. Cells were grown at room temperature in BMGY to an OD600 of about 10. Cells were harvested by centrifugation and transferred to BMMY to induce the production of K3 under control of an AOXI promoter. After 24 hours of induction, cells were removed by centrifugation to yield an essentially clear supernatant. An aliquot of the supernatant was removed for mannosidase assays and the remainder was used for the recovery of secreted soluble K3. A single purification step using CM-sepharose chromatography and an elution gradient of 25 mM NaAc, pH5.0 to 25 mM NaAc, pH5.0, 1M NaCl, resulted in a 95% pure K3 eluting between 300-500 mM NaCl. N-glycan analysis of the K3 derived glycans is shown in FIG. 5D. The earlier removed aliquot of the supernatant was further tested for the presence of secreted mannosidase activity as shown in FIG. 8B. A commercially available standard of Man9-2-AB (Glyko, Novato, Calif.) were added to: BMMY (FIG. 8A), supernatant from the above aliquot (FIG. 8B), and BMMY containing 10 ng of 75 mU/mL of α-1,2-mannosidase from *Trichoderma reesei* (obtained from Contreras et al., WO 02/00856 A2) (FIG. 8C). After incubation for 24 hours at room temperature, samples were analyzed by amino silica HPLC to determine the extent of mannosidase trimming.

Man9-2-AB was used as a substrate and it is evident that after 24 hours of incubation, mannosidase activity was virtually absent in the supernatant of the pFB8 (*Saccharomyces* SEC12 (m)/mouse mannosidase IA Δ187) strain digest (FIG. 7B) and pGC5 (*Saccharomyces* MNS1(m)/mouse mannosidase IB Δ99) strain digest (FIG. 8B) whereas the positive control (purified α-1,2-mannosidase from *T. reesei* obtained from Contreras) leads to complete conversion of $Man_9GlcNAc_2$ to $Man_5GlcNAc_2$ under the same conditions, as shown in FIGS. 7C and 8C. This is conclusive data showing in vivo mannosidase trimming in *P. pastoris* pGC5 strain; and pFB8 strain, which is distinctly different from what has been reported to date (Contreras et al., WO 02/00856 A2).

Figure 9A:
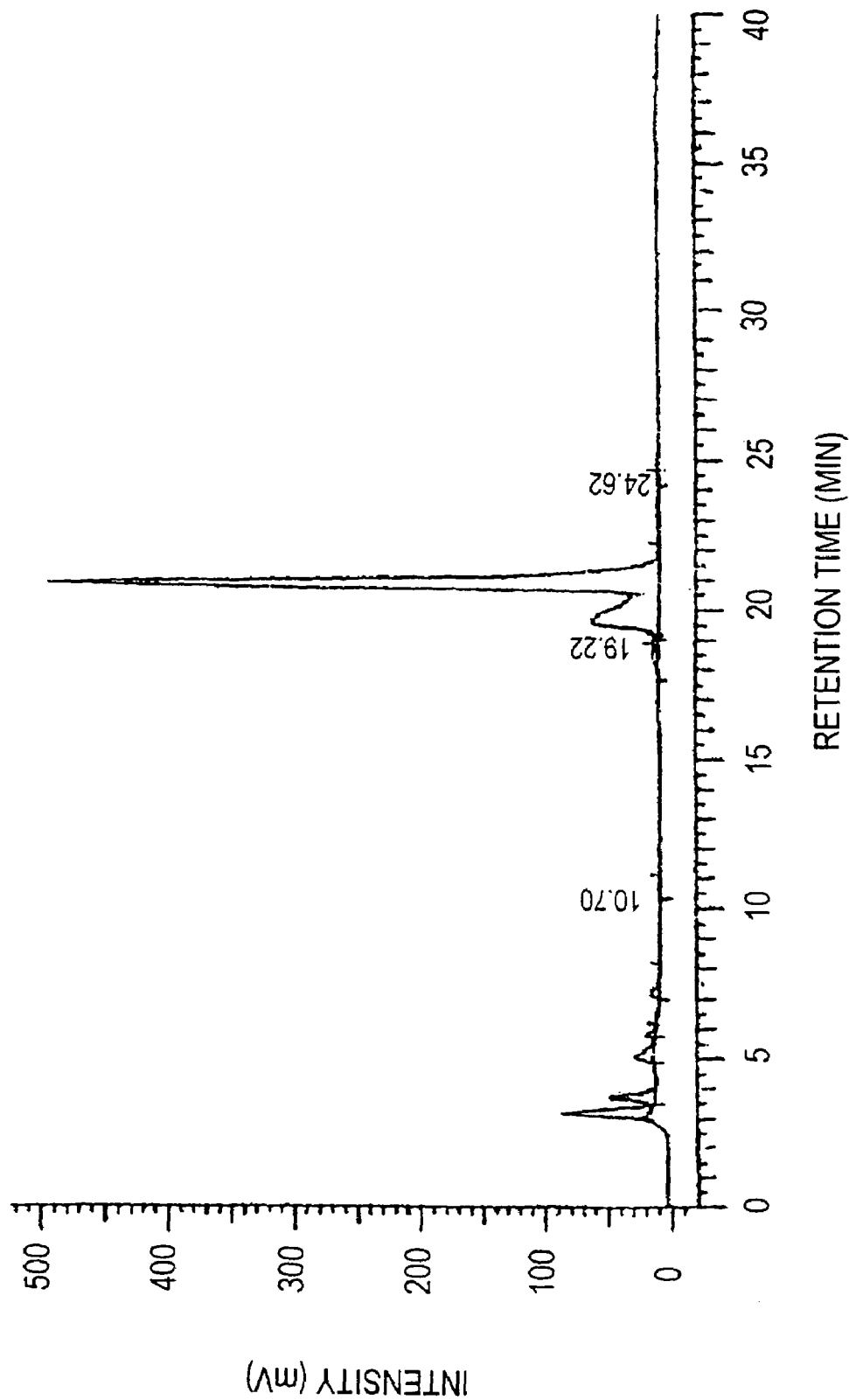
Figure 9B:
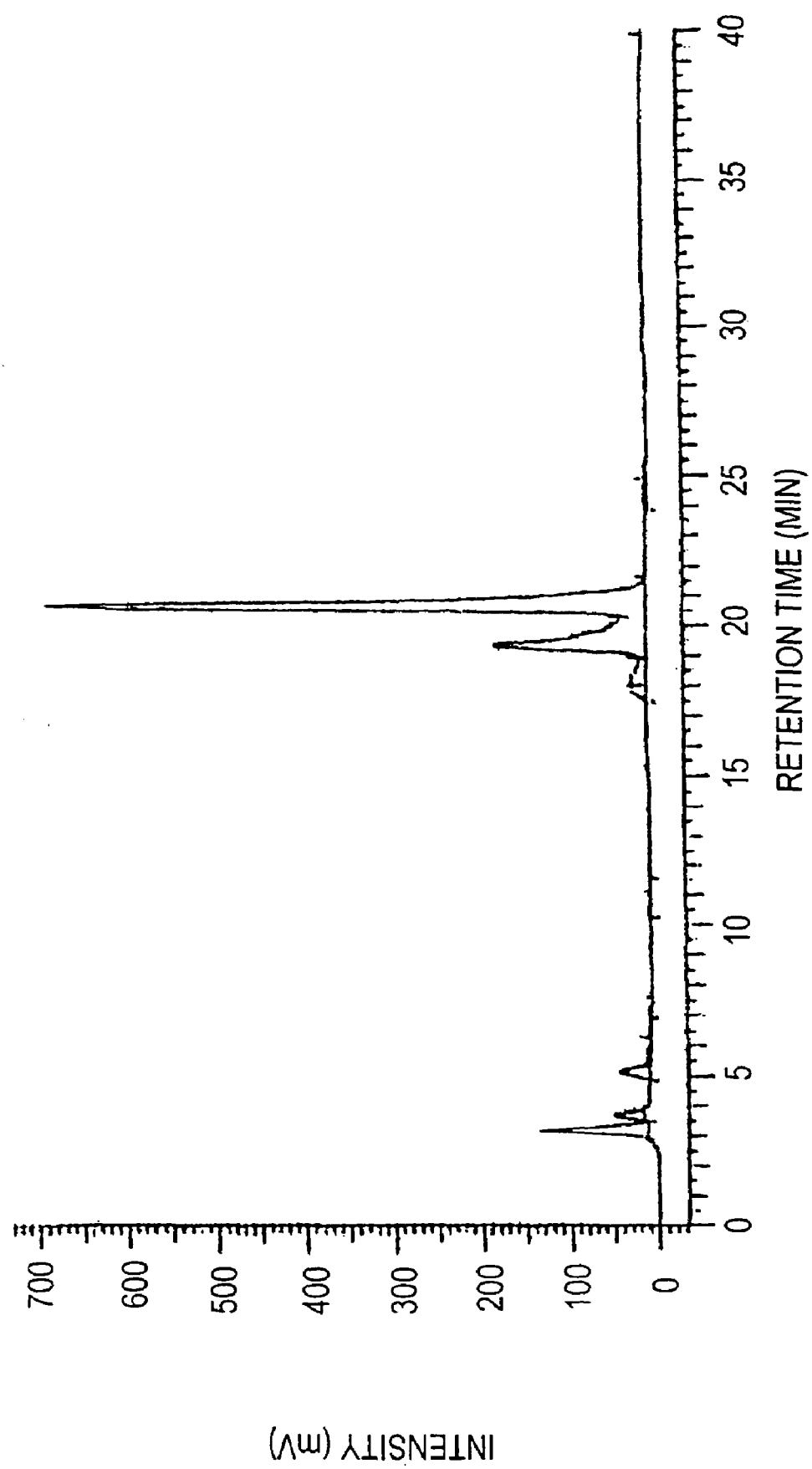

FIG. 9 further substantiates localization and activity of the mannosidase enzyme. *P. pastoris* comprising pBC18-5 (*Saccharomyces* VAN1(s)/*C. elegans* mannosidase IB Δ80) was grown at room temperature in BMGY to an OD600 of about 10. Cells were harvested by centrifugation and transferred to BMMY to induce the production of K3 under control of an AOXI promoter. After 24 hours of induction, cells were removed by centrifugation to yield an essentially clear supernatant. An aliquot of the supernatant was removed for mannosidase assays and the remainder was used for the recovery of secreted soluble K3. A single purification step using CM-sepharose chromatography and an elution gradient 25 mM NaAc, pH5.0 to 25 mM NaAc, pH5.0, 1M NaCl, resulted in a 95% pure K3 eluting between 300-500 mM NaCl. N-glycan analysis of the K3 derived glycans is shown in FIG. 5E. The earlier removed aliquot of the supernatant was further tested for the presence of secreted mannosidase activity as shown in FIG. 9B. A commercially available standard of Man8-2-AB (Glyko, Novato, Calif.) was added to: BMMY (FIG. 9A), supernatant from the above aliquot pBC18-5 (*Saccharomyces* VAN1(s)/*C. elegans* mannosidase IB Δ80) (FIG. 9B), and BMMY containing media from a different fusion construct pDD28-3 (*Saccharomyces* MNN10(m) (from SwissProt 50108)/*H. sapiens* mannosidase IB Δ99) (FIG. 9C). After incubation for 24 hours at room temperature, samples were analyzed by amino silica HPLC to determine the extent of mannosidase trimming. FIG. 9B demonstrates intracellular mannosidase activity in comparison to a fusion construct pDD29-3 (*Saccharomyces* MNN10(m) *H. sapiens* mannosidase IB Δ99) exhibiting a negative result (FIG. 9C).

Example 7 pH Optimum Assay of an Engineered α-1,2-Mannosidase

*P. pastoris* cells comprising plasmid pBB27-2 (*Saccharomyces* MNN10 (s) (from SwissProt 50108)/*C. elegans* mannosidase IB Δ31) were grown at room temperature in BMGY to an OD600 of about 17. About 80 μL of these cells were inoculated into 600 μL BMGY and were grown overnight. Subsequently, cells were harvested by centrifugation and transferred to BMMY to induce the production of K3 (kringle 3 from human plasminogen) under control of an AOX1 promoter. After 24 hours of induction, cells were removed by centrifugation to yield an essentially clear supernatant (pH 6.43). The supernatant was removed for mannosidase pH optimum assays. Fluorescence-labeled $Man_8GlcNAc_2$ (0.5 μg) was added to 20 μL of supernatant adjusted to various pH (FIG. 11) and incubated for 8 hours at room temperature. Following incubation the sample was analyzed by HPLC using an Econosil NH2 4.6×250 mm, 5 micron bead, amino-bound silica column (Altech, Avondale, Pa.). The flow rate was 1.0 ml/min for 40 min and the column was maintained to 30° C. After eluting isocratically (68% A:32% B) for 3 min, a linear solvent gradient (68% A:32% B to 40% A:60% B) was employed over 27 min to elute the glycans (18). Solvent A (acetonitrile) and solvent B (ammonium formate, 50 mM, pH 4.5. The column was equilibrated with solvent (68% A:32% B) for 20 min between runs.

Example 8

Engineering of *P. pastoris* to Produce N-Glycans with the Structure $GlcNAcMan_5GlcNAc_2$ GlcNAc Transferase I activity is required for the maturation of complex and hybrid N-glycans (U.S. Pat. No. 5,834,251). $Man_5GlcNAc_2$ may only be trimmed by mannosidase II, a necessary step in the formation of human glycoforms, after the addition of N-acetylglucosamine to the terminal α-1,3 mannose residue of the trimannose stem by GlcNAc Transferase I (Schachter, 1991 Glycobiology 1(5):453-461). Accordingly, a combinatorial DNA library was prepared including DNA fragments encoding suitably targeted catalytic domains of GlcNAc Transferase I genes from *C. elegans* and *Homo sapiens*; and localization sequences from GLS, MNS, SEC, MNN9, VAN1, ANP1, HOC1, MNN10, MNN11, MNT1, KTR1, KTR2, MNN2, MNN5, YUR1, MNN1, and MNN6 from *S. cerevisiae* and *P. pastoris* putative α-1,2-mannosyltransferases based on the homology from *S. cerevisiae*: D2, D9 and J3, which are KTR homologs. Table 10 includes but does not limit targeting peptide sequences such as SEC and OCH1, from *P. pastoris* and *K. lactis* GnTI, (See Table 6 and Table 10).

TABLE 10

A representative combinatorial library of targeting peptide sequences/catalytic domain for UDP-N-Acetylglucosaminyl Transferase I (GnTI)

| Catalytic Domain | Targeting peptide | | | | |
|---|---|---|---|---|---|
| | OCH1(s) | OCH1(m) | OCH1(l) | MNN9(s) | MNN9(m) |
| Human, GnTI, Δ38 | PB105 | PB106 | PB107 | PB104 | N/A |
| Human, GnTI, Δ86 | NB12 | NB13 | NB14 | NB15 | NB |
| C. elegans, GnTI, Δ88 | OA12 | OA13 | OA14 | OA15 | OA16 |
| C. elegans, GnTI, Δ35 | PA12 | PA13 | PA14 | PA15 | PA16 |
| C. elegans, GnTI, Δ63 | PB12 | PB13 | PB14 | PB15 | PB16 |
| X. leavis, GnTI, Δ33 | QA12 | QA13 | QA14 | QA15 | QA16 |
| X. leavis, GnTI, Δ103 | QB12 | QB13 | QB14 | QB15 | QB16 |

Targeting peptide sequences were selected from OCH1 in *P. pastoris* (long, medium and short) (see Example 4) and MNN9 (SwissProt P39107) in *S. cerevisiae* short, and medium. Catalytic domains were selected from human GnTI with a 38 and 86 amino acid N-terminal deletion, *C. elegans* (gly-12) GnTI with a 35 and 63 amino acid deletion as well as *C. elegans* (gly-14) GnTI with a 88 amino acid N-terminal deletion and *X. leavis* GnTI with a 33 and 103 amino acid N-terminal deletion, respectively.

A portion of the gene encoding human N-acetylglucosaminyl Transferase I (MGATI, Accession# NM002406), lacking the first 154 bp, was amplified by PCR using oligonucleotides 5'-TGGCAGGCGCGCCTCAGTCAGCGCTCTCG-3' (SEQ ID NO: 43) and 5'-AGGTTAATTA AGTGCTAATTC-CAGCTAGG-3' (SEQ ID NO: 44) and vector pHG4.5 (ATCC#79003) as template. The resulting PCR product was cloned into pCR2.1-TOPO and the correct sequence was confirmed. Following digestion with AscI and PacI the truncated GnTI was inserted into plasmid pJN346 to create pNA. After digestion of pJN271 with NotI and AscI, the 120 bp insert was ligated into pNA to generate an in-frame fusion of the MNN9 transmembrane domain with the GnTI, creating pNA 15.

The host organism is a strain of *P. pastoris* that is deficient in hypermannosylation (e.g. an och1 mutant), provides the substrate UDP-GlcNAc in the Golgi and/or ER (i.e. contains a functional UDP-GlcNAc transporter), and provides N-glycans of the structure $Man_5GlcNAc_2$ in the Golgi and/or ER (e.g. *P. pastoris* pFB8 (*Saccharomyces* SEC12 (m)/mouse mannosidase IA Δ187) from above). First, *P. pastoris* pFB8 was transformed with pPB103 containing the *Kluyveromyces lactis* MNN2-2 gene (Genbank AN AF106080) (encoding UDP-GlcNAc transporter) cloned into BamHI and BglII site of pBLADE-SX plasmid (Cereghino et al. Gene 263 (2001) 159-169). Then the aforementioned combinatorial DNA library encoding a combination of exogenous or endogenous GnTI/localization genes was transformed and colonies were selected and analyzed for the presence of the GnTI construct by colony PCR. Our transformation and integration efficiency was generally above 80% and PCR screening can be omitted once robust transformation parameters have been established.

In summary, the methods of the invention yield strains of *P. pastoris* that produce $GlcNAcMan_5GlcNAc_2$ in high yield, as shown in FIG. 10B. At least 60% of the N-glycans are $GlcNAcMan_5GlcNAc_2$. To date, no report exists that describes the formation of $GlcNAcMan_5GlcNAc_2$ on secreted soluble glycoproteins in any yeast. Results presented herein show that addition of the UDP-GlcNAc transporter along with GnTI activity produces a predominant $GlcNAcMan_5GlcNAc_2$ structure, which is confirmed by the peak at 1457 (m/z) (FIG. 10B).

Construction of Strain PBP-3:

The *P. pastoris* strain expressing K3, (Δoch1, arg-, ade-, his-) was transformed successively with the following vectors. First, pFB8 (*Saccharomyces* SEC12 (m)/mouse mannosidase IA Δ187) was transformed in the *P. pastoris* strain by electroporation. Second, pPB103 containing *Kluyveromyces lactis* MNN2-2 gene (Genbank AN AF106080) (encoding UDP-GlcNAc transporter) cloned into pBLADE-SX plasmid (Cereghino et al. Gene 263 (2001) 159-169) digested with BamHI and BglII enzymes was transformed in the *P. pastoris* strain. Third, pPB104 containing *Saccharomyces* MNN9(s)/human GnTI Δ38 encoding gene cloned as NotI-PacI fragment into pJN336 was transformed into the *P. pastoris* strain.

Example 9

Engineering *K. lactis* Cells to Produce N-Glycans with the Structure $Man_5GlcNAc_2$ Identification and Disruption of the *K. lactis* OCH1 Gene The OCH1 gene of the budding yeast *S. cerevisiae* encodes a 1,6-mannosyltransferase that is responsible for the first Golgi localized mannose addition to the $Man_8GlcNAc_2$ N-glycan structure on secreted proteins (Nakanishi-Shindo et al. (1993), *J. Biol. Chem.*; 268(35):26338-45). This mannose transfer is generally recognized as the key initial step in the fungal specific polymannosylation of N-glycan structures (Nakanishi-Shindo et al. (1993) *J. Biol. Chem.* 268(35): 26338-26345; Nakayama et al. (1992) *EMBO J.* 11(7):2511-19; Morin-Ganet et al, *Traffic* 1(1):56-68. (January 2000)). Deletion of this gene in *S. cerevisiae* results in a significantly shorter N-glycan structure that does not include this typical polymannosylation or a growth defect at elevated temperatures (Nakayama et al. (1992) *EMBO J.* 11(7):2511-19).

The Och1p sequence from *S. cerevisiae* was aligned with known homologs from *Candida albicans* (Genbank accession # AAL49987), and *P. pastoris* along with the Hoc1 proteins of *S. cerevisiae* (Neiman et al, *Genetics*, 145(3):637-45 (March 1997) and *K. lactis* (PENDANT EST database) which are related but distinct mannosyltransferases. Regions of high homology that were in common among Och1p homologs but distinct from the Hoc1p homologs were used to design pairs of degenerate primers that were directed against genomic DNA from the *K. lactis* strain MG1/2 (Bianchi et al, *Current Genetics* 12, 185-192 (1987)). PCR amplification with primers RCD33 (CCAGAAGAATTCAATTYTGY-CARTGG) (SEQ ID NO: 45) and RCD34 (CAGT-GAAAATACCTGGNCCNGTCCA) (SEQ ID NO: 46) resulted in a 302 bp product that was cloned and sequenced and the predicted translation was shown to have a high degree of homology to Och1 proteins (>55% to *S. cerevisiae* Och1p).

Figure 12A:
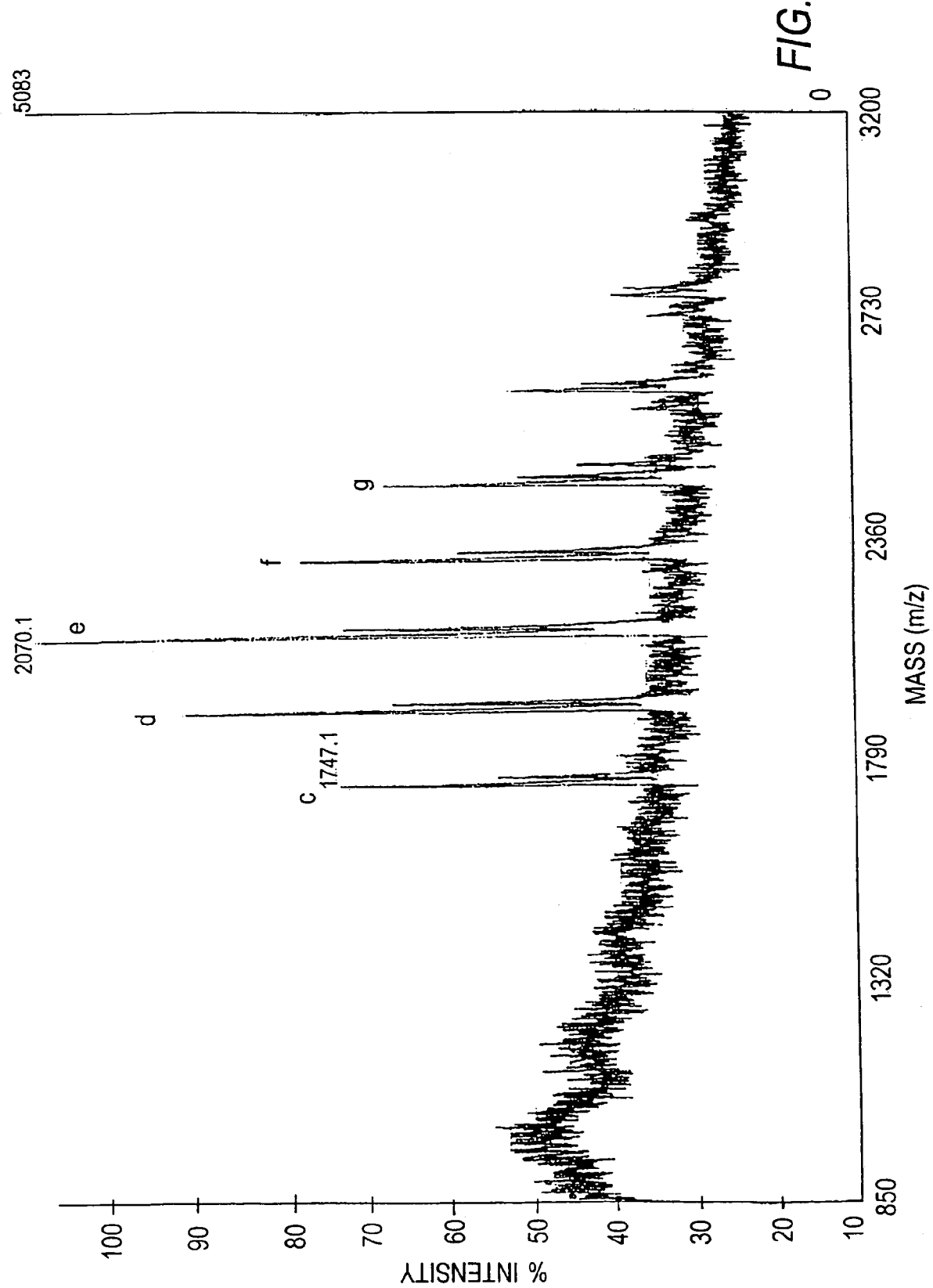

The 302 hp PCR product was used to probe a Southern blot of genomic DNA from *K. lactis* strain (MG1/2) with high stringency (Sambrook et al., *Molecular Cloning: A Laboratory Manual*, 2nd ed., Cold Spring Harbor Laboratory Press, Cold Spring Harbor, N.Y., 1989). Hybridization was observed in a pattern consistent with a single gene indicating that this 302 bp segment corresponds to a portion of the *K. lactis* genome and *K. lactis* (KlOCH1) contains a single copy of the gene. To clone the entire KlOCH1 gene, the Southern blot was used to map the genomic locus. Accordingly, a 5.2 kb BamHI/PstI fragment was cloned by digesting genomic DNA and ligating those fragments in the range of 5.2 kb into pUC19 (New England Biolabs, Beverly, Mass.) to create a *K. lactis* subgenomic library. This subgenomic library was transformed into *E. coli* and several hundred clones were tested by colony PCR using RCD 33/34. The 5.2 kb clone containing the predicted KlOCH1 gene was sequenced and an open reading frame of 1362 bp encoding a predicted protein that is 46.5% identical to the *S. cerevisiae* OCH1 gene. The 5.2 kb sequence was used to make primers for construction of an och1:KAN$^R$ deletion allele using a PCR overlap method (Davidson et al. (2002) *Microbiol.* 148(Pt 8):2607-15). This deletion allele was transformed into two *K. lactis* strains and G418 resistant colonies selected. These colonies were screened by both PCR and for temperature sensitivity to obtain a strain deleted for the OCH1 ORF. The results of the experiment show strains which reveal a mutant PCR pattern, which were characterized by analysis of growth at various temperatures and N-glycan carbohydrate analysis of secreted and cell wall proteins following PNGase digestion. The och1 mutation conferred a temperature sensitivity which allowed strains to grow at 30° C. but not at 35° C. FIG. 12A shows a MALDI-TOF analysis of a wild type *K. lactis* strain producing N-glycans of Man$_8$GlcNAc$_2$ [c] and higher.

Identification, Cloning, and Disruption of the *K. lactis* MNN1 Gene

*S. cerevisiae* MNN1 is the structural gene for the Golgi α-1,3-mannosyltransferase. The product of MNN1 is a 762-amino acid type II membrane protein (Yip et al., *Proc Natl Acad Sci U S A*. 91(7):2723-7. (1994)). Both N-linked and O-linked oligosaccharides isolated from mnn1 mutants lack α-1,3-mannose linkages (Raschke et al., *J Biol Chem.*, 248 (13):4660-6. (Jul. 10, 1973).

The Mnn1p sequence from *S. cerevisiae* was used to search the *K. lactis* translated genomic sequences (PEDANT). One 405 bp DNA sequence encoding a putative protein fragment of significant similarity to Mnn1p was identified. An internal segment of this sequence was subsequently PCR amplified with primers KMN1 (TGCCATCTTTTAGGTCCAGGC-CCGTTC) (SEQ ID NO: 47) and KMN2 (GATCCCAC-GACGCATCGTATTTCTTTC), (SEQ ID NO: 48) and used to probe a Southern blot of genomic DNA from *K. lactis* strain (MG1/2). Based on the Southern hybridization data a 4.2 Kb BamHI-PstI fragment was cloned by generating a size-selected library as described herein. A single clone containing the *K. lactis* MNN1 gene was identified by whole colony PCR using primers KMN1 (SEQ ID NO: 47) and KMN2 (SEQ ID NO: 48) and sequenced. Within this clone a 2241 bp ORF was identified encoding a predicted protein that was 34% identical to the *S. cerevisiae* MNN1 gene. Primers were designed for construction of a mnn1::NAT$^R$ deletion allele using the PCR overlap method (Davidson et al. (2002) *Microbiol.* 148(Pt 8):2607-15).

This disruption allele was transformed into a strain of *K. lactis* by electroporation and nourseothricin resistant transformants were selected and PCR amplified for homologous insertion of the disruption allele. Strains that reveal a mutant PCR pattern may be subjected to N-glycan carbohydrate analysis of a known reporter gene.

Figure 12B:
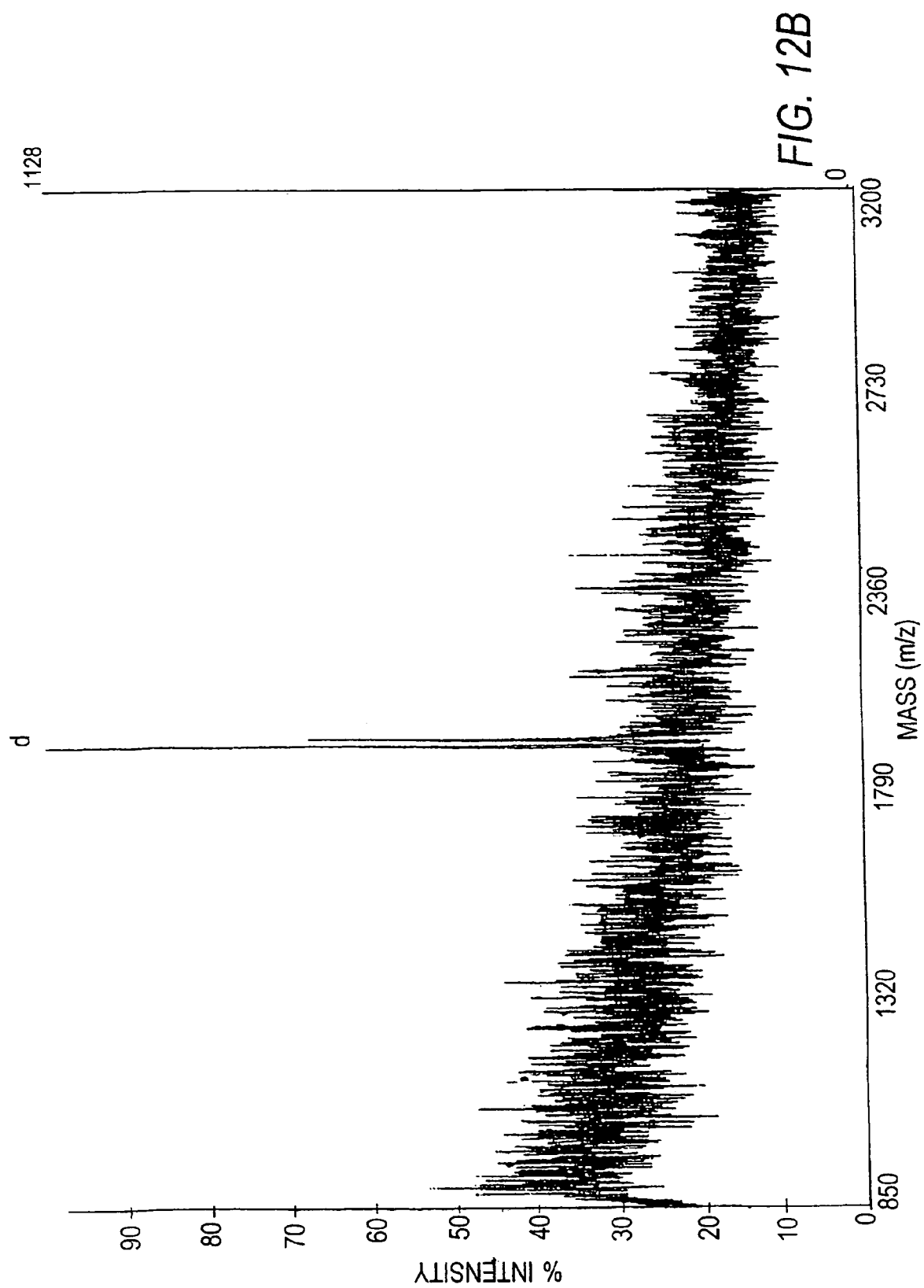

FIG. 12B depicts the N-glycans from the *K. lactis* och1 mnn1 deletion strain observed following PNGase digestion the MALDI-TOF as described herein. The predominant peak at 1908 (m/z) indicated as [d] is consistent with the mass of Man$_9$GlcNAc$_2$.

Additional methods and reagents which can be used in the methods for modifying the glycosylation are described in the literature, such as U.S. Pat. No. 5,955,422, U.S. Pat. No. 4,775,622, U.S. Pat. No. 6,017,743, U.S. Pat. No. 4,925,796, U.S. Pat. No. 5,766,910, U.S. Pat. No. 5,834,251, U.S. Pat. No. 5,910,570, U.S. Pat. No. 5,849,904, U.S. Pat. No. 5,955, 347, U.S. Pat. No. 5,962,294, U.S. Pat. No. 5,135,854, U.S. Pat. No. 4,935,349, U.S. Pat. No. 5,707,828, and U.S. Pat. No. 5,047,335. Appropriate yeast expression systems can be obtained from sources such as the American Type Culture Collection, Rockville, Md. Vectors are commercially available from a variety of sources.

Example 10

Strains, Culture Conditions and Reagents

For the examples below, the following strains, culture conditions and reagents were used. *Escherichia coli* strains TOP10 or DH5α were used for recombinant DNA work.

Protein expression was carried out at room temperature in a 96-well plate format with buffered glycerol-complex medium (BMGY) consisting 1% yeast extract, 2% peptone, 100 mM potassium phosphate buffer, pH 6.0, 1.34% yeast nitrogen base, 4×10$^{-5}$% biotin, and 1% glycerol as a growth medium. The induction medium was buffered methanol-complex medium (BMMY) consisting of 1.5% methanol instead of glycerol in BMGY.

Restriction and modification enzymes were from New England BioLabs (Beverly, Mass.).

Oligonucleotides were obtained from the Dartmouth College Core facility (Hanover, N.H.) or Integrated DNA Technologies (Coralville, Iowa).

Example 11

Cloning and Generation of Expression Vectors to Produce Man$_3$GlcNAc$_2$

Restriction and modification enzymes were from New England BioLabs (Beverly, Mass.). The shuttle vector pVM2 was generated from pUC19 by inverse PCR (Sambrook, J., Fritsch, E. F., and Maniatis, T. (1989) In: Molecular Cloning, a Laboratory Manual 2nd Edition, Cold Spring Harbor N.Y.: Cold Spring Harbor Laboratory Press.) using the primers VJM104 and VJM106 (5'-GCGGCCGCGGATCCCCGGG-TACCGAGCTCGAATTCACT-3' (SEQ ID NO: 107) and 5'-GGGGCGCGCCTTAATTAACGACCTGCAG-GCATGCAAGCTTGGCGTAATCATGGTCAT-3' (SEQ ID NO: 108) respectively, introduced restriction sites NotI, AscI and PacI are underlined).

The roll-in plasmid pJN285 is a derivative of the knock-in plasmid pJN266 that was constructed in the following way. A 0.9-kb fragment of the PpKEX1-5' region was amplified by PCR using primers Kex55 (5'-GGC GAGCTCGGCCTACCCGGCCAAGGCTGAGATCATTT GTCCAGCTTCAGA-3', SEQ ID NO: 27) and Kex53 (5'-GCCCAC GTCGACGGATCCGTTTAAACATCGATTGGAGAGGC TGACACCGCTACTA-3', SEQ ID NO: 28) from *Pichia pastoris* genomic DNA and cloned into pUC19 digested with SacI and SalI. The resulting plasmid was cut with BamHI and SalI, and a 0.8-kb fragment of the KEX1-3' region that had been amplified using primers Kex35 (5'-CG GGATCCACTAGTATTTAAATCATATGTGCGAGTGTAC AACTCTTCCCACATGG-3', SEQ ID NO: 29) and Kex33 (5'-GGACGC GTCGACGGCCTACCCGGCCGTACGAGGAATTTCTCG GATGACTCTTTTC-3', SEQ ID NO: 30) was cloned into pJN262 digested with the same enzymes. This plasmid was cut with BamHI and the 3.8-kb BamHI-BglII fragment of pNKY51 (1) was inserted in each of the two possible orientations resulting in plasmids pJN263 and pJN264. To create an expression cassette with NotI and PacI cloning sites, the GAPDH promoter of *P. pastoris* was amplified using primers Gap5 (5'-CGGGATCCCTCGAGAGATCTTTTTTGTAGAAATGTCTTGGTGCCT-3', SEQ ID NO: 31) and Gap3 (5'-GGACATGCATGCACTAGTGCGGCCGCCACGTGATAGTTGTTCAATTGATTGAAATAGGGACAA-3', SEQ ID NO: 32) and plasmid pGAPZ-A (Invitrogen) as template and cloned into the BamHI-SphI sites of pUC19. The resulting plasmid was cut with SpeI and SphI and the *S. cerevisiae* CYC1 transcriptional terminator region, that had been amplified from pPICZ-A (Invitrogen) using primers Cyc5 (5'-CCTTGCTAGCTTAATTAACCGCGGCACGTCCGACGGCGGCCCACGGGTCCCA-3', SEQ ID NO: 33) and Cyc3 (5'-GGACATGCATGCGGATCCCTTAAGAGCCGGCAGCTTGCAAATTAAAGCCTTCGAGCGTCCC-3', SEQ ID NO: 34), was cloned into the open sites creating pJN261. The GAPDH/CYC1 expression cassette was released by BamHI digestion and cloned either into pJN263 resulting in plasmid pJN265, or into pJN264 resulting in plasmids pJN266 and pJN267 (depending on orientation of the insert). Subsequently the plasmid pJN266 was cut with NgoMIV and SwaI to release the URA-blaster cassette, and a NgoMIV-SwaI fragment containing the PpHIS4 gene, that had been amplified from pPIC3.5 (Invitrogen) using primers JNHIS1 (5'-GCCCAAGCCGGCCTTAAGGGATCTCCTGATGACTGACTCACTGATAATAAAAATACGG-3', SEQ ID NO: 39) and JNHIS2 (5'-GGGCGCGTATTTAAATACTAGTGGATCTATCGAATCTAAATGTAAGTTAAAATCTCTAA-3', SEQ ID NO: 40), was cloned into the open sites to create pJN285.

The pJN348 expression vector is based on plasmid pBLURA-SX (2). First a BamHI fragment containing the GAPDH/CYC1 expression cassette from vector pJN261 was cloned into pBLURA-SX that had been cut with BamHI and BglII to create plasmid pJN338. Subsequently the latter plasmid was cut with NotI and PacI and the two oligonucleotides ExprI (5'-GGCCGCCTGCAGATTTAAATGAATTCGGCGCGCCTTAAT-3', SEQ ID NO: 41) and Expr2 (5'-TAAGGCGCGCCGAATTCATTTAAATCTGCAGGGC-3' (SEQ ID NO: 42), the restriction site AscI is underlined) that had been annealed in vitro, were ligated into the open sites, to create pJN348.

The pPB124 expression vector was constructed in several steps based on pBLADE-SX vector described by Cereghino et al. *Gene* 263 (2001) 159-169. First, BamHI fragment containing GAPDH/CYC1 expression cassette from vector pJN261 (described in Choi et al. *Proc Natl Acad Sci USA*. 2003 Apr. 29; 100(9):5022-7) was cloned into pBLADE-SX vector after BamHI-BglII digest. Next, the XhoI-NotI fragment containing *P. pastoris* GAPDH promoter was replaced with the promoter of *P. pastoris* PMA1 gene that was amplified with PMA1 (5'-TTCCTCGAGATTCAAGCGAATGAGAATAATG-3', SEQ ID NO: 109) and PMA2 (5'-TTGCGGCCGCGAAGTTTTTAAAGGAAAGAGATA-3', SEQ ID NO: 110) primers. The resulting vector was then digested with XbaI-BamHI enzymes to remove ADE1 marker, and after fill-in reaction ligated with blunt-ended BglII-SacI fragment containing nourseothricin resistance marker from vector pAG25 (Goldstein and McCusker, Yeast. 1999 October; 15(14): 1541-53).

Example 12

Generation of Localization Signal/Mannosidase I Catalytic Domain Fusions

Amplification of mouse mannosidase IA. The gene sequence encoding the catalytic domain of mouse mannosidase IA (Genbank: NM_008548, Lal & Moremen 1994) was amplified from mouse liver cDNA (Clontech). Briefly, the forward primer mMIAΔ187-AscI and reverse primer mMIA-PacI (5'-GGCGCGCCGAGCCCGCTGACGCCACCATCCGTGAGAAGAGGGC-3' (SEQ ID NO: 111) and 5'-CCTTAATTAATCATTTCTCTTTGCCATCAATTTCCTTCTTCTGTTCACGG-3' (SEQ ID NO: 26), respectively, introduced AscI and PacI restriction sites are underlined) where used to amplify amino acids 188-655 of the mouse mannosidase IA ORF from mouse liver cDNA (Clontech) with Pfu DNA polymerase (Stratagene). The conditions used for thermo cycling were: 94° C. for 1 min, 1 cycle; 94° C. for 30 sec, 68° C. for 30 sec, 72° C. for 3 min, 30 cycles. Subsequently, 1 µl Taq DNA polymerase (Promega) was added and the reaction further incubated at 72° C. for 10 mm with the 1.4 Kb product being ligated into pCR2.1, giving the plasmid pSH9. Following confirmation of the PCR product by Taq DyeDeoxy terminal sequencing the mouse mannosidase IA was digested with the restriction enzymes AscI and PacI prior to subcloning into the vector pVM2, digested with the same restriction enzymes, generating the plasmid pSH21.

To facilitate the subsequent localization of the truncated mouse mannosidase IA to the yeast Golgi a region of the *S. cerevisiae* Sec12 protein (amino acids 331-432, encoding the transmembrane domain) was amplified with the primers SC125 and SC122 (5'-ATGTGGCGGCGGCCGCCACCATGAACACTATCCACATAATAJLAATTACCGCTTAA CTACGCC-3' (SEQ ID NO: 112) and 5'-GGCGCGCCCCACGCCTAGCACTTTTATGGAATCTACGCTAGGTAC-3' (SEQ ID NO: 113), respectively, introduced NotI and AscI restricition sites are underlined) in the presence of Taq DNA polymerase and *S. cerevisiae* genomic DNA, producing the plasmid pJN305. Following confirmation of the PCR product by Taq DyeDeoxy terminal sequencing the Sec12 fragment, digested with the restriction enzymes NotI and AscI, was subcloned into pSH21 digested with the same enzymes, generating the plasmid pSH29. Subsequently the NotI/PacI fragment of pSH29, encoding the Sec12 fragment in-frame with the truncated mouse mannosidase IA, was subcloned into pJN285 digested with the same enzymes, generating the plasmid pFB8.

Example 13

Generation of Mannosidase II Construct

The catalytic domain of a *Drosophila* mannosidase II (GenBank: X77652, Foster and Roberts 1995), encoding amino acids 75-1108, was amplified from *Drosophila* ovary cDNA using ExTaq DNA polymerase under the thermocycling conditions outlined above, by annealing at 55° C. and extending for 5 minutes. The forward primer dMannIIΔ74_AscI and the reverse primer dMannII_PacI (5'-GGCGCGCCCGCGACGATCCAATAAGACCTCCAC-3' (SEQ ID NO: 69) and 5'-CCTTAATTAATCAGCTTG AGTGACTGCTCACATAAGCGGCGG-3' (SEQ ID NO: 71), respectively, introduced AscI and PacI restriction sites are underlined) were used. Following confirmation of the PCR product by Taq DyeDeoxy terminal sequencing, the plasmid was named pSH214. Subsequently, the *Drosophila* mannosidase II fragment was removed from this plasmid by digestion with the restriction enzymes AscI and PacI, and subcloned into pJN348 digested with the same enzymes, generating the plasmid pSH220.

To facilitate the subsequent localization of the truncated *Drosophila* mannosidase II domain to the Golgi, a region of the *S. cerevisiae* Mnn2 protein (amino acids 1-36, encoding the transmembrane domain) was amplified with the primers Mnn25 and Mnn21 (5'-AGTAAAAT GCGGCCGCCACCATGCTGCTTACCAAAAGGTTTTC AAAGCTGTTC-3' (SEQ ID NO: 114) and 5'-GGCGCGCCCCGACGTGTTCTCATCCATGTATTTGTT TGTAATGAC-3' (SEQ ID NO: 115), respectively, introduced NotI and AscI restricition sites are underlined) in the presence of Taq DNA polymerase and *S. cerevisiae* genomic DNA, producing the plasmid pJN281. Following confirmation of the PCR product by Taq DyeDeoxy terminal sequencing, the Mnn2 fragment was digested with the restriction enzymes NotI and AscI and subcloned into pSH220 digested with the same enzymes, producing an in-frame fusion of the Mnn2 localization signal with the *Drosophila* mannosidase II catalytic domain, generating the plasmid pKD53. The pH optimum of this engineered *Drosophila* mannosidase II catalytic domain was determined to be pH 6.2 using a pH assay essentially as described in Example 7.

Example 14

Mannosidase II Catalytic Domain Library

The library of mannosidase II catalytic domains and leaders showing activity are shown below in Table II. The number of (+)s, as used herein, indicates the relative levels of GlcNAcMan$_3$GlcNA$_2$ production of % neutral glycans. The notation (−) indicates no apparent production of GlcNAcMan$_3$GlcNA$_2$. The notation (+) indicates less than 20% production of GlcNAcMan$_3$GlcNA$_2$. The notation (++) indicates about 20-30% production of GlcNAcMan$_3$GlcNA$_2$. The notation with (+++) indicates about 30-40% production of GlcNAcMan$_3$GlcNA$_2$. The notation with (++++) indicates about 40-50% production of GlcNAcMan$_3$GlcNA$_2$. The notation with (+++++) indicates greater than 50% production of GlcNAcMan$_3$GlcNA$_2$. The notation (NG) indicates that no apparent glycans detected from any colonies transformed with the fusion construct.

TABLE 11

| | Catalytic Domains | | | | |
|---|---|---|---|---|---|
| Leaders | D. melanogaster mannosidase 1I Δ48 | D. melanogaster mannosidase 1I Δ99 | human mannosidase 1I Δ48 | D. melanogaster mannosidase 1I Δ74 | C. elegans mannosidase 1I Δ108 |
| Gls1-s | ++ | − | + | +++++ | +++++ |
| Gls1-m | + | − | − | − | ++ |
| Gls1-l | − | − | − | ++ | ++ |
| Mns1-s | ++ | − | − | ++++ | ++++ |
| Mns1-m | ++ | − | − | ++++ | ++++ |
| Mns1-l | − | − | − | ++ | + |
| S.Sec-s | ++ | − | − | ++++ | ++++ |
| S.Sec-m | ++ | − | + | ++++ | ++++ |
| S.Sec-l | + | − | + | ++++ | ++++ |
| P.Sec-s | ++ | − | + | ++++ | ++++ |
| P.Sec-m | − | − | + | ++++ | ++ |
| P.Och-s | − | − | − | ++ | ++ |
| P.Och-m | − | − | − | +++ | +++ |
| P.Och-l | − | − | − | ++ | ++ |
| Mnn9-s | ++ | − | − | ++++ | +++ |
| Mnn9-m | − | − | − | − | − |
| Mnn9-l | − | − | − | ++ | ++ |
| Van1-s | + | − | − | +++++ | +++++ |
| Van1-m | − | − | − | +++++ | +++++ |
| Van1-l | − | − | − | +++++ | ++++ |
| Anp1-s | − | − | − | +++++ | ++++ |
| Anp1-m | − | − | − | +++++ | ++ |
| Anp1-l | − | − | − | ++++ | +++ |
| Hoc1-s | − | − | − | ++++ | +++ |
| Hoc1-m | − | − | − | ++++ | +++++ |
| Hoc1-l | + | − | − | +++++ | ++ |
| Mnn10-s | − | − | − | + | +++++ |
| Mnn10-m | − | − | − | ++++ | +++++ |
| Mnn10-l | − | − | − | +++ | +++++ |
| Mnn11-s | + | − | − | +++++ | +++++ |
| Mnn11-m | + | − | + | − | +++++ |
| Mnn11-l | − | − | − | ++ | ++ |
| Mnt1-s | + | − | − | +++ | +++++ |
| Mnt1-m | + | + | − | ++++ | +++++ |
| Mnt1-l | + | + | − | +++ | +++++ |
| D2-s | − | − | − | ++ | +++++ |
| D2-m | + | − | − | +++ | +++++ |
| D2-l | − | − | − | + | ++ |
| D9-s | − | − | − | +++ | +++ |
| D9-m | − | − | − | + | +++++ |
| D9-l | − | − | − | + | ++ |

TABLE 11-continued

| | Catalytic Domains | | | | |
|---|---|---|---|---|---|
| Leaders | D. melanogaster mannosidase 1I Δ48 | D. melanogaster mannosidase 1I Δ99 | human mannosidase 1I Δ48 | D. melanogaster mannosidase 1I Δ74 | C. elegans mannosidase 1I Δ108 |
| J3-s | + | − | + | − | ++ |
| J3-m | − | − | − | +++++ | ++++ |
| J3-l | − | − | − | + | + |
| Ktr1-s | + | − | − | +++++ | +++ |
| Ktr1-l | − | − | − | + | ++ |
| Ktr2-s | + | − | − | +++++ | +++++ |
| Ktr2-m | + | − | − | ++ | +++ |
| Ktr2-l | + | − | − | + | ++ |
| Gnt1-s | + | + | − | ++++ | ++++ |
| Gnt1-m | − | − | + | +++++ | +++++ |
| Gnt1-l | − | + | − | ++++ | ++ |
| Mnn2-s | + | + | + | ++++ | ++++ |
| Mnn2-m | + | + | − | ++++ | ++++ |
| Mnn2-l | + | + | − | ++++ | ++++ |
| Mnn5-s | − | + | − | +++ | ++++ |
| Mnn5-m | − | + | − | +++++ | +++++ |
| Mnn5-l | − | + | − | ++ | +++ |
| Yur1-s | − | − | − | ++ | +++ |
| Yur1-m | − | − | − | + | +++ |
| Yur1-l | − | − | − | − | ++++ |
| Mnn1-s | − | + | + | +++++ | +++++ |
| Mnn1-m | + | − | + | +++++ | +++++ |
| Mnn1-l | + | − | + | +++++ | +++ |
| Mnn6-s | − | − | + | ++++ | +++ |
| Mnn6-m | + | − | + | +++++ | ++++ |
| Mnn6-l | − | − | − | ++ | +++ |

Example 15

Generation of GnTII Expression Constructs

The construction of a GnTI expression vector (pNA15) containing a human GnTI gene fused with the N-terminal part of S. cerevisiae MNN9 gene was described previously (Choi et al. Proc Natl Acad Sci USA. 2003 Apr. 29; 100(9):5022-7). In a similar fashion, the rat GnTII gene was cloned. The rat GnTII gene (GenBank accession number U21662) was PCR amplified using Takara EX Taq™ polymerase (Panvera) from rat liver cDNA library (Clontech) with RAT1 (5'-TTCCT-CACTGCAGTCTTCTATAACT-3', SEQ ID NO: 116) and RAT2 (5'-TGGAGACCATGAGGTTCCGCATCTAC-3', SEQ ID NO: 117) primers. The PCR product was then cloned into pCR2.1-TOPO vector (Invitrogen) and sequenced. Using this vector as a template, the AscI-PacI fragment of GnTII, encoding amino-acids 88-443, was amplified with Pfu Turbo polymerase (Stratagene) and primers, RAT44 and RAT11 (5'-TTGGCGCGCCTCCCT AGTGTACCAGT-TGAACTTTG-3' (SEQ ID NO: 118) and 5'-GATTAATTAACTCACTGCAGTCTTCTATAACT-3' (SEQ ID NO: 119) respectively, introduced AscI and PacI restriction sites are underlined). Following confirmation by sequencing, the catalytic domain of rat GnTII was than cloned downstream of the PMA1 promoter as a AscI-PacI fragment in pBP124. In the final step, the gene fragment encoding the S. cerevisiae Mnn2 localization signal was cloned from pJN281 as a NotI-AscI fragment to generate an in-frame fusion with the catalytic domain of GnTII, to generate plasmid pTC53.

Example 16

Reporter Protein Expression, Purification and Release of N-Linked Glycans

The K3 domain, under the control of the alcohol oxidase 1 (AOX1) promoter, was used as a model glycoprotein and was purified using the hexa-histidine tag as reported in Choi et al. Proc Natl Acad Sci USA. 2003 Apr. 29; 100(9):5022-7). The glycans were released and separated from the glycoproteins by a modification of a previously reported method (Papac et al. A. J. S. (1998) Glycobiology 8, 445-454). After the proteins were reduced and carboxymethylated, and the membranes blocked, the wells were washed three times with water. The protein was deglycosylated by the addition of 30 μl of 10 mM $NH_4HCO_3$ pH 8.3 containing one milliunit of N-glycanase (Glyko). After incubation for 16 hr at 37° C., the solution containing the glycans was removed by centrifugation and evaporated to dryness.

Protein Purification

Kringle 3 was purified using a 96-well format on a Beckman BioMek 2000 sample-handling robot (Beckman/Coulter Ranch Cucamonga, Calif.). Kringle 3 was purified from expression media using a C-terminal hexa-histidine tag. The robotic purification was an adaptation of the protocol provided by Novagen for their HisBind resin. Briefly, a 150 uL (μL) settled volume of resin was poured into the wells of a 96-well lysate-binding plate, washed with 3 volumes of water and charged with 5 volumes of 50 mM NiSO4 and washed with 3 volumes of binding buffer (5 mM imidazole, 0.5M NaCl, 20 mM Tris-HCL pH7.9). The protein expression media was diluted 3:2, media/PBS (60 mM PO4, 16 mM KCl, 822 mM NaCl pH7.4) and loaded onto the columns. After draining, the columns were washed with 10 volumes of binding buffer and 6 volumes of wash buffer (30 mM imidazole, 0.5M NaCl, 20 mM Tris-HCl pH7.9) and the protein was eluted with 6 volumes of elution buffer (1M imidazole, 0.5M NaCl, 20 mM Tris-HCl pH7.9). The eluted glycoproteins were evaporated to dryness by lyophilyzation.

Release of N-Linked Glycans

The glycans were released and separated from the glycoproteins by a modification of a previously reported method (Papac, et al. A. J. S. (1998) Glycobiology 8, 445-454). The wells of a 96-well MultiScreen IP (Immobilon-P membrane) plate (Millipore) were wetted with 100 uL of methanol, washed with 3×150 uL of water and 50 uL of RCM buffer (8M urea, 360 mM Tris, 3.2 mM EDTA pH8.6), draining with gentle vacuum after each addition. The dried protein samples were dissolved in 30 uL of RCM buffer and transferred to the wells containing 10 uL of RCM buffer. The wells were drained and washed twice with RCM buffer. The proteins were reduced by addition of 60 uL of 0.1M DTT in RCM buffer for 1hr at 37° C. The wells were washed three times with 300 uL of water and carboxymethylated by addition of 60 uL of 0.1M iodoacetic acid for 30 min in the dark at room temperature. The wells were again washed three times with water and the membranes blocked by the addition of 100 uL of 1% PVP 360 in water for 1 hr at room temperature. The wells were drained and washed three times with 300 uL of water and deglycosylated by the addition of 30 uL of 10 mM $NH_4HCO_3$ pH 8.3 containing one milliunit of N-glycanase (Glyko). After 16 hours at 37° C., the solution containing the glycans was removed by centrifugation and evaporated to dryness.

MALDI/Time-Of-Flight (TOF) Mass Spectrometry.

Molecular weights of the glycans were determined using a Voyager DE PRO linear MALDI-TOF (Applied Biosciences) mass spectrometer using delayed extraction. The dried glycans from each well were dissolved in 15 µl of water and 0.5 µl was spotted on stainless steel sample plates and mixed with 0.5 µl of S-DHB matrix (9 mg/ml of dihydroxybenzoic acid, 1 mg/ml of 5-methoxysalicilic acid in 1:1 water/acetonitrile 0.1% TFA) and allowed to dry. Ions were generated by irradiation with a pulsed nitrogen laser (337 nm) with a 4 ns pulse time. The instrument was operated in the delayed extraction mode with a 125 ns delay and an accelerating voltage of 20 kV. The grid voltage was 93.00%, guide wire voltage was 0.1%, the internal pressure was less than $5×10^{-7}$ torr, and the low mass gate was 875 Da. Spectra were generated from the sum of 100-200 laser pulses and acquired with a 500 MHz digitizer. $Man_5GlcNAc_2$ oligosaccharide was used as an external molecular weight standard. All spectra were generated with the instrument in the positive ion mode.

Miscellaneous:

Proteins were separated by SDS/PAGE according to Laemmli (Laemmli 1970).

Example 17

Generation of Yeast Strain YSH-1

Δoch1, α1,2-Mannosidase, GnTI

The previously reported *P. pastoris* strain BK64 (Choi et al. *Proc Natl Acad Sci USA*. 2003 Apr. 29; 100(9):5022-7), a triple auxotroph (ADE, ARG, HIS) possessing the OCH1 knock-out and expressing the kringle 3 domain (K3) of human plasminogen, was used as the host strain. BK64 was transformed with the plasmid pPB103 linearized with the restriction enzyme EcoNI to introduce the *K. lactis* UDP-N-acetylglucosamine transporter into the host cell, thus creating the strain PBP-1. The mouse MnsI was introduced into this strain by transformation with the plasmid pFB8 linearized with the restriction enzyme EcoNI, generating strain PBP-2. K3 glycan analysis from proteins isolated from strain PBP-2 demonstrated that the primary glycoform present was $Man_5GlcNAc_2$.

Figure 13:
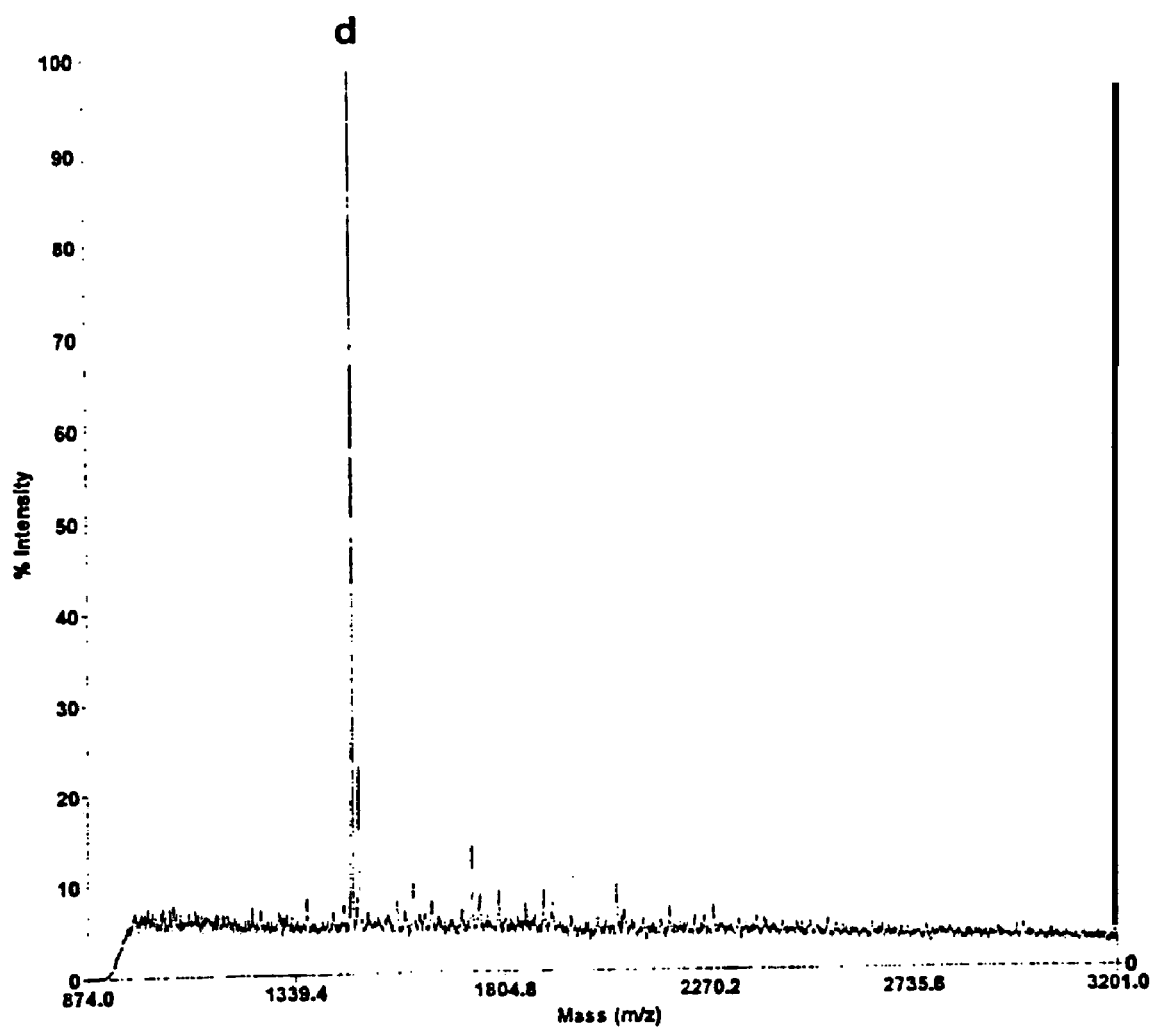
FIG. 13 shows a MALDI-TOF-MS analysis of N-glycans isolated from a kringle 3 glycoprotein produced in a *P. pastoris* YSH-1 (och1 deletion mutant transformed with α-mannosidase and GnT I) showing a predominant peak at 1465 m/z corresponding to the mass of $GlcNAcMan_5GlcNAc_2$ [d].

PBP-2 was subsequently transformed with the human GnTI plasmid pNA15 linearized with the restriction enzyme AatII, generating the strain PBP-3. Analysis of the K3 glycoforms produced in strain PBP-3 demonstrated that the hybrid glycan $GlcNAcMan_5GlcNAc_2$ was the predominant structure. To recover the URA3 marker from PBP-3, this strain was grown in YPD prior to selection on minimal media containing 5-Fluoroorotic (5-FOA, BioVectra) and uracil (Boeke et al., *Mol. Gen. Genet.* 197:345-346 (1984)). The recovered Ura-minus strain producing $GlcNAcMan_5GlcNAc_2$ glycoforms was designated YSH-1. The N-glycan profile from strain YSH-1 is shown in FIG. 13 and displays a predominant peak at 1465 m/z corresponding to the mass of $GlcNAcMan_5GlcNAc_2$ [d].

Example 18

Generation of Yeast Strain YSH-37

*P. pastoris* Expressing Mannosidase II

Figure 14:
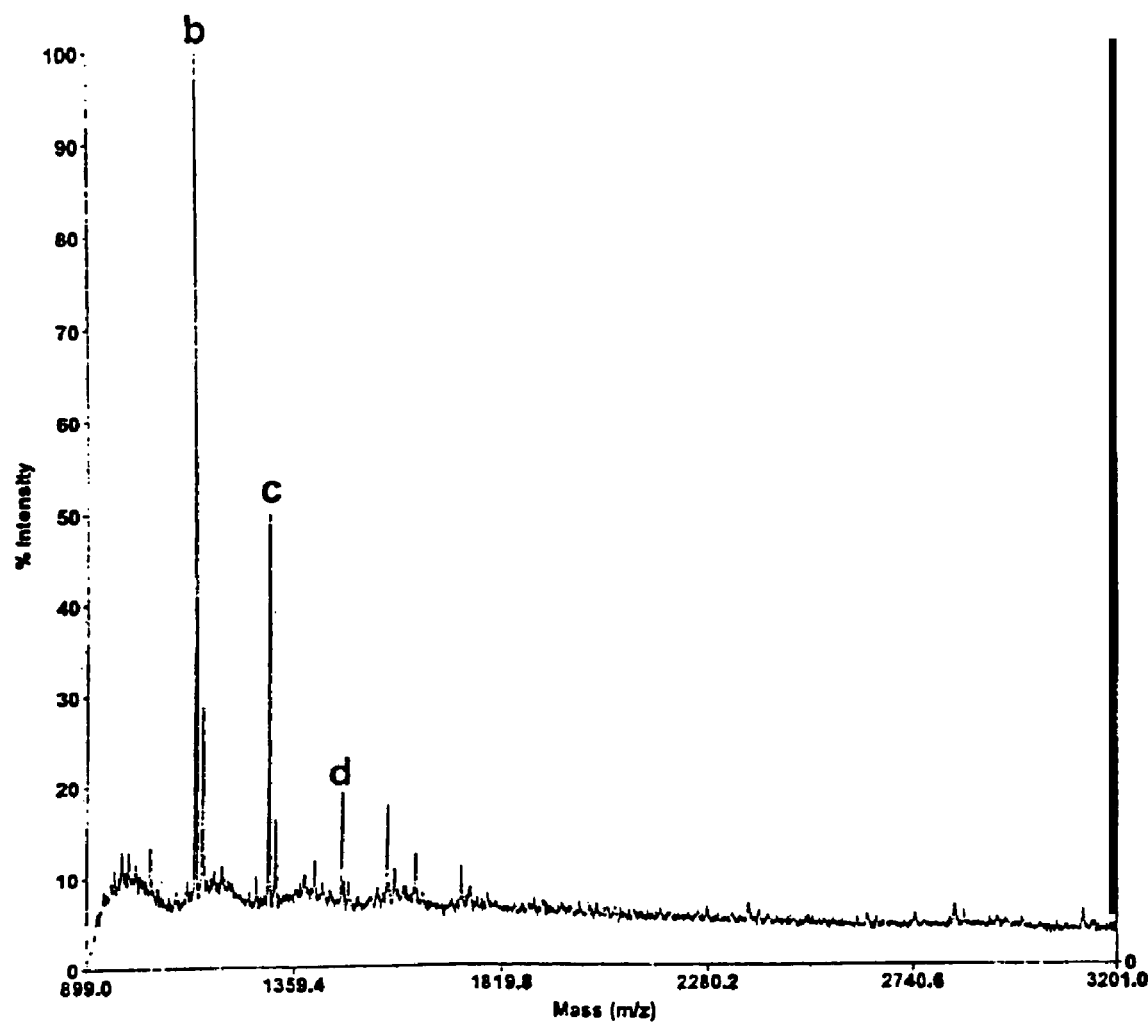
FIG. 14 shows a MALDI-TOF-MS analysis of N-glycans isolated from a kringle 3 glycoprotein produced in a *P. pastoris* YSH-1 transformed with *D. melanogaster* mannosidase II Δ74/*S. cerevisiae* MNN2(s) showing a predominant peak at 1140 m/z corresponding to the mass of $GlcNAcMan_3GlcNAc_2$ [b] and other peaks corresponding to $GlcNAcMan_4GlcNAc_2$ [c] at 1303 m/z and $GlcNAcMan_5GlcNAc_2$ [d] at 1465 m/z. This strain was designated YSH-37.

YSH-1 (Example 17) was transformed with the *D. melanogasier* mannosidase IIΔ74/*S. cerevisiae* MNN2(s) plasmid (pKD53) linearized with the restriction enzyme ApaI, generating strain YSH-37. Analysis of the K3 glycan structures produced in strain YSH-37 (FIG. 14) demonstrated that the predominant glycoform at 1140 m/z corresponds to the mass of $GlcNAcMan_3GlcNAc_2$ [b] and other glycoforms $GlcNAcMan_4GlcNAc_2$ [c] at 1303 m/z and $GlcNAcMan_5GlcNAc_2$ [d] at 1465 m/z.

Example 19

Generation of Yeast Strain YSH-44

Figure 15:
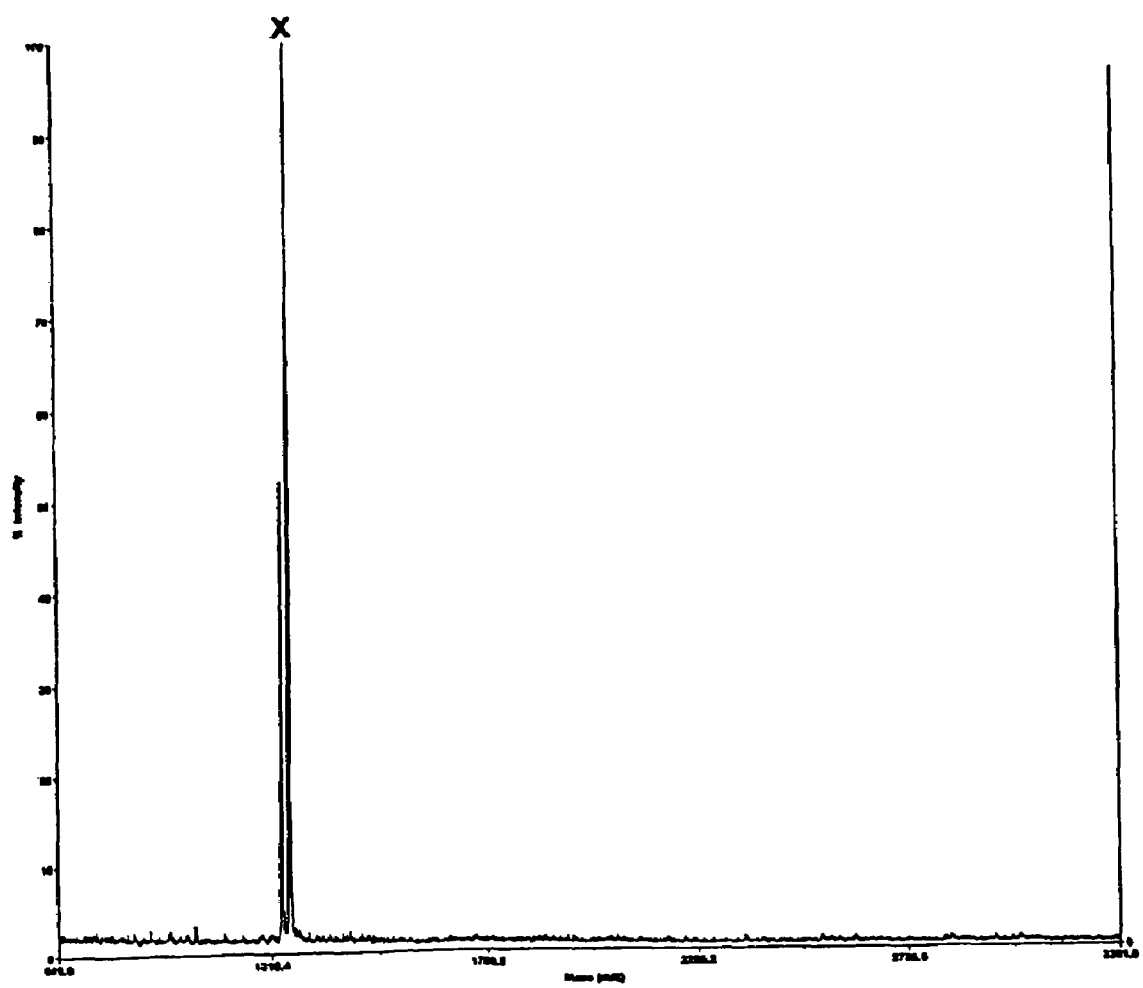
FIG. 15 shows a MALDI-TOF-MS analysis of N-glycans isolated from a kringle 3 glycoprotein produced in a *P. pastoris* YSH-37 transformed with rat GnT II/MNN2 (s) leader showing a predominant peak at 1356 m/z corresponding to the mass of $GlcNAc_2Man_3GlcNAc_2$ [x]. This strain was designated YSH-44.

Strain YSH-37 (Example 18) was transformed with a plasmid encoding a rat GnT II/MNN2 (s) leader, pTC53, linearized with the restriction enzyme EcoRI. The resulting strain, YSH-44, produced a K3 N-glycan having a single glycoform at 1356 m/z, corresponding to the mass of $GlcNAc_2Man_3GlcNAc_2$ [x], by positive mode MALDI-TOF mass spectrometry (FIG. 15).

β-N-Acetylhexosaminidase Digestion

Figure 16:
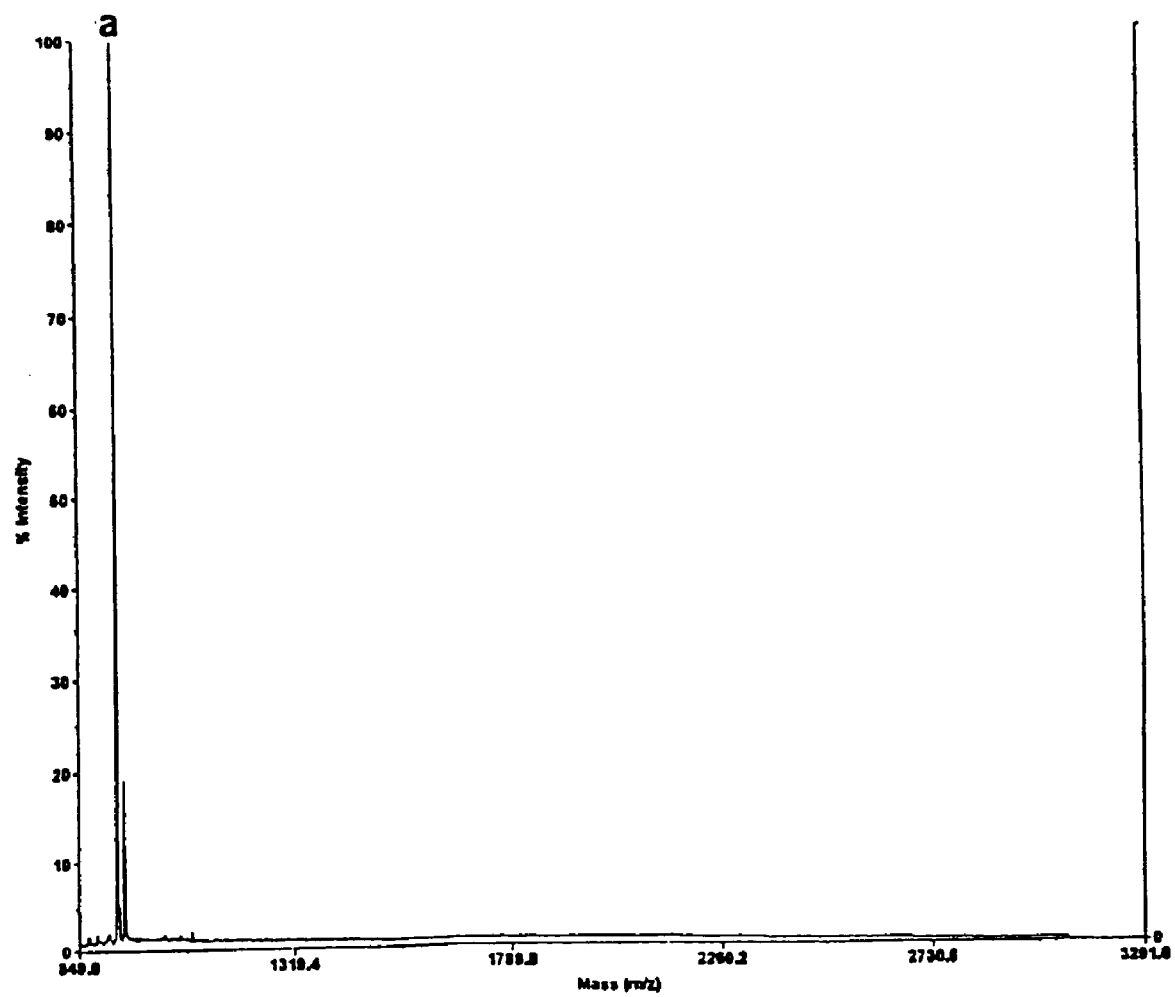
FIG. 16 shows a MALDI-TOF-MS analysis of N-glycans isolated from a kringle 3 glycoprotein produced in a *P. pastoris* YSH-44 ($GlcNAc_2Man_3GlcNAc_2$ [b] produced as shown in FIG. 15) showing a predominant peak at 933 m/z corresponding to the mass of $Man_3GlcNAc_2$ [a] after β-N-acetylhexosaminidase digest.

The glycans from YSH-44 were released and separated from the glycoproteins by a modification of a previously reported method (Papac, et al. A. J. S. (1998) *Glycobiology* 8, 445-454). After the proteins were reduced and carboxymethylated and the membranes blocked, the wells were washed three time with water. The protein was deglycosylated by the addition of 30 µl of 10 mM $NH_4HCO_3$ pH 8.3 containing one milliunit of N-glycanase (Glyko, Novato, Calif.). After a 16 hr digestion at 37° C., the solution containing the glycans was removed by centrifugation and evaporated to dryness. The glycans were then dried in aSC210A speed vac (Thermo Savant, Halbrook, N.Y.). The dried glycans were put in 50 mM $NH_4Ac$ pH 5.0 at 37° C. overnight and 1 mU of hexos (Glyko, Novato, Calif.) was added. The glycans were analyzed and shown to contain a single glycan shown in FIG. 16 at 933 m/z corresponding to the mass of Man$_3$GlcNAc$_2$ [a].

Example 20

Generation of a Yeast Strain with No Apparent Mannosidase II Activity

YSH-1 was transformed with a plasmid encoding a *D. melanogaster* mannosidase IIΔ74/*S. cerevisiae* MNN9(m), plasmid pKD16, linearized with the restriction enzyme EcoRI. The resulting strain produced a single glycoform at 1464 m/z corresponding to the mass of Man$_5$GlcNAc$_2$ [d] by positive mode MALDI-TOF mass spectrometry (FIG. 18). This strain thus expressed no apparent mannosidase II activity from the *D. melanogaster* mannosidase IIΔ74/*S. cerevisiae* MNS1(1) fusion contruct, at least with respect to glycosylation of the K3 reporter glycoprotein.

Example 21

Generation of a Yeast Strain Having Mannosidase II Activity

YSH-1 was transformed with a plasmid encoding a *D. melanogaster* mannosidase IIΔ74/*S. cerevisiae* MNS1(1), plasmid (pKD6), linearized with the restriction enzyme EcoRI. The N-glycan profile of K3 glycoprotein expressed in the resulting strain (FIG. 19) exhibited a predominant peak at 1464 m/z corresponding to the mass of Man$_5$GlcNAc$_2$ [d] and other peaks corresponding to GlcNAcMan$_3$GlcNAc$_2$ [b] at 1139 m/z and GlcNAcMan$_4$GlcNAc$_2$ [c] at 1302 m/z. The resulting yeast strain thus expressed some detectable mannosidase II activity from the *D. melanogaster* mannosidase IIΔ74/*S. cerevisiae* MNS1(1) fusion contruct.

Example 22

Generation of Yeast Strain YSH-27 Having Mannosidase II Activity

YSH-1 was transformed with *D. melanogaster* mannosidase IIΔ74/*S. cerevisiae* GLS1(s) plasmid (pKD1), linearized with the restriction enzyme EcoRI. The N-glycan profile of K3 glycoprotein expressed in the resulting strain, YSH-27, exhibited a predominant peak at 1139 m/z corresponding to the mass of GlcNAcMan$_3$GlcNAc$_2$ [b] (FIG. 20). The resulting strain YSH-27 thus expressed significant levels of mannosidase II activity from the *D. melanogaster* mannosidase IIΔ74/*S. cerevisiae* GLS1(s) fusion contruct.

Example 23

Generation of Yeast Strain YSH-74

Low Mannosidase II Activity

YSH-1 was transformed with *D. melanogaster* mannosidase IIΔ74/*S. cerevisiae* MNS1(m) plasmid (pKD5), linearized with the restriction enzyme EcoRI. The N-glycan profile of K3 glycoprotein expressed in the resulting strain, YSH-74, exhibited a predominant peak at 1140 m/z corresponding to the mass of GlcNAcMan$_3$GlcNAc$_2$ [b] and other peaks corresponding to GlcNAcMan$_4$GlcNAc$_2$ [c] at 1302 m/z and GlcNAcMan$_5$GlcNAc$_2$ [d] at 1464 m/z (FIG. 21). The resulting strain YSH-74 expressed mediocre levels of mannosidase II activity from the *D. melanogaster* mannosidase IIΔ74/*S. cerevisiae* MNS1(m) fusion contruct, at least with respect to glycosylation of the K3 reporter glycoprotein. The glycans from YSH-74 were analyzed further by digestion with *A. saitoi* α-1,2 mannosidase (Glyko, Novato, Calif.), which resulted in glycans exhibiting a predominant peak at 1141 m/z corresponding to the mass of GlcNAcMan$_3$GlcNAc$_2$ [b] (FIG. 22).

Example 24

Mannosidase Assays

Fluorescently-labeled Man$_8$GlcNAc$_2$ (0.5 µg) was added to 20 µL of supernatant and incubated for 30 hours at room temperature. After incubation, the sample was analyzed by HPLC with an Econosil NH$_2$ 4.6×250 mm, 5 micron bead, amino-bound silica column (Altech, Avondale, Pa.). The flow rate was 1.0 ml/min for 40 min and the column was maintained to 30° C. After eluting isocratically (68% A:32% B) for 3 min, a linear solvent gradient (68% A:32% B to 40% A:60% B) was employed over 27 min to elute the glycans (Turco, S. J. (1981) *Anal. Biochem.* 118, 278-283). Solvent A (acetonitrile) and solvent B was an aqueous solution of ammonium formate, 50 mM, pH 4.5. The column was equilibrated with solvent (68% A:32% B) for 20 min between runs.

Example 25

In Vitro Galactose Transfer

Figure 17:
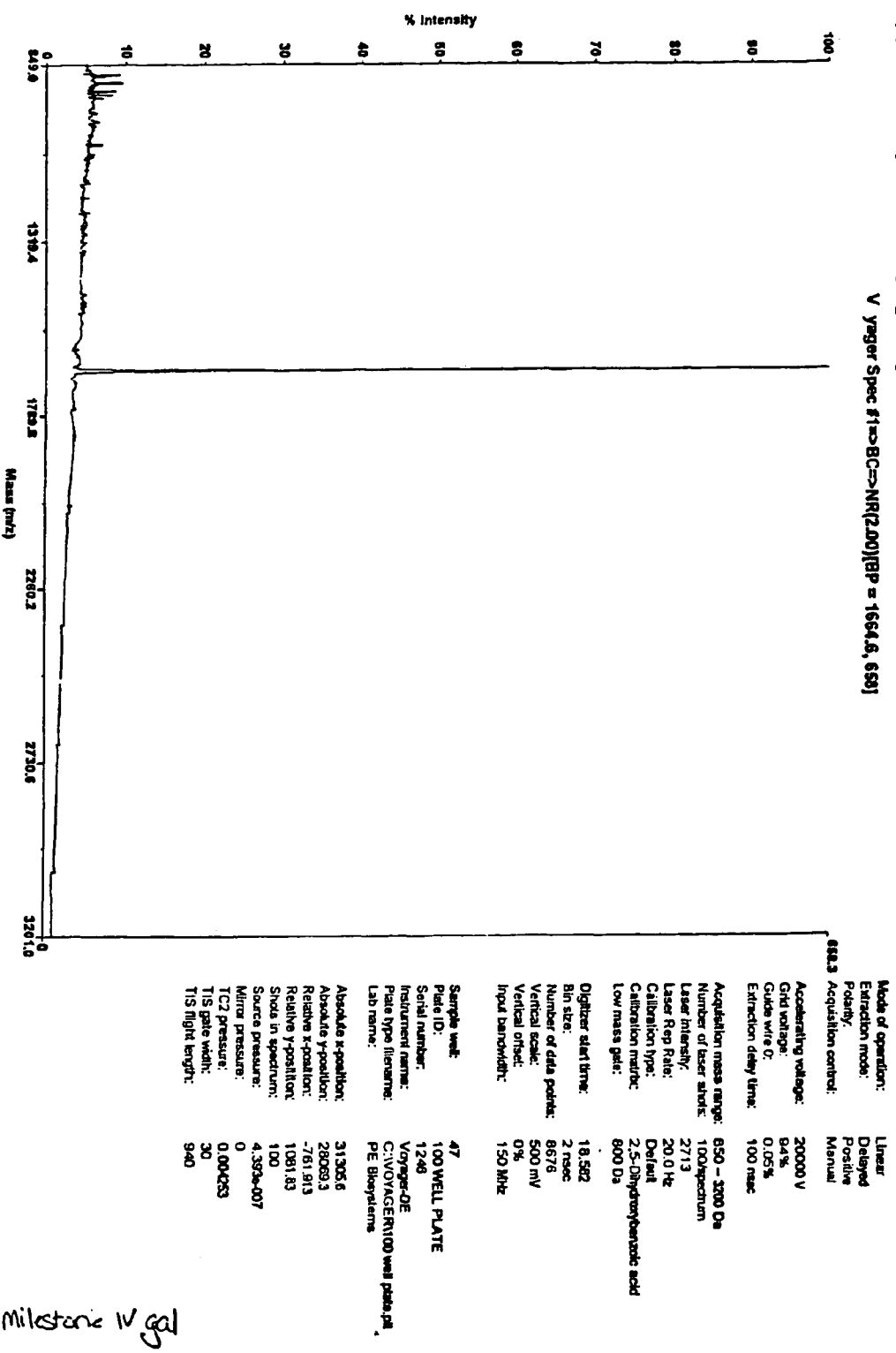
FIG. 17 shows a MALDI-TOF-MS analysis of N-glycans isolated from a kringle 3 glycoprotein produced in a *P. pas-* toris YSH-44 (GlcNAc$_2$Man$_3$GlcNAc$_2$ [b] produced as shown in FIG. 15) showing a predominant peak at 1665 m/z corresponding to the mass of Gal$_2$GlcNAc$_2$Man$_3$GlcNAc$_2$ after addition of β1,4-galactosyltransferase in vitro.

N-linked glycan GlcNAc$_2$Man$_3$GlcNAc$_2$ obtained from strain YSH-44 was used as the substrate for galactose transfer. Twenty mg of this glycan were incubated with 75 mg UDP-Gal and 10 to 50 mU β-1,4-galactosyltranferase (Bovine milk, Calbiochem) in 50 mM NH$_4$HCO$_3$, 1 mM MnCl$_2$, pH7.5 at 37° C. for 16-20 hr. FIG. 17 shows a positive mode MALDI-TOF mass spectrometry displaying a uniform peak at 1665 m/z corresponding to the mass of Gal$_2$GlcNAc$_2$Man$_3$GlcNAc$_2$. The negative control, minus galactosyltransferase, was carried out as described above and showed no transfer of galactose to the substrate GlcNAc$_2$Man$_3$GlcNAc$_2$.

Example 26

Introduction of a Class III Mannosidase into Lower Eukaryotes

A cDNA encoding a class III mannosidase (Jarvis et al. *Glycobiology* 1997 7:113-127) from insect Sf9 cells was amplified using primers specific for the 5' and 3' termini. Subsequently, the cDNA was subcloned into a yeast integration plasmid to investigate the effect of this protein on the N-glycosylation pattern of a secreted reporter protein. A number of truncated products of were produced to generate a library of class III mannosidase constructs with different targeting leader fragments, as described, e.g., in Example 14. In addition to being expressed alone in a desired host strain, resulting fusion proteins are expressed in combination with other glycosylation modifying enzymes to enhance the production of a desired N-glycan structure.

Although the Sf9 mannosidase is the only cloned member of this class III to date, genes and ESTs that show significant homology to this ORF, and in particular the catalytic domain (residues 273 to 2241 of the ORF). A library of class III mannosidases that possess a range of temperature and pH optima is generated. In turn, this will enable the selection of one or more class III mannosidase fusion constructs that perform optimally in modifying the glycosylation pattern of a selected reporter protein to produce a desired N-glycan structure when expressed in a desired host strain such as yeast and filamentous fungi.

Sequence Listings

SEQ ID NO: 1

*M. musculus* α-1,2-mannosidase IA nucleic acid sequence

SEQ ID NO: 2

*M. musculus* α-1,2-mannosidase IA encoded polypeptide sequence

SEQ ID NO: 3 primer for *K. lactis* OCH1 gene: ccagaagaat tcaattytgy cartgg

SEQ ID NO: 4 primer for *K. lactis* OCH1 gene: cagtgaaaat acctggnccn gtcca

SEQ ID NO: 5

Class 2 mannosidase conserved amino acid sequence:

Leu Lys Val Phe Val Val Pro His Ser His Asn Asp Pro Gly Trp Ile Gln Thr Phe Glu Glu Tyr Tyr

SEQ ID NO: 6

Class 2 mannosidase conserved amino acid sequence:

Glu Phe Val Thr Gly Gly Trp Val Met Pro Asp Glu Ala Asn Ser Trp Arg Asn Val Leu Leu Gln Leu Thr Glu Gly Gln Thr Trp Leu Lys Gln Phe Met Asn Val Thr Pro Thr Ala Ser Trp Ala Ile Asp Pro Phe Gly His Ser Pro Thr Met Pro Tyr Ile Leu

SEQ ID NO: 7

Class 2 mannosidase conserved amino acid sequence:

His Met Met Pro Phe Tyr Ser Tyr Asp Ile Pro His Thr Cys Gly Pro Asp Pro Arg Ile Cys Cys Gln Phe Asp Phe Arg Arg Met Pro Gly Gly Arg

SEQ ID NO: 8

Class 2 mannosidase conserved amino acid sequence:

Leu Leu Leu Asp Gln Tyr Arg Lys Lys Ser Glu Leu Phe Arg Thr Asn Val Leu Leu Ile Pro Leu Gly Asp Asp Phe Arg Tyr

SEQ ID NO: 9

Class 2 mannosidase conserved amino acid sequence:

Gln Phe Gly Thr Leu Ser Asp Tyr Phe Asp Ala Leu

SEQ ID NO: 10

Class 2 mannosidase conserved amino acid sequence:

Leu Ser Gly Asp Phe Phe Thr Tyr Ala Asp Arg Ser Asp His

SEQ ID NO: 11

Class 2 mannosidase conserved amino acid sequence:

Tyr Trp Ser Gly Tyr Tyr Thr Ser Arg Pro Phe Tyr Arg Arg Met Asp Arg Val Leu Glu

SEQ ID NO: 12

Class 2 mannosidase conserved amino acid sequence:

Ala Arg Arg Glu Leu Gly Leu Phe Gln His His Asp Ala Ile Thr Gly Thr Ala Arg Asp His Val Val Val Asp Tyr Gly

SEQ ID NO: 13

Class 2 mannosidase conserved amino acid sequence:

Gly Ala Tyr Leu Phe Leu Pro Asp Gly Glu Ala

SEQ ID NO: 14

Class 2 mannosidase conserved amino acid sequence:

Phe Tyr Thr Asp Leu Asn Gly Phe Gln Met Gln Lys Arg Arg

SEQ ID NO: 15

Class 2 mannosidase conserved amino acid sequence:

Lys Leu Pro Leu Gln Ala Asn Tyr Tyr Pro Met Pro Ser Met Ala Tyr Ile Gln Asp Ala Asn Thr Arg Leu Thr Leu Leu Thr Gly Gln Pro Leu Gly Val Ser Ser Leu Ala Ser Gly Gln Leu Glu Val Met Leu Asp Arg Arg Leu Met Ser Asp Asp Asn Arg Gly Leo Gly Gln Gly Val Leu Asp Asn Lys

SEQ ID NO: 16 primer for *K. lactis* MNN1 gene: tgccatcttt taggtccagg cccgttc

SEQ ID NO: 17 primer for *K. lactis* MNN1 gene: gatcccacga cgcatcgtat ttctttc

SEQ ID NO: 18

Primer: ATGGCGAAGGCAGATGGCAGT

SEQ ID NO: 19

Primer: TTAGTCCTTCCAACTTCCTTC

SEQ ID NO: 20

Primer: ACTGCCATCTGCCTTCGCCAT

SEQ ID NO: 21

Primer: GTAATACGACTCACTATAGGGC

SEQ ID NO: 22

Primer: AATTAACCCTCACTAAAGGG

SEQ ID NO: 23

Primer: ATGCCCGTGGGGGGCCTGTTGCCGCTCTTCAGTAGC

SEQ ID NO: 24

Primer: TCATTTCTCTTTGCCATCAATTTCCTTCTTCTGTTCACGG

SEQ ID NO: 25

Primer: GGCGCGCCGACTCCTCCAAGCTGCTCAGCGGGGTCCTGTTCCAC

SEQ ID NO: 26

Primer: CCTTAATTAATCATTTCTCTTTGCCATCAATTTCCTTCTTCTGTTCACGG

SEQ ID NO: 27

Primer: GGCGAGCTCGGCCTACCCGGCCAAGGCTGAGATCATTTGTCCAGCTTCAGA

SEQ ID NO: 28

Primer: GCCCACGTCGACGGATCCGTTTAAACATCGATTGGAGAGGCTGACACCGCTACTA

SEQ ID NO: 29

Primer: CGGGATCCACTAGTATTTAAATCATATGTGCGAGTGTACAACTCTTCCCACATGG

SEQ ID NO: 30

Primer: GGACGCGTCGACGGCCTACCCGGCCGTACGAGGAATTTCTCGGATGACTCTTTTC

SEQ ID NO: 31

Primer: CGGGATCCCTCGAGAGATCTTTTTTGTAGAAATGTCTTGGTGCCT

SEQ ID NO: 32

Primer: GGACATGCATGCACTAGTGCGGCCGCCACGTGATAGTTGTTCAATTGATTGAAATAGGGACAA

SEQ ID NO: 33

Primer: CCTTGCTAGCTTAATTAACCGCGGCACGTCCGACGGCGGCCCACGGGTCCCA

SEQ ID NO: 34

Primer: GGACATGCATGCGGATCCCTTAAGAGCCGGCAGCTTGCAAATTAAAGCCTTCGAGCGTCCC

SEQ ID NO: 35

Primer: GAACCACGTCGACGGCCATTGCGGCCAAAACCTTTTTTCCTATTCAAACACAAGGCATTGC

SEQ ID NO: 36

Primer: CTCCAATACTAGTCGAAGATTATCTTCTACGGTGCCTGGACTC

SEQ ID NO: 37

Primer: TGGAAGGTTTAAACAAAGCTAGAGTAAAATAGATATAGCGAGATTAGAGAATG

SEQ ID NO: 38

Primer: AAGAATTCGGCTGGAAGGCCTTGTACCTTGATGTAGTTCCCGTTTTCATC

SEQ ID NO: 39

Primer: GCCCAA GCCGGCCTTAAGGGATCTCCTGATGACTGACTCACTGATAATAAAAATACGG

SEQ ID NO: 40

Primer: GGGCGCGTATTTAAATACTAGTGGATCTATCGAATCTAAATGTAAGTTAAAATCTCTAA

SEQ ID NO: 41

Primer: GGCCGCCTGCAGATTTAAATGAATTCGGCGCGCCTTAAT

SEQ ID NO: 42

Primer: TAAGGCGCGCCGAATTCATTTAAATCTGCAGGGC

SEQ ID NO: 43

Primer: TGGCAGGCGCGCCTCAGTCAGCGCTCTCG

SEQ ID NO: 44

Primer: AGGTTAATTA AGTGCTAATTCCAGCTAGG

SEQ ID NO: 45

Primer: CCAGAAGAATTCAATTYTGYCARTGG

SEQ ID NO: 46

Primer: CAGTGAAAATACCTGGNCCNGTCCA

SEQ ID NO: 47

Primer: TGCCATCTTTTAGGTCCAGGCCCGTTC

SEQ ID NO: 48

Primer: GATCCCACGACGCATCGTATTTCTTTC

SEQ ID NO: 49

*Arabidopsis thaliana* Mannosidase II (NM_121499)

SEQ ID NO: 50

*C. elegans* Mannosidase II (NM_073 594)

SEQ ID NO: 51

*Ciona intestinalis* mannosidase II (AK116684)

SEQ ID NO: 52

*Drosophila* mannosidase II (X77652)

SEQ ID NO: 53

Human mannosidase II (U31520)

SEQ ID NO: 54

Mouse mannosidase II (X61172)

SEQ ID NO: 55

Rat mannosidase II (XM_218816)

SEQ ID NO: 56

Human mannosidase IIx (D55649)

SEQ ID NO: 57

Insect cell mannosidase III (AF005034)

SEQ ID NO: 58

Human lysosomal mannosidase II (NM_000528)

SEQ ID NO: 59

Human cytoplasmic mannosidase II (NM_006715)

SEQ ID NO: 60 sense primer

5'-GGCGCGCCCTCACTCTCTTCCACTTCGGCGTACCAGGAC-3'

Arabidopsis MannII d69 AscI

SEQ ID NO: 61 antisense primer

5'-CCTTAATTAATCACTTGTGAGGTCGCAGTTCAAGCTTATAAGCTC-3'

Arabidopsis MannII PacI

SEQ ID NO: 62 sense primer

5'-GGGCGCGCCGCGCTCACCAAACGACAAG-CAAATGATTTACGG-3'

*C. elegans* MannII d31 AscI

SEQ ID NO: 63 sense primer

5'-GGCCGCGCCGCTCATATTCATCAAG-TAAAGCAACATATCAAGCC-3'

*C. elegans* MannII d108 AscI

SEQ ID NO: 64 antisense primer

5'-CTTAATTAATTAAAATGATACAA-GAATACTGGAAATATCGTTTGG-3'

*C. elegans* MannII PacI

SEQ ID NO: 65 sense primer

5'-GGCGCGCCACCCTTCAAGACAAACT-TAGTCTGGTGG-3'

*C. intestinalis* MannII d47 AscI

SEQ ID NO: 66 sense primer

5'-GGCGCGCCCTACCACTTATAATGC-CCAAGCAATTTGCG

*C. intestinalis* MannII d100 AscI

SEQ ID NO: 67 antisense primer

5'-CCTTAATTAATTACGTCAGTAC-TATTTTGTAAGCTTGTATCTC-3'

*C. intestinalis* ManII PacI

SEQ ID NO: 68 sense primer

5'-GGCGCGCCCATGAGCTGGAAAATG-GTTTGCAGGAGCACG-3'

*D. melanogaster* MannII d48 AscI

SEQ ID NO: 69 sense primer

5'-GGCGCGCCCGCGACGATCCAATAAGACCTCCAC-3'

*D. melanogaster* MannII d74 AscI

SEQ ID NO: 70 sense primer

5'-GGCGCGCCGACGTGCCCAATGTGGATG-TACAGATGCTG-3'

*D. melanogaster* MannII d99 AscI

SEQ ID NO: 71 antisense primer

5'-CCTTAATTAATCAGCTTGAGTGACTGCT-CACATAAGCGGCGG-3'

*D. melanogaster* MannII PacI

SEQ ID NO: 72 sense primer

5'-GGCGCGCCATAGACCATTTG-GAGCGTTTGCTAGCTGAG-3' human Mann2a d53 AscI

SEQ ID NO: 73 sense primer

5'-GGCGCGCCGCTTCACAAAGTGGAAGTCA-CAATTCAGATGTGC-3' human Man2 d118 AscI

SEQ ID NO: 74 antisense primer

5'-CCCTTAATTAATCACCTCAACTGGAT-TCGGAATGTGCTGATTTC-3' human Mann2A PacI

SEQ ID NO: 75 sense primer

5'-GGCGCGCCGACCATTTG-GAGCGTTTGCTCGCTGAGAAC-3' mouse Man2 d54 AscI

SEQ ID NO: 76 sense primer

5'-GGCGCGCCCTGCAGGCTGACCCCAGAGACTGT-3' mouse Man2 d107 AscI

SEQ ID NO: 77 antisense primer

5'-CCCTTAATTAATCAGGTCCAACG-CAAGCGGATACGGAACGTGCTGATCTC-3' mouse Man2 PacI

SEQ ID NO: 78 sense primer

5'-GGCGCGCCGGTGGGAACTTCCCCAG-GAGCCAAATTTCTG-3' rat MannII AscI d38

SEQ ID NO: 79 sense primer

5'-GGCGCGCCGCGGAGGGCCCACCAGCCCT-GCTGCCCTACCAC-3' rat MannII AscI d81

SEQ ID NO: 80 antisense primer

5'-CCTTAATTAACTAACCCAAGCGCAGGCG-GAAGGTGCTG-3' rat MannII PadI

SEQ ID NO: 81 sense primer

5'-GGCGCGCCCAACACGATCCCACCCGA-CACCAGAATG-3' human MannIIx d29 AscI

SEQ ID NO: 82 sense primer

5'-GGCGCGCCGTGCTGGAGCTGACAGC-CAACGCAGAGGG-3' human MannIIx d74 AscI

SEQ ID NO: 83 sense primer

5'-GGCGCGCCGGTCAGAAGCCAGAGCTGCA-GATGCTCACTG-3' human MannIIx d123 AscI

SEQ ID NO: 84 antisense primer

5'-CCTTAATTAACTAACCCAAGCGGAGGC-GAAAGGTAGCAATC-3' human MannIIx PacI

SEQ ID NO: 85 sense primer

5'-GGCGCGCCCAGAACTATAACAAACCAA-GAATCAGTTACCCAGCC-3'

SfMannIII d36 AscI

SEQ ID NO: 86 antisense primer

5'-CCTTAATTAATTAAAACCTGATCTTG-TAAGTTTTTACCTCCATAGCG-3'

SfMannIII PacI

SEQ ID NO: 87 sense primer

5'-GGCGCGCCATGGGCTACGCGCGGGCT-TCGGGGGTCTGCG-3' human lysosomal MannII AscI

SEQ ID NO: 88 sense primer

5'-GGCGCGCCCCGCCTCTCTGCTTTTTC-CTTTTGTTGCTG-3' human lysosomal MannII d31 AscI

SEQ ID NO:89 antisense primer

5'-CCTTAATTAACTAACCATCCACCTCCT-TCCATTGAACTGAG-3' human lysosomal MannII PacI

SEQ ID NO: 90 sense primer

5'-GGCGCGCCATGGCGGCAGCGCCGTTCT-TGAAGCACTGGCGC-3' human cytosolic MannII AscI

SEQ ID NO: 91 antisense primer

5'-CCTTAATTAATTAGGCTGGGGAAGCA-GAAATTAGGAGTCC-3' human cytosolic MannII PacI

---

What is claimed is:

1. A method for producing a recombinant glycoprotein in a uni- or multicellular fungal host cell which includes an α-1,2-mannosidase activity and a GlcNAc transferase I (GnT I) activity and is diminished or depleted in the activity of an initiating α-1,6-mannosyltransferase, the method comprising the step of expressing in the host cell a nucleic acid encoding a chimeric mannosidase enzyme comprising (a) a *D. melanogaster* mannosidase II catalytic domain fused to a cellular targeting signal peptide selected from the group consisting of Gls1-s, Mns1-s, Mns1-m, S.Sec-s, S.Sec-m, S.Sec-l, P.Sec-s, P.Sec-m, Mnn9-s, Van1-s, Van1-m, Van1-l, Anp1-s, Anp1-m, Anp1-l, Hoc1-s, Hoc1-m, Hoc1-l, Mnn10-m, Mnn11-s, Mnt1-m, J3-m, Ktr1-s, Ktr2-l, Gnt1-s, Gnt1-m, Gnt1-l, Mnn2-s, Mnn2-m, Mnn2-l, Mnn5-m, Mnn1-s, Mnn1-m, Mnn1-l, Mnn6-s, and Mnn6-m or (b) a *C. elegans* mannosidase II catalytic domain fused to a cellular targeting signal peptide selected from the group consisting of Gls1-s, Mns1-s, Mns1-m, S.Sec-s, S.Sec-m, S.Sec-l, P.Sec-s, Van1-s, Van1-m, Van1-l, Anp1-s, Hoc1-l, Mnn10-s, Mnn10-m, Mnn10-l, Mnn11-s, Mnn11-m, Mnt1-s, Mnt1-m, Mnt1-l, D2-s, D2-m, D9-m, J3-m, Ktr2-s, Gnt1-s, Gnt1-m, Mnn2-s, Mnn2-m, Mnn2-l, Mnn5-s, Mnn5-m, Mnn1-s, Mnn1-m, and Mnn6-m, wherein said chimeric mannosidase in (a) or (b) is capable of hydrolyzing in vivo more than 40-50 percent of the Man α-1,3 and/or Man α-1,6 linkages of a GlcNAcMan$_5$GlcNAc$_2$ oligosaccharide substrate, whereby expression of said chimeric mannosidase produces one or more N-glycan structures on a recombinant glycoprotein expressed in said host cell wherein the N-glycan is characterized as having at least the oligosaccharide branch Manα1,3 (Manα1,6) Manβ1,4-GlcNAc β1,4-GlcNAc-Asn.

2. A method for producing a recombinant glycoprotein in a uni- or multicellular fungal host cell which includes an α-1,2-mannosidase and a GlcNAc transferase I (GnT I) and is diminished or depleted in the activity of an initiating α-1,6-mannosyltransferase, the method comprising the step of expressing in the host cell a nucleic acid encoding a chimeric mannosidase enzyme comprising (a) a *D. melanogaster* mannosidase II catalytic domain fused to a cellular targeting signal peptide selected from the group consisting of Gls1-s, Mns1-s, Mns1-m, S.Sec-s, S.Sec-m, S.Sec-l, P.Sec-s, P.Sec-m, Mnn9-s, Van1-s, Van1-m, Van1-l, Anp1-s, Anp1-m, Anp1-l, Hoc1-s, Hoc1-m, Hoc1-l, Mnn10-m, Mnn11-s, Mnt1-m, J3-m, Ktr1-s, Ktr2-s, Gnt1-s, Gnt1-l, Mnn2-s, Mnn2-m, Mnn2-l, Mnn5-m, Mnn1-s, Mnn1-m, Mnn1-l, Mnn6-s, and Mnn6-m or (b) a *C. elegans* mannosidase II catalytic domain fused to a cellular targeting signal peptide selected from the group consisting of Gls1-s, Mns1-s, Mns1-m, S.Sec-s, S.Sec-m, S.Sec-l, P.Sec-s, Van1-s, Van1-m, Van1-l, Anp1-s, Hoc1-m, Mnn10-s, Mnn10-m, Mnn10-l, Mnn11-s, Mnn11-m, Mnt1-s, Mnt1-m, Mnt1-l, D2-s, D2-m, D9-m, J3-m, Ktr2-s, Gnt1-s, Gnt1-m, Mnn2-s, Mnn2-m, Mnn2-l, Mnn5-m, Mnn1-s, Mnn1-m, and Mnn6-m, wherein said chimeric mannosidase in (a) and (b) is capable of hydrolyzing in vivo more than 40-50 percent of the Man α-1,3 and/or Man α-1,6 linkages of a GlcNAcMan$_5$GlcNAc$_2$ oligosaccharide substrate, whereby expression of said chimeric mannosidase produces one or more N-glycan structures on a recombinant glycoprotein expressed in said host cell, wherein the N-glycan is produced within the host cell at a yield of at least 10 mole percent and wherein the N-glycan is characterized as having at least the oligosaccharide branch Manα1,3 (Manα1,6) Manβ1,4-GlcNAc β1,4-GlcNAc-Asn.

3. The method of claim 1 or 2, wherein the oligosaccharide substrate is characterized as Manα1,3 (Manα1,6 Manα1,6) Manβ1,4-GlcNAc β1,4-GlcNAc-Asn; Manα1,3 (Manα1,3 Manα1,6) Manβ1,4-GlcNAc β1,4-GlcNAc-Asn; GlcNAcβ1,2 Manα1,3 (Manα1,6 Manα1,6) Manβ1,4-GlcNAc β1,4-GlcNAc-Asn; GlcNAcβ1,2 Manα1,3 (Manα1,3 Manα1,6) Manβ1,4-GlcNAc β1,4-GlcNAc-Asn; Manα1,3 (Manα1,3 Manα1,6 Manα1,6) Manβ1,4-GlcNAc β1,4-GlcNAc-Asn; GlcNAcβ1,2 Manα1,3 (Manα1,3 Manα1,6 Manα1,6) Manβ1,4-GlcNAc β1,4-GlcNAc-Asn; Manα1,2 Manα1,3 (Manα1,3 Manα1,6 Manα1,6) Manβ1,4-GlcNAc β1,4-GlcNAc-Asn; Manα1,2 Manα1,3 (Manα1,3 Manα1,6) Manβ1,4-GlcNAc β1,4-GlcNAc-Asn; Manα1,2 Manα1,3 (Manα1,6 Manα1,6) Manβ1,4-GlcNAc β1,4-GlcNAc-Asn or high mannan.

4. The method of claim 1 or 2, wherein the chimeric mannosidase comprises a Class IIx mannosidase catalytic domain fused to a cellular targeting signal peptide that targets the chimeric mannosidase to the secretory pathway of the host cell.

5. The method of claim 4, wherein the Class IIx mannosidase enzyme has a substrate specificity for Manα1,3 (Manα1,6 Manα1,6) Manβ1,4-GlcNAc β1,4-GlcNAc-Asn; Manα1,3 (Manα1,3 Manα1,6) Manβ1,4-GLcNAc β1,4-GlcNAc-Asn; or Manα1,2 Manα1,3 (Manα1,3 Manα1,6 Manα1,6) Manβ1,4-GlcNAc β1,4-GlcNAc-Asn.

6. The method of claim 1 or 2, wherein the chimeric mannosidase enzyme comprises a Class III mannosidase catalytic domain fused to a cellular targeting signal peptide that targets the chimeric mannosidase to the secretory pathway of the host cell.

7. The method of claim 6, wherein the Class III mannosidase enzyme has a substrate specificity for Manα1,3 (Manα1,6 Manα1,6) Manβ1,4-GlcNAc β1,4-GlcNAc-Asn; Manα1,3 (Manα1,3 Manα1,6) Manβ1,4-GlcNAc β1,4-GlcNAc-Asn; Manα1,3 (Manα1,3 Manα1,6 Manα1,6) Manβ1,4-GlcNAc β1,4-GlcNAc-Asn; or high mannans.

8. The method of claim 1 or 2, wherein the chimeric mannosidase enzyme is overexpressed.

9. The method of claim 1 or 2, wherein the chimeric mannosidase enzyme is further capable of hydrolyzing a Manα1,2 linkage.

10. The method of claim 1 or 2, wherein the chimeric mannosidase enzyme has a pH optimum of from about 5.0 to about 8.0.

11. The method of claim 1 or 2, wherein the chimeric mannosidase enzyme is localized within the secretory pathway of the host cell.

12. The method of claim 1 or 2, wherein the chimeric mannosidase enzyme is localized within at least one of the ER, Golgi apparatus or the trans Golgi network of the host cell.

13. The method of claim 1 or 2, further comprising the step of isolating the glycoprotein from the host cell.

14. The method of claim 1 or 2, wherein the host cell is selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum* and *Neurospora crassa.*

15. The method of claim 14, wherein the host cell is *Pichia pastoris*.

16. The method of claim 1 or 2, wherein the glycoprotein is a therapeutic protein.

17. The method of claim 16, wherein the therapeutic protein is selected from the group consisting of erythropoietin, cytokines, coagulation factors, soluble IgE receptor α-chain, IgG, IgG fragments, IgM, interleukins, urokinase, chymase, urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin and α-feto protein.

18. The method of claim 1, wherein the N-glycan comprises an oligosaccharide structure selected from the group consisting of $Man_3GlcNAc_2$, $GlcNAcMan_3GlcNAc_2$, and $Man_4GlcNAc_2$.

19. The method of claim 2, wherein the N-glycan comprises an oligosaccharide structure selected from the group consisting of $Man_3GlcNAc_2$, $GlcNAcMan_3GlcNAc_2$, and $Man_4GlcNAc_2$.

20. A method for producing a recombinant glycoprotein in a yeast host cell comprising:
(a) expressing a nucleic acid encoding the recombinant glycoprotein in a yeast host cell that is diminished or depleted in the activity of an initiating α-1,6-mannosyltransferase and expresses an α-1,2-mannosidase activity, a GlcNAc transferase I (GnT I) activity, and a chimeric mannosidase enzyme comprising
(i) a *D. melanogaster* mannosidase II catalytic domain fused to a cellular targeting signal peptide selected from the group consisting of Gls1-s, Mns1-s, Mns1-m, S.Sec-s, S.Sec-m, S.Sec-l, P.Sec-s, P.Sec-m, Mnn9-s, Van1-s, Van1-m, Van1-l, Anp1-s, Anp1-m, Anp1-l, Hoc1-s, Hoc1-m, Hoc1-l, Mnn10-m, Mnn11-s, Mnt1-m, J3-m, Ktr1-s, Ktr2-s, Gnt1-s, Gnt1-m, Gnt1-l, Mnn2-s, Mnn2-m, Mnn2-l, Mnn5-m, Mnn1-s, Mnn1-m, Mnn1-l, Mnn6-s, and Mnn6-m or
(ii) a *C. elegans* mannosidase II catalytic domain fused to a cellular targeting signal peptide selected from the group consisting of Gls1-s, Mns1-s, Mns1-m, S.Sec-s, S.Sec-m, S.Sec-l, P.Sec-s, Van1-s, Van1-m, Van1-l, Anp1-s, Hoc1-m, Mnn10-s, Mnn10-m, Mnn10-l, Mnn11-s, Mnn11-m, Mnt1-s, Mnt1-m, Mnt1-l, D2-s, D2-m, D9-m, J3-m, Ktr2-s, Gnt1-s, Gnt1-m, Mnn2-s, Mnn2-m, Mnn2-l, Mnn5-s, Mnn5-m, Mnn1-s, Mnn1-m, and Mnn6-m wherein said chimeric mannosidase in (a) or (b) is capable of hydrolyzing in vivo more than 40-50 percent of the Man α-1,3 and/or Man α-1,6 linkages of a $GlcNAcMan_5GlcNAc_2$ oligosaccharide substrate and wherein the recombinant glycoprotein expressed in said host cell comprises N-glycans characterized as having at least the oligosaccharide branch Manα1,3 (Manα1,6) Manβ1,4-GlcNAc β1,4-GlcNAc-Asn; and
(b) isolating the recombinant glycoprotein.

21. The method of claim 20, wherein the chimeric mannosidase comprises a Class IIx mannosidase catalytic domain fused to a cellular targeting signal peptide that targets the chimeric mannosidase to the secretory pathway of the host cell.

22. The method of claim 21, wherein the Class IIx mannosidase enzyme has a substrate specificity for Manα1,3 (Manα1,6 Manα1,6) Manβ1,4-GlcNAc β1,4-GlcNAc-Asn; Manα1,3 (Manα1,3 Manα1,6) Man β1,4-GlcNAc β1,4-GlcNAc-Asn; or Manα1,2 Manα1,3 (Manα1,3 Manα1,6 Manα1,6) Man β1,4-GlcNAc β1,4-GlcNAc-Asn.

23. The method of claim 20, wherein the chimeric mannosidase enzyme comprises a Class III mannosidase catalytic domain fused to a cellular targeting signal peptide that targets the chimeric mannosidase to the secretory pathway of the host cell.

24. The method of claim 23, wherein the Class III mannosidase enzyme has a substrate specificity for Manα1,3 (Manα1,6 Manα1,6) Manβ1,4-GlcNAc β1,4-GlcNAc-Asn; Manα1,3 (Manα1,3 Manα1,6) Man β1,4-GlcNAc β1,4-GlcNAc-Asn; or Manα1,3 (Manα1,3 Manα1,6 Manα1,6) Manβ1,4-GlcNAc β1,4-GlcNAc-Asn; or high mannans.

25. The method of claim 20, wherein the yeast host cell is selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis,* and *Candida albicans.*

26. The method of claim 25, wherein the yeast host cell is *Pichia pastoris*.

27. The method of claim 20, wherein the recombinant glycoprotein is a therapeutic protein.

28. The method of claim 27, wherein the therapeutic protein is selected from the group consisting of erythropoietin, cytokines, coagulation factors, soluble IgB receptor α-chain, IgG, IgG fragments, IgM, interleukins, urokinase, chymase, urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin and α-feto protein.

* * * * *

UNITED STATES PATENT AND TRADEMARK OFFICE
CERTIFICATE OF CORRECTION

PATENT NO. : 7,625,756 B2 Page 1 of 1
APPLICATION NO. : 10/616082
DATED : December 1, 2009
INVENTOR(S) : Stephen Hamilton It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 519 days.

Signed and Sealed this

Twenty-first Day of December, 2010

David J. Kappos
*Director of the United States Patent and Trademark Office*

SEQUENCE LISTING

```
<160> NUMBER OF SEQ ID NOS: 119

<210> SEQ ID NO 1
<211> LENGTH: 1968
<212> TYPE: DNA
<213> ORGANISM: Mus musculus
<220> FEATURE:
<221> NAME/KEY: CDS
<222> LOCATION: (1)..(1965)

<400> SEQUENCE: 1 atg ccc gtg ggg ggc ctg ttg ccg ctc ttc agt agc cct ggg ggc ggc      48
Met Pro Val Gly Gly Leu Leu Pro Leu Phe Ser Ser Pro Gly Gly Gly
  1               5                  10                  15 ggc ctg ggc agt ggc ctg ggc ggg ggg ctt ggc ggc ggg agg aag ggg      96
Gly Leu Gly Ser Gly Leu Gly Gly Gly Leu Gly Gly Gly Arg Lys Gly
             20                  25                  30 tct ggc ccc gct gcc ttc cgc ctc acc gag aag ttc gtg ctg ctg ctg     144
Ser Gly Pro Ala Ala Phe Arg Leu Thr Glu Lys Phe Val Leu Leu Leu
         35                  40                  45
```

-continued

| | | |
|---|---|---|
| gtg ttc agc gcc ttc atc acg ctc tgc ttc ggg gca atc ttc ttc ctg<br>Val Phe Ser Ala Phe Ile Thr Leu Cys Phe Gly Ala Ile Phe Phe Leu<br>50                                 55                         60 | | 192 |
| cct gac tcc tcc aag ctg ctc agc ggg gtc ctg ttc cac tcc aac cct<br>Pro Asp Ser Ser Lys Leu Leu Ser Gly Val Leu Phe His Ser Asn Pro<br>65                                 70                         75                       80 | | 240 |
| gcc ttg cag ccg ccg gcg gag cac aag ccc ggg ctc ggg gcg cgt gcg<br>Ala Leu Gln Pro Pro Ala Glu His Lys Pro Gly Leu Gly Ala Arg Ala<br>                      85                         90                       95 | | 288 |
| gag gat gcc gcc gag ggg aga gtc cgg cac cgc gag gaa ggc gcg cct<br>Glu Asp Ala Ala Glu Gly Arg Val Arg His Arg Glu Glu Gly Ala Pro<br>                 100                         105                       110 | | 336 |
| ggg gac cct gga gct gga ctg gaa gac aac tta gcc agg atc cgc gaa<br>Gly Asp Pro Gly Ala Gly Leu Glu Asp Asn Leu Ala Arg Ile Arg Glu<br>         115                        120                       125 | | 384 |
| aac cac gag cgg gct ctc agg gaa gcc aag gag acc ctg cag aag ctg<br>Asn His Glu Arg Ala Leu Arg Glu Ala Lys Glu Thr Leu Gln Lys Leu<br>130                               135                       140 | | 432 |
| ccg gag gag atc caa aga gac att ctg ctg gag aag gaa aag gtg gcc<br>Pro Glu Glu Ile Gln Arg Asp Ile Leu Leu Glu Lys Glu Lys Val Ala<br>145                           150                       155                    160 | | 480 |
| cag gac cag ctg cgt gac aag gat ctg ttt agg ggc ttg ccc aag gtg<br>Gln Asp Gln Leu Arg Asp Lys Asp Leu Phe Arg Gly Leu Pro Lys Val<br>                         165                       170                   175 | | 528 |
| gac ttc ctg ccc ccc gtc ggg gta gag aac cgg gag ccc gct gac gcc<br>Asp Phe Leu Pro Pro Val Gly Val Glu Asn Arg Glu Pro Ala Asp Ala<br>                 180                         185                       190 | | 576 |
| acc atc cgt gag aag agg gca aag atc aaa gag atg atg acc cat gct<br>Thr Ile Arg Glu Lys Arg Ala Lys Ile Lys Glu Met Met Thr His Ala<br>                     195                         200                       205 | | 624 |
| tgg aat aat tat aaa cgc tat gcg tgg ggc ttg aac gaa ctg aaa cct<br>Trp Asn Asn Tyr Lys Arg Tyr Ala Trp Gly Leu Asn Glu Leu Lys Pro<br>         210                        215                       220 | | 672 |
| ata tca aaa gaa ggc cat tca agc agt ttg ttt ggc aac atc aaa gga<br>Ile Ser Lys Glu Gly His Ser Ser Ser Leu Phe Gly Asn Ile Lys Gly<br>225                               230                       235                    240 | | 720 |
| gct aca ata gta gat gcc ctg gat acc ctt ttc att atg ggc atg aag<br>Ala Thr Ile Val Asp Ala Leu Asp Thr Leu Phe Ile Met Gly Met Lys<br>                         245                       250                   255 | | 768 |
| act gaa ttt caa gaa gct aaa tcg tgg att aaa aaa tat tta gat ttt<br>Thr Glu Phe Gln Glu Ala Lys Ser Trp Ile Lys Lys Tyr Leu Asp Phe<br>                 260                         265                       270 | | 816 |
| aat gtg aat gct gaa gtt tct gtt ttt gaa gtc aac ata cgc ttc gtc<br>Asn Val Asn Ala Glu Val Ser Val Phe Glu Val Asn Ile Arg Phe Val<br>275                               280                       285 | | 864 |
| ggt gga ctg ctg tca gcc tac tat ttg tcc gga gag gag ata ttt cga<br>Gly Gly Leu Leu Ser Ala Tyr Tyr Leu Ser Gly Glu Glu Ile Phe Arg<br>         290                        295                       300 | | 912 |
| aag aaa gca gtg gaa ctt ggg gta aaa ttg cta cct gca ttt cat act<br>Lys Lys Ala Val Glu Leu Gly Val Lys Leu Leu Pro Ala Phe His Thr<br>305                             310                       315                    320 | | 960 |
| ccc tct gga ata cct tgg gca ttg ctg aat atg aaa agt ggg atc ggg<br>Pro Ser Gly Ile Pro Trp Ala Leu Leu Asn Met Lys Ser Gly Ile Gly<br>                         325                       330                   335 | | 1008 |
| cgg aac tgg ccc tgg gcc tct gga ggc agc agt atc ctg gcc gaa ttt<br>Arg Asn Trp Pro Trp Ala Ser Gly Gly Ser Ser Ile Leu Ala Glu Phe<br>                 340                         345                       350 | | 1056 |
| gga act ctg cat tta gag ttt atg cac ttg tcc cac tta tca gga gac<br>Gly Thr Leu His Leu Glu Phe Met His Leu Ser His Leu Ser Gly Asp | | 1104 |

```
                355                 360                 365
cca gtc ttt gcc gaa aag gtt atg aaa att cga aca gtg ttg aac aaa     1152
Pro Val Phe Ala Glu Lys Val Met Lys Ile Arg Thr Val Leu Asn Lys
        370                 375                 380 ctg gac aaa cca gaa ggc ctt tat cct aac tat ctg aac ccc agt agt     1200
Leu Asp Lys Pro Glu Gly Leu Tyr Pro Asn Tyr Leu Asn Pro Ser Ser
385                 390                 395                 400 gga cag tgg ggt caa cat cat gtg tcg gtt gga gga ctt gga gac agc     1248
Gly Gln Trp Gly Gln His His Val Ser Val Gly Gly Leu Gly Asp Ser
                405                 410                 415 ttt tat gaa tat ttg ctt aag gcg tgg tta atg tct gac aag aca gat     1296
Phe Tyr Glu Tyr Leu Leu Lys Ala Trp Leu Met Ser Asp Lys Thr Asp
        420                 425                 430 ctc gaa gcc aag aag atg tat ttt gat gct gtt cag gcc atc gag act     1344
Leu Glu Ala Lys Lys Met Tyr Phe Asp Ala Val Gln Ala Ile Glu Thr
                435                 440                 445 cac ttg atc cgc aag tca agt ggg gga cta acg tac atc gca gag tgg     1392
His Leu Ile Arg Lys Ser Ser Gly Gly Leu Thr Tyr Ile Ala Glu Trp
        450                 455                 460 aag ggg ggc ctc ctg gaa cac aag atg ggc cac ctg acg tgc ttt gca     1440
Lys Gly Gly Leu Leu Glu His Lys Met Gly His Leu Thr Cys Phe Ala
465                 470                 475                 480 gga ggc atg ttt gca ctt ggg gca gat gga gct ccg gaa gcc cgg gcc     1488
Gly Gly Met Phe Ala Leu Gly Ala Asp Gly Ala Pro Glu Ala Arg Ala
                485                 490                 495 caa cac tac ctt gaa ctc gga gct gaa att gcc cgc act tgt cat gaa     1536
Gln His Tyr Leu Glu Leu Gly Ala Glu Ile Ala Arg Thr Cys His Glu
        500                 505                 510 tct tat aat cgt aca tat gtg aag ttg gga ccg gaa gcg ttt cga ttt     1584
Ser Tyr Asn Arg Thr Tyr Val Lys Leu Gly Pro Glu Ala Phe Arg Phe
                515                 520                 525 gat ggc ggt gtg gaa gct att gcc acg agg caa aat gaa aag tat tac     1632
Asp Gly Gly Val Glu Ala Ile Ala Thr Arg Gln Asn Glu Lys Tyr Tyr
        530                 535                 540 atc tta cgg ccc gag gtc atc gag aca tac atg tac atg tgg cga ctg     1680
Ile Leu Arg Pro Glu Val Ile Glu Thr Tyr Met Tyr Met Trp Arg Leu
545                 550                 555                 560 act cac gac ccc aag tac agg acc tgg gcc tgg gaa gcc gtg gag gct     1728
Thr His Asp Pro Lys Tyr Arg Thr Trp Ala Trp Glu Ala Val Glu Ala
                565                 570                 575 cta gaa agt cac tgc aga gtg aac gga ggc tac tca ggc tta cgg gat     1776
Leu Glu Ser His Cys Arg Val Asn Gly Gly Tyr Ser Gly Leu Arg Asp
        580                 585                 590 gtt tac att gcc cgt gag agt tat gac gat gtc cag caa agt ttc ttc     1824
Val Tyr Ile Ala Arg Glu Ser Tyr Asp Asp Val Gln Gln Ser Phe Phe
                595                 600                 605 ctg gca gag aca ctg aag tat ttg tac ttg ata ttt tcc gat gat gac     1872
Leu Ala Glu Thr Leu Lys Tyr Leu Tyr Leu Ile Phe Ser Asp Asp Asp
        610                 615                 620 ctt ctt cca cta gaa cac tgg atc ttc aac acc gag gct cat cct ttc     1920
Leu Leu Pro Leu Glu His Trp Ile Phe Asn Thr Glu Ala His Pro Phe
625                 630                 635                 640 cct ata ctc cgt gaa cag aag aag gaa att gat ggc aaa gag aaa tga     1968
Pro Ile Leu Arg Glu Gln Lys Lys Glu Ile Asp Gly Lys Glu Lys
                645                 650                 655

<210> SEQ ID NO 2
<211> LENGTH: 655
<212> TYPE: PRT
<213> ORGANISM: Mus musculus
```

<400> SEQUENCE: 2

```
Met Pro Val Gly Gly Leu Leu Pro Leu Phe Ser Pro Gly Gly Gly
  1               5                  10                  15
Gly Leu Gly Ser Gly Leu Gly Gly Leu Gly Gly Arg Lys Gly
             20                  25                  30
Ser Gly Pro Ala Ala Phe Arg Leu Thr Glu Lys Phe Val Leu Leu
             35                  40                  45
Val Phe Ser Ala Phe Ile Thr Leu Cys Phe Gly Ala Ile Phe Leu
 50                  55                  60
Pro Asp Ser Ser Lys Leu Leu Ser Gly Val Leu Phe His Ser Asn Pro
 65                  70                  75                  80
Ala Leu Gln Pro Pro Ala Glu His Lys Pro Gly Leu Gly Ala Arg Ala
                 85                  90                  95
Glu Asp Ala Ala Glu Gly Arg Val Arg His Arg Glu Gly Ala Pro
                100                 105                 110
Gly Asp Pro Gly Ala Gly Leu Glu Asp Asn Leu Ala Arg Ile Arg Glu
            115                 120                 125
Asn His Glu Arg Ala Leu Arg Glu Ala Lys Glu Thr Leu Gln Lys Leu
            130                 135                 140
Pro Glu Glu Ile Gln Arg Asp Ile Leu Leu Lys Glu Lys Val Ala
145                 150                 155                 160
Gln Asp Gln Leu Arg Asp Lys Asp Leu Phe Arg Gly Leu Pro Lys Val
                165                 170                 175
Asp Phe Leu Pro Pro Val Gly Val Glu Asn Arg Glu Pro Ala Asp Ala
                180                 185                 190
Thr Ile Arg Glu Lys Arg Ala Lys Ile Lys Glu Met Met Thr His Ala
            195                 200                 205
Trp Asn Asn Tyr Lys Arg Tyr Ala Trp Gly Leu Asn Glu Leu Lys Pro
210                 215                 220
Ile Ser Lys Glu Gly His Ser Ser Leu Phe Gly Asn Ile Lys Gly
225                 230                 235                 240
Ala Thr Ile Val Asp Ala Leu Asp Thr Leu Phe Ile Met Gly Met Lys
                245                 250                 255
Thr Glu Phe Gln Glu Ala Lys Ser Trp Ile Lys Lys Tyr Leu Asp Phe
                260                 265                 270
Asn Val Asn Ala Glu Val Ser Val Phe Glu Val Asn Ile Arg Phe Val
            275                 280                 285
Gly Gly Leu Leu Ser Ala Tyr Tyr Leu Ser Gly Glu Glu Ile Phe Arg
            290                 295                 300
Lys Lys Ala Val Glu Leu Gly Val Lys Leu Leu Pro Ala Phe His Thr
305                 310                 315                 320
Pro Ser Gly Ile Pro Trp Ala Leu Leu Asn Met Lys Ser Gly Ile Gly
                325                 330                 335
Arg Asn Trp Pro Trp Ala Ser Gly Gly Ser Ser Ile Leu Ala Glu Phe
                340                 345                 350
Gly Thr Leu His Leu Glu Phe Met His Leu Ser His Leu Ser Gly Asp
            355                 360                 365
Pro Val Phe Ala Glu Lys Val Met Lys Ile Arg Thr Val Leu Asn Lys
            370                 375                 380
Leu Asp Lys Pro Glu Gly Leu Tyr Pro Asn Tyr Leu Asn Pro Ser Ser
385                 390                 395                 400
Gly Gln Trp Gly Gln His His Val Ser Val Gly Gly Leu Gly Asp Ser
```

```
                    405                 410                 415
Phe Tyr Glu Tyr Leu Leu Lys Ala Trp Leu Met Ser Asp Lys Thr Asp
            420                 425                 430

Leu Glu Ala Lys Lys Met Tyr Phe Asp Ala Val Gln Ala Ile Glu Thr
        435                 440                 445

His Leu Ile Arg Lys Ser Ser Gly Gly Leu Thr Tyr Ile Ala Glu Trp
    450                 455                 460

Lys Gly Gly Leu Leu Glu His Lys Met Gly His Leu Thr Cys Phe Ala
465                 470                 475                 480

Gly Gly Met Phe Ala Leu Gly Ala Asp Gly Ala Pro Glu Ala Arg Ala
                485                 490                 495

Gln His Tyr Leu Glu Leu Gly Ala Glu Ile Ala Arg Thr Cys His Glu
            500                 505                 510

Ser Tyr Asn Arg Thr Tyr Val Lys Leu Gly Pro Glu Ala Phe Arg Phe
        515                 520                 525

Asp Gly Gly Val Glu Ala Ile Ala Thr Arg Gln Asn Glu Lys Tyr Tyr
    530                 535                 540

Ile Leu Arg Pro Glu Val Ile Glu Thr Tyr Met Tyr Met Trp Arg Leu
545                 550                 555                 560

Thr His Asp Pro Lys Tyr Arg Thr Trp Ala Trp Glu Ala Val Glu Ala
                565                 570                 575

Leu Glu Ser His Cys Arg Val Asn Gly Gly Tyr Ser Gly Leu Arg Asp
            580                 585                 590

Val Tyr Ile Ala Arg Glu Ser Tyr Asp Val Gln Gln Ser Phe Phe
        595                 600                 605

Leu Ala Glu Thr Leu Lys Tyr Leu Tyr Leu Ile Phe Ser Asp Asp Asp
    610                 615                 620

Leu Leu Pro Leu Glu His Trp Ile Phe Asn Thr Glu Ala His Pro Phe
625                 630                 635                 640

Pro Ile Leu Arg Glu Gln Lys Lys Glu Ile Asp Gly Lys Glu Lys
                645                 650                 655

<210> SEQ ID NO 3
<211> LENGTH: 26
<212> TYPE: DNA
<213> ORGANISM: Kluyveromyces lactis

<400> SEQUENCE: 3
ccagaagaat tcaattytgy cartgg                                        26

<210> SEQ ID NO 4
<211> LENGTH: 25
<212> TYPE: DNA
<213> ORGANISM: Kluyveromyces lactis
<220> FEATURE:
<221> NAME/KEY: modified_base
<222> LOCATION: (17)
<223> OTHER INFORMATION: a, c, g, t, other or unknown
<220> FEATURE:
<221> NAME/KEY: modified_base
<222> LOCATION: (20)
<223> OTHER INFORMATION: a, c, g, t, other or unknown

<400> SEQUENCE: 4
cagtgaaaat acctggnccn gtcca                                         25

<210> SEQ ID NO 5
<211> LENGTH: 23
<212> TYPE: PRT
```

```
<213> ORGANISM: Unknown Organism
<220> FEATURE:
<223> OTHER INFORMATION: Description of Unknown Organism: Class 2
      mannosidase conserved amino acid sequence

<400> SEQUENCE: 5

Leu Lys Val Phe Val Val Pro His Ser His Asn Asp Pro Gly Trp Ile
 1               5                  10                  15

Gln Thr Phe Glu Glu Tyr Tyr
            20

<210> SEQ ID NO 6
<211> LENGTH: 57
<212> TYPE: PRT
<213> ORGANISM: Unknown Organism
<220> FEATURE:
<223> OTHER INFORMATION: Description of Unknown Organism: Class 2
      mannosidase conserved amino acid sequence

<400> SEQUENCE: 6

Glu Phe Val Thr Gly Gly Trp Val Met Pro Asp Glu Ala Asn Ser Trp
 1               5                  10                  15

Arg Asn Val Leu Leu Gln Leu Thr Glu Gly Gln Thr Trp Leu Lys Gln
            20                  25                  30

Phe Met Asn Val Thr Pro Thr Ala Ser Trp Ala Ile Asp Pro Phe Gly
        35                  40                  45

His Ser Pro Thr Met Pro Tyr Ile Leu
    50                  55

<210> SEQ ID NO 7
<211> LENGTH: 33
<212> TYPE: PRT
<213> ORGANISM: Unknown Organism
<220> FEATURE:
<223> OTHER INFORMATION: Description of Unknown Organism: Class 2
      mannosidase conserved amino acid sequence

<400> SEQUENCE: 7

His Met Met Pro Phe Tyr Ser Tyr Asp Ile Pro His Thr Cys Gly Pro
 1               5                  10                  15

Asp Pro Arg Ile Cys Cys Gln Phe Asp Phe Arg Arg Met Pro Gly Gly
            20                  25                  30

Arg

<210> SEQ ID NO 8
<211> LENGTH: 28
<212> TYPE: PRT
<213> ORGANISM: Unknown Organism
<220> FEATURE:
<223> OTHER INFORMATION: Description of Unknown Organism: Class 2
      mannosidase conserved amino acid sequence

<400> SEQUENCE: 8

Leu Leu Leu Asp Gln Tyr Arg Lys Lys Ser Glu Leu Phe Arg Thr Asn
 1               5                  10                  15

Val Leu Leu Ile Pro Leu Gly Asp Asp Phe Arg Tyr
            20                  25

<210> SEQ ID NO 9
<211> LENGTH: 12
<212> TYPE: PRT
<213> ORGANISM: Unknown Organism
<220> FEATURE:
<223> OTHER INFORMATION: Description of Unknown Organism: Class 2
``` mannosidase conserved amino acid sequence

<400> SEQUENCE: 9

Gln Phe Gly Thr Leu Ser Asp Tyr Phe Asp Ala Leu
1               5                   10

<210> SEQ ID NO 10
<211> LENGTH: 14
<212> TYPE: PRT
<213> ORGANISM: Unknown Organism
<220> FEATURE:
<223> OTHER INFORMATION: Description of Unknown Organism: Class 2
      mannosidase conserved amino acid sequence

<400> SEQUENCE: 10

Leu Ser Gly Asp Phe Phe Thr Tyr Ala Asp Arg Ser Asp His
1               5                   10

<210> SEQ ID NO 11
<211> LENGTH: 20
<212> TYPE: PRT
<213> ORGANISM: Unknown Organism
<220> FEATURE:
<223> OTHER INFORMATION: Description of Unknown Organism: Class 2
      mannosidase conserved amino acid sequence

<400> SEQUENCE: 11

Tyr Trp Ser Gly Tyr Tyr Thr Ser Arg Pro Phe Tyr Arg Arg Met Asp
1               5                   10                  15

Arg Val Leu Glu
            20

<210> SEQ ID NO 12
<211> LENGTH: 27
<212> TYPE: PRT
<213> ORGANISM: Unknown Organism
<220> FEATURE:
<223> OTHER INFORMATION: Description of Unknown Organism: Class 2
      mannosidase conserved amino acid sequence

<400> SEQUENCE: 12

Ala Arg Arg Glu Leu Gly Leu Phe Gln His His Asp Ala Ile Thr Gly
1               5                   10                  15

Thr Ala Arg Asp His Val Val Val Asp Tyr Gly
            20                  25

<210> SEQ ID NO 13
<211> LENGTH: 11
<212> TYPE: PRT
<213> ORGANISM: Unknown Organism
<220> FEATURE:
<223> OTHER INFORMATION: Description of Unknown Organism: Class 2
      mannosidase conserved amino acid sequence

<400> SEQUENCE: 13

Gly Ala Tyr Leu Phe Leu Pro Asp Gly Glu Ala
1               5                   10

<210> SEQ ID NO 14
<211> LENGTH: 14
<212> TYPE: PRT
<213> ORGANISM: Unknown Organism
<220> FEATURE:
<223> OTHER INFORMATION: Description of Unknown Organism: Class 2
      mannosidase conserved amino acid sequence

<400> SEQUENCE: 14

```
Phe Tyr Thr Asp Leu Asn Gly Phe Gln Met Gln Lys Arg Arg
  1               5                  10
```

<210> SEQ ID NO 15
<211> LENGTH: 66
<212> TYPE: PRT
<213> ORGANISM: Unknown Organism
<220> FEATURE:
<223> OTHER INFORMATION: Description of Unknown Organism: Class 2
      mannosidase conserved amino acid sequence

<400> SEQUENCE: 15

```
Lys Leu Pro Leu Gln Ala Asn Tyr Tyr Pro Met Pro Ser Met Ala Tyr
  1               5                  10                  15

Ile Gln Asp Ala Asn Thr Arg Leu Thr Leu Leu Thr Gly Gln Pro Leu
             20                  25                  30

Gly Val Ser Ser Leu Ala Ser Gly Gln Leu Glu Val Met Leu Asp Arg
         35                  40                  45

Arg Leu Met Ser Asp Asp Asn Arg Gly Leu Gly Gln Gly Val Leu Asp
     50                  55                  60

Asn Lys
 65
```

<210> SEQ ID NO 16
<211> LENGTH: 27
<212> TYPE: DNA
<213> ORGANISM: Kluyveromyces lactis

<400> SEQUENCE: 16
tgccatcttt taggtccagg cccgttc                                        27

<210> SEQ ID NO 17
<211> LENGTH: 27
<212> TYPE: DNA
<213> ORGANISM: Kluyveromyces lactis

<400> SEQUENCE: 17
gatcccacga cgcatcgtat ttctttc                                        27

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atggcgaagg cagatggcag t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ttagtccttc caacttcctt c                                              21

<210> SEQ ID NO 20
<211> LENGTH: 21

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
actgccatct gccttcgcca t                                              21

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtaatacgac tcactatagg gc                                             22

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aattaaccct cactaaaggg                                                20

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atgcccgtgg ggggcctgtt gccgctcttc agtagc                              36

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcatttctct ttgccatcaa tttccttctt ctgttcacgg                          40

<210> SEQ ID NO 25
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ggcgcgccga ctcctccaag ctgctcagcg gggtcctgtt ccac                     44

<210> SEQ ID NO 26
<211> LENGTH: 50
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 26
ccttaattaa tcatttctct ttgccatcaa tttccttctt ctgttcacgg         50

<210> SEQ ID NO 27
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggcgagctcg gcctacccgg ccaaggctga gatcatttgt ccagcttcag a       51

<210> SEQ ID NO 28
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcccacgtcg acggatccgt ttaaacatcg attggagagg ctgacaccgc tacta   55

<210> SEQ ID NO 29
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgggatccac tagtatttaa atcatatgtg cgagtgtaca actcttccca catgg   55

<210> SEQ ID NO 30
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggacgcgtcg acggcctacc cggccgtacg aggaatttct cggatgactc ttttc   55

<210> SEQ ID NO 31
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cgggatccct cgagagatct tttttgtaga aatgtcttgg tgcct             45

<210> SEQ ID NO 32
<211> LENGTH: 63
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 32
ggacatgcat gcactagtgc ggccgccacg tgatagttgt tcaattgatt gaaataggga    60
caa                                                                  63

<210> SEQ ID NO 33
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ccttgctagc ttaattaacc gcggcacgtc cgacggcggc ccacgggtcc ca            52

<210> SEQ ID NO 34
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggacatgcat gcggatccct taagagccgg cagcttgcaa attaaagcct tcgagcgtcc    60
c                                                                    61

<210> SEQ ID NO 35
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gaaccacgtc gacggccatt gcggccaaaa cctttttttcc tattcaaaca caaggcattg   60
c                                                                    61

<210> SEQ ID NO 36
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ctccaatact agtcgaagat tatcttctac ggtgcctgga ctc                      43

<210> SEQ ID NO 37
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tggaaggttt aaacaaagct agagtaaaat agatatagcg agattagaga atg           53
```

<210> SEQ ID NO 38
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aagaattcgg ctggaaggcc ttgtaccttg atgtagttcc cgttttcatc          50

<210> SEQ ID NO 39
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gcccaagccg gccttaaggg atctcctgat gactgactca ctgataataa aaatacgg   58

<210> SEQ ID NO 40
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gggcgcgtat ttaaatacta gtggatctat cgaatctaaa tgtaagttaa aatctctaa   59

<210> SEQ ID NO 41
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ggccgcctgc agatttaaat gaattcggcg cgccttaat          39

<210> SEQ ID NO 42
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
taaggcgcgc cgaattcatt taaatctgca gggc          34

<210> SEQ ID NO 43
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tggcaggcgc gcctcagtca gcgctctcg          29

-continued

<210> SEQ ID NO 44
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aggttaatta agtgctaatt ccagctagg                                29

<210> SEQ ID NO 45
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccagaagaat tcaattytgy cartgg                                   26

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)
<223> OTHER INFORMATION: a, c, g, t, other or unknown
<220> FEATURE:
<221> NAME/KEY: modified_base
<222> LOCATION: (20)
<223> OTHER INFORMATION: a, c, g, t, other or unknown

<400> SEQUENCE: 46
cagtgaaaat acctggnccn gtcca                                    25

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgccatcttt taggtccagg cccgttc                                  27

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gatcccacga cgcatcgtat ttctttc                                  27

<210> SEQ ID NO 49
<211> LENGTH: 3522
<212> TYPE: DNA
<213> ORGANISM: Arabidopsis thaliana
<220> FEATURE:
<221> NAME/KEY: CDS

<222> LOCATION: (1)..(3519)

<400> SEQUENCE: 49

```
atg ccg ttc tcc tcg tat atc ggc aac agc cgc cgt agc tcc acc ggc      48
Met Pro Phe Ser Ser Tyr Ile Gly Asn Ser Arg Arg Ser Ser Thr Gly
 1               5                  10                  15 gga gga acc ggc ggt tgg ggc caa tct ctt ctt cca aca gcg tta tca      96
Gly Gly Thr Gly Gly Trp Gly Gln Ser Leu Leu Pro Thr Ala Leu Ser
            20                  25                  30 aag tca aaa cta gcg atc aat cga aaa cca cga aaa cga act ctc gta     144
Lys Ser Lys Leu Ala Ile Asn Arg Lys Pro Arg Lys Arg Thr Leu Val
        35                  40                  45 gtc aat ttc atc ttc gcc aac ttc ttc gtc atc gca ctc acc gtc tca     192
Val Asn Phe Ile Phe Ala Asn Phe Phe Val Ile Ala Leu Thr Val Ser
    50                  55                  60 ctc ctc ttc ttc ctc ctc act ctc ttc cac ttc ggc gta cca gga ccg     240
Leu Leu Phe Phe Leu Leu Thr Leu Phe His Phe Gly Val Pro Gly Pro
65                  70                  75                  80 atc tcc tca cga ttc ctt acc tcc aga tcc aat cgg atc gtc aag cca     288
Ile Ser Ser Arg Phe Leu Thr Ser Arg Ser Asn Arg Ile Val Lys Pro
                85                  90                  95 cgg aag aat att aat cgc cga ccc tta aac gat tcc aat tca ggc gcc     336
Arg Lys Asn Ile Asn Arg Arg Pro Leu Asn Asp Ser Asn Ser Gly Ala
            100                 105                 110 gtc gtt gat atc aca act aaa gat cta tac gat agg att gag ttt ctt     384
Val Val Asp Ile Thr Thr Lys Asp Leu Tyr Asp Arg Ile Glu Phe Leu
        115                 120                 125 gat aca gat ggt ggt cca tgg aaa caa ggt tgg aga gtt acg tat aaa     432
Asp Thr Asp Gly Gly Pro Trp Lys Gln Gly Trp Arg Val Thr Tyr Lys
    130                 135                 140 gac gat gag tgg gag aaa gag aag ctc aaa atc ttc gtt gtt cct cat     480
Asp Asp Glu Trp Glu Lys Glu Lys Leu Lys Ile Phe Val Val Pro His
145                 150                 155                 160 tct cat aac gat cct ggt tgg aaa ttg act gta gag gag tat tat cag     528
Ser His Asn Asp Pro Gly Trp Lys Leu Thr Val Glu Glu Tyr Tyr Gln
                165                 170                 175 aga caa tcc aga cat att ctt gac acc att gtt gag act tta tct aag     576
Arg Gln Ser Arg His Ile Leu Asp Thr Ile Val Glu Thr Leu Ser Lys
            180                 185                 190 gat tca aga aga aag ttt ata tgg gag gag atg tca tat ctg gag aga     624
Asp Ser Arg Arg Lys Phe Ile Trp Glu Glu Met Ser Tyr Leu Glu Arg
        195                 200                 205 tgg tgg aga gac gct tca cct aat aaa caa gaa gct ttg act aaa ttg     672
Trp Trp Arg Asp Ala Ser Pro Asn Lys Gln Glu Ala Leu Thr Lys Leu
    210                 215                 220 gtt aag gat ggg cag cta gag att gtt gga ggt ggc tgg gtt atg aat     720
Val Lys Asp Gly Gln Leu Glu Ile Val Gly Gly Gly Trp Val Met Asn
225                 230                 235                 240 gat gag gct aat tca cat tat ttt gcc ata att gaa cag ata gca gag     768
Asp Glu Ala Asn Ser His Tyr Phe Ala Ile Ile Glu Gln Ile Ala Glu
                245                 250                 255 ggt aat atg tgg ctg aat gac aca att ggg gtt att cct aag aat tct     816
Gly Asn Met Trp Leu Asn Asp Thr Ile Gly Val Ile Pro Lys Asn Ser
            260                 265                 270 tgg gct ata gat ccc ttt ggc tat tca tca acc atg gct tat ctt ctc     864
Trp Ala Ile Asp Pro Phe Gly Tyr Ser Ser Thr Met Ala Tyr Leu Leu
        275                 280                 285 cgg cgt atg ggt ttt gaa aac atg ctt att caa agg act cat tac gag     912
Arg Arg Met Gly Phe Glu Asn Met Leu Ile Gln Arg Thr His Tyr Glu
    290                 295                 300
```

```
ctc aag aaa gac ctt gcc cag cat aag aat ctt gaa tat att tgg cgt      960
Leu Lys Lys Asp Leu Ala Gln His Lys Asn Leu Glu Tyr Ile Trp Arg
305                 310                 315                 320 cag agc tgg gat gct atg gaa acc aca gat atc ttt gtt cat atg atg     1008
Gln Ser Trp Asp Ala Met Glu Thr Thr Asp Ile Phe Val His Met Met
                325                 330                 335 ccg ttt tat tca tac gat atc cca cac act tgt gga cca gag cct gca     1056
Pro Phe Tyr Ser Tyr Asp Ile Pro His Thr Cys Gly Pro Glu Pro Ala
            340                 345                 350 att tgc tgt cag ttt gat ttc gct cgg atg cgg gga ttt aag tat gaa     1104
Ile Cys Cys Gln Phe Asp Phe Ala Arg Met Arg Gly Phe Lys Tyr Glu
        355                 360                 365 ctt tgt cca tgg gga aag cac cca gtg gag acc aca cta gaa aat gtg     1152
Leu Cys Pro Trp Gly Lys His Pro Val Glu Thr Thr Leu Glu Asn Val
370                 375                 380 cag gag agg gca tta aag ctt ctg gat caa tac agg aaa aaa tcc act     1200
Gln Glu Arg Ala Leu Lys Leu Leu Asp Gln Tyr Arg Lys Lys Ser Thr
385                 390                 395                 400 cta tat cga act aat aca ctt ctt ata cct ctt gga gat gat ttt agg     1248
Leu Tyr Arg Thr Asn Thr Leu Leu Ile Pro Leu Gly Asp Asp Phe Arg
                405                 410                 415 tac att agt atc gat gaa gcc gag gct cag ttc cgt aac tac cag atg     1296
Tyr Ile Ser Ile Asp Glu Ala Glu Ala Gln Phe Arg Asn Tyr Gln Met
            420                 425                 430 ttg ttt gat cac atc aac tct aat cct agt cta aac gca gaa gca aag     1344
Leu Phe Asp His Ile Asn Ser Asn Pro Ser Leu Asn Ala Glu Ala Lys
        435                 440                 445 ttt ggt act ttg gag gat tat ttc aga aca gtc cga gaa gaa gca gac     1392
Phe Gly Thr Leu Glu Asp Tyr Phe Arg Thr Val Arg Glu Glu Ala Asp
450                 455                 460 aga gtg aat tat tct cgt cct ggt gag gtt ggc tct ggt cag gtt gtt     1440
Arg Val Asn Tyr Ser Arg Pro Gly Glu Val Gly Ser Gly Gln Val Val
465                 470                 475                 480 ggt ttc cct tct ctg tca ggt gac ttc ttt aca tat gca gat agg caa     1488
Gly Phe Pro Ser Leu Ser Gly Asp Phe Phe Thr Tyr Ala Asp Arg Gln
                485                 490                 495 caa gac tat tgg agt ggt tat tat gtt tca aga cct ttc ttc aaa gct     1536
Gln Asp Tyr Trp Ser Gly Tyr Tyr Val Ser Arg Pro Phe Phe Lys Ala
            500                 505                 510 gtt gat cgt gtg ctc gag cat acc ctt cgt gga gct gag atc atg atg     1584
Val Asp Arg Val Leu Glu His Thr Leu Arg Gly Ala Glu Ile Met Met
        515                 520                 525 tca ttt ctg cta ggt tat tgc cat cga att caa tgt gag aaa ttt cca     1632
Ser Phe Leu Leu Gly Tyr Cys His Arg Ile Gln Cys Glu Lys Phe Pro
530                 535                 540 aca agt ttt acg tat aag ttg act gct gca aga aga aat ctg gct ctt     1680
Thr Ser Phe Thr Tyr Lys Leu Thr Ala Ala Arg Arg Asn Leu Ala Leu
545                 550                 555                 560 ttc cag cac cat gat ggg gta act gga act gct aag gat tat gtg gta     1728
Phe Gln His His Asp Gly Val Thr Gly Thr Ala Lys Asp Tyr Val Val
                565                 570                 575 caa gat tac ggc acc cgg atg cat act tca ttg caa gac ctt cag atc     1776
Gln Asp Tyr Gly Thr Arg Met His Thr Ser Leu Gln Asp Leu Gln Ile
            580                 585                 590 ttt atg tct aaa gca atc gaa gtt ctt ctt ggg atc cgc cac gag aaa     1824
Phe Met Ser Lys Ala Ile Glu Val Leu Leu Gly Ile Arg His Glu Lys
        595                 600                 605 gaa aaa tct gat caa tcc cca tca ttt ttc gag gca gag caa atg aga     1872
Glu Lys Ser Asp Gln Ser Pro Ser Phe Phe Glu Ala Glu Gln Met Arg
```

-continued

|  |  |  |  |  |
|---|---|---|---|---|
| 610 | | 615 | | 620 |

| tca | aag | tat | gat | gct | cgg | cca | gtt | cac | aag | cca | att | gct | gcc | cgg | gaa | 1920 |
|---|---|---|---|---|---|---|---|---|---|---|---|---|---|---|---|---|
| Ser | Lys | Tyr | Asp | Ala | Arg | Pro | Val | His | Lys | Pro | Ile | Ala | Ala | Arg | Glu | |
| 625 | | | | 630 | | | | | 635 | | | | | 640 | | |

| gga | aat | tcg | cac | aca | gtt | ata | ctc | ttc | aat | cca | tca | gaa | cag | acg | aga | 1968 |
|---|---|---|---|---|---|---|---|---|---|---|---|---|---|---|---|---|
| Gly | Asn | Ser | His | Thr | Val | Ile | Leu | Phe | Asn | Pro | Ser | Glu | Gln | Thr | Arg | |
| | | | | 645 | | | | | 650 | | | | | 655 | | |

| gag | gag | gtg | gtg | acg | gtt | gtt | gtt | aac | cgc | gct | gaa | atc | tcg | gtt | ttg | 2016 |
|---|---|---|---|---|---|---|---|---|---|---|---|---|---|---|---|---|
| Glu | Glu | Val | Val | Thr | Val | Val | Val | Asn | Arg | Ala | Glu | Ile | Ser | Val | Leu | |
| | | | 660 | | | | | 665 | | | | | 670 | | | |

| gac | tca | aac | tgg | act | tgt | gtc | cct | agc | caa | att | tct | cct | gaa | gtg | cag | 2064 |
|---|---|---|---|---|---|---|---|---|---|---|---|---|---|---|---|---|
| Asp | Ser | Asn | Trp | Thr | Cys | Val | Pro | Ser | Gln | Ile | Ser | Pro | Glu | Val | Gln | |
| | | 675 | | | | | 680 | | | | | 685 | | | | |

| cat | gac | gat | acc | aaa | cta | ttc | acc | ggc | aga | cat | cgc | ctt | tac | tgg | aaa | 2112 |
|---|---|---|---|---|---|---|---|---|---|---|---|---|---|---|---|---|
| His | Asp | Asp | Thr | Lys | Leu | Phe | Thr | Gly | Arg | His | Arg | Leu | Tyr | Trp | Lys | |
| 690 | | | | | 695 | | | | | 700 | | | | | | |

| gct | tcc | atc | cca | gct | ctt | ggt | ctg | aga | aca | tat | ttc | att | gct | aat | ggg | 2160 |
|---|---|---|---|---|---|---|---|---|---|---|---|---|---|---|---|---|
| Ala | Ser | Ile | Pro | Ala | Leu | Gly | Leu | Arg | Thr | Tyr | Phe | Ile | Ala | Asn | Gly | |
| 705 | | | | 710 | | | | | 715 | | | | | 720 | | |

| aat | gtc | gag | tgt | gag | aaa | gct | act | ccg | tct | aaa | ctc | aaa | tac | gct | tct | 2208 |
|---|---|---|---|---|---|---|---|---|---|---|---|---|---|---|---|---|
| Asn | Val | Glu | Cys | Glu | Lys | Ala | Thr | Pro | Ser | Lys | Leu | Lys | Tyr | Ala | Ser | |
| | | | | 725 | | | | | 730 | | | | | 735 | | |

| gag | ttt | gac | cca | ttt | cct | tgt | cct | cct | cca | tat | tcc | tgc | tcc | aaa | ctg | 2256 |
|---|---|---|---|---|---|---|---|---|---|---|---|---|---|---|---|---|
| Glu | Phe | Asp | Pro | Phe | Pro | Cys | Pro | Pro | Pro | Tyr | Ser | Cys | Ser | Lys | Leu | |
| | | | 740 | | | | | 745 | | | | | 750 | | | |

| gac | aac | gac | gtt | act | gag | atc | cga | aat | gaa | cat | cag | act | ctt | gtg | ttt | 2304 |
|---|---|---|---|---|---|---|---|---|---|---|---|---|---|---|---|---|
| Asp | Asn | Asp | Val | Thr | Glu | Ile | Arg | Asn | Glu | His | Gln | Thr | Leu | Val | Phe | |
| | | 755 | | | | | 760 | | | | | 765 | | | | |

| gat | gtg | aag | aac | gga | tca | ctg | cgg | aag | ata | gtc | cat | aga | aac | gga | tca | 2352 |
|---|---|---|---|---|---|---|---|---|---|---|---|---|---|---|---|---|
| Asp | Val | Lys | Asn | Gly | Ser | Leu | Arg | Lys | Ile | Val | His | Arg | Asn | Gly | Ser | |
| 770 | | | | | 775 | | | | | 780 | | | | | | |

| gag | act | gtt | gtg | gga | gaa | gag | ata | ggt | atg | tac | tct | agt | cca | gag | agt | 2400 |
|---|---|---|---|---|---|---|---|---|---|---|---|---|---|---|---|---|
| Glu | Thr | Val | Val | Gly | Glu | Glu | Ile | Gly | Met | Tyr | Ser | Ser | Pro | Glu | Ser | |
| 785 | | | | 790 | | | | | 795 | | | | | 800 | | |

| gga | gct | tac | ctg | ttc | aaa | cca | gat | ggt | gaa | gct | cag | cca | att | gtt | caa | 2448 |
|---|---|---|---|---|---|---|---|---|---|---|---|---|---|---|---|---|
| Gly | Ala | Tyr | Leu | Phe | Lys | Pro | Asp | Gly | Glu | Ala | Gln | Pro | Ile | Val | Gln | |
| | | | | 805 | | | | | 810 | | | | | 815 | | |

| cct | gat | gga | cat | gta | gtc | acc | tct | gag | ggt | ctg | ctg | gtt | caa | gaa | gtc | 2496 |
|---|---|---|---|---|---|---|---|---|---|---|---|---|---|---|---|---|
| Pro | Asp | Gly | His | Val | Val | Thr | Ser | Glu | Gly | Leu | Leu | Val | Gln | Glu | Val | |
| | | | 820 | | | | | 825 | | | | | 830 | | | |

| ttc | tct | tac | cct | aaa | acc | aaa | tgg | gag | aaa | tca | ccc | ctc | tct | cag | aaa | 2544 |
|---|---|---|---|---|---|---|---|---|---|---|---|---|---|---|---|---|
| Phe | Ser | Tyr | Pro | Lys | Thr | Lys | Trp | Glu | Lys | Ser | Pro | Leu | Ser | Gln | Lys | |
| | | 835 | | | | | 840 | | | | | 845 | | | | |

| act | cgt | ctt | tac | act | gga | ggt | aat | acg | ctt | cag | gat | caa | gtg | gtc | gag | 2592 |
|---|---|---|---|---|---|---|---|---|---|---|---|---|---|---|---|---|
| Thr | Arg | Leu | Tyr | Thr | Gly | Gly | Asn | Thr | Leu | Gln | Asp | Gln | Val | Val | Glu | |
| 850 | | | | | 855 | | | | | 860 | | | | | | |

| ata | gaa | tat | cat | gtt | gag | ctt | ctt | ggt | aat | gat | ttt | gat | gac | cgg | gaa | 2640 |
|---|---|---|---|---|---|---|---|---|---|---|---|---|---|---|---|---|
| Ile | Glu | Tyr | His | Val | Glu | Leu | Leu | Gly | Asn | Asp | Phe | Asp | Asp | Arg | Glu | |
| 865 | | | | 870 | | | | | 875 | | | | | 880 | | |

| ttg | att | gtc | cgg | tac | aag | act | gat | gtt | gac | aac | aag | aag | gtc | ttc | tat | 2688 |
|---|---|---|---|---|---|---|---|---|---|---|---|---|---|---|---|---|
| Leu | Ile | Val | Arg | Tyr | Lys | Thr | Asp | Val | Asp | Asn | Lys | Lys | Val | Phe | Tyr | |
| | | | | 885 | | | | | 890 | | | | | 895 | | |

| tca | gat | ctc | aat | ggt | ttc | caa | atg | agc | agg | aga | gaa | act | tat | gat | aag | 2736 |
|---|---|---|---|---|---|---|---|---|---|---|---|---|---|---|---|---|
| Ser | Asp | Leu | Asn | Gly | Phe | Gln | Met | Ser | Arg | Arg | Glu | Thr | Tyr | Asp | Lys | |
| | | | 900 | | | | | 905 | | | | | 910 | | | |

| atc | cct | ctt | caa | gga | aac | tac | tac | cca | atg | cca | tct | ctc | gca | ttt | atc | 2784 |
|---|---|---|---|---|---|---|---|---|---|---|---|---|---|---|---|---|
| Ile | Pro | Leu | Gln | Gly | Asn | Tyr | Tyr | Pro | Met | Pro | Ser | Leu | Ala | Phe | Ile | |
| | | 915 | | | | | 920 | | | | | 925 | | | | |

| caa | gga | tcc | aat | ggt | cag | aga | ttc | tcc | gtg | cac | tct | cgt | caa | tct | ctc | 2832 |

|  |  |
|---|---|
| Gln Gly Ser Asn Gly Gln Arg Phe Ser Val His Ser Arg Gln Ser Leu<br>    930                        935                     940 |  |
| ggt gtt gca agc ctc aaa gag ggt tgg ttg gag att atg ctg gac aga<br>Gly Val Ala Ser Leu Lys Glu Gly Trp Leu Glu Ile Met Leu Asp Arg<br>945                  950                     955                     960 | 2880 |
| cgg ttg gtt cgt gat gac gga cgg ggt cta ggg caa ggt gtg atg gat<br>Arg Leu Val Arg Asp Asp Gly Arg Gly Leu Gly Gln Gly Val Met Asp<br>                        965                     970                     975 | 2928 |
| aac cgc gca atg acc gtg gta ttt cac ctt ctt gcg gaa tct aac att<br>Asn Arg Ala Met Thr Val Val Phe His Leu Leu Ala Glu Ser Asn Ile<br>             980                     985                     990 | 2976 |
| tct caa gca gac cct gct tcc aac act aac ccg agg aac cct tcg ctt<br>Ser Gln Ala Asp Pro Ala Ser Asn Thr Asn Pro Arg Asn Pro Ser Leu<br>        995                     1000                   1005 | 3024 |
| ctc tct cac ctc ata ggt gct cac tta aac tac ccc ata aac aca ttc<br>Leu Ser His Leu Ile Gly Ala His Leu Asn Tyr Pro Ile Asn Thr Phe<br>    1010                   1015                   1020 | 3072 |
| att gcc aag aaa ccg caa gac ata tct gtg cgt gtt cca caa tac ggt<br>Ile Ala Lys Lys Pro Gln Asp Ile Ser Val Arg Val Pro Gln Tyr Gly<br>1025                 1030                 1035                 1040 | 3120 |
| tcc ttt gct cct tta gcc aaa ccg tta cca tgt gac ctc cac att gta<br>Ser Phe Ala Pro Leu Ala Lys Pro Leu Pro Cys Asp Leu His Ile Val<br>                 1045                 1050                 1055 | 3168 |
| aat ttc aag gtt cct cgt cca tcc aaa tac tct cag caa ttg gaa gaa<br>Asn Phe Lys Val Pro Arg Pro Ser Lys Tyr Ser Gln Gln Leu Glu Glu<br>                 1060                 1065                 1070 | 3216 |
| gac aag cca agg ttc gct ctt atc ctc aat aga cga gct tgg gat tca<br>Asp Lys Pro Arg Phe Ala Leu Ile Leu Asn Arg Arg Ala Trp Asp Ser<br>        1075                 1080                 1085 | 3264 |
| gct tat tgc cat aaa gga aga caa gta aac tgc aca agc atg gct aat<br>Ala Tyr Cys His Lys Gly Arg Gln Val Asn Cys Thr Ser Met Ala Asn<br>    1090                   1095                   1100 | 3312 |
| gaa cca gta aac ttt tcc gac atg ttc aaa gat ctt gca gct tca aag<br>Glu Pro Val Asn Phe Ser Asp Met Phe Lys Asp Leu Ala Ala Ser Lys<br>1105                 1110                 1115                 1120 | 3360 |
| gta aaa cca act tca ctg aat ctc ttg caa gaa gat atg gag att ctt<br>Val Lys Pro Thr Ser Leu Asn Leu Leu Gln Glu Asp Met Glu Ile Leu<br>                 1125                 1130                 1135 | 3408 |
| ggg tac gat gac caa gag cta cct cga gat agt tca cag cca cgg gaa<br>Gly Tyr Asp Asp Gln Glu Leu Pro Arg Asp Ser Ser Gln Pro Arg Glu<br>                 1140                 1145                 1150 | 3456 |
| gga cgt gtc tcg atc tct ccc atg gaa ata cga gct tat aag ctt gaa<br>Gly Arg Val Ser Ile Ser Pro Met Glu Ile Arg Ala Tyr Lys Leu Glu<br>        1155                 1160                 1165 | 3504 |
| ctg cga cct cac aag tga<br>Leu Arg Pro His Lys<br>    1170 | 3522 |

```
<210> SEQ ID NO 50
<211> LENGTH: 3432
<212> TYPE: DNA
<213> ORGANISM: Caenorhabditis elegans
<220> FEATURE:
<221> NAME/KEY: CDS
<222> LOCATION: (1)..(3429)

<400> SEQUENCE: 50
```

|  |  |
|---|---|
| atg gga aaa cgc aat ttc tat att atc cta tgt ttg gga gtc ttt ctc<br>Met Gly Lys Arg Asn Phe Tyr Ile Ile Leu Cys Leu Gly Val Phe Leu<br>1                     5                       10                     15 | 48 |
| acc gta tca ctc tat ttg tac aat gga att gaa acc gga gct gaa gcg | 96 |

```
Thr Val Ser Leu Tyr Leu Tyr Asn Gly Ile Glu Thr Gly Ala Glu Ala
            20                  25                  30 ctc acc aaa cga caa gca aat gat tta cgg cgg aaa atc gga aat ttg      144
Leu Thr Lys Arg Gln Ala Asn Asp Leu Arg Arg Lys Ile Gly Asn Leu
        35                  40                  45 gag cat gta gca gaa gaa aat gga aga acg ata gac cgc ttg gaa caa      192
Glu His Val Ala Glu Glu Asn Gly Arg Thr Ile Asp Arg Leu Glu Gln
 50                  55                  60 gaa gtt caa cga gca aaa gct gaa aaa tcg gta gat ttt gat gaa gaa      240
Glu Val Gln Arg Ala Lys Ala Glu Lys Ser Val Asp Phe Asp Glu Glu
 65                  70                  75                  80 aaa gaa aaa acg gaa gaa aaa gaa gta gaa aaa gag gaa aaa gaa gtt      288
Lys Glu Lys Thr Glu Glu Lys Glu Val Glu Lys Glu Lys Glu Val
                85                  90                  95 gca cca gtt cca gtt cga gga aat cgt ggt gaa atg gct cat att cat      336
Ala Pro Val Pro Val Arg Gly Asn Arg Gly Glu Met Ala His Ile His
            100                 105                 110 caa gta aag caa cat atc aag cca act cca tcg atg aaa gat gtt tgt      384
Gln Val Lys Gln His Ile Lys Pro Thr Pro Ser Met Lys Asp Val Cys
        115                 120                 125 gga att aga gaa aac gtc agc att gct cat tca gac ctg cag atg ctc      432
Gly Ile Arg Glu Asn Val Ser Ile Ala His Ser Asp Leu Gln Met Leu
130                 135                 140 gat ctc tat gac acc tgg aag ttc gaa aat cca gac gga ggt gta tgg      480
Asp Leu Tyr Asp Thr Trp Lys Phe Glu Asn Pro Asp Gly Gly Val Trp
145                 150                 155                 160 aaa caa gga tgg aaa att gaa tac gat gca gag aaa gtc aaa tct ctt      528
Lys Gln Gly Trp Lys Ile Glu Tyr Asp Ala Glu Lys Val Lys Ser Leu
                165                 170                 175 cca cgt ttg gaa gtt att gtg ata cct cat tct cat tgt gat ccc gga      576
Pro Arg Leu Glu Val Ile Val Ile Pro His Ser His Cys Asp Pro Gly
            180                 185                 190 tgg att atg act ttc gaa gag tat tac aac aga caa act cgc aat att      624
Trp Ile Met Thr Phe Glu Glu Tyr Tyr Asn Arg Gln Thr Arg Asn Ile
        195                 200                 205 ctt gat gga atg gct aaa cat ttg gca gaa aaa gac gaa atg cgg ttt      672
Leu Asp Gly Met Ala Lys His Leu Ala Glu Lys Asp Glu Met Arg Phe
210                 215                 220 ata tat gca gaa ata tca ttt ttc gaa act tgg tgg aga gac cag gca      720
Ile Tyr Ala Glu Ile Ser Phe Phe Glu Thr Trp Trp Arg Asp Gln Ala
225                 230                 235                 240 gat gaa att aaa aag aaa gtt aaa gga tat ttg gaa gca gga aag ttt      768
Asp Glu Ile Lys Lys Lys Val Lys Gly Tyr Leu Glu Ala Gly Lys Phe
                245                 250                 255 gaa att gtt act ggc gga tgg gtt atg aca gat gaa gct aat gca cat      816
Glu Ile Val Thr Gly Gly Trp Val Met Thr Asp Glu Ala Asn Ala His
            260                 265                 270 tat cac tca atg atc act gaa ttg ttc gaa gga cat gaa tgg att caa      864
Tyr His Ser Met Ile Thr Glu Leu Phe Glu Gly His Glu Trp Ile Gln
        275                 280                 285 aat cat ttg gga aaa agc gcc att cca caa tct cat tgg tca att gat      912
Asn His Leu Gly Lys Ser Ala Ile Pro Gln Ser His Trp Ser Ile Asp
290                 295                 300 cca ttc ggt tta tca cca tca atg cca cat ctt cta act tct gct aat      960
Pro Phe Gly Leu Ser Pro Ser Met Pro His Leu Leu Thr Ser Ala Asn
305                 310                 315                 320 ata acc aat gct gta att caa aga gtt cat tat tcg gtg aaa cgt gag     1008
Ile Thr Asn Ala Val Ile Gln Arg Val His Tyr Ser Val Lys Arg Glu
                325                 330                 335
```

```
ctt gct ctg aaa aag aat ctt gaa ttc tac tgg aga caa tta ttt gga      1056
Leu Ala Leu Lys Lys Asn Leu Glu Phe Tyr Trp Arg Gln Leu Phe Gly
        340                 345                 350 tca act gga cat cct gat ctt cgt tca cat att atg cct ttc tac tct      1104
Ser Thr Gly His Pro Asp Leu Arg Ser His Ile Met Pro Phe Tyr Ser
355                 360                 365 tac gat ata cct cat acg tgt ggc cca gaa ccg tct gtt tgc tgt caa      1152
Tyr Asp Ile Pro His Thr Cys Gly Pro Glu Pro Ser Val Cys Cys Gln
    370                 375                 380 ttc gat ttc cgt aga atg cca gaa ggt gga aaa tca tgt gat tgg gga      1200
Phe Asp Phe Arg Arg Met Pro Glu Gly Gly Lys Ser Cys Asp Trp Gly
385                 390                 395                 400 atc cct cca cag aaa att aac gat gac aat gtg gct cac aga gct gaa      1248
Ile Pro Pro Gln Lys Ile Asn Asp Asp Asn Val Ala His Arg Ala Glu
                405                 410                 415 atg att tat gat caa tat aga aag aaa agt caa ctt ttc aag aat aat      1296
Met Ile Tyr Asp Gln Tyr Arg Lys Lys Ser Gln Leu Phe Lys Asn Asn
            420                 425                 430 gtg att ttc caa cca ctt gga gat gat ttc agg tac gac att gat ttt      1344
Val Ile Phe Gln Pro Leu Gly Asp Asp Phe Arg Tyr Asp Ile Asp Phe
        435                 440                 445 gaa tgg aat tca caa tat gaa aac tat aag aaa ttg ttc gaa tac atg      1392
Glu Trp Asn Ser Gln Tyr Glu Asn Tyr Lys Lys Leu Phe Glu Tyr Met
450                 455                 460 aat tcc aaa tca gaa tgg aat gtt cat gct caa ttc gga act ctt tct      1440
Asn Ser Lys Ser Glu Trp Asn Val His Ala Gln Phe Gly Thr Leu Ser
465                 470                 475                 480 gat tat ttc aag aag ctt gat act gca att tct gcg tct ggc gag caa      1488
Asp Tyr Phe Lys Lys Leu Asp Thr Ala Ile Ser Ala Ser Gly Glu Gln
                485                 490                 495 ctt cca act ttt tct gga gat ttc ttc act tat gcg gac aga gat gat      1536
Leu Pro Thr Phe Ser Gly Asp Phe Phe Thr Tyr Ala Asp Arg Asp Asp
            500                 505                 510 cat tat tgg agt gga tac ttc act tcc cgt cca ttc tat aaa cag ctt      1584
His Tyr Trp Ser Gly Tyr Phe Thr Ser Arg Pro Phe Tyr Lys Gln Leu
        515                 520                 525 gat cgg gtt ctc caa cat tat tta aga tca gct gaa atc gcc ttt acc      1632
Asp Arg Val Leu Gln His Tyr Leu Arg Ser Ala Glu Ile Ala Phe Thr
530                 535                 540 ctt gca aat att gaa gaa gaa gga atg gtt gaa gcg aaa att ttt gag      1680
Leu Ala Asn Ile Glu Glu Glu Gly Met Val Glu Ala Lys Ile Phe Glu
545                 550                 555                 560 aag ctt gtg act gct cga cga gct ctt tca ctt ttc caa cat cac gat      1728
Lys Leu Val Thr Ala Arg Arg Ala Leu Ser Leu Phe Gln His His Asp
                565                 570                 575 ggt gta act ggt acg gca aaa gat cac gtc gtc ttg gat tat ggt cag      1776
Gly Val Thr Gly Thr Ala Lys Asp His Val Val Leu Asp Tyr Gly Gln
            580                 585                 590 aaa atg att gat gct ttg aac gca tgt gag gat att ctt tcg gaa gct      1824
Lys Met Ile Asp Ala Leu Asn Ala Cys Glu Asp Ile Leu Ser Glu Ala
        595                 600                 605 ctt gtt gta ttg ctg gga att gat tca acg aat aag atg cag atg gat      1872
Leu Val Val Leu Leu Gly Ile Asp Ser Thr Asn Lys Met Gln Met Asp
610                 615                 620 gag cat aga gtt aat gaa aac ctt cta ccc gaa aaa cgt gtc tat aaa      1920
Glu His Arg Val Asn Glu Asn Leu Leu Pro Glu Lys Arg Val Tyr Lys
625                 630                 635                 640 att ggg caa aac gtc gta ttg ttc aat act tta tct aga aat cgc aac      1968
Ile Gly Gln Asn Val Val Leu Phe Asn Thr Leu Ser Arg Asn Arg Asn
                645                 650                 655
```

```
-continued gag cca att tgt att caa gtt gat tct ctt gac gct ggt gtc gaa gct    2016
Glu Pro Ile Cys Ile Gln Val Asp Ser Leu Asp Ala Gly Val Glu Ala
        660                 665                 670 gat cct cca att aaa aaa caa caa gtt tcg ccg gtt att gca tat gat    2064
Asp Pro Pro Ile Lys Lys Gln Gln Val Ser Pro Val Ile Ala Tyr Asp
        675                 680                 685 gaa gag aag aaa acg ctt gtt gtc aaa aac gga ata ttc gaa ctt tgc    2112
Glu Glu Lys Lys Thr Leu Val Val Lys Asn Gly Ile Phe Glu Leu Cys
        690                 695                 700 ttc atg tta tca ctt gga cca atg gag tct gtc agt ttc aga ctt gtg    2160
Phe Met Leu Ser Leu Gly Pro Met Glu Ser Val Ser Phe Arg Leu Val
705                 710                 715                 720 aaa aat aca aca aca tcc aaa gtt gaa ata atc acc aat aat gcg gca    2208
Lys Asn Thr Thr Thr Ser Lys Val Glu Ile Ile Thr Asn Asn Ala Ala
                725                 730                 735 gaa ttc aaa gaa aca agt ttt aaa tct tca tcc act tct gga gac ttt    2256
Glu Phe Lys Glu Thr Ser Phe Lys Ser Ser Ser Thr Ser Gly Asp Phe
            740                 745                 750 act gtg aaa aac gac aaa gtt gaa gct gaa ttt gat gga gaa aat gga    2304
Thr Val Lys Asn Asp Lys Val Glu Ala Glu Phe Asp Gly Glu Asn Gly
        755                 760                 765 atg att aaa aga gct acc agt ctt gtt gat gat aaa cca att gat ttg    2352
Met Ile Lys Arg Ala Thr Ser Leu Val Asp Asp Lys Pro Ile Asp Leu
        770                 775                 780 aat tct cac ttt att cat tat gga gca cgg aag tca aag aga aag ttc    2400
Asn Ser His Phe Ile His Tyr Gly Ala Arg Lys Ser Lys Arg Lys Phe
785                 790                 795                 800 gca aat gga aat gaa gac aac ccg gct ggc gca tac ctg ttc ctt ccc    2448
Ala Asn Gly Asn Glu Asp Asn Pro Ala Gly Ala Tyr Leu Phe Leu Pro
                805                 810                 815 gat gga gaa gct aga gaa ctc aaa aaa caa tca agt gat tgg ata ttg    2496
Asp Gly Glu Ala Arg Glu Leu Lys Lys Gln Ser Ser Asp Trp Ile Leu
            820                 825                 830 gta aaa gga gaa gtt gtt caa aaa gtg ttt gca act cca aac aat gat    2544
Val Lys Gly Glu Val Val Gln Lys Val Phe Ala Thr Pro Asn Asn Asp
        835                 840                 845 ctg aaa ata ttg caa acg tac aca ctt tat caa ggg ctt cca tgg att    2592
Leu Lys Ile Leu Gln Thr Tyr Thr Leu Tyr Gln Gly Leu Pro Trp Ile
850                 855                 860 gat ttg gat aat gaa gtt gat gta cgt tcc aag gag aat ttc gag ttg    2640
Asp Leu Asp Asn Glu Val Asp Val Arg Ser Lys Glu Asn Phe Glu Leu
865                 870                 875                 880 gca ctg aga ttc agt tct tca gta aat agt ggt gat gag ttt ttc act    2688
Ala Leu Arg Phe Ser Ser Ser Val Asn Ser Gly Asp Glu Phe Phe Thr
                885                 890                 895 gat ctc aat gga atg caa atg ata aaa agg aga cga caa act aaa tta    2736
Asp Leu Asn Gly Met Gln Met Ile Lys Arg Arg Arg Gln Thr Lys Leu
            900                 905                 910 cca aca cag gcc aat ttc tat ccc atg tct gct ggt gtt tac att gaa    2784
Pro Thr Gln Ala Asn Phe Tyr Pro Met Ser Ala Gly Val Tyr Ile Glu
        915                 920                 925 gac gat act acc aga atg tca att cat tcg gca cag gct ctc gga gtt    2832
Asp Asp Thr Thr Arg Met Ser Ile His Ser Ala Gln Ala Leu Gly Val
        930                 935                 940 agc agt ctc tcg tcg gga caa att gaa ata atg ctt gat cga cga ctt    2880
Ser Ser Leu Ser Ser Gly Gln Ile Glu Ile Met Leu Asp Arg Arg Leu
945                 950                 955                 960 agt tca gat gac aac aga ggt ctt cag caa gga gtt aga gac aac aaa    2928
Ser Ser Asp Asp Asn Arg Gly Leu Gln Gln Gly Val Arg Asp Asn Lys
```

```
                      965              970              975
cga aca gtt gca cat ttc cgt att gtt att gag ccg atg tct tca tcg    2976
Arg Thr Val Ala His Phe Arg Ile Val Ile Glu Pro Met Ser Ser Ser
            980              985              990 agt ggt aat aag aag gaa gaa cga gtt gga ttc cat tca cat gtt ggt    3024
Ser Gly Asn Lys Lys Glu Glu Arg Val Gly Phe His Ser His Val Gly
            995              1000             1005 cat ctc gct acg tgg tct ctt cat tat cct ctt gtc aaa atg att gga    3072
His Leu Ala Thr Trp Ser Leu His Tyr Pro Leu Val Lys Met Ile Gly
            1010             1015             1020 gat gca aca cca aaa tct att tct tcg aaa aat gtg gaa caa gag ctg    3120
Asp Ala Thr Pro Lys Ser Ile Ser Ser Lys Asn Val Glu Gln Glu Leu
1025             1030             1035             1040 aac tgt gac ctg cat cta gtg aca ttt aga aca ctg gca tcg ccg aca    3168
Asn Cys Asp Leu His Leu Val Thr Phe Arg Thr Leu Ala Ser Pro Thr
            1045             1050             1055 act tac gaa gcc aac gaa aga tct acg gca gct gag aag aaa gca gcg    3216
Thr Tyr Glu Ala Asn Glu Arg Ser Thr Ala Ala Glu Lys Lys Ala Ala
            1060             1065             1070 atg gtg atg cat aga gtt gtt cca gac tgt aga tcc agg ctt acc ctc    3264
Met Val Met His Arg Val Val Pro Asp Cys Arg Ser Arg Leu Thr Leu
            1075             1080             1085 cca gac acg tca tgc tta gct act gga tta gaa att gag cca ctc aaa    3312
Pro Asp Thr Ser Cys Leu Ala Thr Gly Leu Glu Ile Glu Pro Leu Lys
            1090             1095             1100 ttg atc tcg aca ctg aag tct gcg aaa aaa acg tca cta acc aat ctt    3360
Leu Ile Ser Thr Leu Lys Ser Ala Lys Lys Thr Ser Leu Thr Asn Leu
1105             1110             1115             1120 tat gaa gga aac aag gct gaa caa ttc cga ctc caa cca aac gat att    3408
Tyr Glu Gly Asn Lys Ala Glu Gln Phe Arg Leu Gln Pro Asn Asp Ile
            1125             1130             1135 tcc agt att ctt gta tca ttt taa                                    3432
Ser Ser Ile Leu Val Ser Phe
            1140

<210> SEQ ID NO 51
<211> LENGTH: 3450
<212> TYPE: DNA
<213> ORGANISM: Ciona intestinalis
<220> FEATURE:
<221> NAME/KEY: CDS
<222> LOCATION: (1)..(3447)

<400> SEQUENCE: 51 atg aag ctc aaa cgc cag ttc tta ttc ttt ggt gga att ctg ttc ttc    48
Met Lys Leu Lys Arg Gln Phe Leu Phe Phe Gly Gly Ile Leu Phe Phe
1               5                   10                  15 ggg agt atc tgg ttt atg ata ggt caa ctt gac act cct aat tcg cca    96
Gly Ser Ile Trp Phe Met Ile Gly Gln Leu Asp Thr Pro Asn Ser Pro
            20                  25                  30 cag aaa gtc aaa ttc tcg gaa ggc agt gaa aat gac caa gtt cga acc    144
Gln Lys Val Lys Phe Ser Glu Gly Ser Glu Asn Asp Gln Val Arg Thr
        35                  40                  45 ctt caa gac aaa ctt agt ctg gtg gaa aaa gaa ttg tta gaa aat cgt    192
Leu Gln Asp Lys Leu Ser Leu Val Glu Lys Glu Leu Leu Glu Asn Arg
    50                  55                  60 aaa ata atg cac aag gtg aaa gat agt cta cag gat atg aca ccc atg    240
Lys Ile Met His Lys Val Lys Asp Ser Leu Gln Asp Met Thr Pro Met
65                  70                  75                  80 aaa aat gtt cat gtg cct atg cag cgc gga gaa ata aga aac aac gtc    288
Lys Asn Val His Val Pro Met Gln Arg Gly Glu Ile Arg Asn Asn Val
```

-continued

```
                      85                       90                       95
aat aaa cct gtg cta cca ctt ata atg ccc aag caa ttt gcg aat gac            336
Asn Lys Pro Val Leu Pro Leu Ile Met Pro Lys Gln Phe Ala Asn Asp
            100                     105                     110 tcc cga atg agt gac acg tgt cct gtg ctc tcg tac tcc ggt ggc aag            384
Ser Arg Met Ser Asp Thr Cys Pro Val Leu Ser Tyr Ser Gly Gly Lys
                115                     120                     125 tcc gat gtt aac atg att aac gtg tat gat cat ctt cca ttt gat gat            432
Ser Asp Val Asn Met Ile Asn Val Tyr Asp His Leu Pro Phe Asp Asp
    130                     135                     140 cca gat ggt gga gtt tgg aaa caa ggt tgg gac atc cag aca tcg gat            480
Pro Asp Gly Gly Val Trp Lys Gln Gly Trp Asp Ile Gln Thr Ser Asp
145                     150                     155                     160 cag gaa tgg gct ggg aga aaa ttg aaa gtg ttc att gtc cct cac tca            528
Gln Glu Trp Ala Gly Arg Lys Leu Lys Val Phe Ile Val Pro His Ser
                165                     170                     175 cat aat gat cct ggt tgg tta aag acg gtg gaa aga tac ttc agc gat            576
His Asn Asp Pro Gly Trp Leu Lys Thr Val Glu Arg Tyr Phe Ser Asp
                180                     185                     190 caa aca caa cat att ctc aat aat att gtg gat gct ttg agt caa gac            624
Gln Thr Gln His Ile Leu Asn Asn Ile Val Asp Ala Leu Ser Gln Asp
        195                     200                     205 cct gca agg aag ttt atc tgg gca gag atg tcg tat ctc tca atg tgg            672
Pro Ala Arg Lys Phe Ile Trp Ala Glu Met Ser Tyr Leu Ser Met Trp
    210                     215                     220 tgg gac att gcc aca cct gat cgt aag cag aaa atg cag aca ctc gtg            720
Trp Asp Ile Ala Thr Pro Asp Arg Lys Gln Lys Met Gln Thr Leu Val
225                     230                     235                     240 aag aat gga cag ctt gag ata gtt acg ggt ggt tgg gtc atg aat gat            768
Lys Asn Gly Gln Leu Glu Ile Val Thr Gly Gly Trp Val Met Asn Asp
                245                     250                     255 gaa gca aac act cat tac ttt gct atg att gat caa ctc att gaa ggt            816
Glu Ala Asn Thr His Tyr Phe Ala Met Ile Asp Gln Leu Ile Glu Gly
            260                     265                     270 atg gaa tgg ttg agg cga aca ttg aat gtt gtt cca aaa agt ggg tgg            864
Met Glu Trp Leu Arg Arg Thr Leu Asn Val Val Pro Lys Ser Gly Trp
        275                     280                     285 gcg att gat ccc ttt ggt cac acc ccc acc atg gct tat ata ctg aaa            912
Ala Ile Asp Pro Phe Gly His Thr Pro Thr Met Ala Tyr Ile Leu Lys
    290                     295                     300 cag atg aag ttc aaa aac atg ctg ata caa aga gtc cat tat gca gtg            960
Gln Met Lys Phe Lys Asn Met Leu Ile Gln Arg Val His Tyr Ala Val
305                     310                     315                     320 aag aag tat ctt gct cag gaa aag tct ctg gaa ttc aga tgg aga caa           1008
Lys Lys Tyr Leu Ala Gln Glu Lys Ser Leu Glu Phe Arg Trp Arg Gln
                325                     330                     335 atg tgg gat tca gct tca agt aca gac atg atg tgt cat ctc atg cct           1056
Met Trp Asp Ser Ala Ser Ser Thr Asp Met Met Cys His Leu Met Pro
            340                     345                     350 ttc tat tca tat gat gtt cct cat act tgt ggc cca gac ccc aag att           1104
Phe Tyr Ser Tyr Asp Val Pro His Thr Cys Gly Pro Asp Pro Lys Ile
        355                     360                     365 tgc tgc cag ttt gat ttt gct cgc tta ccc ggc ggc aag ata acc tgc           1152
Cys Cys Gln Phe Asp Phe Ala Arg Leu Pro Gly Gly Lys Ile Thr Cys
    370                     375                     380 cca tgg aaa gtt cct cct gtt gcc atc act gac tcc aat gta gaa aca           1200
Pro Trp Lys Val Pro Pro Val Ala Ile Thr Asp Ser Asn Val Glu Thr
385                     390                     395                     400 cga gcc gga ata cta ctt gac caa tat aga aaa aag tca aaa ctc ttc           1248
Arg Ala Gly Ile Leu Leu Asp Gln Tyr Arg Lys Lys Ser Lys Leu Phe
```

```
                    -continued

Arg Ala Gly Ile Leu Leu Asp Gln Tyr Arg Lys Lys Ser Lys Leu Phe
                405                 410                 415 aaa agt gac acc ctg ctt att ata tta gga gat gat ttt cgt tat tcg      1296
Lys Ser Asp Thr Leu Leu Ile Ile Leu Gly Asp Asp Phe Arg Tyr Ser
            420                 425                 430 ctg agc aag gaa acc aac gat cag ttt gac aac tac gct cga att atc      1344
Leu Ser Lys Glu Thr Asn Asp Gln Phe Asp Asn Tyr Ala Arg Ile Ile
            435                 440                 445 tcg tat gtg aat tcg cac cca gag tta aac gca aaa ctt cag ttt gga      1392
Ser Tyr Val Asn Ser His Pro Glu Leu Asn Ala Lys Leu Gln Phe Gly
            450                 455                 460 aca tta tcc gaa tat ttt gat gcc atg aaa tct gaa gtg ggg gga gag      1440
Thr Leu Ser Glu Tyr Phe Asp Ala Met Lys Ser Glu Val Gly Gly Glu
465                 470                 475                 480 gaa aaa ctc cca gct tta agt ggt gat ttc ttc act tat gct gat aga      1488
Glu Lys Leu Pro Ala Leu Ser Gly Asp Phe Phe Thr Tyr Ala Asp Arg
                485                 490                 495 gaa gat cac tat tgg agt ggt tac tac act tca cgg cct tac cac aaa      1536
Glu Asp His Tyr Trp Ser Gly Tyr Tyr Thr Ser Arg Pro Tyr His Lys
                500                 505                 510 atg cag gag aga gtc ctg gaa agc cac ctt cga gga gca gaa atg ttg      1584
Met Gln Glu Arg Val Leu Glu Ser His Leu Arg Gly Ala Glu Met Leu
                515                 520                 525 ttt gcg ctc tca tgg ccc aaa atc cag tgg aca gga ctt ggt gaa aca      1632
Phe Ala Leu Ser Trp Pro Lys Ile Gln Trp Thr Gly Leu Gly Glu Thr
530                 535                 540 ttt tca cat gaa ctt tac cca ctg ctg gtc caa gca cgt caa aat ctt      1680
Phe Ser His Glu Leu Tyr Pro Leu Leu Val Gln Ala Arg Gln Asn Leu
545                 550                 555                 560 ggt ttg ttt caa cac cac gat ggt ata aca ggc aca gca aag gat cat      1728
Gly Leu Phe Gln His His Asp Gly Ile Thr Gly Thr Ala Lys Asp His
                565                 570                 575 gtt gtt gtt gat tac ggg aat aaa ctc atg aag agt gtt atg gat gca      1776
Val Val Val Asp Tyr Gly Asn Lys Leu Met Lys Ser Val Met Asp Ala
                580                 585                 590 aag aag gta att tca tac agt gcc caa gtt ctg ttg caa gaa atg atc      1824
Lys Lys Val Ile Ser Tyr Ser Ala Gln Val Leu Leu Gln Glu Met Ile
                595                 600                 605 acg ttt gat cca aat acc atg gta ctt aac tat gat gag gtg tat caa      1872
Thr Phe Asp Pro Asn Thr Met Val Leu Asn Tyr Asp Glu Val Tyr Gln
610                 615                 620 gct cag aac caa caa cct gcg cct gtg gtt gtt aag cta cca acg aag      1920
Ala Gln Asn Gln Gln Pro Ala Pro Val Val Val Lys Leu Pro Thr Lys
625                 630                 635                 640 aat gaa gaa gcg cgg aaa gtc gtt ctc tac aac tct ctg gat tac gac      1968
Asn Glu Glu Ala Arg Lys Val Val Leu Tyr Asn Ser Leu Asp Tyr Asp
                645                 650                 655 aga act ggt gtc gtg cgt cta att gtt acg tca ccc gac gtg gtt gtg      2016
Arg Thr Gly Val Val Arg Leu Ile Val Thr Ser Pro Asp Val Val Val
                660                 665                 670 atg tca gaa aac aaa aac gtc gtt cca tcg caa acc agt ccg atc tgg      2064
Met Ser Glu Asn Lys Asn Val Val Pro Ser Gln Thr Ser Pro Ile Trp
                675                 680                 685 tca gat tcg acg gag atc cgc aca gac cag ttt gaa ctg gtt ttc ctt      2112
Ser Asp Ser Thr Glu Ile Arg Thr Asp Gln Phe Glu Leu Val Phe Leu
                690                 695                 700 tca act gtt ccc gcg ata gga ctg gcg gtg tac aag ata tgg gaa gac      2160
Ser Thr Val Pro Ala Ile Gly Leu Ala Val Tyr Lys Ile Trp Glu Asp
705                 710                 715                 720
```

-continued

| | | |
|---|---|---|
| aac gac gta gca gac acc acg cac tca act gtt aag ttt atc aac ccg<br>Asn Asp Val Ala Asp Thr Thr His Ser Thr Val Lys Phe Ile Asn Pro<br>                    725                  730                735 | 2208 |
| aga gtt ggg ttt tcg aaa cga acc cgc agt aag ttt gta ctc gac gtt<br>Arg Val Gly Phe Ser Lys Arg Thr Arg Ser Lys Phe Val Leu Asp Val<br>          740                  745                  750 | 2256 |
| gag gat agc ggg gag ttt acc atc atg aat gac caa tta gtt gcg cat<br>Glu Asp Ser Gly Glu Phe Thr Ile Met Asn Asp Gln Leu Val Ala His<br>               755                  760              765 | 2304 |
| ttc tct gga caa aac ggg atg ctg cag tca gtc acc act gtg cgt gac<br>Phe Ser Gly Gln Asn Gly Met Leu Gln Ser Val Thr Thr Val Arg Asp<br>     770                  775                  780 | 2352 |
| aac gtt aaa acg cag ctc gga att gaa ttc gtc gct tat act tct cgt<br>Asn Val Lys Thr Gln Leu Gly Ile Glu Phe Val Ala Tyr Thr Ser Arg<br>785                  790                  795              800 | 2400 |
| aat aag aaa gac aag agc ggc gct tac ttg ttc ctg cct gct gga cca<br>Asn Lys Lys Asp Lys Ser Gly Ala Tyr Leu Phe Leu Pro Ala Gly Pro<br>                    805                  810              815 | 2448 |
| gca caa ccg cat gta aca gaa tcc cac cga ccg tta gta agg atc atc<br>Ala Gln Pro His Val Thr Glu Ser His Arg Pro Leu Val Arg Ile Ile<br>               820                  825              830 | 2496 |
| agg ggt cca gtg atg tca acg gtg cat gtt cta cta ccg aac gtt ctg<br>Arg Gly Pro Val Met Ser Thr Val His Val Leu Leu Pro Asn Val Leu<br>         835                  840                  845 | 2544 |
| cat aaa gtt acc cta tac acc ggt act ggt gca ggc acg cag tct tta<br>His Lys Val Thr Leu Tyr Thr Gly Thr Gly Ala Gly Thr Gln Ser Leu<br>850                  855                  860 | 2592 |
| ggc gtc cac gtc tct aac gac gtc gac gtt aga act ggc tac gac aac<br>Gly Val His Val Ser Asn Asp Val Asp Val Arg Thr Gly Tyr Asp Asn<br>865                  870                  875              880 | 2640 |
| aaa gaa ctc agt atg agg tta aac agc gaa gtt tta tcg gga agc aaa<br>Lys Glu Leu Ser Met Arg Leu Asn Ser Glu Val Leu Ser Gly Ser Lys<br>                    885                  890              895 | 2688 |
| ttc ttt acg gat tta aac ggt ttc caa att caa ccc cga acc acg tat<br>Phe Phe Thr Asp Leu Asn Gly Phe Gln Ile Gln Pro Arg Thr Thr Tyr<br>               900                  905                  910 | 2736 |
| tct aaa ctg cca cta caa gca aac ttc tac cca ata ccc aca atg gcg<br>Ser Lys Leu Pro Leu Gln Ala Asn Phe Tyr Pro Ile Pro Thr Met Ala<br>     915                  920                  925 | 2784 |
| ttc ata caa gac gaa aaa tca aga tta act ttg atg acg gcc caa cca<br>Phe Ile Gln Asp Glu Lys Ser Arg Leu Thr Leu Met Thr Ala Gln Pro<br>          930                  935                  940 | 2832 |
| ctg ggt gtt gcc tca ctg aag tca ggt caa ctt gag gtg gtt ttg gat<br>Leu Gly Val Ala Ser Leu Lys Ser Gly Gln Leu Glu Val Val Leu Asp<br>945                  950                  955              960 | 2880 |
| cgc cgt tta atg cag gac gac aac agg ggg gtg ggt caa ggt gtg aaa<br>Arg Arg Leu Met Gln Asp Asp Asn Arg Gly Val Gly Gln Gly Val Lys<br>                    965                  970              975 | 2928 |
| gat aat tta cca act cct gag agt ttc gtg atc atg ctg gaa aga tgg<br>Asp Asn Leu Pro Thr Pro Glu Ser Phe Val Ile Met Leu Glu Arg Trp<br>               980                  985                  990 | 2976 |
| acc gct att gca gcg aaa gaa agc aaa tcg tca gcg aag ctc gcg tat<br>Thr Ala Ile Ala Ala Lys Glu Ser Lys Ser Ser Ala Lys Leu Ala Tyr<br>     995                  1000              1005 | 3024 |
| cca tct atg gct gtg tat cag tca tca tgg gaa ttg cta cac cca ata<br>Pro Ser Met Ala Val Tyr Gln Ser Ser Trp Glu Leu Leu His Pro Ile<br>          1010                  1015              1020 | 3072 |
| cgt cca atg tcg gta aat ggg ccg gta cat ttg aaa gaa gat tac cgc<br>Arg Pro Met Ser Val Asn Gly Pro Val His Leu Lys Glu Asp Tyr Arg<br>1025                 1030                  1035              1040 | 3120 |

-continued

| | |
|---|---|
| tcg ctg cca cag cct tta cca tgc gac gtg cac gtg tta aac ttg cga<br>Ser Leu Pro Gln Pro Leu Pro Cys Asp Val His Val Leu Asn Leu Arg<br>                    1045                      1050                      1055 | 3168 |
| gca att cat tct aaa gat gca gtt gcc cct acc gac caa tcg gct ctg<br>Ala Ile His Ser Lys Asp Ala Val Ala Pro Thr Asp Gln Ser Ala Leu<br>1060                      1065                      1070 | 3216 |
| ctt cta cac aca gtt ggg cgc gaa tgc tcc ttg gac gcg gat aag tat<br>Leu Leu His Thr Val Gly Arg Glu Cys Ser Leu Asp Ala Asp Lys Tyr<br>           1075                      1080                      1085 | 3264 |
| ttc cac cca acg tgc ctc atg cac ggc gtc gag aaa ttg gct atc acg<br>Phe His Pro Thr Cys Leu Met His Gly Val Glu Lys Leu Ala Ile Thr<br>                1090                      1095                      1100 | 3312 |
| atc tcg acg ctt ttt act aac tct ggc atg cgg aag acg tcg ctg tcc<br>Ile Ser Thr Leu Phe Thr Asn Ser Gly Met Arg Lys Thr Ser Leu Ser<br>1105                      1110                      1115                      1120 | 3360 |
| tta caa cac gac ggc tcg ttg ctg gac aac caa ggc ggt att aca gtt<br>Leu Gln His Asp Gly Ser Leu Leu Asp Asn Gln Gly Gly Ile Thr Val<br>                      1125                      1130                      1135 | 3408 |
| tcc cca atg gag ata caa gct tac aaa ata gta ctg acg taa<br>Ser Pro Met Glu Ile Gln Ala Tyr Lys Ile Val Leu Thr<br>           1140                      1145 | 3450 |

<210> SEQ ID NO 52
<211> LENGTH: 3327
<212> TYPE: DNA
<213> ORGANISM: Drosophila sp.
<220> FEATURE:
<221> NAME/KEY: CDS
<222> LOCATION: (1)..(3324)

<400> SEQUENCE: 52

| | |
|---|---|
| atg ttg cga ata cgt cgg cgg ttc gct ttg gta att tgc tcc ggc tgc<br>Met Leu Arg Ile Arg Arg Arg Phe Ala Leu Val Ile Cys Ser Gly Cys<br>1                        5                        10                        15 | 48 |
| ctg ctg gtt ttc ctc agc ctg tac ata atc ctc aat ttt gcg gcg ccg<br>Leu Leu Val Phe Leu Ser Leu Tyr Ile Ile Leu Asn Phe Ala Ala Pro<br>                    20                        25                        30 | 96 |
| gca gcc acc cag ata aag ccc aac tat gag aac att gag aac aag ctg<br>Ala Ala Thr Gln Ile Lys Pro Asn Tyr Glu Asn Ile Glu Asn Lys Leu<br>           35                      40                        45 | 144 |
| cat gag ctg gaa aat ggt ttg cag gag cac ggg gag gag atg cgg aat<br>His Glu Leu Glu Asn Gly Leu Gln Glu His Gly Glu Glu Met Arg Asn<br>      50                      55                        60 | 192 |
| ctc agg gcg cgt ctg gcc aaa aca tcc aat cgc gac gat cca ata aga<br>Leu Arg Ala Arg Leu Ala Lys Thr Ser Asn Arg Asp Asp Pro Ile Arg<br>65                      70                      75                      80 | 240 |
| cct cca ctt aaa gtg gct cgt tcc ccg agg cca ggg caa tgc caa gat<br>Pro Pro Leu Lys Val Ala Arg Ser Pro Arg Pro Gly Gln Cys Gln Asp<br>                    85                        90                        95 | 288 |
| gtg gtc caa gac gtg ccc aat gtg gat gta cag atg ctg gag cta tac<br>Val Val Gln Asp Val Pro Asn Val Asp Val Gln Met Leu Glu Leu Tyr<br>          100                      105                      110 | 336 |
| gat cgc atg tcc ttc aag gac ata gat gga ggc gtg tgg aaa cag ggc<br>Asp Arg Met Ser Phe Lys Asp Ile Asp Gly Gly Val Trp Lys Gln Gly<br>           115                      120                      125 | 384 |
| tgg aac att aag tac gat cca ctg aag tac aac gcc cat cac aaa cta<br>Trp Asn Ile Lys Tyr Asp Pro Leu Lys Tyr Asn Ala His His Lys Leu<br>130                      135                      140 | 432 |
| aaa gtc ttc gtt gtg ccg cac tcg cac aac gat cct gga tgg att cag<br>Lys Val Phe Val Val Pro His Ser His Asn Asp Pro Gly Trp Ile Gln<br>145                      150                      155                      160 | 480 |

| | | |
|---|---|---|
| acg ttt gag gaa tac tac cag cac gac acc aag cac atc ctg tcc aat<br>Thr Phe Glu Glu Tyr Tyr Gln His Asp Thr Lys His Ile Leu Ser Asn<br>               165                     170                  175 | 528 |
| gca cta cgg cat ctg cac gac aat ccc gag atg aag ttc atc tgg gcg<br>Ala Leu Arg His Leu His Asp Asn Pro Glu Met Lys Phe Ile Trp Ala<br>        180                     185                  190 | 576 |
| gaa atc tcc tac ttt gct cgg ttc tat cac gat ttg gga gag aac aaa<br>Glu Ile Ser Tyr Phe Ala Arg Phe Tyr His Asp Leu Gly Glu Asn Lys<br>               195                    200                  205 | 624 |
| aag ctg cag atg aag tcc att gta aag aat gga cag ttg gaa ttt gtg<br>Lys Leu Gln Met Lys Ser Ile Val Lys Asn Gly Gln Leu Glu Phe Val<br>210                    215                  220 | 672 |
| act gga gga tgg gta atg ccg gac gag gcc aac tcc cac tgg cga aac<br>Thr Gly Gly Trp Val Met Pro Asp Glu Ala Asn Ser His Trp Arg Asn<br>225                    230                  235               240 | 720 |
| gta ctg ctg cag ctg acc gaa ggg caa aca tgg ttg aag caa ttc atg<br>Val Leu Leu Gln Leu Thr Glu Gly Gln Thr Trp Leu Lys Gln Phe Met<br>               245                    250                  255 | 768 |
| aat gtc aca ccc act gct tcc tgg gcc atc gat ccc ttc gga cac agt<br>Asn Val Thr Pro Thr Ala Ser Trp Ala Ile Asp Pro Phe Gly His Ser<br>        260                     265                  270 | 816 |
| ccc act atg ccg tac att ttg cag aag agt ggt ttc aag aat atg ctt<br>Pro Thr Met Pro Tyr Ile Leu Gln Lys Ser Gly Phe Lys Asn Met Leu<br>               275                    280                  285 | 864 |
| atc caa agg acg cac tat tcg gtt aag aag gaa ctg gcc caa cag cga<br>Ile Gln Arg Thr His Tyr Ser Val Lys Lys Glu Leu Ala Gln Gln Arg<br>        290                     295                  300 | 912 |
| cag ctt gag ttc ctg tgg cgc cag atc tgg gac aac aaa ggg gac aca<br>Gln Leu Glu Phe Leu Trp Arg Gln Ile Trp Asp Asn Lys Gly Asp Thr<br>305                    310                  315               320 | 960 |
| gct ctc ttc acc cac atg atg ccc ttc tac tcg tac gac att cct cat<br>Ala Leu Phe Thr His Met Met Pro Phe Tyr Ser Tyr Asp Ile Pro His<br>                   325                    330                  335 | 1008 |
| acc tgt ggt cca gat ccc aag gtt tgc tgt cag ttc gat ttc aaa cga<br>Thr Cys Gly Pro Asp Pro Lys Val Cys Cys Gln Phe Asp Phe Lys Arg<br>        340                     345                  350 | 1056 |
| atg ggc tcc ttc ggt ttg agt tgt cca tgg aag gtg ccg ccg cgt aca<br>Met Gly Ser Phe Gly Leu Ser Cys Pro Trp Lys Val Pro Pro Arg Thr<br>               355                    360                  365 | 1104 |
| atc agt gat caa aat gtg gca gca cgc tca gat ctg ctg gtt gat cag<br>Ile Ser Asp Gln Asn Val Ala Ala Arg Ser Asp Leu Leu Val Asp Gln<br>370                    375                  380 | 1152 |
| tgg aag aag aag gcc gag ctg tat cgc aca aac gtg ctg ctg att ccg<br>Trp Lys Lys Lys Ala Glu Leu Tyr Arg Thr Asn Val Leu Leu Ile Pro<br>385                    390                  395               400 | 1200 |
| ttg ggt gac gac ttc cgc ttc aag cag aac acc gag tgg gat gtg cag<br>Leu Gly Asp Asp Phe Arg Phe Lys Gln Asn Thr Glu Trp Asp Val Gln<br>                   405                    410                  415 | 1248 |
| cgc gtg aac tac gaa agg ctg ttc gaa cac atc aac agc cag gcc cac<br>Arg Val Asn Tyr Glu Arg Leu Phe Glu His Ile Asn Ser Gln Ala His<br>        420                     425                  430 | 1296 |
| ttc aat gtc cag gcg cag ttc ggc aca ctg cag gaa tac ttt gat gca<br>Phe Asn Val Gln Ala Gln Phe Gly Thr Leu Gln Glu Tyr Phe Asp Ala<br>               435                    440                  445 | 1344 |
| gtg cac cag gcg gaa agg gcg gga caa gcc gag ttt ccc acg cta agc<br>Val His Gln Ala Glu Arg Ala Gly Gln Ala Glu Phe Pro Thr Leu Ser<br>450                    455                  460 | 1392 |
| ggt gac ttt ttc aca tac gcc gat cga tcg gat aac tat tgg agt ggc<br>Gly Asp Phe Phe Thr Tyr Ala Asp Arg Ser Asp Asn Tyr Trp Ser Gly | 1440 |

```
                  465                 470                 475                 480
tac tac aca tcc cgc ccg tat cat aag cgc atg gac cgc gtc ctg atg          1488
Tyr Tyr Thr Ser Arg Pro Tyr His Lys Arg Met Asp Arg Val Leu Met
                        485                 490                 495 cac tat gta cgt gca gca gaa atg ctt tcc gcc tgg cac tcc tgg gac          1536
His Tyr Val Arg Ala Ala Glu Met Leu Ser Ala Trp His Ser Trp Asp
                500                 505                 510 ggt atg gcc cgc atc gag gaa cgt ctg gag cag gcc cgc agg gag ctg          1584
Gly Met Ala Arg Ile Glu Glu Arg Leu Glu Gln Ala Arg Arg Glu Leu
            515                 520                 525 tca ttg ttc cag cac cac gac ggt ata act ggc aca gca aaa acg cac          1632
Ser Leu Phe Gln His His Asp Gly Ile Thr Gly Thr Ala Lys Thr His
        530                 535                 540 gta gtc gtc gac tac gag caa cgc atg cag gaa gct tta aaa gcc tgt          1680
Val Val Val Asp Tyr Glu Gln Arg Met Gln Glu Ala Leu Lys Ala Cys
545                 550                 555                 560 caa atg gta atg caa cag tcg gtc tac cga ttg ctg aca aag ccc tcc          1728
Gln Met Val Met Gln Gln Ser Val Tyr Arg Leu Leu Thr Lys Pro Ser
                    565                 570                 575 atc tac agt ccg gac ttc agt ttc tcg tac ttt acg ctc gac gac tcc          1776
Ile Tyr Ser Pro Asp Phe Ser Phe Ser Tyr Phe Thr Leu Asp Asp Ser
                580                 585                 590 cgc tgg cca gga tct ggt gtg gag gac agt cga acc acc ata ata ctg          1824
Arg Trp Pro Gly Ser Gly Val Glu Asp Ser Arg Thr Thr Ile Ile Leu
            595                 600                 605 ggc gag gat ata ctg ccc tcc aag cat gtg gtg atg cac aac acc ctg          1872
Gly Glu Asp Ile Leu Pro Ser Lys His Val Val Met His Asn Thr Leu
        610                 615                 620 ccc cac tgg cgg gag cag ctg gtg gac ttt tat gta tcc agt ccg ttt          1920
Pro His Trp Arg Glu Gln Leu Val Asp Phe Tyr Val Ser Ser Pro Phe
625                 630                 635                 640 gta agc gtt acc gac ttg gca aac aat ccg gtg gag gct cag gtg tcc          1968
Val Ser Val Thr Asp Leu Ala Asn Asn Pro Val Glu Ala Gln Val Ser
                    645                 650                 655 ccg gtg tgg agc tgg cac cac gac aca ctc aca aag act atc cac cca          2016
Pro Val Trp Ser Trp His His Asp Thr Leu Thr Lys Thr Ile His Pro
                660                 665                 670 caa ggc tcc acc acc aag tac cgc atc atc ttc aag gct cgg gtg ccg          2064
Gln Gly Ser Thr Thr Lys Tyr Arg Ile Ile Phe Lys Ala Arg Val Pro
            675                 680                 685 ccc atg ggc ttg gcc acc tac gtt tta acc atc tcc gat tcc aag cca          2112
Pro Met Gly Leu Ala Thr Tyr Val Leu Thr Ile Ser Asp Ser Lys Pro
        690                 695                 700 gag cac acc tcg tat gca tcg aat ctc ttg ctc cgt aaa aac ccg act          2160
Glu His Thr Ser Tyr Ala Ser Asn Leu Leu Leu Arg Lys Asn Pro Thr
705                 710                 715                 720 tcg tta cca ttg ggc caa tat ccg gag gat gtg aag ttt ggc gat cct          2208
Ser Leu Pro Leu Gly Gln Tyr Pro Glu Asp Val Lys Phe Gly Asp Pro
                    725                 730                 735 cga gag atc tca ttg cgg gtt ggt aac gga ccc acc ttg gcc ttt tcg          2256
Arg Glu Ile Ser Leu Arg Val Gly Asn Gly Pro Thr Leu Ala Phe Ser
                740                 745                 750 gag cag ggt ctc ctt aag tcc att cag ctt act cag gat agc cca cat          2304
Glu Gln Gly Leu Leu Lys Ser Ile Gln Leu Thr Gln Asp Ser Pro His
            755                 760                 765 gta ccg gtg cac ttc aag ttc ctc aag tat ggc gtt cga tcg cat ggc          2352
Val Pro Val His Phe Lys Phe Leu Lys Tyr Gly Val Arg Ser His Gly
        770                 775                 780 gat aga tcc ggt gcc tat ctg ttc ctg ccc aat gga cca gct tcg cca          2400
```

```
Asp Arg Ser Gly Ala Tyr Leu Phe Leu Pro Asn Gly Pro Ala Ser Pro
785                 790                 795                 800 gtc gag ctt ggc cag cca gtg gtc ctg gtg act aag ggc aaa ctg gag          2448
Val Glu Leu Gly Gln Pro Val Val Leu Val Thr Lys Gly Lys Leu Glu
                805                 810                 815 tcg tcc gtg agc gtg gga ctt ccg agc gtg gtg cac cag acg ata atg          2496
Ser Ser Val Ser Val Gly Leu Pro Ser Val Val His Gln Thr Ile Met
                820                 825                 830 cgc ggt ggt gca cct gag att cgc aat ctg gtg gat ata ggc tca ctg          2544
Arg Gly Gly Ala Pro Glu Ile Arg Asn Leu Val Asp Ile Gly Ser Leu
                835                 840                 845 gac aac acg gag atc gtg atg cgc ttg gag acg cat atc gac agc ggc          2592
Asp Asn Thr Glu Ile Val Met Arg Leu Glu Thr His Ile Asp Ser Gly
850                 855                 860 gat atc ttc tac acg gat ctc aat gga ttg caa ttt atc aag agg cgg          2640
Asp Ile Phe Tyr Thr Asp Leu Asn Gly Leu Gln Phe Ile Lys Arg Arg
865                 870                 875                 880 cgt ttg gac aaa tta cct ttg cag gcc aac tat tat ccc ata cct tct          2688
Arg Leu Asp Lys Leu Pro Leu Gln Ala Asn Tyr Tyr Pro Ile Pro Ser
                885                 890                 895 ggt atg ttc att gag gat gcc aat acg cga ctc act ctc ctc acg ggt          2736
Gly Met Phe Ile Glu Asp Ala Asn Thr Arg Leu Thr Leu Leu Thr Gly
                900                 905                 910 caa ccg ctg ggt gga tct tct ctg gcc tcg ggc gag cta gag att atg          2784
Gln Pro Leu Gly Gly Ser Ser Leu Ala Ser Gly Glu Leu Glu Ile Met
                915                 920                 925 caa gat cgt cgc ctg gcc agc gat gat gaa cgc ggc ctg gga cag ggt          2832
Gln Asp Arg Arg Leu Ala Ser Asp Asp Glu Arg Gly Leu Gly Gln Gly
930                 935                 940 gtt ttg gac aac aag ccg gtg ctg cat att tat cgg ctg gtg ctg gag          2880
Val Leu Asp Asn Lys Pro Val Leu His Ile Tyr Arg Leu Val Leu Glu
945                 950                 955                 960 aag gtt aac aac tgt gtc cga ccg tca aag ctt cat cct gcc ggc tat          2928
Lys Val Asn Asn Cys Val Arg Pro Ser Lys Leu His Pro Ala Gly Tyr
                965                 970                 975 ttg aca agt gcc gca cac aaa gca tcg cag tca ctg ctg gat cca ctg          2976
Leu Thr Ser Ala Ala His Lys Ala Ser Gln Ser Leu Leu Asp Pro Leu
                980                 985                 990 gac aag ttt ata ttc gct gaa aat gag tgg atc ggg gca cag ggg caa          3024
Asp Lys Phe Ile Phe Ala Glu Asn Glu Trp Ile Gly Ala Gln Gly Gln
                995                 1000                1005 ttt ggt ggc gat cat cct tcg gct cgt gag gat ctc gat gtg tcg gtg          3072
Phe Gly Gly Asp His Pro Ser Ala Arg Glu Asp Leu Asp Val Ser Val
    1010                1015                1020 atg aga cgc tta acc aag agc tcg gcc aaa acc cag cga gta ggc tac          3120
Met Arg Arg Leu Thr Lys Ser Ser Ala Lys Thr Gln Arg Val Gly Tyr
1025                1030                1035                1040 gtt ctg cac cgc acc aat ctg atg caa tgc ggc act cca gag gag cat          3168
Val Leu His Arg Thr Asn Leu Met Gln Cys Gly Thr Pro Glu Glu His
                1045                1050                1055 aca cag aag ctg gat gtg tgc cac cta ctg ccg aat gtg gcg aga tgc          3216
Thr Gln Lys Leu Asp Val Cys His Leu Leu Pro Asn Val Ala Arg Cys
                1060                1065                1070 gag cgc acg acg ctg act ttc ctg cag aat ttg gag cac ttg gat ggc          3264
Glu Arg Thr Thr Leu Thr Phe Leu Gln Asn Leu Glu His Leu Asp Gly
                1075                1080                1085 atg gtg gcg ccg gaa gtg tgc ccc atg gaa acc gcc gct tat gtg agc          3312
Met Val Ala Pro Glu Val Cys Pro Met Glu Thr Ala Ala Tyr Val Ser
                1090                1095                1100
```

-continued

```
agt cac tca agc tga                                              3327
Ser His Ser Ser
1105

<210> SEQ ID NO 53
<211> LENGTH: 3435
<212> TYPE: DNA
<213> ORGANISM: Homo sapiens
<220> FEATURE:
<221> NAME/KEY: CDS
<222> LOCATION: (1)..(3432)

<400> SEQUENCE: 53 atg aag tta agc cgc cag ttc acc gtg ttc ggc agt gcg atc ttc tgt    48
Met Lys Leu Ser Arg Gln Phe Thr Val Phe Gly Ser Ala Ile Phe Cys
 1               5                  10                  15 gtg gtg att ttc tcg ctc tac ctg atg ctg gac cgg ggt cac tta gac    96
Val Val Ile Phe Ser Leu Tyr Leu Met Leu Asp Arg Gly His Leu Asp
             20                  25                  30 tac ccc agg aac ccg cgc cgc gag ggc tcc ttc cct cag ggc cag ctc   144
Tyr Pro Arg Asn Pro Arg Arg Glu Gly Ser Phe Pro Gln Gly Gln Leu
         35                  40                  45 tca atg ttg caa gaa aaa ata gac cat ttg gag cgt ttg cta gct gag   192
Ser Met Leu Gln Glu Lys Ile Asp His Leu Glu Arg Leu Leu Ala Glu
     50                  55                  60 aat aat gag atc atc tca aat att aga gac tca gtc atc aat ttg agt   240
Asn Asn Glu Ile Ile Ser Asn Ile Arg Asp Ser Val Ile Asn Leu Ser
 65                  70                  75                  80 gag tct gtg gag gat ggt ccg aaa agt tca caa agc aat ttc agc caa   288
Glu Ser Val Glu Asp Gly Pro Lys Ser Ser Gln Ser Asn Phe Ser Gln
                 85                  90                  95 ggt gct ggc tca cat ctt ctg ccc tca caa tta tcc ctc tca gtt gac   336
Gly Ala Gly Ser His Leu Leu Pro Ser Gln Leu Ser Leu Ser Val Asp
            100                 105                 110 act gca gac tgt ctg ttt gct tca caa agt gga agt cac aat tca gat   384
Thr Ala Asp Cys Leu Phe Ala Ser Gln Ser Gly Ser His Asn Ser Asp
        115                 120                 125 gtg cag atg ttg gat gtt tac agt cta att tct ttt gac aat cca gat   432
Val Gln Met Leu Asp Val Tyr Ser Leu Ile Ser Phe Asp Asn Pro Asp
    130                 135                 140 ggt gga gtt tgg aag caa gga ttt gac att act tat gaa tct aat gaa   480
Gly Gly Val Trp Lys Gln Gly Phe Asp Ile Thr Tyr Glu Ser Asn Glu
145                 150                 155                 160 tgg gac act gaa ccc ctt caa gtc ttt gtg gtg cct cat tcc cat aac   528
Trp Asp Thr Glu Pro Leu Gln Val Phe Val Val Pro His Ser His Asn
                165                 170                 175 gac cca ggt tgg ttg aag act ttc aat gac tac ttt aga gac aag act   576
Asp Pro Gly Trp Leu Lys Thr Phe Asn Asp Tyr Phe Arg Asp Lys Thr
            180                 185                 190 cag tat att ttt aat aac atg gtc cta aag ctg aaa gaa gac tca cgg   624
Gln Tyr Ile Phe Asn Asn Met Val Leu Lys Leu Lys Glu Asp Ser Arg
        195                 200                 205 agg aag ttt att tgg tct gag atc tct tac ctt tca aag tgg tgg gat   672
Arg Lys Phe Ile Trp Ser Glu Ile Ser Tyr Leu Ser Lys Trp Trp Asp
    210                 215                 220 att ata gat att cag aag aag gat gct gtt aaa agt tta ata gaa aat   720
Ile Ile Asp Ile Gln Lys Lys Asp Ala Val Lys Ser Leu Ile Glu Asn
225                 230                 235                 240 ggt cag ctt gaa att gtg aca ggt ggc tgg gtt atg cct gat gaa gct   768
Gly Gln Leu Glu Ile Val Thr Gly Gly Trp Val Met Pro Asp Glu Ala
                245                 250                 255
```

```
act cca cat tat ttt gcc tta att gat caa cta att gaa gga cat cag        816
Thr Pro His Tyr Phe Ala Leu Ile Asp Gln Leu Ile Glu Gly His Gln
        260                 265                 270 tgg ctg gaa aat aat ata gga gtg aaa cct cgg tcc ggc tgg gct att        864
Trp Leu Glu Asn Asn Ile Gly Val Lys Pro Arg Ser Gly Trp Ala Ile
    275                 280                 285 gat ccc ttt gga cac tca cca aca atg gct tat ctt cta aac cgt gct        912
Asp Pro Phe Gly His Ser Pro Thr Met Ala Tyr Leu Leu Asn Arg Ala
290                 295                 300 gga ctt tct cac atg ctt atc cag aga gtt cat tat gca gtt aaa aaa        960
Gly Leu Ser His Met Leu Ile Gln Arg Val His Tyr Ala Val Lys Lys
305                 310                 315                 320 cac ttt gca ctg cat aaa aca ttg gag ttt ttt tgg aga cag aat tgg       1008
His Phe Ala Leu His Lys Thr Leu Glu Phe Phe Trp Arg Gln Asn Trp
                325                 330                 335 gat ctg gga tct gtc aca gat att tta tgc cac atg atg ccc ttc tac       1056
Asp Leu Gly Ser Val Thr Asp Ile Leu Cys His Met Met Pro Phe Tyr
            340                 345                 350 agc tat gac atc cct cac act tgt gga cct gat cct aaa ata tgc tgc       1104
Ser Tyr Asp Ile Pro His Thr Cys Gly Pro Asp Pro Lys Ile Cys Cys
        355                 360                 365 cag ttt gat ttt aaa cgt ctt cct gga ggc aga ttt ggt tgt ccc tgg       1152
Gln Phe Asp Phe Lys Arg Leu Pro Gly Gly Arg Phe Gly Cys Pro Trp
    370                 375                 380 gga gtc ccc cca gaa aca ata cat cct gga aat gtc caa agc agg gct       1200
Gly Val Pro Pro Glu Thr Ile His Pro Gly Asn Val Gln Ser Arg Ala
385                 390                 395                 400 cgg atg cta cta gat cag tac cga aag aag tca aag ctt ttt cga acc       1248
Arg Met Leu Leu Asp Gln Tyr Arg Lys Lys Ser Lys Leu Phe Arg Thr
                405                 410                 415 aaa gtt ctc ctg gct cca cta gga gat gat ttc cgc tac tgt gaa tac       1296
Lys Val Leu Leu Ala Pro Leu Gly Asp Asp Phe Arg Tyr Cys Glu Tyr
            420                 425                 430 acg gaa tgg gat tta cag ttt aag aat tat cag cag ctt ttt gat tat       1344
Thr Glu Trp Asp Leu Gln Phe Lys Asn Tyr Gln Gln Leu Phe Asp Tyr
        435                 440                 445 atg aat tct cag tcc aag ttt aaa gtt aag ata cag ttt gga act tta       1392
Met Asn Ser Gln Ser Lys Phe Lys Val Lys Ile Gln Phe Gly Thr Leu
    450                 455                 460 tca gat ttt ttt gat gcg ctg gat aaa gca gat gaa act cag aga gac       1440
Ser Asp Phe Phe Asp Ala Leu Asp Lys Ala Asp Glu Thr Gln Arg Asp
465                 470                 475                 480 aag ggc caa tcg atg ttc cct gtt tta agt gga gat ttt ttc act tat       1488
Lys Gly Gln Ser Met Phe Pro Val Leu Ser Gly Asp Phe Phe Thr Tyr
                485                 490                 495 gcc gat cga gat gat cat tac tgg agt ggc tat ttt aca tcc aga ccc       1536
Ala Asp Arg Asp Asp His Tyr Trp Ser Gly Tyr Phe Thr Ser Arg Pro
            500                 505                 510 ttt tac aaa cga atg gac aga atc atg gaa tct cat tta agg gct gct       1584
Phe Tyr Lys Arg Met Asp Arg Ile Met Glu Ser His Leu Arg Ala Ala
        515                 520                 525 gaa att ctt tac tat ttc gcc ctg aga caa gct cac aaa tac aag ata       1632
Glu Ile Leu Tyr Tyr Phe Ala Leu Arg Gln Ala His Lys Tyr Lys Ile
    530                 535                 540 aat aaa ttt ctc tca tca tca ctt tac acg gca ctg aca gaa gcc aga       1680
Asn Lys Phe Leu Ser Ser Ser Leu Tyr Thr Ala Leu Thr Glu Ala Arg
545                 550                 555                 560 agg aat ttg gga ctg ttt caa cat cat gat gct atc aca gga act gca       1728
Arg Asn Leu Gly Leu Phe Gln His His Asp Ala Ile Thr Gly Thr Ala
                565                 570                 575
```

-continued

```
aaa gac tgg gtg gtt gtg gat tat ggt acc aga ctt ttt cat tcg tta      1776
Lys Asp Trp Val Val Val Asp Tyr Gly Thr Arg Leu Phe His Ser Leu
        580                 585                 590 atg gtt ttg gag aag ata att gga aat tct gca ttt ctt ctt att ggg      1824
Met Val Leu Glu Lys Ile Ile Gly Asn Ser Ala Phe Leu Leu Ile Gly
            595                 600                 605 aag gac aaa ctc aca tac gac tct tac tct cct gat acc ttc ctg gag      1872
Lys Asp Lys Leu Thr Tyr Asp Ser Tyr Ser Pro Asp Thr Phe Leu Glu
        610                 615                 620 atg gat ttg aaa caa aaa tca caa gat tct ctg cca caa aaa aat ata      1920
Met Asp Leu Lys Gln Lys Ser Gln Asp Ser Leu Pro Gln Lys Asn Ile
625                 630                 635                 640 ata agg ctg agt gcg gag cca agg tac ctt gtg gtc tat aat cct tta      1968
Ile Arg Leu Ser Ala Glu Pro Arg Tyr Leu Val Val Tyr Asn Pro Leu
                645                 650                 655 gaa caa gac cga atc tcg ttg gtc tca gtc tat gtg agt tcc ccg aca      2016
Glu Gln Asp Arg Ile Ser Leu Val Ser Val Tyr Val Ser Ser Pro Thr
        660                 665                 670 gtg caa gtg ttc tct gct tca gga aaa cct gtg gaa gtt caa gtc agc      2064
Val Gln Val Phe Ser Ala Ser Gly Lys Pro Val Glu Val Gln Val Ser
            675                 680                 685 gca gtt tgg gat aca gca aat act att tca gaa aca gcc tat gag atc      2112
Ala Val Trp Asp Thr Ala Asn Thr Ile Ser Glu Thr Ala Tyr Glu Ile
        690                 695                 700 tct ttt cga gca cat ata ccg cca ttg gga ctg aaa gtg tat aag att      2160
Ser Phe Arg Ala His Ile Pro Pro Leu Gly Leu Lys Val Tyr Lys Ile
705                 710                 715                 720 ttg gaa tca gca agt tca aat tca cat tta gct gat tat gtc ttg tat      2208
Leu Glu Ser Ala Ser Ser Asn Ser His Leu Ala Asp Tyr Val Leu Tyr
                725                 730                 735 aag aat aaa gta gaa gat agc gga att ttc acc ata aag aat atg ata      2256
Lys Asn Lys Val Glu Asp Ser Gly Ile Phe Thr Ile Lys Asn Met Ile
        740                 745                 750 aat act gaa gaa ggt ata aca cta gag aac tcc ttt gtt tta ctt cgg      2304
Asn Thr Glu Glu Gly Ile Thr Leu Glu Asn Ser Phe Val Leu Leu Arg
            755                 760                 765 ttt gat caa act gga ctt atg aag caa atg atg act aaa gaa gat ggt      2352
Phe Asp Gln Thr Gly Leu Met Lys Gln Met Met Thr Lys Glu Asp Gly
        770                 775                 780 aaa cac cat gaa gta aat gtg caa ttt tca tgg tat gga acc aca att      2400
Lys His His Glu Val Asn Val Gln Phe Ser Trp Tyr Gly Thr Thr Ile
785                 790                 795                 800 aaa aga gac aaa agt ggt gcc tac ctc ttc tta cct gat ggt aat gcc      2448
Lys Arg Asp Lys Ser Gly Ala Tyr Leu Phe Leu Pro Asp Gly Asn Ala
                805                 810                 815 aag cct tat gtt tac aca aca ccg ccc ttt gtc aga gtg aca cat gga      2496
Lys Pro Tyr Val Tyr Thr Thr Pro Pro Phe Val Arg Val Thr His Gly
        820                 825                 830 agg att tat tcg gaa gtg act tgc ttt ttt gac cat gtt act cat aga      2544
Arg Ile Tyr Ser Glu Val Thr Cys Phe Phe Asp His Val Thr His Arg
            835                 840                 845 gtc cga cta tac cac ata cag gga ata gaa gga cag tct gtg gaa gtt      2592
Val Arg Leu Tyr His Ile Gln Gly Ile Glu Gly Gln Ser Val Glu Val
        850                 855                 860 tcc aat att gtg gac atc cga aaa gta tat aac cgt gag att gca atg      2640
Ser Asn Ile Val Asp Ile Arg Lys Val Tyr Asn Arg Glu Ile Ala Met
865                 870                 875                 880 aaa att tct tct gat ata aaa agc caa aat aga ttt tat act gac cta      2688
Lys Ile Ser Ser Asp Ile Lys Ser Gln Asn Arg Phe Tyr Thr Asp Leu
```

| | | |
|---|---|---|
| aat ggg tac cag att caa cct aga atg aca ctg agc aaa ttg cct ctt<br>Asn Gly Tyr Gln Ile Gln Pro Arg Met Thr Leu Ser Lys Leu Pro Leu<br>900 905 910 | | 2736 |
| caa gca aat gtc tat ccc atg acc aca atg gcc tat atc cag gat gcc<br>Gln Ala Asn Val Tyr Pro Met Thr Met Ala Tyr Ile Gln Asp Ala<br>915 920 925 | | 2784 |
| aaa cat cgt ttg aca ctg ctc tct gct cag tca tta ggg gtt tcg agt<br>Lys His Arg Leu Thr Leu Leu Ser Ala Gln Ser Leu Gly Val Ser Ser<br>930 935 940 | | 2832 |
| ttg aat agt ggt cag att gaa gtt atc atg gat cga aga ctc atg caa<br>Leu Asn Ser Gly Gln Ile Glu Val Ile Met Asp Arg Arg Leu Met Gln<br>945 950 955 960 | | 2880 |
| gat gat aat cgt ggc ctt gag caa ggt atc cag gat aac aag att aca<br>Asp Asp Asn Arg Gly Leu Glu Gln Gly Ile Gln Asp Asn Lys Ile Thr<br>965 970 975 | | 2928 |
| gct aat cta ttt cga ata cta cta gaa aaa aga agt gct gtt aat acg<br>Ala Asn Leu Phe Arg Ile Leu Leu Glu Lys Arg Ser Ala Val Asn Thr<br>980 985 990 | | 2976 |
| gaa gaa gaa aag aag tcg gtc agt tat cct tct ctc ctt agc cac ata<br>Glu Glu Glu Lys Lys Ser Val Ser Tyr Pro Ser Leu Leu Ser His Ile<br>995 1000 1005 | | 3024 |
| act tct tct ctc atg aat cat cca gtc att cca atg gca aat aag ttc<br>Thr Ser Ser Leu Met Asn His Pro Val Ile Pro Met Ala Asn Lys Phe<br>1010 1015 1020 | | 3072 |
| tcc tca cct acc ctt gag ctg caa ggt gaa ttc tct cca tta cag tca<br>Ser Ser Pro Thr Leu Glu Leu Gln Gly Glu Phe Ser Pro Leu Gln Ser<br>1025 1030 1035 1040 | | 3120 |
| tct ttg cct tgt gac att cat ctg gtt aat ttg aga aca ata cag tca<br>Ser Leu Pro Cys Asp Ile His Leu Val Asn Leu Arg Thr Ile Gln Ser<br>1045 1050 1055 | | 3168 |
| aag gtg ggc aat ggg cac tcc aat gag gca gcc ttg atc ctc cac aga<br>Lys Val Gly Asn Gly His Ser Asn Glu Ala Ala Leu Ile Leu His Arg<br>1060 1065 1070 | | 3216 |
| aaa ggg ttt gat tgt cgg ttc tct agc aaa ggc aca ggg ctg ttt tgt<br>Lys Gly Phe Asp Cys Arg Phe Ser Ser Lys Gly Thr Gly Leu Phe Cys<br>1075 1080 1085 | | 3264 |
| tct act act cag gga aag ata ttg gta cag aaa ctt tta aac aag ttt<br>Ser Thr Thr Gln Gly Lys Ile Leu Val Gln Lys Leu Leu Asn Lys Phe<br>1090 1095 1100 | | 3312 |
| att gtc gaa agt ctc aca cct tca tca cta tcc ttg atg cat tca cct<br>Ile Val Glu Ser Leu Thr Pro Ser Ser Leu Ser Leu Met His Ser Pro<br>1105 1110 1115 1120 | | 3360 |
| ccc ggc act cag aat ata agt gag atc aac ttg agt cca atg gaa atc<br>Pro Gly Thr Gln Asn Ile Ser Glu Ile Asn Leu Ser Pro Met Glu Ile<br>1125 1130 1135 | | 3408 |
| agc aca ttc cga atc cag ttg agg tga<br>Ser Thr Phe Arg Ile Gln Leu Arg<br>1140 | | 3435 |

<210> SEQ ID NO 54
<211> LENGTH: 3453
<212> TYPE: DNA
<213> ORGANISM: Mus musculus
<220> FEATURE:
<221> NAME/KEY: CDS
<222> LOCATION: (1)..(3450)

<400> SEQUENCE: 54

| | |
|---|---|
| atg aag tta agt cgc cag ttc acc gtg ttt ggc agc gcg atc ttc tgc<br>Met Lys Leu Ser Arg Gln Phe Thr Val Phe Gly Ser Ala Ile Phe Cys | 48 |

-continued

|   |   |   |   |   |   |   |   |   |   |   |   |   |   |   |   |   |
|---|---|---|---|---|---|---|---|---|---|---|---|---|---|---|---|---|
| 1 |   |   |   | 5 |   |   |   |   | 10 |   |   |   |   | 15 |   |   |

```
gtc gta atc ttc tca ctc tac ctg atg ctg gac agg ggt cac ttg gac    96
Val Val Ile Phe Ser Leu Tyr Leu Met Leu Asp Arg Gly His Leu Asp
             20                  25                  30 tac cct cgg ggc ccg cgc cag gag ggc tcc ttt ccg cag ggc cag ctt   144
Tyr Pro Arg Gly Pro Arg Gln Glu Gly Ser Phe Pro Gln Gly Gln Leu
         35                  40                  45 tca ata ttg caa gaa aag att gac cat ttg gag cgt ttg ctc gct gag   192
Ser Ile Leu Gln Glu Lys Ile Asp His Leu Glu Arg Leu Leu Ala Glu
     50                  55                  60 aac aac gag atc atc tca aat atc aga gac tca gtc atc aac ctg agc   240
Asn Asn Glu Ile Ile Ser Asn Ile Arg Asp Ser Val Ile Asn Leu Ser
 65                  70                  75                  80 gag tct gtg gag gac ggc ccg cgg gga tca cca ggc aac gcc agc caa   288
Glu Ser Val Glu Asp Gly Pro Arg Gly Ser Pro Gly Asn Ala Ser Gln
                 85                  90                  95 ggc tcc atc cac ctc cac tcg cca cag ttg gcc ctg cag gct gac ccc   336
Gly Ser Ile His Leu His Ser Pro Gln Leu Ala Leu Gln Ala Asp Pro
            100                 105                 110 aga gac tgt ttg ttt gct tca cag agt ggg agt cag ccc cgg gat gtg   384
Arg Asp Cys Leu Phe Ala Ser Gln Ser Gly Ser Gln Pro Arg Asp Val
        115                 120                 125 cag atg ttg gat gtt tac gat ctg att cct ttt gat aat cca gat ggt   432
Gln Met Leu Asp Val Tyr Asp Leu Ile Pro Phe Asp Asn Pro Asp Gly
    130                 135                 140 gga gtt tgg aag caa gga ttt gac att aag tat gaa gcg gat gag tgg   480
Gly Val Trp Lys Gln Gly Phe Asp Ile Lys Tyr Glu Ala Asp Glu Trp
145                 150                 155                 160 gac cat gag ccc ctg caa gtg ttt gtg gtg cct cac tcc cat aat gac   528
Asp His Glu Pro Leu Gln Val Phe Val Val Pro His Ser His Asn Asp
                165                 170                 175 cca ggt tgg ttg aag act ttc aat gac tac ttt aga gac aag act cag   576
Pro Gly Trp Leu Lys Thr Phe Asn Asp Tyr Phe Arg Asp Lys Thr Gln
            180                 185                 190 tat att ttt aat aac atg gtc cta aag ctg aaa gaa gac tca agc agg   624
Tyr Ile Phe Asn Asn Met Val Leu Lys Leu Lys Glu Asp Ser Ser Arg
        195                 200                 205 aag ttt atg tgg tct gag atc tct tac ctt gca aaa tgg tgg gat att   672
Lys Phe Met Trp Ser Glu Ile Ser Tyr Leu Ala Lys Trp Trp Asp Ile
    210                 215                 220 ata gat att ccg aag aag gaa gct gtt aaa agt tta cta cag aat ggt   720
Ile Asp Ile Pro Lys Lys Glu Ala Val Lys Ser Leu Leu Gln Asn Gly
225                 230                 235                 240 cag ctg gaa att gtg acc ggt ggc tgg gtt atg cct gat gaa gcc act   768
Gln Leu Glu Ile Val Thr Gly Gly Trp Val Met Pro Asp Glu Ala Thr
                245                 250                 255 cca cat tat ttt gcc tta att gac caa cta att gaa ggg cac caa tgg   816
Pro His Tyr Phe Ala Leu Ile Asp Gln Leu Ile Glu Gly His Gln Trp
            260                 265                 270 ctg gaa aaa aat cta gga gtg aaa cct cga tcg ggc tgg gcc ata gat   864
Leu Glu Lys Asn Leu Gly Val Lys Pro Arg Ser Gly Trp Ala Ile Asp
        275                 280                 285 ccc ttt ggt cat tca ccc aca atg gct tat ctt cta aag cgt gct gga   912
Pro Phe Gly His Ser Pro Thr Met Ala Tyr Leu Leu Lys Arg Ala Gly
    290                 295                 300 ttt tca cac atg ctc atc cag aga gtc cat tat gca atc aaa aaa cac   960
Phe Ser His Met Leu Ile Gln Arg Val His Tyr Ala Ile Lys Lys His
305                 310                 315                 320 ttc tct ttg cat aaa acg ctg gag ttt ttc tgg aga cag aat tgg gat  1008
```

```
                Phe Ser Leu His Lys Thr Leu Glu Phe Phe Trp Arg Gln Asn Trp Asp
                                325                 330                 335 ctt gga tct gct aca gac att ttg tgc cat atg atg ccc ttc tac agc         1056
Leu Gly Ser Ala Thr Asp Ile Leu Cys His Met Met Pro Phe Tyr Ser
            340                 345                 350 tac gac atc cct cac acc tgt ggg cct gat cct aaa ata tgc tgc cag         1104
Tyr Asp Ile Pro His Thr Cys Gly Pro Asp Pro Lys Ile Cys Cys Gln
        355                 360                 365 ttt gat ttt aaa cgg ctt cct gga ggc aga tat ggt tgt ccc tgg gga         1152
Phe Asp Phe Lys Arg Leu Pro Gly Gly Arg Tyr Gly Cys Pro Trp Gly
    370                 375                 380 gtt ccc cca gaa gca ata tct cct gga aat gtc caa agc agg gct cag         1200
Val Pro Pro Glu Ala Ile Ser Pro Gly Asn Val Gln Ser Arg Ala Gln
385                 390                 395                 400 atg cta ttg gat cag tac cgg aaa aag tca aaa ctt ttc cgc act aaa         1248
Met Leu Leu Asp Gln Tyr Arg Lys Lys Ser Lys Leu Phe Arg Thr Lys
                405                 410                 415 gtt ctg ctg gct cca ctg gga gac gac ttt cgg ttc agt gaa tac aca         1296
Val Leu Leu Ala Pro Leu Gly Asp Asp Phe Arg Phe Ser Glu Tyr Thr
            420                 425                 430 gag tgg gat ctg cag tgc agg aac tac gag caa ctg ttc agt tac atg         1344
Glu Trp Asp Leu Gln Cys Arg Asn Tyr Glu Gln Leu Phe Ser Tyr Met
        435                 440                 445 aac tcg cag cct cat ctg aaa gtg aag atc cag ttt gga acc ttg tca         1392
Asn Ser Gln Pro His Leu Lys Val Lys Ile Gln Phe Gly Thr Leu Ser
    450                 455                 460 gat tat ttc gac gca ttg gag aaa gcg gtg gca gcc gag aag aag agt         1440
Asp Tyr Phe Asp Ala Leu Glu Lys Ala Val Ala Ala Glu Lys Lys Ser
465                 470                 475                 480 agc cag tct gtg ttc cct gcc ctg agt gga gac ttc ttc acg tac gct         1488
Ser Gln Ser Val Phe Pro Ala Leu Ser Gly Asp Phe Phe Thr Tyr Ala
                485                 490                 495 gac aga gac gac cat tac tgg agt ggc tac ttc acg tcc aga cct ttc         1536
Asp Arg Asp Asp His Tyr Trp Ser Gly Tyr Phe Thr Ser Arg Pro Phe
            500                 505                 510 tac aaa cga atg gac aga ata atg gaa tct cgt ata agg gct gct gaa         1584
Tyr Lys Arg Met Asp Arg Ile Met Glu Ser Arg Ile Arg Ala Ala Glu
        515                 520                 525 att ctt tac cag ttg gcc ttg aaa caa gct cag aaa tac aag ata aat         1632
Ile Leu Tyr Gln Leu Ala Leu Lys Gln Ala Gln Lys Tyr Lys Ile Asn
    530                 535                 540 aaa ttt ctt tca tca cct cat tac aca aca ctg aca gaa gcc aga agg         1680
Lys Phe Leu Ser Ser Pro His Tyr Thr Thr Leu Thr Glu Ala Arg Arg
545                 550                 555                 560 aac tta gga cta ttt cag cat cat gat gcc atc aca gga acc gcg aaa         1728
Asn Leu Gly Leu Phe Gln His His Asp Ala Ile Thr Gly Thr Ala Lys
                565                 570                 575 gac tgg gtg gtt gtg gac tat ggt acc aga ctc ttt cag tca tta aat         1776
Asp Trp Val Val Val Asp Tyr Gly Thr Arg Leu Phe Gln Ser Leu Asn
            580                 585                 590 tct ttg gag aag ata att gga gat tct gca ttt ctt ctc att tta aag         1824
Ser Leu Glu Lys Ile Ile Gly Asp Ser Ala Phe Leu Leu Ile Leu Lys
        595                 600                 605 gac aaa aag ctg tac cag tca gat cct tcc aaa gcc ttc tta gag atg         1872
Asp Lys Lys Leu Tyr Gln Ser Asp Pro Ser Lys Ala Phe Leu Glu Met
    610                 615                 620 gat acg aag caa agt tca caa gat tct ctg ccc caa aaa att ata ata         1920
Asp Thr Lys Gln Ser Ser Gln Asp Ser Leu Pro Gln Lys Ile Ile Ile
625                 630                 635                 640
```

```
caa ctg agc gca cag gag cca agg tac ctt gtg gtc tac aat ccc ttt    1968
Gln Leu Ser Ala Gln Glu Pro Arg Tyr Leu Val Val Tyr Asn Pro Phe
            645                 650                 655 gaa caa gaa cgg cat tca gtg gtg tcc atc cgg gta aac tcc gcc aca    2016
Glu Gln Glu Arg His Ser Val Val Ser Ile Arg Val Asn Ser Ala Thr
        660                 665                 670 ggg aaa gtg ctg tct gat tcg gga aaa ccg gtg gag gtt caa gtc agt    2064
Gly Lys Val Leu Ser Asp Ser Gly Lys Pro Val Glu Val Gln Val Ser
    675                 680                 685 gca gtt tgg aac gac atg agg aca att tca caa gca gcc tat gag gtt    2112
Ala Val Trp Asn Asp Met Arg Thr Ile Ser Gln Ala Ala Tyr Glu Val
690                 695                 700 tct ttt cta gct cat ata cca cca ctg gga ctg aaa gtg ttt aag atc    2160
Ser Phe Leu Ala His Ile Pro Pro Leu Gly Leu Lys Val Phe Lys Ile
705                 710                 715                 720 tta gag tca caa agt tca agc tca cac ttg gct gat tat gtc cta tat    2208
Leu Glu Ser Gln Ser Ser Ser Ser His Leu Ala Asp Tyr Val Leu Tyr
                725                 730                 735 aat aat gat gga cta gca gaa aat gga ata ttc cac gtg aag aac atg    2256
Asn Asn Asp Gly Leu Ala Glu Asn Gly Ile Phe His Val Lys Asn Met
            740                 745                 750 gtg gat gct gga gat gcc ata aca ata gag aat ccc ttc ctg gcg att    2304
Val Asp Ala Gly Asp Ala Ile Thr Ile Glu Asn Pro Phe Leu Ala Ile
        755                 760                 765 tgg ttt gac cga tct ggg ctg atg gag aaa gtg aga agg aaa gaa gac    2352
Trp Phe Asp Arg Ser Gly Leu Met Glu Lys Val Arg Arg Lys Glu Asp
    770                 775                 780 agt aga cag cat gaa ctg aag gtc cag ttc ctg tgg tac gga acc acc    2400
Ser Arg Gln His Glu Leu Lys Val Gln Phe Leu Trp Tyr Gly Thr Thr
785                 790                 795                 800 aac aaa agg gac aag agc ggt gcc tac ctc ttc ctg cct gac ggg cag    2448
Asn Lys Arg Asp Lys Ser Gly Ala Tyr Leu Phe Leu Pro Asp Gly Gln
                805                 810                 815 ggc cag cca tat gtt tcc cta aga ccg ccc ttt gtc aga gtg aca cgt    2496
Gly Gln Pro Tyr Val Ser Leu Arg Pro Pro Phe Val Arg Val Thr Arg
            820                 825                 830 gga agg atc tac tca gat gtg acc tgt ttc ctc gaa cac gtt act cac    2544
Gly Arg Ile Tyr Ser Asp Val Thr Cys Phe Leu Glu His Val Thr His
        835                 840                 845 aaa gtc cgc ctg tac aac att cag gga ata gaa ggt cag tcc atg gaa    2592
Lys Val Arg Leu Tyr Asn Ile Gln Gly Ile Glu Gly Gln Ser Met Glu
    850                 855                 860 gtt tct aat att gta aac atc agg aat gtg cat aac cgt gag att gta    2640
Val Ser Asn Ile Val Asn Ile Arg Asn Val His Asn Arg Glu Ile Val
865                 870                 875                 880 atg aga att tca tct aaa ata aac aac caa aat aga tat tat act gac    2688
Met Arg Ile Ser Ser Lys Ile Asn Asn Gln Asn Arg Tyr Tyr Thr Asp
                885                 890                 895 cta aat gga tat cag att cag cct aga agg acc atg agc aaa ttg cct    2736
Leu Asn Gly Tyr Gln Ile Gln Pro Arg Arg Thr Met Ser Lys Leu Pro
            900                 905                 910 ctt caa gcc aac gtt tac ccg atg tgc aca atg gcg tat atc cag gat    2784
Leu Gln Ala Asn Val Tyr Pro Met Cys Thr Met Ala Tyr Ile Gln Asp
        915                 920                 925 gct gag cac cgg ctc acg ctg ctc tct gct cag tct cta ggt gct tcc    2832
Ala Glu His Arg Leu Thr Leu Leu Ser Ala Gln Ser Leu Gly Ala Ser
    930                 935                 940 agc atg gct tct ggt cag att gaa gtc ttc atg gat cga agg ctc atg    2880
Ser Met Ala Ser Gly Gln Ile Glu Val Phe Met Asp Arg Arg Leu Met
945                 950                 955                 960
```

```
cag gat gat aac cgt ggc ctt ggg caa ggc gtc cat gac aat aag att    2928
Gln Asp Asp Asn Arg Gly Leu Gly Gln Gly Val His Asp Asn Lys Ile
                965                 970                 975 aca gct aat ttg ttt cga atc ctc ctc gag aag aga agc gct gtg aac    2976
Thr Ala Asn Leu Phe Arg Ile Leu Leu Glu Lys Arg Ser Ala Val Asn
            980                 985                 990 atg gaa gaa gaa aag aag agc cct gtc agc tac cct tcc ctc ctc agc    3024
Met Glu Glu Glu Lys Lys Ser Pro Val Ser Tyr Pro Ser Leu Leu Ser
        995                1000                1005 cac atg act tcg tcc ttc ctc aac cat ccc ttt ctc ccc atg gta cta    3072
His Met Thr Ser Ser Phe Leu Asn His Pro Phe Leu Pro Met Val Leu
    1010                1015                1020 agt ggc cag ctc ccc tcc cct gcc ttt gag ctg ctg agt gaa ttt cct    3120
Ser Gly Gln Leu Pro Ser Pro Ala Phe Glu Leu Leu Ser Glu Phe Pro
1025                1030                1035                1040 ctg ctg cag tcc tct cta cct tgt gat atc cat ctg gtc aac ctg cgg    3168
Leu Leu Gln Ser Ser Leu Pro Cys Asp Ile His Leu Val Asn Leu Arg
                1045                1050                1055 aca ata caa tca aag atg ggc aaa ggc tat tcg gat gag gca gcc ttg    3216
Thr Ile Gln Ser Lys Met Gly Lys Gly Tyr Ser Asp Glu Ala Ala Leu
            1060                1065                1070 atc ctc cac agg aaa ggg ttt gat tgc cag ttc tcc agc aga ggc atc    3264
Ile Leu His Arg Lys Gly Phe Asp Cys Gln Phe Ser Ser Arg Gly Ile
        1075                1080                1085 ggg cta ccc tgt tcc act act cag gga aag atg tca gtt ctg aaa ctt    3312
Gly Leu Pro Cys Ser Thr Thr Gln Gly Lys Met Ser Val Leu Lys Leu
    1090                1095                1100 ttc aac aag ttt gct gtg gag agt ctc gtc cct tcc tct ctg tcc ttg    3360
Phe Asn Lys Phe Ala Val Glu Ser Leu Val Pro Ser Ser Leu Ser Leu
1105                1110                1115                1120 atg cac tcc cct cca gat gcc cag aac atg agt gaa gtc agc ctg agc    3408
Met His Ser Pro Pro Asp Ala Gln Asn Met Ser Glu Val Ser Leu Ser
                1125                1130                1135 ccc atg gag atc agc acg ttc cgt atc cgc ttg cgt tgg acc tga        3453
Pro Met Glu Ile Ser Thr Phe Arg Ile Arg Leu Arg Trp Thr
            1140                1145                1150

<210> SEQ ID NO 55
<211> LENGTH: 3840
<212> TYPE: DNA
<213> ORGANISM: Rattus norvegicus
<220> FEATURE:
<221> NAME/KEY: CDS
<222> LOCATION: (1)..(3837)

<400> SEQUENCE: 55 atg gcc tgt ata ggt gga gcc cag ggg caa cgg cag gcc gtg gaa aag     48
Met Ala Cys Ile Gly Gly Ala Gln Gly Gln Arg Gln Ala Val Glu Lys
  1               5                  10                  15 gaa cct tcc cac caa ggg tat ccg tgg aag cca atg acc aat ggc agc     96
Glu Pro Ser His Gln Gly Tyr Pro Trp Lys Pro Met Thr Asn Gly Ser
             20                  25                  30 tgc tca gaa ctg gca ttg ctc agc aaa acc cga atg tac tgt cac cag    144
Cys Ser Glu Leu Ala Leu Leu Ser Lys Thr Arg Met Tyr Cys His Gln
         35                  40                  45 gga tgt gtc agg cca ccc agg act gac gtg aaa aac ttc aag acc aca    192
Gly Cys Val Arg Pro Pro Arg Thr Asp Val Lys Asn Phe Lys Thr Thr
     50                  55                  60 act gat act cag agt gtg cct ggt gtc agt atg aag ctg aaa aag cag    240
Thr Asp Thr Gln Ser Val Pro Gly Val Ser Met Lys Leu Lys Lys Gln
 65                  70                  75                  80
```

-continued

| | |
|---|---|
| gtg aca gtg tgc ggg gct gct atc ttc tgt gtg gcc gtc ttt tcc ctg<br>Val Thr Val Cys Gly Ala Ala Ile Phe Cys Val Ala Val Phe Ser Leu<br>                        85                          90                        95 | 288 |
| tac cta atg ctg gac cga gtg cag cat gat cct gcc aga cac cag aat<br>Tyr Leu Met Leu Asp Arg Val Gln His Asp Pro Ala Arg His Gln Asn<br>                100                        105                      110 | 336 |
| ggt ggg aac ttc ccc agg agc caa att tct gtg cta cag aac cgg atc<br>Gly Gly Asn Phe Pro Arg Ser Gln Ile Ser Val Leu Gln Asn Arg Ile<br>     115                        120                      125 | 384 |
| gaa cag ctg gaa cag ctg ctg gaa gaa aac cat gag atc ata agc cat<br>Glu Gln Leu Glu Gln Leu Leu Glu Glu Asn His Glu Ile Ile Ser His<br>130                        135                      140 | 432 |
| atc aag gac tct gtg ctg gaa ctg aca gcc aat gcg gag ggc cca cca<br>Ile Lys Asp Ser Val Leu Glu Leu Thr Ala Asn Ala Glu Gly Pro Pro<br>145                        150                      155                      160 | 480 |
| gcc ctg ctg ccc tac cac aca gcc aac ggc tcc tgg gct gtg ctc ccc<br>Ala Leu Leu Pro Tyr His Thr Ala Asn Gly Ser Trp Ala Val Leu Pro<br>                165                        170                      175 | 528 |
| gag ccc cgg ccc agc ttc ttc tct gta tcc cct gag gac tgc cag ttt<br>Glu Pro Arg Pro Ser Phe Phe Ser Val Ser Pro Glu Asp Cys Gln Phe<br>                  180                        185                      190 | 576 |
| gct ttg ggg ggc cgg ggt cag aag cca gag cta cag atg tta act gtg<br>Ala Leu Gly Gly Arg Gly Gln Lys Pro Glu Leu Gln Met Leu Thr Val<br>     195                        200                      205 | 624 |
| tct gag gat ttg ccg ttt gac aat gtg gag ggc ggc gtg tgg agg caa<br>Ser Glu Asp Leu Pro Phe Asp Asn Val Glu Gly Gly Val Trp Arg Gln<br>210                        215                      220 | 672 |
| ggc ttc gac atc tcc tac agc cca aat gac tgg gat gct gaa gac ctg<br>Gly Phe Asp Ile Ser Tyr Ser Pro Asn Asp Trp Asp Ala Glu Asp Leu<br>225                        230                      235                      240 | 720 |
| cag gtg ttt gtg gtg cct cac tcc cac aat gat cca ggt gaa gag cca<br>Gln Val Phe Val Val Pro His Ser His Asn Asp Pro Gly Glu Glu Pro<br>                245                        250                      255 | 768 |
| gca ggc ccc agc cgc agc gtg cag ggt ggg ctt tct ggt gac agg cgc<br>Ala Gly Pro Ser Arg Ser Val Gln Gly Gly Leu Ser Gly Asp Arg Arg<br>                  260                        265                      270 | 816 |
| tgg atc aag act ttt gac aag tac tac acg gaa caa acc caa cac atc<br>Trp Ile Lys Thr Phe Asp Lys Tyr Tyr Thr Glu Gln Thr Gln His Ile<br>     275                        280                      285 | 864 |
| ctc aac agc atg gtg tcc aag ctg cag gaa gat ccc cga cgg cgc ttt<br>Leu Asn Ser Met Val Ser Lys Leu Gln Glu Asp Pro Arg Arg Arg Phe<br>290                        295                      300 | 912 |
| ctc tgg gca gaa gtc tcc ttc ttc gcc aag tgg tgg gac aac atc agt<br>Leu Trp Ala Glu Val Ser Phe Phe Ala Lys Trp Trp Asp Asn Ile Ser<br>305                        310                      315                      320 | 960 |
| gcc cag aaa agg gca gca gtt cga agg ctg gtg gga aat ggg cag ctg<br>Ala Gln Lys Arg Ala Ala Val Arg Arg Leu Val Gly Asn Gly Gln Leu<br>                  325                        330                      335 | 1008 |
| gaa att gca acg ggt gga tgg gtg atg cca gat gag gcc aac tcc cat<br>Glu Ile Ala Thr Gly Gly Trp Val Met Pro Asp Glu Ala Asn Ser His<br>                340                        345                      350 | 1056 |
| tac ttt gcc ctg gtg ggg cag ctc atc gag ggg ccc ccg cca gta cgc<br>Tyr Phe Ala Leu Val Gly Gln Leu Ile Glu Gly Pro Pro Pro Val Arg<br>                  355                        360                      365 | 1104 |
| agg gca gtg gac ccc ttt gga cac agc tcc acc atg cct tac ctg ctg<br>Arg Ala Val Asp Pro Phe Gly His Ser Ser Thr Met Pro Tyr Leu Leu<br>370                        375                      380 | 1152 |
| cgc cgt gcc aac ctg acc agc atg cta att cag agg gtg cat tac gcc<br>Arg Arg Ala Asn Leu Thr Ser Met Leu Ile Gln Arg Val His Tyr Ala | 1200 |

-continued

```
                385                 390                 395                 400
atc aag aag cac ttt gcg gcc act cac agc ctg gag ttc atg tgg agg         1248
Ile Lys Lys His Phe Ala Ala Thr His Ser Leu Glu Phe Met Trp Arg
                405                 410                 415 cag aca tgg gat tca gac tcc agc aca gac atc ttc tgc cac atg atg         1296
Gln Thr Trp Asp Ser Asp Ser Ser Thr Asp Ile Phe Cys His Met Met
                420                 425                 430 ccc ttc tac agc tac gac gtc cca cac acc tgt ggc cct gat ccc aag         1344
Pro Phe Tyr Ser Tyr Asp Val Pro His Thr Cys Gly Pro Asp Pro Lys
                435                 440                 445 atc tgc tgc cag ttt gat ttc aaa cgt ctg ccg ggt ggg aga atc aat         1392
Ile Cys Cys Gln Phe Asp Phe Lys Arg Leu Pro Gly Gly Arg Ile Asn
        450                 455                 460 tgt cct tgg aag gtg ccg ccg cgg gct atc aca gag gcc aac gtg gca         1440
Cys Pro Trp Lys Val Pro Pro Arg Ala Ile Thr Glu Ala Asn Val Ala
465                 470                 475                 480 gac agg gca gcc ctg ctc ctg gac cag tac cgg aag aag tcc cgg ctg         1488
Asp Arg Ala Ala Leu Leu Leu Asp Gln Tyr Arg Lys Lys Ser Arg Leu
                485                 490                 495 ttt cga agc agt gtc ctc ctt gtg ccg ctg ggt gat gac ttc cga tat         1536
Phe Arg Ser Ser Val Leu Leu Val Pro Leu Gly Asp Asp Phe Arg Tyr
                500                 505                 510 gac aag ccc cag gaa tgg gat gcc cag ttc ttc aac tat caa cgg ctc         1584
Asp Lys Pro Gln Glu Trp Asp Ala Gln Phe Phe Asn Tyr Gln Arg Leu
                515                 520                 525 ttt gac ttc ctc aac agc aag ccg gag ttc cac gta cag gca cag ttt         1632
Phe Asp Phe Leu Asn Ser Lys Pro Glu Phe His Val Gln Ala Gln Phe
        530                 535                 540 ggg acc ctc tct gag tat ttt gat gcc ctg tat aag agg aca gga gtg         1680
Gly Thr Leu Ser Glu Tyr Phe Asp Ala Leu Tyr Lys Arg Thr Gly Val
545                 550                 555                 560 gag cct ggt gcc cgg cct cca ggg ttt cct gtg ctg agt ggg gac ttc         1728
Glu Pro Gly Ala Arg Pro Pro Gly Phe Pro Val Leu Ser Gly Asp Phe
                565                 570                 575 ttc tcc tat gct gac cgg gag gac cac tac tgg aca ggc tat tac act         1776
Phe Ser Tyr Ala Asp Arg Glu Asp His Tyr Trp Thr Gly Tyr Tyr Thr
                580                 585                 590 tcc cgg cct ttc tat aag agc ttg gac cgc gtg cta gaa act cac ctt         1824
Ser Arg Pro Phe Tyr Lys Ser Leu Asp Arg Val Leu Glu Thr His Leu
                595                 600                 605 cgt ggg gca gag gtt cta tac agc ctg gct ttg gcg cat gcc cgc cgt         1872
Arg Gly Ala Glu Val Leu Tyr Ser Leu Ala Leu Ala His Ala Arg Arg
        610                 615                 620 tct gga ctg act ggc cag tat ccg ctg tct gat tac gct gtc ctg acg         1920
Ser Gly Leu Thr Gly Gln Tyr Pro Leu Ser Asp Tyr Ala Val Leu Thr
625                 630                 635                 640 gaa gct cgt cgt aca ctg ggc ctc ttc cag cac cac gat gcc atc acc         1968
Glu Ala Arg Arg Thr Leu Gly Leu Phe Gln His His Asp Ala Ile Thr
                645                 650                 655 gga act gcc aag gag gca gtt gta gta gac tat ggg gtc agg ttg ctg         2016
Gly Thr Ala Lys Glu Ala Val Val Val Asp Tyr Gly Val Arg Leu Leu
                660                 665                 670 cgt tcc ctg gtc agc cta aag cag gtc atc atc aat gct gcc cac tac         2064
Arg Ser Leu Val Ser Leu Lys Gln Val Ile Ile Asn Ala Ala His Tyr
        675                 680                 685 ctg gtg ctg ggg gac aag gag acc tac agc ttt gac cct agg gca ccc         2112
Leu Val Leu Gly Asp Lys Glu Thr Tyr Ser Phe Asp Pro Arg Ala Pro
690                 695                 700 ttc ctc caa atg gtg agc cag gcc tgg cga ggc tct cag agc acc ctc         2160
```

-continued

```
      Phe Leu Gln Met Val Ser Gln Ala Trp Arg Gly Ser Gln Ser Thr Leu
      705                 710                 715                 720 cac ccc agc gcg gcc ctt gtt cct gct gct gct gct tct gcc ctg ctg      2208
His Pro Ser Ala Ala Leu Val Pro Ala Ala Ala Ala Ser Ala Leu Leu
                725                 730                 735 ccg cag cga gct cct agg ttt gtg gtg gtc ttt aac cca ctg gaa cag      2256
Pro Gln Arg Ala Pro Arg Phe Val Val Val Phe Asn Pro Leu Glu Gln
            740                 745                 750 gag cgg ctc agt gtg gtg tcc ctg ctg gtc aac tca ccc cga gtg cga      2304
Glu Arg Leu Ser Val Val Ser Leu Leu Val Asn Ser Pro Arg Val Arg
        755                 760                 765 gtg ctt tca gag gag ggt cag ccc ttg tct gtg cag atc agt gtg cag      2352
Val Leu Ser Glu Glu Gly Gln Pro Leu Ser Val Gln Ile Ser Val Gln
    770                 775                 780 tgg agc tcc gcc acc aac atg gtc ccc gat gtc tac cag gtg tca gtg      2400
Trp Ser Ser Ala Thr Asn Met Val Pro Asp Val Tyr Gln Val Ser Val
785                 790                 795                 800 cct gtc cgc ctg cca gcc ctg ggc ctg ggt gtg ctg cag ctg cag cca      2448
Pro Val Arg Leu Pro Ala Leu Gly Leu Gly Val Leu Gln Leu Gln Pro
                805                 810                 815 gat ctc gat gga ccc tac aca ctg cag tct tcg gtg cat gtc tac ctg      2496
Asp Leu Asp Gly Pro Tyr Thr Leu Gln Ser Ser Val His Val Tyr Leu
            820                 825                 830 aac ggc gtg aaa ctg tct gtc agc agg caa aca aca ttc cct ctc cgt      2544
Asn Gly Val Lys Leu Ser Val Ser Arg Gln Thr Thr Phe Pro Leu Arg
        835                 840                 845 gtt gtg gac tcg ggc acc agt gac ttc gcc atc agc aat cga tac atg      2592
Val Val Asp Ser Gly Thr Ser Asp Phe Ala Ile Ser Asn Arg Tyr Met
    850                 855                 860 cag gtc tgg ttc tcc ggc ctt act ggg ctt ctc aag agc gtc cga cgt      2640
Gln Val Trp Phe Ser Gly Leu Thr Gly Leu Leu Lys Ser Val Arg Arg
865                 870                 875                 880 gtg gac gaa gag cag gaa cag cag gtg gac atg aag ctc ttc gtc tat      2688
Val Asp Glu Glu Gln Glu Gln Gln Val Asp Met Lys Leu Phe Val Tyr
                885                 890                 895 gga acc cgc aca tcc aag gat aag agt ggt gcc tac ctc ttc ctg cct      2736
Gly Thr Arg Thr Ser Lys Asp Lys Ser Gly Ala Tyr Leu Phe Leu Pro
            900                 905                 910 gat aac gag gct aag ccc tat gtc cct aag aaa cct cct gtg ctg cgc      2784
Asp Asn Glu Ala Lys Pro Tyr Val Pro Lys Lys Pro Pro Val Leu Arg
        915                 920                 925 gtc acc gaa ggc cct ttc ttc tca gag gtg gct gcg tat tat gag cac      2832
Val Thr Glu Gly Pro Phe Phe Ser Glu Val Ala Ala Tyr Tyr Glu His
    930                 935                 940 ttt cac caa gtg att cga ctt tac aac ctg cca ggg gta gag ggg ctg      2880
Phe His Gln Val Ile Arg Leu Tyr Asn Leu Pro Gly Val Glu Gly Leu
945                 950                 955                 960 tct ctg gac gtg tcg ttc cag gtg gac atc agg gac tac gtg aac aag      2928
Ser Leu Asp Val Ser Phe Gln Val Asp Ile Arg Asp Tyr Val Asn Lys
                965                 970                 975 gag cta gcc ctg cgc atc cac aca gac atc gac agc cag ggc act ttc      2976
Glu Leu Ala Leu Arg Ile His Thr Asp Ile Asp Ser Gln Gly Thr Phe
            980                 985                 990 ttc aca gac ctc aat ggc ttt cag gta cag ccc cgg aag tat ctg aag      3024
Phe Thr Asp Leu Asn Gly Phe Gln Val Gln Pro Arg Lys Tyr Leu Lys
        995                 1000                1005 aag ttg ccc ctg cag gct aat ttc tac cct atg cca gtc atg gcc tac      3072
Lys Leu Pro Leu Gln Ala Asn Phe Tyr Pro Met Pro Val Met Ala Tyr
    1010                1015                1020
```

-continued

```
atc cag gat tcc cag agg cgc ctc acg ctg cac act gct cag gct ctg         3120
Ile Gln Asp Ser Gln Arg Arg Leu Thr Leu His Thr Ala Gln Ala Leu
1025                1030                1035                1040 ggt gtc tcc agc ctc ggc aat ggc cag ctg gag gtg atc ttg gac cga         3168
Gly Val Ser Ser Leu Gly Asn Gly Gln Leu Glu Val Ile Leu Asp Arg
            1045                1050                1055 agg cta atg cag gat gac aac cgg gga cta ggc caa ggg ctc aaa gac         3216
Arg Leu Met Gln Asp Asp Asn Arg Gly Leu Gly Gln Gly Leu Lys Asp
        1060                1065                1070 aac aag atc acc tgc aac cat ttc cgc ctc ctg tta gaa cgt cga acc         3264
Asn Lys Ile Thr Cys Asn His Phe Arg Leu Leu Leu Glu Arg Arg Thr
    1075                1080                1085 ctg atg agc cct gag gtc caa cag gag cgc tct aca agc tac ccg tcc         3312
Leu Met Ser Pro Glu Val Gln Gln Glu Arg Ser Thr Ser Tyr Pro Ser
1090                1095                1100 ctc ctc agc cac atg act tcc atg tac ctc aac aca cct cct ctg gtc         3360
Leu Leu Ser His Met Thr Ser Met Tyr Leu Asn Thr Pro Pro Leu Val
1105                1110                1115                1120 tta ccg gtg gcc aag agg gag agc acc agc ccc act ctg cac tct ttc         3408
Leu Pro Val Ala Lys Arg Glu Ser Thr Ser Pro Thr Leu His Ser Phe
            1125                1130                1135 cac cct ctg gct tct ccg ttg ccc tgc gat ttc cat ctg ctc aat ctg         3456
His Pro Leu Ala Ser Pro Leu Pro Cys Asp Phe His Leu Leu Asn Leu
        1140                1145                1150 cgc atg ctc ccc gcc gag gtg agt gtc ccg gtc cgt gcc aat cct cac         3504
Arg Met Leu Pro Ala Glu Val Ser Val Pro Val Arg Ala Asn Pro His
    1155                1160                1165 cat cag gct gag cct tgc ctt ctt ggc aga cat gct gct gac cct cca         3552
His Gln Ala Glu Pro Cys Leu Leu Gly Arg His Ala Ala Asp Pro Pro
1170                1175                1180 ccg ctc ttg tcc ctg act gtc ttc cag gac acc ttg ccc gcg gct gat         3600
Pro Leu Leu Ser Leu Thr Val Phe Gln Asp Thr Leu Pro Ala Ala Asp
1185                1190                1195                1200 gct gct ctc atc cta cac cgc aag ggt ttt gac tgt ggc ctt gaa gcc         3648
Ala Ala Leu Ile Leu His Arg Lys Gly Phe Asp Cys Gly Leu Glu Ala
            1205                1210                1215 aag aac ctg ggc ttc aac tgt acc aca agc caa ggc aag ctg gcc ctg         3696
Lys Asn Leu Gly Phe Asn Cys Thr Thr Ser Gln Gly Lys Leu Ala Leu
        1220                1225                1230 ggg agc ctc ttc cat ggc ctg gat gtg cta ttc ctg cag ccc acc tct         3744
Gly Ser Leu Phe His Gly Leu Asp Val Leu Phe Leu Gln Pro Thr Ser
    1235                1240                1245 ttg act ttg cta tac cct ctg gcc tcg ccc tcc aac agc act gac atc         3792
Leu Thr Leu Leu Tyr Pro Leu Ala Ser Pro Ser Asn Ser Thr Asp Ile
1250                1255                1260 tct ctg gag ccc atg gag atc agc acc ttc cgc ctg cgc ttg ggt tag        3840
Ser Leu Glu Pro Met Glu Ile Ser Thr Phe Arg Leu Arg Leu Gly
1265                1270                1275

<210> SEQ ID NO 56
<211> LENGTH: 3420
<212> TYPE: DNA
<213> ORGANISM: Homo sapiens
<220> FEATURE:
<221> NAME/KEY: CDS
<222> LOCATION: (1)..(3417)

<400> SEQUENCE: 56 atg aag ctg aaa aag cag gtg aca gtg tgt ggg gct gcc atc ttc tgt          48
Met Lys Leu Lys Lys Gln Val Thr Val Cys Gly Ala Ala Ile Phe Cys
1               5                   10                  15
```

-continued

| | |
|---|---|
| gtg gca gtc ttc tcg ctc tac ctc atg ctg gac cga gtg caa cac gat<br>Val Ala Val Phe Ser Leu Tyr Leu Met Leu Asp Arg Val Gln His Asp<br>                  20                        25                      30 | 96 |
| ccc acc cga cac cag aat ggt ggg aac ttc ccc cgg agc caa att tct<br>Pro Thr Arg His Gln Asn Gly Gly Asn Phe Pro Arg Ser Gln Ile Ser<br>                  35                        40                      45 | 144 |
| gtg ctg cag aac cgc att gag cag ctg gag cag ctt ttg gag gag aac<br>Val Leu Gln Asn Arg Ile Glu Gln Leu Glu Gln Leu Leu Glu Glu Asn<br>        50                        55                        60 | 192 |
| cat gag att atc agc cat atc aag gac tcc gtg ctg gag ctg aca gcc<br>His Glu Ile Ile Ser His Ile Lys Asp Ser Val Leu Glu Leu Thr Ala<br>65                        70                        75                        80 | 240 |
| aac gca gag ggc ccg ccc gcc atg ctg ccc tac tac acg gtc aat ggc<br>Asn Ala Glu Gly Pro Pro Ala Met Leu Pro Tyr Tyr Thr Val Asn Gly<br>                        85                        90                        95 | 288 |
| tcc tgg gtg gtg cca ccg gag ccc cgg ccc agc ttc ttc tcc atc tcc<br>Ser Trp Val Val Pro Pro Glu Pro Arg Pro Ser Phe Phe Ser Ile Ser<br>                  100                     105                   110 | 336 |
| ccg cag gac tgc cag ttt gct ttg ggg ggc cgg ggt cag aag cca gag<br>Pro Gln Asp Cys Gln Phe Ala Leu Gly Gly Arg Gly Gln Lys Pro Glu<br>              115                     120                    125 | 384 |
| ctg cag atg ctc act gtg tcg gag gag ctg ccg ttt gac aac gtg gat<br>Leu Gln Met Leu Thr Val Ser Glu Glu Leu Pro Phe Asp Asn Val Asp<br>130                        135                     140 | 432 |
| ggt ggt gtg tgg agg caa ggc ttc gac atc tcc tac gac ccg cac gac<br>Gly Gly Val Trp Arg Gln Gly Phe Asp Ile Ser Tyr Asp Pro His Asp<br>145                        150                     155                    160 | 480 |
| tgg gat gct gaa gac ctg cag gtg ttt gtg gtg ccc cac tct cac aat<br>Trp Asp Ala Glu Asp Leu Gln Val Phe Val Val Pro His Ser His Asn<br>                  165                     170                   175 | 528 |
| gac cca ggc tgg atc aag acc ttt gac aag tac tac aca gag cag acc<br>Asp Pro Gly Trp Ile Lys Thr Phe Asp Lys Tyr Tyr Thr Glu Gln Thr<br>              180                     185                    190 | 576 |
| caa cac atc ctc aat agc atg gtg tct aag ctg cag gag gac ccc cgg<br>Gln His Ile Leu Asn Ser Met Val Ser Lys Leu Gln Glu Asp Pro Arg<br>              195                     200                    205 | 624 |
| cgg cgc ttc ctc tgg gca gag gtc tcc ttc ttc gcc aag tgg tgg gac<br>Arg Arg Phe Leu Trp Ala Glu Val Ser Phe Phe Ala Lys Trp Trp Asp<br>210                        215                     220 | 672 |
| aac atc aat gtc caa aag aga gcg gca gtc cga agg ctg gtg gga aac<br>Asn Ile Asn Val Gln Lys Arg Ala Ala Val Arg Arg Leu Val Gly Asn<br>225                        230                     235                    240 | 720 |
| ggg cag ctg gag att gcg aca gga ggc tgg gtg atg cca gat gag gcc<br>Gly Gln Leu Glu Ile Ala Thr Gly Gly Trp Val Met Pro Asp Glu Ala<br>                  245                     250                   255 | 768 |
| aat tcc cac tac ttt gca ttg att gac cag ctc atc gaa gga cac cag<br>Asn Ser His Tyr Phe Ala Leu Ile Asp Gln Leu Ile Glu Gly His Gln<br>              260                     265                    270 | 816 |
| tgg ctg gag aga aat ctt ggt gca acc ccc cgc tct ggc tgg gca gtg<br>Trp Leu Glu Arg Asn Leu Gly Ala Thr Pro Arg Ser Gly Trp Ala Val<br>        275                        280                     285 | 864 |
| gac ccc ttt gga tac agc tcc acc atg cct tac ctg ctg cgc cgt gcc<br>Asp Pro Phe Gly Tyr Ser Ser Thr Met Pro Tyr Leu Leu Arg Arg Ala<br>290                        295                     300 | 912 |
| aac ctc acc agc atg ctg att cag aga gtg cac tat gcc atc aag aag<br>Asn Leu Thr Ser Met Leu Ile Gln Arg Val His Tyr Ala Ile Lys Lys<br>305                        310                     315                    320 | 960 |
| cac ttt gct gcc acc cac agc cta gag ttc atg tgg agg cag aca tgg<br>His Phe Ala Ala Thr His Ser Leu Glu Phe Met Trp Arg Gln Thr Trp<br>                  325                     330                   335 | 1008 |

-continued

```
gac tcg gac tcc agc aca gac atc ttc tgt cac atg atg ccc ttc tac     1056
Asp Ser Asp Ser Ser Thr Asp Ile Phe Cys His Met Met Pro Phe Tyr
        340                 345                 350 agc tat gac gtc ccc cat acc tgt ggc cca gat ccc aag atc tgc tgc     1104
Ser Tyr Asp Val Pro His Thr Cys Gly Pro Asp Pro Lys Ile Cys Cys
            355                 360                 365 caa ttt gat ttc aaa cgc ctg cct ggt ggg cgc atc aac tgc cct tgg     1152
Gln Phe Asp Phe Lys Arg Leu Pro Gly Gly Arg Ile Asn Cys Pro Trp
370                 375                 380 aag gtg cca ccc cgg gcc atc aca gag gcc aac gtg gca gag agg gca     1200
Lys Val Pro Pro Arg Ala Ile Thr Glu Ala Asn Val Ala Glu Arg Ala
385                 390                 395                 400 gcc ctg ctt ctg gac caa tac cgg aag aag tcc cag ctg ttc cga agc     1248
Ala Leu Leu Leu Asp Gln Tyr Arg Lys Lys Ser Gln Leu Phe Arg Ser
                405                 410                 415 aac gtc ctc ctg gtg cct ctt gga gat gac ttc cga tat gac aag ccc     1296
Asn Val Leu Leu Val Pro Leu Gly Asp Asp Phe Arg Tyr Asp Lys Pro
            420                 425                 430 cag gag tgg gat gcc cag ttc ttc aac tac caa cgg ctc ttt gac ttc     1344
Gln Glu Trp Asp Ala Gln Phe Phe Asn Tyr Gln Arg Leu Phe Asp Phe
        435                 440                 445 ttc aac agc agg cct aac ctc cat gtg cag gcc cag ttt ggc act ctt     1392
Phe Asn Ser Arg Pro Asn Leu His Val Gln Ala Gln Phe Gly Thr Leu
450                 455                 460 tct gac tat ttt gat gcc ctg tac aag agg aca ggg gtg gag cca ggg     1440
Ser Asp Tyr Phe Asp Ala Leu Tyr Lys Arg Thr Gly Val Glu Pro Gly
465                 470                 475                 480 gcc cgg cct cca ggg ttt cct gtg ctg agc ggg gat ttc ttc tcc tat     1488
Ala Arg Pro Pro Gly Phe Pro Val Leu Ser Gly Asp Phe Phe Ser Tyr
                485                 490                 495 gcg gac cgg gag gat cat tac tgg aca ggc tat tac act tcc cgg ccc     1536
Ala Asp Arg Glu Asp His Tyr Trp Thr Gly Tyr Tyr Thr Ser Arg Pro
            500                 505                 510 ttc tac aag agc tta gac cga gtc ctg gaa gcc cac ctg cgg ggg gca     1584
Phe Tyr Lys Ser Leu Asp Arg Val Leu Glu Ala His Leu Arg Gly Ala
        515                 520                 525 gag gtt ctg tac agc ctg gct gca gct cac gct cgc cgc tct ggt ctg     1632
Glu Val Leu Tyr Ser Leu Ala Ala Ala His Ala Arg Arg Ser Gly Leu
530                 535                 540 gct ggc cgg tac cca ctg tct gat ttc acc ctc ctg acg gaa gct cgg     1680
Ala Gly Arg Tyr Pro Leu Ser Asp Phe Thr Leu Leu Thr Glu Ala Arg
545                 550                 555                 560 cgc aca ttg ggg ctc ttc cag cat cac gat gcc atc act ggc acg gcc     1728
Arg Thr Leu Gly Leu Phe Gln His His Asp Ala Ile Thr Gly Thr Ala
                565                 570                 575 aag gag gct gtg gtg gtg gac tat ggg gtc agg ctt ctg cgc tcc ctt     1776
Lys Glu Ala Val Val Val Asp Tyr Gly Val Arg Leu Leu Arg Ser Leu
            580                 585                 590 gtc aac ctg aag cag gtc atc att cat gca gcc cac tat ctg gtg ctg     1824
Val Asn Leu Lys Gln Val Ile Ile His Ala Ala His Tyr Leu Val Leu
        595                 600                 605 ggg gac aag gag acc tac cac ttt gac cct gag gcg ccc ttc ctc caa     1872
Gly Asp Lys Glu Thr Tyr His Phe Asp Pro Glu Ala Pro Phe Leu Gln
610                 615                 620 gtg gat gac act cgc tta agt cac gac gcc ctc cca gag cgc acg gtg     1920
Val Asp Asp Thr Arg Leu Ser His Asp Ala Leu Pro Glu Arg Thr Val
625                 630                 635                 640 atc cag ctg gat tcc tcg ccc agg ttt gtg gtc cta ttc aac cca ctg     1968
Ile Gln Leu Asp Ser Ser Pro Arg Phe Val Val Leu Phe Asn Pro Leu
```

-continued

```
                   645                 650                 655
gaa cag gag cga ttc agc atg gtg tcc ctg ctg gtc aac tct ccc cgc      2016
Glu Gln Glu Arg Phe Ser Met Val Ser Leu Leu Val Asn Ser Pro Arg
                660                 665                 670 gtg cgt gtc ctt tcg gag gag ggt cag ccc ctg gcc gtg cag atc agc      2064
Val Arg Val Leu Ser Glu Glu Gly Gln Pro Leu Ala Val Gln Ile Ser
            675                 680                 685 gca cac tgg agc tct gcc acc gag gcg gtc cct gac gtc tac cag gtg      2112
Ala His Trp Ser Ser Ala Thr Glu Ala Val Pro Asp Val Tyr Gln Val
        690                 695                 700 tct gtg cct gtc cgc ctg cca gcc ctg ggc ctg ggc gtg ctg cag cta      2160
Ser Val Pro Val Arg Leu Pro Ala Leu Gly Leu Gly Val Leu Gln Leu
705                 710                 715                 720 cag ctg ggc ctg gat ggg cac cgc acg ctg ccc tcc tct gtg cgc atc      2208
Gln Leu Gly Leu Asp Gly His Arg Thr Leu Pro Ser Ser Val Arg Ile
                725                 730                 735 tac ctg cac ggc cgg cag ctg tcc gtc agc agg cac gaa gcg ttt cct      2256
Tyr Leu His Gly Arg Gln Leu Ser Val Ser Arg His Glu Ala Phe Pro
            740                 745                 750 ctc cgt gtc att gac tct ggc acc agc gac ttc gcc ctc agc aac cgc      2304
Leu Arg Val Ile Asp Ser Gly Thr Ser Asp Phe Ala Leu Ser Asn Arg
        755                 760                 765 tac atg cag gtc tgg ttc tca ggc ctt act ggg ctc ctc aag agc atc      2352
Tyr Met Gln Val Trp Phe Ser Gly Leu Thr Gly Leu Leu Lys Ser Ile
770                 775                 780 cga agg gtg gat gag gag cac gag cag cag gtg gac atg cag gtc ctt      2400
Arg Arg Val Asp Glu Glu His Glu Gln Gln Val Asp Met Gln Val Leu
785                 790                 795                 800 gtc tat ggc acc cgt acg tcc aaa gac aag agt gga gcc tac ctc ttc      2448
Val Tyr Gly Thr Arg Thr Ser Lys Asp Lys Ser Gly Ala Tyr Leu Phe
                805                 810                 815 ctg ccc gat ggc gag gct agc cct acg tcc cca agg agc ccc ccg tgc      2496
Leu Pro Asp Gly Glu Ala Ser Pro Thr Ser Pro Arg Ser Pro Pro Cys
            820                 825                 830 tgc gtg tca ctg aag gcc ctt tct tct cag agg tgg ttg cgt act atg      2544
Cys Val Ser Leu Lys Ala Leu Ser Ser Gln Arg Trp Leu Arg Thr Met
        835                 840                 845 agc aca ttc acc agg cgg tcc ggc ttt aca atc tgc cag ggg tgg agg      2592
Ser Thr Phe Thr Arg Arg Ser Gly Phe Thr Ile Cys Gln Gly Trp Arg
850                 855                 860 ggc tgt ctc tgg aca tat cat ccc tgg tgg aca tcc ggg act acg tca      2640
Gly Cys Leu Trp Thr Tyr His Pro Trp Trp Thr Ser Gly Thr Thr Ser
865                 870                 875                 880 aca agg agc tgg ccc tgc aca tcc ata cag aca tcg aca gcc agg gtg      2688
Thr Arg Ser Trp Pro Cys Thr Ser Ile Gln Thr Ser Thr Ala Arg Val
                885                 890                 895 cag ccc cga cgg tat ctg aag aag ctc ccc ctc cag gcc aac ttc tac      2736
Gln Pro Arg Arg Tyr Leu Lys Lys Leu Pro Leu Gln Ala Asn Phe Tyr
            900                 905                 910 ccc atg cca gtc atg gcc tat atc cag gac gca cag aag cgc ctc acg      2784
Pro Met Pro Val Met Ala Tyr Ile Gln Asp Ala Gln Lys Arg Leu Thr
        915                 920                 925 ctg cac act gcc cag gcc ctg ggt gtc tct agc ctc aaa gat ggc cag      2832
Leu His Thr Ala Gln Ala Leu Gly Val Ser Ser Leu Lys Asp Gly Gln
930                 935                 940 ctg gag gtg atc ttg gac cgg cgg ctg atg cag gat gac aac cgg ggc      2880
Leu Glu Val Ile Leu Asp Arg Arg Leu Met Gln Asp Asp Asn Arg Gly
945                 950                 955                 960 cta ggc caa ggg ctc aag gac aac aag aga acc tgc aac cgt ttc cgc      2928
```

```
Leu Gly Gln Gly Leu Lys Asp Asn Lys Arg Thr Cys Asn Arg Phe Arg
            965                 970                 975 ctc ctg cta gag cgg cga acc gtg ggc agt gag gtc caa gat agc cac      2976
Leu Leu Leu Glu Arg Arg Thr Val Gly Ser Glu Val Gln Asp Ser His
        980                 985                 990 tct acc agc tac cca tcc ctc ctc agc cac ctg acc tcc atg tac ctg      3024
Ser Thr Ser Tyr Pro Ser Leu Leu Ser His Leu Thr Ser Met Tyr Leu
            995                 1000                1005 aac gcc ccg gcg ctc gct ctg cct gta gcc agg atg cag ctc cca ggc      3072
Asn Ala Pro Ala Leu Ala Leu Pro Val Ala Arg Met Gln Leu Pro Gly
        1010                1015                1020 cct ggt ctg cgc tca ttt cat cct ctg gct tcc tca ctg ccc tgt gac      3120
Pro Gly Leu Arg Ser Phe His Pro Leu Ala Ser Ser Leu Pro Cys Asp
1025                1030                1035                1040 ttc cac ctg ctc aac cta cgt acg ctc cag gct gag gag gac acc cta      3168
Phe His Leu Leu Asn Leu Arg Thr Leu Gln Ala Glu Glu Asp Thr Leu
                1045                1050                1055 ccc tcg gcg gag acc gca ctc atc tta cac cgc aag ggt ttt gac tgc      3216
Pro Ser Ala Glu Thr Ala Leu Ile Leu His Arg Lys Gly Phe Asp Cys
            1060                1065                1070 ggc ctg gag gcc aag aac ttg ggc ttc aac tgc acc aca agc caa ggc      3264
Gly Leu Glu Ala Lys Asn Leu Gly Phe Asn Cys Thr Thr Ser Gln Gly
        1075                1080                1085 aag gta gcc ctg ggc agc ctt ttc cat ggc ctg gat gtg gta ttc ctt      3312
Lys Val Ala Leu Gly Ser Leu Phe His Gly Leu Asp Val Val Phe Leu
    1090                1095                1100 cag cca acc tcc ttg acg tta ctg tac cct ctg gcc tcc ccg tcc aac      3360
Gln Pro Thr Ser Leu Thr Leu Leu Tyr Pro Leu Ala Ser Pro Ser Asn
1105                1110                1115                1120 agc act gac gtc tat ttg gag ccc atg gag att gct acc ttt cgc ctc      3408
Ser Thr Asp Val Tyr Leu Glu Pro Met Glu Ile Ala Thr Phe Arg Leu
                1125                1130                1135 cgc ttg ggt tag                                                       3420
Arg Leu Gly <210> SEQ ID NO 57
<211> LENGTH: 3393
<212> TYPE: DNA
<213> ORGANISM: Spodoptera frugiperda
<220> FEATURE:
<221> NAME/KEY: CDS
<222> LOCATION: (1)..(3390)

<400> SEQUENCE: 57 atg agg act cgt gtc ctt cgt tgc cgg ccg ttc tcc acc cgg atc ctg       48
Met Arg Thr Arg Val Leu Arg Cys Arg Pro Phe Ser Thr Arg Ile Leu
1               5                   10                  15 ctg ctg ctg cta ttt gtc ctt gcg ttt ggg gtc tac tgc tat ttc tac       96
Leu Leu Leu Leu Phe Val Leu Ala Phe Gly Val Tyr Cys Tyr Phe Tyr
                20                  25                  30 aat gca tct cct cag aac tat aac aaa cca aga atc agt tac cca gcc      144
Asn Ala Ser Pro Gln Asn Tyr Asn Lys Pro Arg Ile Ser Tyr Pro Ala
            35                  40                  45 agt atg gag cac ttc aaa tct tcc ctc act cac acc gtc aag agc cga      192
Ser Met Glu His Phe Lys Ser Ser Leu Thr His Thr Val Lys Ser Arg
        50                  55                  60 gac gag cca act ccg gat caa tgc cct gca ttg aag gaa agc gaa gcg      240
Asp Glu Pro Thr Pro Asp Gln Cys Pro Ala Leu Lys Glu Ser Glu Ala
65                  70                  75                  80 gac atc gac acc gtg gcg ata tac cca act ttt gat ttt cag ccg agc      288
Asp Ile Asp Thr Val Ala Ile Tyr Pro Thr Phe Asp Phe Gln Pro Ser
```

-continued

```
                    85                      90                      95
tgg ttg cgt aca aag gaa ttt tgg gac aag tcc ttc gag gat cgg tat      336
Trp Leu Arg Thr Lys Glu Phe Trp Asp Lys Ser Phe Glu Asp Arg Tyr
            100                     105                     110 gaa aga att cat aac gac act aca cgg cct aga ctg aag gta atc gtg      384
Glu Arg Ile His Asn Asp Thr Thr Arg Pro Arg Leu Lys Val Ile Val
            115                     120                     125 gtt cct cac tca cac aac gac ccg gga tgg ctg aag acg ttt gaa cag      432
Val Pro His Ser His Asn Asp Pro Gly Trp Leu Lys Thr Phe Glu Gln
            130                     135                     140 tac ttc gag tgg aag acc aag aac att atc aac aac ata gtg aac aaa      480
Tyr Phe Glu Trp Lys Thr Lys Asn Ile Ile Asn Asn Ile Val Asn Lys
145                     150                     155                     160 ctg cac cag tac ccc aac atg acc ttc att tgg acc gag ata tcg ttt      528
Leu His Gln Tyr Pro Asn Met Thr Phe Ile Trp Thr Glu Ile Ser Phe
            165                     170                     175 ctg aat gcc tgg tgg gaa agg tcg cac cct gtc aaa caa aag gca ttg      576
Leu Asn Ala Trp Trp Glu Arg Ser His Pro Val Lys Gln Lys Ala Leu
            180                     185                     190 aaa aaa ctt atc aaa gaa ggt cgt ctc gag atc acg acg ggc ggc tgg      624
Lys Lys Leu Ile Lys Glu Gly Arg Leu Glu Ile Thr Thr Gly Gly Trp
            195                     200                     205 gtg atg ccg gac gaa gcc tgc acg cat atc tat gcg cta att gac cag      672
Val Met Pro Asp Glu Ala Cys Thr His Ile Tyr Ala Leu Ile Asp Gln
210                     215                     220 ttt att gaa gga cat cac tgg gtg aaa act aat ctc ggc gtc atc ccg      720
Phe Ile Glu Gly His His Trp Val Lys Thr Asn Leu Gly Val Ile Pro
225                     230                     235                     240 aag aca gga tgg tct att gac ccc ttc ggc cac ggg gcc act gtg cct      768
Lys Thr Gly Trp Ser Ile Asp Pro Phe Gly His Gly Ala Thr Val Pro
            245                     250                     255 tac ctg cta gac cag agc ggc ctt gag gga acc att ata cag aga atc      816
Tyr Leu Leu Asp Gln Ser Gly Leu Glu Gly Thr Ile Ile Gln Arg Ile
            260                     265                     270 cat tat gcg tgg aaa cag tgg ctg gcg gag cga cag att gag gag ttt      864
His Tyr Ala Trp Lys Gln Trp Leu Ala Glu Arg Gln Ile Glu Glu Phe
            275                     280                     285 tac tgg ctg gcg agt tgg gct act acg aag ccg tcc atg ata gtg cac      912
Tyr Trp Leu Ala Ser Trp Ala Thr Thr Lys Pro Ser Met Ile Val His
            290                     295                     300 aat cag ccg ttt gat att tat tca ata aaa agc acg tgt ggc ccg cac      960
Asn Gln Pro Phe Asp Ile Tyr Ser Ile Lys Ser Thr Cys Gly Pro His
305                     310                     315                     320 cct tca att tgt ctc agt ttc gac ttc agg aag att ccc ggc gaa tat     1008
Pro Ser Ile Cys Leu Ser Phe Asp Phe Arg Lys Ile Pro Gly Glu Tyr
            325                     330                     335 tct gaa tac aca gct aag cac gaa gac atc acg gaa cac aac ttg cac     1056
Ser Glu Tyr Thr Ala Lys His Glu Asp Ile Thr Glu His Asn Leu His
            340                     345                     350 agc aag gca aag act ttg ata gag gag tac gac cgt atc ggg tcc ctg     1104
Ser Lys Ala Lys Thr Leu Ile Glu Glu Tyr Asp Arg Ile Gly Ser Leu
            355                     360                     365 act cca cac aac gtg gtg ctg gtg ccg ctc gga gac gac ttc aga tac     1152
Thr Pro His Asn Val Val Leu Val Pro Leu Gly Asp Asp Phe Arg Tyr
            370                     375                     380 gag tac agc gtc gag ttt gat gcc caa tac gtc aat tat atg aaa atg     1200
Glu Tyr Ser Val Glu Phe Asp Ala Gln Tyr Val Asn Tyr Met Lys Met
385                     390                     395                     400 ttt aac tac atc aat gct cac aag gaa atc ttc aac gct gac gta cag     1248
```

-continued

```
            Phe Asn Tyr Ile Asn Ala His Lys Glu Ile Phe Asn Ala Asp Val Gln
                        405                 410                 415 ttc gga act cct ctc gat tac ttt aac gcc atg aaa gaa aga cat caa         1296
Phe Gly Thr Pro Leu Asp Tyr Phe Asn Ala Met Lys Glu Arg His Gln
            420                 425                 430 aat ata ccc agc tta aag gga gat ttc ttc gtt tac tcc gat att ttc         1344
Asn Ile Pro Ser Leu Lys Gly Asp Phe Phe Val Tyr Ser Asp Ile Phe
            435                 440                 445 agc gaa ggt aaa cca gcg tac tgg tca ggt tac tac act act aga ccc         1392
Ser Glu Gly Lys Pro Ala Tyr Trp Ser Gly Tyr Tyr Thr Thr Arg Pro
            450                 455                 460 tac caa aaa atc ctc gcc cgt cag ttc gaa cac caa ctg cga tcg gca         1440
Tyr Gln Lys Ile Leu Ala Arg Gln Phe Glu His Gln Leu Arg Ser Ala
465                 470                 475                 480 gag att tta ttc acc ctt gta tcg aac tac atc aga cag atg ggt cgc         1488
Glu Ile Leu Phe Thr Leu Val Ser Asn Tyr Ile Arg Gln Met Gly Arg
            485                 490                 495 caa gga gag ttc gga gct tct gag aaa aag tta gaa aaa tct tac gag         1536
Gln Gly Glu Phe Gly Ala Ser Glu Lys Lys Leu Glu Lys Ser Tyr Glu
            500                 505                 510 cag ctt atc tat gct cga cgg aac ttg ggt ctg ttt caa cat cac gat         1584
Gln Leu Ile Tyr Ala Arg Arg Asn Leu Gly Leu Phe Gln His His Asp
            515                 520                 525 gcg att act gga aca tca aag tcc agt gtg atg caa gat tac gga acc         1632
Ala Ile Thr Gly Thr Ser Lys Ser Ser Val Met Gln Asp Tyr Gly Thr
            530                 535                 540 aaa ctg ttc aca agt ctg tat cac tgc atc cgc ctg cag gag gcc gcg         1680
Lys Leu Phe Thr Ser Leu Tyr His Cys Ile Arg Leu Gln Glu Ala Ala
545                 550                 555                 560 ctc acc acc atc atg ttg cct gac cag tcg ttg cac tcg cag agc att         1728
Leu Thr Thr Ile Met Leu Pro Asp Gln Ser Leu His Ser Gln Ser Ile
            565                 570                 575 ata caa agc gag gtt gag tgg gaa act tac gga aaa ccg ccc aag aag         1776
Ile Gln Ser Glu Val Glu Trp Glu Thr Tyr Gly Lys Pro Pro Lys Lys
            580                 585                 590 ctg caa gtg tcc ttc att gac aag aag aaa gtt ata ctt ttt aat ccg         1824
Leu Gln Val Ser Phe Ile Asp Lys Lys Lys Val Ile Leu Phe Asn Pro
            595                 600                 605 ttg gct gag act cga act gaa gtg gtc acg gtt aga tcc aac acg tcc         1872
Leu Ala Glu Thr Arg Thr Glu Val Val Thr Val Arg Ser Asn Thr Ser
            610                 615                 620 aac atc cgg gtg tac gat aca cac aag agg aag cac gtc ttg tat cag         1920
Asn Ile Arg Val Tyr Asp Thr His Lys Arg Lys His Val Leu Tyr Gln
625                 630                 635                 640 ata atg ccc agc atc aca atc caa gac aac ggc aag agt atc gta agc         1968
Ile Met Pro Ser Ile Thr Ile Gln Asp Asn Gly Lys Ser Ile Val Ser
            645                 650                 655 gac acc acg ttc gac ata atg ttc gtg gcc acc atc ccg ccc ctc acc         2016
Asp Thr Thr Phe Asp Ile Met Phe Val Ala Thr Ile Pro Pro Leu Thr
            660                 665                 670 tcc atc tcg tac aag ctg cag gag cac acc aac act tcc cac cac tgc         2064
Ser Ile Ser Tyr Lys Leu Gln Glu His Thr Asn Thr Ser His His Cys
            675                 680                 685 gtc att ttc tgc aac aac tgc gaa caa tac cag aaa tcc aat gtg ttc         2112
Val Ile Phe Cys Asn Asn Cys Glu Gln Tyr Gln Lys Ser Asn Val Phe
            690                 695                 700 caa att aag aaa atg atg cct ggt gac ata caa tta gaa aat gca gtg         2160
Gln Ile Lys Lys Met Met Pro Gly Asp Ile Gln Leu Glu Asn Ala Val
705                 710                 715                 720
```

```
cta aaa ctt ctc gtt aat agg aac acc ggc ttt ctg aga caa gtc tat    2208
Leu Lys Leu Leu Val Asn Arg Asn Thr Gly Phe Leu Arg Gln Val Tyr
            725                 730                 735 aga aag gac atc cgg aag aga act gtc gtt gac gta caa ttc ggc gca    2256
Arg Lys Asp Ile Arg Lys Arg Thr Val Val Asp Val Gln Phe Gly Ala
        740                 745                 750 tat caa agt gcc caa aga cat tct ggt gct tac ctc ttc atg cct cat    2304
Tyr Gln Ser Ala Gln Arg His Ser Gly Ala Tyr Leu Phe Met Pro His
            755                 760                 765 tac gac tca cct gag aag aat gtt ctg cat ccc tac act aat cag aac    2352
Tyr Asp Ser Pro Glu Lys Asn Val Leu His Pro Tyr Thr Asn Gln Asn
        770                 775                 780 aac atg caa gat gat aac ata atc ata gtg tcc gga cct att tct acg    2400
Asn Met Gln Asp Asp Asn Ile Ile Ile Val Ser Gly Pro Ile Ser Thr
785                 790                 795                 800 gaa atc acg acc atg tac ttg ccc ttc ttg gtg cac act att agg ata    2448
Glu Ile Thr Thr Met Tyr Leu Pro Phe Leu Val His Thr Ile Arg Ile
                805                 810                 815 tac aac gtg ccg gac ccg gta ctg tcg cgt gct att cta tta gag acc    2496
Tyr Asn Val Pro Asp Pro Val Leu Ser Arg Ala Ile Leu Leu Glu Thr
            820                 825                 830 gat gta gat ttc gag gcg cca cct aag aac aga gag act gag tta ttt    2544
Asp Val Asp Phe Glu Ala Pro Pro Lys Asn Arg Glu Thr Glu Leu Phe
        835                 840                 845 atg aga tta cag act gat ata caa aac ggt gac att ccc gaa ttt tac    2592
Met Arg Leu Gln Thr Asp Ile Gln Asn Gly Asp Ile Pro Glu Phe Tyr
850                 855                 860 acc gat cag aac gga ttc cag tac caa aag agg gtc aaa gtg aat aaa    2640
Thr Asp Gln Asn Gly Phe Gln Tyr Gln Lys Arg Val Lys Val Asn Lys
865                 870                 875                 880 cta gga ata gaa gct aat tac tac ccg atc act acc atg gcg tgc ctg    2688
Leu Gly Ile Glu Ala Asn Tyr Tyr Pro Ile Thr Thr Met Ala Cys Leu
            885                 890                 895 caa gac gag gag acc cgg ctc act ctg ctg acg aac cac gct caa ggc    2736
Gln Asp Glu Glu Thr Arg Leu Thr Leu Leu Thr Asn His Ala Gln Gly
        900                 905                 910 gct gct gca tac gaa cca gga cgc tta gaa gtc atg ctc gat cgt cga    2784
Ala Ala Ala Tyr Glu Pro Gly Arg Leu Glu Val Met Leu Asp Arg Arg
            915                 920                 925 act ctt tat gat gac ttc aga gga atc ggt gaa gga gta gtc gat aac    2832
Thr Leu Tyr Asp Asp Phe Arg Gly Ile Gly Glu Gly Val Val Asp Asn
        930                 935                 940 aaa ccg acg act ttc cag aac tgg att tta att gaa tcc atg cca ggc    2880
Lys Pro Thr Thr Phe Gln Asn Trp Ile Leu Ile Glu Ser Met Pro Gly
945                 950                 955                 960 gtg acg cga gcc aag aga gac act agt gaa cca ggt ttc aaa ttt gtt    2928
Val Thr Arg Ala Lys Arg Asp Thr Ser Glu Pro Gly Phe Lys Phe Val
            965                 970                 975 aat gaa cgt cgt ttt ggc ccc ggc cag aag gaa agc cct tac caa gta    2976
Asn Glu Arg Arg Phe Gly Pro Gly Gln Lys Glu Ser Pro Tyr Gln Val
        980                 985                 990 ccg tcg cag act gcg gac tac ctg agc agg atg ttc aat tac ccg gtg    3024
Pro Ser Gln Thr Ala Asp Tyr Leu Ser Arg Met Phe Asn Tyr Pro Val
            995                 1000                1005 aac gtg tac ctg gtg gac act agc gag gtt ggc gag atc gag gtg aag    3072
Asn Val Tyr Leu Val Asp Thr Ser Glu Val Gly Glu Ile Glu Val Lys
        1010                1015                1020 ccg tac cag tcg ttc ctg cag agc ttc ccg ccc ggc atc cac ctg gtc    3120
Pro Tyr Gln Ser Phe Leu Gln Ser Phe Pro Pro Gly Ile His Leu Val
1025                1030                1035                1040
```

| | | |
|---|---|---|
| acc ctg cgc acc atc acc gac gac gtg ctc gaa ctc ttc ccc agc aac<br>Thr Leu Arg Thr Ile Thr Asp Asp Val Leu Glu Leu Phe Pro Ser Asn<br>          1045                    1050                 1055 | | 3168 |
| gaa agc tac atg gta ctg cac cga cca gga tac agc tgc gct gtc gga<br>Glu Ser Tyr Met Val Leu His Arg Pro Gly Tyr Ser Cys Ala Val Gly<br>        1060                   1065                 1070 | | 3216 |
| gag aag cca gtc gcc aag tct ccc aag ttt tcg tcc aaa acc agg ttc<br>Glu Lys Pro Val Ala Lys Ser Pro Lys Phe Ser Ser Lys Thr Arg Phe<br>       1075                    1080                1085 | | 3264 |
| aat ggt ctg aac att cag aac atc act gca gtc agc ctg acc ggc ctg<br>Asn Gly Leu Asn Ile Gln Asn Ile Thr Ala Val Ser Leu Thr Gly Leu<br>       1090                    1095                1100 | | 3312 |
| aag tca ctc cga cct ctc aca ggt ctg agt gac atc cac ctg aac gct<br>Lys Ser Leu Arg Pro Leu Thr Gly Leu Ser Asp Ile His Leu Asn Ala<br>1105                  1110                1115                1120 | | 3360 |
| atg gag gta aaa act tac aag atc agg ttt taa<br>Met Glu Val Lys Thr Tyr Lys Ile Arg Phe<br>               1125                    1130 | | 3393 |

<210> SEQ ID NO 58
<211> LENGTH: 3033
<212> TYPE: DNA
<213> ORGANISM: Homo sapiens
<220> FEATURE:
<221> NAME/KEY: CDS
<222> LOCATION: (1)..(3030)

<400> SEQUENCE: 58

| | | |
|---|---|---|
| atg ggc tac gcg cgg gct tcg ggg gtc tgc gct cgc ggc tgc ctg gac<br>Met Gly Tyr Ala Arg Ala Ser Gly Val Cys Ala Arg Gly Cys Leu Asp<br>1                     5                    10                   15 | | 48 |
| tca gca ggc ccc tgg acc atg tcc cgc gcc ctg cgg cca ccg ctc ccg<br>Ser Ala Gly Pro Trp Thr Met Ser Arg Ala Leu Arg Pro Pro Leu Pro<br>                20                   25                   30 | | 96 |
| cct ctc tgc ttt ttc ctt ttg ctg gcg gct gcc ggt gct cgg gcc<br>Pro Leu Cys Phe Phe Leu Leu Leu Leu Ala Ala Ala Gly Ala Arg Ala<br>             35                  40                 45 | | 144 |
| ggg gga tac gag aca tgc ccc aca gtg cag ccg aac atg ctg aac gtg<br>Gly Gly Tyr Glu Thr Cys Pro Thr Val Gln Pro Asn Met Leu Asn Val<br>  50                   55                   60 | | 192 |
| cac ctg ctg cct cac aca cat gat gac gtg ggc tgg ctc aaa acc gtg<br>His Leu Leu Pro His Thr His Asp Asp Val Gly Trp Leu Lys Thr Val<br>65                  70                  75                  80 | | 240 |
| gac cag tac ttt tat gga atc aag aat gac atc cag cac gcc ggt gtg<br>Asp Gln Tyr Phe Tyr Gly Ile Lys Asn Asp Ile Gln His Ala Gly Val<br>                   85                   90                  95 | | 288 |
| cag tac atc ctg gac tcg gtc atc tct gcc ttg ctg gca gat ccc acc<br>Gln Tyr Ile Leu Asp Ser Val Ile Ser Ala Leu Leu Ala Asp Pro Thr<br>            100                 105                110 | | 336 |
| cgt cgc ttc att tac gtg gag att gcc ttc ttc tcc cgt tgg tgg cac<br>Arg Arg Phe Ile Tyr Val Glu Ile Ala Phe Phe Ser Arg Trp Trp His<br>          115                  120                125 | | 384 |
| cag cag aca aat gcc aca cag gaa gtc gtg cga gac ctt gtg cgc cag<br>Gln Gln Thr Asn Ala Thr Gln Glu Val Val Arg Asp Leu Val Arg Gln<br> 130                  135                140 | | 432 |
| ggg cgc ctg gag ttc gcc aat ggt ggc tgg gtg atg aac gat gag gca<br>Gly Arg Leu Glu Phe Ala Asn Gly Gly Trp Val Met Asn Asp Glu Ala<br>145                   150                  155                  160 | | 480 |
| gcc acc cac tac ggt gcc atc gtg gac cag atg aca ctt ggg ctg cgc<br>Ala Thr His Tyr Gly Ala Ile Val Asp Gln Met Thr Leu Gly Leu Arg<br>                   165                   170                 175 | | 528 |

-continued

| | | |
|---|---|---|
| ttt ctg gag gac aca ttt ggc aat gat ggg cga ccc cgt gtg gcc tgg<br>Phe Leu Glu Asp Thr Phe Gly Asn Asp Gly Arg Pro Arg Val Ala Trp<br>180 185 190 | 576 |
| cac att gac ccc ttc ggc cac tct cgg gag cag gcc tcg ctg ttt gcg<br>His Ile Asp Pro Phe Gly His Ser Arg Glu Gln Ala Ser Leu Phe Ala<br>195 200 205 | 624 |
| cag atg ggc ttc gac ggc ttc ttc ttt ggg cgc ctt gat tat caa gat<br>Gln Met Gly Phe Asp Gly Phe Phe Phe Gly Arg Leu Asp Tyr Gln Asp<br>210 215 220 | 672 |
| aag tgg gta cgg atg cag aag ctg gag atg gag cag gtg tgg cgg gcc<br>Lys Trp Val Arg Met Gln Lys Leu Glu Met Glu Gln Val Trp Arg Ala<br>225 230 235 240 | 720 |
| agc acc agc ctg aag ccc ccg acc gcg gac ctc ttc act ggt gtg ctt<br>Ser Thr Ser Leu Lys Pro Pro Thr Ala Asp Leu Phe Thr Gly Val Leu<br>245 250 255 | 768 |
| ccc aat ggt tac aac ccg cca agg aat ctg tgc tgg gat gtg ctg tgt<br>Pro Asn Gly Tyr Asn Pro Pro Arg Asn Leu Cys Trp Asp Val Leu Cys<br>260 265 270 | 816 |
| gtc gat cag ccg ctg gtg gag gac cct cgc agc ccc gag tac aac gcc<br>Val Asp Gln Pro Leu Val Glu Asp Pro Arg Ser Pro Glu Tyr Asn Ala<br>275 280 285 | 864 |
| aag gag ctg gtc gat tac ttc cta aat gtg gcc act gcc cag ggc cgg<br>Lys Glu Leu Val Asp Tyr Phe Leu Asn Val Ala Thr Ala Gln Gly Arg<br>290 295 300 | 912 |
| tat tac cgc acc aac cac act gtg atg acc atg ggc tcg gac ttc caa<br>Tyr Tyr Arg Thr Asn His Thr Val Met Thr Met Gly Ser Asp Phe Gln<br>305 310 315 320 | 960 |
| tat gag aat gcc aac atg tgg ttc aag aac ctt gac aag ctc atc cgg<br>Tyr Glu Asn Ala Asn Met Trp Phe Lys Asn Leu Asp Lys Leu Ile Arg<br>325 330 335 | 1008 |
| ctg gta aat gcg cag cag gca aaa gga agc agt gtc cat gtt ctc tac<br>Leu Val Asn Ala Gln Gln Ala Lys Gly Ser Ser Val His Val Leu Tyr<br>340 345 350 | 1056 |
| tcc acc ccc gct tgt tac ctc tgg gag ctg aac aag gcc aac ctc acc<br>Ser Thr Pro Ala Cys Tyr Leu Trp Glu Leu Asn Lys Ala Asn Leu Thr<br>355 360 365 | 1104 |
| tgg tca gtg aaa cat gac gac ttc ttc cct tac gcg gat ggc ccc cac<br>Trp Ser Val Lys His Asp Asp Phe Phe Pro Tyr Ala Asp Gly Pro His<br>370 375 380 | 1152 |
| cag ttc tgg acc ggt tac ttt tcc agt cgg ccg gcc ctc aaa cgc tac<br>Gln Phe Trp Thr Gly Tyr Phe Ser Ser Arg Pro Ala Leu Lys Arg Tyr<br>385 390 395 400 | 1200 |
| gag cgc ctc agc tac aac ttc ctg cag gtg tgc aac cag ctg gag gcg<br>Glu Arg Leu Ser Tyr Asn Phe Leu Gln Val Cys Asn Gln Leu Glu Ala<br>405 410 415 | 1248 |
| ctg gtg ggc ctg gcg gcc aac gtg gga ccc tat ggc tcc gga gac agt<br>Leu Val Gly Leu Ala Ala Asn Val Gly Pro Tyr Gly Ser Gly Asp Ser<br>420 425 430 | 1296 |
| gca ccc ctc aat gag gcg atg gct gtg ctc cag cat cac gac gcc gtc<br>Ala Pro Leu Asn Glu Ala Met Ala Val Leu Gln His His Asp Ala Val<br>435 440 445 | 1344 |
| agc ggc acc tcc cgc cag cac gtg gcc aac gac tac gcg cgc cag ctt<br>Ser Gly Thr Ser Arg Gln His Val Ala Asn Asp Tyr Ala Arg Gln Leu<br>450 455 460 | 1392 |
| gcg gca ggc tgg ggg cct tgc gag gtt ctt ctg agc aac gcg ctg gcg<br>Ala Ala Gly Trp Gly Pro Cys Glu Val Leu Leu Ser Asn Ala Leu Ala<br>465 470 475 480 | 1440 |
| cgg ctc aga ggc ttc aaa gat cac ttc acc ttt tgc caa cag cta aac<br>Arg Leu Arg Gly Phe Lys Asp His Phe Thr Phe Cys Gln Gln Leu Asn | 1488 |

-continued

```
                485                 490                 495
atc agc atc tgc ccg ctc agc cag acg gcg gcg cgc ttc cag gtc atc    1536
Ile Ser Ile Cys Pro Leu Ser Gln Thr Ala Ala Arg Phe Gln Val Ile
            500                 505                 510 gtt tat aat ccc ctg ggg cgg aag gtg aat tgg atg gta cgg ctg ccg    1584
Val Tyr Asn Pro Leu Gly Arg Lys Val Asn Trp Met Val Arg Leu Pro
        515                 520                 525 gtc agc gaa ggc gtt ttc gtt gtg aag gac ccc aat ggc agg aca gtg    1632
Val Ser Glu Gly Val Phe Val Val Lys Asp Pro Asn Gly Arg Thr Val
    530                 535                 540 ccc agc gat gtg gta ata ttt ccc agc tca gac agc cag gcg cac cct    1680
Pro Ser Asp Val Val Ile Phe Pro Ser Ser Asp Ser Gln Ala His Pro
545                 550                 555                 560 ccg gag ctg ctg ttc tca gcc tca ctg ccc gcc ctg ggc ttc agc acc    1728
Pro Glu Leu Leu Phe Ser Ala Ser Leu Pro Ala Leu Gly Phe Ser Thr
                565                 570                 575 tat tca gta gcc cag gtg cct cgc tgg aag ccc cag gcc cgc gca cca    1776
Tyr Ser Val Ala Gln Val Pro Arg Trp Lys Pro Gln Ala Arg Ala Pro
            580                 585                 590 cag ccc atc ccc aga aga tcc tgg tcc cct gct tta acc atc gaa aat    1824
Gln Pro Ile Pro Arg Arg Ser Trp Ser Pro Ala Leu Thr Ile Glu Asn
        595                 600                 605 gag cac atc cgg gca acg ttt gat cct gac aca ggg ctg ttg atg gag    1872
Glu His Ile Arg Ala Thr Phe Asp Pro Asp Thr Gly Leu Leu Met Glu
    610                 615                 620 att atg aac atg aat cag caa ctc ctg ctg cct gtt cgc cag acc ttc    1920
Ile Met Asn Met Asn Gln Gln Leu Leu Leu Pro Val Arg Gln Thr Phe
625                 630                 635                 640 ttc tgg tac aac gcc agt ata ggt gac aac gaa agt gac cag gcc tca    1968
Phe Trp Tyr Asn Ala Ser Ile Gly Asp Asn Glu Ser Asp Gln Ala Ser
                645                 650                 655 ggt gcc tac atc ttc aga ccc aac caa cag aaa ccg ctg cct gtg agc    2016
Gly Ala Tyr Ile Phe Arg Pro Asn Gln Gln Lys Pro Leu Pro Val Ser
            660                 665                 670 cgc tgg gct cag atc cac ctg gtg aag aca ccc ttg gtg cag gag gtg    2064
Arg Trp Ala Gln Ile His Leu Val Lys Thr Pro Leu Val Gln Glu Val
        675                 680                 685 cac cag aac ttc tca gct tgg tgt tcc cag gtg gtt cgc ctg tac cca    2112
His Gln Asn Phe Ser Ala Trp Cys Ser Gln Val Val Arg Leu Tyr Pro
    690                 695                 700 gga cag cgg cac ctg gag cta gag tgg tcg gtg ggg ccg ata cct gtg    2160
Gly Gln Arg His Leu Glu Leu Glu Trp Ser Val Gly Pro Ile Pro Val
705                 710                 715                 720 ggc gac acc tgg ggg aag gag gtc atc agc cgt ttt gac aca ccg ctg    2208
Gly Asp Thr Trp Gly Lys Glu Val Ile Ser Arg Phe Asp Thr Pro Leu
                725                 730                 735 gag aca aag gga cgc ttc tac aca gac agc aat ggc cgg gag atc ctg    2256
Glu Thr Lys Gly Arg Phe Tyr Thr Asp Ser Asn Gly Arg Glu Ile Leu
            740                 745                 750 gag agg agg cgg gat tat cga ccc acc tgg aaa ctg aac cag acg gag    2304
Glu Arg Arg Arg Asp Tyr Arg Pro Thr Trp Lys Leu Asn Gln Thr Glu
        755                 760                 765 ccc gtg gca gga aac tac tat cca gtc aac acc cgg att tac atc acg    2352
Pro Val Ala Gly Asn Tyr Tyr Pro Val Asn Thr Arg Ile Tyr Ile Thr
    770                 775                 780 gat gga aac atg cag ctg act gtg ctg act gac cgc tcc cag ggg ggc    2400
Asp Gly Asn Met Gln Leu Thr Val Leu Thr Asp Arg Ser Gln Gly Gly
785                 790                 795                 800 agc agc ctg aga gat ggc tcg ctg gag ctc atg gtg cac cga agg ctg    2448
Ser Ser Leu Arg Asp Gly Ser Leu Glu Leu Met Val His Arg Arg Leu
```

```
Ser Ser Leu Arg Asp Gly Ser Leu Glu Leu Met Val His Arg Arg Leu
            805                 810                 815 ctg aag gac gat gga cgc gga gta tcg gag cca cta atg gag aac ggg     2496
Leu Lys Asp Asp Gly Arg Gly Val Ser Glu Pro Leu Met Glu Asn Gly
        820                 825                 830 tcg ggg gcg tgg gtg cga ggg cgc cac ctg gtg ctg ctg gac aca gcc     2544
Ser Gly Ala Trp Val Arg Gly Arg His Leu Val Leu Leu Asp Thr Ala
            835                 840                 845 cag gct gca gcc gcc gga cac cgg ctc ctg gcg gag cag gag gtc ctg     2592
Gln Ala Ala Ala Ala Gly His Arg Leu Leu Ala Glu Gln Glu Val Leu
        850                 855                 860 gcc cct cag gtg gtg ctg gcc ccg ggt ggc ggc gcc gcc tac aat ctc     2640
Ala Pro Gln Val Val Leu Ala Pro Gly Gly Gly Ala Ala Tyr Asn Leu
865                 870                 875                 880 ggg gct cct ccg cgc acg cag ttc tca ggg ctg cgc agg gac ctg ccg     2688
Gly Ala Pro Pro Arg Thr Gln Phe Ser Gly Leu Arg Arg Asp Leu Pro
                885                 890                 895 ccc tcg gtg cac ctg ctc acg ctg gcc agc tgg ggc ccc gaa atg gtg     2736
Pro Ser Val His Leu Leu Thr Leu Ala Ser Trp Gly Pro Glu Met Val
            900                 905                 910 ctg ctg cgc ttg gag cac cag ttt gcc gta gga gag gat tcc gga cgt     2784
Leu Leu Arg Leu Glu His Gln Phe Ala Val Gly Glu Asp Ser Gly Arg
        915                 920                 925 aac ctg agc gcc ccc gtt acc ttg aac ttg agg gac ctg ttc tcc acc     2832
Asn Leu Ser Ala Pro Val Thr Leu Asn Leu Arg Asp Leu Phe Ser Thr
930                 935                 940 ttc acc atc acc cgc ctg cag gag acc acg ctg gtg gcc aac cag ctc     2880
Phe Thr Ile Thr Arg Leu Gln Glu Thr Thr Leu Val Ala Asn Gln Leu
945                 950                 955                 960 cgc gag gca gcc tcc agg ctc aag tgg aca aca aac aca ggc ccc aca     2928
Arg Glu Ala Ala Ser Arg Leu Lys Trp Thr Thr Asn Thr Gly Pro Thr
                965                 970                 975 ccc cac caa act ccg tac cag ctg gac ccg gcc aac atc acg ctg gaa     2976
Pro His Gln Thr Pro Tyr Gln Leu Asp Pro Ala Asn Ile Thr Leu Glu
            980                 985                 990 ccc atg gaa atc cgc act ttc ctg gcc tca gtt caa tgg aag gag gtg     3024
Pro Met Glu Ile Arg Thr Phe Leu Ala Ser Val Gln Trp Lys Glu Val
        995                 1000                1005 gat ggt tag                                                         3033
Asp Gly
    1010

<210> SEQ ID NO 59
<211> LENGTH: 3189
<212> TYPE: DNA
<213> ORGANISM: Homo sapiens
<220> FEATURE:
<221> NAME/KEY: CDS
<222> LOCATION: (1)..(3186)

<400> SEQUENCE: 59 atg gcg gca gcg ccg ttc ttg aag cac tgg cgc acc act ttt gag cgg     48
Met Ala Ala Ala Pro Phe Leu Lys His Trp Arg Thr Thr Phe Glu Arg
1               5                   10                  15 gtg gag aag ttc gtg tcc ccg atc tac ttc acc gac tgt aac ctc cgc     96
Val Glu Lys Phe Val Ser Pro Ile Tyr Phe Thr Asp Cys Asn Leu Arg
            20                  25                  30 ggc agg ctt ttt ggg gcc agc tgc cct gtg gct gtg ctc tcc agc ttc    144
Gly Arg Leu Phe Gly Ala Ser Cys Pro Val Ala Val Leu Ser Ser Phe
        35                  40                  45 ctg acg ccg gag aga ctt ccc tac cag gag gca gtc cag cgg gac ttc    192
```

-continued

```
            Leu Thr Pro Glu Arg Leu Pro Tyr Gln Glu Ala Val Gln Arg Asp Phe
                50                  55                  60 cgc ccc gcg cag gtc ggc gac agc ttc gga ccc aca tgg tgg acc tgc        240
Arg Pro Ala Gln Val Gly Asp Ser Phe Gly Pro Thr Trp Trp Thr Cys
 65                  70                  75                  80 tgg ttc cgg gtg gag ctg acc atc cca gag gca tgg gtg ggc cag gaa        288
Trp Phe Arg Val Glu Leu Thr Ile Pro Glu Ala Trp Val Gly Gln Glu
                 85                  90                  95 gtt cac ctt tgc tgg gaa agt gat gga gaa ggt ctg gtg tgg cgt gat        336
Val His Leu Cys Trp Glu Ser Asp Gly Glu Gly Leu Val Trp Arg Asp
                100                 105                 110 gga gaa cct gtc cag ggt tta acc aaa gag ggt gag aag acc agc tat        384
Gly Glu Pro Val Gln Gly Leu Thr Lys Glu Gly Glu Lys Thr Ser Tyr
            115                 120                 125 gtc ctg act gac agg ctg ggg gaa aga gac ccc cga agc ctc act ctc        432
Val Leu Thr Asp Arg Leu Gly Glu Arg Asp Pro Arg Ser Leu Thr Leu
        130                 135                 140 tat gtg gaa gta gcc tgc aat ggg ctc ctg ggg gcc ggg aag gga agc        480
Tyr Val Glu Val Ala Cys Asn Gly Leu Leu Gly Ala Gly Lys Gly Ser
145                 150                 155                 160 atg att gca gcc cct gac cct gag aag ata ttc cag ctg agc cgg gct        528
Met Ile Ala Ala Pro Asp Pro Glu Lys Ile Phe Gln Leu Ser Arg Ala
                165                 170                 175 gag cta gct gtg ttc cac cgg gat gtc cac atg ctc ctg gtg gat ctg        576
Glu Leu Ala Val Phe His Arg Asp Val His Met Leu Leu Val Asp Leu
            180                 185                 190 gag ctg ctg ctg ggc ata gcc aag ggc ctc ggg aag gac aac cag cgc        624
Glu Leu Leu Leu Gly Ile Ala Lys Gly Leu Gly Lys Asp Asn Gln Arg
        195                 200                 205 agc ttc cag gcc ctg tac aca gcc aat cag atg gtg aac gtg tgt gac        672
Ser Phe Gln Ala Leu Tyr Thr Ala Asn Gln Met Val Asn Val Cys Asp
    210                 215                 220 cct gcc cag ccc gag acc ttc cca gtg gcc cag gcc ctg gcc tcc agg        720
Pro Ala Gln Pro Glu Thr Phe Pro Val Ala Gln Ala Leu Ala Ser Arg
225                 230                 235                 240 ttc ttt ggc caa cat ggg ggt gaa agc caa cac acc att cat gcc aca        768
Phe Phe Gly Gln His Gly Gly Glu Ser Gln His Thr Ile His Ala Thr
                245                 250                 255 ggg cac tgc cac att gat aca gcc tgg ctt tgg ccc ttc aaa gag act        816
Gly His Cys His Ile Asp Thr Ala Trp Leu Trp Pro Phe Lys Glu Thr
            260                 265                 270 gtg agg aaa tgt gcc cgg agc tgg gtg acc gcc ctg cag ctc atg gag        864
Val Arg Lys Cys Ala Arg Ser Trp Val Thr Ala Leu Gln Leu Met Glu
        275                 280                 285 cgg aac cct gag ttc atc ttt gcc tgc tcc cag gcg cag cag ctg gaa        912
Arg Asn Pro Glu Phe Ile Phe Ala Cys Ser Gln Ala Gln Gln Leu Glu
    290                 295                 300 tgg gtg aag agc cgc tac cct ggc ctg tac tcc cgc atc cag gag ttt        960
Trp Val Lys Ser Arg Tyr Pro Gly Leu Tyr Ser Arg Ile Gln Glu Phe
305                 310                 315                 320 gcg tgc cgt ggg cag ttt gtg cct gtg ggg ggc acc tgg gtg gaa atg       1008
Ala Cys Arg Gly Gln Phe Val Pro Val Gly Gly Thr Trp Val Glu Met
                325                 330                 335 gat ggg aac ctg ccc agt gga gag gcc atg gtg agg cag ttt ttg cag       1056
Asp Gly Asn Leu Pro Ser Gly Glu Ala Met Val Arg Gln Phe Leu Gln
            340                 345                 350 ggc cag aac ttc ttt ctg cag gag ttt ggg aag atg tgc tct gag ttc       1104
Gly Gln Asn Phe Phe Leu Gln Glu Phe Gly Lys Met Cys Ser Glu Phe
        355                 360                 365
```

-continued

| | |
|---|---|
| tgg ctg ccg gac acc ttt ggc tac tca gca cag ctc ccc cag atc atg<br>Trp Leu Pro Asp Thr Phe Gly Tyr Ser Ala Gln Leu Pro Gln Ile Met<br>370                         375                     380 | 1152 |
| cac ggc tgt ggc atc agg cgc ttt ctc acc cag aaa ttg agc tgg aat<br>His Gly Cys Gly Ile Arg Arg Phe Leu Thr Gln Lys Leu Ser Trp Asn<br>385                         390                     395                  400 | 1200 |
| ttg gtg aac tcc ttc cca cac cat aca ttt ttc tgg gag ggc ctg gat<br>Leu Val Asn Ser Phe Pro His His Thr Phe Phe Trp Glu Gly Leu Asp<br>                       405                     410                     415 | 1248 |
| ggc tcc cgt gta ctg gtc cac ttc cca cct ggc gac tcc tat ggg atg<br>Gly Ser Arg Val Leu Val His Phe Pro Pro Gly Asp Ser Tyr Gly Met<br>                420                         425                     430 | 1296 |
| cag ggc agc gtg gag gag gtg ctg aag acc gtg gcc aac aac cgg gac<br>Gln Gly Ser Val Glu Glu Val Leu Lys Thr Val Ala Asn Asn Arg Asp<br>              435                       440                     445 | 1344 |
| aag ggg cgg gcc aac cac agt gcc ttc ctc ttt ggc ttt ggg gat ggg<br>Lys Gly Arg Ala Asn His Ser Ala Phe Leu Phe Gly Phe Gly Asp Gly<br>450                         455                     460 | 1392 |
| ggt ggt ggc ccc acc cag acc atg ctg gac cgc ctg aag cgc ctg agc<br>Gly Gly Gly Pro Thr Gln Thr Met Leu Asp Arg Leu Lys Arg Leu Ser<br>465                         470                     475                  480 | 1440 |
| aat acg gat ggg ctg ccc agg gtg cag cta tct tct cca aga cag ctc<br>Asn Thr Asp Gly Leu Pro Arg Val Gln Leu Ser Ser Pro Arg Gln Leu<br>                       485                     490                     495 | 1488 |
| ttc tca gca ctg gag agt gac tca gag cag ctg tgc acg tgg gtt ggg<br>Phe Ser Ala Leu Glu Ser Asp Ser Glu Gln Leu Cys Thr Trp Val Gly<br>                      500                     505                   510 | 1536 |
| gag ctc ttc ttg gag ctg cac aat ggc aca tac acc acc cat gcc cag<br>Glu Leu Phe Leu Glu Leu His Asn Gly Thr Tyr Thr Thr His Ala Gln<br>              515                     520                     525 | 1584 |
| atc aag aag ggg aac cgg gaa tgt gag cgg atc ctg cac gac gtg gag<br>Ile Lys Lys Gly Asn Arg Glu Cys Glu Arg Ile Leu His Asp Val Glu<br>530                         535                     540 | 1632 |
| ctg ctc agt agc ctg gcc ctg gcc cgc agt gcc cag ttc cta tac cca<br>Leu Leu Ser Ser Leu Ala Leu Ala Arg Ser Ala Gln Phe Leu Tyr Pro<br>545                         550                     555                  560 | 1680 |
| gca gcc cag ctg cag cac ctc tgg agg ctc ctt ctt ctg aac cag ttc<br>Ala Ala Gln Leu Gln His Leu Trp Arg Leu Leu Leu Leu Asn Gln Phe<br>                      565                     570                   575 | 1728 |
| cat gat gtg gtg act gga agc tgc atc cag atg gtg gca gag gaa gcc<br>His Asp Val Val Thr Gly Ser Cys Ile Gln Met Val Ala Glu Glu Ala<br>              580                     585                     590 | 1776 |
| atg tgc cat tat gaa gac atc cgt tcc cat ggc aat aca ctg ctc agc<br>Met Cys His Tyr Glu Asp Ile Arg Ser His Gly Asn Thr Leu Leu Ser<br>                     595                     600                   605 | 1824 |
| gct gca gcc gca gcc ctg tgt gct ggg gag cca ggt cct gag ggc ctc<br>Ala Ala Ala Ala Ala Leu Cys Ala Gly Glu Pro Gly Pro Glu Gly Leu<br>610                         615                     620 | 1872 |
| ctc atc gtc aac aca ctg ccc tgg aag cgg atc gaa gtg atg gcc ctg<br>Leu Ile Val Asn Thr Leu Pro Trp Lys Arg Ile Glu Val Met Ala Leu<br>625                         630                     635                  640 | 1920 |
| ccc aaa ccg ggc ggg gcc cac agc cta gcc ctg gtg aca gtg ccc agc<br>Pro Lys Pro Gly Gly Ala His Ser Leu Ala Leu Val Thr Val Pro Ser<br>                      645                     650                     655 | 1968 |
| atg ggc tat gct cct gtt cct ccc ccc acc tca ctg cag ccc ctg ctg<br>Met Gly Tyr Ala Pro Val Pro Pro Pro Thr Ser Leu Gln Pro Leu Leu<br>                     660                     665                    670 | 2016 |
| ccc cag cag cct gtg ttc gta gtg caa gag act gat ggc tcc gtg act<br>Pro Gln Gln Pro Val Phe Val Val Gln Glu Thr Asp Gly Ser Val Thr<br>                 675                     680                     685 | 2064 |

```
                                                        -continued ctg gac aat ggc atc atc cga gtg aag ctg gac cca act ggt cgc ctg        2112
Leu Asp Asn Gly Ile Ile Arg Val Lys Leu Asp Pro Thr Gly Arg Leu
    690             695                 700 acg tcc ttg gtc ctg gtg gcc tct ggc agg gag gcc att gct gag ggc        2160
Thr Ser Leu Val Leu Val Ala Ser Gly Arg Glu Ala Ile Ala Glu Gly
705             710                 715                 720 gcc gtg ggg aac cag ttt gtg cta ttt gat gat gtc ccc ttg tac tgg        2208
Ala Val Gly Asn Gln Phe Val Leu Phe Asp Asp Val Pro Leu Tyr Trp
                725                 730                 735 gat gca tgg gac gtc atg gac tac cac ctg gag aca cgg aag cct gtg        2256
Asp Ala Trp Asp Val Met Asp Tyr His Leu Glu Thr Arg Lys Pro Val
            740                 745                 750 ctg ggc cag gca ggg acc ctg gca gtg ggc acc gag ggc ggc ctg cgg        2304
Leu Gly Gln Ala Gly Thr Leu Ala Val Gly Thr Glu Gly Gly Leu Arg
        755                 760                 765 ggc agc gcc tgg ttc ttg cta cag atc agc ccc aac agt cgg ctt agc        2352
Gly Ser Ala Trp Phe Leu Leu Gln Ile Ser Pro Asn Ser Arg Leu Ser
    770                 775                 780 cag gag gtt gtg ctg gac gtt ggc tgc ccc tat gtc cgc ttc cac acc        2400
Gln Glu Val Val Leu Asp Val Gly Cys Pro Tyr Val Arg Phe His Thr
785             790                 795                 800 gag gta cac tgg cat gag gcc cac aag ttc ctg aag gtg gag ttc cct        2448
Glu Val His Trp His Glu Ala His Lys Phe Leu Lys Val Glu Phe Pro
                805                 810                 815 gct cgc gtg cgg agt tcc cag gcc acc tat gag atc cag ttt ggg cac        2496
Ala Arg Val Arg Ser Ser Gln Ala Thr Tyr Glu Ile Gln Phe Gly His
            820                 825                 830 ctg cag cga cct acc cac tac aat acc tct tgg gac tgg gct cga ttt        2544
Leu Gln Arg Pro Thr His Tyr Asn Thr Ser Trp Asp Trp Ala Arg Phe
        835                 840                 845 gag gtg tgg gcc cat cgc tgg atg gat ctg tca gaa cac ggc ttt ggg        2592
Glu Val Trp Ala His Arg Trp Met Asp Leu Ser Glu His Gly Phe Gly
    850                 855                 860 ctg gcc ctg ctc aac gac tgc aag tat ggc gcg tca gtg cga ggc agc        2640
Leu Ala Leu Leu Asn Asp Cys Lys Tyr Gly Ala Ser Val Arg Gly Ser
865             870                 875                 880 atc ctc agc ctc tcg ctc ttg cgg gcg cct aaa gcc ccg gac gct act        2688
Ile Leu Ser Leu Ser Leu Leu Arg Ala Pro Lys Ala Pro Asp Ala Thr
                885                 890                 895 gct gac acg ggg cgc cac gag ttc acc tat gca ctg atg ccg cac aag        2736
Ala Asp Thr Gly Arg His Glu Phe Thr Tyr Ala Leu Met Pro His Lys
            900                 905                 910 ggc tct ttc cag gat gct ggc gtt atc caa gct gcc tac agc cta aac        2784
Gly Ser Phe Gln Asp Ala Gly Val Ile Gln Ala Ala Tyr Ser Leu Asn
        915                 920                 925 ttc ccc ctg ttg gct ctg cca gcc ccc agc cca gcg ccc gcc acc tcc        2832
Phe Pro Leu Leu Ala Leu Pro Ala Pro Ser Pro Ala Pro Ala Thr Ser
    930                 935                 940 tgg agt gcg ttt tcc gtg tct tca ccc gcg gtc gta ttg gag acc gtc        2880
Trp Ser Ala Phe Ser Val Ser Ser Pro Ala Val Val Leu Glu Thr Val
945             950                 955                 960 aag cag gcg gag agc agc ccc cag cgc cgc tcg ctg gtc ctg agg ctg        2928
Lys Gln Ala Glu Ser Ser Pro Gln Arg Arg Ser Leu Val Leu Arg Leu
                965                 970                 975 tat gag gcc cac ggc agc cac gtg gac tgc tgg ctg cac ttg tcg ctg        2976
Tyr Glu Ala His Gly Ser His Val Asp Cys Trp Leu His Leu Ser Leu
            980                 985                 990 ccg gtt cag gag gcc atc ctc tgc gat ctc ttg gag cga cca gac cct        3024
Pro Val Gln Glu Ala Ile Leu Cys Asp Leu Leu Glu Arg Pro Asp Pro
```

```
                995                 1000                1005
gct ggc cac ttg act tcg gga caa ccg cct gaa gct cac ctt ttc tcc      3072
Ala Gly His Leu Thr Ser Gly Gln Pro Pro Glu Ala His Leu Phe Ser
        1010                1015                1020 ctt cca agt gct gtc cct gtt gct cgt gct tca gcc tcc gcc aca ctg      3120
Leu Pro Ser Ala Val Pro Val Ala Arg Ala Ser Ala Ser Ala Thr Leu
1025                1030                1035                1040 agt ccc tgg ggc tgg ggt ttt gtt tgt aga agg ctc tgg gga ctc cta      3168
Ser Pro Trp Gly Trp Gly Phe Val Cys Arg Arg Leu Trp Gly Leu Leu
                1045                1050                1055 att tct gct tcc cca gcc taa                                          3189
Ile Ser Ala Ser Pro Ala
            1060

<210> SEQ ID NO 60
<211> LENGTH: 39
<212> TYPE: DNA
<213> ORGANISM: Arabidopsis thaliana

<400> SEQUENCE: 60
ggcgcgccct cactctcttc cacttcggcg taccaggac                           39

<210> SEQ ID NO 61
<211> LENGTH: 45
<212> TYPE: DNA
<213> ORGANISM: Arabidopsis thaliana

<400> SEQUENCE: 61
ccttaattaa tcacttgtga ggtcgcagtt caagcttata agctc                    45

<210> SEQ ID NO 62
<211> LENGTH: 42
<212> TYPE: DNA
<213> ORGANISM: Caenorhabditis elegans

<400> SEQUENCE: 62
gggcgcgccg cgctcaccaa acgacaagca aatgatttac gg                       42

<210> SEQ ID NO 63
<211> LENGTH: 44
<212> TYPE: DNA
<213> ORGANISM: Caenorhabditis elegans

<400> SEQUENCE: 63
gggcgcgccg ctcatattca tcaagtaaag caacatatca agcc                     44

<210> SEQ ID NO 64
<211> LENGTH: 45
<212> TYPE: DNA
<213> ORGANISM: Caenorhabditis elegans

<400> SEQUENCE: 64
cttaattaat taaaatgata caagaatact ggaaatatcg tttgg                    45

<210> SEQ ID NO 65
<211> LENGTH: 36
<212> TYPE: DNA
<213> ORGANISM: Ciona intestinalis

<400> SEQUENCE: 65
ggcgcgccac ccttcaagac aaacttagtc tggtgg                              36
```

```
<210> SEQ ID NO 66
<211> LENGTH: 38
<212> TYPE: DNA
<213> ORGANISM: Ciona intestinalis

<400> SEQUENCE: 66
ggcgcgccct accacttata atgcccaagc aatttgcg                              38

<210> SEQ ID NO 67
<211> LENGTH: 43
<212> TYPE: DNA
<213> ORGANISM: Ciona intestinalis

<400> SEQUENCE: 67
ccttaattaa ttacgtcagt actattttgt aagcttgtat ctc                        43

<210> SEQ ID NO 68
<211> LENGTH: 39
<212> TYPE: DNA
<213> ORGANISM: Drosophila melanogaster

<400> SEQUENCE: 68
ggcgcgccca tgagctggaa aatggtttgc aggagcacg                             39

<210> SEQ ID NO 69
<211> LENGTH: 33
<212> TYPE: DNA
<213> ORGANISM: Drosophila melanogaster

<400> SEQUENCE: 69
ggcgcgcccg cgacgatcca ataagacctc cac                                   33

<210> SEQ ID NO 70
<211> LENGTH: 38
<212> TYPE: DNA
<213> ORGANISM: Drosophila melanogaster

<400> SEQUENCE: 70
ggcgcgccga cgtgcccaat gtggatgtac agatgctg                              38

<210> SEQ ID NO 71
<211> LENGTH: 42
<212> TYPE: DNA
<213> ORGANISM: Drosophila melanogaster

<400> SEQUENCE: 71
ccttaattaa tcagcttgag tgactgctca cataagcggc gg                         42

<210> SEQ ID NO 72
<211> LENGTH: 38
<212> TYPE: DNA
<213> ORGANISM: Homo sapiens

<400> SEQUENCE: 72
ggcgcgccat agaccatttg gagcgtttgc tagctgag                              38

<210> SEQ ID NO 73
<211> LENGTH: 42
<212> TYPE: DNA
<213> ORGANISM: Homo sapiens

<400> SEQUENCE: 73
ggcgcgccgc ttcacaaagt ggaagtcaca attcagatgt gc                         42
```

```
<210> SEQ ID NO 74
<211> LENGTH: 44
<212> TYPE: DNA
<213> ORGANISM: Homo sapiens

<400> SEQUENCE: 74
cccttaatta atcacctcaa ctggattcgg aatgtgctga tttc            44

<210> SEQ ID NO 75
<211> LENGTH: 38
<212> TYPE: DNA
<213> ORGANISM: Mus musculus

<400> SEQUENCE: 75
ggcgcgccga ccatttggag cgtttgctcg ctgagaac                   38

<210> SEQ ID NO 76
<211> LENGTH: 32
<212> TYPE: DNA
<213> ORGANISM: Mus musculus

<400> SEQUENCE: 76
ggcgcgccct gcaggctgac cccagagact gt                         32

<210> SEQ ID NO 77
<211> LENGTH: 50
<212> TYPE: DNA
<213> ORGANISM: Mus musculus

<400> SEQUENCE: 77
cccttaatta atcaggtcca acgcaagcgg atacggaacg tgctgatctc      50

<210> SEQ ID NO 78
<211> LENGTH: 39
<212> TYPE: DNA
<213> ORGANISM: Rattus norvegicus

<400> SEQUENCE: 78
ggcgcgccgg tgggaacttc cccaggagcc aaatttctg                  39

<210> SEQ ID NO 79
<211> LENGTH: 41
<212> TYPE: DNA
<213> ORGANISM: Rattus norvegicus

<400> SEQUENCE: 79
ggcgcgccgc ggagggccca ccagccctgc tgccctacca c               41

<210> SEQ ID NO 80
<211> LENGTH: 38
<212> TYPE: DNA
<213> ORGANISM: Rattus norvegicus

<400> SEQUENCE: 80
ccttaattaa ctaacccaag cgcaggcgga aggtgctg                   38

<210> SEQ ID NO 81
<211> LENGTH: 36
<212> TYPE: DNA
<213> ORGANISM: Homo sapiens

<400> SEQUENCE: 81
ggcgcgccca acacgatccc acccgacacc agaatg                     36
```

<210> SEQ ID NO 82
<211> LENGTH: 37
<212> TYPE: DNA
<213> ORGANISM: Homo sapiens

<400> SEQUENCE: 82
ggcgcgccgt gctggagctg acagccaacg cagaggg                              37

<210> SEQ ID NO 83
<211> LENGTH: 39
<212> TYPE: DNA
<213> ORGANISM: Homo sapiens

<400> SEQUENCE: 83
ggcgcgccgg tcagaagcca gagctgcaga tgctcactg                            39

<210> SEQ ID NO 84
<211> LENGTH: 41
<212> TYPE: DNA
<213> ORGANISM: Homo sapiens

<400> SEQUENCE: 84
ccttaattaa ctaacccaag cggaggcgaa aggtagcaat c                         41

<210> SEQ ID NO 85
<211> LENGTH: 44
<212> TYPE: DNA
<213> ORGANISM: Unknown Organism
<220> FEATURE:
<223> OTHER INFORMATION: Description of Unknown Organism: SfMannIII d36
      AscI

<400> SEQUENCE: 85
ggcgcgccca gaactataac aaaccaagaa tcagttaccc agcc                      44

<210> SEQ ID NO 86
<211> LENGTH: 47
<212> TYPE: DNA
<213> ORGANISM: Unknown Organism
<220> FEATURE:
<223> OTHER INFORMATION: Description of Unknown Organism: SfMannIII PacI

<400> SEQUENCE: 86
ccttaattaa ttaaaacctg atcttgtaag tttttacctc catagcg                   47

<210> SEQ ID NO 87
<211> LENGTH: 39
<212> TYPE: DNA
<213> ORGANISM: Homo sapiens

<400> SEQUENCE: 87
ggcgcgccat gggctacgcg cgggcttcgg gggtctgcg                            39

<210> SEQ ID NO 88
<211> LENGTH: 38
<212> TYPE: DNA
<213> ORGANISM: Homo sapiens

<400> SEQUENCE: 88
ggcgcgcccc gcctctctgc tttttccttt tgttgctg                             38

<210> SEQ ID NO 89
<211> LENGTH: 41

<212> TYPE: DNA
<213> ORGANISM: Homo sapiens

<400> SEQUENCE: 89
ccttaattaa ctaaccatcc acctccttcc attgaactga g      41

<210> SEQ ID NO 90
<211> LENGTH: 41
<212> TYPE: DNA
<213> ORGANISM: Homo sapiens

<400> SEQUENCE: 90
ggcgcgccat ggcggcagcg ccgttcttga agcactggcg c      41

<210> SEQ ID NO 91
<211> LENGTH: 40
<212> TYPE: DNA
<213> ORGANISM: Homo sapiens

<400> SEQUENCE: 91
ccttaattaa ttaggctggg gaagcagaaa ttaggagtcc      40

<210> SEQ ID NO 92
<211> LENGTH: 1143
<212> TYPE: PRT
<213> ORGANISM: Caenorhabditis elegans

<400> SEQUENCE: 92

```
Met Gly Lys Arg Asn Phe Tyr Ile Ile Leu Cys Leu Gly Val Phe Leu
  1               5                  10                  15

Thr Val Ser Leu Tyr Leu Tyr Asn Gly Ile Glu Thr Gly Ala Glu Ala
             20                  25                  30

Leu Thr Lys Arg Gln Ala Asn Asp Leu Arg Arg Lys Ile Gly Asn Leu
         35                  40                  45

Glu His Val Ala Glu Glu Asn Gly Arg Thr Ile Asp Arg Leu Glu Gln
     50                  55                  60

Glu Val Gln Arg Ala Lys Ala Glu Lys Ser Val Asp Phe Asp Glu Glu
 65                  70                  75                  80

Lys Glu Lys Thr Glu Glu Lys Glu Val Glu Lys Glu Lys Glu Val
                 85                  90                  95

Ala Pro Val Pro Val Arg Gly Asn Arg Gly Glu Met Ala His Ile His
            100                 105                 110

Gln Val Lys Gln His Ile Lys Pro Thr Pro Ser Met Lys Asp Val Cys
        115                 120                 125

Gly Ile Arg Glu Asn Val Ser Ile Ala His Ser Asp Leu Gln Met Leu
    130                 135                 140

Asp Leu Tyr Asp Thr Trp Lys Phe Glu Asn Pro Asp Gly Gly Val Trp
145                 150                 155                 160

Lys Gln Gly Trp Lys Ile Glu Tyr Asp Ala Glu Lys Val Lys Ser Leu
                165                 170                 175

Pro Arg Leu Glu Val Ile Val Ile Pro His Ser His Cys Asp Pro Gly
            180                 185                 190

Trp Ile Met Thr Phe Glu Glu Tyr Tyr Asn Arg Gln Thr Arg Asn Ile
        195                 200                 205

Leu Asp Gly Met Ala Lys His Leu Ala Glu Lys Asp Glu Met Arg Phe
    210                 215                 220

Ile Tyr Ala Glu Ile Ser Phe Phe Glu Thr Trp Trp Arg Asp Gln Ala
225                 230                 235                 240
```

```
Asp Glu Ile Lys Lys Val Lys Gly Tyr Leu Glu Ala Gly Lys Phe
                245                 250                 255
Glu Ile Val Thr Gly Gly Trp Val Met Thr Asp Glu Ala Asn Ala His
            260                 265                 270
Tyr His Ser Met Ile Thr Glu Leu Phe Glu Gly His Glu Trp Ile Gln
        275                 280                 285
Asn His Leu Gly Lys Ser Ala Ile Pro Gln Ser His Trp Ser Ile Asp
    290                 295                 300
Pro Phe Gly Leu Ser Pro Ser Met Pro His Leu Leu Thr Ser Ala Asn
305                 310                 315                 320
Ile Thr Asn Ala Val Ile Gln Arg Val His Tyr Ser Val Lys Arg Glu
                325                 330                 335
Leu Ala Leu Lys Lys Asn Leu Glu Phe Tyr Trp Arg Gln Leu Phe Gly
            340                 345                 350
Ser Thr Gly His Pro Asp Leu Arg Ser His Ile Met Pro Phe Tyr Ser
        355                 360                 365
Tyr Asp Ile Pro His Thr Cys Gly Pro Glu Pro Ser Val Cys Cys Gln
    370                 375                 380
Phe Asp Phe Arg Arg Met Pro Glu Gly Gly Lys Ser Cys Asp Trp Gly
385                 390                 395                 400
Ile Pro Pro Gln Lys Ile Asn Asp Asp Asn Val Ala His Arg Ala Glu
                405                 410                 415
Met Ile Tyr Asp Gln Tyr Arg Lys Lys Ser Gln Leu Phe Lys Asn Asn
            420                 425                 430
Val Ile Phe Gln Pro Leu Gly Asp Asp Phe Arg Tyr Asp Ile Asp Phe
        435                 440                 445
Glu Trp Asn Ser Gln Tyr Glu Asn Tyr Lys Lys Leu Phe Glu Tyr Met
    450                 455                 460
Asn Ser Lys Ser Glu Trp Asn Val His Ala Gln Phe Gly Thr Leu Ser
465                 470                 475                 480
Asp Tyr Phe Lys Lys Leu Asp Thr Ala Ile Ser Ala Ser Gly Glu Gln
                485                 490                 495
Leu Pro Thr Phe Ser Gly Asp Phe Phe Thr Tyr Ala Asp Arg Asp Asp
            500                 505                 510
His Tyr Trp Ser Gly Tyr Phe Thr Ser Arg Pro Phe Tyr Lys Gln Leu
        515                 520                 525
Asp Arg Val Leu Gln His Tyr Leu Arg Ser Ala Glu Ile Ala Phe Thr
    530                 535                 540
Leu Ala Asn Ile Glu Glu Gly Met Val Glu Ala Lys Ile Phe Glu
545                 550                 555                 560
Lys Leu Val Thr Ala Arg Arg Ala Leu Ser Leu Phe Gln His His Asp
                565                 570                 575
Gly Val Thr Gly Thr Ala Lys Asp His Val Val Leu Asp Tyr Gly Gln
            580                 585                 590
Lys Met Ile Asp Ala Leu Asn Ala Cys Glu Asp Ile Leu Ser Glu Ala
        595                 600                 605
Leu Val Val Leu Leu Gly Ile Asp Ser Thr Asn Lys Met Gln Met Asp
    610                 615                 620
Glu His Arg Val Asn Glu Asn Leu Leu Pro Lys Arg Val Tyr Lys
625                 630                 635                 640
Ile Gly Gln Asn Val Val Leu Phe Asn Thr Leu Ser Arg Asn Arg Asn
                645                 650                 655
```

-continued

```
Glu Pro Ile Cys Ile Gln Val Asp Ser Leu Asp Ala Gly Val Glu Ala
        660                 665                 670

Asp Pro Pro Ile Lys Lys Gln Gln Val Ser Pro Val Ile Ala Tyr Asp
        675                 680                 685

Glu Glu Lys Lys Thr Leu Val Val Lys Asn Gly Ile Phe Glu Leu Cys
        690                 695                 700

Phe Met Leu Ser Leu Gly Pro Met Glu Ser Val Ser Phe Arg Leu Val
705                 710                 715                 720

Lys Asn Thr Thr Thr Ser Lys Val Glu Ile Ile Thr Asn Asn Ala Ala
                725                 730                 735

Glu Phe Lys Glu Thr Ser Phe Lys Ser Ser Thr Ser Gly Asp Phe
        740                 745                 750

Thr Val Lys Asn Asp Lys Val Glu Ala Glu Phe Asp Gly Glu Asn Gly
        755                 760                 765

Met Ile Lys Arg Ala Thr Ser Leu Val Asp Asp Lys Pro Ile Asp Leu
770                 775                 780

Asn Ser His Phe Ile His Tyr Gly Ala Arg Lys Ser Lys Arg Lys Phe
785                 790                 795                 800

Ala Asn Gly Asn Glu Asp Asn Pro Ala Gly Ala Tyr Leu Phe Leu Pro
                805                 810                 815

Asp Gly Glu Ala Arg Glu Leu Lys Lys Gln Ser Ser Asp Trp Ile Leu
        820                 825                 830

Val Lys Gly Glu Val Val Gln Lys Val Phe Ala Thr Pro Asn Asn Asp
        835                 840                 845

Leu Lys Ile Leu Gln Thr Tyr Thr Leu Tyr Gln Gly Leu Pro Trp Ile
        850                 855                 860

Asp Leu Asp Asn Glu Val Asp Val Arg Ser Lys Glu Asn Phe Glu Leu
865                 870                 875                 880

Ala Leu Arg Phe Ser Ser Val Asn Ser Gly Asp Glu Phe Phe Thr
                885                 890                 895

Asp Leu Asn Gly Met Gln Met Ile Lys Arg Arg Gln Thr Lys Leu
        900                 905                 910

Pro Thr Gln Ala Asn Phe Tyr Pro Met Ser Ala Gly Val Tyr Ile Glu
        915                 920                 925

Asp Asp Thr Thr Arg Met Ser Ile His Ser Ala Gln Ala Leu Gly Val
930                 935                 940

Ser Ser Leu Ser Ser Gly Gln Ile Glu Ile Met Leu Asp Arg Arg Leu
945                 950                 955                 960

Ser Ser Asp Asp Asn Arg Gly Leu Gln Gln Gly Val Arg Asp Asn Lys
                965                 970                 975

Arg Thr Val Ala His Phe Arg Ile Val Ile Glu Pro Met Ser Ser Ser
        980                 985                 990

Ser Gly Asn Lys Lys Glu Glu Arg Val Gly Phe His Ser His Val Gly
        995                 1000                1005

His Leu Ala Thr Trp Ser Leu His Tyr Pro Leu Val Lys Met Ile Gly
        1010                1015                1020

Asp Ala Thr Pro Lys Ser Ile Ser Ser Lys Asn Val Glu Gln Glu Leu
1025                1030                1035                1040

Asn Cys Asp Leu His Leu Val Thr Phe Arg Thr Leu Ala Ser Pro Thr
                1045                1050                1055

Thr Tyr Glu Ala Asn Glu Arg Ser Thr Ala Ala Glu Lys Lys Ala Ala
        1060                1065                1070

Met Val Met His Arg Val Val Pro Asp Cys Arg Ser Arg Leu Thr Leu
```

-continued

```
                     1075                1080                1085
Pro Asp Thr Ser Cys Leu Ala Thr Gly Leu Glu Ile Glu Pro Leu Lys
    1090                1095                1100
Leu Ile Ser Thr Leu Lys Ser Ala Lys Thr Ser Leu Thr Asn Leu
1105                1110                1115                1120
Tyr Glu Gly Asn Lys Ala Glu Gln Phe Arg Leu Gln Pro Asn Asp Ile
                1125                1130                1135
Ser Ser Ile Leu Val Ser Phe
            1140

<210> SEQ ID NO 93
<211> LENGTH: 1279
<212> TYPE: PRT
<213> ORGANISM: Rattus norvegicus

<400> SEQUENCE: 93

Met Ala Cys Ile Gly Gly Ala Gln Gly Gln Arg Gln Ala Val Glu Lys
 1               5                  10                  15
Glu Pro Ser His Gln Gly Tyr Pro Trp Lys Pro Met Thr Asn Gly Ser
                20                  25                  30
Cys Ser Glu Leu Ala Leu Leu Ser Lys Thr Arg Met Tyr Cys His Gln
            35                  40                  45
Gly Cys Val Arg Pro Pro Arg Thr Asp Val Lys Asn Phe Lys Thr Thr
        50                  55                  60
Thr Asp Thr Gln Ser Val Pro Gly Val Ser Met Lys Leu Lys Lys Gln
 65                  70                  75                  80
Val Thr Val Cys Gly Ala Ala Ile Phe Cys Val Ala Val Phe Ser Leu
                85                  90                  95
Tyr Leu Met Leu Asp Arg Val Gln His Asp Pro Ala Arg His Gln Asn
                100                 105                 110
Gly Gly Asn Phe Pro Arg Ser Gln Ile Ser Val Leu Gln Asn Arg Ile
            115                 120                 125
Glu Gln Leu Glu Gln Leu Leu Glu Glu Asn His Glu Ile Ile Ser His
        130                 135                 140
Ile Lys Asp Ser Val Leu Glu Leu Thr Ala Asn Ala Glu Gly Pro Pro
145                 150                 155                 160
Ala Leu Leu Pro Tyr His Thr Ala Asn Gly Ser Trp Ala Val Leu Pro
                165                 170                 175
Glu Pro Arg Pro Ser Phe Phe Ser Val Ser Pro Glu Asp Cys Gln Phe
                180                 185                 190
Ala Leu Gly Gly Arg Gly Gln Lys Pro Glu Leu Gln Met Leu Thr Val
            195                 200                 205
Ser Glu Asp Leu Pro Phe Asp Asn Val Glu Gly Val Trp Arg Gln
        210                 215                 220
Gly Phe Asp Ile Ser Tyr Ser Pro Asn Asp Trp Asp Ala Glu Asp Leu
225                 230                 235                 240
Gln Val Phe Val Val Pro His Ser His Asn Asp Pro Gly Glu Glu Pro
                245                 250                 255
Ala Gly Pro Ser Arg Ser Val Gln Gly Gly Leu Ser Gly Asp Arg Arg
                260                 265                 270
Trp Ile Lys Thr Phe Asp Lys Tyr Tyr Thr Glu Gln Thr Gln His Ile
            275                 280                 285
Leu Asn Ser Met Val Ser Lys Leu Gln Glu Asp Pro Arg Arg Arg Phe
        290                 295                 300
```

-continued

```
Leu Trp Ala Glu Val Ser Phe Phe Ala Lys Trp Trp Asp Asn Ile Ser
305                 310                 315                 320

Ala Gln Lys Arg Ala Ala Val Arg Arg Leu Val Gly Asn Gly Gln Leu
            325                 330                 335

Glu Ile Ala Thr Gly Gly Trp Val Met Pro Asp Glu Ala Asn Ser His
        340                 345                 350

Tyr Phe Ala Leu Val Gly Gln Leu Ile Glu Gly Pro Pro Val Arg
    355                 360                 365

Arg Ala Val Asp Pro Phe Gly His Ser Ser Thr Met Pro Tyr Leu Leu
370                 375                 380

Arg Arg Ala Asn Leu Thr Ser Met Leu Ile Gln Arg Val His Tyr Ala
385                 390                 395                 400

Ile Lys Lys His Phe Ala Ala Thr His Ser Leu Glu Phe Met Trp Arg
                405                 410                 415

Gln Thr Trp Asp Ser Asp Ser Ser Thr Asp Ile Phe Cys His Met Met
            420                 425                 430

Pro Phe Tyr Ser Tyr Asp Val Pro His Thr Cys Gly Pro Asp Pro Lys
            435                 440                 445

Ile Cys Cys Gln Phe Asp Phe Lys Arg Leu Pro Gly Gly Arg Ile Asn
        450                 455                 460

Cys Pro Trp Lys Val Pro Pro Arg Ala Ile Thr Glu Ala Asn Val Ala
465                 470                 475                 480

Asp Arg Ala Ala Leu Leu Leu Asp Gln Tyr Arg Lys Lys Ser Arg Leu
                485                 490                 495

Phe Arg Ser Ser Val Leu Leu Val Pro Leu Gly Asp Asp Phe Arg Tyr
            500                 505                 510

Asp Lys Pro Gln Glu Trp Asp Ala Gln Phe Phe Asn Tyr Gln Arg Leu
            515                 520                 525

Phe Asp Phe Leu Asn Ser Lys Pro Glu Phe His Val Gln Ala Gln Phe
530                 535                 540

Gly Thr Leu Ser Glu Tyr Phe Asp Ala Leu Tyr Lys Arg Thr Gly Val
545                 550                 555                 560

Glu Pro Gly Ala Arg Pro Pro Gly Phe Pro Val Leu Ser Gly Asp Phe
                565                 570                 575

Phe Ser Tyr Ala Asp Arg Glu Asp His Tyr Trp Thr Gly Tyr Tyr Thr
            580                 585                 590

Ser Arg Pro Phe Tyr Lys Ser Leu Asp Arg Val Leu Glu Thr His Leu
            595                 600                 605

Arg Gly Ala Glu Val Leu Tyr Ser Leu Ala Leu Ala His Ala Arg Arg
610                 615                 620

Ser Gly Leu Thr Gly Gln Tyr Pro Leu Ser Asp Tyr Ala Val Leu Thr
625                 630                 635                 640

Glu Ala Arg Arg Thr Leu Gly Leu Phe Gln His His Asp Ala Ile Thr
                645                 650                 655

Gly Thr Ala Lys Glu Ala Val Val Asp Tyr Gly Val Arg Leu Leu
            660                 665                 670

Arg Ser Leu Val Ser Leu Lys Gln Val Ile Ile Asn Ala Ala His Tyr
            675                 680                 685

Leu Val Leu Gly Asp Lys Glu Thr Tyr Ser Phe Asp Pro Arg Ala Pro
            690                 695                 700

Phe Leu Gln Met Val Ser Gln Ala Trp Arg Gly Ser Gln Ser Thr Leu
705                 710                 715                 720

His Pro Ser Ala Ala Leu Val Pro Ala Ala Ala Ala Ser Ala Leu Leu
```

-continued

```
            725                 730                 735
Pro Gln Arg Ala Pro Arg Phe Val Val Phe Asn Pro Leu Glu Gln
            740                 745                 750
Glu Arg Leu Ser Val Val Ser Leu Leu Val Asn Ser Pro Arg Val Arg
            755                 760                 765
Val Leu Ser Glu Glu Gly Gln Pro Leu Ser Val Gln Ile Ser Val Gln
            770                 775                 780
Trp Ser Ser Ala Thr Asn Met Val Pro Asp Val Tyr Gln Val Ser Val
785                 790                 795                 800
Pro Val Arg Leu Pro Ala Leu Gly Leu Gly Val Leu Gln Leu Gln Pro
            805                 810                 815
Asp Leu Asp Gly Pro Tyr Thr Leu Gln Ser Ser Val His Val Tyr Leu
            820                 825                 830
Asn Gly Val Lys Leu Ser Val Ser Arg Gln Thr Thr Phe Pro Leu Arg
            835                 840                 845
Val Val Asp Ser Gly Thr Ser Asp Phe Ala Ile Ser Asn Arg Tyr Met
            850                 855                 860
Gln Val Trp Phe Ser Gly Leu Thr Gly Leu Leu Lys Ser Val Arg Arg
865                 870                 875                 880
Val Asp Glu Glu Gln Glu Gln Val Asp Met Lys Leu Phe Val Tyr
            885                 890                 895
Gly Thr Arg Thr Ser Lys Asp Lys Ser Gly Ala Tyr Leu Phe Leu Pro
            900                 905                 910
Asp Asn Glu Ala Lys Pro Tyr Val Pro Lys Pro Val Leu Arg
            915                 920                 925
Val Thr Glu Gly Pro Phe Phe Ser Glu Val Ala Ala Tyr Tyr Glu His
            930                 935                 940
Phe His Gln Val Ile Arg Leu Tyr Asn Leu Pro Gly Val Glu Gly Leu
945                 950                 955                 960
Ser Leu Asp Val Ser Phe Gln Val Asp Ile Arg Asp Tyr Val Asn Lys
            965                 970                 975
Glu Leu Ala Leu Arg Ile His Thr Asp Ile Asp Ser Gln Gly Thr Phe
            980                 985                 990
Phe Thr Asp Leu Asn Gly Phe Gln Val Gln Pro Arg Lys Tyr Leu Lys
            995                 1000                1005
Lys Leu Pro Leu Gln Ala Asn Phe Tyr Pro Met Pro Val Met Ala Tyr
            1010                1015                1020
Ile Gln Asp Ser Gln Arg Arg Leu Thr Leu His Thr Ala Gln Ala Leu
1025                1030                1035                1040
Gly Val Ser Ser Leu Gly Asn Gly Gln Leu Glu Val Ile Leu Asp Arg
            1045                1050                1055
Arg Leu Met Gln Asp Asp Asn Arg Gly Leu Gly Gln Gly Leu Lys Asp
            1060                1065                1070
Asn Lys Ile Thr Cys Asn His Phe Arg Leu Leu Glu Arg Arg Thr
            1075                1080                1085
Leu Met Ser Pro Glu Val Gln Gln Glu Arg Ser Thr Ser Tyr Pro Ser
            1090                1095                1100
Leu Leu Ser His Met Thr Ser Met Tyr Leu Asn Thr Pro Pro Leu Val
1105                1110                1115                1120
Leu Pro Val Ala Lys Arg Glu Ser Thr Ser Pro Thr Leu His Ser Phe
            1125                1130                1135
His Pro Leu Ala Ser Pro Leu Pro Cys Asp Phe His Leu Leu Asn Leu
            1140                1145                1150
```

Arg Met Leu Pro Ala Glu Val Ser Val Pro Val Arg Ala Asn Pro His
         1155                1160                1165

His Gln Ala Glu Pro Cys Leu Leu Gly Arg His Ala Ala Asp Pro Pro
    1170                1175                1180

Pro Leu Leu Ser Leu Thr Val Phe Gln Asp Thr Leu Pro Ala Ala Asp
1185                1190                1195                1200

Ala Ala Leu Ile Leu His Arg Lys Gly Phe Asp Cys Gly Leu Glu Ala
             1205                1210                1215

Lys Asn Leu Gly Phe Asn Cys Thr Thr Ser Gln Gly Lys Leu Ala Leu
         1220                1225                1230

Gly Ser Leu Phe His Gly Leu Asp Val Leu Phe Leu Gln Pro Thr Ser
         1235                1240                1245

Leu Thr Leu Leu Tyr Pro Leu Ala Ser Pro Ser Asn Ser Thr Asp Ile
         1250                1255                1260

Ser Leu Glu Pro Met Glu Ile Ser Thr Phe Arg Leu Arg Leu Gly
1265                1270                1275

<210> SEQ ID NO 94
<211> LENGTH: 1149
<212> TYPE: PRT
<213> ORGANISM: Ciona intestinalis

<400> SEQUENCE: 94

Met Lys Leu Lys Arg Gln Phe Leu Phe Phe Gly Gly Ile Leu Phe Phe
1               5                   10                  15

Gly Ser Ile Trp Phe Met Ile Gly Gln Leu Asp Thr Pro Asn Ser Pro
            20                  25                  30

Gln Lys Val Lys Phe Ser Glu Gly Ser Glu Asn Asp Gln Val Arg Thr
        35                  40                  45

Leu Gln Asp Lys Leu Ser Leu Val Glu Lys Glu Leu Leu Glu Asn Arg
    50                  55                  60

Lys Ile Met His Lys Val Lys Asp Ser Leu Gln Asp Met Thr Pro Met
65                  70                  75                  80

Lys Asn Val His Val Pro Met Gln Arg Gly Glu Ile Arg Asn Asn Val
                85                  90                  95

Asn Lys Pro Val Leu Pro Leu Ile Met Pro Lys Gln Phe Ala Asn Asp
            100                 105                 110

Ser Arg Met Ser Asp Thr Cys Pro Val Leu Ser Tyr Ser Gly Gly Lys
        115                 120                 125

Ser Asp Val Asn Met Ile Asn Val Tyr Asp His Leu Pro Phe Asp Asp
    130                 135                 140

Pro Asp Gly Gly Val Trp Lys Gln Gly Trp Asp Ile Gln Thr Ser Asp
145                 150                 155                 160

Gln Glu Trp Ala Gly Arg Lys Leu Lys Val Phe Ile Val Pro His Ser
                165                 170                 175

His Asn Asp Pro Gly Trp Leu Lys Thr Val Glu Arg Tyr Phe Ser Asp
            180                 185                 190

Gln Thr Gln His Ile Leu Asn Asn Ile Val Asp Ala Leu Ser Gln Asp
        195                 200                 205

Pro Ala Arg Lys Phe Ile Trp Ala Glu Met Ser Tyr Leu Ser Met Trp
    210                 215                 220

Trp Asp Ile Ala Thr Pro Asp Arg Lys Gln Lys Met Gln Thr Leu Val
225                 230                 235                 240

Lys Asn Gly Gln Leu Glu Ile Val Thr Gly Gly Trp Val Met Asn Asp

-continued

```
                245                 250                 255
Glu Ala Asn Thr His Tyr Phe Ala Met Ile Asp Gln Leu Ile Glu Gly
            260                 265                 270
Met Glu Trp Leu Arg Arg Thr Leu Asn Val Val Pro Lys Ser Gly Trp
        275                 280                 285
Ala Ile Asp Pro Phe Gly His Thr Pro Thr Met Ala Tyr Ile Leu Lys
    290                 295                 300
Gln Met Lys Phe Lys Asn Met Leu Ile Gln Arg Val His Tyr Ala Val
305                 310                 315                 320
Lys Lys Tyr Leu Ala Gln Glu Lys Ser Leu Glu Phe Arg Trp Arg Gln
                325                 330                 335
Met Trp Asp Ser Ala Ser Ser Thr Asp Met Met Cys His Leu Met Pro
            340                 345                 350
Phe Tyr Ser Tyr Asp Val Pro His Thr Cys Gly Pro Asp Pro Lys Ile
        355                 360                 365
Cys Cys Gln Phe Asp Phe Ala Arg Leu Pro Gly Gly Lys Ile Thr Cys
    370                 375                 380
Pro Trp Lys Val Pro Pro Val Ala Ile Thr Asp Ser Asn Val Glu Thr
385                 390                 395                 400
Arg Ala Gly Ile Leu Leu Asp Gln Tyr Arg Lys Lys Ser Lys Leu Phe
                405                 410                 415
Lys Ser Asp Thr Leu Leu Ile Ile Leu Gly Asp Asp Phe Arg Tyr Ser
            420                 425                 430
Leu Ser Lys Glu Thr Asn Asp Gln Phe Asp Asn Tyr Ala Arg Ile Ile
        435                 440                 445
Ser Tyr Val Asn Ser His Pro Glu Leu Asn Ala Lys Leu Gln Phe Gly
    450                 455                 460
Thr Leu Ser Glu Tyr Phe Asp Ala Met Lys Ser Glu Val Gly Gly Glu
465                 470                 475                 480
Glu Lys Leu Pro Ala Leu Ser Gly Asp Phe Phe Thr Tyr Ala Asp Arg
                485                 490                 495
Glu Asp His Tyr Trp Ser Gly Tyr Tyr Thr Ser Arg Pro Tyr His Lys
            500                 505                 510
Met Gln Glu Arg Val Leu Glu Ser His Leu Arg Gly Ala Glu Met Leu
        515                 520                 525
Phe Ala Leu Ser Trp Pro Lys Ile Gln Trp Thr Gly Leu Gly Glu Thr
    530                 535                 540
Phe Ser His Glu Leu Tyr Pro Leu Leu Val Gln Ala Arg Gln Asn Leu
545                 550                 555                 560
Gly Leu Phe Gln His His Asp Gly Ile Thr Gly Thr Ala Lys Asp His
                565                 570                 575
Val Val Val Asp Tyr Gly Asn Lys Leu Met Lys Ser Val Met Asp Ala
            580                 585                 590
Lys Lys Val Ile Ser Tyr Ser Ala Gln Val Leu Leu Gln Glu Met Ile
        595                 600                 605
Thr Phe Asp Pro Asn Thr Met Val Leu Asn Tyr Asp Glu Val Tyr Gln
    610                 615                 620
Ala Gln Asn Gln Gln Pro Ala Pro Val Val Lys Leu Pro Thr Lys
625                 630                 635                 640
Asn Glu Glu Ala Arg Lys Val Val Leu Tyr Asn Ser Leu Asp Tyr Asp
                645                 650                 655
Arg Thr Gly Val Val Arg Leu Ile Val Thr Ser Pro Asp Val Val
            660                 665                 670
```

```
Met Ser Glu Asn Lys Asn Val Val Pro Ser Gln Thr Ser Pro Ile Trp
            675                 680                 685

Ser Asp Ser Thr Glu Ile Arg Thr Asp Gln Phe Glu Leu Val Phe Leu
        690                 695                 700

Ser Thr Val Pro Ala Ile Gly Leu Ala Val Tyr Lys Ile Trp Glu Asp
705                 710                 715                 720

Asn Asp Val Ala Asp Thr Thr His Ser Thr Val Lys Phe Ile Asn Pro
                725                 730                 735

Arg Val Gly Phe Ser Lys Arg Thr Arg Ser Lys Phe Val Leu Asp Val
            740                 745                 750

Glu Asp Ser Gly Glu Phe Thr Ile Met Asn Asp Gln Leu Val Ala His
            755                 760                 765

Phe Ser Gly Gln Asn Gly Met Leu Gln Ser Val Thr Thr Val Arg Asp
        770                 775                 780

Asn Val Lys Thr Gln Leu Gly Ile Glu Phe Val Ala Tyr Thr Ser Arg
785                 790                 795                 800

Asn Lys Lys Asp Lys Ser Gly Ala Tyr Leu Phe Leu Pro Ala Gly Pro
                805                 810                 815

Ala Gln Pro His Val Thr Glu Ser His Arg Pro Leu Val Arg Ile Ile
            820                 825                 830

Arg Gly Pro Val Met Ser Thr Val His Val Leu Leu Pro Asn Val Leu
            835                 840                 845

His Lys Val Thr Leu Tyr Thr Gly Thr Gly Ala Gly Thr Gln Ser Leu
            850                 855                 860

Gly Val His Val Ser Asn Asp Val Asp Val Arg Thr Gly Tyr Asp Asn
865                 870                 875                 880

Lys Glu Leu Ser Met Arg Leu Asn Ser Glu Val Leu Ser Gly Ser Lys
                885                 890                 895

Phe Phe Thr Asp Leu Asn Gly Phe Gln Ile Gln Pro Arg Thr Thr Tyr
            900                 905                 910

Ser Lys Leu Pro Leu Gln Ala Asn Phe Tyr Pro Ile Pro Thr Met Ala
            915                 920                 925

Phe Ile Gln Asp Glu Lys Ser Arg Leu Thr Leu Met Thr Ala Gln Pro
930                 935                 940

Leu Gly Val Ala Ser Leu Lys Ser Gly Gln Leu Glu Val Val Leu Asp
945                 950                 955                 960

Arg Arg Leu Met Gln Asp Asp Asn Arg Gly Val Gly Gln Gly Val Lys
            965                 970                 975

Asp Asn Leu Pro Thr Pro Glu Ser Phe Val Ile Met Leu Glu Arg Trp
            980                 985                 990

Thr Ala Ile Ala Ala Lys Glu Ser Lys Ser Ala Lys Leu Ala Tyr
            995                 1000                1005

Pro Ser Met Ala Val Tyr Gln Ser Ser Trp Glu Leu Leu His Pro Ile
            1010                1015                1020

Arg Pro Met Ser Val Asn Gly Pro Val His Leu Lys Glu Asp Tyr Arg
1025                1030                1035                1040

Ser Leu Pro Gln Pro Leu Pro Cys Asp Val His Val Leu Asn Leu Arg
                1045                1050                1055

Ala Ile His Ser Lys Asp Ala Val Ala Pro Thr Asp Gln Ser Ala Leu
            1060                1065                1070

Leu Leu His Thr Val Gly Arg Glu Cys Ser Leu Asp Ala Asp Lys Tyr
            1075                1080                1085
```

```
Phe His Pro Thr Cys Leu Met His Gly Val Glu Lys Leu Ala Ile Thr
    1090                1095                1100

Ile Ser Thr Leu Phe Thr Asn Ser Gly Met Arg Lys Thr Ser Leu Ser
1105                1110                1115                1120

Leu Gln His Asp Gly Ser Leu Leu Asp Asn Gly Gly Ile Thr Val
            1125                1130                1135

Ser Pro Met Glu Ile Gln Ala Tyr Lys Ile Val Leu Thr
            1140                1145

<210> SEQ ID NO 95
<211> LENGTH: 1173
<212> TYPE: PRT
<213> ORGANISM: Arabidopsis thaliana

<400> SEQUENCE: 95

Met Pro Phe Ser Ser Tyr Ile Gly Asn Ser Arg Arg Ser Thr Gly
  1               5                  10                  15

Gly Gly Thr Gly Gly Trp Gly Gln Ser Leu Leu Pro Thr Ala Leu Ser
                20                  25                  30

Lys Ser Lys Leu Ala Ile Asn Arg Lys Pro Arg Lys Arg Thr Leu Val
             35                  40                  45

Val Asn Phe Ile Phe Ala Asn Phe Val Ile Ala Leu Thr Val Ser
         50                  55                  60

Leu Leu Phe Phe Leu Leu Thr Leu Phe His Phe Gly Val Pro Gly Pro
 65                  70                  75                  80

Ile Ser Ser Arg Phe Leu Thr Ser Arg Ser Asn Arg Ile Val Lys Pro
                 85                  90                  95

Arg Lys Asn Ile Asn Arg Arg Pro Leu Asn Asp Ser Asn Ser Gly Ala
                100                 105                 110

Val Val Asp Ile Thr Thr Lys Asp Leu Tyr Asp Arg Ile Glu Phe Leu
            115                 120                 125

Asp Thr Asp Gly Gly Pro Trp Lys Gln Gly Trp Arg Val Thr Tyr Lys
130                 135                 140

Asp Asp Glu Trp Glu Lys Glu Lys Leu Lys Ile Phe Val Val Pro His
145                 150                 155                 160

Ser His Asn Asp Pro Gly Trp Lys Leu Thr Val Glu Glu Tyr Tyr Gln
                165                 170                 175

Arg Gln Ser Arg His Ile Leu Asp Thr Ile Val Glu Thr Leu Ser Lys
            180                 185                 190

Asp Ser Arg Arg Lys Phe Ile Trp Glu Glu Met Ser Tyr Leu Glu Arg
        195                 200                 205

Trp Trp Arg Asp Ala Ser Pro Asn Lys Gln Glu Ala Leu Thr Lys Leu
210                 215                 220

Val Lys Asp Gly Gln Leu Glu Ile Val Gly Gly Trp Val Met Asn
225                 230                 235                 240

Asp Glu Ala Asn Ser His Tyr Phe Ala Ile Glu Gln Ile Ala Glu
                245                 250                 255

Gly Asn Met Trp Leu Asn Asp Thr Ile Gly Val Ile Pro Lys Asn Ser
            260                 265                 270

Trp Ala Ile Asp Pro Phe Gly Tyr Ser Ser Thr Met Ala Tyr Leu Leu
        275                 280                 285

Arg Arg Met Gly Phe Glu Asn Met Leu Ile Gln Arg Thr His Tyr Glu
    290                 295                 300

Leu Lys Lys Asp Leu Ala Gln His Lys Asn Leu Glu Tyr Ile Trp Arg
305                 310                 315                 320
```

```
Gln Ser Trp Asp Ala Met Glu Thr Thr Asp Ile Phe Val His Met Met
                325                 330                 335
Pro Phe Tyr Ser Tyr Asp Ile Pro His Thr Cys Gly Pro Glu Pro Ala
            340                 345                 350
Ile Cys Cys Gln Phe Asp Phe Ala Arg Met Arg Gly Phe Lys Tyr Glu
        355                 360                 365
Leu Cys Pro Trp Gly Lys His Pro Val Glu Thr Thr Leu Glu Asn Val
    370                 375                 380
Gln Glu Arg Ala Leu Lys Leu Leu Asp Gln Tyr Arg Lys Lys Ser Thr
385                 390                 395                 400
Leu Tyr Arg Thr Asn Thr Leu Leu Ile Pro Leu Gly Asp Asp Phe Arg
                405                 410                 415
Tyr Ile Ser Ile Asp Glu Ala Glu Ala Gln Phe Arg Asn Tyr Gln Met
            420                 425                 430
Leu Phe Asp His Ile Asn Ser Asn Pro Ser Leu Asn Ala Glu Ala Lys
        435                 440                 445
Phe Gly Thr Leu Glu Asp Tyr Phe Arg Thr Val Arg Glu Glu Ala Asp
    450                 455                 460
Arg Val Asn Tyr Ser Arg Pro Gly Glu Val Gly Ser Gly Gln Val Val
465                 470                 475                 480
Gly Phe Pro Ser Leu Ser Gly Asp Phe Thr Tyr Ala Asp Arg Gln
                485                 490                 495
Gln Asp Tyr Trp Ser Gly Tyr Tyr Val Ser Arg Pro Phe Phe Lys Ala
            500                 505                 510
Val Asp Arg Val Leu Glu His Thr Leu Arg Gly Ala Glu Ile Met Met
        515                 520                 525
Ser Phe Leu Leu Gly Tyr Cys His Arg Ile Gln Cys Glu Lys Phe Pro
    530                 535                 540
Thr Ser Phe Thr Tyr Lys Leu Thr Ala Ala Arg Arg Asn Leu Ala Leu
545                 550                 555                 560
Phe Gln His His Asp Gly Val Thr Gly Thr Ala Lys Asp Tyr Val Val
                565                 570                 575
Gln Asp Tyr Gly Thr Arg Met His Thr Ser Leu Gln Asp Leu Gln Ile
            580                 585                 590
Phe Met Ser Lys Ala Ile Glu Val Leu Leu Gly Ile Arg His Glu Lys
        595                 600                 605
Glu Lys Ser Asp Gln Ser Pro Ser Phe Phe Glu Ala Glu Gln Met Arg
    610                 615                 620
Ser Lys Tyr Asp Ala Arg Pro Val His Lys Pro Ile Ala Ala Arg Glu
625                 630                 635                 640
Gly Asn Ser His Thr Val Ile Leu Phe Asn Pro Ser Glu Gln Thr Arg
                645                 650                 655
Glu Glu Val Val Thr Val Val Asn Arg Ala Glu Ile Ser Val Leu
            660                 665                 670
Asp Ser Asn Trp Thr Cys Val Pro Ser Gln Ile Ser Pro Glu Val Gln
        675                 680                 685
His Asp Asp Thr Lys Leu Phe Thr Gly Arg His Arg Leu Tyr Trp Lys
    690                 695                 700
Ala Ser Ile Pro Ala Leu Gly Leu Arg Thr Tyr Phe Ile Ala Asn Gly
705                 710                 715                 720
Asn Val Glu Cys Glu Lys Ala Thr Pro Ser Lys Leu Lys Tyr Ala Ser
                725                 730                 735
```

-continued

```
Glu Phe Asp Pro Phe Pro Cys Pro Pro Tyr Ser Cys Ser Lys Leu
                740                 745                 750

Asp Asn Asp Val Thr Glu Ile Arg Asn Glu His Gln Thr Leu Val Phe
        755                 760                 765

Asp Val Lys Asn Gly Ser Leu Arg Lys Ile Val His Arg Asn Gly Ser
    770                 775                 780

Glu Thr Val Val Gly Glu Ile Gly Met Tyr Ser Ser Pro Glu Ser
785                 790                 795                 800

Gly Ala Tyr Leu Phe Lys Pro Asp Gly Glu Ala Gln Pro Ile Val Gln
                805                 810                 815

Pro Asp Gly His Val Val Thr Ser Glu Gly Leu Leu Val Gln Glu Val
                820                 825                 830

Phe Ser Tyr Pro Lys Thr Lys Trp Glu Lys Ser Pro Leu Ser Gln Lys
                835                 840                 845

Thr Arg Leu Tyr Thr Gly Gly Asn Thr Leu Gln Asp Gln Val Val Glu
    850                 855                 860

Ile Glu Tyr His Val Glu Leu Leu Gly Asn Asp Phe Asp Asp Arg Glu
865                 870                 875                 880

Leu Ile Val Arg Tyr Lys Thr Asp Val Asp Asn Lys Lys Val Phe Tyr
                885                 890                 895

Ser Asp Leu Asn Gly Phe Gln Met Ser Arg Arg Glu Thr Tyr Asp Lys
            900                 905                 910

Ile Pro Leu Gln Gly Asn Tyr Tyr Pro Met Pro Ser Leu Ala Phe Ile
            915                 920                 925

Gln Gly Ser Asn Gly Gln Arg Phe Ser Val His Ser Arg Gln Ser Leu
            930                 935                 940

Gly Val Ala Ser Leu Lys Glu Gly Trp Leu Glu Ile Met Leu Asp Arg
945                 950                 955                 960

Arg Leu Val Arg Asp Asp Gly Arg Gly Leu Gly Gln Gly Val Met Asp
                965                 970                 975

Asn Arg Ala Met Thr Val Val Phe His Leu Leu Ala Glu Ser Asn Ile
            980                 985                 990

Ser Gln Ala Asp Pro Ala Ser Asn Thr Asn Pro Arg Asn Pro Ser Leu
        995                 1000                1005

Leu Ser His Leu Ile Gly Ala His Leu Asn Tyr Pro Ile Asn Thr Phe
    1010                1015                1020

Ile Ala Lys Lys Pro Gln Asp Ile Ser Val Arg Val Pro Gln Tyr Gly
1025                1030                1035                1040

Ser Phe Ala Pro Leu Ala Lys Pro Leu Pro Cys Asp Leu His Ile Val
                1045                1050                1055

Asn Phe Lys Val Pro Arg Pro Ser Lys Tyr Ser Gln Gln Leu Glu Glu
                1060                1065                1070

Asp Lys Pro Arg Phe Ala Leu Ile Leu Asn Arg Arg Ala Trp Asp Ser
        1075                1080                1085

Ala Tyr Cys His Lys Gly Arg Gln Val Asn Cys Thr Ser Met Ala Asn
        1090                1095                1100

Glu Pro Val Asn Phe Ser Asp Met Phe Lys Asp Leu Ala Ala Ser Lys
1105                1110                1115                1120

Val Lys Pro Thr Ser Leu Asn Leu Leu Gln Glu Asp Met Glu Ile Leu
                1125                1130                1135

Gly Tyr Asp Asp Gln Glu Leu Pro Arg Asp Ser Ser Gln Pro Arg Glu
            1140                1145                1150

Gly Arg Val Ser Ile Ser Pro Met Glu Ile Arg Ala Tyr Lys Leu Glu
```

-continued

```
            1155                1160                1165

Leu Arg Pro His Lys
    1170

<210> SEQ ID NO 96
<211> LENGTH: 1108
<212> TYPE: PRT
<213> ORGANISM: Drosophila sp.

<400> SEQUENCE: 96

Met Leu Arg Ile Arg Arg Phe Ala Leu Val Ile Cys Ser Gly Cys
  1               5                  10                  15

Leu Leu Val Phe Leu Ser Leu Tyr Ile Ile Leu Asn Phe Ala Ala Pro
                 20                  25                  30

Ala Ala Thr Gln Ile Lys Pro Asn Tyr Glu Asn Ile Glu Asn Lys Leu
             35                  40                  45

His Glu Leu Glu Asn Gly Leu Gln His Gly Glu Glu Met Arg Asn
     50                  55                  60

Leu Arg Ala Arg Leu Ala Lys Thr Ser Asn Arg Asp Asp Pro Ile Arg
 65                  70                  75                  80

Pro Pro Leu Lys Val Ala Arg Ser Pro Arg Pro Gly Gln Cys Gln Asp
                 85                  90                  95

Val Val Gln Asp Val Pro Asn Val Asp Val Gln Met Leu Glu Leu Tyr
                100                 105                 110

Asp Arg Met Ser Phe Lys Asp Ile Asp Gly Gly Val Trp Lys Gln Gly
                115                 120                 125

Trp Asn Ile Lys Tyr Asp Pro Leu Lys Tyr Asn Ala His His Lys Leu
    130                 135                 140

Lys Val Phe Val Val Pro His Ser His Asn Asp Pro Gly Trp Ile Gln
145                 150                 155                 160

Thr Phe Glu Glu Tyr Tyr Gln His Asp Thr Lys His Ile Leu Ser Asn
                165                 170                 175

Ala Leu Arg His Leu His Asp Asn Pro Glu Met Lys Phe Ile Trp Ala
                180                 185                 190

Glu Ile Ser Tyr Phe Ala Arg Phe Tyr His Asp Leu Gly Glu Asn Lys
            195                 200                 205

Lys Leu Gln Met Lys Ser Ile Val Lys Asn Gly Gln Leu Glu Phe Val
    210                 215                 220

Thr Gly Gly Trp Val Met Pro Asp Glu Ala Asn Ser His Trp Arg Asn
225                 230                 235                 240

Val Leu Leu Gln Leu Thr Glu Gly Gln Thr Trp Leu Lys Gln Phe Met
                245                 250                 255

Asn Val Thr Pro Thr Ala Ser Trp Ala Ile Asp Pro Phe Gly His Ser
                260                 265                 270

Pro Thr Met Pro Tyr Ile Leu Gln Lys Ser Gly Phe Lys Asn Met Leu
            275                 280                 285

Ile Gln Arg Thr His Tyr Ser Val Lys Lys Glu Leu Ala Gln Gln Arg
    290                 295                 300

Gln Leu Glu Phe Leu Trp Arg Gln Ile Trp Asp Asn Lys Gly Asp Thr
305                 310                 315                 320

Ala Leu Phe Thr His Met Met Pro Phe Tyr Ser Tyr Asp Ile Pro His
                325                 330                 335

Thr Cys Gly Pro Asp Pro Lys Val Cys Cys Gln Phe Asp Phe Lys Arg
                340                 345                 350
```

```
Met Gly Ser Phe Gly Leu Ser Cys Pro Trp Lys Val Pro Pro Arg Thr
        355                 360                 365
Ile Ser Asp Gln Asn Val Ala Ala Arg Ser Asp Leu Leu Val Asp Gln
        370                 375                 380
Trp Lys Lys Ala Glu Leu Tyr Arg Thr Asn Val Leu Leu Ile Pro
385                 390                 395                 400
Leu Gly Asp Asp Phe Arg Phe Lys Gln Asn Thr Glu Trp Asp Val Gln
                405                 410                 415
Arg Val Asn Tyr Glu Arg Leu Phe Glu His Ile Asn Ser Gln Ala His
                420                 425                 430
Phe Asn Val Gln Ala Gln Phe Gly Thr Leu Gln Glu Tyr Phe Asp Ala
                435                 440                 445
Val His Gln Ala Glu Arg Ala Gly Gln Ala Glu Phe Pro Thr Leu Ser
450                 455                 460
Gly Asp Phe Phe Thr Tyr Ala Asp Arg Ser Asp Asn Tyr Trp Ser Gly
465                 470                 475                 480
Tyr Tyr Thr Ser Arg Pro Tyr His Lys Arg Met Asp Arg Val Leu Met
                485                 490                 495
His Tyr Val Arg Ala Ala Glu Met Leu Ser Ala Trp His Ser Trp Asp
                500                 505                 510
Gly Met Ala Arg Ile Glu Glu Arg Leu Glu Gln Ala Arg Arg Glu Leu
                515                 520                 525
Ser Leu Phe Gln His His Asp Gly Ile Thr Gly Thr Ala Lys Thr His
                530                 535                 540
Val Val Val Asp Tyr Glu Gln Arg Met Gln Glu Ala Leu Lys Ala Cys
545                 550                 555                 560
Gln Met Val Met Gln Ser Val Tyr Arg Leu Leu Thr Lys Pro Ser
                565                 570                 575
Ile Tyr Ser Pro Asp Phe Ser Phe Ser Tyr Phe Thr Leu Asp Asp Ser
                580                 585                 590
Arg Trp Pro Gly Ser Gly Val Glu Asp Ser Arg Thr Thr Ile Ile Leu
                595                 600                 605
Gly Glu Asp Ile Leu Pro Ser Lys His Val Val Met His Asn Thr Leu
                610                 615                 620
Pro His Trp Arg Glu Gln Leu Val Asp Phe Tyr Val Ser Ser Pro Phe
625                 630                 635                 640
Val Ser Val Thr Asp Leu Ala Asn Asn Pro Val Glu Ala Gln Val Ser
                645                 650                 655
Pro Val Trp Ser Trp His His Asp Thr Leu Thr Lys Thr Ile His Pro
                660                 665                 670
Gln Gly Ser Thr Thr Lys Tyr Arg Ile Ile Phe Lys Ala Arg Val Pro
                675                 680                 685
Pro Met Gly Leu Ala Thr Tyr Val Leu Thr Ile Ser Asp Ser Lys Pro
                690                 695                 700
Glu His Thr Ser Tyr Ala Ser Asn Leu Leu Arg Lys Asn Pro Thr
705                 710                 715                 720
Ser Leu Pro Leu Gly Gln Tyr Pro Glu Asp Val Lys Phe Gly Asp Pro
                725                 730                 735
Arg Glu Ile Ser Leu Arg Val Gly Asn Gly Pro Thr Leu Ala Phe Ser
                740                 745                 750
Glu Gln Gly Leu Leu Lys Ser Ile Gln Leu Thr Gln Asp Ser Pro His
                755                 760                 765
Val Pro Val His Phe Lys Phe Leu Lys Tyr Gly Val Arg Ser His Gly
```

```
                    770                 775                 780
Asp Arg Ser Gly Ala Tyr Leu Phe Leu Pro Asn Gly Pro Ala Ser Pro
785                 790                 795                 800

Val Glu Leu Gly Gln Pro Val Leu Val Thr Lys Gly Lys Leu Glu
                805                 810                 815

Ser Ser Val Ser Val Gly Leu Pro Ser Val His Gln Thr Ile Met
                820                 825                 830

Arg Gly Gly Ala Pro Glu Ile Arg Asn Leu Val Asp Ile Gly Ser Leu
                835                 840                 845

Asp Asn Thr Glu Ile Val Met Arg Leu Glu Thr His Ile Asp Ser Gly
850                 855                 860

Asp Ile Phe Tyr Thr Asp Leu Asn Gly Leu Gln Phe Ile Lys Arg Arg
865                 870                 875                 880

Arg Leu Asp Lys Leu Pro Leu Gln Ala Asn Tyr Tyr Pro Ile Pro Ser
                885                 890                 895

Gly Met Phe Ile Glu Asp Ala Asn Thr Arg Leu Thr Leu Leu Thr Gly
                900                 905                 910

Gln Pro Leu Gly Gly Ser Ser Leu Ala Ser Gly Glu Leu Glu Ile Met
                915                 920                 925

Gln Asp Arg Arg Leu Ala Ser Asp Glu Arg Gly Leu Gly Gln Gly
                930                 935                 940

Val Leu Asp Asn Lys Pro Val Leu His Ile Tyr Arg Leu Val Leu Glu
945                 950                 955                 960

Lys Val Asn Asn Cys Val Arg Pro Ser Lys Leu His Pro Ala Gly Tyr
                965                 970                 975

Leu Thr Ser Ala Ala His Lys Ala Ser Gln Ser Leu Leu Asp Pro Leu
                980                 985                 990

Asp Lys Phe Ile Phe Ala Glu Asn Glu Trp Ile Gly Ala Gln Gly Gln
                995                 1000                1005

Phe Gly Gly Asp His Pro Ser Ala Arg Glu Asp Leu Asp Val Ser Val
                1010                1015                1020

Met Arg Arg Leu Thr Lys Ser Ser Ala Lys Thr Gln Arg Val Gly Tyr
1025                1030                1035                1040

Val Leu His Arg Thr Asn Leu Met Gln Cys Gly Thr Pro Glu His
                1045                1050                1055

Thr Gln Lys Leu Asp Val Cys His Leu Leu Pro Asn Val Ala Arg Cys
                1060                1065                1070

Glu Arg Thr Thr Leu Thr Phe Leu Gln Asn Leu Glu His Leu Asp Gly
                1075                1080                1085

Met Val Ala Pro Glu Val Cys Pro Met Glu Thr Ala Ala Tyr Val Ser
                1090                1095                1100

Ser His Ser Ser
1105

<210> SEQ ID NO 97
<211> LENGTH: 1144
<212> TYPE: PRT
<213> ORGANISM: Homo sapiens

<400> SEQUENCE: 97

Met Lys Leu Ser Arg Gln Phe Thr Val Phe Gly Ser Ala Ile Phe Cys
  1               5                  10                  15

Val Val Ile Phe Ser Leu Tyr Leu Met Leu Asp Arg Gly His Leu Asp
                 20                  25                  30
```

-continued

```
Tyr Pro Arg Asn Pro Arg Arg Glu Gly Ser Phe Pro Gln Gly Gln Leu
     35                  40                  45

Ser Met Leu Gln Glu Lys Ile Asp His Leu Glu Arg Leu Leu Ala Glu
 50                  55                  60

Asn Asn Glu Ile Ile Ser Asn Ile Arg Asp Ser Val Ile Asn Leu Ser
 65                  70                  75                  80

Glu Ser Val Glu Asp Gly Pro Lys Ser Ser Gln Ser Asn Phe Ser Gln
             85                  90                  95

Gly Ala Gly Ser His Leu Leu Pro Ser Gln Leu Ser Leu Ser Val Asp
                100                 105                 110

Thr Ala Asp Cys Leu Phe Ala Ser Gln Ser Gly Ser His Asn Ser Asp
             115                 120                 125

Val Gln Met Leu Asp Val Tyr Ser Leu Ile Ser Phe Asp Asn Pro Asp
 130                 135                 140

Gly Gly Val Trp Lys Gln Gly Phe Asp Ile Thr Tyr Glu Ser Asn Glu
145                 150                 155                 160

Trp Asp Thr Glu Pro Leu Gln Val Phe Val Val Pro His Ser His Asn
                165                 170                 175

Asp Pro Gly Trp Leu Lys Thr Phe Asn Asp Tyr Phe Arg Asp Lys Thr
                180                 185                 190

Gln Tyr Ile Phe Asn Asn Met Val Leu Lys Leu Lys Glu Asp Ser Arg
         195                 200                 205

Arg Lys Phe Ile Trp Ser Glu Ile Ser Tyr Leu Ser Lys Trp Trp Asp
     210                 215                 220

Ile Ile Asp Ile Gln Lys Lys Asp Ala Val Lys Ser Leu Ile Glu Asn
225                 230                 235                 240

Gly Gln Leu Glu Ile Val Thr Gly Gly Trp Val Met Pro Asp Glu Ala
                245                 250                 255

Thr Pro His Tyr Phe Ala Leu Ile Asp Gln Leu Ile Glu Gly His Gln
                260                 265                 270

Trp Leu Glu Asn Asn Ile Gly Val Lys Pro Arg Ser Gly Trp Ala Ile
         275                 280                 285

Asp Pro Phe Gly His Ser Pro Thr Met Ala Tyr Leu Leu Asn Arg Ala
     290                 295                 300

Gly Leu Ser His Met Leu Ile Gln Arg Val His Tyr Ala Val Lys Lys
305                 310                 315                 320

His Phe Ala Leu His Lys Thr Leu Glu Phe Phe Trp Arg Gln Asn Trp
                325                 330                 335

Asp Leu Gly Ser Val Thr Asp Ile Leu Cys His Met Met Pro Phe Tyr
                340                 345                 350

Ser Tyr Asp Ile Pro His Thr Cys Gly Pro Asp Pro Lys Ile Cys Cys
         355                 360                 365

Gln Phe Asp Phe Lys Arg Leu Pro Gly Gly Arg Phe Gly Cys Pro Trp
     370                 375                 380

Gly Val Pro Pro Glu Thr Ile His Pro Gly Asn Val Gln Ser Arg Ala
385                 390                 395                 400

Arg Met Leu Leu Asp Gln Tyr Arg Lys Lys Ser Lys Leu Phe Arg Thr
                405                 410                 415

Lys Val Leu Leu Ala Pro Leu Gly Asp Asp Phe Arg Tyr Cys Glu Tyr
                420                 425                 430

Thr Glu Trp Asp Leu Gln Phe Lys Asn Tyr Gln Gln Leu Phe Asp Tyr
         435                 440                 445

Met Asn Ser Gln Ser Lys Phe Lys Val Lys Ile Gln Phe Gly Thr Leu
```

```
        450                 455                 460
Ser Asp Phe Phe Asp Ala Leu Asp Lys Ala Asp Glu Thr Gln Arg Asp
465                 470                 475                 480

Lys Gly Gln Ser Met Phe Pro Val Leu Ser Gly Asp Phe Phe Thr Tyr
                485                 490                 495

Ala Asp Arg Asp Asp His Tyr Trp Ser Gly Tyr Phe Thr Ser Arg Pro
            500                 505                 510

Phe Tyr Lys Arg Met Asp Arg Ile Met Glu Ser His Leu Arg Ala Ala
        515                 520                 525

Glu Ile Leu Tyr Tyr Phe Ala Leu Arg Gln Ala His Lys Tyr Lys Ile
    530                 535                 540

Asn Lys Phe Leu Ser Ser Leu Tyr Thr Ala Leu Thr Glu Ala Arg
545                 550                 555                 560

Arg Asn Leu Gly Leu Phe Gln His His Asp Ala Ile Thr Gly Thr Ala
                565                 570                 575

Lys Asp Trp Val Val Asp Tyr Gly Thr Arg Leu Phe His Ser Leu
            580                 585                 590

Met Val Leu Glu Lys Ile Ile Gly Asn Ser Ala Phe Leu Leu Ile Gly
        595                 600                 605

Lys Asp Lys Leu Thr Tyr Asp Ser Tyr Ser Pro Asp Thr Phe Leu Glu
    610                 615                 620

Met Asp Leu Lys Gln Lys Ser Gln Asp Ser Leu Pro Gln Lys Asn Ile
625                 630                 635                 640

Ile Arg Leu Ser Ala Glu Pro Arg Tyr Leu Val Val Tyr Asn Pro Leu
                645                 650                 655

Glu Gln Asp Arg Ile Ser Leu Val Ser Val Tyr Val Ser Ser Pro Thr
            660                 665                 670

Val Gln Val Phe Ser Ala Ser Gly Lys Pro Val Glu Val Gln Val Ser
        675                 680                 685

Ala Val Trp Asp Thr Ala Asn Thr Ile Ser Glu Thr Ala Tyr Glu Ile
    690                 695                 700

Ser Phe Arg Ala His Ile Pro Pro Leu Gly Leu Lys Val Tyr Lys Ile
705                 710                 715                 720

Leu Glu Ser Ala Ser Ser Asn Ser His Leu Ala Asp Tyr Val Leu Tyr
                725                 730                 735

Lys Asn Lys Val Glu Asp Ser Gly Ile Phe Thr Ile Lys Asn Met Ile
            740                 745                 750

Asn Thr Glu Glu Gly Ile Thr Leu Glu Asn Ser Phe Val Leu Leu Arg
        755                 760                 765

Phe Asp Gln Thr Gly Leu Met Lys Gln Met Met Thr Lys Glu Asp Gly
    770                 775                 780

Lys His His Glu Val Asn Val Gln Phe Ser Trp Tyr Gly Thr Thr Ile
785                 790                 795                 800

Lys Arg Asp Lys Ser Gly Ala Tyr Leu Phe Leu Pro Asp Gly Asn Ala
                805                 810                 815

Lys Pro Tyr Val Tyr Thr Thr Pro Pro Phe Val Arg Val Thr His Gly
            820                 825                 830

Arg Ile Tyr Ser Glu Val Thr Cys Phe Phe Asp His Val Thr His Arg
        835                 840                 845

Val Arg Leu Tyr His Ile Gln Gly Ile Glu Gly Gln Ser Val Glu Val
    850                 855                 860

Ser Asn Ile Val Asp Ile Arg Lys Val Tyr Asn Arg Glu Ile Ala Met
865                 870                 875                 880
```

-continued

Lys Ile Ser Ser Asp Ile Lys Ser Gln Asn Arg Phe Tyr Thr Asp Leu
              885                 890                 895

Asn Gly Tyr Gln Ile Gln Pro Arg Met Thr Leu Ser Lys Leu Pro Leu
          900                 905                 910

Gln Ala Asn Val Tyr Pro Met Thr Thr Met Ala Tyr Ile Gln Asp Ala
          915                 920                 925

Lys His Arg Leu Thr Leu Leu Ser Ala Gln Ser Leu Gly Val Ser Ser
          930                 935                 940

Leu Asn Ser Gly Gln Ile Glu Val Ile Met Asp Arg Arg Leu Met Gln
945                 950                 955                 960

Asp Asp Asn Arg Gly Leu Glu Gln Gly Ile Gln Asp Asn Lys Ile Thr
              965                 970                 975

Ala Asn Leu Phe Arg Ile Leu Leu Glu Lys Arg Ser Ala Val Asn Thr
          980                 985                 990

Glu Glu Glu Lys Lys Ser Val Ser Tyr Pro Ser Leu Leu Ser His Ile
          995                 1000                1005

Thr Ser Ser Leu Met Asn His Pro Val Ile Pro Met Ala Asn Lys Phe
      1010                1015                1020

Ser Ser Pro Thr Leu Glu Leu Gln Gly Glu Phe Ser Pro Leu Gln Ser
1025                1030                1035                1040

Ser Leu Pro Cys Asp Ile His Leu Val Asn Leu Arg Thr Ile Gln Ser
              1045                1050                1055

Lys Val Gly Asn Gly His Ser Asn Glu Ala Ala Leu Ile Leu His Arg
          1060                1065                1070

Lys Gly Phe Asp Cys Arg Phe Ser Ser Lys Gly Thr Gly Leu Phe Cys
          1075                1080                1085

Ser Thr Thr Gln Gly Lys Ile Leu Val Gln Lys Leu Leu Asn Lys Phe
          1090                1095                1100

Ile Val Glu Ser Leu Thr Pro Ser Ser Leu Ser Leu Met His Ser Pro
1105                1110                1115                1120

Pro Gly Thr Gln Asn Ile Ser Glu Ile Asn Leu Ser Pro Met Glu Ile
              1125                1130                1135

Ser Thr Phe Arg Ile Gln Leu Arg
          1140

<210> SEQ ID NO 98
<211> LENGTH: 1150
<212> TYPE: PRT
<213> ORGANISM: Mus musculus

<400> SEQUENCE: 98

Met Lys Leu Ser Arg Gln Phe Thr Val Phe Gly Ser Ala Ile Phe Cys
1               5                   10                  15

Val Val Ile Phe Ser Leu Tyr Leu Met Leu Asp Arg Gly His Leu Asp
            20                  25                  30

Tyr Pro Arg Gly Pro Arg Gln Glu Gly Ser Phe Pro Gln Gly Gln Leu
        35                  40                  45

Ser Ile Leu Gln Glu Lys Ile Asp His Leu Glu Arg Leu Leu Ala Glu
    50                  55                  60

Asn Asn Glu Ile Ile Ser Asn Ile Arg Asp Ser Val Ile Asn Leu Ser
65                  70                  75                  80

Glu Ser Val Glu Asp Gly Pro Arg Gly Ser Pro Gly Asn Ala Ser Gln
            85                  90                  95

Gly Ser Ile His Leu His Ser Pro Gln Leu Ala Leu Gln Ala Asp Pro

-continued

```
                100                 105                 110
Arg Asp Cys Leu Phe Ala Ser Gln Ser Gly Ser Gln Pro Arg Asp Val
            115                 120                 125
Gln Met Leu Asp Val Tyr Asp Leu Ile Pro Phe Asp Asn Pro Asp Gly
    130                 135                 140
Gly Val Trp Lys Gln Gly Phe Asp Ile Lys Tyr Glu Ala Asp Glu Trp
145                 150                 155                 160
Asp His Glu Pro Leu Gln Val Phe Val Pro His Ser His Asn Asp
                165                 170                 175
Pro Gly Trp Leu Lys Thr Phe Asn Asp Tyr Phe Arg Asp Lys Thr Gln
            180                 185                 190
Tyr Ile Phe Asn Asn Met Val Leu Lys Leu Lys Glu Asp Ser Ser Arg
        195                 200                 205
Lys Phe Met Trp Ser Glu Ile Ser Tyr Leu Ala Lys Trp Trp Asp Ile
            210                 215                 220
Ile Asp Ile Pro Lys Lys Glu Ala Val Lys Ser Leu Leu Gln Asn Gly
225                 230                 235                 240
Gln Leu Glu Ile Val Thr Gly Gly Trp Val Met Pro Asp Glu Ala Thr
                245                 250                 255
Pro His Tyr Phe Ala Leu Ile Asp Gln Leu Ile Glu Gly His Gln Trp
            260                 265                 270
Leu Glu Lys Asn Leu Gly Val Lys Pro Arg Ser Gly Trp Ala Ile Asp
        275                 280                 285
Pro Phe Gly His Ser Pro Thr Met Ala Tyr Leu Leu Lys Arg Ala Gly
    290                 295                 300
Phe Ser His Met Leu Ile Gln Arg Val His Tyr Ala Ile Lys Lys His
305                 310                 315                 320
Phe Ser Leu His Lys Thr Leu Glu Phe Phe Trp Arg Gln Asn Trp Asp
                325                 330                 335
Leu Gly Ser Ala Thr Asp Ile Leu Cys His Met Met Pro Phe Tyr Ser
            340                 345                 350
Tyr Asp Ile Pro His Thr Cys Gly Pro Asp Pro Lys Ile Cys Cys Gln
        355                 360                 365
Phe Asp Phe Lys Arg Leu Pro Gly Gly Arg Tyr Gly Cys Pro Trp Gly
    370                 375                 380
Val Pro Pro Glu Ala Ile Ser Pro Gly Asn Val Gln Ser Arg Ala Gln
385                 390                 395                 400
Met Leu Leu Asp Gln Tyr Arg Lys Lys Ser Lys Leu Phe Arg Thr Lys
                405                 410                 415
Val Leu Leu Ala Pro Leu Gly Asp Asp Phe Arg Phe Ser Glu Tyr Thr
            420                 425                 430
Glu Trp Asp Leu Gln Cys Arg Asn Tyr Glu Gln Leu Phe Ser Tyr Met
        435                 440                 445
Asn Ser Gln Pro His Leu Lys Val Lys Ile Gln Phe Gly Thr Leu Ser
    450                 455                 460
Asp Tyr Phe Asp Ala Leu Glu Lys Ala Val Ala Ala Glu Lys Lys Ser
465                 470                 475                 480
Ser Gln Ser Val Phe Pro Ala Leu Ser Gly Asp Phe Phe Thr Tyr Ala
                485                 490                 495
Asp Arg Asp Asp His Tyr Trp Ser Gly Tyr Phe Thr Ser Arg Pro Phe
            500                 505                 510
Tyr Lys Arg Met Asp Arg Ile Met Glu Ser Arg Ile Arg Ala Ala Glu
        515                 520                 525
```

```
Ile Leu Tyr Gln Leu Ala Leu Lys Gln Ala Gln Lys Tyr Lys Ile Asn
    530                 535                 540

Lys Phe Leu Ser Ser Pro His Tyr Thr Thr Leu Thr Glu Ala Arg Arg
545                 550                 555                 560

Asn Leu Gly Leu Phe Gln His His Asp Ala Ile Thr Gly Thr Ala Lys
                565                 570                 575

Asp Trp Val Val Val Asp Tyr Gly Thr Arg Leu Phe Gln Ser Leu Asn
            580                 585                 590

Ser Leu Glu Lys Ile Ile Gly Asp Ser Ala Phe Leu Leu Ile Leu Lys
        595                 600                 605

Asp Lys Lys Leu Tyr Gln Ser Asp Pro Ser Lys Ala Phe Leu Glu Met
    610                 615                 620

Asp Thr Lys Gln Ser Ser Gln Asp Ser Leu Pro Gln Lys Ile Ile Ile
625                 630                 635                 640

Gln Leu Ser Ala Gln Glu Pro Arg Tyr Leu Val Val Tyr Asn Pro Phe
                645                 650                 655

Glu Gln Glu Arg His Ser Val Val Ser Ile Arg Val Asn Ser Ala Thr
            660                 665                 670

Gly Lys Val Leu Ser Asp Ser Gly Lys Pro Val Glu Val Gln Val Ser
        675                 680                 685

Ala Val Trp Asn Asp Met Arg Thr Ile Ser Gln Ala Ala Tyr Glu Val
    690                 695                 700

Ser Phe Leu Ala His Ile Pro Pro Leu Gly Leu Lys Val Phe Lys Ile
705                 710                 715                 720

Leu Glu Ser Gln Ser Ser Ser His Leu Ala Asp Tyr Val Leu Tyr
                725                 730                 735

Asn Asn Asp Gly Leu Ala Glu Asn Gly Ile Phe His Val Lys Asn Met
            740                 745                 750

Val Asp Ala Gly Asp Ala Ile Thr Ile Glu Asn Pro Phe Leu Ala Ile
        755                 760                 765

Trp Phe Asp Arg Ser Gly Leu Met Glu Lys Val Arg Arg Lys Glu Asp
    770                 775                 780

Ser Arg Gln His Glu Leu Lys Val Gln Phe Leu Trp Tyr Gly Thr Thr
785                 790                 795                 800

Asn Lys Arg Asp Lys Ser Gly Ala Tyr Leu Phe Leu Pro Asp Gly Gln
                805                 810                 815

Gly Gln Pro Tyr Val Ser Leu Arg Pro Pro Phe Val Arg Val Thr Arg
            820                 825                 830

Gly Arg Ile Tyr Ser Asp Val Thr Cys Phe Leu Glu His Val Thr His
        835                 840                 845

Lys Val Arg Leu Tyr Asn Ile Gln Gly Ile Glu Gly Gln Ser Met Glu
    850                 855                 860

Val Ser Asn Ile Val Asn Ile Arg Asn Val His Asn Arg Glu Ile Val
865                 870                 875                 880

Met Arg Ile Ser Ser Lys Ile Asn Asn Gln Asn Arg Tyr Tyr Thr Asp
                885                 890                 895

Leu Asn Gly Tyr Gln Ile Gln Pro Arg Arg Thr Met Ser Lys Leu Pro
            900                 905                 910

Leu Gln Ala Asn Val Tyr Pro Met Cys Thr Met Ala Tyr Ile Gln Asp
        915                 920                 925

Ala Glu His Arg Leu Thr Leu Leu Ser Ala Gln Ser Leu Gly Ala Ser
    930                 935                 940
```

```
Ser Met Ala Ser Gly Gln Ile Glu Val Phe Met Asp Arg Arg Leu Met
945                 950                 955                 960

Gln Asp Asp Asn Arg Gly Leu Gly Gln Gly Val His Asp Asn Lys Ile
                965                 970                 975

Thr Ala Asn Leu Phe Arg Ile Leu Leu Glu Lys Arg Ser Ala Val Asn
            980                 985                 990

Met Glu Glu Lys Lys Ser Pro Val Ser Tyr Pro Ser Leu Leu Ser
        995                 1000                1005

His Met Thr Ser Ser Phe Leu Asn His Pro Phe Leu Pro Met Val Leu
    1010                1015                1020

Ser Gly Gln Leu Pro Ser Pro Ala Phe Glu Leu Leu Ser Glu Phe Pro
1025                1030                1035                1040

Leu Leu Gln Ser Ser Leu Pro Cys Asp Ile His Leu Val Asn Leu Arg
                1045                1050                1055

Thr Ile Gln Ser Lys Met Gly Lys Gly Tyr Ser Asp Glu Ala Ala Leu
            1060                1065                1070

Ile Leu His Arg Lys Gly Phe Asp Cys Gln Phe Ser Ser Arg Gly Ile
        1075                1080                1085

Gly Leu Pro Cys Ser Thr Thr Gln Gly Lys Met Ser Val Leu Lys Leu
    1090                1095                1100

Phe Asn Lys Phe Ala Val Glu Ser Leu Val Pro Ser Ser Leu Ser Leu
1105                1110                1115                1120

Met His Ser Pro Pro Asp Ala Gln Asn Met Ser Glu Val Ser Leu Ser
                1125                1130                1135

Pro Met Glu Ile Ser Thr Phe Arg Ile Arg Leu Arg Trp Thr
                1140                1145                1150

<210> SEQ ID NO 99
<211> LENGTH: 1139
<212> TYPE: PRT
<213> ORGANISM: Homo sapiens

<400> SEQUENCE: 99

Met Lys Leu Lys Lys Gln Val Thr Val Cys Gly Ala Ala Ile Phe Cys
1               5                   10                  15

Val Ala Val Phe Ser Leu Tyr Leu Met Leu Asp Arg Val Gln His Asp
                20                  25                  30

Pro Thr Arg His Gln Asn Gly Gly Asn Phe Pro Arg Ser Gln Ile Ser
            35                  40                  45

Val Leu Gln Asn Arg Ile Glu Gln Leu Glu Gln Leu Leu Glu Glu Asn
        50                  55                  60

His Glu Ile Ile Ser His Ile Lys Asp Ser Val Leu Glu Leu Thr Ala
65                  70                  75                  80

Asn Ala Glu Gly Pro Pro Ala Met Leu Pro Tyr Tyr Thr Val Asn Gly
                85                  90                  95

Ser Trp Val Val Pro Pro Glu Pro Arg Pro Ser Phe Ser Ile Ser
                100                 105                 110

Pro Gln Asp Cys Gln Phe Ala Leu Gly Gly Arg Gly Gln Lys Pro Glu
            115                 120                 125

Leu Gln Met Leu Thr Val Ser Glu Glu Leu Pro Phe Asp Asn Val Asp
        130                 135                 140

Gly Gly Val Trp Arg Gln Gly Phe Asp Ile Ser Tyr Asp Pro His Asp
145                 150                 155                 160

Trp Asp Ala Glu Asp Leu Gln Val Phe Val Val Pro His Ser His Asn
                165                 170                 175
```

-continued

```
Asp Pro Gly Trp Ile Lys Thr Phe Asp Lys Tyr Tyr Thr Glu Gln Thr
            180                 185                 190

Gln His Ile Leu Asn Ser Met Val Ser Lys Leu Gln Glu Asp Pro Arg
            195                 200                 205

Arg Arg Phe Leu Trp Ala Glu Val Ser Phe Phe Ala Lys Trp Trp Asp
210                 215                 220

Asn Ile Asn Val Gln Lys Arg Ala Ala Val Arg Arg Leu Val Gly Asn
225                 230                 235                 240

Gly Gln Leu Glu Ile Ala Thr Gly Gly Trp Val Met Pro Asp Glu Ala
                245                 250                 255

Asn Ser His Tyr Phe Ala Leu Ile Asp Gln Leu Ile Glu Gly His Gln
            260                 265                 270

Trp Leu Glu Arg Asn Leu Gly Ala Thr Pro Arg Ser Gly Trp Ala Val
            275                 280                 285

Asp Pro Phe Gly Tyr Ser Ser Thr Met Pro Tyr Leu Leu Arg Arg Ala
            290                 295                 300

Asn Leu Thr Ser Met Leu Ile Gln Arg Val His Tyr Ala Ile Lys Lys
305                 310                 315                 320

His Phe Ala Ala Thr His Ser Leu Glu Phe Met Trp Arg Gln Thr Trp
                325                 330                 335

Asp Ser Asp Ser Ser Thr Asp Ile Phe Cys His Met Met Pro Phe Tyr
            340                 345                 350

Ser Tyr Asp Val Pro His Thr Cys Gly Pro Asp Pro Lys Ile Cys Cys
            355                 360                 365

Gln Phe Asp Phe Lys Arg Leu Pro Gly Gly Arg Ile Asn Cys Pro Trp
            370                 375                 380

Lys Val Pro Pro Arg Ala Ile Thr Glu Ala Asn Val Ala Glu Arg Ala
385                 390                 395                 400

Ala Leu Leu Leu Asp Gln Tyr Arg Lys Lys Ser Gln Leu Phe Arg Ser
                405                 410                 415

Asn Val Leu Leu Val Pro Leu Gly Asp Asp Phe Arg Tyr Asp Lys Pro
            420                 425                 430

Gln Glu Trp Asp Ala Gln Phe Phe Asn Tyr Gln Arg Leu Phe Asp Phe
            435                 440                 445

Phe Asn Ser Arg Pro Asn Leu His Val Gln Ala Gln Phe Gly Thr Leu
450                 455                 460

Ser Asp Tyr Phe Asp Ala Leu Tyr Lys Arg Thr Gly Val Glu Pro Gly
465                 470                 475                 480

Ala Arg Pro Pro Gly Phe Pro Val Leu Ser Gly Asp Phe Phe Ser Tyr
                485                 490                 495

Ala Asp Arg Glu Asp His Tyr Trp Thr Gly Tyr Tyr Thr Ser Arg Pro
            500                 505                 510

Phe Tyr Lys Ser Leu Asp Arg Val Leu Glu Ala His Leu Arg Gly Ala
            515                 520                 525

Glu Val Leu Tyr Ser Leu Ala Ala Ala His Ala Arg Arg Ser Gly Leu
            530                 535                 540

Ala Gly Arg Tyr Pro Leu Ser Asp Phe Thr Leu Leu Thr Glu Ala Arg
545                 550                 555                 560

Arg Thr Leu Gly Leu Phe Gln His His Asp Ala Ile Thr Gly Thr Ala
                565                 570                 575

Lys Glu Ala Val Val Val Asp Tyr Gly Val Arg Leu Leu Arg Ser Leu
            580                 585                 590
```

-continued

```
Val Asn Leu Lys Gln Val Ile Ile His Ala Ala His Tyr Leu Val Leu
            595                 600                 605

Gly Asp Lys Glu Thr Tyr His Phe Asp Pro Glu Ala Pro Phe Leu Gln
        610                 615                 620

Val Asp Asp Thr Arg Leu Ser His Asp Ala Leu Pro Glu Arg Thr Val
625                 630                 635                 640

Ile Gln Leu Asp Ser Ser Pro Arg Phe Val Leu Phe Asn Pro Leu
                645                 650                 655

Glu Gln Glu Arg Phe Ser Met Val Ser Leu Leu Val Asn Ser Pro Arg
                660                 665                 670

Val Arg Val Leu Ser Glu Glu Gly Gln Pro Leu Ala Val Gln Ile Ser
                675                 680                 685

Ala His Trp Ser Ser Ala Thr Glu Ala Val Pro Asp Val Tyr Gln Val
        690                 695                 700

Ser Val Pro Val Arg Leu Pro Ala Leu Gly Leu Gly Val Leu Gln Leu
705                 710                 715                 720

Gln Leu Gly Leu Asp Gly His Arg Thr Leu Pro Ser Ser Val Arg Ile
                725                 730                 735

Tyr Leu His Gly Arg Gln Leu Ser Val Ser Arg His Glu Ala Phe Pro
            740                 745                 750

Leu Arg Val Ile Asp Ser Gly Thr Ser Asp Phe Ala Leu Ser Asn Arg
        755                 760                 765

Tyr Met Gln Val Trp Phe Ser Gly Leu Thr Gly Leu Leu Lys Ser Ile
        770                 775                 780

Arg Arg Val Asp Glu Glu His Glu Gln Gln Val Asp Met Gln Val Leu
785                 790                 795                 800

Val Tyr Gly Thr Arg Thr Ser Lys Asp Lys Ser Gly Ala Tyr Leu Phe
                805                 810                 815

Leu Pro Asp Gly Glu Ala Ser Pro Thr Ser Pro Arg Ser Pro Pro Cys
            820                 825                 830

Cys Val Ser Leu Lys Ala Leu Ser Ser Gln Arg Trp Leu Arg Thr Met
        835                 840                 845

Ser Thr Phe Thr Arg Arg Ser Gly Phe Thr Ile Cys Gln Gly Trp Arg
        850                 855                 860

Gly Cys Leu Trp Thr Tyr His Pro Trp Trp Thr Ser Gly Thr Thr Ser
865                 870                 875                 880

Thr Arg Ser Trp Pro Cys Thr Ser Ile Gln Thr Ser Thr Ala Arg Val
                885                 890                 895

Gln Pro Arg Arg Tyr Leu Lys Lys Leu Pro Leu Gln Ala Asn Phe Tyr
            900                 905                 910

Pro Met Pro Val Met Ala Tyr Ile Gln Asp Ala Gln Lys Arg Leu Thr
        915                 920                 925

Leu His Thr Ala Gln Ala Leu Gly Val Ser Ser Leu Lys Asp Gly Gln
        930                 935                 940

Leu Glu Val Ile Leu Asp Arg Arg Leu Met Gln Asp Asp Asn Arg Gly
945                 950                 955                 960

Leu Gly Gln Gly Leu Lys Asp Asn Lys Arg Thr Cys Asn Arg Phe Arg
                965                 970                 975

Leu Leu Leu Glu Arg Arg Thr Val Gly Ser Glu Val Gln Asp Ser His
            980                 985                 990

Ser Thr Ser Tyr Pro Ser Leu Leu Ser His Leu Thr Ser Met Tyr Leu
        995                 1000                1005

Asn Ala Pro Ala Leu Ala Leu Pro Val Ala Arg Met Gln Leu Pro Gly
```

```
          1010                1015                1020
Pro Gly Leu Arg Ser Phe His Pro Leu Ala Ser Ser Leu Pro Cys Asp
1025                1030                1035                1040

Phe His Leu Leu Asn Leu Arg Thr Leu Gln Ala Glu Glu Asp Thr Leu
                1045                1050                1055

Pro Ser Ala Glu Thr Ala Leu Ile Leu His Arg Lys Gly Phe Asp Cys
            1060                1065                1070

Gly Leu Glu Ala Lys Asn Leu Gly Phe Asn Cys Thr Ser Gln Gly
        1075                1080                1085

Lys Val Ala Leu Gly Ser Leu Phe His Gly Leu Asp Val Val Phe Leu
    1090                1095                1100

Gln Pro Thr Ser Leu Thr Leu Leu Tyr Pro Leu Ala Ser Pro Ser Asn
1105                1110                1115                1120

Ser Thr Asp Val Tyr Leu Glu Pro Met Glu Ile Ala Thr Phe Arg Leu
                1125                1130                1135

Arg Leu Gly

<210> SEQ ID NO 100
<211> LENGTH: 1130
<212> TYPE: PRT
<213> ORGANISM: Spodoptera frugiperda

<400> SEQUENCE: 100

Met Arg Thr Arg Val Leu Arg Cys Arg Pro Phe Ser Thr Arg Ile Leu
 1               5                  10                  15

Leu Leu Leu Leu Phe Val Leu Ala Phe Gly Val Tyr Cys Tyr Phe Tyr
                20                  25                  30

Asn Ala Ser Pro Gln Asn Tyr Asn Lys Pro Arg Ile Ser Tyr Pro Ala
            35                  40                  45

Ser Met Glu His Phe Lys Ser Ser Leu Thr His Thr Val Lys Ser Arg
        50                  55                  60

Asp Glu Pro Thr Pro Asp Gln Cys Pro Ala Leu Lys Glu Ser Glu Ala
65                  70                  75                  80

Asp Ile Asp Thr Val Ala Ile Tyr Pro Thr Phe Asp Phe Gln Pro Ser
                85                  90                  95

Trp Leu Arg Thr Lys Glu Phe Trp Asp Lys Ser Phe Glu Asp Arg Tyr
            100                 105                 110

Glu Arg Ile His Asn Asp Thr Thr Arg Pro Arg Leu Lys Val Ile Val
        115                 120                 125

Val Pro His Ser His Asn Asp Pro Gly Trp Leu Lys Thr Phe Glu Gln
    130                 135                 140

Tyr Phe Glu Trp Lys Thr Lys Asn Ile Ile Asn Asn Ile Val Asn Lys
145                 150                 155                 160

Leu His Gln Tyr Pro Asn Met Thr Phe Ile Trp Thr Glu Ile Ser Phe
                165                 170                 175

Leu Asn Ala Trp Trp Glu Arg Ser His Pro Val Lys Gln Lys Ala Leu
            180                 185                 190

Lys Lys Leu Ile Lys Glu Gly Arg Leu Glu Ile Thr Thr Gly Gly Trp
        195                 200                 205

Val Met Pro Asp Glu Ala Cys Thr His Ile Tyr Ala Leu Ile Asp Gln
    210                 215                 220

Phe Ile Glu Gly His His Trp Val Lys Thr Asn Leu Gly Val Ile Pro
225                 230                 235                 240

Lys Thr Gly Trp Ser Ile Asp Pro Phe Gly His Gly Ala Thr Val Pro
```

-continued

```
            245                 250                 255
Tyr Leu Leu Asp Gln Ser Gly Leu Glu Gly Thr Ile Ile Gln Arg Ile
            260                 265                 270
His Tyr Ala Trp Lys Gln Trp Leu Ala Glu Arg Gln Ile Glu Glu Phe
            275                 280                 285
Tyr Trp Leu Ala Ser Trp Ala Thr Thr Lys Pro Ser Met Ile Val His
            290                 295                 300
Asn Gln Pro Phe Asp Ile Tyr Ser Ile Lys Ser Thr Cys Gly Pro His
305                 310                 315                 320
Pro Ser Ile Cys Leu Ser Phe Asp Phe Arg Lys Ile Pro Gly Glu Tyr
            325                 330                 335
Ser Glu Tyr Thr Ala Lys His Glu Asp Ile Thr Glu His Asn Leu His
            340                 345                 350
Ser Lys Ala Lys Thr Leu Ile Glu Glu Tyr Asp Arg Ile Gly Ser Leu
            355                 360                 365
Thr Pro His Asn Val Val Leu Val Pro Leu Gly Asp Asp Phe Arg Tyr
            370                 375                 380
Glu Tyr Ser Val Glu Phe Asp Ala Gln Tyr Val Asn Tyr Met Lys Met
385                 390                 395                 400
Phe Asn Tyr Ile Asn Ala His Lys Glu Ile Phe Asn Ala Asp Val Gln
            405                 410                 415
Phe Gly Thr Pro Leu Asp Tyr Phe Asn Ala Met Lys Glu Arg His Gln
            420                 425                 430
Asn Ile Pro Ser Leu Lys Gly Asp Phe Phe Val Tyr Ser Asp Ile Phe
            435                 440                 445
Ser Glu Gly Lys Pro Ala Tyr Trp Ser Gly Tyr Tyr Thr Thr Arg Pro
450                 455                 460
Tyr Gln Lys Ile Leu Ala Arg Gln Phe Glu His Gln Leu Arg Ser Ala
465                 470                 475                 480
Glu Ile Leu Phe Thr Leu Val Ser Asn Tyr Ile Arg Gln Met Gly Arg
            485                 490                 495
Gln Gly Glu Phe Gly Ala Ser Glu Lys Lys Leu Glu Lys Ser Tyr Glu
            500                 505                 510
Gln Leu Ile Tyr Ala Arg Arg Asn Leu Gly Leu Phe Gln His His Asp
            515                 520                 525
Ala Ile Thr Gly Thr Ser Lys Ser Ser Val Met Gln Asp Tyr Gly Thr
            530                 535                 540
Lys Leu Phe Thr Ser Leu Tyr His Cys Ile Arg Leu Gln Glu Ala Ala
545                 550                 555                 560
Leu Thr Thr Ile Met Leu Pro Asp Gln Ser Leu His Ser Gln Ser Ile
            565                 570                 575
Ile Gln Ser Glu Val Glu Trp Glu Thr Tyr Gly Lys Pro Pro Lys Lys
            580                 585                 590
Leu Gln Val Ser Phe Ile Asp Lys Lys Val Ile Leu Phe Asn Pro
            595                 600                 605
Leu Ala Glu Thr Arg Thr Glu Val Val Thr Val Arg Ser Asn Thr Ser
            610                 615                 620
Asn Ile Arg Val Tyr Asp Thr His Lys Arg Lys His Val Leu Tyr Gln
625                 630                 635                 640
Ile Met Pro Ser Ile Thr Ile Gln Asp Asn Gly Lys Ser Ile Val Ser
            645                 650                 655
Asp Thr Thr Phe Asp Ile Met Phe Val Ala Thr Ile Pro Pro Leu Thr
            660                 665                 670
```

```
Ser Ile Ser Tyr Lys Leu Gln Glu His Thr Asn Thr Ser His His Cys
        675                 680                 685
Val Ile Phe Cys Asn Asn Cys Glu Gln Tyr Gln Lys Ser Asn Val Phe
    690                 695                 700
Gln Ile Lys Lys Met Met Pro Gly Asp Ile Gln Leu Glu Asn Ala Val
705                 710                 715                 720
Leu Lys Leu Leu Val Asn Arg Asn Thr Gly Phe Leu Arg Gln Val Tyr
            725                 730                 735
Arg Lys Asp Ile Arg Lys Arg Thr Val Val Asp Val Gln Phe Gly Ala
            740                 745                 750
Tyr Gln Ser Ala Gln Arg His Ser Gly Ala Tyr Leu Phe Met Pro His
            755                 760                 765
Tyr Asp Ser Pro Glu Lys Asn Val Leu His Pro Tyr Thr Asn Gln Asn
            770                 775                 780
Asn Met Gln Asp Asp Asn Ile Ile Ile Val Ser Gly Pro Ile Ser Thr
785                 790                 795                 800
Glu Ile Thr Thr Met Tyr Leu Pro Phe Leu Val His Thr Ile Arg Ile
                805                 810                 815
Tyr Asn Val Pro Asp Pro Val Leu Ser Arg Ala Ile Leu Leu Glu Thr
            820                 825                 830
Asp Val Asp Phe Glu Ala Pro Pro Lys Asn Arg Glu Thr Glu Leu Phe
            835                 840                 845
Met Arg Leu Gln Thr Asp Ile Gln Asn Gly Asp Ile Pro Glu Phe Tyr
            850                 855                 860
Thr Asp Gln Asn Gly Phe Gln Tyr Gln Lys Arg Val Lys Val Asn Lys
865                 870                 875                 880
Leu Gly Ile Glu Ala Asn Tyr Tyr Pro Ile Thr Thr Met Ala Cys Leu
                885                 890                 895
Gln Asp Glu Glu Thr Arg Leu Thr Leu Leu Thr Asn His Ala Gln Gly
                900                 905                 910
Ala Ala Ala Tyr Glu Pro Gly Arg Leu Glu Val Met Leu Asp Arg Arg
            915                 920                 925
Thr Leu Tyr Asp Asp Phe Arg Gly Ile Gly Glu Gly Val Val Asp Asn
930                 935                 940
Lys Pro Thr Thr Phe Gln Asn Trp Ile Leu Ile Glu Ser Met Pro Gly
945                 950                 955                 960
Val Thr Arg Ala Lys Arg Asp Thr Ser Glu Pro Gly Phe Lys Phe Val
                965                 970                 975
Asn Glu Arg Arg Phe Gly Pro Gly Gln Lys Glu Ser Pro Tyr Gln Val
            980                 985                 990
Pro Ser Gln Thr Ala Asp Tyr Leu Ser Arg Met Phe Asn Tyr Pro Val
            995                1000                1005
Asn Val Tyr Leu Val Asp Thr Ser Glu Val Gly Glu Ile Glu Val Lys
        1010                1015                1020
Pro Tyr Gln Ser Phe Leu Gln Ser Phe Pro Pro Gly Ile His Leu Val
1025                1030                1035                1040
Thr Leu Arg Thr Ile Thr Asp Asp Val Leu Glu Leu Phe Pro Ser Asn
            1045                1050                1055
Glu Ser Tyr Met Val Leu His Arg Pro Gly Tyr Ser Cys Ala Val Gly
            1060                1065                1070
Glu Lys Pro Val Ala Lys Ser Pro Lys Phe Ser Ser Lys Thr Arg Phe
            1075                1080                1085
```

```
Asn Gly Leu Asn Ile Gln Asn Ile Thr Ala Val Ser Leu Thr Gly Leu
        1090                1095                1100

Lys Ser Leu Arg Pro Leu Thr Gly Leu Ser Asp Ile His Leu Asn Ala
1105                1110                1115                1120

Met Glu Val Lys Thr Tyr Lys Ile Arg Phe
                1125                1130

<210> SEQ ID NO 101
<211> LENGTH: 1010
<212> TYPE: PRT
<213> ORGANISM: Homo sapiens

<400> SEQUENCE: 101

Met Gly Tyr Ala Arg Ala Ser Gly Val Cys Ala Arg Gly Cys Leu Asp
  1               5                  10                  15

Ser Ala Gly Pro Trp Thr Met Ser Arg Ala Leu Arg Pro Pro Leu Pro
             20                  25                  30

Pro Leu Cys Phe Phe Leu Leu Leu Ala Ala Gly Ala Arg Ala
         35                  40                  45

Gly Gly Tyr Glu Thr Cys Pro Thr Val Gln Pro Asn Met Leu Asn Val
 50                  55                  60

His Leu Leu Pro His Thr His Asp Asp Val Gly Trp Leu Lys Thr Val
 65                  70                  75                  80

Asp Gln Tyr Phe Tyr Gly Ile Lys Asn Asp Ile Gln His Ala Gly Val
                 85                  90                  95

Gln Tyr Ile Leu Asp Ser Val Ile Ser Ala Leu Leu Ala Asp Pro Thr
            100                 105                 110

Arg Arg Phe Ile Tyr Val Glu Ile Ala Phe Phe Ser Arg Trp Trp His
        115                 120                 125

Gln Gln Thr Asn Ala Thr Gln Glu Val Val Arg Asp Leu Val Arg Gln
    130                 135                 140

Gly Arg Leu Glu Phe Ala Asn Gly Gly Trp Val Met Asn Asp Glu Ala
145                 150                 155                 160

Ala Thr His Tyr Gly Ala Ile Val Asp Gln Met Thr Leu Gly Leu Arg
                165                 170                 175

Phe Leu Glu Asp Thr Phe Gly Asn Asp Gly Arg Pro Arg Val Ala Trp
            180                 185                 190

His Ile Asp Pro Phe Gly His Ser Arg Glu Gln Ala Ser Leu Phe Ala
        195                 200                 205

Gln Met Gly Phe Asp Gly Phe Phe Gly Arg Leu Asp Tyr Gln Asp
    210                 215                 220

Lys Trp Val Arg Met Gln Lys Leu Glu Met Glu Gln Val Trp Arg Ala
225                 230                 235                 240

Ser Thr Ser Leu Lys Pro Pro Thr Ala Asp Leu Phe Thr Gly Val Leu
                245                 250                 255

Pro Asn Gly Tyr Asn Pro Pro Arg Asn Leu Cys Trp Asp Val Leu Cys
            260                 265                 270

Val Asp Gln Pro Leu Val Glu Asp Pro Arg Ser Pro Glu Tyr Asn Ala
        275                 280                 285

Lys Glu Leu Val Asp Tyr Phe Leu Asn Val Ala Thr Ala Gln Gly Arg
    290                 295                 300

Tyr Tyr Arg Thr Asn His Thr Val Met Thr Met Gly Ser Asp Phe Gln
305                 310                 315                 320

Tyr Glu Asn Ala Asn Met Trp Phe Lys Asn Leu Asp Lys Leu Ile Arg
                325                 330                 335
```

```
Leu Val Asn Ala Gln Gln Ala Lys Gly Ser Ser Val His Val Leu Tyr
            340                 345                 350

Ser Thr Pro Ala Cys Tyr Leu Trp Glu Leu Asn Lys Ala Asn Leu Thr
            355                 360                 365

Trp Ser Val Lys His Asp Asp Phe Phe Pro Tyr Ala Asp Gly Pro His
            370                 375                 380

Gln Phe Trp Thr Gly Tyr Phe Ser Ser Arg Pro Ala Leu Lys Arg Tyr
385                 390                 395                 400

Glu Arg Leu Ser Tyr Asn Phe Leu Gln Val Cys Asn Gln Leu Glu Ala
            405                 410                 415

Leu Val Gly Leu Ala Ala Asn Val Gly Pro Tyr Gly Ser Gly Asp Ser
            420                 425                 430

Ala Pro Leu Asn Glu Ala Met Ala Val Leu Gln His Asp Ala Val
            435                 440                 445

Ser Gly Thr Ser Arg Gln His Val Ala Asn Asp Tyr Ala Arg Gln Leu
            450                 455                 460

Ala Ala Gly Trp Gly Pro Cys Glu Val Leu Leu Ser Asn Ala Leu Ala
465                 470                 475                 480

Arg Leu Arg Gly Phe Lys Asp His Phe Thr Phe Cys Gln Gln Leu Asn
            485                 490                 495

Ile Ser Ile Cys Pro Leu Ser Gln Thr Ala Ala Arg Phe Gln Val Ile
            500                 505                 510

Val Tyr Asn Pro Leu Gly Arg Lys Val Asn Trp Met Val Arg Leu Pro
            515                 520                 525

Val Ser Glu Gly Val Phe Val Val Lys Asp Pro Asn Gly Arg Thr Val
            530                 535                 540

Pro Ser Asp Val Val Ile Phe Pro Ser Ser Asp Ser Gln Ala His Pro
545                 550                 555                 560

Pro Glu Leu Leu Phe Ser Ala Ser Leu Pro Ala Leu Gly Phe Ser Thr
            565                 570                 575

Tyr Ser Val Ala Gln Val Pro Arg Trp Lys Pro Gln Ala Arg Ala Pro
            580                 585                 590

Gln Pro Ile Pro Arg Arg Ser Trp Ser Pro Ala Leu Thr Ile Glu Asn
            595                 600                 605

Glu His Ile Arg Ala Thr Phe Asp Pro Asp Thr Gly Leu Leu Met Glu
            610                 615                 620

Ile Met Asn Met Asn Gln Gln Leu Leu Leu Pro Val Arg Gln Thr Phe
625                 630                 635                 640

Phe Trp Tyr Asn Ala Ser Ile Gly Asp Asn Glu Ser Asp Gln Ala Ser
            645                 650                 655

Gly Ala Tyr Ile Phe Arg Pro Asn Gln Gln Lys Pro Leu Pro Val Ser
            660                 665                 670

Arg Trp Ala Gln Ile His Leu Val Lys Thr Pro Leu Val Gln Glu Val
            675                 680                 685

His Gln Asn Phe Ser Ala Trp Cys Ser Gln Val Val Arg Leu Tyr Pro
            690                 695                 700

Gly Gln Arg His Leu Glu Leu Glu Trp Ser Val Gly Pro Ile Pro Val
705                 710                 715                 720

Gly Asp Thr Trp Gly Lys Glu Val Ile Ser Arg Phe Asp Thr Pro Leu
            725                 730                 735

Glu Thr Lys Gly Arg Phe Tyr Thr Asp Ser Asn Gly Arg Glu Ile Leu
            740                 745                 750
```

```
Glu Arg Arg Arg Asp Tyr Arg Pro Thr Trp Lys Leu Asn Gln Thr Glu
    755                 760                 765

Pro Val Ala Gly Asn Tyr Tyr Pro Val Asn Thr Arg Ile Tyr Ile Thr
770                 775                 780

Asp Gly Asn Met Gln Leu Thr Val Leu Thr Asp Arg Ser Gln Gly Gly
785                 790                 795                 800

Ser Ser Leu Arg Asp Gly Ser Leu Glu Leu Met Val His Arg Arg Leu
                805                 810                 815

Leu Lys Asp Asp Gly Arg Gly Val Ser Glu Pro Leu Met Glu Asn Gly
                820                 825                 830

Ser Gly Ala Trp Val Arg Gly Arg His Leu Val Leu Leu Asp Thr Ala
                835                 840                 845

Gln Ala Ala Ala Gly His Arg Leu Leu Ala Glu Gln Glu Val Leu
    850                 855                 860

Ala Pro Gln Val Val Leu Ala Pro Gly Gly Gly Ala Ala Tyr Asn Leu
865                 870                 875                 880

Gly Ala Pro Pro Arg Thr Gln Phe Ser Gly Leu Arg Arg Asp Leu Pro
                885                 890                 895

Pro Ser Val His Leu Leu Thr Leu Ala Ser Trp Gly Pro Glu Met Val
                900                 905                 910

Leu Leu Arg Leu Glu His Gln Phe Ala Val Gly Glu Asp Ser Gly Arg
                915                 920                 925

Asn Leu Ser Ala Pro Val Thr Leu Asn Leu Arg Asp Leu Phe Ser Thr
                930                 935                 940

Phe Thr Ile Thr Arg Leu Gln Glu Thr Thr Leu Val Ala Asn Gln Leu
945                 950                 955                 960

Arg Glu Ala Ala Ser Arg Leu Lys Trp Thr Thr Asn Thr Gly Pro Thr
                965                 970                 975

Pro His Gln Thr Pro Tyr Gln Leu Asp Pro Ala Asn Ile Thr Leu Glu
                980                 985                 990

Pro Met Glu Ile Arg Thr Phe Leu Ala Ser Val Gln Trp Lys Glu Val
            995                 1000                1005

Asp Gly
    1010

<210> SEQ ID NO 102
<211> LENGTH: 1062
<212> TYPE: PRT
<213> ORGANISM: Homo sapiens

<400> SEQUENCE: 102

Met Ala Ala Ala Pro Phe Leu Lys His Trp Arg Thr Thr Phe Glu Arg
  1               5                  10                  15

Val Glu Lys Phe Val Ser Pro Ile Tyr Phe Thr Asp Cys Asn Leu Arg
                 20                  25                  30

Gly Arg Leu Phe Gly Ala Ser Cys Pro Val Ala Val Leu Ser Ser Phe
             35                  40                  45

Leu Thr Pro Glu Arg Leu Pro Tyr Gln Glu Ala Val Gln Arg Asp Phe
     50                  55                  60

Arg Pro Ala Gln Val Gly Asp Ser Phe Gly Pro Thr Trp Thr Cys
 65                  70                  75                  80

Trp Phe Arg Val Glu Leu Thr Ile Pro Glu Ala Trp Val Gly Gln Glu
                 85                  90                  95

Val His Leu Cys Trp Glu Ser Asp Gly Glu Gly Leu Val Trp Arg Asp
            100                 105                 110
```

-continued

```
Gly Glu Pro Val Gln Gly Leu Thr Lys Glu Gly Glu Lys Thr Ser Tyr
        115                 120                 125
Val Leu Thr Asp Arg Leu Gly Glu Arg Asp Pro Arg Ser Leu Thr Leu
130                 135                 140
Tyr Val Glu Val Ala Cys Asn Gly Leu Leu Gly Ala Gly Lys Gly Ser
145                 150                 155                 160
Met Ile Ala Ala Pro Asp Pro Glu Lys Ile Phe Gln Leu Ser Arg Ala
                165                 170                 175
Glu Leu Ala Val Phe His Arg Asp Val His Met Leu Leu Val Asp Leu
            180                 185                 190
Glu Leu Leu Gly Ile Ala Lys Gly Leu Gly Lys Asp Asn Gln Arg
        195                 200                 205
Ser Phe Gln Ala Leu Tyr Thr Ala Asn Gln Met Val Asn Val Cys Asp
    210                 215                 220
Pro Ala Gln Pro Glu Thr Phe Pro Val Ala Gln Ala Leu Ala Ser Arg
225                 230                 235                 240
Phe Phe Gly Gln His Gly Gly Glu Ser Gln His Thr Ile His Ala Thr
                245                 250                 255
Gly His Cys His Ile Asp Thr Ala Trp Leu Trp Pro Phe Lys Glu Thr
            260                 265                 270
Val Arg Lys Cys Ala Arg Ser Trp Val Thr Ala Leu Gln Leu Met Glu
        275                 280                 285
Arg Asn Pro Glu Phe Ile Phe Ala Cys Ser Gln Ala Gln Gln Leu Glu
    290                 295                 300
Trp Val Lys Ser Arg Tyr Pro Gly Leu Tyr Ser Arg Ile Gln Glu Phe
305                 310                 315                 320
Ala Cys Arg Gly Gln Phe Val Pro Val Gly Thr Trp Val Glu Met
                325                 330                 335
Asp Gly Asn Leu Pro Ser Gly Glu Ala Met Val Arg Gln Phe Leu Gln
            340                 345                 350
Gly Gln Asn Phe Phe Leu Gln Glu Phe Gly Lys Met Cys Ser Glu Phe
        355                 360                 365
Trp Leu Pro Asp Thr Phe Gly Tyr Ser Ala Gln Leu Pro Gln Ile Met
    370                 375                 380
His Gly Cys Gly Ile Arg Arg Phe Leu Thr Gln Lys Leu Ser Trp Asn
385                 390                 395                 400
Leu Val Asn Ser Phe Pro His His Thr Phe Phe Trp Glu Gly Leu Asp
                405                 410                 415
Gly Ser Arg Val Leu Val His Phe Pro Pro Gly Asp Ser Tyr Gly Met
            420                 425                 430
Gln Gly Ser Val Glu Glu Val Leu Lys Thr Val Ala Asn Asn Arg Asp
        435                 440                 445
Lys Gly Arg Ala Asn His Ser Ala Phe Leu Phe Gly Phe Gly Asp Gly
    450                 455                 460
Gly Gly Pro Thr Gln Thr Met Leu Asp Arg Leu Lys Arg Leu Ser
465                 470                 475                 480
Asn Thr Asp Gly Leu Pro Arg Val Gln Leu Ser Ser Pro Arg Gln Leu
                485                 490                 495
Phe Ser Ala Leu Glu Ser Asp Ser Glu Gln Leu Cys Thr Trp Val Gly
            500                 505                 510
Glu Leu Phe Leu Glu Leu His Asn Gly Thr Tyr Thr Thr His Ala Gln
        515                 520                 525
```

-continued

```
Ile Lys Lys Gly Asn Arg Glu Cys Glu Arg Ile Leu His Asp Val Glu
        530                 535                 540

Leu Leu Ser Ser Leu Ala Leu Ala Arg Ser Ala Gln Phe Leu Tyr Pro
545                 550                 555                 560

Ala Ala Gln Leu Gln His Leu Trp Arg Leu Leu Leu Asn Gln Phe
                565                 570                 575

His Asp Val Val Thr Gly Ser Cys Ile Gln Met Val Ala Glu Glu Ala
            580                 585                 590

Met Cys His Tyr Glu Asp Ile Arg Ser His Gly Asn Thr Leu Leu Ser
        595                 600                 605

Ala Ala Ala Ala Leu Cys Ala Glu Pro Gly Pro Glu Gly Leu
        610                 615                 620

Leu Ile Val Asn Thr Leu Pro Trp Lys Arg Ile Glu Val Met Ala Leu
625                 630                 635                 640

Pro Lys Pro Gly Gly Ala His Ser Leu Ala Leu Val Thr Val Pro Ser
                645                 650                 655

Met Gly Tyr Ala Pro Val Pro Pro Thr Ser Leu Gln Pro Leu Leu
                660                 665                 670

Pro Gln Gln Pro Val Phe Val Val Gln Glu Thr Asp Gly Ser Val Thr
            675                 680                 685

Leu Asp Asn Gly Ile Ile Arg Val Lys Leu Asp Pro Thr Gly Arg Leu
        690                 695                 700

Thr Ser Leu Val Leu Val Ala Ser Gly Arg Glu Ala Ile Ala Glu Gly
705                 710                 715                 720

Ala Val Gly Asn Gln Phe Val Leu Phe Asp Asp Val Pro Leu Tyr Trp
                725                 730                 735

Asp Ala Trp Asp Val Met Asp Tyr His Leu Glu Thr Arg Lys Pro Val
            740                 745                 750

Leu Gly Gln Ala Gly Thr Leu Ala Val Gly Thr Glu Gly Gly Leu Arg
                755                 760                 765

Gly Ser Ala Trp Phe Leu Leu Gln Ile Ser Pro Asn Ser Arg Leu Ser
770                 775                 780

Gln Glu Val Val Leu Asp Val Gly Cys Pro Tyr Val Arg Phe His Thr
785                 790                 795                 800

Glu Val His Trp His Glu Ala His Lys Phe Leu Lys Val Glu Phe Pro
            805                 810                 815

Ala Arg Val Arg Ser Ser Gln Ala Thr Tyr Glu Ile Gln Phe Gly His
                820                 825                 830

Leu Gln Arg Pro Thr His Tyr Asn Thr Ser Trp Asp Trp Ala Arg Phe
        835                 840                 845

Glu Val Trp Ala His Arg Trp Met Asp Leu Ser Glu His Gly Phe Gly
        850                 855                 860

Leu Ala Leu Leu Asn Asp Cys Lys Tyr Gly Ala Ser Val Arg Gly Ser
865                 870                 875                 880

Ile Leu Ser Leu Ser Leu Leu Arg Ala Pro Lys Ala Pro Asp Ala Thr
                885                 890                 895

Ala Asp Thr Gly Arg His Glu Phe Thr Tyr Ala Leu Met Pro His Lys
                900                 905                 910

Gly Ser Phe Gln Asp Ala Gly Val Ile Gln Ala Ala Tyr Ser Leu Asn
            915                 920                 925

Phe Pro Leu Leu Ala Leu Pro Ala Pro Ser Pro Ala Pro Ala Thr Ser
        930                 935                 940

Trp Ser Ala Phe Ser Val Ser Ser Pro Ala Val Val Leu Glu Thr Val
```

```
                945                 950                 955                 960
Lys Gln Ala Glu Ser Ser Pro Gln Arg Arg Ser Leu Val Leu Arg Leu
                965                 970                 975

Tyr Glu Ala His Gly Ser His Val Asp Cys Trp Leu His Leu Ser Leu
            980                 985                 990

Pro Val Gln Glu Ala Ile Leu Cys Asp Leu Leu Glu Arg Pro Asp Pro
        995                 1000                1005

Ala Gly His Leu Thr Ser Gly Gln Pro Pro Glu Ala His Leu Phe Ser
    1010                1015                1020

Leu Pro Ser Ala Val Pro Val Ala Arg Ala Ser Ala Ser Ala Thr Leu
1025                1030                1035                1040

Ser Pro Trp Gly Trp Gly Phe Val Cys Arg Arg Leu Trp Gly Leu Leu
                1045                1050                1055

Ile Ser Ala Ser Pro Ala
            1060

<210> SEQ ID NO 103
<211> LENGTH: 26
<212> TYPE: DNA
<213> ORGANISM: Saccharomyces cerevisiae
<220> FEATURE:
<221> NAME/KEY: modified_base
<222> LOCATION: (9)
<223> OTHER INFORMATION: a, c, g or t
<220> FEATURE:
<221> NAME/KEY: modified_base
<222> LOCATION: (12)
<223> OTHER INFORMATION: a, c, g or t
<220> FEATURE:
<221> NAME/KEY: modified_base
<222> LOCATION: (18)
<223> OTHER INFORMATION: a, c, g or t

<400> SEQUENCE: 103
taytggmgng tngarcynga yathaa                                        26

<210> SEQ ID NO 104
<211> LENGTH: 20
<212> TYPE: DNA
<213> ORGANISM: Saccharomyces cerevisiae
<220> FEATURE:
<221> NAME/KEY: modified_base
<222> LOCATION: (6)
<223> OTHER INFORMATION: a, c, g or t
<220> FEATURE:
<221> NAME/KEY: modified_base
<222> LOCATION: (12)
<223> OTHER INFORMATION: a, c, g or t

<400> SEQUENCE: 104 gcrtcnccccc anckytcrta                                              20

<210> SEQ ID NO 105
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

His Asp Glu Leu
  1

<210> SEQ ID NO 106
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Lys Asp Glu Leu
  1

<210> SEQ ID NO 107
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gcggccgcgg atccccgggt accgagctcg aattcact                         38

<210> SEQ ID NO 108
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
ggggcgcgcc ttaattaacg acctgcaggc atgcaagctt ggcgtaatca tggtcat    57

<210> SEQ ID NO 109
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ttcctcgaga ttcaagcgaa tgagaataat g                                31

<210> SEQ ID NO 110
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
ttgcggccgc gaagttttta aaggaaagag ata                              33

<210> SEQ ID NO 111
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
ggcgcgccga gcccgctgac gccaccatcc gtgagaagag ggc                   43

<210> SEQ ID NO 112
```

```
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
atgtggcggc ggccgccacc atgaacacta tccacataat aaaattaccg cttaactacg    60
cc                                                                   62

<210> SEQ ID NO 113
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ggcgcgcccc acgcctagca cttttatgga atctacgcta ggtac                    45

<210> SEQ ID NO 114
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
agtaaaatgc ggccgccacc atgctgctta ccaaaaggtt ttcaaagctg ttc           53

<210> SEQ ID NO 115
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
ggcgcgcccc gacgtgttct catccatgta tttgtttgta atgac                    45

<210> SEQ ID NO 116
<211> LENGTH: 25
<212> TYPE: DNA
<213> ORGANISM: Rattus norvegicus

<400> SEQUENCE: 116
ttcctcactg cagtcttcta taact                                          25

<210> SEQ ID NO 117
<211> LENGTH: 26
<212> TYPE: DNA
<213> ORGANISM: Rattus norvegicus

<400> SEQUENCE: 117
tggagaccat gaggttccgc atctac                                         26

<210> SEQ ID NO 118
<211> LENGTH: 35
<212> TYPE: DNA
<213> ORGANISM: Rattus norvegicus

<400> SEQUENCE: 118
```

-continued

```
ttggcgcgcc tccctagtgt accagttgaa ctttg                    35

<210> SEQ ID NO 119
<211> LENGTH: 32
<212> TYPE: DNA
<213> ORGANISM: Rattus norvegicus

<400> SEQUENCE: 119
gattaattaa ctcactgcag tcttctataa ct                       32
```